US011371990B2

(12) United States Patent
Gerwien et al.

(10) Patent No.: US 11,371,990 B2
(45) Date of Patent: Jun. 28, 2022

(54) METHODS FOR IDENTIFYING CANDIDATE BIOMARKERS

(71) Applicant: Cowper Sciences Inc., Chandler, AZ (US)

(72) Inventors: Robert William Gerwien, San Ramon, CA (US); Theodore Michael Tarasow, San Ramon, CA (US); Jonathan Scott Melnick, San Ramon, CA (US); Kathryn Frances Sykes, San Ramon, CA (US); Michael William Rowe, San Ramon, CA (US)

(73) Assignee: COWPER SCIENCES INC., Chandler, AZ (US)

( * ) Notice: Subject to any disclaimer, the term of this patent is extended or adjusted under 35 U.S.C. 154(b) by 648 days.

(21) Appl. No.: 16/348,704

(22) PCT Filed: Nov. 10, 2017

(86) PCT No.: PCT/US2017/061194
§ 371 (c)(1),
(2) Date: Aug. 12, 2019

(87) PCT Pub. No.: WO2018/089858
PCT Pub. Date: May 17, 2018

(65) Prior Publication Data
US 2020/0209236 A1 Jul. 2, 2020

Related U.S. Application Data

(60) Provisional application No. 62/581,581, filed on Nov. 3, 2017, provisional application No. 62/522,636, filed
(Continued)

(51) Int. Cl.
G01N 33/564 (2006.01)

(52) U.S. Cl.
CPC ..... *G01N 33/564* (2013.01); *G01N 2800/102* (2013.01); *G01N 2800/104* (2013.01)

(58) Field of Classification Search
CPC .......... G01N 33/564; G01N 2800/102; G01N 2800/104; G01N 33/56905; C07K 14/4713; C07K 9/00; C40B 30/04
See application file for complete search history.

(56) References Cited

U.S. PATENT DOCUMENTS 5,143,854 A 9/1992 Pirrung et al.
5,424,186 A 6/1995 Fodor et al.
(Continued)

FOREIGN PATENT DOCUMENTS

CN 1438324 A 8/2003
CN 102099372 A 6/2011
(Continued)

OTHER PUBLICATIONS

Williams et al, "Diagnosis and early detection of CNS-SLE in MRL/lpr mice using peptide microarrays," BMC Immunology, vol. 15, Iss. 23, p. 1-19, Jun. 7, 2014. (Year: 2014).*
(Continued)

Primary Examiner — Jennifer Wecker
Assistant Examiner — Michael Paul Shimek
(74) Attorney, Agent, or Firm — Wilson Sonsini Goodrich & Rosati

(57) ABSTRACT

The disclosed embodiments concern methods, devices, and systems for identifying candidate biomarkers useful for the diagnosis, prognosis, monitoring and screening and/or as targets for the treatment of diseases and conditions in subjects, in particular autoimmune and infectious diseases. The identification of candidate biomarkers is predicated on identifying discriminating peptides present on a peptide array, which can distinguish samples from different subjects
(Continued)

having different health conditions by the binding patterns of antibodies present in the samples.

20 Claims, 167 Drawing Sheets

Specification includes a Sequence Listing.

Related U.S. Application Data on Jun. 20, 2017, provisional application No. 62/522,052, filed on Jun. 19, 2017, provisional application No. 62/462,320, filed on Feb. 22, 2017, provisional application No. 62/421,182, filed on Nov. 11, 2016.

(56) References Cited

U.S. PATENT DOCUMENTS

| | | | |
|---|---|---|---|
| 5,449,754 A | 9/1995 | Nishioka | |
| 5,571,639 A | 11/1996 | Hubbell et al. | |
| 5,593,839 A | 1/1997 | Hubbell et al. | |
| 5,595,915 A | 1/1997 | Geysen | |
| 5,677,195 A | 10/1997 | Winkler et al. | |
| 5,759,774 A | 6/1998 | Hackett et al. | |
| 5,919,523 A | 7/1999 | Sundberg et al. | |
| 6,083,763 A | 7/2000 | Balch | |
| 6,309,831 B1 | 10/2001 | Goldberg et al. | |
| 6,329,209 B1 | 12/2001 | Wagner et al. | |
| 6,346,413 B1 | 2/2002 | Fodor et al. | |
| 6,346,423 B1 | 2/2002 | Schembri | |
| 6,359,125 B1 | 3/2002 | Kim et al. | |
| 6,365,418 B1 | 4/2002 | Wagner et al. | |
| 6,387,631 B1 | 5/2002 | Arnold et al. | |
| 6,399,365 B2 | 6/2002 | Besemer et al. | |
| 6,465,183 B2 | 10/2002 | Wolber | |
| 6,475,808 B1 | 11/2002 | Wagner et al. | |
| 6,475,809 B1 | 11/2002 | Wagner et al. | |
| 6,489,159 B1 | 12/2002 | Chenchik et al. | |
| 6,496,309 B1 | 12/2002 | Bliton et al. | |
| 6,511,277 B1 | 1/2003 | Norris et al. | |
| 6,545,748 B1 | 4/2003 | Trozera | |
| 6,567,163 B1 | 5/2003 | Sandstrom | |
| 6,569,671 B1 | 5/2003 | Okamoto et al. | |
| 6,573,369 B2 | 6/2003 | Henderson et al. | |
| 6,604,902 B2 | 8/2003 | Norris et al. | |
| 6,620,584 B1 | 9/2003 | Chee et al. | |
| 6,630,358 B1 | 10/2003 | Wagner et al. | |
| 6,660,479 B2 | 12/2003 | Kim et al. | |
| 6,706,875 B1 | 3/2004 | Goldberg et al. | |
| 6,723,517 B1 | 4/2004 | Bamdad | |
| 6,733,977 B2 | 5/2004 | Besemer et al. | |
| 6,780,582 B1 | 8/2004 | Wagner et al. | |
| 6,806,954 B2 | 10/2004 | Sandstrom | |
| 6,824,669 B1 | 11/2004 | Li et al. | |
| 6,877,665 B2 | 4/2005 | Challa et al. | |
| 6,890,760 B1 | 5/2005 | Webb | |
| 6,897,073 B2 | 5/2005 | Wagner et al. | |
| 6,919,181 B2 | 7/2005 | Hargreaves | |
| 6,989,267 B2 | 1/2006 | Kim et al. | |
| 6,989,276 B2 | 1/2006 | Thompson et al. | |
| 7,006,680 B2 | 2/2006 | Gulati | |
| 7,081,954 B2 | 7/2006 | Sandstrom | |
| 7,108,472 B2 | 9/2006 | Norris et al. | |
| 7,130,458 B2 | 10/2006 | Bartell | |
| 7,148,058 B2 | 12/2006 | Charych et al. | |
| 7,247,469 B2 | 7/2007 | Wagner et al. | |
| 7,354,721 B2 | 4/2008 | Tchaga | |
| 7,466,851 B2 | 12/2008 | Gulati | |
| 7,507,480 B2 | 3/2009 | Sugama | |
| 7,522,271 B2 | 4/2009 | Sandstrom | |
| 7,534,563 B2 | 5/2009 | Hargreaves | |
| 7,569,343 B2 | 8/2009 | Marton et al. | |
| 7,588,906 B2 | 9/2009 | Brueggemeier et al. | |
| 7,622,295 B2 | 11/2009 | Cabezas | |
| 7,682,797 B2 | 3/2010 | Thompson et al. | |
| 7,682,798 B2 | 3/2010 | Thompson et al. | |
| 7,695,919 B2 | 4/2010 | Apel et al. | |
| 7,723,125 B2 | 5/2010 | Tchaga | |
| 7,884,183 B2 | 2/2011 | Von et al. | |
| 7,909,889 B2 | 3/2011 | Charrier et al. | |
| 7,993,583 B2 | 8/2011 | Dugan et al. | |
| 8,073,626 B2 | 12/2011 | Troup et al. | |
| 8,148,141 B2 | 4/2012 | Nokihara et al. | |
| 8,242,058 B2 | 8/2012 | Raines et al. | |
| RE44,031 E | 2/2013 | Apel et al. | |
| 8,969,255 B2 | 3/2015 | Johnston et al. | |
| 9,970,932 B2 | 5/2018 | Woodbury et al. | |
| 2003/0003516 A1 | 1/2003 | Robinson et al. | |
| 2003/0082579 A1 | 5/2003 | Felgner et al. | |
| 2003/0207467 A1 | 11/2003 | Snyder et al. | |
| 2004/0038307 A1 | 2/2004 | Lee et al. | |
| 2004/0038556 A1 | 2/2004 | French et al. | |
| 2004/0048311 A1 | 3/2004 | Ault-Riche et al. | |
| 2004/0063902 A1 | 4/2004 | Miranda | |
| 2004/0071705 A1 | 4/2004 | Sato et al. | |
| 2005/0009204 A1 | 1/2005 | Fang et al. | |
| 2005/0048566 A1 | 3/2005 | Delisi et al. | |
| 2005/0064395 A1 | 3/2005 | Israel et al. | |
| 2005/0255491 A1 | 11/2005 | Lee et al. | |
| 2006/0013971 A1 | 1/2006 | Chen et al. | |
| 2006/0052948 A1 | 3/2006 | Gorlach | |
| 2007/0003954 A1 | 1/2007 | Kodadek et al. | |
| 2007/0015172 A1 | 1/2007 | Zhang et al. | |
| 2007/0020678 A1 | 1/2007 | Ault-Riche et al. | |
| 2007/0099256 A1 | 5/2007 | Sundararajan et al. | |
| 2007/0122841 A1 | 5/2007 | Rajasekaran et al. | |
| 2008/0026485 A1 | 1/2008 | Hueber et al. | |
| 2008/0124719 A1 | 5/2008 | Chung et al. | |
| 2008/0188618 A1 | 8/2008 | Greving et al. | |
| 2008/0193965 A1 | 8/2008 | Zeng et al. | |
| 2008/0207507 A1 | 8/2008 | Lau et al. | |
| 2009/0054251 A1 | 2/2009 | O'Connor et al. | |
| 2009/0131278 A1 | 5/2009 | Wagner et al. | |
| 2009/0142792 A1 | 6/2009 | Robinson et al. | |
| 2009/0176664 A1 | 7/2009 | Chu | |
| 2010/0035765 A1 | 2/2010 | Kodadek | |
| 2010/0064393 A1 | 3/2010 | Berka et al. | |
| 2010/0210478 A1 | 8/2010 | Gao et al. | |
| 2010/0261205 A1 | 10/2010 | Kakuta et al. | |
| 2011/0046015 A1 | 2/2011 | Honda et al. | |
| 2011/0065594 A1 | 3/2011 | Thompson et al. | |
| 2011/0105366 A1 | 5/2011 | Lebl et al. | |
| 2011/0190149 A1 | 8/2011 | Tainsky et al. | |
| 2011/0275537 A1 | 11/2011 | Rychlewski et al. | |
| 2011/0301057 A1 | 12/2011 | Propheter et al. | |
| 2011/0301058 A1 | 12/2011 | Cheng et al. | |
| 2011/0319291 A1 | 12/2011 | Vrijbloed et al. | |
| 2012/0004130 A1 | 1/2012 | Mattoon et al. | |
| 2012/0134920 A1 | 5/2012 | D'Souza et al. | |
| 2012/0189702 A1 | 7/2012 | Gupta | |
| 2012/0190574 A1 | 7/2012 | Johnston et al. | |
| 2012/0238477 A1 | 9/2012 | Albert et al. | |
| 2013/0071860 A1 | 3/2013 | Hale et al. | |
| 2013/0079242 A1 | 3/2013 | Johnston et al. | |
| 2013/0079250 A1 | 3/2013 | Johnston et al. | |
| 2013/0143756 A1 | 6/2013 | Johnston et al. | |
| 2013/0310265 A1 | 11/2013 | Menegatti et al. | |
| 2014/0087963 A1 | 3/2014 | Johnston et al. | |
| 2014/0135225 A1 | 5/2014 | Crow et al. | |
| 2014/0342939 A1 | 11/2014 | Cohen et al. | |
| 2015/0108344 A1 | 4/2015 | Anderson et al. | |
| 2015/0119289 A1 | 4/2015 | Chen et al. | |
| 2015/0217258 A1 | 8/2015 | Woodbury et al. | |
| 2015/0241420 A1 | 8/2015 | Johnston et al. | |
| 2016/0041158 A1 | 2/2016 | Woodbury et al. | |
| 2016/0067667 A1 | 3/2016 | Rajasekaran et al. | |
| 2016/0131662 A1 | 5/2016 | Kodadek | |
| 2017/0030906 A1 | 2/2017 | Mesa et al. | |
| 2017/0106344 A1 | 4/2017 | Woodbury et al. | |
| 2017/0212101 A1 | 7/2017 | Zhu et al. | |

(56) References Cited

U.S. PATENT DOCUMENTS

| | | |
|---|---|---|
| 2020/0064345 A1 | 2/2020 | Sykes et al. |
| 2020/0116715 A1 | 4/2020 | Gerwien et al. |

FOREIGN PATENT DOCUMENTS

| | | |
|---|---|---|
| EP | 0476014 B1 | 8/1994 |
| EP | 0728520 A1 | 8/1996 |
| EP | 1785726 A1 | 5/2007 |
| JP | 2002540382 A | 11/2002 |
| JP | 2012508011 A | 4/2012 |
| JP | 2012530906 A | 12/2012 |
| JP | 2013188212 A | 9/2013 |
| JP | 2015528912 A | 10/2015 |
| JP | 2016502095 A | 1/2016 |
| WO | WO-9015070 A1 | 12/1990 |
| WO | WO-9118980 A1 | 12/1991 |
| WO | WO-9306121 A1 | 4/1993 |
| WO | WO-9408051 A1 | 4/1994 |
| WO | WO-9512608 A1 | 5/1995 |
| WO | WO-9530642 A1 | 11/1995 |
| WO | WO-9535503 A1 | 12/1995 |
| WO | WO-9609668 A1 | 3/1996 |
| WO | WO-9727329 A1 | 7/1997 |
| WO | WO-0004382 A1 | 1/2000 |
| WO | WO-0156691 A2 | 8/2001 |
| WO | WO-02097051 A2 | 12/2002 |
| WO | WO-03019192 A1 | 3/2003 |
| WO | WO-2004053068 A2 | 6/2004 |
| WO | WO-2005050224 A2 | 6/2005 |
| WO | WO-2007068240 A2 | 6/2007 |
| WO | WO-2007147141 A2 | 12/2007 |
| WO | WO-2008048970 A2 | 4/2008 |
| WO | WO-2008085185 A2 | 7/2008 |
| WO | WO-2008151146 A2 | 12/2008 |
| WO | WO-2009140039 A2 | 11/2009 |
| WO | WO-2010043668 A1 | 4/2010 |
| WO | WO-2010053587 A2 | 5/2010 |
| WO | WO-2010148365 A2 | 12/2010 |
| WO | WO-2011026200 A2 | 3/2011 |
| WO | WO-2011045745 A1 | 4/2011 |
| WO | WO-2011109440 A1 | 9/2011 |
| WO | WO-2011150168 A1 | 12/2011 |
| WO | WO-2012007622 A1 | 1/2012 |
| WO | WO-2012055069 A1 | 5/2012 |
| WO | WO-2014062981 A1 | 4/2014 |
| WO | WO-2014036312 A3 | 5/2015 |
| WO | WO-2015095136 A1 | 6/2015 |
| WO | WO-2016005295 A1 | 1/2016 |
| WO | WO-2016040703 A1 | 3/2016 |
| WO | WO-2017223116 A2 | 12/2017 |
| WO | WO-2017223117 A1 | 12/2017 |
| WO | WO-2017223116 A3 | 2/2018 |
| WO | WO-2018089554 A1 | 5/2018 |
| WO | WO-2018089556 A1 | 5/2018 |
| WO | WO-2018156808 A2 | 8/2018 |
| WO | WO-2018236838 A2 | 12/2018 |

OTHER PUBLICATIONS

Alpert et al., A clinically meaningful metric of immune age derived from high-dimensional longitudinal monitoring. Nature Medicine. 25(3):487-495 (2019). doi: 10.1038/s41591-019-0381-y. Epub Mar. 6, 2019.

Anic et al., New classification criteria for systemic lupus erthematosus correlate with disease activity. Croat Med J. 55: 514-519 (2014).

Benjamini e al. Controlling the false discovery rate: a practical and powerful approach to multiple testing. Journal of the Royal Statistical Society. Series B (Methodological), pp. 289-300 (1995).

Bern, C.: Chagas' Disease. N Engl J Med. 373(19): 1881-1882 (2015).

Bern et al.: An estimate of the burden of Chagas disease in the United States. Clin Infect Dis. 49(5): e52-e54 (2009).

Bombardier et al., Derivation of the SLEDAI. Arthritis and Rheumatism 35(6) (1992).

Buscaglia et al.: The surface coat of the mammal-dwelling infective trypomastigote stage of Trypanosoma cruzi is formed by highly diverse immunogenic mucins. J Biol Chem. 279(16): 15860-15869 (2004).

Busch et al.: Virus and antibody dynamics in acute west nile virus infection. J Infect Dis. 198(7): 984-993 (2008).

Carmona et al., Towards High-throughput Immunomics for Infectious Diseases: Use of Next-generation Peptide Microarrays for Rapid Discovery and Mapping of Antigenic Determinants. Mol Cell Proteomics 14(7):1871-1884 (2015).

Chatelain, E.: Chagas disease research and development: Is there light at the end of the tunnel? Comput Struct Biotechnol J. 15: 98-103 (2016; eCollection 2017).

Cheng et al.: Immunoblot assay using recombinant antigens as a supplemental test to confirm the presence of antibodies to Trypanosoma cruzi. Clin Vaccine Immunol. 14(4): 355-361 (2007).

Choung et al., Determination of B-Cell Epitopes in Patients with Celiac Disease: Peptide Microarrays. Plos One 11(1): e014777 (2016).

Clayton, J.: Chagas disease 101. Nature. 465(7301): S4-S5 (2010).

Cooley et al., High throughput selection of effective serodiagnostics for Trypanosoma cruzi infection. PLoS Negl Trop Dis 2(10):e316 (2008).

Cortes et al., Support-vector networks. Machine Learning. 1995; 20:273-297.

Crooks, et al. WebLogo: a sequence logo generator. Genome Res. Jun. 2004;14(6):1188-90.

De Pablos et al.: Multigene families in Trypanosoma cruzi and their role in infectivity. Infect Immun. 80(7): 2258-2264 (2012).

De Rycker et al.: Identification of Trypanocidal Activity for Known Clinical Compounds Using a New Trypanosoma cruzi Hit-Discovery Screening Cascade. PLoS Negl Trop Dis.10(4): e0004584 (2016).

DeLong et al. Comparing the areas under two or more correlated receiver operating characteristic curves: a nonparametric approach. Biometrics (1988); 44(3) 837-845.

European Application No. 17816082.6 Extended European Search Report dated Apr. 9, 2020.

European Application No. 18821115 Search Report dated Apr. 9, 2021.

European Application No. 18757099 Search Report dated Jan. 18, 2021.

Gomes et al.: Diagnosis of Chagas disease: what has been achieved? What remains to be done with regard to diagnosis and follow up studies? Mem Inst Oswaldo Cruz. 104 Suppl 1: 115-121 (2009).

Granjon et al.: Development of a Novel Multiplex Immunoassay Multi-cruzi for the Serological Confirmation of Chagas Disease. PLoS Negl Trop Dis. 10(4): e0004596 (2016).

Haft et al.: Human orthologs of yeast vacuolar protein sorting proteins Vps26, 29, and 35: assembly into multimeric complexes. Mol Biol Cell. 11(12): 4105-4116 (2000).

International Application No. PCT/US2018/019287 International Search Report and Written Opinion dated Aug. 10, 2018.

Issa et al.: Antitrypanosomal agents: treatment or threat? Lancet. 376(9743): 768 (2010).

Jeong JS, Jiang L, Albino E, et al., Rapid identification of monospecific monoclonal antibodies using a human proteome microarray, Mol Cell Proteomics, 2012;11(6):O111.016253. doi:10.1074/mcp.O111.016253.

Jollymore, M. "Virus research aims to prevent or reverse immune-system aging," Nova Scotia Health Authority Research Annual Report 2017, Feb. 21, 2018, pp. 1-2. Retrieved from the Internet:http://www.nshealth.ca/news/virus-research-aims-prevent-or-reverse-immune-system-aging Oct. 15, 2019.

Keating et al.: Inflammatory and cardiac biomarkers are differentially expressed in clinical stages of Chagas disease. Int J Cardiol. 199: 451-459 (2015).

Lander et al.: Localization and developmental regulation of a dispersed gene family 1 protein in Trypanosoma cruzi. Infect Immun. 78(1): 231-240 (2010).

(56) References Cited

OTHER PUBLICATIONS

Manson et al., Systemic Lupus Erythematosus. Orphanet J Rare Dis 1:6 (2006).
McCullough et al.: The nation's changing blood supply system. JAMA. 269(17): 2239-2245 (1993).
Morillo et al.: Randomized Trial of Benznidazole for Chronic Chagas' Cardiomyopathy. N Engl J Med. 373(14): 1295-1306 (2015).
Moudgil et al. Cytokines in autoimmunity: Role in induction, regulation, and treatment, J. Interferon & Cytokine Res, 31(10):695-703 (2011).
Neufing et al., Exposure and Binding of Selected Immunodominant La/SSB Epitopes on Human Apoptotic Cells. Arthritis Rheum 52(12): 3934-3942 (2005).
Oliveira et al.: Perspectives in Chagas disease treatment. Glob Heart. 10(3): 189-192 (2015).
PCT/US2019/028791 International Search Report and Written Opinion dated Oct. 15, 2019.
Pecoul et al.: The Benefit Trial: Where Do We Go from Here? PLoS Negl Trop Dis. 10(2): e0004343 (2016).
Perez et al.: Chagas disease: the challenge of polyparasitism? Trends Parasitol. 30(4): 176-182 (2014).
Pinazo et al.: Biological markers for evaluating therapeutic efficacy in Chagas disease, a systematic review. Expert Rev Anti Infect Ther. 12(4): 479-496 (2014).
Pinazo et al.: Immunosuppression and Chagas disease: a management challenge. PLoS Negl Trop Dis. 7(1): e1965 (2013).
Praast et al.: Evaluation of the Abbott Architect Chagas prototype assay. Diagn Microbiol Infect Dis. 69(1): 74-81 (2011).
Rassi et al.: Chagas disease. Lancet. 375(9723): 1388-1402 (2010).
Remesar et al.: Bimodal distribution of Trypanosoma cruzi antibody levels in blood donors from a highly endemic area of Argentina: what is the significance of low-reactive samples? Transfusion. 55(10): 2499-2504 (2015).
Sodre et al.: Proteomic map of Trypanosoma cruzi CL Brener: the reference strain of the genome project. Arch Microbiol. 191(2): 177-184. Epub Nov. 11, 2008. (2009).
Sokolove et al., Development and deployment of antigen arrays for investigation of B-cell specificity in autoimmune disease. Frontiers in Bioscience E4: 320-330 (2012).
Steverding, D.: The history of Chagas disease. Parasit Vectors. 7: 317 (2014).
Tarasow et al., Immunosignature Autoantibody Profiles Provide Mechanistic Insight into Systemic Lupus Erythematosus and Differentiation from Symptomatically Overlapping Diseases. Retrieved from http://www.healthtell.com/wp-content/uploads/2018/06/5-HealthTell_ACR2017_poster_SLE (2017).
Tobler et al.: Evaluation of a new enzyme-linked immunosorbent assay for detection of Chagas antibody in US blood donors. Transfusion. 47(1): 90-96 (2007).
Torzewski et al., Animal Models of C-Reactive Protein. Hindawl Publishing Corporation, Mediators of Inflammation, pp. 1-7 (2014).
U.S. Appl. No. 16/312,131 Non-Final Office Action dated May 12, 2021.
U.S. Appl. No. 16/312,168 Non-Final Office Action dated Feb. 18, 2021.
Van Der Vekiens et al., Human and equine cardiovascular endocrinology: beware to compare. Cardiovascular Endocrinology 2(4): 67-76 (2013).
Viotti et al.: Long-term cardiac outcomes of treating chronic Chagas disease with benznidazole versus no treatment: a nonrandomized trial. Ann Intern Med. 144(10): 724-734 (2006).
Viotti et al.: Side effects of benznidazole as treatment in chronic Chagas disease: fears and realities. Expert Rev Anti Infect Ther. 7(2): 157-163 (2009).
Wang et al., Plasma Autoantibodies Associated With Basal-like Breast Cancers. Cancer Epidemiol Biomarkers Prev 24(9): 1332-1340 (2015).

Agarwal, et al. Disregulated expression of the Th2 cytokine gene in patients with intraoral squamous cell carcinoma. Immunol Invest. Feb. 2003;32(1-2):17-30.
Altschul et al. Local alignment statistics. Meth. Enzymol. 266:460-480 (1996).
Anderson, et al. The human plasma proteome: history, character, and diagnostic prospects. Mol Cell Proteomics. Nov. 2002;1(11):845-67.
Andresen, et al. Deciphering the Antibodyome—Peptide Arrays for Serum Antibody Diagnostics, Current Proteomics, 6(1):1-12 (2009).
Assayag et al. High Resolution Computed Tomography Scoring Systems for Evaluating Interstitial Lung Disease in Systemic Sclerosis Patients. Rheumatology S1:003 (2012).
Bailey. MEME: discovering and analyzing DNA and protein sequence motifs. (2006) Nucleic Acids Res. 34(suppl 2): W369-W373.
Bauer et al., Identification and Quantification of a New Family of Peptide Endocannabinoids (Pepcans) Showing Negative Allosteric Modulation at CB1 Receptors, Journal of Biological Chemistry (2012) 287(44); 36944-36967.
Berglund, et al. A Genecentric Human Protein Atlas for Express Profiles Based on antibodies. Oct. 1, 2008, Molecular and Cellular Proteomics, 7, pp. 2019-2027.
Boltz, et al. Peptide microarrays for carbohydrate recognition. Analyst. Apr. 2009;134(4):650-2. doi: 10.1039/b823156g. Epub Feb. 11, 2009.
Borrebaeck. Antibodies in diagnostics—from immunoassays to protein chips. Immunol Today. Aug. 2000;21(8):379-82.
Breitling F. et al. High-density peptide arrays. Mol. BioSyst., vol. 5, pp. 224-234, 2009.
Brown, et al. Statistical methods for analyzing immunosignatures. BMC Bioinformatics. Aug. 19, 2011;12:349. doi: 10.1186/1471-2105-12-349.
Brown, et al. The preclinical natural history of serous ovarian cancer: defining the target for early detection. PLoS Med. Jul. 2009;6(7):e1000114. doi: 10.1371/journal.pmed.1000114. Epub Jul. 28, 2009.
Brusic, et al. Information technologies for vaccine research. Expert Rev Vaccines. Jun. 2005;4(3):407-17.
Butler, et al. The immunochemistry of sandwich ELISAs—VI. Greater than 90% of monoclonal and 75% of polyclonal anti-fluorescyl capture antibodies (CAbs) are denatured by passive adsorption. Mol Immunol. Sep. 1993;30(13):1165-75.
Butler. Solid supports in enzyme-linked immunosorbent assay and other solid-phase immunoassays. Methods. Sep. 2000;22(1):4-23.
Canadian Patent Application No. 2,882,801 Office Action dated Jun. 14, 2019.
Casey, et al. Phage display of peptides in ligand selection for use in affinity chromatography. Methods Mol Biol. 2008;421:111-24.
Cenci, et al. Managing and exploiting stress in the antibody factory. FEBS Lett. Jul. 31, 2007;581(19):3652-7. Epub Apr. 24, 2007.
Cerecedo, et al. Mapping of the IgE and IgG4 sequential epitopes of milk allergens with a peptide microarray-based immunoassay. J Allergy Clin Immunol. Sep. 2008;122(3):589-94. doi: 10.1016/j.jaci.2008.06.040.
Chase, et al. Evaluation of biological sample preparation for immunosignature-based diagnostics. Clin Vaccine Immunol. Mar. 2012;19(3):352-8. doi: 10.1128/CVI.05667-11. Epub Jan. 11, 2012.
Chase et al,. Evaluation of biological sample preparation for immunosignature-based diagnostics. Clinical Vaccine and Immunology. 19(3):352-358 (2012).
Chene, P., Challenges in Design of Biochemical Assays for the Identification of Small Molecules to Target Multiple Conformations of Protein Kinases. Drug Discovery Today, 13(11/12); 522-529 (2008).
Christian, R.B., et al. (1992) Simplified methods for construction, assessment and rapid screening of peptide libraries in bacteriophage. Journal of Molecular Biology 227, 711-718.
Cooperman, et al. Cell division rates of primary human precursor B cells in culture reflect in vivo rates. Stem Cells. 2004;22(6):1111-20.
Cretich, et al. Epitope mapping of human chromogranin A by peptide microarrays. Methods Mol Biol. 2009;570:221-32. doi: 10.1007/978-1-60327-394-7_10.

(56) References Cited

OTHER PUBLICATIONS

Cretich. Protein and peptide arrays: Recent trends and new directions. (2006) Biomol. Eng. 23: 77-88 (2006).

Daver, et al. The usefulness of prostate-specific antigen and prostatic acid phosphatase in clinical practice. Am J Clin Oncol. 1988;11 Suppl 2:S53-60.

de Paz, J.L. et la. Exploration of the use of an acylsulfonamide safety-catch linker for the polymer-supported synthesis of hyaluronic acid oligosaccharides. Carbohydr Res. Mar. 30, 2010;345(5):565-71. Epub Jan. 4, 2010.

Derda, et al. Diversity of phage-displayed libraries of peptides during panning and amplification. Molecules. Feb. 21, 2011;16(2):1776-803. doi: 10.3390/molecules16021776.

Diehnelt, et al. Discovery of high-affinity protein binding ligands-backwards. PLoS One. May 19, 2010;5(5):e10728. doi: 10.1371/journal.pone.0010728.

Draghici. Statistics and Data Analysis for Microarrays Using R and Bioconductor. Chapman & Hall/CRC. 2012.

Engvall, et al. Enzyme-linked immunosorbent assay (ELISA). Quantitative assay of immunoglobulin G. Immunochemistry. Sep. 1971;8(9):871-4.

EP 10790305.6 Extended European Search Report dated Aug. 20, 2013.

European Patent Application No. 13 833992.4 European Search Report dated Apr. 25, 2016.

Falsey, J.R., et al. Peptide and small molecule microarray for high throughput cell adhesion and functional assays. Bioconjugate Chem. (2001) 12, 346-353.

Favoino et al. Autoantibodies recognizing the amino terminal 1-17 segment of CENP-A display unique specificities in systemic sclerosis. PLoS One 8(4):e61453 (2013).

Fodor. Multiplexed biochemical assays with biological chips. Nature 364:555-556 (1993).

Folgori, A., et al. A general strategy to identify mimotopes of pathological antigens using only random peptide libraries and human sera. (1994) EMBO Journal, vol. 13, No. 9, pp. 2236-2243.

Foong, et al. Bacterial glycoprofiling by using random sequence peptide microarrays. Chembiochem. Mar. 23, 2009;10(5):877-88. doi: 10.1002/cbic.200800716.

Foong, et al. Current advances in peptide and small molecule microarray technologies. Curr Opin Chem Biol. Apr. 2012;16(1-2):234-42. doi: 10.1016/j.cbpa.2011.12.007. Epub Jan. 3, 2012.

Forster, et al. The bulk of the peripheral B-cell pool in mice is stable and not rapidly renewed from the bone marrow. Proc Natl Acad Sci U S A. Jun. 1990;87(12):4781-4.

Frith. Discovering Sequence Motifs with Arbitrary Insertions and Deletions. (2008) PLOS Comput. Biol. 4: e1000071.

Fu et al., Exploring peptide space for enzyme modulators, J. Am. Chem. Soc., Apr. 2010, 6419-6424, vol. 132, No. 18.

Fu, et al. Peptide-modified surfaces for enzyme immobilization. PLoS One. Apr. 8, 2011;6(4):e18692. doi: 10.1371/journal.pone.0018692.

Gallina, et al. Prediction of pathological stage is inaccurate in men with PSA values above 20 ng/mL. Eur Urol. Nov. 2007;52(5):1374-80. Epub Dec. 11, 2006.

Geysen, et al. Use of peptide synthesis to probe viral antigens for epitopes to a resolution of a single amino acid. Proc Natl Acad Sci U S A. Jul. 1984;81(13):3998-4002.

Greving, et al. High-throughput screening in two dimensions: binding intensity and off-rate on a peptide microarray. Anal Biochem. Jul. 1, 2010;402(1):93-5. doi: 10.1016/j.ab.2010.03.002. Epub Mar. 6, 2010.

Greving, et al. Thermodynamic additivity of sequence variations: an algorithm for creating high affinity peptides without large libraries or structural information. PLoS One. Nov. 11, 2010;5(11):e15432. doi: 10.1371/journal.pone.0015432.

Gupta, N., et al. Engineering a synthetic ligand for tumor necrosis factor-alpha.(2011) Bioconjugate Chemistry, vol. 22, pp. 1473-1478.

Halperin et al. Exploring Antidbody Recognition of Sequence Space Through Random-Sequence Peptide Microarrays. Molecular & Cellular Proteomics 10.3:1-10 (2011).

Halperin, R.F., Stafford, P. and Johnson S.A. Exploring Antibody Recognition of Sequence Space through Random-Sequence Peptide Microarrays. (2011) Molecular Cell Proteomics, vol. 10, No. 3, pp. 1-10.

Hanash, S. Disease proteomics. (Mar. 2003) Nature vol. 422, pp. 226-232.

Hao, et al. Homeostasis of peripheral B cells in the absence of B cell influx from the bone marrow. J Exp Med. Oct. 15, 2001;194(8):1151-64.

Hecker et al. Computational analysis of high-density peptide microarray data with application from systemic sclerosis to multiple sclerosis. Autoimmunity Reviews 11:180-190 (2012).

Henikoff et al. Amino acid substitution matrices from protein blocks. PNAS USA 89(22):10915-10919 (1992).

Hori, et al. Mathematical model identifies blood biomarker-based early cancer detection strategies and limitations. Sci Transl Med. Nov. 16, 2011;3(109):109ra116. doi: 10.1126/scitranslmed.3003110.

Huang, et al. MIMOX: a web tool for phage display based epitope mapping. BMC Bioinformatics. Oct. 12, 2006;7:451.

Hughes, et al. Immunosignaturing can detect products from molecular markers in brain cancer. PLoS One. 2012;7(7):e40201. doi: 10.1371/journal.pone.0040201. Epub Jul. 16, 2012.

International search report and written opinion dated Oct. 22, 2012 for PCT/US2012/036631.

International search report and written opinion dated Feb. 3, 2014 for PCT/US2013/057373.

International search report and Written opinion dated Apr. 28, 2015 for PCT/US2013/057373.

International search report dated Dec. 20, 2013 for PCT/US2013/065541.

Janeway, et al. Immunobiology: The Immune System in Health and Disease. Current Biology Limited. 1997.

Jonassen. Efficient discovery of conserved patterns using a pattern graph. (1997) Comput. Appl. Biosci. 13: 509-22.

Kroening, et al. Autoreactive antibodies raised by self derived de novo peptides can identify unrelated antigens on protein microarrays. Are autoantibodies really autoantibodies? Exp Mol Pathol. Jun. 2012;92(3):304-11. doi: 10.1016/j.yexmp.2012.03.002. Epub Mar. 8, 2012.

Kukreja et al. Comparative study of classification algorithms for immunosignaturing data. BMC Bioinformatics 13:139 (2012).

Kukreja, M., et al. Immunosignaturing Microarrays Distinguish Antibody Profiles of Related Pancreatic Diseases. (2012) Journal of Proteomics & Bioinformatics, vol. S6, pp. 001.

Legutki et al., A general method for characterization of humoral immunity induced by a vaccine or infection. Vaccine. 28(28):4529-4537 (2010).

Legutki, J.B., et al. Scalable high-density peptide arrays for comprehensive health monitoring. Nature Communications, vol. 5, p. 4785; (Sep. 3, 2014).

Lewczuk, et al. Amyloid beta peptides in plasma in early diagnosis of Alzheimer's disease: A multicenter study with multiplexing. Exp Neurol. Jun. 2010;223(2):366-70. doi: 10.1016/j.expneurol.2009.07.024. Epub Aug. 5, 2009.

Lin, et al. Development of a novel peptide microarray for large-scale epitope mapping of food allergens. J Allergy Clin Immunol. Aug. 2009;124(2):315-22, 322.e1-3. doi: 10.1016/j.jaci.2009.05.024. Epub Jul. 3, 2009.

Lisnevskaia et al. Systemic lupus erythematosus. Lancet 384(9957):1878-88 (2014).

Liu et al. Towards proteome-wide production of monoclonal antibody by phage display. J Mol Biol. 315(5):1063-1073 (2002).

Liu, R., et al. Combinatorial peptide library methods for immunobiology research. (2003) Experimental Hematology vol. 31, pp. 11-30.

Lorenz, P., et al. Probing the epitope signatures of IgG antibodies in human serum from patients with autoimmune disease. (2009) Methods in Molecular Biology, Epitope Mapping Protocls, vol. 524, pp. 247-258.

(56) References Cited

OTHER PUBLICATIONS

MacKey, et al. Getting more from less: algorithms for rapid protein identification with multiple short peptide sequences. Mol Cell Proteomics. Feb. 2002;1(2):139-47.
McDade, et al. What a Drop Can Do: Dried Blood Spots as a Minimally Invasive Method for Integrating Biomarkers Into Population-Based Research, Demography 44(4):899-925 (2007).
Medsger et al. Assessment of disease severity and prognosis. Clin Exper Rheumatol 21:S42-S46 (2003).
Merbl, et al. A Systems Immunology Approach to the Host-Tumor Interaction: Large-Scale Patterns of Natural Autoantibodies Distinguish Healthy and Tumor-Bearing Mice. PLoS One vol. 4, Issue 6, p. e6053. Jun. 2009.
"Mestas, et al., Of Mice and Not Men: Differences Between Mouse and Human Immunology, The Journal of Immunology, 172;2731-2738 (2004)."
Min et al. Peptide arrays: towards routine implementation. Current Opinion in Chemical Biology vol. 8, pp. 554-558, 2004.
Miseta, Attila et al. Relationship Between the Occurrence of Cysteine in Proteins and the Complexity of Organisms. (2000) Mol. Biol. Evol., vol. 17, pp. 1232-1239.
Mitra et al., Self-assembly of cyclic metal-DNA nanostructures using ruthenium tris(bipyridine)-branchedoligonucleotides. Agnewandte Chemie. 43(43):5804-5808 (2004).
Mohan, S., et al. Association energetics of cross-reactive and specific antibodies. (Feb. 17, 2009) Biochemistry vol. 48, No. 6, pp. 1390-1398.
Moller, et al. DNA probes on chip surfaces studied by scanning force microscopy using specific binding of colloidal gold. Nucleic Acids Res. Oct. 15, 2000;28(20):E91.
Moreau, et al. Discontinuous epitope prediction based on mimotope analysis. Bioinformatics. May 1, 2006;22(9):1088-95. Epub Jan. 24, 2006.
Navalkar, K.A. et al. Peptide based diagnostics: Are random-sequence peptides more useful than tiling proteome sequences? Journal of Immunological Methods, vol. 417, pp. 10-21 (2015).
Neuman De Vegvar, et al. Microarray profiling of antiviral antibodies for the development of diagnostics, vaccines, and therapeutics. (2004) Clinical Immunology, vol. 111 pp. 196-201.
No Author. Affymetrix, GeneChip Human Genome Arrays Data Sheet, pp. 1-4 (2003).
No Author. NSB9 Amine Slide, NSB Postech, 2007, http://www.nsbpostech.com/2007/products/slide.html.
No Author. Pubchem CID 110154. Created: Aug. 8, 2005. Date accessed: Feb. 26, 2018, pp. 1-15.
Nobrega, A., et al. Functional diversity and clonal frequencies of reactivity in the available antibody repertoire. (1998) European Journal of Immunology vol. 28, pp. 1204-1215.
Office action dated Apr. 8, 2013 for U.S. Appl. No. 13/379,080.
Office action dated Sep. 12, 2014 for U.S. Appl. No. 13/379,080.
Office action dated Sep. 20, 2013 for U.S. Appl. No. 13/624,332.
Office action dated Sep. 20, 2013 for U.S. Appl. No. 13/624,386.
Office action dated Oct. 3, 2013 for U.S. Appl. No. 13/379,080.
Oglesby et al. Impact of Early Versus Late Systemic Lupus Erythematosus Diagnosis on Clinical and Economic Outcomes. Applied Health Economics & Health Policy 12(2):179-90 (2014).
Panicker, R.C., et al. Recent advances in peptide-based microarray technologies. (2004) Combinatorial Chemistry & High Throughput Screening vol. 7, pp. 547-556.
PCT/US2017/038391 International Search Report and Written Opinion dated Dec. 11, 2017.
PCT/US2017/038391 Invitation to Pay Additional Fees dated Oct. 5, 2017.
PCT/US2017/038392 International Search Report and Written Opinion dated Sep. 8, 2017.
PCT/US2017/060721 International Preliminary Report on Patentability dated May 23, 2019.
PCT/US2017/060721 International Search Report and Written Opinion dated Feb. 26, 2018.
PCT/US2017/060724 International Preliminary Report on Patentability dated May 23, 2019.
PCT/US2017/060724 International Search Report and Written Opinion dated Mar. 13, 2018.
PCT/US2018/038240 International Search Report and Written Opinion dated Dec. 27, 2018.
PCT/US2019/017326 International Search Report and Written Opinion dated Jun. 3, 2019.
Perez-Gordo, et al. Epitope mapping of Atlantic salmon major allergen by peptide microarray immunoassay. Int Arch Allergy Immunol. 2012;157(1):31-40. doi: 10.1159/000324677. Epub Sep. 5, 2011.
Price et al., On silico peptide microarrays for high-resolution mapping of antibody epitopes and diverse protein-protein interactions, Nat Med, Sep. 2012, 1434-40, vol. 18, No. 9.
Quackenbush, et al. Computational Analysis of Microarray Data, Nature Reviews, 2;418-427 (2001).
Quintana, et al., Antigen-chip technology for accessing global information about the state of the body. 2006 Lupus vol. 15, pp. 428-430.
Quintana, et al. The Natural autoantibody repertoire and autoimmune disease. Biomedicine & Pharmacotheraphy vol. 58 (2004) pp. 276-281.
Reddy, et al. Identification of candidate IgG biomarkers for Alzheimer's disease via combinatorial library screening. Cell. Jan. 7, 2011;144(1):132-42. doi: 10.1016/j.cell.2010.11.054.
Reddy, et al., Protein fingerprinting in complex mixtures with peptoid microarrays. Proc. Of The Nat'l Academy of Sciences, Nat'l Academy of Sciences, US, 102(36):12672-12677 Sep. 2005.
Reineke, et al., Epitope Mapping Protocols, Method in Molecular Biology 524, 2nd Edition, Huma Press. 1-447 (2009).
Reineke, et al. Identification Of Distinct Antibody Epitopes and mimotopes from a peptide array of 5520 randomly generated sequences. Journal of Immunological Methods vol. 267 (2002) pp. 37-51.
Restrepo, et al. Application of immunosignatures to the assessment of Alzheimer's disease. Ann Neurol. Aug. 2011;70(2):286-95. doi: 10.1002/ana.22405.
Rigoutsos. In Silico Pattern-Based Analysis of the Human Cytomegalovirus Genome. (1998) Bioinformatics 14: 55-67.
Roobol. Contemporary role of prostate cancer gene 3 in the management of prostate cancer. Curr Opin Urol. May 2011;21(3):225-9. doi: 10.1097/MOU.0b013e328344939c.
Shreffler, W.G., et al. IgE and IgG4 epitope mapping by microarray immunoassay reveals the diversity of immune response to the peanut allergen, Ara h 2. (2005) J Allergy Clin Immunol vol. 116, No. 4, pp. 893-899.
PCT/US2019/017326 Invitation to Pay Additional Fees dated Apr. 12, 2019.
Stafford, et al. Physical characterization of the "immunosignaturing effect". Mol Cell Proteomics. Apr. 2012;11(4):M111.011593. doi: 10.1074/mcp.M111.011593. Epub Jan. 18, 2012.
Stafford P, and Johnston,Microarray technology displays the complexities of the humoral immune response. Expert Rev. Mol. Diagn. vol. 11, No. 1, pp. 5-8, Jan. 2011.
Stafford, P., et al. Immunosignature system for diagnosis of cancer. PNAS, vol. 111, No. 30; pp. E3072-E3080 (Jul. 14, 2014).
States et al. Improved sensitivity of nucleic acid database searches using application-specific scoring matrices. Methods 3:66-70 (1991).
Sulzer, et al. Memory in idiotypic networks due to competition between proliferation and differentiation. Bull Math Biol. Nov. 1993;55(6):1133-82.
Szardenings, M. Phage display of random peptide libraries: applications, limits, and potential. (2003) Journal of Receptors and Signal Transduction, vol. 23, No. 4, pp. 307-349.
Tan et al. Autoantibodies to fibrillin 1 in systemic sclerosis: ethnic differences in antigen recognition and lack of correlation with specific clinical features or HLA alleles. Arthritis Rheum 43(11):2464-71 (2000).
Tang et al., Current Developments in SELDI Affinity Technology, Mass Spectrometry Reviews 23;34-44 (2004).

(56) References Cited

OTHER PUBLICATIONS

Tedesco, et al. A new strategy for the early diagnosis of rheumatoid arthritis: a combined approach. Autoimmun Rev. Jan. 2009;8(3):233-7. doi: 10.1016/j.autrev.2008.07.031. Epub Aug. 15, 2008.
Thompson, et al. Prostate-specific antigen in the early detection of prostate cancer. CMAJ. Jun. 19, 2007;176(13):1853-8.
Thorpe, I.F., and Brooks, C.L., Molecular evolution of affinity and flexibility in the immune system. (May 22, 2007) PNAS vol. 104, No. 21, pp. 8821-8826.
Uhlen, M., et al. Generation and validation of affinity reagents on a proteome-wide level. (2009) Journal of Molecular Recognition, vol. 22, pp. 57-64.
United States Patent and Trademark Office, Subject Matter Eligibility Examples: Life Sciences, Subject Matter Eligibility Update, 2016, 1-31.
U.S. Appl. No. 13/379,080 Advisory Action dated Mar. 4, 2014.
U.S. Appl. No. 13/379,080 Final Office Action dated Jul. 21, 2015.
U.S. Appl. No. 13/379,080 Final Office action dated Apr. 8, 2013.
U.S. Appl. No. 13/379,080 Final Office action dated Oct. 3, 2013.
U.S. Appl. No. 13/379,080 Final Office action dated Sep. 12, 2014.
U.S. Appl. No. 13/379,080 Office Action dated Aug. 4, 2016.
U.S. Appl. No. 13/379,080 Office action dated Oct. 11, 2012.
U.S. Appl. No. 13/379,080 Restriction Requirement dated Mar. 29, 2016.
U.S. Appl. No. 13/624,332 Advisory Action dated Mar. 4, 2014.
U.S. Appl. No. 13/624,332 Advisory Office Action dated Aug. 2, 2017.
U.S. Appl. No. 13/624,332 Final action dated Sep. 20, 2013.
U.S. Appl. No. 13/624,332 Final Office Action dated Feb. 28, 2018.
U.S. Appl. No. 13/624,332 Non-Final Office Action dated Oct. 3, 2017.
U.S. Appl. No. 13/624,332 Office Action dated Feb. 8, 2016.
U.S. Appl. No. 13/624,332 Office action dated Jan. 22, 2013.
U.S. Appl. No. 13/624,332 Office Action dated Jul. 18, 2016.
U.S. Appl. No. 13/624,386 Advisory Action dated Mar. 4, 2014.
U.S. Appl. No. 13/624,386 Final action dated Sep. 20, 2013.
"U.S. Appl. No. 13/624,386 Notice of Allowance dated Mar. 13, 2017".
U.S. Appl. No. 13/624,386 Office action dated Jan. 23, 2013.
U.S. Appl. No. 13/624,386 Office Action dated Jan. 7, 2016.
U.S. Appl. No. 13/624,386 Office Action dated Jul. 25, 2016.
U.S. Appl. No. 13/683,778 Notice of Allowance dated Nov. 24, 2014.
U.S. Appl. No. 13/683,778 Office Action dated Oct. 1, 2013.
U.S. Appl. No. 14/014,168 Advisory Office Action dated Dec. 16, 2016.
U.S. Appl. No. 14/014,168 Advisory Office Action dated Jan. 3, 2018.
U.S. Appl. No. 14/014,168 Final Office Action dated Sep. 18, 2017.
U.S. Appl. No. 14/014,168 Office Action dated Feb. 21, 2017.
U.S. Appl. No. 14/014,168 Office Action dated Jan. 6, 2016.
U.S. Appl. No. 14/014,168 Restriction Requirement dated Oct. 1, 2015.
U.S. Appl. No. 14/424,022 Final Office Action dated Sep. 7, 2018.
U.S. Appl. No. 15/621,877 Non-Final Office Action dated Sep. 13, 2018.
U.S. Appl. No. 13/624,332 Advisory Office Action dated Oct. 13, 2016.
U.S. Appl. No. 13/624,386 Office Action dated Nov. 28, 2016.
U.S. Appl. No. 14/014,168 Final Office Action dated Sep. 1, 2016.
Usami, et al. The effect of pH, hydrogen peroxide and temperature on the stability of human monoclonal antibody. J Pharm Biomed Anal. Jun. 1996;14(8-10):1133-40.
Volk, et al. The accuracy of primary care patients' self-reports of prostate-specific antigen testing. Am J Prev Med. Jan. 2002;22(1):56-8.
Wang, Y., et al. Detection of Mammary Tumor Virus ENV Gene-like Sequences in Human Breast Cancer. (Nov. 15, 1995) Cancer Research vol. 55, pp. 5173-5179.
Waterboer et al., Bried Blood Spot Samples For Seroepidemiology of Infections With Human Papillomaviruses, Helicobacter pylori, Hepatitis C Virus, and JC Virus, Cancer, Epidemiology, Biomarkers and Prevention, 2011,21 (2), 288-293.
Yang, et al. Segmentation and intensity estimation for microarray images with saturated pixels. BMC Bioinformatics. Nov. 30, 2011;12:462. doi: 10.1186/1471-2105-12-462.
Zhou, Z.H., et al. Properties and function of polyreactive antibodies and polyreactive antigen-binding B cells. (Dec. 2007) J. Autoimmun. vol. 29, No. 4, pp. 219-228.
Zou et al. Regularization and Variable Selection via the Elastic Net. J R Statist Soc B 67(Part 2):301-320 (2005).
Zundel, et al. Development and evaluation of an enzyme-linked immunoassay for the prostate: specific antigen utilizing two monoclonal antibodies. Urol Res. 1990;18(5):327-30.

\* cited by examiner

FIG. 5

Box 3: Major Clinical Manifestations of Systemic Sclerosis

Cutaneous
- Diffuse edema of hands and feet (early stages)
- Progressive skin tightening
- Sclerodactyly
- Calcinosis
- Telangiectasias
- Digital ulcers and pits
- Contractures
- Hyperpigmentation, hypopigmentation, salt and pepper skin
- Characteristic facies Vascular
- Raynaud's phenomenon
- Nailfold capillary changes
- Digital ischemia and ulcers
- Vasculitic leg ulcers (rare)

Pulmonary
- Interstitial lung disease, including alveolitis and interstitial fibrosis
- Pulmonary hypertension
- Recurrent aspiration pneumonitis caused by esophageal reflux and dysmotility
- Chest wall restriction (decreased thoracic compliance)
- Respiratory muscle weakness Cardiac
- Cardiomyopathy (systolic and diastolic dysfunction): Congestive heart failure
- Conduction defects
    - Septal infarction pattern
    - Ventricular conduction abnormalities
    - Arrhythmias
    - Heart blocks
- Pericarditis or pericardial effusion (impending renal crisis)

Renal
- Scleroderma renal crisis (hypertension, renal failure MAHA)

FIG. 5, Continued

Musculoskeletal and Rheumatologic
- Arthralgia
- Tendon friction rubs (relatively specific for diffuse scleroderma)
- Inflammatory arthritis, erosive arthropathy (rare)
- Myopathy, myositis Gastrointestinal
- Gastroesophageal reflux
- Esophageal dysmotility, aperistaltic esophagus
- Esophageal stricture
- Adenocarcinoma arising in Barrett's esophagus (occasionally)
- Watermelon stomach (gastric antral vascular ectasias [GAVE]): Iron-deficiency anemia
- Decreased peristalsis throughout GI tract, leading to bloating, early satiety, stasis, and pseudo-obstruction
- Bacterial overgrowth and malabsorptive diarrhea, alternating diarrhea and constipation
- Megacolon (rare)
- Colonic wide-mouth diverticula (usually asymptomatic)
- Pneumatosis cystoides intestinalis
- Primary biliary cirrhosis
- Anal incontinence Endocrine
- Hypothyroidism Neurologic
- Carpal tunnel syndrome
- Trigeminal neuralgia

FIG. 6

Box 4: American College of Rheumatology Diagnostic Criteria for Systemic Sclerosis Major Criterion

- Proximal sclerodermatous skin changes (proximal to the metacarpophalangeal joints)

Minor Criteria
- Sclerodactyly
- Digital pitting scars of fingertips or loss of substance of the distal finger pads
- Bibasilar pulmonary fibrosis

FIG. 7

Classification Criteria for Polymyositis and Dermatomyositis*

1. Skin lesions

Heliotrope: red-purple edematous erythema on the upper palpebral

Gottron's sign: red-purple keratotic, atrophic erythema or macules on the extensor surface if finger joints Erythema on the extensor surface of extremity joints, slight raised red-purple erythema over elbows or knees 2. Proximal muscle weakness (upper or lower extremity and trunk)

3. Elevated serum creatine kinase or aldolase level

4. Muscle pain on grasping or spontaneous pain

5. Myogenic changes on electromyography (short-duration, polyphasic motor unit potentials with spontaneous fibrillation potentials)

6. Positive anti-Jo-1 antibody test (histidyl-tRNA synthetase)

7. Nondestructive arthritis or arthralgias

8. Systemic inflammatory signs (temperature: more than 37°C [98.6°F] at axilla, elevated serum C-reactive protein level or accelerated erythrocyte sedimentation rate of more than 20 mm per hour by Westergren)

9. Pathologic findings compatible with inflammatory myositis (inflammatory infiltration of skeletal evidence of active regeneration may be seen)

---

\* —Patients presenting with at least one finding from item 1 and four findings from items 2 through 9 are said to have dermatomyositis (sensitivity, 94.1 percent [127/135] and specificity of skin lesions against systemic lupus erythema and systemic sclerosis, 90.3 percent [214/237]). Patients presenting with at least four findings from items 2 through 9 are said to have polymyositis (sensitivity, 98.9 percent [180/182] and specificity of polymyositis and dermatomyositis against all control diseases combined, 95.2 percent [373/392]).

FIG. 8A

| motif | n | n.lib | enrich | p | fdr | padj.holm | Pr_seqs.m | PLR |
|---|---|---|---|---|---|---|---|---|
| FAGE | 3 | 4 | 12.42717 | 2.12E-06 | 0.000155 | 0.000918 | 0.75 | 375.027 |
| KRR | 15 | 174 | 8.068678 | 2.01E-11 | 7.45E-09 | 2.23E-08 | 0.086207 | 11.7933 |
| WWY | 7 | 89 | 7.361536 | 8.66E-06 | 0.000453 | 0.009443 | 0.078652 | 10.6715 |
| KKRW | 3 | 7 | 7.101243 | 1.82E-05 | 0.000798 | 0.007816 | 0.428571 | 93.75675 |
| LKK | 8 | 107 | 6.997882 | 2.90E-06 | 0.000161 | 0.003165 | 0.074766 | 10.10174 |
| KRFF | 5 | 13 | 6.37291 | 4.26E-08 | 9.34E-06 | 1.86E-05 | 0.384615 | 78.13063 |
| ASDD | 3 | 8 | 6.213587 | 2.89E-05 | 0.000976 | 0.012372 | 0.375 | 75.0054 |
| LKSF | 3 | 8 | 6.213587 | 2.89E-05 | 0.000976 | 0.012372 | 0.375 | 75.0054 |
| WYW | 14 | 213 | 6.151894 | 3.27E-09 | 4.53E-07 | 3.60E-06 | 0.065728 | 8.794603 |
| GES | 7 | 108 | 6.066451 | 3.07E-05 | 0.001362 | 0.033318 | 0.064815 | 8.66399 |
| KKR | 18 | 283 | 5.953145 | 3.38E-11 | 9.39E-09 | 3.74E-08 | 0.063604 | 8.491177 |
| KRW | 11 | 185 | 5.565207 | 4.22E-07 | 3.35E-05 | 0.000463 | 0.059459 | 7.902868 |
| VKR | 16 | 277 | 5.406306 | 1.65E-09 | 2.90E-07 | 1.82E-06 | 0.057762 | 7.663387 |
| YWY | 10 | 174 | 5.379119 | 1.91E-06 | 0.000118 | 0.002087 | 0.057471 | 7.6225 |
| LKR | 16 | 279 | 5.367551 | 1.83E-09 | 2.90E-07 | 2.02E-06 | 0.057348 | 7.60511 |
| KRY | 12 | 215 | 5.224 | 2.52E-07 | 2.33E-05 | 0.000277 | 0.055814 | 7.389695 |
| KSF | 8 | 144 | 5.199815 | 2.57E-05 | 0.00119 | 0.027962 | 0.055556 | 7.353471 |
| YWW | 9 | 164 | 5.136402 | 8.98E-06 | 0.000453 | 0.009781 | 0.054878 | 7.258587 |
| PKAR | 3 | 10 | 4.97087 | 6.12E-05 | 0.001679 | 0.026008 | 0.3 | 53.57529 |
| WWYW | 3 | 10 | 4.97087 | 6.12E-05 | 0.001679 | 0.026008 | 0.3 | 53.57529 |
| YFY | 8 | 155 | 4.830796 | 4.35E-05 | 0.001788 | 0.047138 | 0.051613 | 6.803211 |
| AKR | 21 | 412 | 4.770704 | 5.16E-11 | 1.15E-08 | 5.71E-08 | 0.050971 | 6.714038 |
| VKKR | 4 | 14 | 4.734162 | 4.04E-06 | 0.000222 | 0.001747 | 0.285714 | 50.0036 |
| KRF | 28 | 554 | 4.730517 | 4.31E-14 | 4.79E-11 | 4.79E-11 | 0.050542 | 6.654471 |
| HKR | 13 | 264 | 4.608927 | 3.40E-07 | 2.90E-05 | 0.000374 | 0.049242 | 6.47457 |

FIG. 8B

| motif | n | n.lib | enrich | p | fdr | padj.holm | Pr_seqs.motif | PLR |
|---|---|---|---|---|---|---|---|---|
| Y | 789 | 56760 | 1.72706 | 6.29E-56 | 5.03E-55 | 5.03E-55 | 0.013901 | 1.7622 |
| K | 637 | 62082 | 1.274813 | 1.92E-13 | 7.68E-13 | 1.34E-12 | 0.010261 | 1.295968 |
| R | 630 | 63785 | 1.227142 | 1.18E-10 | 3.14E-10 | 7.06E-10 | 0.009877 | 1.247022 |
| F | 699 | 75858 | 1.14485 | 1.08E-07 | 2.17E-07 | 5.42E-07 | 0.009215 | 1.162619 |
| S | 722 | 81297 | 1.103407 | 5.54E-06 | 8.86E-06 | 2.22E-05 | 0.008881 | 1.120155 |
| W | 530 | 58364 | 1.128246 | 7.95E-05 | 0.000106 | 0.000239 | 0.009081 | 1.145602 |
| G | 922 | 111145 | 1.030656 | 0.000118 | 0.000135 | 0.000239 | 0.008295 | 1.045683 |
| A | 518 | 57451 | 1.120224 | 0.000193 | 0.000193 | 0.000239 | 0.009016 | 1.137384 |

FIG. 8C

| peptide | p.value | p.bon | mean1 | mean2 |
|---|---|---|---|---|
| GPRPQYHED | 8.86E-46 | 1.12E-40 | 3.707997373 | 3.91088824 |
| GPRPSGNLD | 1.58E-44 | 1.99E-39 | 3.397069873 | 3.738576773 |
| AKGRSAWFVSG | 8.35E-30 | 1.05E-24 | 3.362914364 | 3.255045798 |
| GPRENEYQHF | 6.12E-28 | 7.71E-23 | 3.765333521 | 3.901974824 |
| QVKSFPYVG | 2.50E-27 | 3.15E-22 | 3.501555599 | 3.296352493 |
| RLKKLFAG | 5.65E-27 | 7.12E-22 | 3.281041422 | 3.159967943 |
| ANPKRLVPFG | 1.74E-26 | 2.19E-21 | 3.539750541 | 3.293925928 |
| GQRRWLG | 2.32E-26 | 2.93E-21 | 3.287624203 | 3.177969221 |
| AVKKLFGLD | 9.43E-26 | 1.19E-20 | 3.303018784 | 3.137108443 |
| SPVAKRVHFS | 2.90E-25 | 3.65E-20 | 3.304197835 | 3.186545691 |
| KRGKRLLSWQG | 4.40E-25 | 5.55E-20 | 3.349281951 | 3.235756346 |
| RPRSLAQFG | 4.79E-25 | 6.03E-20 | 3.497425962 | 3.303037261 |
| QRKRGVLPFD | 5.65E-25 | 7.12E-20 | 3.461077028 | 3.128049971 |
| KAYEDPDG | 1.04E-24 | 1.31E-19 | 3.536935068 | 3.653689054 |
| VKKRAWRVFE | 2.32E-24 | 2.92E-19 | 3.313402946 | 3.212991066 |
| EHSVKRLFS | 2.95E-24 | 3.71E-19 | 3.420175248 | 3.293613999 |
| FNQSDPSPLD | 3.00E-24 | 3.78E-19 | 3.539551105 | 3.646161901 |
| KSAYKSGLFG | 3.36E-24 | 4.23E-19 | 3.423996496 | 3.317633937 |
| GRRSVFSG | 3.89E-24 | 4.91E-19 | 3.450877988 | 3.289645676 |
| FSHGVSEEG | 4.08E-24 | 5.14E-19 | 3.565746652 | 3.664233729 |
| PRARSAWPQDG | 5.11E-24 | 6.44E-19 | 3.566575755 | 3.382991964 |
| VKRGHPLFS | 5.30E-24 | 6.68E-19 | 3.267074394 | 3.152675122 |
| NKPLKRYLD | 5.84E-24 | 7.35E-19 | 3.404790227 | 3.292371434 |
| KRVAKRSAPWFG | 7.28E-24 | 9.18E-19 | 3.280377985 | 3.160416679 |
| KGRSLLFE | 7.75E-24 | 9.77E-19 | 3.514528664 | 3.393017759 |
| SKRWPWVG | 7.75E-24 | 9.77E-19 | 3.399040784 | 3.313805994 |
| SSGLKRFG | 9.78E-24 | 1.23E-18 | 3.312149078 | 3.174847868 |
| SKRRWFSG | 2.06E-23 | 2.59E-18 | 3.415882186 | 3.312829999 |
| FGEQDADG | 2.63E-23 | 3.32E-18 | 3.502857626 | 3.613244841 |
| QSRKVPWLD | 3.80E-23 | 4.79E-18 | 3.402154438 | 3.277434228 |
| KQRGRSVFG | 7.41E-23 | 9.33E-18 | 3.34672362 | 3.220002464 |
| AGFRKRLFG | 7.86E-23 | 9.90E-18 | 3.293410409 | 3.206338472 |
| AKRRYVARFD | 1.01E-22 | 1.28E-17 | 3.407488995 | 3.309521844 |
| PKRFLSHWG | 1.03E-22 | 1.30E-17 | 3.554336757 | 3.465497181 |
| YSGESEQDG | 1.10E-22 | 1.39E-17 | 3.549732089 | 3.659240428 |
| HPFKKHFG | 1.17E-22 | 1.47E-17 | 3.310190197 | 3.21022248 |
| LDQAKRFFG | 1.86E-22 | 2.35E-17 | 3.463213747 | 3.309102479 |
| YGPRRHPYANG | 2.38E-22 | 3.00E-17 | 3.487242048 | 3.598946428 |
| QHSQKRSNFFS | 4.74E-22 | 5.98E-17 | 3.294375033 | 3.199996472 |
| KSGYEEPEG | 5.67E-22 | 7.14E-17 | 3.543882456 | 3.645221603 |
| PKKRSWNYRLD | 6.06E-22 | 7.64E-17 | 3.412885539 | 3.303161449 |
| KKRYFQLG | 6.67E-22 | 8.40E-17 | 3.401790596 | 3.305611111 |
| FGDDSDG | 7.39E-22 | 9.31E-17 | 3.517898195 | 3.624013977 |
| GAQKRVSRWVSG | 7.83E-22 | 9.87E-17 | 3.303936854 | 3.203733001 |

FIG. 8C, continued

| peptide | p.value | p.bon | mean1 | mean2 |
|---|---|---|---|---|
| ALKSFRD | 8.30E-22 | 1.05E-16 | 3.378269932 | 3.265273661 |
| PSRKRFFD | 8.40E-22 | 1.06E-16 | 3.417539354 | 3.261548894 |
| VGELKRVFS | 1.58E-21 | 1.99E-16 | 3.435138128 | 3.329740449 |
| FGHDDEG | 1.62E-21 | 2.04E-16 | 3.497454077 | 3.596169515 |
| KVARLYGDG | 1.69E-21 | 2.12E-16 | 3.531074202 | 3.380660108 |
| VGVKRSRLE | 1.71E-21 | 2.16E-16 | 3.247207945 | 3.144981103 |

FIG. 10A

| motif | n | n.lib | enrich | p | fdr | padj.holm | Pr_seqs | PLR |
|---|---|---|---|---|---|---|---|---|
| YDEK | 2 | 2 | 17.8669 | 5.49E-05 | 0.0018 | 0.01575 | 1 | Inf |
| PVRR | 2 | 3 | 11.9112 | 0.00016 | 0.00284 | 0.04571 | 0.66667 | 250.018 |
| SNPV | 3 | 5 | 10.7201 | 4.02E-06 | 0.00047 | 0.00118 | 0.6 | 187.514 |
| DKYE | 3 | 6 | 8.93343 | 8.00E-06 | 0.00047 | 0.00234 | 0.5 | 125.009 |
| DVHY | 3 | 6 | 8.93343 | 8.00E-06 | 0.00047 | 0.00234 | 0.5 | 125.009 |
| NPDQ | 3 | 6 | 8.93343 | 8.00E-06 | 0.00047 | 0.00234 | 0.5 | 125.009 |
| QEEF | 3 | 7 | 7.65723 | 1.39E-05 | 0.00068 | 0.00404 | 0.42857 | 93.7568 |
| NPE | 10 | 134 | 7.47587 | 8.59E-08 | 9.65E-05 | 9.65E-05 | 0.07463 | 10.0814 |
| DEV | 7 | 103 | 6.80812 | 1.39E-05 | 0.00312 | 0.01552 | 0.06796 | 9.11524 |
| EDWP | 4 | 11 | 6.49704 | 9.53E-07 | 0.00028 | 0.00028 | 0.36364 | 71.4337 |
| EDFP | 3 | 10 | 5.36006 | 4.69E-05 | 0.00173 | 0.01351 | 0.3 | 53.5753 |
| PLVD | 3 | 11 | 4.87278 | 6.42E-05 | 0.00189 | 0.01835 | 0.27273 | 46.8784 |
| SPD | 9 | 186 | 4.84726 | 1.35E-05 | 0.00312 | 0.01508 | 0.04839 | 6.35639 |
| LVD | 10 | 216 | 4.63781 | 6.68E-06 | 0.0025 | 0.00748 | 0.0463 | 6.0684 |
| LRDP | 3 | 12 | 4.46672 | 8.51E-05 | 0.00193 | 0.02424 | 0.25 | 41.6697 |
| PARR | 3 | 12 | 4.46672 | 8.51E-05 | 0.00193 | 0.02424 | 0.25 | 41.6697 |
| PELE | 3 | 12 | 4.46672 | 8.51E-05 | 0.00193 | 0.02424 | 0.25 | 41.6697 |
| PEYK | 3 | 13 | 4.12312 | 0.00011 | 0.00232 | 0.03101 | 0.23077 | 37.5027 |
| VVVS | 3 | 14 | 3.82861 | 0.00014 | 0.00257 | 0.03911 | 0.21429 | 34.0934 |
| YDPV | 3 | 14 | 3.82861 | 0.00014 | 0.00257 | 0.03911 | 0.21429 | 34.0934 |
| DPA | 11 | 303 | 3.63678 | 2.29E-05 | 0.0043 | 0.02566 | 0.0363 | 4.70924 |
| E.P | 51 | 2430 | 2.80423 | 1.49E-10 | 1.77E-08 | 1.77E-08 | 0.02099 | 2.67989 |
| D..P | 39 | 2129 | 2.46511 | 6.03E-07 | 1.76E-05 | 6.88E-05 | 0.01832 | 2.3327 |
| PE | 58 | 3143 | 2.44722 | 1.40E-09 | 1.69E-07 | 1.69E-07 | 0.01845 | 2.35025 |
| D...P | 25 | 1399 | 2.44005 | 9.29E-05 | 0.00391 | 0.01032 | 0.01787 | 2.27455 |

FIG. 10B

| motif | n | n.lib | enrich | p | fdr | padj.holm | Pr_seqs | PLR |
|---|---|---|---|---|---|---|---|---|
| D | 969 | 98037 | 1.30318 | 6.37E-27 | 5.10E-26 | 5.10E-26 | 0.00988 | 1.24793 |
| E | 867 | 88289 | 1.29474 | 2.48E-22 | 9.92E-22 | 1.74E-21 | 0.00982 | 1.23977 |
| P | 538 | 56321 | 1.25945 | 1.77E-10 | 4.71E-10 | 1.06E-09 | 0.00955 | 1.20565 |
| V | 564 | 68411 | 1.08699 | 0.00065 | 0.00104 | 0.00259 | 0.00824 | 1.03918 |
| G | 903 | 1E+05 | 1.07119 | 6.01E-07 | 1.20E-06 | 3.00E-06 | 0.00812 | 1.02396 |
| S | 633 | 81297 | 1.0266 | 0.0144 | 0.01921 | 0.04321 | 0.00779 | 0.98099 |

FIG. 12A

SSc-Renal crisis+ v SSc-Renal crisis-

| motif | n | n.lib | enrich | p | fdr | padj.holm | Pr_seqs.m | PLR |
|---|---|---|---|---|---|---|---|---|
| DGLH | 2 | 4 | 9.317495 | 0.000105 | 0.000984 | 0.009979 | 0.5 | 251.018 |
| NPGS | 2 | 4 | 9.317495 | 0.000105 | 0.000984 | 0.009979 | 0.5 | 251.018 |
| NPHP | 2 | 4 | 9.317495 | 0.000105 | 0.000984 | 0.009979 | 0.5 | 251.018 |
| PLN | 7 | 123 | 7.922963 | 1.00E-06 | 0.000385 | 0.000655 | 0.056911 | 15.14764 |
| PEV | 7 | 126 | 7.734321 | 1.18E-06 | 0.000385 | 0.000769 | 0.055556 | 14.76576 |
| PESQ | 2 | 5 | 7.453996 | 0.000175 | 0.001199 | 0.016061 | 0.4 | 167.3453 |
| PFHP | 2 | 5 | 7.453996 | 0.000175 | 0.001199 | 0.016061 | 0.4 | 167.3453 |
| PFLP | 2 | 5 | 7.453996 | 0.000175 | 0.001199 | 0.016061 | 0.4 | 167.3453 |
| VESV | 2 | 5 | 7.453996 | 0.000175 | 0.001199 | 0.016061 | 0.4 | 167.3453 |
| P.....P | 26 | 782 | 7.169625 | 5.44E-15 | 2.64E-13 | 5.22E-13 | 0.033248 | 8.632894 |
| PVES | 3 | 9 | 6.211664 | 6.09E-06 | 0.000408 | 0.000627 | 0.333333 | 125.509 |
| PEVA | 2 | 6 | 6.211664 | 0.000261 | 0.001281 | 0.022718 | 0.333333 | 125.509 |
| PQDK | 2 | 6 | 6.211664 | 0.000261 | 0.001281 | 0.022718 | 0.333333 | 125.509 |
| PWDQ | 2 | 6 | 6.211664 | 0.000261 | 0.001281 | 0.022718 | 0.333333 | 125.509 |
| PYEV | 2 | 6 | 6.211664 | 0.000261 | 0.001281 | 0.022718 | 0.333333 | 125.509 |
| WELP | 2 | 6 | 6.211664 | 0.000261 | 0.001281 | 0.022718 | 0.333333 | 125.509 |
| P....P | 29 | 1155 | 5.717851 | 9.99E-14 | 1.90E-12 | 9.09E-12 | 0.025108 | 6.46494 |
| YHDS | 3 | 10 | 5.590497 | 8.67E-06 | 0.000408 | 0.000884 | 0.3 | 107.5791 |
| P.....A | 20 | 798 | 5.404518 | 9.77E-10 | 1.35E-08 | 8.89E-08 | 0.025063 | 6.452905 |
| ANYP | 2 | 7 | 5.324283 | 0.000365 | 0.001391 | 0.029894 | 0.285714 | 100.4072 |
| EVYH | 2 | 7 | 5.324283 | 0.000365 | 0.001391 | 0.029894 | 0.285714 | 100.4072 |
| PDAE | 2 | 7 | 5.324283 | 0.000365 | 0.001391 | 0.029894 | 0.285714 | 100.4072 |
| PDRD | 2 | 7 | 5.324283 | 0.000365 | 0.001391 | 0.029894 | 0.285714 | 100.4072 |
| PLNE | 2 | 7 | 5.324283 | 0.000365 | 0.001391 | 0.029894 | 0.285714 | 100.4072 |
| YRND | 2 | 7 | 5.324283 | 0.000365 | 0.001391 | 0.029894 | 0.285714 | 100.4072 |

FIG. 12B

| motif | n | n.lib | enrich | p | fdr | padj.holm | Pr_seqs.motif | PLR |
|---|---|---|---|---|---|---|---|---|
| P | 600 | 56321 | 2.585501 | 1.36275467947878E-105 | 9.53928275635149E-105 | 9.53928275635149E-105 | 0.010653 | 2.702945 |
| D | 532 | 98037 | 1.316999 | 2.40E-16 | 8.40E-16 | 1.44E-15 | 0.005427 | 1.369587 |
| E | 444 | 88289 | 1.220507 | 7.36E-09 | 1.72E-08 | 3.68E-08 | 0.005029 | 1.268735 |

FIG. 14A

| motif | n | n.lib | enrich | p | fdr | padj.holm | Pr_seqs.m | PLR |
|---|---|---|---|---|---|---|---|---|
| HHAP | 2 | 2 | 18.02843 | 1.63E-05 | 0.000512 | 0.002497 | 1 | Inf |
| RYY | 9 | 90 | 13.07211 | 1.46E-10 | 2.92E-08 | 8.74E-08 | 0.1 | 27.89089 |
| RVWW | 2 | 3 | 12.01895 | 4.88E-05 | 0.000958 | 0.007325 | 0.666667 | 502.036 |
| RRY | 9 | 99 | 11.88373 | 3.47E-10 | 5.03E-08 | 2.07E-07 | 0.090909 | 25.1018 |
| RYR | 13 | 183 | 9.286196 | 1.03E-12 | 6.16E-10 | 6.16E-10 | 0.071038 | 19.19549 |
| LGNW | 2 | 4 | 9.014216 | 9.74E-05 | 0.001495 | 0.014513 | 0.5 | 251.018 |
| PYYY | 2 | 4 | 9.014216 | 9.74E-05 | 0.001495 | 0.014513 | 0.5 | 251.018 |
| RY | 99 | 2725 | 8.902886 | 1.35E-59 | 1.28E-57 | 1.28E-57 | 0.03633 | 9.463359 |
| RYK | 11 | 190 | 7.568062 | 5.03E-10 | 5.03E-08 | 3E-07 | 0.057895 | 15.42569 |
| GHRY | 2 | 5 | 7.211373 | 0.000162 | 0.001495 | 0.023637 | 0.4 | 167.3453 |
| RRLV | 2 | 5 | 7.211373 | 0.000162 | 0.001495 | 0.023637 | 0.4 | 167.3453 |
| RYRW | 2 | 5 | 7.211373 | 0.000162 | 0.001495 | 0.023637 | 0.4 | 167.3453 |
| RYSW | 2 | 5 | 7.211373 | 0.000162 | 0.001495 | 0.023637 | 0.4 | 167.3453 |
| VRYR | 2 | 5 | 7.211373 | 0.000162 | 0.001495 | 0.023637 | 0.4 | 167.3453 |
| YRRN | 2 | 5 | 7.211373 | 0.000162 | 0.001495 | 0.023637 | 0.4 | 167.3453 |
| RYH | 9 | 164 | 7.173717 | 3E-08 | 2.57E-06 | 1.78E-05 | 0.054878 | 14.57524 |
| HRY | 6 | 110 | 7.13024 | 6.39E-06 | 0.000239 | 0.003742 | 0.054545 | 14.48181 |
| SRY | 6 | 110 | 7.13024 | 6.39E-06 | 0.000239 | 0.003742 | 0.054545 | 14.48181 |
| R....Y | 31 | 1090 | 6.85769 | 1.16E-16 | 1.17E-14 | 1.17E-14 | 0.02844 | 7.348025 |
| RYHY | 3 | 8 | 6.760662 | 3.64E-06 | 0.00019 | 0.000563 | 0.375 | 150.6108 |
| VRY | 6 | 121 | 6.482036 | 1.1E-05 | 0.000331 | 0.006411 | 0.049587 | 13.09659 |
| R..Y | 52 | 1963 | 6.439458 | 1.22E-25 | 1.27E-23 | 1.27E-23 | 0.02649 | 6.830422 |
| YVR | 6 | 125 | 6.274611 | 1.33E-05 | 0.00038 | 0.007704 | 0.048 | 12.65637 |
| RYG | 7 | 146 | 6.267448 | 2.55E-06 | 0.000128 | 0.001503 | 0.047945 | 12.64119 |
| YKY | 7 | 152 | 6.020049 | 3.33E-06 | 0.000154 | 0.00196 | 0.046053 | 12.11811 |

FIG. 14B

| motif | n | n.lib | enrich | p | fdr | padj.holm | Pr_seqs.motif | PLR |
|---|---|---|---|---|---|---|---|---|
| R | 598 | 63785 | 2.33422 | 3.84E-89 | 2.31E-88 | 2.31E-88 | 0.009375 | 2.375627 |
| Y | 457 | 56760 | 2.004624 | 9.22E-49 | 2.77E-48 | 4.61E-48 | 0.008051 | 2.037462 |
| S | 436 | 81297 | 1.335276 | 1.84E-13 | 3.68E-13 | 7.36E-13 | 0.005363 | 1.353481 |
| H | 348 | 65939 | 1.314002 | 1.55E-09 | 2.32E-09 | 4.64E-09 | 0.005278 | 1.331803 |
| K | 304 | 62082 | 1.219178 | 1.33E-05 | 1.60E-05 | 2.66E-05 | 0.004897 | 1.235221 |
| F | 329 | 75858 | 1.079826 | 0.009229 | 0.009229 | 0.009229 | 0.004337 | 1.09342 |

FIG. 16A

| motif | n | n.lib | enrich | p | fdr | padj.holm | Pr_seqs.m | PLR |
|---|---|---|---|---|---|---|---|---|
| GFVQ | 2 | 2 | 17.46913 | 5.63E-05 | 0.001593 | 0.017016 | 1 | Inf |
| PPFR | 2 | 2 | 17.46913 | 5.63E-05 | 0.001593 | 0.017016 | 1 | Inf |
| LRYG | 3 | 4 | 13.10185 | 1.68E-06 | 0.000262 | 0.000521 | 0.75 | 375.027 |
| PPRN | 2 | 3 | 11.64609 | 0.000168 | 0.003077 | 0.04995 | 0.666667 | 250.018 |
| PVRR | 2 | 3 | 11.64609 | 0.000168 | 0.003077 | 0.04995 | 0.666667 | 250.018 |
| YYYD | 2 | 3 | 11.64609 | 0.000168 | 0.003077 | 0.04995 | 0.666667 | 250.018 |
| PPR | 14 | 130 | 10.80912 | 1.92E-12 | 2.17E-09 | 2.17E-09 | 0.107692 | 15.08729 |
| VRR | 9 | 95 | 9.508773 | 5.30E-08 | 1.50E-05 | 5.98E-05 | 0.094737 | 13.08234 |
| YDEY | 3 | 6 | 8.734565 | 8.31E-06 | 0.000862 | 0.002569 | 0.5 | 125.009 |
| YYD | 10 | 124 | 8.094386 | 4.56E-08 | 1.50E-05 | 5.15E-05 | 0.080645 | 10.9657 |
| SYEE | 3 | 7 | 7.48677 | 1.45E-05 | 0.001066 | 0.004456 | 0.428571 | 93.75675 |
| RRS | 12 | 193 | 6.240645 | 3.89E-08 | 1.50E-05 | 4.39E-05 | 0.062176 | 8.28789 |
| LRY | 7 | 115 | 6.109501 | 3.04E-05 | 0.00357 | 0.034206 | 0.06087 | 8.102435 |
| PARR | 4 | 12 | 5.823043 | 1.50E-06 | 0.000262 | 0.000465 | 0.333333 | 62.5045 |
| EKKD | 3 | 9 | 5.823043 | 3.43E-05 | 0.001222 | 0.010472 | 0.333333 | 62.5045 |
| RNYA | 3 | 9 | 5.823043 | 3.43E-05 | 0.001222 | 0.010472 | 0.333333 | 62.5045 |
| RYG | 8 | 146 | 5.499747 | 1.79E-05 | 0.002707 | 0.02014 | 0.054795 | 7.246899 |
| DDY | 8 | 158 | 5.082045 | 3.15E-05 | 0.00357 | 0.035413 | 0.050633 | 6.667147 |
| ARSQ | 3 | 11 | 4.764308 | 6.67E-05 | 0.001728 | 0.020006 | 0.272727 | 46.87838 |
| NEVD | 3 | 12 | 4.367282 | 8.84E-05 | 0.002115 | 0.026436 | 0.25 | 41.66967 |
| SYA | 11 | 290 | 3.807152 | 1.70E-05 | 0.002707 | 0.019134 | 0.037931 | 4.92867 |
| YSG | 17 | 457 | 3.73369 | 1.28E-07 | 2.90E-05 | 0.000144 | 0.037199 | 4.829893 |
| SGLF | 4 | 21 | 3.327453 | 1.71E-05 | 0.001066 | 0.005262 | 0.190476 | 29.41388 |
| R....G | 98 | 4448 | 3.021096 | 2.99E-21 | 3.08E-19 | 3.08E-19 | 0.022032 | 2.816295 |
| QRS | 14 | 469 | 2.996131 | 1.91E-05 | 0.002707 | 0.021521 | 0.029851 | 3.846431 |

FIG. 16B

| motif | n | n.lib | enrich | p | fdr | padj.holm | Pr_seqs.motif | PLR |
|---|---|---|---|---|---|---|---|---|
| S | 882 | 81297 | 1.418235 | 6.13E-34 | 4.29E-33 | 4.29E-33 | 0.010849 | 1.371112 |
| G | 1027 | 111145 | 1.20791 | 7.53E-20 | 2.63E-19 | 4.52E-19 | 0.00924 | 1.165879 |
| Y | 568 | 56760 | 1.308158 | 1.15E-13 | 2.68E-13 | 5.75E-13 | 0.010007 | 1.263616 |
| R | 620 | 63785 | 1.270654 | 4.72E-13 | 8.27E-13 | 1.89E-12 | 0.00972 | 1.227034 |
| A | 487 | 57451 | 1.108117 | 0.000749 | 0.001048 | 0.002246 | 0.008477 | 1.068734 |
| Q | 491 | 60519 | 1.060581 | 0.013081 | 0.014598 | 0.026162 | 0.008113 | 1.022513 |
| V | 547 | 68411 | 1.045239 | 0.014598 | 0.014598 | 0.026162 | 0.007996 | 1.007602 |

FIG. 18A

| motif | n | n.lib | enrich | p | fdr | padj.holm | Pr_seqs.m | PLR |
|---|---|---|---|---|---|---|---|---|
| DEHH | 2 | 2 | 18.06433 | 6.44E-05 | 0.002268 | 0.021124 | 1 | Inf |
| PPFR | 2 | 2 | 18.06433 | 6.44E-05 | 0.002268 | 0.021124 | 1 | Inf |
| VDDH | 3 | 4 | 13.54825 | 2.05E-06 | 0.000344 | 0.000686 | 0.75 | 375.027 |
| PVRQ | 3 | 5 | 10.8386 | 5.11E-06 | 0.00057 | 0.0017 | 0.6 | 187.5135 |
| PLRR | 3 | 6 | 9.032165 | 1.01E-05 | 0.00085 | 0.003369 | 0.5 | 125.009 |
| VDE | 14 | 156 | 8.797687 | 4.88E-11 | 5.79E-08 | 5.79E-08 | 0.089744 | 12.32483 |
| PRR | 11 | 132 | 8.16928 | 1.23E-08 | 4.89E-06 | 1.46E-05 | 0.083333 | 11.36445 |
| DDH | 9 | 108 | 8.16928 | 2.60E-07 | 6.17E-05 | 0.000307 | 0.083333 | 11.36445 |
| PVR | 10 | 124 | 7.905755 | 7.71E-08 | 2.29E-05 | 9.14E-05 | 0.080645 | 10.9657 |
| DYYG | 4 | 10 | 7.225732 | 8.37E-07 | 0.000281 | 0.000281 | 0.4 | 83.33933 |
| DEH | 9 | 125 | 7.058258 | 8.98E-07 | 0.000152 | 0.001062 | 0.072 | 9.698974 |
| PRN | 9 | 125 | 7.058258 | 8.98E-07 | 0.000152 | 0.001062 | 0.072 | 9.698974 |
| PPR | 9 | 130 | 6.786787 | 1.25E-06 | 0.000165 | 0.001472 | 0.069231 | 9.29819 |
| PRK | 8 | 121 | 6.481413 | 6.82E-06 | 0.000737 | 0.008034 | 0.066116 | 8.850195 |
| EEH | 7 | 112 | 6.12696 | 3.68E-05 | 0.002912 | 0.043159 | 0.0625 | 8.333933 |
| HPDE | 3 | 9 | 6.021443 | 4.19E-05 | 0.002268 | 0.013856 | 0.333333 | 62.5045 |
| PPRK | 3 | 9 | 6.021443 | 4.19E-05 | 0.002268 | 0.013856 | 0.333333 | 62.5045 |
| NPE | 8 | 134 | 5.852619 | 1.44E-05 | 0.001426 | 0.016958 | 0.059701 | 7.937079 |
| HFP | 14 | 236 | 5.81542 | 1.09E-08 | 4.89E-06 | 1.29E-05 | 0.059322 | 7.88345 |
| VDD | 8 | 137 | 5.724459 | 1.69E-05 | 0.001546 | 0.019897 | 0.058394 | 7.752496 |
| KHVR | 3 | 10 | 5.419299 | 5.94E-05 | 0.002268 | 0.019557 | 0.3 | 53.57529 |
| RNH | 11 | 208 | 5.184351 | 1.24E-06 | 0.000165 | 0.001459 | 0.052885 | 6.980198 |
| EEHS | 3 | 11 | 4.926636 | 8.12E-05 | 0.002268 | 0.026485 | 0.272727 | 46.87838 |
| PRNR | 3 | 11 | 4.926636 | 8.12E-05 | 0.002268 | 0.026485 | 0.272727 | 46.87838 |
| RAYK | 3 | 11 | 4.926636 | 8.12E-05 | 0.002268 | 0.026485 | 0.272727 | 46.87838 |

FIG. 18B

| motif | n | n.lib | enrich | p | fdr | padj. holm | Pr_seqs. motif | PLR |
|---|---|---|---|---|---|---|---|---|
| P | 697 | 56321 | 1.547734 | 1.55E-34 | 7.74E-34 | 7.74E-34 | 0.012375 | 1.566433 |
| R | 722 | 63785 | 1.415639 | 1.03E-25 | 2.57E-25 | 4.11E-25 | 0.011319 | 1.431212 |
| K | 633 | 62082 | 1.275181 | 1.94E-13 | 3.23E-13 | 5.82E-13 | 0.010196 | 1.287746 |
| H | 649 | 65939 | 1.230938 | 2.56E-11 | 3.21E-11 | 5.13E-11 | 0.009842 | 1.242623 |
| D | 805 | 98037 | 1.026927 | 0.001503 | 0.001503 | 0.001503 | 0.008211 | 1.03497 |

FIG. 20A

| motif | n | n.lib | enrich | p | fdr | padj.holm | Pr_seqs.m | PLR |
|---|---|---|---|---|---|---|---|---|
| RWYY | 2 | 2 | 16.77991 | 6.39E-05 | 0.001788 | 0.025988 | 1 | Inf |
| VWWW | 2 | 2 | 16.77991 | 6.39E-05 | 0.001788 | 0.025988 | 1 | Inf |
| GES | 10 | 108 | 8.576619 | 1.99E-08 | 4.59E-06 | 2.17E-05 | 0.092593 | 12.75602 |
| YGE | 11 | 122 | 8.351658 | 5.19E-09 | 1.89E-06 | 5.66E-06 | 0.090164 | 12.38828 |
| KKRW | 3 | 7 | 7.191389 | 1.74E-05 | 0.001046 | 0.007216 | 0.428571 | 93.75675 |
| ASDD | 3 | 8 | 6.292465 | 2.77E-05 | 0.001294 | 0.011449 | 0.375 | 75.0054 |
| YWGN | 3 | 8 | 6.292465 | 2.77E-05 | 0.001294 | 0.011449 | 0.375 | 75.0054 |
| KDE | 9 | 135 | 6.175165 | 1.66E-06 | 0.000199 | 0.0018 | 0.066667 | 8.929214 |
| WYW | 12 | 213 | 5.21845 | 2.01E-07 | 3.14E-05 | 0.000218 | 0.056338 | 7.463224 |
| NFW | 8 | 143 | 5.181957 | 2.25E-05 | 0.001637 | 0.024241 | 0.055944 | 7.407941 |
| KRFF | 4 | 13 | 5.163048 | 2.75E-06 | 0.000231 | 0.001144 | 0.307692 | 55.55956 |
| YWW | 9 | 164 | 5.083215 | 8.16E-06 | 0.000743 | 0.008832 | 0.054878 | 7.258587 |
| ASEE | 3 | 11 | 4.576338 | 8.02E-05 | 0.001982 | 0.03249 | 0.272727 | 46.87838 |
| SDSY | 3 | 11 | 4.576338 | 8.02E-05 | 0.001982 | 0.03249 | 0.272727 | 46.87838 |
| QRSQ | 3 | 12 | 4.194977 | 0.000106 | 0.00235 | 0.042848 | 0.25 | 41.66967 |
| WFPH | 3 | 12 | 4.194977 | 0.000106 | 0.00235 | 0.042848 | 0.25 | 41.66967 |
| GYG | 10 | 222 | 4.172409 | 1.47E-05 | 0.001148 | 0.015887 | 0.045045 | 5.896651 |
| ESD | 17 | 382 | 4.122165 | 2.10E-08 | 4.59E-06 | 2.29E-05 | 0.044503 | 5.822337 |
| SED | 55 | 1344 | 3.790559 | 4.03E-22 | 4.41E-19 | 4.41E-19 | 0.040923 | 5.333976 |
| DED | 23 | 570 | 3.7376 | 4.96E-10 | 2.71E-07 | 5.42E-07 | 0.040351 | 5.25632 |
| GSE | 17 | 436 | 3.611622 | 1.39E-07 | 2.53E-05 | 0.000151 | 0.038991 | 5.071964 |
| W..W | 63 | 2236 | 3.525676 | 4.34E-17 | 4.47E-15 | 4.47E-15 | 0.028175 | 3.624283 |
| SSE | 17 | 455 | 3.460807 | 2.52E-07 | 3.44E-05 | 0.000274 | 0.037363 | 4.851947 |
| WY | 66 | 2413 | 3.42858 | 3.30E-17 | 1.82E-15 | 3.60E-15 | 0.027352 | 3.515379 |
| EED | 16 | 469 | 3.159999 | 1.82E-06 | 0.000199 | 0.001972 | 0.034115 | 4.415329 |

FIG. 20B

| motif | n | n.lib | enrich | p | fdr | padj.holm | Pr_seqs.motif | PLR |
|---|---|---|---|---|---|---|---|---|
| Y | 745 | 56760 | 1.646241 | 1.74E-45 | 1.22E-44 | 1.22E-44 | 0.013125 | 1.662621 |
| W | 637 | 58364 | 1.368907 | 3.44E-19 | 1.20E-18 | 2.06E-18 | 0.010914 | 1.379437 |
| S | 790 | 81297 | 1.218799 | 7.02E-14 | 1.64E-13 | 3.51E-13 | 0.009717 | 1.22669 |
| G | 954 | 111145 | 1.076559 | 1.32E-07 | 2.30E-07 | 5.27E-07 | 0.008583 | 1.08229 |
| D | 836 | 98037 | 1.069537 | 9.54E-06 | 1.34E-05 | 2.86E-05 | 0.008527 | 1.075169 |
| F | 630 | 75858 | 1.041642 | 0.006944 | 0.008101 | 0.013888 | 0.008305 | 1.046893 |

FIG. 22A

| motif | n | n.lib | enrich | p | fdr | padj.holm | Pr seqs. | PLR |
|---|---|---|---|---|---|---|---|---|
| SAY | 8 | 111 | 7.15427 | 3.25E-06 | 0.00334 | 0.00399 | 0.07207 | 9.70944 |
| RQYQ | 3 | 8 | 6.87164 | 2.68E-05 | 0.00425 | 0.00776 | 0.375 | 75.0054 |
| SAYE | 3 | 10 | 5.49731 | 5.67E-05 | 0.00425 | 0.01638 | 0.3 | 53.5753 |
| HEH | 8 | 146 | 5.4392 | 2.43E-05 | 0.00994 | 0.02978 | 0.05479 | 7.2469 |
| HVEV | 3 | 11 | 4.99755 | 7.75E-05 | 0.00425 | 0.02216 | 0.27273 | 46.8784 |
| DKS | 10 | 200 | 4.96327 | 5.43E-06 | 0.00334 | 0.00667 | 0.05 | 6.57942 |
| NHNV | 3 | 12 | 4.58109 | 0.0001 | 0.00425 | 0.02916 | 0.25 | 41.6697 |
| R....   | 18 | 737 | 3.06844 | 3.19E-05 | 0.00094 | 0.00366 | 0.02442 | 3.12957 |
| H....   | 30 | 1351 | 2.78984 | 6.49E-07 | 7.47E-05 | 7.66E-05 | 0.02221 | 2.83896 |
| DYWK | 4 | 27 | 2.71472 | 5.90E-05 | 0.00425 | 0.01699 | 0.14815 | 21.7407 |
| H....   | 32 | 1548 | 2.59712 | 1.27E-06 | 7.47E-05 | 0.00015 | 0.02067 | 2.63871 |
| H....   | 35 | 1787 | 2.47512 | 2.23E-06 | 0.00028 | 0.00028 | 0.01959 | 2.49733 |
| DKSG | 4 | 30 | 2.44325 | 9.04E-05 | 0.00425 | 0.02576 | 0.13333 | 19.2322 |
| HH | 47 | 2453 | 2.42312 | 6.52E-08 | 8.02E-06 | 8.02E-06 | 0.01916 | 2.44199 |
| H...V | 42 | 2221 | 2.39673 | 3.99E-07 | 3.31E-05 | 5.39E-05 | 0.01891 | 2.40954 |
| H....   | 34 | 1803 | 2.36917 | 4.95E-06 | 0.00019 | 0.00057 | 0.01886 | 2.40266 |
| H....   | 22 | 1189 | 2.33826 | 0.00035 | 0.01102 | 0.04304 | 0.0185 | 2.35664 |
| S.Y | 47 | 2555 | 2.32759 | 2.24E-07 | 3.04E-05 | 3.04E-05 | 0.0184 | 2.34267 |
| K....   | 23 | 1271 | 2.28684 | 0.00031 | 0.01102 | 0.03855 | 0.0181 | 2.30385 |
| EK | 50 | 2803 | 2.25591 | 2.61E-07 | 1.61E-05 | 3.19E-05 | 0.01784 | 2.27041 |
| H...F | 48 | 2708 | 2.24652 | 4.91E-07 | 3.31E-05 | 6.58E-05 | 0.01773 | 2.2558 |
| DK | 49 | 2835 | 2.18583 | 1.02E-06 | 4.18E-05 | 0.00012 | 0.01728 | 2.19865 |
| SS | 46 | 2662 | 2.18536 | 1.56E-06 | 4.78E-05 | 0.00019 | 0.01728 | 2.19817 |
| S..R | 40 | 2436 | 2.07913 | 2.52E-05 | 0.00165 | 0.00313 | 0.01642 | 2.08696 |
| H...Q | 29 | 1773 | 2.07304 | 0.00035 | 0.01187 | 0.04642 | 0.01636 | 2.0787 |

FIG. 22B

| motif | n | n.lib | enrich | p | fdr | padj.holm | Pr seqs. | PLR |
|---|---|---|---|---|---|---|---|---|
| K | 578 | 62082 | 1.17696 | 2.14E-07 | 1.07E-06 | 1.93E-06 | 0.00931 | 1.1748 |
| H | 606 | 65939 | 1.1618 | 3.92E-07 | 1.31E-06 | 3.14E-06 | 0.00919 | 1.15953 |
| S | 728 | 81297 | 1.13203 | 1.43E-07 | 1.07E-06 | 1.43E-06 | 0.00895 | 1.12955 |
| R | 567 | 63785 | 1.12373 | 4.01E-05 | 0.0001 | 0.00028 | 0.00889 | 1.1212 |
| Q | 522 | 60519 | 1.09038 | 0.00142 | 0.00237 | 0.00711 | 0.00863 | 1.08763 |
| A | 487 | 57451 | 1.0716 | 0.00813 | 0.01161 | 0.03251 | 0.00848 | 1.06873 |
| G | 897 | 1E+05 | 1.02024 | 0.00048 | 0.00095 | 0.00286 | 0.00807 | 1.0171 |

FIG. 24A

| motif | n | n.lib | enrich | p | fdr | padj.holm | Pr_seqs.m | PLR |
|---|---|---|---|---|---|---|---|---|
| PDLQ | 2 | 2 | 15.90948 | 6.82E-05 | 0.001545 | 0.026925 | 1 | Inf |
| PDSV | 2 | 2 | 15.90948 | 6.82E-05 | 0.001545 | 0.026925 | 1 | Inf |
| PDVV | 2 | 2 | 15.90948 | 6.82E-05 | 0.001545 | 0.026925 | 1 | Inf |
| PERA | 2 | 2 | 15.90948 | 6.82E-05 | 0.001545 | 0.026925 | 1 | Inf |
| PGSL | 2 | 2 | 15.90948 | 6.82E-05 | 0.001545 | 0.026925 | 1 | Inf |
| PGD | 16 | 111 | 12.94505 | 1.64E-15 | 5.86E-13 | 1.76E-12 | 0.144144 | 21.05415 |
| PDS | 17 | 119 | 12.82947 | 2.54E-16 | 2.72E-13 | 2.72E-13 | 0.142857 | 20.83483 |
| PQES | 4 | 5 | 12.72759 | 2.31E-08 | 9.41E-06 | 9.41E-06 | 0.8 | 500.036 |
| PDD | 15 | 112 | 12.02763 | 3.81E-14 | 8.16E-12 | 4.07E-11 | 0.133929 | 19.33129 |
| PDH | 17 | 127 | 12.02131 | 7.80E-16 | 4.18E-13 | 8.36E-13 | 0.133858 | 19.31957 |
| PPE | 16 | 127 | 11.31418 | 1.45E-14 | 3.89E-12 | 1.55E-11 | 0.125984 | 18.01932 |
| PEE | 15 | 124 | 10.86366 | 1.76E-13 | 2.36E-11 | 1.88E-10 | 0.120968 | 17.20307 |
| P.....A | 75 | 798 | 10.40835 | 4.10E-52 | 2.50E-50 | 2.50E-50 | 0.093985 | 12.96774 |
| PGE | 14 | 122 | 10.30564 | 2.33E-12 | 2.50E-10 | 2.48E-09 | 0.114754 | 16.20487 |
| PEQ | 13 | 115 | 10.15202 | 1.71E-11 | 1.53E-09 | 1.81E-08 | 0.113043 | 15.93252 |
| PPD | 14 | 127 | 9.899906 | 4.07E-12 | 3.96E-10 | 4.32E-09 | 0.110236 | 15.48784 |
| PGS | 13 | 121 | 9.648609 | 3.28E-11 | 2.35E-09 | 3.47E-08 | 0.107438 | 15.04738 |
| PDHQ | 3 | 5 | 9.54569 | 5.56E-06 | 0.000756 | 0.002256 | 0.6 | 187.5135 |
| PDA | 17 | 167 | 9.141957 | 7.94E-14 | 1.42E-11 | 8.47E-11 | 0.101796 | 14.16769 |
| PEH | 13 | 129 | 9.050246 | 7.41E-11 | 4.96E-09 | 7.83E-08 | 0.100775 | 14.00963 |
| PDV | 11 | 111 | 8.899722 | 2.53E-09 | 1.08E-07 | 2.65E-06 | 0.099099 | 13.75099 |
| PDR | 12 | 122 | 8.833405 | 5.24E-10 | 2.96E-08 | 5.53E-07 | 0.098361 | 13.63735 |
| P.....Q | 75 | 954 | 8.706356 | 1.31E-46 | 4.00E-45 | 7.86E-45 | 0.078616 | 10.6663 |
| PDE | 12 | 124 | 8.690931 | 6.34E-10 | 3.23E-08 | 6.67E-07 | 0.096774 | 13.39382 |
| PDL | 12 | 124 | 8.690931 | 6.34E-10 | 3.23E-08 | 6.67E-07 | 0.096774 | 13.39382 |

FIG. 24B

| motif | n | n.lib | enrich | p | fdr | padj.holm | Pr_seqs.motif | PLR |
|---|---|---|---|---|---|---|---|---|
| P | 1406 | 56321 | 3.063067 | 2.9149873 | 2.0404911 | 2.0404911 | 0.024964 | 3.200631 |
| E | 901 | 88289 | 1.25216 | 3.57E-19 | 1.25E-18 | 2.14E-18 | 0.010205 | 1.288885 |
| D | 942 | 98037 | 1.178969 | 2.06E-14 | 4.82E-14 | 1.03E-13 | 0.009609 | 1.212817 |
| S | 785 | 81297 | 1.184777 | 2.18E-11 | 3.82E-11 | 8.73E-11 | 0.009656 | 1.21885 |
| G | 953 | 111145 | 1.05207 | 5.13E-06 | 7.19E-06 | 1.54E-05 | 0.008574 | 1.081145 |
| Q | 526 | 60519 | 1.066438 | 0.007134 | 0.008323 | 0.014268 | 0.008691 | 1.09604 |

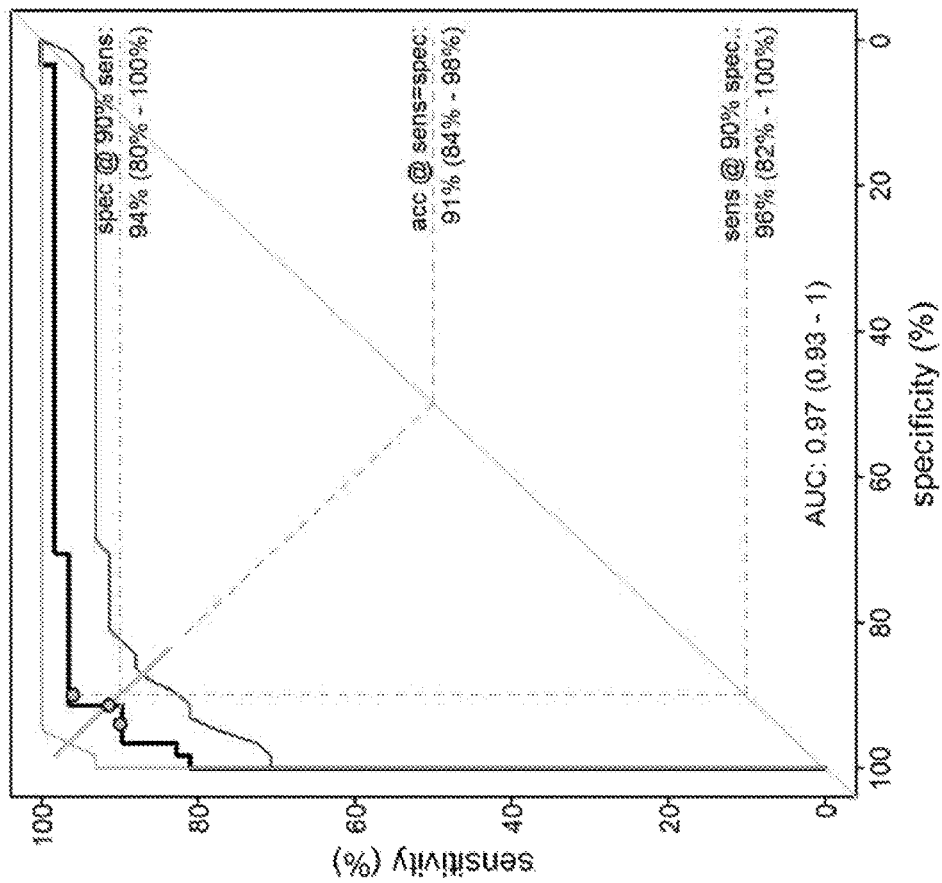
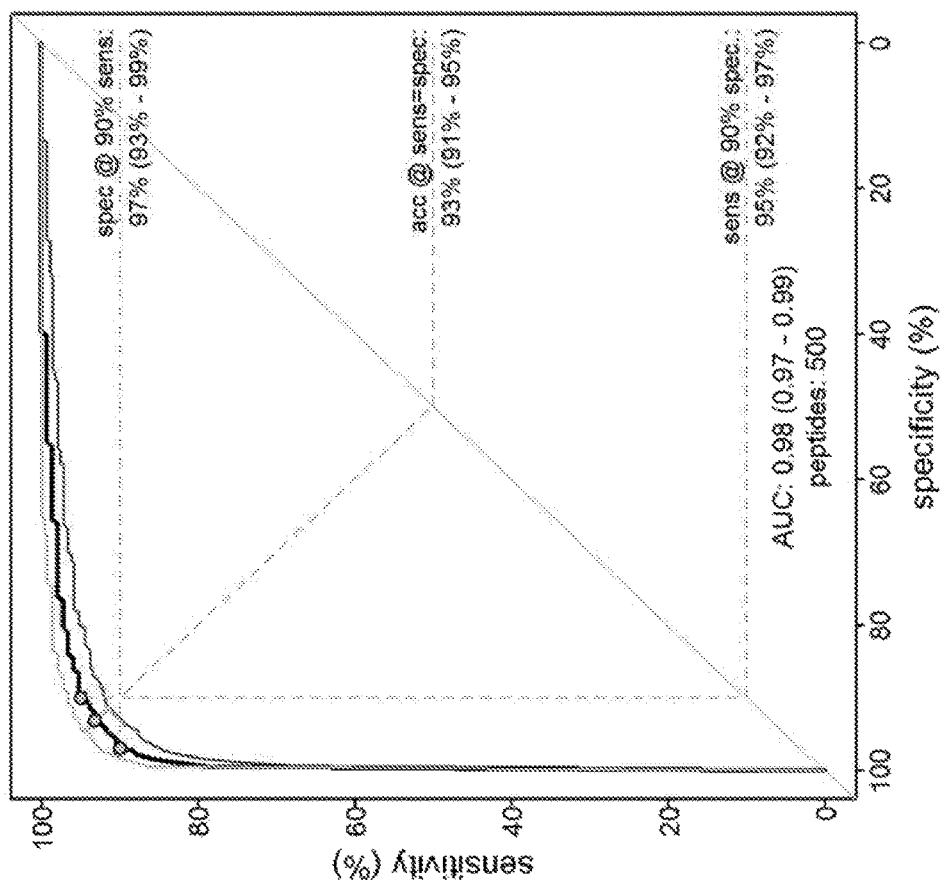
FIG. 31A
FIG. 31B

FIG. 36A

CHAGAS v HEALTHY [[Chags+ v -]]

| motif | n | n.lib | enrich | p | fdr | padj.holm | Pr_seqs.motif | PLR |
|---|---|---|---|---|---|---|---|---|
| R | 361 | 63785 | 1.931345036 | 2.74E-36 | 2.19E-35 | 2.19E-35 | 0.005659638 | 1.932752841 |
| D | 388 | 98037 | 1.350557062 | 8.01E-14 | 3.20E-13 | 5.61E-13 | 0.003957689 | 1.349232123 |
| K | 227 | 62082 | 1.247760931 | 4.52E-05 | 0.00012044 | 0.00027099 | 0.003656454 | 1.24615996 |

FIG. 36B

| motif | n | n.lib | enrich | p | fdr | padj.holm | Pr_seqs.motif | PLR |
|---|---|---|---|---|---|---|---|---|
| R.....D | 43 | 3126 | 4.441082485 | 1.57E-16 | 1.54E-14 | 1.54E-14 | 0.013755598 | 4.736065258 |
| R.....G | 42 | 3967 | 3.418191954 | 1.74E-12 | 8.51E-11 | 1.69E-10 | 0.010587346 | 3.633560337 |
| R....G | 34 | 4448 | 2.549921336 | 6.15E-07 | 1.91E-05 | 5.60E-05 | 0.007643885 | 2.615587994 |
| R....Y | 15 | 1090 | 4.590684067 | 1.22E-06 | 2.84E-05 | 0.000109986 | 0.013761468 | 4.738114393 |
| L....P | 13 | 999 | 4.341007223 | 1.11E-05 | 0.000200334 | 0.000985592 | 0.013013013 | 4.477021545 |
| V....D | 27 | 3614 | 2.492230808 | 1.29E-05 | 0.000200334 | 0.001137379 | 0.007470946 | 2.555966365 |
| R....S | 22 | 2648 | 2.771515708 | 1.72E-05 | 0.000228585 | 0.001496863 | 0.008308157 | 2.844793232 |
| R....A | 13 | 1132 | 3.830977222 | 3.98E-05 | 0.000462713 | 0.003423081 | 0.011484099 | 3.944900128 |
| P....K | 13 | 1441 | 3.009483841 | 0.000410088 | 0.004237577 | 0.034857486 | 0.009021513 | 3.091276781 |
| R...D | 39 | 4160 | 3.133924946 | 4.89E-10 | 4.50E-08 | 4.50E-08 | 0.009375 | 3.213547617 |
| R...G | 40 | 5064 | 2.64048442 | 3.05E-08 | 1.40E-06 | 2.77E-06 | 0.007898894 | 2.703541918 |
| R...P | 20 | 1607 | 4.160364998 | 1.13E-07 | 2.52E-06 | 1.01E-05 | 0.012445551 | 4.27933037 |
| L...D | 34 | 4135 | 2.748658074 | 1.33E-07 | 2.52E-06 | 1.19E-05 | 0.008222491 | 2.815217119 |
| R...Y | 20 | 1627 | 4.109223449 | 1.37E-07 | 2.52E-06 | 1.20E-05 | 0.012292563 | 4.226071747 |
| Y...D | 31 | 4211 | 2.460898873 | 4.32E-06 | 5.87E-05 | 0.000376192 | 0.007361672 | 2.518304022 |
| A...D | 31 | 4218 | 2.456814878 | 4.47E-06 | 5.87E-05 | 0.000384059 | 0.007349455 | 2.514093817 |
| L...E | 26 | 3517 | 2.471259174 | 2.34E-05 | 0.000268642 | 0.001985612 | 0.007392664 | 2.528984957 |
| R...A | 16 | 1669 | 3.204652631 | 4.78E-05 | 0.000488252 | 0.004012155 | 0.009586579 | 3.286774252 |
| R...L | 20 | 2485 | 2.690425171 | 6.49E-05 | 0.000597532 | 0.005390781 | 0.00804829 | 2.755090181 |
| R..D | 117 | 4553 | 8.697362324 | 2.60E-69 | 2.58E-67 | 2.58E-67 | 0.025697342 | 8.956061585 |
| R..E | 55 | 4027 | 4.622537161 | 2.68E-20 | 1.33E-18 | 2.63E-18 | 0.01365781 | 4.701930405 |
| D..G | 38 | 5277 | 2.437226288 | 8.68E-07 | 2.87E-05 | 8.42E-05 | 0.007201061 | 2.462963326 |
| D..D | 31 | 4457 | 2.354064787 | 1.56E-05 | 0.000386429 | 0.001498876 | 0.006955351 | 2.378335023 |

FIG. 36C

| motif | n | n.lib | enrich | p | fdr | padj.holm | Pr_seqs.motif | PLR |
|---|---|---|---|---|---|---|---|---|
| V..V | 20 | 2794 | 2.422718442 | 0.000301792 | 0.005975482 | 0.02867024 | 0.007158196 | 2.448196574 |
| R.V | 57 | 3312 | 5.833859935 | 1.25E-25 | 1.22E-23 | 1.22E-23 | 0.017210145 | 5.946297173 |
| R.L | 42 | 3760 | 3.786456012 | 5.80E-13 | 2.84E-11 | 5.63E-11 | 0.011170213 | 3.835859151 |
| R.F | 36 | 4316 | 2.827434384 | 4.56E-08 | 1.49E-06 | 4.38E-06 | 0.008341057 | 2.856153069 |
| Y.D | 36 | 4808 | 2.538104576 | 5.69E-07 | 1.39E-05 | 5.40E-05 | 0.007487521 | 2.561679618 |
| D.D | 31 | 3872 | 2.713924837 | 8.87E-07 | 1.74E-05 | 8.34E-05 | 0.008006198 | 2.740565168 |
| R.Y | 23 | 2632 | 2.962193478 | 5.58E-06 | 9.12E-05 | 0.000519023 | 0.008738602 | 2.993480986 |
| L.D | 35 | 5977 | 1.984980565 | 0.000148851 | 0.00208392 | 0.013694329 | 0.00585578 | 2.000129631 |
| R.R | 20 | 2789 | 2.430820844 | 0.000299963 | 0.003674552 | 0.027296674 | 0.007171029 | 2.452617298 |
| P.R | 22 | 3233 | 2.306685824 | 0.000389383 | 0.004239944 | 0.035044437 | 0.006804825 | 2.326511064 |
| LR | 49 | 2602 | 6.413256029 | 7.75E-24 | 7.21E-22 | 7.21E-22 | 0.018831668 | 6.517304496 |
| VD | 49 | 6351 | 2.627506249 | 2.31E-09 | 1.08E-07 | 2.13E-07 | 0.00771532 | 2.640221894 |
| DY | 35 | 3798 | 3.138360827 | 6.64E-09 | 2.06E-07 | 6.04E-07 | 0.009215377 | 3.158323218 |
| RQ | 27 | 2445 | 3.760751964 | 9.62E-09 | 2.24E-07 | 8.66E-07 | 0.011042945 | 3.791667226 |
| FR | 28 | 2724 | 3.500585733 | 2.30E-08 | 4.27E-07 | 2.04E-06 | 0.010279001 | 3.526638062 |
| RR | 26 | 2464 | 3.593539598 | 4.34E-08 | 6.10E-07 | 3.81E-06 | 0.010551948 | 3.621282398 |
| RD | 38 | 4729 | 2.736554318 | 5.17E-08 | 6.10E-07 | 4.50E-06 | 0.008035525 | 2.750685326 |
| RE | 39 | 4933 | 2.692422938 | 5.24E-08 | 6.10E-07 | 4.51E-06 | 0.00790594 | 2.705972564 |
| RK | 23 | 2345 | 3.340217748 | 8.70E-07 | 8.99E-06 | 7.40E-05 | 0.009808102 | 3.363476267 |
| VR | 22 | 2494 | 3.004111321 | 7.77E-06 | 7.23E-05 | 0.000652887 | 0.008821171 | 3.022017406 |
| FD | 52 | 9168 | 1.931605927 | 9.08E-06 | 7.67E-05 | 0.000753417 | 0.005671902 | 1.936965004 |
| KR | 38 | 5930 | 2.18232131 | 1.50E-05 | 0.000116093 | 0.001228343 | 0.006408094 | 2.189997431 |
| VE | 39 | 6640 | 2.000259391 | 7.70E-05 | 0.000550942 | 0.006238083 | 0.005873494 | 2.006215684 |
| RL | 35 | 5845 | 2.039263374 | 0.000119931 | 0.000796686 | 0.0095945 | 0.005988024 | 2.045571475 |
| YD | 23 | 3244 | 2.414553212 | 0.00020634 | 0.001240587 | 0.016300899 | 0.007090012 | 2.424710305 |
| DG | 82 | 18509 | 1.508761826 | 0.000224677 | 0.001240587 | 0.017524783 | 0.004430277 | 1.511060885 |
| RY | 20 | 2725 | 2.499500796 | 0.000226774 | 0.001240587 | 0.017524783 | 0.00733945 | 2.510645951 |
| RQV | 10 | 201 | 8.044970355 | 6.49E-10 | 2.76E-07 | 2.76E-07 | 0.049751244 | 17.77826518 |
| LRK | 7 | 98 | 11.55027887 | 2.01E-08 | 4.28E-06 | 8.54E-06 | 0.071428571 | 26.12037422 |
| GVE | 8 | 261 | 4.956441506 | 1.33E-06 | 0.000174507 | 0.000564163 | 0.030651341 | 10.73722893 |
| LRE | 7 | 187 | 6.053087321 | 1.64E-06 | 0.000174507 | 0.000693111 | 0.037433155 | 13.2053003 |
| PRR | 6 | 132 | 7.350177461 | 3.00E-06 | 0.000255235 | 0.001264191 | 0.045454545 | 16.16975547 |
| RRL | 7 | 238 | 4.75599718 | 7.98E-06 | 0.000566494 | 0.003359073 | 0.029411765 | 10.28984439 |
| LRV | 7 | 264 | 4.287603519 | 1.56E-05 | 0.000853763 | 0.006539468 | 0.026515152 | 9.248848459 |
| RQL | 6 | 177 | 5.481488276 | 1.60E-05 | 0.000853763 | 0.006717872 | 0.033898305 | 11.91455666 |
| PGK | 5 | 140 | 5.775139433 | 6.44E-05 | 0.002732802 | 0.026938566 | 0.035714286 | 12.57647648 |
| YRQ | 5 | 142 | 5.693799441 | 6.89E-05 | 0.002732802 | 0.028739553 | 0.035211268 | 12.39287828 |
| REF | 5 | 144 | 5.614718894 | 7.36E-05 | 0.002732802 | 0.03062951 | 0.034722222 | 12.21456348 |
| EVD | 6 | 237 | 4.093769725 | 8.14E-05 | 0.002732802 | 0.033761414 | 0.025316456 | 8.81986662 |

FIG. 36D

| motif | n | n.lib | enrich | p | fdr | padj.holm | Pr_seqs.motif | PLR |
|---|---|---|---|---|---|---|---|---|
| LDY | 6 | 245 | 3.960095611 | 9.75E-05 | 0.002732802 | 0.040380359 | 0.024489796 | 8.524640959 |
| REV | 5 | 153 | 5.284441312 | 9.80E-05 | 0.002732802 | 0.040457379 | 0.032679739 | 11.47178598 |
| RKR | 6 | 248 | 3.912191229 | 0.000104227 | 0.002732802 | 0.042941332 | 0.024193548 | 8.418963592 |
| RYV | 5 | 157 | 5.149805864 | 0.000110567 | 0.002732802 | 0.045443128 | 0.031847134 | 11.16989687 |
| RLV | 5 | 159 | 5.085028432 | 0.000117319 | 0.002732802 | 0.04810086 | 0.031446541 | 11.02483327 |
| ARP | 5 | 160 | 5.053247004 | 0.000120811 | 0.002732802 | 0.049411834 | 0.03125 | 10.95370532 |
| RQVD | 5 | 22 | 4.517570837 | 5.41E-09 | 4.92E-07 | 4.92E-07 | 0.227272727 | 99.87201908 |
| REFD | 4 | 17 | 4.677014514 | 1.69E-07 | 7.69E-06 | 1.52E-05 | 0.235294118 | 104.4814969 |
| RQLD | 4 | 21 | 3.786154606 | 4.21E-07 | 1.28E-05 | 3.75E-05 | 0.19047619 | 79.89761526 |
| PRRD | 3 | 9 | 6.625770561 | 2.08E-06 | 4.73E-05 | 0.000182779 | 0.333333333 | 169.7824324 |
| RNYD | 3 | 10 | 5.963193505 | 2.96E-06 | 5.39E-05 | 0.00025758 | 0.3 | 145.5277992 |
| REVD | 3 | 15 | 3.975462336 | 1.11E-05 | 0.000144343 | 0.000954888 | 0.2 | 84.89121622 |
| RYVD | 3 | 15 | 3.975462336 | 1.11E-05 | 0.000144343 | 0.000954888 | 0.2 | 84.89121622 |
| RLVD | 3 | 16 | 3.72699594 | 1.36E-05 | 0.000155106 | 0.001145398 | 0.1875 | 78.36112266 |
| RSVD | 3 | 17 | 3.507760885 | 1.65E-05 | 0.000167049 | 0.00137127 | 0.176470588 | 72.76389961 |
| RKRD | 3 | 20 | 2.981596752 | 2.75E-05 | 0.000242905 | 0.002256295 | 0.15 | 59.92321145 |
| DYAD | 3 | 21 | 2.839615955 | 3.20E-05 | 0.000242905 | 0.002594545 | 0.142857143 | 56.59414414 |
| RELE | 3 | 21 | 2.839615955 | 3.20E-05 | 0.000242905 | 0.002594545 | 0.142857143 | 56.59414414 |
| RQFD | 3 | 24 | 2.48466396 | 4.84E-05 | 0.000338982 | 0.00382565 | 0.125 | 48.50926641 |
| HRSV | 2 | 5 | 7.950924673 | 8.52E-05 | 0.000430541 | 0.006642625 | 0.4 | 226.3765766 |
| LRKF | 2 | 5 | 7.950924673 | 8.52E-05 | 0.000430541 | 0.006642625 | 0.4 | 226.3765766 |
| LRYV | 2 | 5 | 7.950924673 | 8.52E-05 | 0.000430541 | 0.006642625 | 0.4 | 226.3765766 |
| RVVR | 2 | 5 | 7.950924673 | 8.52E-05 | 0.000430541 | 0.006642625 | 0.4 | 226.3765766 |
| VRRL | 2 | 5 | 7.950924673 | 8.52E-05 | 0.000430541 | 0.006642625 | 0.4 | 226.3765766 |
| EVDG | 4 | 79 | 1.006446161 | 9.24E-05 | 0.000442363 | 0.006742394 | 0.050632911 | 18.11012613 |
| LREV | 2 | 6 | 6.625770561 | 0.000127494 | 0.000552472 | 0.009179536 | 0.333333333 | 169.7824324 |
| RKQD | 2 | 6 | 6.625770561 | 0.000127494 | 0.000552472 | 0.009179536 | 0.333333333 | 169.7824324 |
| LREF | 2 | 7 | 5.679231909 | 0.000178143 | 0.000704826 | 0.012469997 | 0.285714286 | 135.8259459 |
| LRVV | 2 | 7 | 5.679231909 | 0.000178143 | 0.000704826 | 0.012469997 | 0.285714286 | 135.8259459 |
| FRLV | 2 | 8 | 4.969327921 | 0.000237061 | 0.0008629 | 0.016120118 | 0.25 | 113.1882883 |
| GVEQ | 2 | 8 | 4.969327921 | 0.000237061 | 0.0008629 | 0.016120118 | 0.25 | 113.1882883 |
| FDDD | 2 | 9 | 4.417180374 | 0.000304198 | 0.000954552 | 0.020077061 | 0.222222222 | 97.01853282 |
| GKAV | 2 | 9 | 4.417180374 | 0.000304198 | 0.000954552 | 0.020077061 | 0.222222222 | 97.01853282 |
| LDFY | 2 | 9 | 4.417180374 | 0.000304198 | 0.000954552 | 0.020077061 | 0.222222222 | 97.01853282 |
| VVRL | 2 | 9 | 4.417180374 | 0.000304198 | 0.000954552 | 0.020077061 | 0.222222222 | 97.01853282 |
| LRKV | 2 | 10 | 3.975462336 | 0.000379506 | 0.001079221 | 0.023529385 | 0.2 | 84.89121622 |
| LRQV | 2 | 10 | 3.975462336 | 0.000379506 | 0.001079221 | 0.023529385 | 0.2 | 84.89121622 |
| YRQL | 2 | 10 | 3.975462336 | 0.000379506 | 0.001079221 | 0.023529385 | 0.2 | 84.89121622 |

FIG. 36E

| motif | n | n.lib | enrich | p | fdr | padj.holm | Pr_seqs.motif | PLR |
|---|---|---|---|---|---|---|---|---|
| RDKD | 2 | 11 | 3.61405667 | 0.000462937 | 0.001201291 | 0.027313285 | 0.181818182 | 75.45885886 |
| RDYD | 2 | 11 | 3.61405667 | 0.000462937 | 0.001201291 | 0.027313285 | 0.181818182 | 75.45885886 |
| RSAD | 2 | 11 | 3.61405667 | 0.000462937 | 0.001201291 | 0.027313285 | 0.181818182 | 75.45885886 |
| ARDY | 2 | 12 | 3.31288528 | 0.000554442 | 0.001201291 | 0.031048762 | 0.166666667 | 67.91297297 |
| GVEN | 2 | 12 | 3.31288528 | 0.000554442 | 0.001201291 | 0.031048762 | 0.166666667 | 67.91297297 |
| KYHD | 2 | 12 | 3.31288528 | 0.000554442 | 0.001201291 | 0.031048762 | 0.166666667 | 67.91297297 |
| RAHD | 2 | 12 | 3.31288528 | 0.000554442 | 0.001201291 | 0.031048762 | 0.166666667 | 67.91297297 |
| RSHS | 2 | 12 | 3.31288528 | 0.000554442 | 0.001201291 | 0.031048762 | 0.166666667 | 67.91297297 |
| RVLK | 2 | 12 | 3.31288528 | 0.000554442 | 0.001201291 | 0.031048762 | 0.166666667 | 67.91297297 |
| YRYW | 2 | 12 | 3.31288528 | 0.000554442 | 0.001201291 | 0.031048762 | 0.166666667 | 67.91297297 |
| GQPA | 2 | 13 | 3.058047951 | 0.000653974 | 0.00132248 | 0.032044706 | 0.153846154 | 61.73906634 |
| LDYD | 2 | 13 | 3.058047951 | 0.000653974 | 0.00132248 | 0.032044706 | 0.153846154 | 61.73906634 |
| VFYD | 2 | 13 | 3.058047951 | 0.000653974 | 0.00132248 | 0.032044706 | 0.153846154 | 61.73906634 |
| FRKR | 2 | 14 | 2.839615955 | 0.000761484 | 0.001414184 | 0.035028241 | 0.142857143 | 56.59414414 |
| RAVD | 2 | 14 | 2.839615955 | 0.000761484 | 0.001414184 | 0.035028241 | 0.142857143 | 56.59414414 |
| VDAD | 2 | 14 | 2.839615955 | 0.000761484 | 0.001414184 | 0.035028241 | 0.142857143 | 56.59414414 |
| YLDY | 2 | 14 | 2.839615955 | 0.000761484 | 0.001414184 | 0.035028241 | 0.142857143 | 56.59414414 |
| QPAE | 2 | 15 | 2.650308224 | 0.000876924 | 0.001534618 | 0.036830822 | 0.133333333 | 52.24074844 |
| QVDA | 2 | 15 | 2.650308224 | 0.000876924 | 0.001534618 | 0.036830822 | 0.133333333 | 52.24074844 |
| RDLD | 2 | 15 | 2.650308224 | 0.000876924 | 0.001534618 | 0.036830822 | 0.133333333 | 52.24074844 |
| RGVE | 2 | 16 | 2.48466396 | 0.001000249 | 0.00168784 | 0.039009698 | 0.125 | 48.50926641 |
| FDVF | 2 | 17 | 2.338507257 | 0.001131409 | 0.00168784 | 0.042993556 | 0.117647059 | 45.27531532 |
| FEYS | 2 | 17 | 2.338507257 | 0.001131409 | 0.00168784 | 0.042993556 | 0.117647059 | 45.27531532 |
| HLVD | 2 | 17 | 2.338507257 | 0.001131409 | 0.00168784 | 0.042993556 | 0.117647059 | 45.27531532 |
| HQKS | 2 | 17 | 2.338507257 | 0.001131409 | 0.00168784 | 0.042993556 | 0.117647059 | 45.27531532 |
| RLLD | 2 | 17 | 2.338507257 | 0.001131409 | 0.00168784 | 0.042993556 | 0.117647059 | 45.27531532 |
| RYVE | 2 | 17 | 2.338507257 | 0.001131409 | 0.00168784 | 0.042993556 | 0.117647059 | 45.27531532 |
| VDGY | 2 | 17 | 2.338507257 | 0.001131409 | 0.00168784 | 0.042993556 | 0.117647059 | 45.27531532 |
| VEVD | 2 | 17 | 2.338507257 | 0.001131409 | 0.00168784 | 0.042993556 | 0.117647059 | 45.27531532 |
| HLQR | 2 | 18 | 2.208590187 | 0.001270359 | 0.001806292 | 0.042993556 | 0.111111111 | 42.44560811 |
| VDPA | 2 | 18 | 2.208590187 | 0.001270359 | 0.001806292 | 0.042993556 | 0.111111111 | 42.44560811 |
| YDYA | 2 | 18 | 2.208590187 | 0.001270359 | 0.001806292 | 0.042993556 | 0.111111111 | 42.44560811 |
| FDYF | 2 | 19 | 2.092348598 | 0.001417052 | 0.001924653 | 0.042993556 | 0.105263158 | 39.94880763 |
| KHKH | 2 | 19 | 2.092348598 | 0.001417052 | 0.001924653 | 0.042993556 | 0.105263158 | 39.94880763 |
| RYFD | 2 | 19 | 2.092348598 | 0.001417052 | 0.001924653 | 0.042993556 | 0.105263158 | 39.94880763 |
| DGHE | 2 | 20 | 1.987731168 | 0.001571441 | 0.002014101 | 0.042993556 | 0.1 | 37.72942943 |
| FDYA | 2 | 20 | 1.987731168 | 0.001571441 | 0.002014101 | 0.042993556 | 0.1 | 37.72942943 |
| KYNK | 2 | 20 | 1.987731168 | 0.001571441 | 0.002014101 | 0.042993556 | 0.1 | 37.72942943 |
| RYLE | 2 | 20 | 1.987731168 | 0.001571441 | 0.002014101 | 0.042993556 | 0.1 | 37.72942943 |

FIG. 36F

| motif | n | n.lib | enrich | p | fdr | padj.holm | Pr_seqs.motif | PLR |
|---|---|---|---|---|---|---|---|---|
| LDFD | 2 | 21 | 1.893077303 | 0.00173348 | 0.002160913 | 0.042993556 | 0.095238095 | 35.74366999 |
| RQKE | 2 | 21 | 1.893077303 | 0.00173348 | 0.002160913 | 0.042993556 | 0.095238095 | 35.74366999 |
| RFLD | 2 | 22 | 1.807028335 | 0.001903122 | 0.002309121 | 0.042993556 | 0.090909091 | 33.95648649 |
| SAQK | 2 | 22 | 1.807028335 | 0.001903122 | 0.002309121 | 0.042993556 | 0.090909091 | 33.95648649 |
| DWVD | 2 | 23 | 1.728461885 | 0.002080322 | 0.002458562 | 0.042993556 | 0.086956522 | 32.33951094 |
| RFFD | 2 | 23 | 1.728461885 | 0.002080322 | 0.002458562 | 0.042993556 | 0.086956522 | 32.33951094 |
| RQLE | 2 | 24 | 1.65644264 | 0.002265034 | 0.00264254 | 0.042993556 | 0.083333333 | 30.86953317 |
| RKVE | 2 | 25 | 1.590184935 | 0.002457212 | 0.00283046 | 0.042993556 | 0.08 | 29.52737955 |
| KKRD | 2 | 27 | 1.472393458 | 0.002863788 | 0.003217342 | 0.042993556 | 0.074074074 | 27.16518919 |
| RQVE | 2 | 27 | 1.472393458 | 0.002863788 | 0.003217342 | 0.042993556 | 0.074074074 | 27.16518919 |
| DPVS | 2 | 28 | 1.419807977 | 0.003078094 | 0.003374778 | 0.042993556 | 0.071428571 | 26.12037422 |
| DYFG | 2 | 28 | 1.419807977 | 0.003078094 | 0.003374778 | 0.042993556 | 0.071428571 | 26.12037422 |
| DYFD | 2 | 29 | 1.370849082 | 0.003299687 | 0.003574661 | 0.042993556 | 0.068965517 | 25.15295295 |
| FRLG | 2 | 30 | 1.325154112 | 0.003528522 | 0.003733669 | 0.042993556 | 0.066666667 | 24.2546332 |
| RRVD | 2 | 30 | 1.325154112 | 0.003528522 | 0.003733669 | 0.042993556 | 0.066666667 | 24.2546332 |
| KKRH | 2 | 33 | 1.204685557 | 0.004258037 | 0.004403197 | 0.042993556 | 0.060606061 | 21.90741064 |
| RRLE | 2 | 33 | 1.204685557 | 0.004258037 | 0.004403197 | 0.042993556 | 0.060606061 | 21.90741064 |
| RRLD | 2 | 34 | 1.169253628 | 0.004515398 | 0.004616868 | 0.042993556 | 0.058823529 | 21.22280405 |
| DPLS | 2 | 36 | 1.104295093 | 0.005051144 | 0.005107268 | 0.042993556 | 0.055555556 | 19.97440382 |
| DVFG | 2 | 39 | 1.019349317 | 0.005906675 | 0.005906675 | 0.042993556 | 0.051282051 | 18.35485756 |
| FDVFG | 2 | 3 | 1.149972929 | 2.56E-05 | 2.56E-05 | 2.56E-05 | 0.666666667 | 679.1297297 |

FIG. 37A

Chagas v others (HBV, HCV, WNV) – top 1000 peptides

| motif | n | n.lib | enrich | p | fdr | padj.holm | Pr_seqs.motif | PLR |
|---|---|---|---|---|---|---|---|---|
| RRY | 13 | 99 | 11.23386 | 1.60E-12 | 2.37E-10 | 1.41E-09 | 0.131313131 | 18.89671 |
| RYP | 12 | 97 | 10.58352 | 2.36E-11 | 2.61E-09 | 2.07E-08 | 0.12371134 | 17.64833 |
| HRSV | 3 | 5 | 9.684373 | 4.93E-06 | 0.00015 | 0.00272351 | 0.6 | 187.5135 |
| LRYV | 3 | 5 | 9.684373 | 4.93E-06 | 0.00015 | 0.00272351 | 0.6 | 187.5135 |
| VRYR | 3 | 5 | 9.684373 | 4.93E-06 | 0.00015 | 0.00272351 | 0.6 | 187.5135 |
| ALRY | 4 | 7 | 9.223213 | 1.36E-07 | 1.54E-05 | 7.64E-05 | 0.571428571 | 166.6787 |
| RQY | 10 | 94 | 9.10108 | 4.85E-09 | 2.59E-07 | 4.22E-06 | 0.106382979 | 14.88202 |
| RAY | 10 | 95 | 9.005279 | 5.38E-09 | 2.65E-07 | 4.67E-06 | 0.105263158 | 14.70694 |
| RYR | 19 | 183 | 8.882256 | 1.06E-15 | 4.68E-13 | 9.35E-13 | 0.103825137 | 14.48275 |
| VRY | 12 | 121 | 8.484312 | 3.25E-10 | 2.62E-08 | 2.84E-07 | 0.099173554 | 13.76246 |
| RSY | 20 | 207 | 8.265715 | 7.68E-16 | 4.68E-13 | 6.81E-13 | 0.096618357 | 13.36995 |
| R...Y | 106 | 1627 | 8.166611 | 3.10E-60 | 2.76E-58 | 2.76E-58 | 0.065150584 | 8.712001 |
| LRGY | 5 | 10 | 8.070311 | 7.65E-09 | 1.44E-06 | 4.32E-06 | 0.5 | 125.009 |
| REVD | 7 | 15 | 7.53229 | 1.20E-11 | 6.80E-09 | 6.80E-09 | 0.466666667 | 109.3829 |
| YSR | 12 | 137 | 7.493444 | 1.37E-09 | 8.10E-08 | 1.20E-06 | 0.087591241 | 12.00086 |
| R.....Y | 41 | 671 | 7.47805 | 2.90E-23 | 5.88E-22 | 2.26E-21 | 0.061102832 | 8.135506 |
| RSR | 13 | 149 | 7.464107 | 3.00E-10 | 2.62E-08 | 2.63E-07 | 0.087248322 | 11.94939 |
| RRHY | 5 | 11 | 7.336647 | 1.39E-08 | 1.97E-06 | 7.85E-06 | 0.454545455 | 104.1742 |
| RYS | 13 | 154 | 7.221766 | 4.52E-10 | 3.34E-08 | 3.95E-07 | 0.084415584 | 11.52565 |
| RYQ | 18 | 215 | 7.162338 | 2.50E-13 | 4.85E-11 | 2.21E-10 | 0.08372093 | 11.42214 |
| SRY | 9 | 110 | 6.999558 | 2.80E-07 | 6.36E-06 | 0.0002375 | 0.081818182 | 11.13942 |
| RASY | 3 | 7 | 6.91741 | 1.71E-05 | 0.000345 | 0.00926568 | 0.428571429 | 93.75675 |
| RPYP | 3 | 7 | 6.91741 | 1.71E-05 | 0.000345 | 0.00926568 | 0.428571429 | 93.75675 |
| RRYR | 3 | 7 | 6.91741 | 1.71E-05 | 0.000345 | 0.00926568 | 0.428571429 | 93.75675 |
| VSRY | 3 | 7 | 6.91741 | 1.71E-05 | 0.000345 | 0.00926568 | 0.428571429 | 93.75675 |

FIG. 37B

| motif | n | n.lib | enrich | p | fdr | padj.holm | Pr_seqs.motif | PLR |
|---|---|---|---|---|---|---|---|---|
| R | 1389 | 63785 | 2.744297 | 9.98E-274 | 3.99E-273 | 3.99E-273 | 0.02177628 | 2.782831 |
| Y | 816 | 56760 | 1.811737 | 3.42E-66 | 6.84E-66 | 1.03E-65 | 0.014376321 | 1.823383 |
| S | 850 | 81297 | 1.317625 | 3.62E-23 | 4.83E-23 | 7.25E-23 | 0.01045549 | 1.32084 |
| V | 613 | 68411 | 1.129229 | 7.52E-06 | 7.52E-06 | 7.52E-06 | 0.008960547 | 1.130277 |

FIG. 38A

HBV v OTHER (Chagas, HCV, and WNV) top 1000 discriminating peptides

| motif | n | n.lib | enrich | p | fdr | padj.holm | Pr_seqs.motif | PLR |
|---|---|---|---|---|---|---|---|---|
| WKW | 18 | 172 | 8.779645 | 1.86E-14 | 2.56E-12 | 1.78E-11 | 0.104651163 | 14.61144 |
| FKF | 21 | 228 | 7.727114 | 1.71E-15 | 3.31E-13 | 1.65E-12 | 0.092105263 | 12.68207 |
| FWF | 16 | 174 | 7.714426 | 3.82E-12 | 4.09E-10 | 3.65E-09 | 0.091954023 | 12.65914 |
| KFW | 16 | 176 | 7.626762 | 4.55E-12 | 4.39E-10 | 4.35E-09 | 0.090909091 | 12.5009 |
| FKV | 21 | 250 | 7.047128 | 1.08E-14 | 1.74E-12 | 1.04E-11 | 0.084 | 11.46371 |
| WKF | 32 | 381 | 7.046247 | 1.39E-21 | 1.34E-18 | 1.34E-18 | 0.083989501 | 11.46214 |
| WKA | 14 | 168 | 6.991199 | 3.09E-10 | 2.29E-08 | 2.94E-07 | 0.083333333 | 11.36445 |
| W.....W | 51 | 795 | 6.788037 | 3.01E-26 | 3.59E-24 | 3.59E-24 | 0.064150943 | 8.569165 |
| LWVA | 3 | 7 | 6.723382 | 2.22E-05 | 0.000551 | 0.0132336 | 0.428571429 | 93.75675 |
| WVK | 11 | 142 | 6.498861 | 5.14E-08 | 2.16E-06 | 4.85E-05 | 0.077464789 | 10.49694 |
| FRF | 19 | 248 | 6.427392 | 1.01E-12 | 1.22E-10 | 9.65E-10 | 0.076612903 | 10.37193 |
| WWK | 15 | 196 | 6.420488 | 2.41E-10 | 1.93E-08 | 2.30E-07 | 0.076530612 | 10.35986 |
| FWK | 18 | 246 | 6.138613 | 8.49E-12 | 7.45E-10 | 8.11E-09 | 0.073170732 | 9.869132 |
| FWV | 15 | 205 | 6.138613 | 4.50E-10 | 2.90E-08 | 4.28E-07 | 0.073170732 | 9.869132 |
| WKV | 29 | 419 | 5.806532 | 1.94E-17 | 6.22E-15 | 1.86E-14 | 0.069212411 | 9.295541 |
| WKL | 28 | 407 | 5.771604 | 7.98E-17 | 1.92E-14 | 7.67E-14 | 0.068796069 | 9.235493 |
| KLW | 11 | 161 | 5.731914 | 1.85E-07 | 5.96E-06 | 0.0001733 | 0.068322981 | 9.167327 |
| FVW | 7 | 104 | 5.646737 | 3.47E-05 | 0.000523 | 0.0312669 | 0.067307692 | 9.021268 |
| KVW | 11 | 164 | 5.627062 | 2.23E-07 | 6.73E-06 | 0.0002083 | 0.067073171 | 8.987575 |
| WKAW | 5 | 14 | 5.602818 | 9.17E-08 | 1.14E-05 | 5.65E-05 | 0.357142857 | 69.44944 |
| VHF | 16 | 241 | 5.569752 | 5.00E-10 | 3.01E-08 | 4.75E-07 | 0.066390041 | 8.889529 |
| HFW | 12 | 186 | 5.412541 | 9.72E-08 | 3.48E-06 | 9.14E-05 | 0.064516129 | 8.62131 |
| EWKW | 4 | 12 | 5.229297 | 2.64E-06 | 0.000164 | 0.0016194 | 0.333333333 | 62.5045 |
| WKWL | 4 | 12 | 5.229297 | 2.64E-06 | 0.000164 | 0.0016194 | 0.333333333 | 62.5045 |
| WVKL | 4 | 12 | 5.229297 | 2.64E-06 | 0.000164 | 0.0016194 | 0.333333333 | 62.5045 |

FIG. 38B

| motif | n | n.lib | enrich | p | fdr | padj.holm | Pr_seqs.motif | PLR |
|---|---|---|---|---|---|---|---|---|
| W | 936 | 58364 | 1.903574 | 7.34E-87 | 2.57E-86 | 4.40E-86 | 0.016037283 | 2.03748 |
| F | 1119 | 75858 | 1.750926 | 3.17E-87 | 2.22E-86 | 2.22E-86 | 0.014751246 | 1.871648 |
| K | 731 | 62082 | 1.397625 | 2.05E-24 | 3.58E-24 | 8.18E-24 | 0.01177475 | 1.489488 |
| V | 793 | 68411 | 1.375898 | 2.89E-25 | 6.75E-25 | 1.45E-24 | 0.011591703 | 1.466061 |
| L | 713 | 71596 | 1.182061 | 1.13E-09 | 1.59E-09 | 3.40E-09 | 0.009958657 | 1.257444 |
| A | 536 | 57451 | 1.107404 | 0.000424 | 0.000494 | 0.000847 | 0.00932969 | 1.177279 |
| H | 579 | 65939 | 1.042258 | 0.016899 | 0.016899 | 0.0168994 | 0.008780843 | 1.107408 |

FIG. 39A

HCV v OTHER 500 (HBV, Chagas, WNV)

| motif | n | n.lib | enrich | p | fdr | padj.holm | Pr seqs.motif | PLR |
|---|---|---|---|---|---|---|---|---|
| LRK | 8 | 98 | 11.26068 | 7.41E-09 | 1.12E-06 | 4.48E-06 | 0.081632653 | 22.31271 |
| LREE | 3 | 5 | 11.23753 | 6.37E-07 | 2.49E-05 | 9.81E-05 | 0.6 | 376.527 |
| YSSR | 3 | 5 | 11.23753 | 6.37E-07 | 2.49E-05 | 9.81E-05 | 0.6 | 376.527 |
| PGK | 11 | 140 | 10.83841 | 1.74E-11 | 1.05E-08 | 1.05E-08 | 0.078571429 | 21.40464 |
| GDKW | 4 | 7 | 10.70241 | 8.89E-09 | 6.93E-07 | 1.38E-06 | 0.571428571 | 334.6907 |
| LRRK | 2 | 4 | 9.364611 | 9.56E-05 | 0.000785 | 0.013484 | 0.5 | 251.018 |
| PGKQ | 2 | 4 | 9.364611 | 9.56E-05 | 0.000785 | 0.013484 | 0.5 | 251.018 |
| RYPN | 2 | 4 | 9.364611 | 9.56E-05 | 0.000785 | 0.013484 | 0.5 | 251.018 |
| RYSF | 2 | 4 | 9.364611 | 9.56E-05 | 0.000785 | 0.013484 | 0.5 | 251.018 |
| LRE | 11 | 187 | 8.114316 | 3.92E-10 | 7.93E-08 | 2.37E-07 | 0.058823529 | 15.68863 |
| REV | 9 | 153 | 8.114316 | 1.54E-08 | 1.64E-06 | 9.26E-06 | 0.058823529 | 15.68863 |
| RYS | 9 | 154 | 8.061626 | 1.62E-08 | 1.64E-06 | 9.78E-06 | 0.058441558 | 15.58043 |
| RYV | 9 | 157 | 7.907582 | 1.92E-08 | 1.67E-06 | 1.15E-05 | 0.057324841 | 15.26461 |
| FDDK | 2 | 5 | 7.491689 | 0.000159 | 0.000954 | 0.0217776 | 0.4 | 167.3453 |
| LLPR | 2 | 5 | 7.491689 | 0.000159 | 0.000954 | 0.0217776 | 0.4 | 167.3453 |
| LLRY | 2 | 5 | 7.491689 | 0.000159 | 0.000954 | 0.0217776 | 0.4 | 167.3453 |
| LPRR | 2 | 5 | 7.491689 | 0.000159 | 0.000954 | 0.0217776 | 0.4 | 167.3453 |
| LRYV | 2 | 5 | 7.491689 | 0.000159 | 0.000954 | 0.0217776 | 0.4 | 167.3453 |
| SADD | 2 | 5 | 7.491689 | 0.000159 | 0.000954 | 0.0217776 | 0.4 | 167.3453 |
| VAAD | 2 | 5 | 7.491689 | 0.000159 | 0.000954 | 0.0217776 | 0.4 | 167.3453 |
| REE | 8 | 154 | 7.16589 | 2.52E-07 | 1.91E-05 | 0.0001511 | 0.051948052 | 13.75441 |
| PRY | 7 | 137 | 7.048202 | 1.59E-06 | 0.000107 | 0.0009505 | 0.051094891 | 13.51635 |
| LRR | 5 | 99 | 6.966837 | 5.33E-05 | 0.001507 | 0.0313119 | 0.050505051 | 13.35202 |
| GPR | 13 | 270 | 6.641718 | 1.22E-10 | 3.71E-08 | 7.40E-08 | 0.048148148 | 12.69741 |
| R...Y | 43 | 1627 | 6.447478 | 1.43E-21 | 1.33E-19 | 1.33E-19 | 0.02642901 | 6.814251 |

FIG. 39B

| motif | n | n.lib | enrich | p | fdr | padj.holm | Pr seqs.motif | PLR |
|---|---|---|---|---|---|---|---|---|
| R | 525 | 63785 | 2.061935 | 1.46E-60 | 1.32E-59 | 1.32E-59 | 0.008230775 | 2.083219 |
| Y | 347 | 56760 | 1.531515 | 2.48E-17 | 1.12E-16 | 1.99E-16 | 0.00611346 | 1.544028 |
| D | 461 | 98037 | 1.177999 | 9.17E-08 | 2.75E-07 | 6.42E-07 | 0.004702306 | 1.18594 |
| G | 489 | 111145 | 1.102181 | 1.63E-05 | 3.66E-05 | 9.77E-05 | 0.004399658 | 1.109274 |

FIG. 40A

WNV v OTHER 1000 (HBV, HCV, Chagas)

| motif | n | n.lib | enrich | p | fdr | padj.holm | Pr_seqs.motif | PLR |
|---|---|---|---|---|---|---|---|---|
| HKWW | 3 | 4 | 12.27113 | 2.22E-06 | 0.00011 | 0.0011886 | 0.75 | 375.027 |
| WKK | 20 | 152 | 11.64225 | 3.09E-18 | 3.11E-15 | 3.11E-15 | 0.131578947 | 18.94076 |
| WEKK | 4 | 6 | 10.90767 | 6.80E-08 | 1.29E-05 | 3.70E-05 | 0.666666667 | 250.018 |
| KEW | 20 | 176 | 10.05467 | 5.78E-17 | 2.92E-14 | 5.82E-14 | 0.113636364 | 16.02679 |
| PQWW | 3 | 5 | 9.816905 | 5.51E-06 | 0.000177 | 0.002931 | 0.6 | 187.5135 |
| KWW | 10 | 93 | 9.5141 | 5.88E-09 | 2.69E-07 | 5.80E-06 | 0.107526882 | 15.06133 |
| K....W | 85 | 1271 | 7.959864 | 9.85E-48 | 8.67E-46 | 8.67E-46 | 0.066876475 | 8.95933 |
| KDW | 16 | 179 | 7.908928 | 3.05E-12 | 4.39E-10 | 3.06E-09 | 0.089385475 | 12.27082 |
| WKW | 15 | 172 | 7.716378 | 2.05E-11 | 2.59E-09 | 2.06E-08 | 0.087209302 | 11.94354 |
| WEK | 12 | 140 | 7.584097 | 2.50E-09 | 1.26E-07 | 2.47E-06 | 0.085714286 | 11.71959 |
| K..W | 134 | 2194 | 7.418298 | 2.30E-70 | 1.96E-68 | 1.96E-68 | 0.061075661 | 8.131653 |
| WDK | 10 | 120 | 7.373428 | 6.91E-08 | 2.11E-06 | 6.74E-05 | 0.083333333 | 11.36445 |
| HWK | 19 | 229 | 7.341229 | 1.12E-13 | 2.26E-11 | 1.13E-10 | 0.082969432 | 11.31034 |
| WKWD | 4 | 9 | 7.271781 | 5.60E-07 | 6.32E-05 | 0.0003039 | 0.444444444 | 100.0072 |
| QKW | 15 | 183 | 7.252552 | 4.98E-11 | 4.42E-09 | 4.97E-08 | 0.081967213 | 11.16152 |
| WKP | 14 | 171 | 7.244069 | 2.20E-10 | 1.48E-08 | 2.19E-07 | 0.081871345 | 11.1473 |
| K.....W | 44 | 715 | 7.20496 | 9.25E-24 | 8.69E-22 | 8.69E-22 | 0.061538462 | 8.197311 |
| K...W | 100 | 1684 | 7.161044 | 1.44E-51 | 1.41E-49 | 1.41E-49 | 0.059382423 | 7.891982 |
| WHK | 11 | 137 | 7.104325 | 2.27E-08 | 8.17E-07 | 2.23E-05 | 0.080291971 | 10.91348 |
| HPW | 19 | 239 | 7.034065 | 2.42E-13 | 4.06E-11 | 2.43E-10 | 0.079497908 | 10.79623 |
| KEWA | 3 | 7 | 7.012075 | 1.90E-05 | 0.000473 | 0.009999 | 0.428571429 | 93.75675 |
| KWK | 16 | 206 | 6.872321 | 2.58E-11 | 2.88E-09 | 2.58E-08 | 0.077669903 | 10.52707 |
| NKW | 13 | 168 | 6.846754 | 1.92E-09 | 1.02E-07 | 1.90E-06 | 0.077380952 | 10.48463 |
| WPK | 11 | 143 | 6.806241 | 3.54E-08 | 1.19E-06 | 3.47E-05 | 0.076923077 | 10.41742 |
| KWH | 14 | 185 | 6.69587 | 6.22E-10 | 3.92E-08 | 6.18E-07 | 0.075675676 | 10.23465 |

FIG. 40B

| motif | n | n.lib | enrich | p | fdr | padj.holm | Pr_seqs.motif | PLR |
|---|---|---|---|---|---|---|---|---|
| K | 1005 | 62082 | 1.990158 | 4.33E-105 | 1.73E-104 | 1.73E-104 | 0.016188267 | 2.056978 |
| W | 922 | 58364 | 1.942106 | 4.68E-90 | 9.37E-90 | 1.41E-89 | 0.015797409 | 2.006516 |
| H | 699 | 65939 | 1.303233 | 7.30E-17 | 9.74E-17 | 1.46E-16 | 0.010600707 | 1.339382 |
| P | 516 | 56321 | 1.126332 | 0.0001354 | 0.0001354 | 0.00013538 | 0.009161769 | 1.155894 |

FIG. 41A

CHAGAS v HBV 1000

| motif | n | n.lib | enrich | p | fdr | padj.holm | Pr_seqs.motif | PLR |
|---|---|---|---|---|---|---|---|---|
| LRYV | 3 | 5 | 9.846808 | 5.03E-06 | 0.00025609 | 0.00245232 | 0.6 | 187.5135 |
| ALRY | 4 | 7 | 9.377912 | 1.39E-07 | 2.30E-05 | 6.88E-05 | 0.571428571 | 166.6787 |
| RYP | 10 | 97 | 9.129637 | 6.93E-09 | 1.16E-06 | 6.92E-06 | 0.103092784 | 14.36885 |
| QQYR | 3 | 6 | 8.205673 | 9.99E-06 | 0.00041293 | 0.0048553 | 0.5 | 125.009 |
| RAYS | 3 | 6 | 8.205673 | 9.99E-06 | 0.00041293 | 0.0048553 | 0.5 | 125.009 |
| YSR | 12 | 137 | 7.75686 | 1.45E-09 | 3.65E-07 | 1.45E-06 | 0.087591241 | 12.00086 |
| RAY | 8 | 95 | 7.457472 | 1.07E-06 | 5.97E-05 | 0.00105613 | 0.084210526 | 11.49508 |
| RPYP | 3 | 7 | 7.033434 | 1.74E-05 | 0.0006157 | 0.0084112 | 0.428571429 | 93.75675 |
| VSRY | 3 | 7 | 7.033434 | 1.74E-05 | 0.0006157 | 0.0084112 | 0.428571429 | 93.75675 |
| LRY | 9 | 115 | 6.930585 | 4.27E-07 | 2.94E-05 | 0.00042322 | 0.07826087 | 10.61397 |
| YSS | 10 | 130 | 6.812114 | 1.16E-07 | 1.05E-05 | 0.00011484 | 0.076923077 | 10.41742 |
| REVD | 6 | 15 | 6.564539 | 1.22E-09 | 6.03E-07 | 6.03E-07 | 0.4 | 83.33933 |
| LRGY | 4 | 10 | 6.564539 | 8.20E-07 | 0.0001017 | 0.00040433 | 0.4 | 83.33933 |
| RYV | 11 | 157 | 6.204664 | 7.10E-08 | 7.91E-06 | 7.06E-05 | 0.070063694 | 9.418486 |
| GPRR | 3 | 8 | 6.154255 | 2.76E-05 | 0.00072153 | 0.01323926 | 0.375 | 75.0054 |
| NPRY | 3 | 8 | 6.154255 | 2.76E-05 | 0.00072153 | 0.01323926 | 0.375 | 75.0054 |
| RNS | 10 | 150 | 5.903832 | 4.39E-07 | 2.94E-05 | 0.00043466 | 0.066666667 | 8.929214 |
| RYQ | 14 | 215 | 5.766534 | 3.13E-09 | 6.28E-07 | 3.13E-06 | 0.065116279 | 8.707095 |
| RYA | 16 | 246 | 5.759836 | 2.45E-10 | 1.23E-07 | 2.46E-07 | 0.06504065 | 8.696278 |
| RYS | 10 | 154 | 5.750486 | 5.60E-07 | 3.51E-05 | 0.00055337 | 0.064935065 | 8.681181 |
| ALR | 9 | 140 | 5.692981 | 2.23E-06 | 0.00010637 | 0.00218915 | 0.064285714 | 8.588405 |
| SRY | 7 | 110 | 5.635476 | 3.18E-05 | 0.00070931 | 0.0305187 | 0.063636364 | 8.495757 |
| GPR | 17 | 270 | 5.575841 | 1.13E-10 | 1.13E-07 | 1.13E-07 | 0.062962963 | 8.399814 |
| GRY | 8 | 129 | 5.491937 | 1.06E-05 | 0.00033132 | 0.01027445 | 0.062015504 | 8.265058 |
| RYVD | 5 | 15 | 5.470449 | 9.10E-08 | 2.26E-05 | 4.50E-05 | 0.333333333 | 62.5045 |

FIG. 41B

| motif | n | n.lib | enrich | p | fdr | padj.holm | Pr_seqs.m | PLR |
|---|---|---|---|---|---|---|---|---|
| R | 1032 | 63785 | 2.03062 | 8.40E-114 | 5.88E-113 | 5.88E-113 | 0.016179 | 2.055827 |
| Y | 760 | 56760 | 1.680501 | 1.57E-49 | 5.50E-49 | 9.43E-49 | 0.01339 | 1.696551 |
| S | 902 | 81297 | 1.392514 | 5.55E-32 | 1.29E-31 | 2.77E-31 | 0.011095 | 1.402551 |
| A | 575 | 57451 | 1.256139 | 5.21E-11 | 9.12E-11 | 2.08E-10 | 0.010009 | 1.263805 |
| V | 624 | 68411 | 1.144791 | 1.19E-06 | 1.39E-06 | 2.38E-06 | 0.009121 | 1.150746 |
| Q | 550 | 60519 | 1.140613 | 1.62E-05 | 1.62E-05 | 1.62E-05 | 0.009088 | 1.146508 |
| G | 953 | 111145 | 1.076144 | 1.44E-07 | 2.02E-07 | 4.33E-07 | 0.008574 | 1.081145 |

FIG. 42A

CHAGAS v HCV 1000

| motif | n | n.lib | enrich | p | fdr | padj.holm | Pr_seqs.motif | PLR |
|---|---|---|---|---|---|---|---|---|
| RYR | 21 | 183 | 9.791189 | 5.73E-18 | 5.11E-15 | 5.114E-15 | 0.114754098 | 16.20487 |
| HRSV | 3 | 5 | 9.674559 | 5.2E-06 | 0.000179 | 0.0028658 | 0.6 | 187.5135 |
| LRYV | 3 | 5 | 9.674559 | 5.2E-06 | 0.000179 | 0.0028658 | 0.6 | 187.5135 |
| VRYR | 3 | 5 | 9.674559 | 5.2E-06 | 0.000179 | 0.0028658 | 0.6 | 187.5135 |
| YSSR | 3 | 5 | 9.674559 | 5.2E-06 | 0.000179 | 0.0028658 | 0.6 | 187.5135 |
| RASY | 4 | 7 | 9.213865 | 1.46E-07 | 1.64E-05 | 8.154E-05 | 0.571428571 | 166.6787 |
| R...Y | 116 | 1627 | 8.774977 | 5.28E-69 | 4.76E-67 | 4.756E-67 | 0.071296865 | 9.596985 |
| PRY | 14 | 137 | 8.719161 | 8.98E-12 | 8.9E-10 | 7.934E-09 | 0.102189781 | 14.22867 |
| RYV | 16 | 157 | 8.69536 | 3.13E-13 | 6.98E-11 | 2.784E-10 | 0.101910828 | 14.18542 |
| RSR | 15 | 149 | 8.589585 | 2.04E-12 | 3.03E-10 | 1.811E-09 | 0.100671141 | 13.99354 |
| R.....Y | 48 | 671 | 8.560694 | 2.47E-29 | 2.15E-27 | 2.15E-27 | 0.071535022 | 9.631512 |
| RYS | 15 | 154 | 8.310703 | 3.31E-12 | 3.69E-10 | 2.925E-09 | 0.097402597 | 13.49018 |
| LRGY | 5 | 10 | 8.062132 | 8.36E-09 | 2.35E-06 | 4.696E-06 | 0.5 | 125.009 |
| RYP | 9 | 97 | 7.916587 | 1.07E-07 | 2.9E-06 | 9.231E-05 | 0.092783505 | 12.78501 |
| YRR | 13 | 143 | 7.756656 | 2.15E-10 | 1.37E-08 | 1.892E-07 | 0.090909091 | 12.5009 |
| VRY | 11 | 121 | 7.756656 | 5.21E-09 | 2.11E-07 | 4.54E-06 | 0.090909091 | 12.5009 |
| SRY | 10 | 110 | 7.756656 | 2.58E-08 | 8.52E-07 | 2.233E-05 | 0.090909091 | 12.5009 |
| RRY | 9 | 99 | 7.756656 | 1.28E-07 | 3.27E-06 | 0.00011 | 0.090909091 | 12.5009 |
| REVD | 7 | 15 | 7.524657 | 1.36E-11 | 7.64E-09 | 7.644E-09 | 0.466666667 | 109.3829 |
| R....Y | 67 | 1090 | 7.479609 | 1.87E-36 | 1.74E-34 | 1.74E-34 | 0.06146789 | 8.187295 |
| YSR | 12 | 137 | 7.473566 | 1.62E-09 | 7.42E-08 | 1.419E-06 | 0.087591241 | 12.00086 |
| LRY | 10 | 115 | 7.41941 | 3.95E-08 | 1.22E-06 | 3.414E-05 | 0.086956522 | 11.90562 |
| RGY | 19 | 220 | 7.368823 | 4.07E-14 | 1.21E-11 | 3.626E-11 | 0.086363636 | 11.81677 |
| RRHY | 5 | 11 | 7.329211 | 1.52E-08 | 2.86E-06 | 8.537E-06 | 0.454545455 | 104.1742 |
| QYR | 14 | 163 | 7.328374 | 9.41E-11 | 6.46E-09 | 8.285E-08 | 0.085889571 | 11.74581 |

FIG. 42B

| motif | n | n.lib | enrich | p | fdr | padj.holm | Pr_seqs.motif | PLR |
|---|---|---|---|---|---|---|---|---|
| R | 1353 | 63785 | 2.641794 | 2.41E-250 | 1.20E-249 | 1.20E-249 | 0.021211884 | 2.709142 |
| Y | 862 | 56760 | 1.891405 | 1.97E-78 | 4.92E-78 | 7.88E-78 | 0.015186751 | 1.927757 |
| S | 797 | 81297 | 1.220966 | 3.81E-14 | 6.36E-14 | 1.14E-13 | 0.00980356 | 1.237667 |
| V | 594 | 68411 | 1.081385 | 0.000776 | 0.000776 | 0.000916 | 0.008682814 | 1.094937 |
| G | 910 | 111145 | 1.019697 | 0.000458 | 0.0005725 | 0.000916 | 0.008187503 | 1.031961 |

FIG. 43A

CHAGAS v WNV 1000

| motif | n | n.lib | enrich | p | fdr | padj.holm | Pr_seqs.motif | PLR |
|---|---|---|---|---|---|---|---|---|
| NGD | 39 | 135 | 26.40327 | 4.04E-49 | 4.10E-46 | 4.10E-46 | 0.288888889 | 50.78491 |
| ENGD | 3 | 4 | 12.61276 | 1.89E-06 | 9.50E-05 | 0.00084 | 0.75 | 375.027 |
| NGDS | 4 | 6 | 11.21134 | 5.50E-08 | 6.21E-06 | 2.47E-05 | 0.666666667 | 250.018 |
| DNG | 22 | 193 | 10.41819 | 5.99E-19 | 3.04E-16 | 6.08E-16 | 0.113989637 | 16.08303 |
| RNGE | 3 | 5 | 10.09021 | 4.70E-06 | 0.000194 | 0.002083 | 0.6 | 187.5135 |
| NGS | 14 | 130 | 9.842638 | 2.99E-12 | 7.58E-10 | 3.02E-09 | 0.107692308 | 15.08729 |
| NGE | 13 | 131 | 9.069824 | 5.03E-11 | 1.02E-08 | 5.08E-08 | 0.099236641 | 13.77218 |
| ANGD | 4 | 8 | 8.408507 | 2.53E-07 | 1.91E-05 | 0.0001136 | 0.5 | 125.009 |
| DRNG | 4 | 8 | 8.408507 | 2.53E-07 | 1.91E-05 | 0.0001136 | 0.5 | 125.009 |
| KEWP | 3 | 6 | 8.408507 | 9.35E-06 | 0.000249 | 0.0041042 | 0.5 | 125.009 |
| NGDD | 3 | 6 | 8.408507 | 9.35E-06 | 0.000249 | 0.0041042 | 0.5 | 125.009 |
| NGDV | 3 | 6 | 8.408507 | 9.35E-06 | 0.000249 | 0.0041042 | 0.5 | 125.009 |
| WEKK | 3 | 6 | 8.408507 | 9.35E-06 | 0.000249 | 0.0041042 | 0.5 | 125.009 |
| REVD | 7 | 15 | 7.84794 | 1.07E-11 | 1.99E-09 | 4.84E-09 | 0.466666667 | 109.3829 |
| REV | 13 | 153 | 7.765666 | 3.53E-10 | 5.97E-08 | 3.57E-07 | 0.08496732 | 11.60798 |
| NGH | 11 | 131 | 7.674467 | 8.97E-09 | 1.01E-06 | 9.04E-06 | 0.083969466 | 11.45916 |
| WDK | 10 | 120 | 7.616327 | 4.54E-08 | 3.29E-06 | 4.55E-05 | 0.083333333 | 11.36445 |
| DNGD | 4 | 9 | 7.474228 | 4.53E-07 | 2.93E-05 | 0.0002022 | 0.444444444 | 100.0072 |
| LRDV | 3 | 7 | 7.207291 | 1.63E-05 | 0.00035 | 0.0070428 | 0.428571429 | 93.75675 |
| VNGD | 3 | 7 | 7.207291 | 1.63E-05 | 0.00035 | 0.0070428 | 0.428571429 | 93.75675 |
| RNG | 11 | 145 | 6.933484 | 2.59E-08 | 2.02E-06 | 2.60E-05 | 0.075862069 | 10.26193 |
| KQW | 6 | 82 | 6.687506 | 4.83E-05 | 0.001217 | 0.0471102 | 0.073170732 | 9.869132 |
| PKW | 10 | 138 | 6.622893 | 1.70E-07 | 9.10E-06 | 0.0001698 | 0.072463768 | 9.766328 |
| KWP | 7 | 97 | 6.595582 | 1.24E-05 | 0.000408 | 0.0122604 | 0.072164948 | 9.722922 |
| LRK | 7 | 98 | 6.52828 | 1.33E-05 | 0.000422 | 0.0131007 | 0.071428571 | 9.616077 |

FIG. 43B

| motif | n | n.lib | enrich | p | fdr | padj.holm | Pr_seqs.motif | PLR |
|---|---|---|---|---|---|---|---|---|
| K | 664 | 62082 | 1.362393 | 8.05E-20 | 3.22E-19 | 5.63E-19 | 0.010695532 | 1.351493 |
| W | 620 | 58364 | 1.353153 | 1.21E-17 | 3.22E-17 | 7.25E-17 | 0.010622987 | 1.342227 |
| D | 1012 | 98037 | 1.314894 | 2.26E-29 | 1.81E-28 | 1.81E-28 | 0.010322633 | 1.303882 |
| H | 625 | 65939 | 1.207363 | 1.24E-09 | 1.98E-09 | 4.96E-09 | 0.009478457 | 1.196231 |
| R | 599 | 63785 | 1.196213 | 1.27E-08 | 1.69E-08 | 3.80E-08 | 0.009390923 | 1.185079 |
| E | 803 | 88289 | 1.158535 | 2.41E-10 | 4.82E-10 | 1.21E-09 | 0.009095131 | 1.147409 |
| G | 910 | 111145 | 1.042921 | 2.71E-05 | 3.10E-05 | 5.42E-05 | 0.008187503 | 1.031961 |

FIG. 44A

HBV v HCV 500

| motif | n | n.lib | enrich | p | fdr | padj.holm | Pr_seqs.motif | PLR |
|---|---|---|---|---|---|---|---|---|
| FFA | 8 | 101 | 9.08707 | 1.78E-08 | 8.82E-07 | 1.04E-05 | 0.079207921 | 21.59295 |
| AWF | 25 | 325 | 8.824943 | 3.66E-23 | 2.18E-20 | 2.18E-20 | 0.076923077 | 20.91817 |
| VLLK | 2 | 4 | 8.456997 | 0.000116 | 0.000958 | 0.02882921 | 0.5 | 251.018 |
| WWLA | 2 | 4 | 8.456997 | 0.000116 | 0.000958 | 0.02882921 | 0.5 | 251.018 |
| FAW | 18 | 260 | 7.942449 | 2.71E-16 | 8.08E-14 | 1.61E-13 | 0.069230769 | 18.67076 |
| LFA | 15 | 234 | 7.354119 | 2.46E-13 | 3.67E-11 | 1.46E-10 | 0.064102564 | 17.19301 |
| FWF | 11 | 174 | 7.252683 | 4.30E-10 | 3.66E-08 | 2.54E-07 | 0.063218391 | 16.93987 |
| LWVA | 3 | 7 | 7.248855 | 2.95E-06 | 9.45E-05 | 0.00080601 | 0.428571429 | 188.2635 |
| FAL | 12 | 190 | 7.245743 | 7.04E-11 | 7.00E-09 | 4.16E-08 | 0.063157895 | 16.92256 |
| FHFA | 2 | 5 | 6.765598 | 0.000192 | 0.001167 | 0.0457912 | 0.4 | 167.3453 |
| FHFV | 2 | 5 | 6.765598 | 0.000192 | 0.001167 | 0.0457912 | 0.4 | 167.3453 |
| FVNL | 2 | 5 | 6.765598 | 0.000192 | 0.001167 | 0.0457912 | 0.4 | 167.3453 |
| HFFA | 2 | 5 | 6.765598 | 0.000192 | 0.001167 | 0.0457912 | 0.4 | 167.3453 |
| NWAV | 2 | 5 | 6.765598 | 0.000192 | 0.001167 | 0.0457912 | 0.4 | 167.3453 |
| WFK | 8 | 147 | 6.243497 | 3.28E-07 | 1.11E-05 | 0.00019026 | 0.054421769 | 14.44708 |
| VWF | 8 | 153 | 5.998654 | 4.45E-07 | 1.33E-05 | 0.0002567 | 0.052287582 | 13.84927 |
| VFF | 9 | 174 | 5.934014 | 9.35E-08 | 3.98E-06 | 5.45E-05 | 0.051724138 | 13.69189 |
| F..F | 83 | 3193 | 5.879595 | 8.37E-37 | 8.62E-35 | 8.62E-35 | 0.025994363 | 6.699194 |
| F.F | 84 | 3264 | 5.853106 | 2.67E-37 | 2.51E-35 | 2.51E-35 | 0.025735294 | 6.630664 |
| FWFA | 3 | 9 | 5.637998 | 7.04E-06 | 0.000164 | 0.00188648 | 0.333333333 | 125.509 |
| HFF | 8 | 163 | 5.630639 | 7.19E-07 | 1.95E-05 | 0.00041329 | 0.049079755 | 12.95577 |
| FKF | 11 | 228 | 5.534943 | 7.33E-09 | 4.37E-07 | 4.30E-06 | 0.048245614 | 12.72441 |
| WF | 88 | 3645 | 5.506241 | 2.98E-37 | 2.77E-35 | 2.77E-35 | 0.024142661 | 6.210173 |
| VWV | 8 | 170 | 5.398789 | 9.87E-07 | 2.45E-05 | 0.00056537 | 0.047058824 | 12.39595 |
| FAWF | 6 | 19 | 5.341261 | 1.88E-10 | 5.25E-08 | 5.25E-08 | 0.315789474 | 115.8545 |

FIG. 44B

| motif | n | n.lib | enrich | p | fdr | padj.holm | Pr_seqs.motif | PLR |
|---|---|---|---|---|---|---|---|---|
| F | 731 | 75858 | 2.261851 | 1.69E-105 | 1.01E-104 | 1.01E-104 | 0.009636426 | 2.442453 |
| W | 513 | 58364 | 2.0631 | 1.85E-58 | 5.54E-58 | 9.23E-58 | 0.008789665 | 2.225929 |
| V | 467 | 68411 | 1.602282 | 7.51E-28 | 1.50E-27 | 3.00E-27 | 0.006826388 | 1.725324 |
| L | 463 | 71596 | 1.51789 | 3.84E-23 | 5.76E-23 | 1.15E-22 | 0.006466842 | 1.63386 |
| A | 325 | 57451 | 1.327803 | 4.40E-09 | 5.28E-09 | 8.80E-09 | 0.005656995 | 1.428086 |
| H | 299 | 65939 | 1.064331 | 0.0368037 | 0.0368037 | 0.0368037 | 0.004534494 | 1.143424 |

FIG. 45A

HBV v WNV top 1000

| motif | n | n.lib | enrich | p | fdr | padj.holm | Pr_seqs.motif | PLR |
|---|---|---|---|---|---|---|---|---|
| WKK | 18 | 152 | 10.35137 | 1.82E-15 | 2.71E-13 | 1.89E-12 | 0.118421053 | 16.79225 |
| WKW | 20 | 172 | 10.16414 | 7.31E-17 | 1.52E-14 | 7.59E-14 | 0.11627907 | 16.44855 |
| PQWW | 3 | 5 | 9.462475 | 6.25E-06 | 0.000245 | 0.0034769 | 0.6 | 187.5135 |
| KFW | 18 | 176 | 8.939822 | 2.43E-14 | 3.17E-12 | 2.52E-11 | 0.102272727 | 14.24153 |
| KFWF | 5 | 10 | 7.885396 | 1.14E-08 | 5.27E-06 | 6.46E-06 | 0.5 | 125.009 |
| FWVK | 3 | 6 | 7.885396 | 1.24E-05 | 0.000321 | 0.0068095 | 0.5 | 125.009 |
| WHK | 12 | 137 | 7.65649 | 2.92E-09 | 1.52E-07 | 2.99E-06 | 0.087591241 | 12.00086 |
| HWK | 19 | 229 | 7.25249 | 2.12E-13 | 2.46E-11 | 2.20E-10 | 0.082969432 | 11.31034 |
| W.....W | 53 | 795 | 7.223312 | 2.38E-28 | 2.50E-26 | 2.50E-26 | 0.066666667 | 8.929214 |
| WKF | 31 | 381 | 7.112229 | 1.19E-20 | 1.24E-17 | 1.24E-17 | 0.081364829 | 11.07223 |
| KVW | 13 | 164 | 6.928968 | 2.21E-09 | 1.21E-07 | 2.27E-06 | 0.079268293 | 10.76236 |
| WKVK | 3 | 7 | 6.758911 | 2.16E-05 | 0.000455 | 0.011732 | 0.428571429 | 93.75675 |
| WWK | 15 | 196 | 6.689663 | 2.16E-10 | 1.73E-08 | 2.23E-07 | 0.076530612 | 10.35986 |
| KWH | 14 | 185 | 6.614931 | 9.90E-10 | 6.45E-08 | 1.02E-06 | 0.075675676 | 10.23465 |
| HPW | 18 | 239 | 6.5833 | 4.61E-12 | 4.37E-10 | 4.76E-09 | 0.075313808 | 10.18173 |
| K.....W | 43 | 715 | 6.516135 | 1.40E-21 | 3.68E-20 | 1.43E-19 | 0.06013986 | 7.999088 |
| WKV | 31 | 419 | 6.467206 | 1.86E-19 | 9.68E-17 | 1.93E-16 | 0.07398568 | 9.987832 |
| WK | 255 | 4685 | 6.459334 | 4.49E-119 | 4.27E-117 | 4.27E-117 | 0.054429029 | 7.195778 |
| WKL | 30 | 407 | 6.443115 | 7.78E-19 | 2.71E-16 | 8.10E-16 | 0.073710074 | 9.947666 |
| K....W | 72 | 1271 | 6.340348 | 2.49E-34 | 2.52E-32 | 2.52E-32 | 0.056648308 | 7.506796 |
| HLW | 15 | 207 | 6.334173 | 4.63E-10 | 3.22E-08 | 4.76E-07 | 0.072463768 | 9.766328 |
| NKWH | 4 | 10 | 6.308317 | 1.10E-06 | 6.24E-05 | 0.0006137 | 0.4 | 83.33933 |
| W....W | 70 | 1246 | 6.287907 | 3.38E-33 | 1.71E-31 | 3.38E-31 | 0.056179775 | 7.441012 |
| WKA | 12 | 168 | 6.243685 | 2.91E-08 | 1.32E-06 | 2.97E-05 | 0.071428571 | 9.616077 |
| WKH | 30 | 435 | 6.028386 | 4.89E-18 | 1.27E-15 | 5.08E-15 | 0.068965517 | 9.259926 |

FIG. 45B

| motif | n | n.lib | enrich | p | fdr | padj.holm | Pr_seqs.motif | PLR |
|---|---|---|---|---|---|---|---|---|
| W | 988 | 58364 | 2.022012 | 3.41E-106 | 2.04E-105 | 2.04E-105 | 0.016928243 | 2.152623 |
| K | 960 | 62082 | 1.847045 | 2.57E-83 | 7.70E-83 | 1.28E-82 | 0.015463419 | 1.963428 |
| F | 778 | 75858 | 1.22504 | 1.12E-13 | 2.24E-13 | 4.47E-13 | 0.010256005 | 1.295378 |
| H | 603 | 65939 | 1.092312 | 0.000325 | 0.0004871 | 0.0009743 | 0.009144816 | 1.153735 |
| V | 596 | 68411 | 1.04062 | 0.014439 | 0.0173269 | 0.0288782 | 0.008712049 | 1.098656 |

FIG. 46A

HCV v WNV top 500 peptides

| motif | n | n.lib | enrich | p | fdr | padj.holm | Pr_seqs.motif | PLR |
|---|---|---|---|---|---|---|---|---|
| WEKK | 4 | 6 | 11.698 | 4.84E-09 | 9.19E-07 | 9.19E-07 | 0.666666667 | 502.036 |
| WKK | 13 | 152 | 11.0247 | 1.61E-13 | 1.02E-10 | 1.02E-10 | 0.085526316 | 23.4765 |
| KEW | 12 | 176 | 8.78889 | 2.01E-11 | 4.23E-09 | 1.27E-08 | 0.068181818 | 18.3672 |
| EKK | 7 | 115 | 7.84631 | 6.83E-07 | 3.93E-05 | 0.0004255 | 0.060869565 | 16.2697 |
| YSAR | 3 | 7 | 7.52012 | 2.64E-06 | 0.00016 | 0.0004971 | 0.428571429 | 188.264 |
| K...W | 53 | 1684 | 7.27642 | 2.40E-28 | 2.81E-26 | 2.81E-26 | 0.031472684 | 8.15693 |
| DGRW | 2 | 5 | 7.01878 | 0.000179 | 0.001359 | 0.0300309 | 0.4 | 167.345 |
| HPKW | 2 | 5 | 7.01878 | 0.000179 | 0.001359 | 0.0300309 | 0.4 | 167.345 |
| KELW | 2 | 5 | 7.01878 | 0.000179 | 0.001359 | 0.0300309 | 0.4 | 167.345 |
| GPR | 14 | 270 | 6.68389 | 1.73E-11 | 4.23E-09 | 1.09E-08 | 0.051851852 | 13.7275 |
| GPRR | 3 | 8 | 6.58011 | 4.22E-06 | 0.00016 | 0.0007886 | 0.375 | 150.611 |
| NKEF | 3 | 8 | 6.58011 | 4.22E-06 | 0.00016 | 0.0007886 | 0.375 | 150.611 |
| K..W | 61 | 2194 | 6.53027 | 8.67E-30 | 8.23E-28 | 8.23E-28 | 0.027803099 | 7.17867 |
| HPK | 10 | 198 | 6.51029 | 1.69E-08 | 1.79E-06 | 1.06E-05 | 0.050505051 | 13.352 |
| KDW | 9 | 179 | 6.48119 | 9.11E-08 | 8.24E-06 | 5.71E-05 | 0.05027933 | 13.2892 |
| WEK | 7 | 140 | 6.44518 | 2.55E-06 | 0.000116 | 0.001584 | 0.05 | 13.2115 |
| K.W | 70 | 2598 | 6.40471 | 2.40E-33 | 2.45E-31 | 2.45E-31 | 0.026943803 | 6.95066 |
| NKK | 9 | 184 | 6.30507 | 1.15E-07 | 9.11E-06 | 7.21E-05 | 0.048913043 | 12.9095 |
| K.....W | 20 | 715 | 6.08523 | 2.19E-10 | 2.52E-08 | 2.52E-08 | 0.027972028 | 7.22354 |
| K....W | 34 | 1271 | 6.05961 | 2.04E-16 | 2.41E-14 | 2.41E-14 | 0.02675059 | 6.89944 |
| KFW | 8 | 176 | 5.85926 | 1.01E-06 | 5.33E-05 | 0.0006286 | 0.045454545 | 11.9532 |
| WKKE | 4 | 12 | 5.84898 | 1.56E-07 | 1.49E-05 | 2.96E-05 | 0.333333333 | 125.509 |
| HKDW | 2 | 6 | 5.84898 | 0.000267 | 0.001802 | 0.0438494 | 0.333333333 | 125.509 |
| KKPW | 2 | 6 | 5.84898 | 0.000267 | 0.001802 | 0.0438494 | 0.333333333 | 125.509 |
| W.K | 70 | 2950 | 5.64049 | 4.58E-30 | 2.33E-28 | 4.62E-28 | 0.023728814 | 6.10113 |

FIG. 46B

| motif | n | n.lib | enrich | p | fdr | padj.holm | Pr_seqs.motif | PLR |
|---|---|---|---|---|---|---|---|---|
| K | 512 | 62082 | 1.98543 | 5.36E-54 | 3.22E-53 | 3.22E-53 | 0.008247157 | 2.0874 |
| W | 367 | 58364 | 1.51381 | 1.38E-17 | 4.14E-17 | 6.91E-17 | 0.006288123 | 1.58842 |
| R | 353 | 63785 | 1.332313 | 3.19E-10 | 6.38E-10 | 1.28E-09 | 0.005534217 | 1.396919 |
| Y | 291 | 56760 | 1.234243 | 1.31E-05 | 1.97E-05 | 3.94E-05 | 0.00512685 | 1.293564 |
| P | 274 | 56321 | 1.171198 | 0.000658 | 0.000789 | 0.0013154 | 0.00486497 | 1.227165 |

FIG. 47A

MULTICLASS top 1000 peptides

| motif | n | n.lib | enrich | p | fdr | padj.holm | Pr_seqs.motif | PLR |
|---|---|---|---|---|---|---|---|---|
| LRYV | 3 | 5 | 10.33072 | 5.24E-06 | 0.00029 | 0.0021963 | 0.6 | 187.5135 |
| RYP | 9 | 97 | 8.696814 | 1.09E-07 | 2.45E-05 | 0.0001222 | 0.092783505 | 12.78501 |
| WEKK | 3 | 6 | 8.608937 | 1.04E-05 | 0.000492 | 0.0043452 | 0.5 | 125.009 |
| REVD | 7 | 15 | 8.035008 | 1.38E-11 | 5.88E-09 | 5.88E-09 | 0.466666667 | 109.3829 |
| YLLP | 4 | 9 | 7.652388 | 5.24E-07 | 7.37E-05 | 0.0002216 | 0.444444444 | 100.0072 |
| KFWF | 4 | 10 | 6.887149 | 8.67E-07 | 7.37E-05 | 0.000366 | 0.4 | 83.33933 |
| KWWK | 4 | 10 | 6.887149 | 8.67E-07 | 7.37E-05 | 0.000366 | 0.4 | 83.33933 |
| LRK | 7 | 98 | 6.695167 | 1.62E-05 | 0.001082 | 0.0179625 | 0.071428571 | 9.616077 |
| GPR | 19 | 270 | 6.595979 | 1.65E-12 | 1.85E-09 | 1.85E-09 | 0.07037037 | 9.462833 |
| RYV | 11 | 157 | 6.567234 | 8.01E-08 | 2.24E-05 | 8.95E-05 | 0.070063694 | 9.418486 |
| GPRR | 3 | 8 | 6.456703 | 2.88E-05 | 0.000942 | 0.0119041 | 0.375 | 75.0054 |
| KFW | 12 | 176 | 6.390841 | 2.82E-08 | 1.05E-05 | 3.15E-05 | 0.068181818 | 9.147 |
| DRY | 7 | 108 | 6.075244 | 3.05E-05 | 0.001801 | 0.0336612 | 0.064814815 | 8.66399 |
| YGPR | 4 | 12 | 5.739291 | 2.02E-06 | 0.000143 | 0.0008476 | 0.333333333 | 62.5045 |
| RAVY | 3 | 9 | 5.739291 | 4.30E-05 | 0.001141 | 0.017662 | 0.333333333 | 62.5045 |
| SRYG | 3 | 9 | 5.739291 | 4.30E-05 | 0.001141 | 0.017662 | 0.333333333 | 62.5045 |
| PRR | 8 | 132 | 5.680747 | 1.36E-05 | 0.001019 | 0.0150908 | 0.060606061 | 8.065097 |
| RAV | 9 | 153 | 5.513667 | 5.09E-06 | 0.000558 | 0.0056612 | 0.058823529 | 7.813063 |
| REV | 9 | 153 | 5.513667 | 5.09E-06 | 0.000558 | 0.0056612 | 0.058823529 | 7.813063 |
| LRKV | 3 | 10 | 5.165362 | 6.10E-05 | 0.001441 | 0.0248955 | 0.3 | 53.57529 |
| WKK | 8 | 152 | 4.933281 | 3.76E-05 | 0.002009 | 0.0414316 | 0.052631579 | 6.944944 |
| WKW | 9 | 172 | 4.904599 | 1.31E-05 | 0.001019 | 0.0144795 | 0.052325581 | 6.902337 |
| WWK | 10 | 196 | 4.782262 | 5.47E-06 | 0.000558 | 0.0060796 | 0.051020408 | 6.720914 |
| RVV | 9 | 177 | 4.766051 | 1.64E-05 | 0.001082 | 0.0181388 | 0.050847458 | 6.696911 |
| PKWK | 3 | 11 | 4.695784 | 8.34E-05 | 0.001772 | 0.0339406 | 0.272727273 | 46.87838 |

FIG. 47B

| motif | n | n.lib | enrich | p | fdr | padj.holm | Pr_seqs.motif | PLR |
|---|---|---|---|---|---|---|---|---|
| R | 782 | 63785 | 1.524215 | 1.64E-37 | 1.15E-36 | 1.15E-36 | 0.012259936 | 1.551625 |
| Y | 603 | 56760 | 1.320788 | 3.83E-15 | 1.34E-14 | 2.30E-14 | 0.010623679 | 1.342316 |
| K | 580 | 62082 | 1.161503 | 1.04E-06 | 2.44E-06 | 5.22E-06 | 0.009342483 | 1.178908 |
| W | 527 | 58364 | 1.122597 | 0.000131 | 0.000229 | 0.0005231 | 0.009029539 | 1.139059 |
| V | 585 | 68411 | 1.063134 | 0.003423 | 0.004793 | 0.0102699 | 0.008551256 | 1.078204 |
| A | 488 | 57451 | 1.05604 | 0.019788 | 0.023086 | 0.0395757 | 0.008494195 | 1.070948 |

FIG. 48A

| peptide | order clustered | Discrimination, Chagas + vs - | | | Pearson correlation, log₂(intensity) vs. T. cruzi ELISA (S/CO) | | | | | |
|---|---|---|---|---|---|---|---|---|---|---|
| | | intensity ratio mean(+)/mean(-) | t-test p-value | rank | All 2015 Donors | | | 2015 Chagas+ Donors Only | | |
| | | | | | r | p-value | r | p-value | FDR | rank |
| KRHRHQPEG | 1 | 0.89 | 2.8E-07 | 328 | -0.26 | 1.3E-06 | -0.09 | 0.26 | 1.00 | 253 |
| RSHRASD | 2 | 0.89 | 1.2E-07 | 259 | -0.27 | 6.7E-07 | -0.06 | 0.45 | 1.00 | 291 |
| NSHSGKHLQRLF | 3 | 0.88 | 5.8E-11 | 119 | -0.34 | 1.0E-10 | -0.07 | 0.39 | 1.00 | 279 |
| GRHSRREG | 4 | 0.90 | 4.9E-08 | 214 | -0.30 | 3.1E-08 | -0.03 | 0.72 | 1.00 | 327 |
| KAQYKQRD | 5 | 0.88 | 7.5E-08 | 225 | -0.27 | 3.9E-07 | -0.09 | 0.28 | 1.00 | 260 |
| RWRDRFGQKSE | 6 | 0.89 | 1.4E-08 | 178 | -0.30 | 3.1E-08 | -0.01 | 0.89 | 1.00 | 350 |
| KYSYLDYKG | 7 | 0.90 | 3.1E-07 | 338 | -0.24 | 8.5E-06 | 0.07 | 0.39 | 1.00 | 281 |
| RWQHQKSPEG | 8 | 0.89 | 4.0E-08 | 210 | -0.28 | 1.4E-07 | -0.05 | 0.55 | 1.00 | 308 |
| EWRGRKRD | 9 | 0.89 | 2.5E-07 | 315 | -0.26 | 9.5E-07 | -0.08 | 0.32 | 1.00 | 273 |
| KSGSHQKRE | 10 | 0.86 | 4.3E-10 | 136 | -0.33 | 9.6E-10 | -0.10 | 0.23 | 1.00 | 251 |
| KQVDAHKRFG | 11 | 0.89 | 1.3E-07 | 264 | -0.24 | 8.3E-06 | 0.00 | 0.99 | 1.00 | 368 |
| SAFRKRDG | 12 | 0.90 | 9.1E-08 | 236 | -0.28 | 1.3E-07 | -0.03 | 0.68 | 1.00 | 321 |
| VLGREKQHG | 13 | 0.89 | 2.5E-08 | 195 | -0.29 | 9.7E-08 | 0.02 | 0.77 | 1.00 | 336 |
| SFRKRHEG | 14 | 0.90 | 1.2E-07 | 250 | -0.29 | 4.0E-08 | -0.09 | 0.30 | 1.00 | 267 |
| RFRRWDG | 15 | 0.90 | 1.6E-07 | 277 | -0.25 | 2.8E-06 | 0.03 | 0.69 | 1.00 | 325 |
| KKHYRSDDG | 16 | 0.88 | 1.9E-07 | 290 | -0.24 | 9.2E-06 | 0.05 | 0.58 | 1.00 | 310 |
| KFHQWKVSD | 17 | 0.89 | 1.9E-07 | 296 | -0.24 | 7.4E-06 | 0.02 | 0.78 | 1.00 | 337 |
| NKDRARRDG | 18 | 0.89 | 2.3E-07 | 310 | -0.26 | 1.5E-06 | -0.10 | 0.22 | 1.00 | 249 |
| WGQHKRSRDG | 19 | 0.88 | 1.3E-09 | 149 | -0.31 | 7.2E-09 | 0.03 | 0.76 | 1.00 | 333 |
| SSYKGAHG | 20 | 0.90 | 4.1E-10 | 134 | -0.34 | 8.8E-11 | -0.16 | 0.06 | 1.00 | 213 |
| VDKARHQHS | 21 | 0.90 | 1.3E-07 | 263 | -0.27 | 7.2E-07 | 0.00 | 0.98 | 1.00 | 364 |
| RSHSNSGKLE | 22 | 0.89 | 1.4E-07 | 266 | -0.27 | 4.8E-07 | -0.05 | 0.58 | 1.00 | 311 |
| SWRHKFDG | 23 | 0.91 | 1.9E-08 | 189 | -0.30 | 2.1E-08 | -0.02 | 0.85 | 1.00 | 346 |

FIG. 48B

| | | | | | | | | | |
|---|---|---|---|---|---|---|---|---|---|
| KKRERWQEG | 24 | 0.88 | 7.7E-08 | 227 | -0.29 | 7.5E-08 | -0.09 | 0.29 | 1.00 | 263 |
| HKHAKRGDG | 25 | 0.89 | 2.3E-07 | 306 | -0.24 | 1.2E-05 | 0.06 | 0.45 | 1.00 | 292 |
| KWHKKRHSE | 26 | 0.88 | 2.6E-08 | 199 | -0.28 | 2.4E-07 | -0.01 | 0.89 | 1.00 | 351 |
| KSKWANKEG | 27 | 0.87 | 1.6E-07 | 279 | -0.31 | 6.7E-09 | -0.24 | 0.0029 | 0.66 | 180 |
| KKKKRHED | 28 | 0.87 | 3.2E-07 | 341 | -0.29 | 1.0E-07 | -0.07 | 0.43 | 1.00 | 287 |
| KLHKHKSE | 29 | 0.87 | 7.9E-10 | 143 | -0.34 | 2.3E-10 | -0.10 | 0.22 | 1.00 | 250 |
| KYSKSKHE | 30 | 0.88 | 1.4E-08 | 177 | -0.30 | 1.6E-08 | -0.08 | 0.32 | 1.00 | 272 |
| KSKRDAWGYEG | 31 | 0.89 | 3.4E-07 | 346 | -0.25 | 2.7E-06 | -0.09 | 0.30 | 1.00 | 268 |
| GAMYNKYDG | 32 | 0.89 | 1.5E-07 | 275 | -0.29 | 1.1E-07 | -0.14 | 0.09 | 1.00 | 222 |
| KFSWYQDKG | 33 | 0.88 | 1.2E-08 | 175 | -0.31 | 4.6E-09 | -0.12 | 0.15 | 1.00 | 234 |
| KKEVGYKDG | 34 | 0.86 | 2.3E-07 | 311 | -0.26 | 1.9E-06 | -0.07 | 0.40 | 1.00 | 282 |
| HKYKSRSE | 35 | 0.87 | 1.1E-08 | 173 | -0.29 | 3.8E-08 | -0.01 | 0.93 | 1.00 | 355 |
| KSWGPQHWYKE | 36 | 0.88 | 2.0E-07 | 297 | -0.26 | 1.1E-06 | -0.18 | 0.03 | 1.00 | 207 |
| KSSHFNKEG | 37 | 0.89 | 5.0E-08 | 215 | -0.29 | 6.4E-08 | -0.16 | 0.06 | 1.00 | 212 |
| FSREKNKG | 38 | 0.90 | 1.3E-08 | 176 | -0.30 | 1.5E-08 | -0.11 | 0.17 | 1.00 | 239 |
| QSLKKRD | 39 | 0.89 | 3.9E-07 | 355 | -0.29 | 1.1E-07 | -0.09 | 0.29 | 1.00 | 262 |
| LWEGKRRG | 40 | 0.89 | 2.3E-07 | 308 | -0.29 | 7.8E-08 | -0.11 | 0.20 | 1.00 | 246 |
| YDYKKYWKG | 41 | 0.89 | 7.2E-08 | 222 | -0.28 | 2.9E-07 | -0.05 | 0.57 | 1.00 | 309 |
| KAARKDG | 42 | 0.87 | 2.7E-07 | 325 | -0.25 | 2.3E-06 | -0.03 | 0.76 | 1.00 | 331 |
| SRKQDG | 43 | 0.89 | 2.5E-07 | 316 | -0.26 | 2.1E-06 | -0.06 | 0.49 | 1.00 | 297 |
| RSKKDDG | 44 | 0.88 | 2.1E-07 | 302 | -0.27 | 8.5E-07 | -0.13 | 0.11 | 1.00 | 224 |
| KWGKKFSE | 45 | 0.86 | 2.2E-07 | 304 | -0.27 | 6.4E-07 | -0.05 | 0.58 | 1.00 | 312 |
| VAQSKREKRFG | 46 | 0.90 | 8.2E-08 | 230 | -0.28 | 2.2E-07 | -0.08 | 0.31 | 1.00 | 270 |
| KAGSSG | 47 | 0.88 | 2.0E-08 | 190 | -0.26 | 9.0E-07 | 0.09 | 0.30 | 1.00 | 266 |
| SNDRKRFG | 48 | 0.90 | 7.7E-08 | 226 | -0.28 | 1.4E-07 | -0.08 | 0.33 | 1.00 | 275 |
| NAKPSYG | 49 | 0.88 | 1.2E-07 | 253 | -0.24 | 8.0E-06 | 0.04 | 0.60 | 1.00 | 315 |

FIG. 48C

| | | | | | | | | |
|---|---|---|---|---|---|---|---|---|
| GSKHWQRSE | 50 | 0.88 | 1.1E-07 | 248 | -0.25 | 4.0E-06 | 0.01 | 0.93 | 356 |
| KQGSRSDG | 51 | 0.88 | 8.9E-08 | 235 | -0.25 | 4.2E-06 | 0.04 | 0.65 | 318 |
| KAGFEKHSG | 52 | 0.89 | 1.8E-07 | 285 | -0.25 | 3.1E-06 | 0.01 | 0.88 | 349 |
| KLHHKVLD | 53 | 0.88 | 1.5E-07 | 274 | -0.23 | 1.4E-05 | 0.06 | 0.48 | 295 |
| KLAEWHVKLG | 54 | 0.88 | 3.3E-07 | 344 | -0.25 | 4.0E-06 | -0.03 | 0.72 | 328 |
| KLEKKHPKDG | 55 | 0.86 | 1.5E-07 | 273 | -0.26 | 1.3E-06 | -0.02 | 0.77 | 335 |
| EKMHFKHLF | 56 | 0.89 | 1.4E-07 | 271 | -0.26 | 9.3E-07 | -0.09 | 0.28 | 258 |
| SRKKRSED | 57 | 0.87 | 1.6E-07 | 278 | -0.28 | 3.2E-07 | -0.08 | 0.31 | 269 |
| GDKHKHVLS | 58 | 0.85 | 9.0E-09 | 167 | -0.29 | 9.7E-08 | 0.00 | 1.00 | 370 |
| KAEGKHYKG | 59 | 0.85 | 9.6E-08 | 239 | -0.28 | 1.6E-07 | -0.11 | 0.18 | 242 |
| KMDHQRG | 60 | 0.85 | 3.1E-07 | 339 | -0.26 | 1.1E-06 | -0.07 | 0.41 | 283 |
| EQEDKFDRSG | 61 | 0.84 | 2.5E-07 | 318 | -0.31 | 1.0E-08 | -0.13 | 0.13 | 228 |
| SNDVSPVLSE | 62 | 0.85 | 1.8E-07 | 287 | -0.27 | 7.7E-07 | 0.06 | 0.45 | 293 |
| FRWHYKRED | 63 | 0.90 | 2.9E-07 | 332 | -0.25 | 2.5E-06 | 0.08 | 0.32 | 271 |
| FRHHARSED | 64 | 0.90 | 6.0E-09 | 163 | -0.29 | 7.3E-08 | 0.11 | 0.18 | 244 |
| FFWHQSDG | 65 | 0.88 | 2.5E-08 | 194 | -0.28 | 2.8E-07 | 0.07 | 0.44 | 289 |
| LWLYPNKRG | 66 | 0.88 | 1.2E-07 | 251 | -0.27 | 4.7E-07 | -0.06 | 0.50 | 301 |
| FKWKRHDG | 67 | 0.89 | 1.6E-08 | 180 | -0.27 | 3.3E-07 | 0.05 | 0.55 | 307 |
| AWFHKRQDG | 68 | 0.89 | 1.9E-07 | 295 | -0.24 | 1.1E-05 | 0.09 | 0.30 | 265 |
| LFFHQKSG | 69 | 0.86 | 1.3E-07 | 261 | -0.25 | 3.6E-06 | 0.06 | 0.49 | 296 |
| FWKHKHGAVD | 70 | 0.89 | 2.7E-07 | 323 | -0.25 | 2.5E-06 | 0.02 | 0.85 | 345 |
| LFHLQRPG | 71 | 0.89 | 2.4E-07 | 313 | -0.25 | 3.5E-06 | 0.04 | 0.59 | 313 |
| SHFKRSHSE | 72 | 0.90 | 3.5E-07 | 350 | -0.27 | 8.2E-07 | 0.06 | 0.51 | 303 |
| FQHLYKRAG | 73 | 0.89 | 8.7E-08 | 233 | -0.28 | 2.9E-07 | 0.07 | 0.43 | 285 |
| VYHRKRD | 74 | 0.89 | 9.8E-08 | 240 | -0.28 | 1.5E-07 | 0.06 | 0.50 | 300 |
| YRYWKRGQPAD | 75 | 0.88 | 1.5E-10 | 124 | -0.35 | 3.0E-11 | -0.08 | 0.33 | 276 |
| AALKWRDG | 76 | 0.89 | 1.3E-07 | 260 | -0.27 | 5.2E-07 | 0.05 | 0.52 | 304 |

FIG. 48D

| | | | | | | | | | |
|---|---|---|---|---|---|---|---|---|---|
| SFMKKRDG | 77 | 0.89 | 9.4E-09 | 168 | -0.28 | 2.1E-07 | 0.01 | 0.95 | 1.00 | 358 |
| SYHFQKPG | 78 | 0.90 | 1.3E-07 | 265 | -0.25 | 3.8E-06 | 0.12 | 0.14 | 1.00 | 230 |
| VKHKYWREG | 79 | 0.90 | 7.9E-08 | 228 | -0.26 | 1.9E-06 | 0.02 | 0.83 | 1.00 | 342 |
| LMHMGRSG | 80 | 0.89 | 1.4E-07 | 270 | -0.25 | 2.6E-06 | 0.13 | 0.11 | 1.00 | 223 |
| VRHRKVEG | 81 | 0.91 | 1.1E-07 | 247 | -0.23 | 1.9E-05 | 0.09 | 0.27 | 1.00 | 257 |
| LAHRQHSG | 82 | 0.90 | 8.6E-08 | 231 | -0.27 | 5.6E-07 | 0.11 | 0.18 | 1.00 | 240 |
| RFHKHRDG | 83 | 0.88 | 4.6E-09 | 156 | -0.29 | 8.5E-08 | 0.06 | 0.44 | 1.00 | 290 |
| KQYSAQKD | 84 | 0.87 | 2.9E-08 | 203 | -0.28 | 1.8E-07 | -0.11 | 0.18 | 1.00 | 241 |
| KKYRQKEG | 85 | 0.85 | 2.9E-08 | 204 | -0.24 | 7.5E-06 | -0.02 | 0.85 | 1.00 | 347 |
| RYYRKDG | 86 | 0.88 | 2.6E-08 | 196 | -0.27 | 8.1E-07 | 0.04 | 0.62 | 1.00 | 316 |
| RLYSRKRE | 87 | 0.87 | 1.8E-08 | 184 | -0.28 | 2.5E-07 | 0.01 | 0.91 | 1.00 | 353 |
| KGYFQWNKSD | 88 | 0.88 | 1.7E-07 | 283 | -0.26 | 1.1E-06 | -0.03 | 0.74 | 1.00 | 330 |
| SRYRYANDG | 89 | 0.89 | 5.5E-09 | 162 | -0.27 | 3.2E-07 | 0.00 | 0.97 | 1.00 | 361 |
| KLYAYAQQG | 90 | 0.91 | 3.3E-07 | 345 | -0.26 | 1.1E-06 | 0.00 | 0.98 | 1.00 | 365 |
| AVEDLVPAVE | 91 | 1.55 | 1.6E-08 | 182 | 0.29 | 3.9E-08 | -0.02 | 0.84 | 1.00 | 343 |
| GVENLFDEG | 92 | 2.15 | 9.8E-17 | 51 | 0.44 | 2.7E-17 | -0.11 | 0.20 | 1.00 | 248 |
| GLEHLVDG | 93 | 2.28 | 2.1E-16 | 53 | 0.45 | 5.7E-18 | -0.12 | 0.14 | 1.00 | 232 |
| GVEHLAWG | 94 | 2.06 | 2.3E-17 | 44 | 0.46 | 3.4E-19 | -0.08 | 0.36 | 1.00 | 278 |
| GVEQLGKHSD | 95 | 1.53 | 1.0E-09 | 144 | 0.30 | 2.9E-08 | -0.04 | 0.60 | 1.00 | 314 |
| GADELFG | 96 | 1.39 | 6.6E-09 | 155 | 0.27 | 4.7E-07 | -0.09 | 0.26 | 1.00 | 254 |
| GVENWVSDG | 97 | 1.44 | 1.0E-07 | 242 | 0.24 | 1.1E-05 | -0.21 | 0.01 | 1.00 | 198 |
| GFEDLPQEG | 98 | 1.76 | 6.6E-13 | 93 | 0.36 | 2.1E-11 | -0.12 | 0.17 | 1.00 | 235 |
| EPHYHVNKVD | 99 | 1.48 | 2.2E-07 | 305 | 0.20 | 0.0003 | -0.11 | 0.17 | 1.00 | 238 |
| DYSDQVSG | 100 | 1.47 | 1.0E-08 | 171 | 0.29 | 6.3E-08 | 0.09 | 0.29 | 1.00 | 264 |
| QRGFVSGKED | 101 | 1.23 | 3.0E-08 | 205 | 0.26 | 1.1E-06 | -0.12 | 0.15 | 1.00 | 233 |
| GWGHLSEQSG | 102 | 1.19 | 1.1E-07 | 244 | 0.25 | 3.6E-06 | -0.09 | 0.28 | 1.00 | 261 |
| YMKLPEDYEWVG | 103 | 1.34 | 2.6E-08 | 200 | 0.38 | 3.1E-13 | 0.37 | 1.4E-05 | 0.01 | 49 |

FIG. 48E

| | | | | | | | | |
|---|---|---|---|---|---|---|---|---|
| WHWKGVLPED | 104 | 1.23 | 1.7E-07 | 280 | 0.32 | 2.3E-09 | 0.27 | 0.0010 | 0.37 | 167 |
| ASPYNQVKPYED | 105 | 1.32 | 2.9E-10 | 128 | 0.45 | 3.2E-18 | 0.43 | 1.6E-07 | 0.0004 | 18 |
| ASPRSPFEVE | 106 | 1.34 | 4.1E-10 | 133 | 0.41 | 3.5E-15 | 0.31 | 0.0001 | 0.09 | 118 |
| ARPPYQPAED | 107 | 1.43 | 1.4E-09 | 150 | 0.38 | 3.0E-13 | 0.46 | 1.7E-08 | 1.7E-04 | 14 |
| AWGSAVEVD | 108 | 1.25 | 1.1E-07 | 245 | 0.32 | 1.3E-09 | 0.11 | 0.18 | 1.00 | 243 |
| ARPEQDYFG | 109 | 1.21 | 0.0003 | 5355 | 0.28 | 2.0E-07 | 0.32 | 1.8E-04 | 0.07 | 112 |
| AKPQWAFED | 110 | 1.15 | 9.3E-05 | 3013 | 0.29 | 5.3E-08 | 0.32 | 0.0001 | 0.09 | 117 |
| ARPNEWGYFD | 111 | 1.21 | 3.8E-10 | 130 | 0.38 | 3.8E-13 | 0.28 | 0.0006 | 0.27 | 149 |
| ARGDYYLEG | 112 | 1.22 | 1.1E-08 | 174 | 0.36 | 2.1E-11 | 0.19 | 0.02 | 1.00 | 201 |
| ADPYSYAALSD | 113 | 1.21 | 2.4E-08 | 193 | 0.35 | 5.7E-11 | 0.18 | 0.03 | 1.00 | 206 |
| AEPYRYWQWLE | 114 | 1.15 | 1.2E-07 | 254 | 0.30 | 1.7E-08 | 0.15 | 0.06 | 1.00 | 216 |
| AKWYENFSD | 115 | 1.18 | 1.1E-07 | 249 | 0.30 | 1.6E-08 | 0.14 | 0.08 | 1.00 | 220 |
| AYPSYAVED | 116 | 1.27 | 1.0E-09 | 145 | 0.42 | 6.3E-16 | 0.30 | 0.0003 | 0.17 | 135 |
| AQGWDSSGVFE | 117 | 1.24 | 1.7E-08 | 183 | 0.35 | 4.0E-11 | 0.21 | 0.01 | 1.00 | 196 |
| AADVVWHSD | 118 | 1.15 | 3.8E-07 | 354 | 0.24 | 1.1E-05 | -0.02 | 0.78 | 1.00 | 338 |
| DRYYADG | 119 | 1.28 | 1.4E-07 | 268 | 0.33 | 1.0E-09 | 0.16 | 0.05 | 1.00 | 211 |
| DRYWSDYDG | 120 | 1.23 | 6.1E-09 | 164 | 0.33 | 5.4E-10 | 0.14 | 0.08 | 1.00 | 219 |
| DRWYALDG | 121 | 1.20 | 2.1E-07 | 301 | 0.29 | 6.4E-08 | 0.14 | 0.09 | 1.00 | 221 |
| DRSFPYWDG | 122 | 1.22 | 3.0E-08 | 206 | 0.31 | 4.7E-09 | 0.13 | 0.12 | 1.00 | 227 |
| VPRRFDQRED | 123 | 1.25 | 2.8E-07 | 329 | 0.30 | 1.4E-08 | 0.27 | 0.0009 | 0.34 | 161 |
| QRGGAFDWVD | 124 | 1.30 | 2.2E-08 | 192 | 0.29 | 5.7E-08 | 0.11 | 0.20 | 1.00 | 247 |
| SRGFELSE | 125 | 1.33 | 9.9E-08 | 241 | 0.31 | 9.7E-09 | 0.15 | 0.07 | 1.00 | 217 |
| GQRAFEYSD | 126 | 1.22 | 4.5E-08 | 212 | 0.29 | 4.3E-08 | 0.01 | 0.92 | 1.00 | 354 |
| EPRRLDYDG | 127 | 1.37 | 1.5E-07 | 276 | 0.34 | 1.3E-10 | 0.33 | 1.5E-04 | 0.05 | 95 |
| RRDLDFSD | 128 | 1.83 | 4.8E-10 | 139 | 0.37 | 4.0E-12 | 0.35 | 1.2E-04 | 0.03 | 73 |

FIG. 48F

| | | | | | | | | |
|---|---|---|---|---|---|---|---|---|
| GRELEWQFS | 129 | 1.39 | 3.2E-07 | 342 | 0.32 | 2.4E-09 | 0.31 | 0.0002 | 0.12 | 124 |
| VVRLQLSE | 130 | 1.16 | 7.4E-08 | 224 | 0.31 | 9.0E-09 | 0.09 | 0.28 | 1.00 | 259 |
| GPFVRVLFS | 131 | 1.20 | 2.9E-08 | 202 | 0.29 | 7.8E-08 | 0.07 | 0.43 | 1.00 | 288 |
| PSQLWVKFG | 132 | 1.18 | 1.8E-07 | 289 | 0.27 | 6.6E-07 | 0.04 | 0.65 | 1.00 | 319 |
| RQVLRFVSE | 133 | 1.17 | 3.6E-07 | 351 | 0.25 | 2.5E-06 | 0.05 | 0.53 | 1.00 | 306 |
| RVNFRVLKYE | 134 | 1.14 | 1.2E-07 | 252 | 0.29 | 4.4E-08 | 0.03 | 0.69 | 1.00 | 324 |
| DRRLRVLSG | 135 | 1.18 | 3.3E-08 | 208 | 0.28 | 1.3E-07 | 0.01 | 0.90 | 1.00 | 352 |
| PLVLRVPKG | 136 | 1.21 | 3.8E-09 | 153 | 0.32 | 2.3E-09 | 0.03 | 0.73 | 1.00 | 329 |
| PLNFKRLAVFS | 137 | 1.16 | 1.9E-07 | 294 | 0.28 | 3.0E-07 | 0.01 | 0.87 | 1.00 | 348 |
| QFRLGFAG | 138 | 1.15 | 5.7E-08 | 217 | 0.29 | 4.3E-08 | 0.03 | 0.68 | 1.00 | 323 |
| KLVHLRVG | 139 | 1.15 | 4.7E-08 | 213 | 0.27 | 4.0E-07 | -0.01 | 0.94 | 1.00 | 357 |
| VRVVRLG | 140 | 1.16 | 3.4E-07 | 347 | 0.24 | 8.2E-06 | -0.06 | 0.49 | 1.00 | 298 |
| RLNFRLVG | 141 | 1.17 | 1.2E-07 | 256 | 0.26 | 1.7E-06 | 0.00 | 0.97 | 1.00 | 363 |
| YQLLLKG | 142 | 1.14 | 3.6E-07 | 352 | 0.24 | 7.9E-06 | 0.02 | 0.84 | 1.00 | 344 |
| AVLKARFNKHF | 143 | 1.13 | 1.8E-07 | 284 | 0.26 | 1.1E-06 | 0.03 | 0.68 | 1.00 | 322 |
| PSAVKLFRLG | 144 | 1.16 | 2.8E-07 | 327 | 0.25 | 3.2E-06 | -0.02 | 0.77 | 1.00 | 334 |
| YRVLKLSADPVS | 145 | 1.14 | 2.4E-07 | 314 | 0.24 | 7.9E-06 | 0.02 | 0.81 | 1.00 | 341 |
| LPRPPKLFG | 146 | 1.19 | 9.4E-08 | 237 | 0.28 | 1.4E-07 | 0.05 | 0.52 | 1.00 | 305 |
| PPKYVSARFS | 147 | 1.17 | 1.9E-07 | 293 | 0.25 | 2.8E-06 | 0.00 | 0.99 | 1.00 | 369 |
| PARFRVALLSD | 148 | 1.18 | 2.8E-09 | 152 | 0.31 | 8.6E-09 | 0.04 | 0.64 | 1.00 | 317 |
| ALRVVLKD | 149 | 1.18 | 2.8E-08 | 201 | 0.30 | 3.4E-08 | 0.02 | 0.80 | 1.00 | 340 |
| ALRAVVLS | 150 | 1.23 | 1.3E-11 | 108 | 0.34 | 1.8E-10 | 0.00 | 0.98 | 1.00 | 366 |
| VRFEVVLG | 151 | 1.22 | 1.8E-08 | 185 | 0.27 | 3.3E-07 | 0.00 | 0.96 | 1.00 | 360 |
| VPWKALRLF | 152 | 1.16 | 3.5E-07 | 348 | 0.24 | 6.9E-06 | 0.00 | 0.99 | 1.00 | 367 |
| AVRLKFREG | 153 | 1.14 | 1.1E-07 | 246 | 0.30 | 3.7E-08 | 0.12 | 0.17 | 1.00 | 236 |
| LRVVRFG | 154 | 1.20 | 1.9E-08 | 186 | 0.29 | 5.6E-08 | 0.03 | 0.76 | 1.00 | 332 |
| AVLWDYFDG | 155 | 1.15 | 3.9E-07 | 356 | 0.29 | 1.1E-07 | 0.07 | 0.42 | 1.00 | 284 |

FIG. 48G

| | | | | | | | | | |
|---|---|---|---|---|---|---|---|---|---|
| VWSKFEYED | 156 | 1.14 | 1.0E-08 | 170 | 0.30 | 2.2E-08 | 0.07 | 0.39 | 1.00 | 280 |
| FVSYSDYED | 157 | 1.15 | 6.1E-08 | 219 | 0.31 | 6.1E-09 | 0.15 | 0.06 | 1.00 | 215 |
| LYENRFEYSD | 158 | 1.17 | 2.9E-07 | 331 | 0.27 | 6.1E-07 | 0.08 | 0.32 | 1.00 | 274 |
| FYDWDED | 159 | 1.16 | 4.5E-10 | 137 | 0.34 | 1.0E-10 | 0.08 | 0.35 | 1.00 | 277 |
| SFDYFDAFD | 160 | 1.16 | 8.6E-08 | 232 | 0.27 | 3.2E-07 | 0.06 | 0.49 | 1.00 | 299 |
| YKSLDFYD | 161 | 1.22 | 1.2E-07 | 255 | 0.29 | 1.0E-07 | 0.07 | 0.43 | 1.00 | 286 |
| GYSSAWVSE | 162 | 1.23 | 1.1E-08 | 172 | 0.30 | 2.4E-08 | 0.00 | 0.96 | 1.00 | 359 |
| YWLDYDSALS | 163 | 1.16 | 2.0E-07 | 299 | 0.28 | 2.4E-07 | 0.12 | 0.14 | 1.00 | 229 |
| AAYLDYSD | 164 | 1.12 | 2.3E-07 | 307 | 0.30 | 2.8E-08 | 0.12 | 0.14 | 1.00 | 231 |
| YVVEFDSG | 165 | 1.17 | 2.6E-07 | 320 | 0.32 | 2.3E-09 | 0.16 | 0.06 | 1.00 | 214 |
| YKSYQWLEYED | 166 | 1.13 | 8.9E-08 | 234 | 0.30 | 3.0E-08 | 0.11 | 0.20 | 1.00 | 245 |
| NVFYDYADVED | 167 | 1.15 | 3.1E-08 | 207 | 0.29 | 6.0E-08 | 0.06 | 0.50 | 1.00 | 302 |
| AGWYSDWFSD | 168 | 1.12 | 3.1E-07 | 337 | 0.28 | 1.8E-07 | 0.09 | 0.27 | 1.00 | 255 |
| WLDSAWFPPSE | 169 | 1.15 | 5.3E-08 | 216 | 0.31 | 4.7E-09 | 0.03 | 0.71 | 1.00 | 326 |
| YYESYAED | 170 | 1.15 | 2.4E-10 | 127 | 0.35 | 6.4E-11 | 0.10 | 0.23 | 1.00 | 252 |
| FQEPYPYQED | 171 | 1.14 | 1.8E-07 | 286 | 0.28 | 2.4E-07 | 0.02 | 0.79 | 1.00 | 339 |
| YDWVNAKFD | 172 | 1.20 | 3.2E-07 | 343 | 0.26 | 1.3E-06 | -0.04 | 0.66 | 1.00 | 320 |
| QKRWLDAPFD | 173 | 1.20 | 2.1E-07 | 303 | 0.31 | 4.2E-09 | 0.16 | 0.05 | 1.00 | 210 |
| DWGSWFG | 174 | 1.16 | 3.0E-07 | 335 | 0.27 | 6.1E-07 | 0.00 | 0.97 | 1.00 | 362 |
| FRSGLDFDG | 175 | 1.19 | 2.4E-07 | 312 | 0.29 | 4.2E-08 | 0.17 | 0.04 | 1.00 | 209 |
| YVDKDFRFG | 176 | 1.14 | 1.4E-07 | 272 | 0.30 | 2.4E-08 | 0.13 | 0.12 | 1.00 | 226 |
| YSGVDWFPNSD | 177 | 1.13 | 2.6E-07 | 321 | 0.28 | 1.9E-07 | 0.11 | 0.17 | 1.00 | 237 |
| RYQFEDNYFG | 178 | 1.13 | 9.4E-08 | 238 | 0.28 | 1.9E-07 | 0.06 | 0.46 | 1.00 | 294 |
| VRQVDGHEG | 179 | 5.27 | 4.0E-28 | 8 | 0.66 | 7.4E-43 | 0.42 | 1.1E-06 | 0.0006 | 19 |
| FRQVEGPVD | 180 | 5.59 | 9.6E-31 | 5 | 0.64 | 2.6E-40 | 0.32 | 1.7E-04 | 0.06 | 110 |
| LRALEPHSE | 181 | 4.79 | 1.7E-28 | 7 | 0.68 | 1.2E-47 | 0.39 | 1.1E-05 | 0.0046 | 34 |
| FRQLEKHD | 182 | 3.41 | 3.0E-22 | 19 | 0.57 | 1.6E-30 | 0.37 | 1.6E-05 | 0.01 | 53 |

FIG. 48H

| | | | | | | | | |
|---|---|---|---|---|---|---|---|---|
| LREVDQVDG | 183 | 7.28 | 1.6E-35 | 1 | 0.66 | 9.2E-43 | 0.38 | 1.2E-05 | 0.0063 | 41 |
| FRLVDEG | 184 | 2.91 | 3.1E-31 | 4 | 0.64 | 2.8E-39 | 0.32 | 1.7E-04 | 0.06 | 111 |
| LREVPWKE | 185 | 4.81 | 3.2E-32 | 2 | 0.65 | 7.8E-41 | 0.38 | 1.2E-05 | 0.0054 | 37 |
| VRLVDPED | 186 | 5.28 | 1.6E-30 | 6 | 0.63 | 5.5E-39 | 0.35 | 1.2E-04 | 0.03 | 70 |
| LRYLEPADG | 187 | 3.21 | 4.7E-25 | 12 | 0.62 | 1.3E-36 | 0.42 | 1.1E-06 | 0.0008 | 21 |
| LRYVDPAQKRD | 188 | 3.17 | 4.4E-24 | 13 | 0.57 | 2.1E-30 | 0.33 | 1.6E-04 | 0.05 | 107 |
| VRRVDPYFD | 189 | 2.39 | 8.6E-24 | 15 | 0.64 | 8.6E-40 | 0.41 | 1.2E-06 | 0.0011 | 24 |
| LREFDYFSE | 190 | 2.39 | 8.1E-24 | 14 | 0.60 | 6.1E-34 | 0.34 | 1.3E-04 | 0.04 | 88 |
| SRQVDPLSE | 191 | 3.95 | 1.0E-19 | 26 | 0.49 | 1.5E-21 | 0.33 | 1.5E-04 | 0.05 | 104 |
| FREADLED | 192 | 3.89 | 4.7E-26 | 9 | 0.58 | 5.6E-31 | 0.27 | 0.0010 | 0.36 | 165 |
| LRKVEAHSG | 193 | 3.14 | 1.1E-21 | 21 | 0.54 | 9.8E-27 | 0.42 | 1.1E-06 | 0.0007 | 20 |
| VRRLDKED | 194 | 4.18 | 1.3E-25 | 10 | 0.64 | 1.8E-40 | 0.46 | 1.7E-08 | 1.6E-04 | 13 |
| FRKLEMDG | 195 | 4.21 | 1.5E-25 | 11 | 0.60 | 4.8E-34 | 0.44 | 1.3E-07 | 0.0002 | 16 |
| VRKVDWEG | 196 | 5.15 | 2.6E-31 | 3 | 0.68 | 8.5E-47 | 0.42 | 1.1E-06 | 0.0008 | 22 |
| MRALDFDAHG | 197 | 2.71 | 4.1E-18 | 38 | 0.53 | 6.5E-26 | 0.36 | 1.8E-05 | 0.02 | 58 |
| LRLWDPSDG | 198 | 2.97 | 8.9E-19 | 34 | 0.51 | 3.6E-23 | 0.34 | 1.2E-04 | 0.03 | 75 |
| GRQLDPEG | 199 | 3.80 | 7.3E-22 | 20 | 0.53 | 4.5E-26 | 0.35 | 1.2E-04 | 0.03 | 69 |
| QRQFDAQLAKLE | 200 | 3.38 | 2.6E-21 | 22 | 0.55 | 6.4E-28 | 0.34 | 1.3E-04 | 0.03 | 82 |
| RRSFDGDG | 201 | 2.03 | 6.3E-12 | 105 | 0.40 | 4.2E-14 | 0.35 | 1.1E-04 | 0.02 | 67 |
| GRNFDKREG | 202 | 1.70 | 4.2E-10 | 135 | 0.32 | 2.2E-09 | 0.29 | 0.0004 | 0.20 | 141 |
| YRQADFSG | 203 | 1.97 | 2.7E-13 | 88 | 0.46 | 3.8E-19 | 0.29 | 0.0004 | 0.22 | 145 |
| YRLVDYQALED | 204 | 2.13 | 7.4E-15 | 72 | 0.45 | 5.9E-18 | 0.28 | 0.0006 | 0.28 | 154 |
| LRKFMHVED | 205 | 2.41 | 2.8E-16 | 56 | 0.52 | 2.4E-24 | 0.41 | 1.3E-06 | 0.0012 | 27 |
| FRLLDLSG | 206 | 1.78 | 1.7E-11 | 112 | 0.39 | 1.9E-13 | 0.33 | 1.5E-04 | 0.05 | 99 |
| LREFHVEG | 207 | 1.72 | 5.8E-13 | 92 | 0.45 | 3.9E-18 | 0.41 | 1.3E-06 | 0.0012 | 26 |
| YRKVDYALE | 208 | 1.76 | 1.8E-11 | 113 | 0.44 | 4.9E-17 | 0.34 | 1.3E-04 | 0.03 | 84 |
| MRRVDGWWEG | 209 | 2.23 | 1.8E-17 | 42 | 0.49 | 4.2E-22 | 0.33 | 1.6E-04 | 0.06 | 109 |

FIG. 48I

| | | | | | | | | | |
|---|---|---|---|---|---|---|---|---|---|
| NREFDDYHG | 210 | 2.15 | 8.5E-15 | 51 | 0.48 | 2.8E-20 | 0.31 | 0.0002 | 0.11 | 119 |
| QRLFESDHREG | 211 | 2.09 | 8.9E-16 | 63 | 0.50 | 4.8E-23 | 0.34 | 1.3E-04 | 0.04 | 90 |
| FPQREGYKVD | 212 | 1.85 | 1.6E-14 | 75 | 0.48 | 8.5E-21 | 0.33 | 1.5E-04 | 0.05 | 102 |
| FVKRDED | 213 | 2.58 | 8.5E-15 | 52 | 0.43 | 1.6E-16 | 0.28 | 0.0006 | 0.28 | 153 |
| FRAHDNVED | 214 | 2.29 | 1.6E-14 | 76 | 0.42 | 7.5E-16 | 0.25 | 0.0025 | 0.62 | 179 |
| AREFDFYG | 215 | 2.18 | 7.1E-18 | 40 | 0.53 | 1.6E-25 | 0.38 | 1.2E-05 | 0.0055 | 39 |
| QRELDFYALS | 216 | 2.20 | 5.7E-19 | 32 | 0.51 | 6.1E-24 | 0.34 | 1.2E-04 | 0.03 | 78 |
| LREYENHDG | 217 | 2.29 | 3.8E-16 | 58 | 0.51 | 2.1E-23 | 0.41 | 1.4E-06 | 0.0016 | 29 |
| HREVDGAHFD | 218 | 2.43 | 3.2E-16 | 57 | 0.45 | 1.9E-18 | 0.36 | 1.6E-05 | 0.01 | 55 |
| ARDLDHSWHSD | 219 | 2.14 | 4.1E-15 | 59 | 0.49 | 1.4E-21 | 0.38 | 1.3E-05 | 0.0071 | 45 |
| ERYVDGYHD | 220 | 1.94 | 1.8E-15 | 69 | 0.47 | 7.1E-20 | 0.35 | 1.2E-04 | 0.02 | 68 |
| ERLLDYG | 221 | 2.32 | 1.6E-18 | 35 | 0.52 | 6.2E-25 | 0.39 | 1.9E-06 | 0.0035 | 32 |
| ERQFDVFG | 222 | 2.09 | 2.6E-14 | 80 | 0.40 | 2.0E-14 | 0.27 | 0.0010 | 0.36 | 162 |
| GRSADYQFD | 223 | 2.19 | 9.7E-16 | 64 | 0.48 | 9.8E-21 | 0.27 | 0.0010 | 0.36 | 164 |
| NRDFDGPVVD | 224 | 2.31 | 1.7E-15 | 68 | 0.45 | 8.4E-18 | 0.33 | 1.4E-04 | 0.05 | 93 |
| GRDYDAWVS | 225 | 1.90 | 5.6E-14 | 84 | 0.42 | 4.1E-16 | 0.28 | 0.0006 | 0.28 | 151 |
| GRSLDDG | 226 | 2.35 | 4.3E-14 | 82 | 0.44 | 3.3E-17 | 0.38 | 1.2E-05 | 0.0067 | 43 |
| HRQLDGWNFD | 227 | 1.99 | 2.3E-16 | 55 | 0.50 | 9.0E-23 | 0.38 | 1.2E-05 | 0.0055 | 38 |
| GRRLEDLDG | 228 | 2.43 | 1.0E-15 | 65 | 0.44 | 1.2E-17 | 0.33 | 1.6E-04 | 0.06 | 108 |
| GRHLDYEYKSE | 229 | 1.86 | 1.2E-14 | 74 | 0.52 | 1.2E-24 | 0.36 | 1.7E-05 | 0.01 | 56 |
| SRFLDHED | 230 | 1.78 | 2.0E-11 | 114 | 0.39 | 2.4E-13 | 0.33 | 1.6E-04 | 0.05 | 106 |
| LRPLEVDG | 231 | 3.52 | 1.6E-22 | 18 | 0.57 | 6.1E-30 | 0.39 | 1.1E-05 | 0.0046 | 35 |
| VRPVERDG | 232 | 2.35 | 1.8E-15 | 70 | 0.47 | 3.0E-20 | 0.32 | 1.9E-04 | 0.08 | 114 |
| RRYVDSDG | 233 | 2.90 | 1.9E-18 | 36 | 0.51 | 1.4E-23 | 0.39 | 1.2E-05 | 0.0054 | 36 |
| GRAVDKVLD | 234 | 2.74 | 1.4E-15 | 52 | 0.47 | 3.4E-20 | 0.33 | 1.5E-04 | 0.05 | 94 |
| SRLVEEG | 235 | 2.70 | 2.8E-15 | 71 | 0.45 | 3.7E-18 | 0.35 | 1.1E-04 | 0.02 | 66 |
| SRSVDPAHVD | 236 | 2.99 | 6.0E-17 | 48 | 0.46 | 5.8E-19 | 0.34 | 1.3E-04 | 0.03 | 80 |

FIG. 48J

| | | | | | | | | | |
|---|---|---|---|---|---|---|---|---|---|
| HRSVDAEG | 237 | 2.23 | 4.9E-13 | 91 | 0.38 | 6.7E-13 | 0.33 | 1.5E-04 | 0.05 | 97 |
| HRHVDWDPNQLE | 238 | 1.71 | 6.0E-10 | 141 | 0.35 | 2.5E-11 | 0.31 | 0.0002 | 0.11 | 121 |
| LRAHDED | 239 | 2.46 | 5.8E-16 | 60 | 0.45 | 4.2E-18 | 0.31 | 0.0002 | 0.12 | 126 |
| QRFAVDADMSD | 240 | 2.15 | 7.6E-13 | 94 | 0.35 | 3.0E-11 | 0.22 | 0.0090 | 1.00 | 194 |
| QRNYDFG | 241 | 1.78 | 8.6E-11 | 122 | 0.42 | 4.9E-16 | 0.28 | 0.0007 | 0.30 | 156 |
| QRHVDGFNWAG | 242 | 1.66 | 2.6E-08 | 198 | 0.27 | 7.4E-07 | 0.26 | 0.0013 | 0.42 | 171 |
| QRHVEGVYQLWG | 243 | 1.42 | 1.2E-07 | 258 | 0.27 | 3.7E-07 | 0.22 | 0.0083 | 1.00 | 193 |
| LRKFDVFG | 244 | 1.98 | 2.0E-17 | 43 | 0.50 | 1.1E-22 | 0.41 | 1.2E-06 | 0.0011 | 25 |
| ERLFDFENWG | 245 | 1.84 | 1.4E-13 | 86 | 0.41 | 2.3E-15 | 0.31 | 0.0002 | 0.11 | 120 |
| GRLFDWQGED | 246 | 1.91 | 3.0E-17 | 45 | 0.52 | 2.9E-24 | 0.30 | 0.0002 | 0.13 | 127 |
| KRLFDYARFPED | 247 | 1.59 | 4.2E-13 | 89 | 0.44 | 2.0E-17 | 0.36 | 1.1E-04 | 0.02 | 59 |
| QRLYDWQPRD | 248 | 1.80 | 1.4E-15 | 66 | 0.49 | 4.6E-22 | 0.34 | 1.3E-04 | 0.04 | 89 |
| LPRREDYNQFE | 249 | 2.38 | 1.5E-19 | 29 | 0.50 | 3.6E-22 | 0.29 | 0.0005 | 0.23 | 148 |
| FPRRDFED | 250 | 2.25 | 1.0E-22 | 17 | 0.58 | 1.2E-31 | 0.36 | 1.1E-04 | 0.02 | 60 |
| FPSRDGALE | 251 | 2.58 | 3.3E-18 | 37 | 0.45 | 1.7E-18 | 0.29 | 0.0004 | 0.22 | 146 |
| LPNRDSLG | 252 | 2.36 | 2.3E-16 | 54 | 0.44 | 4.4E-17 | 0.27 | 0.0010 | 0.36 | 166 |
| LPLRENQG | 253 | 1.85 | 1.1E-12 | 98 | 0.38 | 1.2E-12 | 0.23 | 0.0044 | 0.81 | 186 |
| LRKSDLSD | 254 | 2.21 | 4.3E-13 | 90 | 0.41 | 2.6E-15 | 0.33 | 1.4E-04 | 0.04 | 92 |
| LRDKDRWSD | 255 | 2.30 | 4.7E-14 | 83 | 0.44 | 1.1E-17 | 0.29 | 0.00003 | 0.18 | 137 |
| VRRLYED | 256 | 1.29 | 1.1E-05 | 1199 | 0.29 | 6.7E-08 | 0.33 | 1.5E-04 | 0.05 | 101 |
| LRRVLSENE | 257 | 1.28 | 1.6E-05 | 1379 | 0.34 | 2.5E-10 | 0.37 | 1.4E-05 | 0.01 | 48 |
| LRKLSLED | 258 | 1.87 | 3.7E-11 | 116 | 0.43 | 3.8E-16 | 0.41 | 1.3E-06 | 0.0012 | 28 |
| LRKVPVEG | 259 | 1.30 | 3.9E-06 | 779 | 0.28 | 1.1E-07 | 0.37 | 1.4E-05 | 0.01 | 50 |
| PGVGHKHFG | 260 | 1.47 | 2.0E-11 | 115 | 0.44 | 5.0E-17 | 0.46 | 1.6E-08 | 1.6E-04 | 12 |
| PGKFQRPRD | 261 | 1.34 | 2.8E-07 | 326 | 0.32 | 1.5E-09 | 0.44 | 1.4E-07 | 0.00003 | 17 |
| PAVGKQVLKRVS | 262 | 1.27 | 7.2E-08 | 223 | 0.33 | 8.7E-10 | 0.22 | 0.0069 | 0.97 | 191 |
| PGKWFKSG | 263 | 1.41 | 1.6E-11 | 110 | 0.45 | 6.9E-18 | 0.37 | 1.6E-05 | 0.01 | 52 |

FIG. 48K

| | | | | | | | | | | |
|---|---|---|---|---|---|---|---|---|---|---|
| PGRHAKYNKVS | 264 | 1.33 | 5.4E-10 | 140 | 0.40 | 2.9E-14 | 0.31 | 0.0002 | 0.12 | 125 |
| AQAVARDKDG | 265 | 1.53 | 1.4E-07 | 269 | 0.30 | 2.8E-08 | 0.30 | 0.0003 | 0.16 | 133 |
| PGHDWKGQVS | 266 | 1.44 | 3.0E-07 | 334 | 0.31 | 5.9E-09 | 0.40 | 1.5E-06 | 0.0021 | 31 |
| PGKERHLVD | 267 | 2.74 | 9.1E-23 | 16 | 0.60 | 1.5E-34 | 0.70 | 1.1E-21 | 1.2E-16 | 1 |
| PGSAQKEYNHL | 268 | 2.34 | 4.1E-18 | 39 | 0.55 | 9.6E-28 | 0.61 | 1.3E-15 | 1.9E-11 | 4 |
| PGSGAKEFSG | 269 | 2.00 | 1.6E-12 | 99 | 0.43 | 2.1E-16 | 0.52 | 1.3E-10 | 1.4E-06 | 10 |
| PGFEQKPAQG | 270 | 2.21 | 2.8E-19 | 31 | 0.56 | 1.0E-28 | 0.62 | 1.1E-15 | 1.6E-11 | 3 |
| PGWEPKYASG | 271 | 1.92 | 9.0E-20 | 25 | 0.55 | 1.7E-27 | 0.58 | 1.2E-13 | 1.5E-09 | 6 |
| PAKEAKEPHADG | 272 | 3.01 | 1.4E-19 | 28 | 0.57 | 7.6E-30 | 0.57 | 1.8E-13 | 1.1E-08 | 7 |
| PGRGAKQHD | 273 | 2.33 | 2.8E-19 | 30 | 0.58 | 8.0E-32 | 0.65 | 1.7E-18 | 1.5E-13 | 2 |
| PGVEQRRLG | 274 | 2.14 | 6.6E-19 | 33 | 0.57 | 6.8E-30 | 0.59 | 1.5E-14 | 1.1E-09 | 5 |
| PGKAVYAVSD | 275 | 1.83 | 8.1E-12 | 106 | 0.44 | 2.2E-17 | 0.47 | 1.3E-08 | 1.4E-04 | 11 |
| PGKSVLNREG | 276 | 1.37 | 3.0E-07 | 333 | 0.30 | 2.5E-08 | 0.40 | 1.4E-06 | 0.0018 | 30 |
| VGKAVKHD | 277 | 1.96 | 1.1E-12 | 97 | 0.48 | 9.7E-21 | 0.54 | 1.1E-11 | 1.2E-07 | 8 |
| PGRAQRHMDG | 278 | 1.61 | 1.1E-12 | 95 | 0.49 | 1.1E-21 | 0.54 | 1.2E-11 | 1.2E-07 | 9 |
| VGRQVDYKFD | 279 | 1.34 | 1.9E-08 | 188 | 0.36 | 2.0E-11 | 0.33 | 1.5E-04 | 0.05 | 103 |
| VLRRLEREG | 280 | 1.46 | 1.3E-07 | 262 | 0.32 | 2.8E-09 | 0.38 | 1.2E-05 | 0.0070 | 44 |
| LRSWDYNEG | 281 | 1.42 | 2.0E-07 | 300 | 0.29 | 6.6E-08 | 0.24 | 0.0036 | 0.73 | 182 |
| HWLRQVED | 282 | 1.29 | 8.0E-08 | 229 | 0.34 | 3.0E-10 | 0.29 | 0.0004 | 0.20 | 140 |
| LLRYVEDG | 283 | 1.49 | 1.3E-10 | 123 | 0.39 | 2.0E-13 | 0.27 | 0.0011 | 0.38 | 169 |
| YRKQDAWD | 284 | 1.27 | 2.5E-05 | 1658 | 0.28 | 2.8E-07 | 0.35 | 1.2E-04 | 0.03 | 71 |
| LRKWEDG | 285 | 1.42 | 2.4E-06 | 639 | 0.28 | 2.6E-07 | 0.35 | 1.1E-04 | 0.02 | 64 |
| YRGQFDKDYLG | 286 | 1.30 | 1.8E-07 | 288 | 0.36 | 1.1E-11 | 0.34 | 1.3E-04 | 0.04 | 91 |
| LRRYLEDG | 287 | 1.20 | 1.4E-06 | 527 | 0.29 | 7.3E-08 | 0.32 | 1.9E-04 | 0.08 | 115 |
| VRGVEAWFD | 288 | 1.27 | 1.7E-07 | 282 | 0.31 | 9.2E-09 | 0.17 | 0.04 | 1.00 | 208 |
| ARLLEFEWQKD | 289 | 1.31 | 4.9E-09 | 160 | 0.36 | 6.7E-12 | 0.30 | 0.0002 | 0.14 | 130 |
| YRGVELWFD | 290 | 1.40 | 1.8E-12 | 100 | 0.41 | 3.1E-15 | 0.26 | 0.0018 | 0.51 | 175 |

FIG. 48L

| | | | | | | | | | |
|---|---|---|---|---|---|---|---|---|---|
| LRDFHFD | 291 | 1.32 | 1.3E-09 | 148 | 0.37 | 2.9E-12 | 0.27 | 0.0008 | 0.33 | 157 |
| YRSADVFYD | 292 | 1.39 | 4.6E-10 | 138 | 0.35 | 3.0E-11 | 0.18 | 0.03 | 1.00 | 205 |
| LPRYDED | 293 | 1.57 | 2.6E-09 | 151 | 0.35 | 2.2E-11 | 0.36 | 1.8E-05 | 0.02 | 57 |
| LPYHDRLDQHLD | 294 | 1.27 | 2.7E-07 | 324 | 0.29 | 5.6E-08 | 0.21 | 0.01 | 1.00 | 197 |
| VRYFEQLEG | 295 | 1.38 | 1.2E-09 | 147 | 0.39 | 8.8E-14 | 0.33 | 1.6E-04 | 0.05 | 105 |
| VRVADGWRD | 296 | 1.23 | 3.6E-07 | 353 | 0.31 | 4.6E-09 | 0.19 | 0.02 | 1.00 | 203 |
| KQRWVEVDG | 297 | 1.44 | 2.1E-08 | 191 | 0.33 | 6.8E-10 | 0.34 | 1.3E-04 | 0.03 | 81 |
| LRFAEVG | 298 | 1.25 | 5.8E-06 | 894 | 0.29 | 1.1E-07 | 0.34 | 1.3E-04 | 0.04 | 87 |
| LPFRDPG | 299 | 1.27 | 6.0E-08 | 218 | 0.31 | 6.0E-09 | 0.29 | 0.0003 | 0.19 | 139 |
| NRQFDWLPWSG | 300 | 1.28 | 7.0E-08 | 221 | 0.32 | 2.5E-09 | 0.23 | 0.0055 | 0.88 | 189 |
| RAMFDYADHEG | 301 | 1.39 | 4.9E-09 | 159 | 0.36 | 1.8E-11 | 0.19 | 0.02 | 1.00 | 202 |
| RSSFDEDG | 302 | 1.46 | 1.2E-07 | 257 | 0.28 | 3.1E-07 | 0.18 | 0.03 | 1.00 | 204 |
| PKLYDGHEMVE | 303 | 1.49 | 2.9E-07 | 330 | 0.27 | 5.7E-07 | 0.26 | 0.0014 | 0.43 | 172 |
| PRQVDWKEYEG | 304 | 2.31 | 1.1E-12 | 96 | 0.40 | 4.8E-14 | 0.38 | 1.2E-05 | 0.0063 | 42 |
| PPRRDVSE | 305 | 1.71 | 4.9E-09 | 158 | 0.30 | 3.0E-08 | 0.30 | 0.0002 | 0.14 | 131 |
| ARDYDGNPFSG | 306 | 2.08 | 1.4E-15 | 67 | 0.46 | 1.2E-18 | 0.28 | 0.0005 | 0.28 | 152 |
| ERYYDG | 307 | 1.41 | 1.6E-08 | 181 | 0.35 | 2.9E-11 | 0.27 | 0.0011 | 0.38 | 168 |
| WRNYDPYVE | 308 | 1.27 | 3.7E-08 | 209 | 0.38 | 8.5E-13 | 0.34 | 1.2E-04 | 0.03 | 79 |
| WRQSDGVVPDG | 309 | 1.39 | 1.6E-08 | 179 | 0.33 | 1.1E-09 | 0.20 | 0.01 | 1.00 | 199 |
| ARPYDWENKVD | 310 | 1.51 | 5.4E-11 | 118 | 0.45 | 4.4E-18 | 0.42 | 1.2E-06 | 0.0009 | 23 |
| ARPADVDYFG | 311 | 1.56 | 5.9E-11 | 120 | 0.42 | 7.3E-16 | 0.37 | 1.6E-05 | 0.01 | 54 |
| QVWRQVDAD | 312 | 1.55 | 3.7E-10 | 129 | 0.36 | 1.7E-11 | 0.27 | 0.0008 | 0.33 | 158 |
| FREVANVED | 313 | 1.62 | 4.1E-08 | 211 | 0.31 | 9.5E-09 | 0.31 | 0.0002 | 0.11 | 122 |
| YRQVHEAWD | 314 | 1.59 | 1.5E-11 | 109 | 0.41 | 6.0E-15 | 0.26 | 0.0017 | 0.49 | 174 |
| NRPVDGYPFG | 315 | 1.57 | 2.6E-08 | 197 | 0.31 | 5.9E-09 | 0.25 | 0.0022 | 0.56 | 177 |
| YRSSDPVSNWSD | 316 | 1.44 | 2.5E-07 | 317 | 0.28 | 2.2E-07 | 0.09 | 0.27 | 1.00 | 256 |
| AKARDYGVED | 317 | 1.29 | 2.4E-06 | 636 | 0.32 | 2.9E-09 | 0.36 | 1.1E-04 | 0.02 | 61 |

FIG. 48M

| | | | | | | | | | |
|---|---|---|---|---|---|---|---|---|---|
| LRWGHFED | 318 | 1.32 | 2.5E-07 | 319 | 0.30 | 1.6E-08 | 0.23 | 0.0053 | 0.87 | 188 |
| HPQRDNPYHVE | 319 | 1.56 | 1.9E-08 | 187 | 0.31 | 7.7E-09 | 0.26 | 0.0014 | 0.44 | 173 |
| YPRRDRED | 320 | 1.37 | 1.0E-07 | 243 | 0.31 | 6.5E-09 | 0.22 | 0.0073 | 0.99 | 192 |
| QYRQLDHDG | 321 | 1.76 | 9.4E-12 | 107 | 0.39 | 8.0E-14 | 0.32 | 1.8E-04 | 0.07 | 113 |
| AFRELEASG | 322 | 1.49 | 6.5E-10 | 142 | 0.42 | 1.9E-15 | 0.25 | 0.0025 | 0.61 | 178 |
| SKYHDLFD | 323 | 1.35 | 2.3E-07 | 309 | 0.28 | 1.2E-07 | 0.23 | 0.0050 | 0.86 | 187 |
| FRNHEVFD | 324 | 1.54 | 3.9E-10 | 131 | 0.34 | 9.8E-11 | 0.30 | 0.0003 | 0.17 | 136 |
| LKYHDAFSD | 325 | 1.34 | 3.2E-07 | 340 | 0.31 | 6.1E-09 | 0.13 | 0.11 | 1.00 | 225 |
| NRNYDKFEG | 326 | 1.60 | 4.8E-09 | 157 | 0.36 | 1.9E-11 | 0.29 | 0.0003 | 0.18 | 138 |
| KRWYDAMD | 327 | 1.46 | 6.6E-08 | 220 | 0.35 | 2.3E-11 | 0.29 | 0.0004 | 0.21 | 144 |
| QRHFDPDAVEKRV | 328 | 1.99 | 3.7E-12 | 104 | 0.41 | 4.8E-15 | 0.34 | 1.3E-04 | 0.03 | 83 |
| FQRAVDWHE | 329 | 1.47 | 4.3E-09 | 155 | 0.35 | 4.8E-11 | 0.30 | 0.0003 | 0.17 | 134 |
| YRYVEDWPSD | 330 | 1.80 | 1.9E-14 | 78 | 0.50 | 1.0E-22 | 0.35 | 1.1E-04 | 0.02 | 65 |
| LRNSDPQVED | 331 | 2.41 | 6.6E-14 | 85 | 0.43 | 2.5E-16 | 0.30 | 0.0002 | 0.13 | 129 |
| FRQAED | 332 | 2.03 | 3.4E-12 | 102 | 0.39 | 1.1E-13 | 0.28 | 0.0007 | 0.29 | 155 |
| YREYDGQPAED | 333 | 2.51 | 6.9E-20 | 24 | 0.53 | 2.9E-25 | 0.34 | 1.3E-04 | 0.04 | 86 |
| YRRVEDAEAKD | 334 | 2.87 | 9.2E-17 | 50 | 0.55 | 4.9E-19 | 0.34 | 1.3E-04 | 0.04 | 86 |
| LAERDYADG | 335 | 1.78 | 1.2E-17 | 41 | 0.48 | 7.2E-21 | 0.30 | 0.0002 | 0.15 | 132 |
| FPERDKRLG | 336 | 1.60 | 3.9E-11 | 117 | 0.39 | 2.0E-13 | 0.29 | 0.0004 | 0.20 | 143 |
| FRLEDGAGLED | 337 | 1.58 | 1.1E-09 | 146 | 0.33 | 5.4E-10 | 0.27 | 0.0010 | 0.36 | 163 |
| LRFFDPAEG | 338 | 2.17 | 7.8E-09 | 166 | 0.34 | 3.1E-10 | 0.27 | 0.0012 | 0.40 | 170 |
| FRPFDNDG | 339 | 1.62 | 2.0E-20 | 23 | 0.53 | 2.9E-25 | 0.35 | 1.1E-04 | 0.02 | 63 |
| LRYFDYLD | 340 | 1.72 | 9.2E-17 | 50 | 0.46 | 4.9E-19 | 0.24 | 0.0040 | 0.77 | 184 |
| FRYFDPLSD | 341 | 1.51 | 1.7E-14 | 77 | 0.46 | 1.3E-18 | 0.34 | 1.2E-04 | 0.03 | 74 |
| PRFFDDDG | 342 | 1.75 | 2.5E-14 | 79 | 0.45 | 2.1E-18 | 0.34 | 1.2E-04 | 0.03 | 76 |
| YRQLELDWSG | 343 | 1.94 | 5.9E-17 | 47 | 0.51 | 1.0E-23 | 0.37 | 1.4E-05 | 0.0098 | 46 |
| ERWVDPKRFE | 344 | 1.68 | 1.0E-19 | 27 | 0.52 | 1.1E-24 | 0.35 | 1.1E-04 | 0.02 | 62 |
| | | | 3.7E-12 | 103 | 0.39 | 6.0E-14 | 0.24 | 0.0031 | 0.68 | 181 |

FIG. 48N

| | | | | | | | | |
|---|---|---|---|---|---|---|---|---|
| LARQIDWWVD | 345 | 1.94 | 5.0E-17 | 46 | 0.52 | 2.9E-24 | 0.33 | 1.5E-04 | 0.05 | 98 |
| LRVAEFEG | 346 | 2.27 | 6.2E-17 | 49 | 0.49 | 3.4E-21 | 0.28 | 0.0006 | 0.27 | 150 |
| SPLRDGPFE | 347 | 2.26 | 8.1E-15 | 73 | 0.42 | 2.2E-15 | 0.29 | 0.0004 | 0.22 | 147 |
| QRVVEYQWFD | 348 | 1.93 | 3.6E-14 | 81 | 0.41 | 3.7E-15 | 0.20 | 0.02 | 1.00 | 200 |
| LRDYELFD | 349 | 1.54 | 4.1E-10 | 132 | 0.36 | 1.7E-11 | 0.25 | 0.0020 | 0.54 | 176 |
| HRELEVFSG | 350 | 1.36 | 1.4E-07 | 267 | 0.29 | 6.1E-08 | 0.21 | 0.01 | 1.00 | 195 |
| LREWEGAQFE | 351 | 1.49 | 1.0E-08 | 169 | 0.32 | 1.7E-09 | 0.23 | 0.0056 | 0.89 | 190 |
| LRWFQED | 352 | 1.39 | 2.0E-07 | 298 | 0.32 | 3.6E-09 | 0.32 | 0.0001 | 0.09 | 116 |
| LRWQDPSD | 353 | 1.52 | 3.0E-07 | 336 | 0.27 | 3.4E-07 | 0.27 | 0.0009 | 0.33 | 160 |
| HRGVDGRVD | 354 | 1.38 | 2.6E-07 | 322 | 0.32 | 2.6E-09 | 0.34 | 1.3E-04 | 0.03 | 85 |
| SRSFEHDG | 355 | 1.44 | 4.2E-07 | 364 | 0.29 | 7.0E-08 | 0.37 | 1.5E-05 | 0.01 | 51 |
| VRVFDDDG | 356 | 1.89 | 2.2E-13 | 87 | 0.46 | 2.4E-19 | 0.45 | 1.9E-08 | 1.8E-04 | 15 |
| RREFDGVLS | 357 | 1.80 | 1.7E-11 | 111 | 0.45 | 5.8E-18 | 0.39 | 1.1E-05 | 0.0046 | 33 |
| RRSVDYWWSE | 358 | 1.95 | 7.2E-11 | 121 | 0.34 | 1.1E-10 | 0.30 | 0.00002 | 0.13 | 128 |
| HRWODG | 359 | 1.56 | 4.1E-07 | 363 | 0.27 | 3.4E-07 | 0.33 | 1.5E-04 | 0.05 | 100 |
| VVREVDG | 360 | 1.50 | 3.5E-07 | 349 | 0.28 | 2.7E-07 | 0.29 | 0.0004 | 0.20 | 142 |
| FQQREQISE | 361 | 1.74 | 4.3E-09 | 154 | 0.28 | 1.7E-07 | 0.15 | 0.08 | 1.00 | 218 |
| VRQYEDG | 362 | 1.82 | 1.7E-10 | 126 | 0.41 | 9.3E-15 | 0.38 | 1.2E-05 | 0.0063 | 40 |
| GPSREPEG | 363 | 1.51 | 1.9E-07 | 292 | 0.26 | 2.2E-06 | 0.24 | 0.0040 | 0.77 | 185 |
| VRLADSED | 364 | 2.14 | 2.4E-12 | 101 | 0.40 | 3.1E-14 | 0.31 | 0.0002 | 0.12 | 123 |
| HRSVEPSE | 365 | 1.58 | 1.9E-07 | 291 | 0.23 | 2.0E-05 | 0.24 | 0.0038 | 0.75 | 183 |
| LRAAEDG | 366 | 1.88 | 1.5E-10 | 125 | 0.41 | 6.4E-15 | 0.37 | 1.4E-05 | 0.01 | 47 |
| LRQVQISE | 367 | 1.47 | 1.6E-06 | 556 | 0.29 | 6.2E-08 | 0.33 | 1.5E-04 | 0.05 | 96 |
| LRQKEFDG | 368 | 1.66 | 5.4E-09 | 161 | 0.36 | 1.8E-11 | 0.27 | 0.0008 | 0.33 | 159 |
| GRFLDPAKD | 369 | 1.43 | 1.7E-07 | 281 | 0.28 | 1.5E-07 | 0.35 | 1.2E-04 | 0.03 | 72 |
| YRKLHEPD | 370 | 1.42 | 4.9E-07 | 387 | 0.31 | 5.3E-09 | 0.34 | 1.2E-04 | 0.03 | 77 |

FIG. 49A

Physicians Global Assessment _____

| 0 | 1 | 2 | 3 |
|---|---|---|---|
| None | Mild | Med | Severe |

SLEDAI SCORE

Check box: If descriptor is present at the time of visit or in the proceeding 10 days

| Wt | Present | Descriptor | Definition |
|---|---|---|---|
| 8 | ☐ | Seizure | Recent onset. Exclude metabolic, infectious or drug cause |
| 8 | ☐ | Psychosis | Altered ability to function in normal activity due to severe disturbance in the perception of reality. Include hallucinations, incoherence, marked loose associations, impoverished thought content, marked illogical thinking, bizarre, disorganized, or catatonic behavior. Excluded uremia and drug causes. |
| 8 | ☐ | Organic Brain Syndrome | Altered mental function with impaired orientation, memory or other intelligent function, with rapid onset fluctuating clinical features. Include clouding of consciousness with reduced capacity to focus, and inability to sustain attention to environment, plus at least two of the following: perceptual disturbance, incoherent speech, insomnia or daytime drowsiness, or increased or decreased psychomotor activity. Exclude metabolic, infectious or drug causes. |
| 8 | ☐ | Visual Disturbance | Retinal changes of SLE. Include cytoid bodies, retinal hemorrhages, serious exodate or hemorrhages in the choroids, or optic neuritis. Exclude hypertension, infection, or drug causes. |
| 8 | ☐ | Cranial Nerve Disorder | New onset of sensory or motor neuropathy involving cranial nerves. |
| 8 | ☐ | Lupus Headache | Severe persistent headache: may be migrainous, but must be non-responsive to narcotic analgesia. |
| 8 | ☐ | CVA | New onset of cerebrovascular accident(s). Exclude arteriosclerosis |
| 8 | ☐ | Vasculitis | Ulceration, gangrene, tender finger nodules, periungual, infarction, splinter hemorrhages, or biopsy or angiogram proof of vasculitis |
| 4 | ☐ | Arthritis | More than 2 joints with pain and signs of inflammation (i.e. tenderness, swelling, or effusion). |
| 4 | ☐ | Myositis | Proximal muscle aching/weakness, associated with elevated creatine phosphokinase/adolase or electromyogram changes or a biopsy showing myositis. |
| 4 | ☐ | Urinary Casts | Heme-granular or red blood cell casts |
| 4 | ☐ | Hematuria | >5 red blood cells/high power field. Exclude stone, infection or other cause. |
| 4 | ☐ | Proteinuria | >0.5 gm/24 hours. New onset or recent increase of more than 0.5 gm/24 hours. |
| 4 | ☐ | Pyuria | >5 white blood cells/high power field. Exclude infection. |
| 2 | ☐ | New Rash | New onset or recurrence of inflammatory type rash. |
| 2 | ☐ | Alopecia | New onset or recurrence of abnormal, patchy or diffuse loss of hair. |
| 2 | ☐ | Mucosal Ulcers | New onset or recurrence of oral or nasal ulcerations |

FIG. 49B

| 2 | ☐ | Pleurisy | Pleuritic chest pain with pleural rub or effusion, or pleural thickening. |
| 2 | ☐ | Pericarditis | Pericardial pain with at least 1 of the following: rub, effusion, or electrocardiogram confirmation. |
| 2 | ☐ | Low Complement | Decrease in CH50, C3, or C4 below the lower limit of normal for testing laboratory. |
| 2 | ☐ | Increased DNA binding | >25% binding by Farr assay or above normal range for testing laboratory. |
| 1 | ☐ | Fever | >38°C. Exclude infectious cause |
| 1 | ☐ | Thrombocytopenia | <100,000 platelets/mm3 |
| 1 | ☐ | Leukopenia | <3,000 White blood cell/mm3. Exclude drug causes. |

_____ TOTAL SCORE (Sum of weights next to descriptors marked present)

| Mild or Moderate Flare ☐ | Severe Flare ☐ |
|---|---|
| ☐ Change in SLEDAI > 3 points | ☐ Change in SLEDAI > 12 |
| ☐ New/worse discoid, photosensitive, profundus, cutaneous vasculitis, bullous lupus Nasopharyngeal ulcers Pleuritis Pericarditis Arthritis Fever (SLE) | ☐ New/worse CNS-SLE Vasculitis Nephritis Myositis Plt < 60,000 Home anemia: Hb <7% or decrease in Hb > 3% Requiring: double prednisone Prednisone>0.5 mg/kg/day hospitalization |
| ☐ Increase in Prednisone, but not to >0.5 mg/kg/day | ☐ Prednisone >0.5 mg/kg/day |
| ☐ Added NSAID or Plaquenil | ☐ New Cytoxan, Azathioprine, Methotrexate, Hospitalization (SLE) |
| ☐ ≥1.0 Increase in PGA, but not to more than 2.5 | ☐ Increase in PGA to > 2.5 |

Peptides that Distinguish Active vs. Inactive SLE

Classifiers of Active vs. Inactive SLE

IMS Model

C3 antiDNA

UPCR

| SLEDAI | 0 | 1-3 | 4-5 | 6-7 | 8-9 | 10-11 | 12-15 | 15-27 |
|---|---|---|---|---|---|---|---|---|
| first | 49 | 23 | 14 | 20 | 19 | 15 | 25 | 18 |
| later | 53 | 13 | 17 | 20 | 32 | 13 | 14 | 11 |

FIG. 60A

| motif | n | n.lib | enrich | p | fdr | padj.holm | Pr_seqs.motif | PLR |
|---|---|---|---|---|---|---|---|---|
| K | 850 | 62082 | 2.52962046 | 1.41E-145 | 5.63E-145 | 5.63E-145 | 0.01369157 | 2.47787185 |
| R | 795 | 63785 | 2.30277077 | 6.62E-115 | 1.32E-114 | 1.99E-114 | 0.01246375 | 2.2528576 |
| H.K | 84 | 2524 | 6.10780767 | 1.55E-38 | 1.41E-36 | 1.41E-36 | 0.03328051 | 6.14508197 |
| R.K | 87 | 2758 | 5.81149826 | 2.52E-38 | 2.37E-36 | 2.37E-36 | 0.0315446 | 5.81411456 |
| RR | 81 | 2464 | 6.03308901 | 7.65E-37 | 3.29E-35 | 6.89E-35 | 0.03287338 | 6.06735208 |
| RK | 79 | 2345 | 6.18272118 | 1.08E-36 | 3.29E-35 | 9.65E-35 | 0.0336887 | 6.22308032 |
| KR | 123 | 5930 | 3.80667531 | 2.43E-35 | 5.53E-34 | 2.14E-33 | 0.02074199 | 3.78086792 |
| HR | 77 | 2470 | 5.72122713 | 1.37E-33 | 2.49E-32 | 1.19E-31 | 0.03117409 | 5.74362725 |
| RH | 122 | 6470 | 3.46053653 | 2.54E-31 | 3.86E-30 | 2.19E-29 | 0.01885626 | 3.4305293 |
| H | 563 | 65939 | 1.57749568 | 3.36E-31 | 4.47E-31 | 6.71E-31 | 0.00853819 | 1.53719255 |
| K..K | 73 | 2501 | 5.47277836 | 1.55E-30 | 1.43E-28 | 1.43E-28 | 0.02918832 | 5.36676277 |
| RG | 98 | 4727 | 3.80483555 | 2.05E-28 | 2.66E-27 | 1.74E-26 | 0.02073197 | 3.77900194 |
| R.R | 73 | 2789 | 4.82211393 | 1.74E-27 | 8.20E-26 | 1.62E-25 | 0.02617426 | 4.79768041 |
| K.K | 71 | 2686 | 4.86984863 | 5.09E-27 | 1.47E-25 | 4.68E-25 | 0.02643336 | 4.84646272 |
| K.R | 73 | 2850 | 4.71890378 | 6.26E-27 | 1.47E-25 | 5.70E-25 | 0.02561404 | 4.69229384 |
| H.K | 71 | 2779 | 4.7068778 | 3.60E-26 | 6.77E-25 | 3.24E-24 | 0.02554876 | 4.68002216 |
| K..G | 99 | 5512 | 3.36763238 | 1.27E-24 | 4.50E-23 | 1.15E-22 | 0.01796081 | 3.26464068 |
| R..K | 64 | 2434 | 4.93012683 | 1.47E-24 | 4.50E-23 | 1.32E-22 | 0.02629417 | 4.82025316 |
| R...R | 57 | 1942 | 5.52507679 | 1.66E-24 | 1.41E-22 | 1.41E-22 | 0.02935118 | 5.39761273 |
| K.....G | 78 | 3846 | 3.78255433 | 3.62E-24 | 3.08E-22 | 3.08E-22 | 0.02028081 | 3.69506369 |
| H.R | 68 | 2810 | 4.45826331 | 7.61E-24 | 1.19E-22 | 6.77E-22 | 0.02419329 | 4.42669584 |
| KG | 85 | 4297 | 3.63035412 | 1.53E-23 | 1.74E-22 | 1.29E-21 | 0.01978124 | 3.60220798 |
| KH | 98 | 5687 | 3.1625583 | 1.10E-22 | 1.04E-21 | 9.15E-21 | 0.01723228 | 3.12989801 |
| KK | 63 | 2534 | 4.56277818 | 1.14E-22 | 1.04E-21 | 9.37E-21 | 0.02486188 | 4.5509915 |
| K....K | 47 | 1441 | 6.11926437 | 1.43E-22 | 1.32E-20 | 1.32E-20 | 0.03261624 | 6.01829268 |
| K.G | 107 | 6718 | 2.93431612 | 2.48E-22 | 3.33E-21 | 2.18E-20 | 0.01592736 | 2.88904856 |
| R.H | 65 | 2863 | 4.18268472 | 1.92E-21 | 2.26E-20 | 1.67E-19 | 0.02270346 | 4.14671194 |
| K...G | 88 | 5075 | 3.26406887 | 2.14E-21 | 9.08E-20 | 1.79E-19 | 0.0173399 | 3.14978945 |
| R..R | 60 | 2521 | 4.46248836 | 4.94E-21 | 1.14E-19 | 4.40E-19 | 0.02380008 | 4.35188948 |
| K..R | 60 | 2593 | 4.33857815 | 1.88E-20 | 3.45E-19 | 1.65E-18 | 0.02313922 | 4.23818792 |
| H..K | 57 | 2392 | 4.46799185 | 4.43E-20 | 6.79E-19 | 3.85E-18 | 0.02382943 | 4.35738758 |
| K....G | 75 | 4409 | 3.19143868 | 2.18E-18 | 1.00E-16 | 1.98E-16 | 0.01701066 | 3.08894785 |
| R....G | 75 | 4448 | 3.16345619 | 3.48E-18 | 1.07E-16 | 3.13E-16 | 0.01686151 | 3.0613995 |
| K...R | 49 | 1997 | 4.61881645 | 3.79E-18 | 1.07E-16 | 3.14E-16 | 0.02453681 | 4.48998973 |
| R.....G | 69 | 3967 | 3.24404405 | 4.38E-18 | 1.86E-16 | 3.68E-16 | 0.0173935 | 3.15969728 |
| R...K | 47 | 1862 | 4.75150149 | 6.19E-18 | 1.32E-16 | 5.08E-16 | 0.02524168 | 4.62231405 |
| R.G | 99 | 7019 | 2.59850211 | 2.49E-17 | 2.60E-16 | 2.14E-15 | 0.01410457 | 2.55368497 |

FIG. 60B

| motif | n | n.lib | enrich | p | fdr | padj.holm | Pr_seqs.motif | PLR |
|---|---|---|---|---|---|---|---|---|
| R..G | 81 | 5272 | 2.88076816 | 1.40E-16 | 1.84E-15 | 1.21E-14 | 0.01536419 | 2.78530148 |
| R..H | 54 | 2660 | 3.80636836 | 3.40E-16 | 3.91E-15 | 2.89E-14 | 0.02030075 | 3.69877206 |
| H..R | 46 | 2001 | 4.32736404 | 4.29E-16 | 7.39E-15 | 3.48E-14 | 0.02298851 | 4.2 |
| R....K | 39 | 1480 | 4.94388353 | 6.07E-16 | 1.40E-14 | 5.40E-14 | 0.02635135 | 4.83102012 |
| H.....G | 64 | 3982 | 3.01276568 | 2.13E-15 | 6.03E-14 | 1.77E-13 | 0.01615346 | 2.93073371 |
| K..K | 43 | 1839 | 4.40148691 | 2.16E-15 | 3.05E-14 | 1.72E-13 | 0.02338227 | 4.2736637 |
| H....R | 38 | 1485 | 4.80089804 | 3.55E-15 | 6.53E-14 | 3.12E-13 | 0.02558923 | 4.68762958 |
| H..R | 50 | 2513 | 3.73057871 | 8.88E-15 | 9.08E-14 | 7.46E-13 | 0.01989654 | 3.62362972 |
| HKR | 18 | 264 | 7.33710284 | 1.27E-14 | 9.47E-12 | 9.47E-12 | 0.06818182 | 13.0609756 |
| R...G | 74 | 5064 | 2.7507474 | 1.91E-14 | 2.32E-13 | 1.51E-12 | 0.01461295 | 2.64709419 |
| H......K | 28 | 878 | 5.94789602 | 4.62E-14 | 9.82E-13 | 3.79E-12 | 0.03189066 | 5.88 |
| G | 723 | 111145 | 1.20185066 | 6.07E-14 | 6.07E-14 | 6.07E-14 | 0.00650502 | 1.16874808 |
| R....K | 28 | 910 | 5.73873924 | 1.09E-13 | 1.86E-12 | 8.85E-12 | 0.03076923 | 5.66666667 |
| KRG | 22 | 504 | 4.89729864 | 1.44E-13 | 4.30E-11 | 1.08E-10 | 0.04365079 | 8.1473029 |
| RHK | 15 | 186 | 8.67829368 | 1.73E-13 | 4.30E-11 | 1.29E-10 | 0.08064516 | 15.6578947 |
| K...R | 36 | 1536 | 4.3972041 | 2.38E-13 | 3.66E-12 | 2.07E-11 | 0.0234375 | 4.284 |
| RRH | 17 | 278 | 6.58051909 | 3.98E-13 | 7.43E-11 | 2.96E-10 | 0.06115108 | 11.6264368 |
| K.H | 53 | 3076 | 3.17433429 | 4.86E-13 | 4.57E-12 | 4.13E-11 | 0.01723017 | 3.12950711 |
| K.....K | 27 | 909 | 5.53987204 | 6.72E-13 | 9.52E-12 | 5.38E-11 | 0.02970297 | 5.46428571 |
| KHK | 14 | 168 | 8.96757013 | 7.00E-13 | 1.03E-10 | 5.20E-10 | 0.08333333 | 16.2272727 |
| RHR | 14 | 170 | 8.86206931 | 8.23E-13 | 1.03E-10 | 6.11E-10 | 0.08235294 | 16.0192308 |
| K..H | 48 | 2694 | 3.34073739 | 1.47E-12 | 1.35E-11 | 1.22E-10 | 0.01781737 | 3.23809524 |
| R.....R | 28 | 1035 | 5.04565479 | 2.29E-12 | 2.78E-11 | 1.81E-10 | 0.02705314 | 4.9832572 |
| H...K | 38 | 1855 | 3.85613626 | 4.41E-12 | 4.69E-11 | 3.44E-10 | 0.02048518 | 3.7330765 |
| KA | 45 | 2500 | 3.30345141 | 7.87E-12 | 6.51E-11 | 6.38E-10 | 0.018 | 3.27189409 |
| R...R | 34 | 1610 | 3.96203566 | 1.76E-11 | 2.31E-10 | 1.51E-09 | 0.02111801 | 3.85088832 |
| RRG | 13 | 175 | 7.99394823 | 1.98E-11 | 2.11E-09 | 1.46E-08 | 0.07428571 | 14.3240741 |
| RY | 46 | 2725 | 3.09803802 | 3.76E-11 | 2.85E-10 | 3.01E-09 | 0.01688073 | 3.06494961 |
| K....S | 43 | 2579 | 3.12811314 | 7.22E-11 | 8.30E-10 | 6.13E-09 | 0.01667313 | 3.02661672 |
| K..W | 34 | 1684 | 3.80057685 | 8.37E-11 | 7.90E-10 | 6.44E-09 | 0.02019802 | 3.67818182 |
| H....K | 31 | 1447 | 4.01937477 | 9.51E-11 | 9.72E-10 | 7.98E-09 | 0.02142364 | 3.90783898 |
| K.S | 63 | 4736 | 2.4558959 | 1.52E-10 | 1.29E-09 | 1.27E-08 | 0.01333051 | 2.41164486 |
| R..Y | 36 | 1963 | 3.43859393 | 4.06E-10 | 3.39E-09 | 3.33E-08 | 0.01833928 | 3.33471718 |
| KS | 59 | 4483 | 2.41588122 | 1.08E-09 | 7.55E-09 | 8.52E-08 | 0.01316377 | 2.38107619 |
| HRG | 11 | 159 | 7.4447752 | 1.47E-09 | 1.37E-07 | 1.09E-06 | 0.06918239 | 13.2668919 |
| RW | 41 | 2540 | 2.96241268 | 1.50E-09 | 9.74E-09 | 1.17E-07 | 0.01614173 | 2.92857143 |
| R.S | 61 | 4818 | 2.33252421 | 2.01E-09 | 1.58E-08 | 1.67E-07 | 0.01266086 | 2.28894261 |

FIG. 60C

| motif | n | n.lib | enrich | p | fdr | padj.holm | Pr_seqs.motif | PLR |
|---|---|---|---|---|---|---|---|---|
| K..N | 37 | 2204 | 3.14766732 | 2.43E-09 | 1.86E-08 | 1.97E-07 | 0.01678766 | 3.04776188 |
| RKK | 9 | 94 | 10.3031657 | 2.59E-09 | 2.15E-07 | 1.91E-06 | 0.09574468 | 18.9 |
| K...F | 42 | 2764 | 2.86038137 | 2.76E-09 | 2.35E-08 | 2.10E-07 | 0.01519537 | 2.75422483 |
| YK | 53 | 3988 | 2.43902436 | 5.75E-09 | 3.49E-08 | 4.43E-07 | 0.01328987 | 2.40419314 |
| H...G | 61 | 5083 | 2.25903216 | 7.24E-09 | 5.60E-08 | 5.43E-07 | 0.01200079 | 2.1681681 |
| K.W | 40 | 2598 | 2.8365077 | 7.34E-09 | 5.31E-08 | 6.02E-07 | 0.01539646 | 2.79124316 |
| R...H | 35 | 2155 | 3.05726763 | 1.13E-08 | 8.04E-08 | 8.40E-07 | 0.0162413 | 2.94693396 |
| KGG | 9 | 114 | 8.49559276 | 1.43E-08 | 1.07E-06 | 1.06E-05 | 0.07894737 | 15.3 |
| R....H | 29 | 1618 | 3.36267442 | 1.87E-08 | 1.72E-07 | 1.55E-06 | 0.01792336 | 3.25770925 |
| AK | 54 | 4281 | 2.31496244 | 2.31E-08 | 1.32E-07 | 1.76E-06 | 0.01261388 | 2.28034067 |
| RYH | 10 | 164 | 6.56183668 | 2.72E-08 | 1.85E-06 | 2.00E-05 | 0.06097561 | 11.5909091 |
| G...K | 32 | 1931 | 3.11946698 | 3.01E-08 | 1.97E-07 | 2.19E-06 | 0.01657172 | 3.00789889 |
| K..S | 48 | 3660 | 2.45900178 | 3.06E-08 | 2.17E-07 | 2.45E-06 | 0.01311475 | 2.37209302 |
| KV | 63 | 5427 | 2.13047354 | 3.60E-08 | 1.93E-07 | 2.70E-06 | 0.01160862 | 2.09647651 |
| KF | 57 | 4754 | 2.20044793 | 6.94E-08 | 3.51E-07 | 5.13E-06 | 0.0119899 | 2.1661699 |
| KAA | 8 | 99 | 8.69582558 | 7.59E-08 | 4.49E-06 | 5.59E-05 | 0.08080808 | 15.6923077 |
| L...K | 26 | 1431 | 3.40878063 | 7.68E-08 | 6.42E-07 | 6.30E-06 | 0.01816911 | 3.30320285 |
| RHF | 18 | 696 | 2.78303901 | 7.82E-08 | 4.49E-06 | 5.75E-05 | 0.02586207 | 4.73893805 |
| KRH | 17 | 627 | 2.91767832 | 9.16E-08 | 4.89E-06 | 6.72E-05 | 0.02711324 | 4.97459016 |
| K.....R | 21 | 1005 | 3.89720351 | 9.81E-08 | 1.04E-06 | 7.65E-06 | 0.02089552 | 3.80945122 |
| WK | 56 | 4685 | 2.1936829 | 9.88E-08 | 4.73E-07 | 7.21E-06 | 0.01195304 | 2.15942968 |
| K.F | 52 | 4274 | 2.24146493 | 1.27E-07 | 8.51E-07 | 1.03E-05 | 0.01216659 | 2.19848413 |
| KQ | 35 | 2401 | 2.67529268 | 2.48E-07 | 1.13E-06 | 1.78E-05 | 0.01457726 | 2.64053254 |
| KHR | 9 | 159 | 6.09117971 | 2.53E-07 | 1.26E-05 | 0.00018535 | 0.05660377 | 10.71 |
| K.Y | 37 | 2649 | 2.57325537 | 2.79E-07 | 1.75E-06 | 2.23E-05 | 0.01396753 | 2.52852221 |
| HRK | 7 | 80 | 9.41594864 | 2.88E-07 | 1.34E-05 | 0.00021086 | 0.0875 | 17.1164384 |
| GK | 41 | 3075 | 2.44700104 | 3.10E-07 | 1.34E-06 | 2.20E-05 | 0.01333333 | 2.41216216 |
| R.F | 51 | 4316 | 2.17696708 | 3.22E-07 | 1.89E-06 | 2.54E-05 | 0.0118165 | 2.13446659 |
| HKN | 7 | 82 | 9.18629136 | 3.42E-07 | 1.50E-05 | 0.00024965 | 0.08536585 | 16.66 |
| H......R | 20 | 994 | 3.75269669 | 3.53E-07 | 3.33E-06 | 2.71E-05 | 0.02013072 | 3.66529774 |
| K.L | 47 | 3853 | 2.24730475 | 3.82E-07 | 2.11E-06 | 2.98E-05 | 0.01219829 | 2.20428271 |
| G..K | 34 | 2370 | 2.68985743 | 3.94E-07 | 2.59E-06 | 3.12E-05 | 0.01434599 | 2.59803082 |
| NK | 58 | 5166 | 2.06048287 | 4.30E-07 | 1.78E-06 | 3.01E-05 | 0.01122726 | 2.02682067 |
| GR | 39 | 2888 | 2.47835112 | 5.22E-07 | 2.07E-06 | 3.60E-05 | 0.01350416 | 2.44348894 |
| KRR | 9 | 174 | 5.56607801 | 5.40E-07 | 2.24E-05 | 0.00039452 | 0.05172414 | 9.73636364 |
| RKA | 7 | 92 | 8.18778143 | 7.51E-07 | 2.95E-05 | 0.00054749 | 0.07608696 | 14.7 |
| H....G | 50 | 4443 | 2.11134416 | 7.88E-07 | 6.04E-06 | 6.38E-05 | 0.01125366 | 2.03164125 |

FIG. 60D

| motif | n | n.lib | enrich | p | fdr | padj.holm | Pr_seqs.motif | PLR |
|---|---|---|---|---|---|---|---|---|
| HKK | 7 | 97 | 7.76573084 | 1.08E-06 | 4.02E-05 | 0.00078319 | 0.07216495 | 13.8833333 |
| F...K | 29 | 1950 | 2.79947166 | 1.13E-06 | 6.84E-06 | 8.11E-05 | 0.01487179 | 2.69469027 |
| K.V | 43 | 3538 | 2.23910133 | 1.32E-06 | 6.92E-06 | 0.000102 | 0.01215376 | 2.19613734 |
| HKF | 9 | 194 | 4.99225554 | 1.34E-06 | 4.75E-05 | 0.00097149 | 0.04639175 | 8.68378378 |
| R...N | 22 | 1259 | 3.27840264 | 1.40E-06 | 9.89E-06 | 0.0001118 | 0.01747419 | 3.17461601 |
| RHG | 15 | 605 | 2.66803739 | 1.54E-06 | 5.22E-05 | 0.00111556 | 0.02479339 | 4.53813559 |
| K...Q | 27 | 1793 | 2.83462859 | 2.07E-06 | 1.13E-05 | 0.00014691 | 0.01505856 | 2.7290487 |
| R..F | 40 | 3238 | 2.32340627 | 2.10E-06 | 1.22E-05 | 0.00016378 | 0.01239157 | 2.23964868 |
| Y..K | 33 | 2446 | 2.5296252 | 2.12E-06 | 1.22E-05 | 0.00016378 | 0.01349141 | 2.44115209 |
| K...Y | 25 | 1582 | 2.97472085 | 2.13E-06 | 1.13E-05 | 0.00014899 | 0.01580278 | 2.86608863 |
| GRG | 9 | 208 | 4.65623834 | 2.37E-06 | 7.70E-05 | 0.00171804 | 0.04326923 | 8.07286432 |
| KKH | 10 | 268 | 4.01532991 | 2.49E-06 | 7.75E-05 | 0.00180267 | 0.03731343 | 6.91860465 |
| GRKK | 3 | 6 | 8.36593216 | 3.00E-06 | 0.00034723 | 0.00079684 | 0.5 | 178.5 |
| RRGS | 3 | 6 | 8.36593216 | 3.00E-06 | 0.00034723 | 0.00079684 | 0.5 | 178.5 |
| K.A | 35 | 2677 | 2.40870046 | 3.02E-06 | 1.45E-05 | 0.00022955 | 0.01307434 | 2.36468584 |
| K.N | 35 | 2681 | 2.40510672 | 3.09E-06 | 1.45E-05 | 0.00023163 | 0.01305483 | 2.36111111 |
| RKV | 9 | 219 | 4.42236335 | 3.61E-06 | 0.00010777 | 0.0026077 | 0.04109589 | 7.65 |
| H...H | 29 | 2080 | 2.62450468 | 3.86E-06 | 1.93E-05 | 0.00026629 | 0.01394231 | 2.52389078 |
| H..N | 30 | 2175 | 2.58619153 | 3.95E-06 | 2.14E-05 | 0.00030035 | 0.0137931 | 2.4965035 |
| KKR | 10 | 283 | 3.80250324 | 4.03E-06 | 0.00011248 | 0.00290873 | 0.03533569 | 6.53846154 |
| A.K | 38 | 3043 | 2.30061934 | 4.06E-06 | 1.74E-05 | 0.00030017 | 0.01248768 | 2.25723794 |
| RKF | 8 | 167 | 5.15501038 | 4.07E-06 | 0.00011248 | 0.0029312 | 0.04790419 | 8.98113208 |
| K.F | 34 | 2593 | 2.41568066 | 4.08E-06 | 1.74E-05 | 0.00030017 | 0.01311223 | 2.37162954 |
| RN | 33 | 2474 | 2.44799013 | 5.05E-06 | 1.91E-05 | 0.00034311 | 0.01333873 | 2.41315035 |
| Y.K | 38 | 3099 | 2.25904635 | 5.07E-06 | 2.07E-05 | 0.00036486 | 0.01226202 | 2.2159425 |
| S...R | 23 | 1473 | 2.92947927 | 5.11E-06 | 3.28E-05 | 0.0004038 | 0.01561439 | 2.83137931 |
| HKRR | 3 | 7 | 7.170799 | 5.22E-06 | 0.00034723 | 0.00137846 | 0.42857143 | 133.875 |
| HRLN | 3 | 7 | 7.170799 | 5.22E-06 | 0.00034723 | 0.00137846 | 0.42857143 | 133.875 |
| K...L | 28 | 2033 | 2.58396122 | 5.35E-06 | 3.28E-05 | 0.00041698 | 0.01377275 | 2.49276808 |
| K...V | 30 | 2249 | 2.51098714 | 6.18E-06 | 2.92E-05 | 0.00042033 | 0.01333926 | 2.41324921 |
| KHG | 13 | 515 | 2.71639018 | 6.18E-06 | 0.00016492 | 0.00445095 | 0.02524272 | 4.62250996 |
| K...H | 29 | 2141 | 2.54972897 | 6.61E-06 | 2.96E-05 | 0.00044266 | 0.01354507 | 2.45099432 |
| RRL | 9 | 238 | 4.06931754 | 7.06E-06 | 0.0001818 | 0.00507456 | 0.03781513 | 7.01528384 |
| R...S | 37 | 3095 | 2.25036912 | 7.71E-06 | 3.21E-05 | 0.00050873 | 0.01195477 | 2.15974493 |
| S...K | 27 | 1933 | 2.62932699 | 7.92E-06 | 3.31E-05 | 0.00051582 | 0.01396793 | 2.52859391 |
| KRW | 8 | 185 | 4.6534418 | 8.61E-06 | 0.00021442 | 0.0061828 | 0.04324324 | 8.06779661 |
| R..S | 41 | 3596 | 2.13777929 | 8.90E-06 | 4.55E-05 | 0.00066731 | 0.01140156 | 2.05864979 |

Fig. 60E

| motif | n | n.lib | enrich | p | fdr | padj.holm | Pr_seqs.motif | PLR |
|---|---|---|---|---|---|---|---|---|
| R...N | 25 | 1726 | 2.7265402 | 9.30E-06 | 3.59E-05 | 0.00059491 | 0.01448436 | 2.62345679 |
| R....L | 27 | 2003 | 2.52899607 | 1.13E-05 | 6.53E-05 | 0.00087383 | 0.01347978 | 2.43901822 |
| KKW | 6 | 92 | 7.01809836 | 1.14E-05 | 0.00026726 | 0.00820872 | 0.06521739 | 12.4534884 |
| VHR | 6 | 92 | 7.01809836 | 1.14E-05 | 0.00026726 | 0.00820872 | 0.06521739 | 12.4534884 |
| KVHR | 3 | 9 | 5.57728811 | 1.24E-05 | 0.00066135 | 0.00325705 | 0.33333333 | 89.25 |
| K....S | 28 | 2183 | 2.3922367 | 1.25E-05 | 0.00010588 | 0.00094671 | 0.01282639 | 2.31925754 |
| QX | 56 | 5559 | 1.84878654 | 1.28E-05 | 4.66E-05 | 0.00085698 | 0.01007375 | 1.81646375 |
| RRK | 6 | 97 | 6.65634072 | 1.55E-05 | 0.00035103 | 0.01108761 | 0.06185567 | 11.7692308 |
| K..F | 38 | 3306 | 2.15515961 | 1.79E-05 | 8.68E-05 | 0.00132805 | 0.01149425 | 2.0755814 |
| RRF | 8 | 206 | 4.17906181 | 1.87E-05 | 0.00041053 | 0.01336937 | 0.03883495 | 7.21212121 |
| AKA | 7 | 150 | 5.02183927 | 1.92E-05 | 0.00041053 | 0.01371472 | 0.04666667 | 8.73776224 |
| R....F | 24 | 1758 | 2.5461983 | 1.93E-05 | 0.00014948 | 0.00145085 | 0.01365188 | 2.47058824 |
| RKS | 7 | 155 | 4.85984446 | 2.38E-05 | 0.00049285 | 0.01691121 | 0.04516129 | 8.44256757 |
| Y...X | 26 | 1945 | 2.51632325 | 2.40E-05 | 8.88E-05 | 0.00151425 | 0.01336761 | 2.41844711 |
| KKWR | 3 | 11 | 4.56323572 | 2.42E-05 | 0.00080546 | 0.00632254 | 0.27272727 | 66.9375 |
| RHRG | 3 | 11 | 4.56323572 | 2.42E-05 | 0.00080546 | 0.00632254 | 0.27272727 | 66.9375 |
| RRHY | 3 | 11 | 4.56323572 | 2.42E-05 | 0.00080546 | 0.00632254 | 0.27272727 | 66.9375 |
| HRH | 9 | 279 | 3.47131747 | 2.48E-05 | 0.00050101 | 0.0176439 | 0.03225806 | 5.95 |
| R...V | 29 | 2283 | 2.39113874 | 2.68E-05 | 9.49E-05 | 0.00166196 | 0.01270258 | 2.29658385 |
| KRWHF | 2 | 2 | 1.567276 | 2.79E-05 | 3.72E-05 | 0.00011173 | 1 | Inf |
| LWKHG | 2 | 2 | 1.567276 | 2.79E-05 | 3.72E-05 | 0.00011173 | 1 | Inf |
| WKHRG | 2 | 2 | 1.567276 | 2.79E-05 | 3.72E-05 | 0.00011173 | 1 | Inf |
| KRK | 7 | 160 | 4.70797432 | 2.91E-05 | 0.00055752 | 0.02066625 | 0.04375 | 8.16666667 |
| YYK | 7 | 160 | 4.70797432 | 2.91E-05 | 0.00055752 | 0.02066625 | 0.04375 | 8.16666667 |
| K....H | 23 | 1666 | 2.59010982 | 3.44E-05 | 0.0001836 | 0.00261139 | 0.01380552 | 2.49878271 |
| Y.R | 37 | 3279 | 2.07885132 | 3.48E-05 | 0.00013629 | 0.00247053 | 0.01128393 | 2.03716841 |
| G....K | 20 | 1334 | 2.81280422 | 3.59E-05 | 0.0001836 | 0.00269413 | 0.0149925 | 2.71689498 |
| SR | 33 | 2763 | 2.19193904 | 3.61E-05 | 0.00012186 | 0.00238184 | 0.01194354 | 2.15769231 |
| KY | 32 | 2610 | 2.2501159 | 3.62E-05 | 0.00012186 | 0.00238184 | 0.01226054 | 2.21567106 |
| RWK | 8 | 227 | 3.79245257 | 3.73E-05 | 0.00068678 | 0.02644117 | 0.03524229 | 6.52054795 |
| KVG | 13 | 613 | 2.28212225 | 3.77E-05 | 0.00068678 | 0.0266501 | 0.02120718 | 3.8675 |
| KN | 30 | 2422 | 2.27322557 | 3.84E-05 | 0.00012467 | 0.00245496 | 0.01238646 | 2.23871237 |
| F..K | 29 | 2332 | 2.33167568 | 4.05E-05 | 0.00017814 | 0.00295286 | 0.01243568 | 2.24772036 |
| HG | 52 | 5251 | 1.81742603 | 4.06E-05 | 0.00012734 | 0.00255654 | 0.00990288 | 1.78534334 |
| K..V | 33 | 2821 | 2.19335811 | 4.07E-05 | 0.00017814 | 0.00295286 | 0.01169798 | 2.11280488 |
| R....A | 18 | 1132 | 2.98326215 | 4.14E-05 | 0.00020027 | 0.00306066 | 0.01590106 | 2.88420108 |
| AKAK | 3 | 13 | 3.86119946 | 4.17E-05 | 0.00123111 | 0.01074679 | 0.23076923 | 53.55 |

FIG. 60F

| motif | n | n.lib | enrich | p | fdr | padj.holm | Pr_seqs.motif | PLR |
|---|---|---|---|---|---|---|---|---|
| RNK | 8 | 231 | 3.72678239 | 4.22E-05 | 0.00075122 | 0.02981958 | 0.03463203 | 6.40358744 |
| KL | 50 | 5031 | 1.82394234 | 6.00E-05 | 0.00018191 | 0.00371816 | 0.00993838 | 1.79180887 |
| R....H | 18 | 1200 | 2.79763538 | 6.45E-05 | 0.00045723 | 0.00477667 | 0.015 | 2.71827411 |
| RHXL | 3 | 15 | 3.34637286 | 6.57E-05 | 0.00150751 | 0.01689528 | 0.2 | 44.625 |
| HKS | 7 | 182 | 4.13887852 | 6.58E-05 | 0.0011434 | 0.04640172 | 0.03846154 | 7.14 |
| RQR | 8 | 247 | 3.48537139 | 6.75E-05 | 0.00114551 | 0.04750127 | 0.03238866 | 5.9748954 |
| R...P | 22 | 1607 | 2.57703011 | 7.00E-05 | 0.00023789 | 0.00426797 | 0.01369011 | 2.47760252 |
| NKX | 7 | 184 | 4.09389071 | 7.05E-05 | 0.00117005 | 0.04955097 | 0.03804348 | 7.05932203 |
| R..L | 34 | 3036 | 2.09978989 | 7.74E-05 | 0.00032378 | 0.00549729 | 0.01119895 | 2.02165223 |
| W...K | 24 | 1853 | 2.43808314 | 7.81E-05 | 0.00025522 | 0.00468403 | 0.01295197 | 2.34226353 |
| NKYK | 3 | 16 | 3.13722456 | 8.06E-05 | 0.00150751 | 0.02063067 | 0.1875 | 41.1923077 |
| K....N | 14 | 798 | 3.27208816 | 8.30E-05 | 0.00054276 | 0.00605972 | 0.01754386 | 3.1875 |
| R...Y | 22 | 1627 | 2.5453518 | 8.33E-05 | 0.00026237 | 0.0049172 | 0.01352183 | 2.44672897 |
| KFSG | 5 | 82 | 1.02023563 | 8.35E-05 | 0.00150751 | 0.02128916 | 0.06097561 | 11.5909091 |
| RWHFD | 2 | 3 | 1.04485066 | 8.35E-05 | 8.35E-05 | 0.00011173 | 0.66666667 | 357 |
| FHHK | 2 | 3 | 11.1545762 | 8.50E-05 | 0.00150751 | 0.02159252 | 0.66666667 | 357 |
| KKPH | 2 | 3 | 11.1545762 | 8.50E-05 | 0.00150751 | 0.02159252 | 0.66666667 | 357 |
| LHHN | 2 | 3 | 11.1545762 | 8.50E-05 | 0.00150751 | 0.02159252 | 0.66666667 | 357 |
| R....D | 37 | 3539 | 1.96149182 | 8.54E-05 | 0.00039299 | 0.00623652 | 0.01045493 | 1.88592233 |
| SK | 31 | 2652 | 2.14527806 | 8.63E-05 | 0.00024739 | 0.00526705 | 0.01168929 | 2.11121709 |
| HY | 33 | 2865 | 2.11390142 | 8.70E-05 | 0.00024739 | 0.00526705 | 0.01151832 | 2.07997881 |
| K.P | 25 | 1958 | 2.39401029 | 0.00011001 | 0.00042928 | 0.00770084 | 0.01276813 | 2.30858769 |
| K.Y | 25 | 1962 | 2.38912953 | 0.00011139 | 0.00042928 | 0.00772709 | 0.0127421 | 2.30382034 |
| G....R | 16 | 1034 | 2.88601973 | 0.0001136 | 0.00068971 | 0.00817917 | 0.01547389 | 2.80550098 |
| KRSH | 3 | 18 | 2.78864405 | 0.00011649 | 0.00167972 | 0.02924016 | 0.16666667 | 35.7 |
| NKKH | 3 | 18 | 2.78864405 | 0.00011649 | 0.00167972 | 0.02924016 | 0.16666667 | 35.7 |
| SPNL | 3 | 18 | 2.78864405 | 0.00011649 | 0.00167972 | 0.02924016 | 0.16666667 | 35.7 |
| HREG | 4 | 47 | 1.42398845 | 0.00011998 | 0.00167972 | 0.02975509 | 0.08510638 | 16.6046512 |
| LK | 32 | 2804 | 2.10249558 | 0.00012088 | 0.00045451 | 0.00846153 | 0.01141227 | 2.06060606 |
| K...P | 21 | 1567 | 2.52268478 | 0.00013467 | 0.00040882 | 0.0078109 | 0.0134014 | 2.42464424 |
| K..L | 33 | 3014 | 2.05290751 | 0.00013706 | 0.0005044 | 0.00932035 | 0.01094891 | 1.97601476 |
| S..K | 28 | 2351 | 2.23307903 | 0.00014897 | 0.00052712 | 0.00998092 | 0.01190983 | 2.1515282 |
| Q.K | 31 | 2711 | 2.10666412 | 0.00016098 | 0.00056605 | 0.01110793 | 0.01143489 | 2.06473881 |
| RHKR | 3 | 20 | 2.50977965 | 0.00016146 | 0.00173325 | 0.03987954 | 0.15 | 31.5 |
| RWKG | 3 | 20 | 2.50977965 | 0.00016146 | 0.00173325 | 0.03987954 | 0.15 | 31.5 |
| H.N | 31 | 2715 | 2.10356038 | 0.00016259 | 0.00056605 | 0.01110793 | 0.01141805 | 2.0616617 |
| K.....H | 17 | 1180 | 2.68699443 | 0.00016309 | 0.0009242 | 0.0115797 | 0.01440678 | 2.60920034 |

FIG. 60G

| motif | n | n.lib | enrich | p | fdr | padj.holm | Pr_seqs.motif | PLR |
|---|---|---|---|---|---|---|---|---|
| L..K | 24 | 1914 | 2.36038038 | 0.000166 | 0.00048656 | 0.00946217 | 0.01253918 | 2.26666667 |
| H..G | 49 | 5204 | 1.76545838 | 0.00016666 | 0.00056789 | 0.01099977 | 0.00941583 | 1.69670223 |
| HFRN | 2 | 4 | 8.36593216 | 0.00016942 | 0.00173325 | 0.04150678 | 0.5 | 178.5 |
| KAAY | 2 | 4 | 8.36593216 | 0.00016942 | 0.00173325 | 0.04150678 | 0.5 | 178.5 |
| KGGQ | 2 | 4 | 8.36593216 | 0.00016942 | 0.00173325 | 0.04150678 | 0.5 | 178.5 |
| KHYP | 2 | 4 | 8.36593216 | 0.00016942 | 0.00173325 | 0.04150678 | 0.5 | 178.5 |
| KPHP | 2 | 4 | 8.36593216 | 0.00016942 | 0.00173325 | 0.04150678 | 0.5 | 178.5 |
| P.K | 34 | 3122 | 2.00636129 | 0.00017185 | 0.00057692 | 0.01151389 | 0.01089045 | 1.96534974 |
| A..K | 28 | 2397 | 2.19022478 | 0.00017644 | 0.00057973 | 0.01146851 | 0.01168127 | 2.10975095 |
| HKRG | 3 | 21 | 2.39026633 | 0.00018761 | 0.00178234 | 0.04502753 | 0.14285714 | 29.75 |
| RWHF | 3 | 21 | 2.39026633 | 0.00018761 | 0.00178234 | 0.04502753 | 0.14285714 | 29.75 |
| S.R | 32 | 2918 | 2.02035558 | 0.00019043 | 0.00061724 | 0.01256812 | 0.01096642 | 1.97920998 |
| RS | 48 | 5032 | 1.75063667 | 0.00020761 | 0.00057251 | 0.01224919 | 0.00953895 | 1.71910112 |
| S..R | 28 | 2436 | 2.15515961 | 0.00021043 | 0.00066759 | 0.01346781 | 0.01149425 | 2.0755814 |
| R.Y | 30 | 2632 | 2.09989941 | 0.00022308 | 0.00069899 | 0.01450029 | 0.01139818 | 2.05803228 |
| K...S | 33 | 3089 | 2.01098449 | 0.00022919 | 0.00064938 | 0.01283485 | 0.01068307 | 1.92751963 |
| K..Q | 27 | 2322 | 2.1802196 | 0.00024867 | 0.00076259 | 0.01566625 | 0.01162791 | 2.1 |
| A..R | 29 | 2575 | 2.11163794 | 0.0003112 | 0.00092355 | 0.01929421 | 0.01126214 | 2.03318832 |
| H....S | 29 | 2649 | 2.05390986 | 0.00031487 | 0.00137942 | 0.0226704 | 0.01094753 | 1.97576336 |
| RF | 50 | 5413 | 1.69522518 | 0.00034688 | 0.00092841 | 0.02011885 | 0.00923702 | 1.6641805 |
| H..Q | 22 | 1773 | 2.33575149 | 0.00035564 | 0.00097354 | 0.01955993 | 0.01240835 | 2.24271845 |
| K....V | 18 | 1384 | 2.42569542 | 0.00035911 | 0.00190775 | 0.0251374 | 0.01300578 | 2.35212299 |
| H..S | 32 | 3062 | 1.96724061 | 0.00036651 | 0.00097354 | 0.01979141 | 0.01045069 | 1.88514851 |
| K...N | 17 | 1244 | 2.56385748 | 0.00038496 | 0.00160982 | 0.02733191 | 0.01366559 | 2.47310513 |
| R.N | 29 | 2636 | 2.02682249 | 0.00039706 | 0.00120398 | 0.0254116 | 0.01100152 | 1.98561565 |
| S.K | 31 | 2871 | 1.98926033 | 0.00042443 | 0.00124677 | 0.02673933 | 0.01079763 | 1.94841549 |
| R..W | 21 | 1655 | 2.38854807 | 0.00043382 | 0.00111741 | 0.02299237 | 0.01268882 | 2.29406365 |
| R.W | 29 | 2681 | 1.99280271 | 0.00047751 | 0.00136017 | 0.02960535 | 0.01081686 | 1.95192308 |
| Y....K | 18 | 1399 | 2.41390475 | 0.00052926 | 0.00211352 | 0.03704793 | 0.01286633 | 2.32657495 |
| Y..R | 28 | 2577 | 2.03724051 | 0.00054628 | 0.00157055 | 0.03332306 | 0.01086535 | 1.96076893 |
| Y....R | 19 | 1525 | 2.33748642 | 0.00055135 | 0.00211352 | 0.03804342 | 0.01245902 | 2.25199203 |
| R.....S | 24 | 2150 | 2.08196121 | 0.00058965 | 0.00294823 | 0.0406856 | 0.01116279 | 2.01505174 |
| N.R | 32 | 3078 | 1.91533385 | 0.0006851 | 0.0018941 | 0.04179103 | 0.01039636 | 1.87524622 |
| A...K | 22 | 1896 | 2.1842233 | 0.00069761 | 0.00174403 | 0.03627576 | 0.01160338 | 2.09551761 |
| F.K | 30 | 2875 | 1.92241226 | 0.00073275 | 0.00196795 | 0.04396477 | 0.01043478 | 1.88224956 |

FIG. 61

| Peptide Sequence | r.Ein.1st | p.Ein.1st | r.Ein.max | p.Ein.max | r.Ein.chng | p.Ein.chng | mean.r | min.r2 |
|---|---|---|---|---|---|---|---|---|
| RHKYYG | 0.453151517 | 1.18E-10 | 0.490671239 | 1.77E-12 | 0.452105136 | 4.26E-10 | 0.465309297 | 0.204399054 |
| RRLRSWKG | 0.444668344 | 2.86E-10 | 0.47079275 | 1.75E-11 | 0.441812279 | 1.16E-09 | 0.452424458 | 0.19519809 |
| RGYHLYHEKG | 0.441398846 | 3.99E-10 | 0.477650813 | 8.08E-12 | 0.479507649 | 2.48E-11 | 0.466185769 | 0.194832942 |
| KHRWSGRLG | 0.455380401 | 9.36E-11 | 0.455618229 | 9.13E-11 | 0.440809201 | 1.28E-09 | 0.450602611 | 0.194312752 |
| HHDWKHRG | 0.43110546 | 1.11E-09 | 0.454310381 | 1.05E-10 | 0.438648104 | 1.58E-09 | 0.441354648 | 0.185851918 |
| RKAFGRG | 0.436033275 | 6.84E-10 | 0.456053785 | 8.71E-11 | 0.430283113 | 3.45E-09 | 0.440790058 | 0.185143558 |
| RRLHRHSG | 0.442401722 | 3.60E-10 | 0.455108229 | 9.63E-11 | 0.427210585 | 4.58E-09 | 0.441573512 | 0.182508884 |
| HSQKARAVG | 0.428077047 | 1.50E-09 | 0.47929073 | 6.70E-12 | 0.426956169 | 4.69E-09 | 0.444774649 | 0.18229157 |
| AHRPRKRG | 0.468458035 | 2.27E-11 | 0.480346714 | 5.93E-12 | 0.4253097 | 5.45E-09 | 0.45803815 | 0.180888341 |
| SKRHKYVG | 0.425023414 | 2.01E-09 | 0.454151984 | 1.07E-10 | 0.451163995 | 4.68E-10 | 0.443446464 | 0.180644902 |
| NHRNDWQRHL | 0.430240571 | 1.21E-09 | 0.466345825 | 2.86E-11 | 0.424350221 | 5.94E-09 | 0.440312205 | 0.18007311 |
| RKKHYKRG | 0.424201688 | 2.17E-09 | 0.471385994 | 1.64E-11 | 0.48526565 | 1.32E-11 | 0.460284444 | 0.179947072 |
| RSRHRQRLS | 0.423491242 | 2.33E-09 | 0.463395957 | 3.96E-11 | 0.463646924 | 1.33E-10 | 0.450178041 | 0.179344832 |
| RLHGRGRDG | 0.421022128 | 2.94E-09 | 0.444346697 | 2.96E-10 | 0.422439752 | 7.07E-09 | 0.429269526 | 0.177259633 |
| HFRQRQRD | 0.42050417 | 3.09E-09 | 0.451236754 | 1.45E-10 | 0.4354572 | 2.13E-09 | 0.435732708 | 0.176823757 |
| HLNRWRYKD | 0.422057206 | 2.67E-09 | 0.444917836 | 2.79E-10 | 0.419464851 | 9.23E-09 | 0.428813298 | 0.175950761 |
| YHEGRNSRG | 0.427385184 | 1.60E-09 | 0.479798202 | 6.32E-12 | 0.418531105 | 1.00E-08 | 0.44190483 | 0.175168286 |
| RRPRARG | 0.438210431 | 5.50E-10 | 0.4504788 | 1.57E-10 | 0.418411309 | 1.01E-08 | 0.43570018 | 0.175068023 |
| KHPYYAYKG | 0.417437649 | 4.13E-09 | 0.468596428 | 2.23E-11 | 0.426713723 | 4.79E-09 | 0.4375826 | 0.174254191 |
| HRWHREG | 0.416812218 | 4.38E-09 | 0.434305204 | 8.12E-10 | 0.439837196 | 1.41E-09 | 0.430318206 | 0.173732425 |
| QHRHKKDG | 0.415942207 | 4.75E-09 | 0.446318899 | 2.41E-10 | 0.416767012 | 1.17E-08 | 0.426342706 | 0.17300792 |
| QHVNAKAKVE | 0.414672641 | 5.35E-09 | 0.458401327 | 6.78E-11 | 0.414926474 | 1.38E-08 | 0.429333481 | 0.171953399 |
| RHFRYQLKDG | 0.437570295 | 5.87E-10 | 0.460514982 | 5.40E-11 | 0.414207195 | 1.47E-08 | 0.437430824 | 0.1715676 |
| KRRGHSNLFS | 0.416896033 | 4.34E-09 | 0.430846612 | 1.14E-09 | 0.414002953 | 1.50E-08 | 0.420581866 | 0.171398445 |
| WYARKDRG | 0.431975475 | 1.02E-09 | 0.449909155 | 1.66E-10 | 0.413238171 | 1.60E-08 | 0.4317076 | 0.170765786 |
| RHFRNKEFG | 0.417575536 | 4.08E-09 | 0.458959361 | 6.39E-11 | 0.412668695 | 1.68E-08 | 0.429734531 | 0.170295452 |
| KSRFANRYG | 0.416707666 | 4.42E-09 | 0.456602839 | 8.22E-11 | 0.412667455 | 1.68E-08 | 0.42865932 | 0.170294428 |
| RHGKAAKD | 0.412242549 | 6.69E-09 | 0.434376717 | 8.07E-10 | 0.414029667 | 1.49E-08 | 0.420216311 | 0.169943919 |
| HSARKRKVG | 0.412161606 | 6.74E-09 | 0.465066592 | 3.30E-11 | 0.425565123 | 5.32E-09 | 0.434264441 | 0.16987719 |
| VRKSQKRG | 0.452237237 | 1.30E-10 | 0.475843096 | 9.92E-12 | 0.411512314 | 1.86E-08 | 0.446530882 | 0.169342384 |
| HDKKHFPRDG | 0.411092581 | 7.44E-09 | 0.453006205 | 1.20E-10 | 0.413445771 | 1.57E-08 | 0.425848186 | 0.16899711 |
| RGDKVLSFD | 0.444780416 | 2.83E-10 | 0.451552003 | 1.40E-10 | 0.410889206 | 1.96E-08 | 0.435740542 | 0.16882994 |
| QHLEKFPRWKG | 0.417683714 | 4.04E-09 | 0.439256317 | 4.95E-10 | 0.410621074 | 2.01E-08 | 0.422520368 | 0.168609666 |
| YHRRGNRLE | 0.433075663 | 9.17E-10 | 0.454812369 | 9.94E-11 | 0.410553667 | 2.02E-08 | 0.4328139 | 0.168554314 |
| RRRFFG | 0.410451878 | 7.89E-09 | 0.414988675 | 5.19E-09 | 0.458815884 | 2.17E-10 | 0.428085479 | 0.168470744 |
| RRKEWRFSD | 0.410313996 | 7.99E-09 | 0.44434877 | 2.95E-10 | 0.478971975 | 2.63E-11 | 0.444544914 | 0.168357575 |
| FYERHKLG | 0.410275549 | 8.02E-09 | 0.427126477 | 1.64E-09 | 0.431699659 | 3.03E-09 | 0.423033895 | 0.168326026 |
| HKGYGG | 0.40983778 | 8.35E-09 | 0.447287743 | 2.18E-10 | 0.411505891 | 1.86E-08 | 0.422877138 | 0.167967006 |
| AKQAHVAKVE | 0.419808417 | 3.30E-09 | 0.465350468 | 3.20E-11 | 0.40978442 | 2.16E-08 | 0.431647769 | 0.167923271 |
| RYRYHYKFE | 0.409223497 | 8.83E-09 | 0.418860379 | 3.61E-09 | 0.41321049 | 1.60E-08 | 0.413764789 | 0.167463871 |
| GKKPHLSG | 0.424240464 | 2.17E-09 | 0.454002471 | 1.08E-10 | 0.408669476 | 2.38E-08 | 0.428970804 | 0.167010741 |
| SPHKRLAKVS | 0.41233243 | 6.64E-09 | 0.453068381 | 1.20E-10 | 0.408287743 | 2.46E-08 | 0.424562851 | 0.166698881 |
| PRGRHSYRWRD | 0.40822762 | 9.67E-09 | 0.421861905 | 2.72E-09 | 0.43041706 | 3.41E-09 | 0.420168861 | 0.16664979 |
| RSKAANVSD | 0.408220657 | 9.67E-09 | 0.424028534 | 2.21E-09 | 0.45124454 | 4.64E-10 | 0.427831244 | 0.166644105 |
| KYRRWHFD | 0.435320539 | 7.35E-10 | 0.43277792 | 9.45E-10 | 0.408027694 | 2.51E-08 | 0.425375384 | 0.166486599 |
| HRKLPLFD | 0.407958441 | 9.91E-09 | 0.448806594 | 1.87E-10 | 0.418362101 | 1.02E-08 | 0.425042379 | 0.16643009 |
| RRHYPAFEG | 0.41069003 | 7.72E-09 | 0.42649275 | 1.74E-09 | 0.407871526 | 2.55E-08 | 0.415018102 | 0.166359182 |
| VKKKRSG | 0.407374516 | 1.04E-08 | 0.42734475 | 1.61E-09 | 0.414648732 | 1.41E-08 | 0.416455999 | 0.165953996 |
| KFRWWDG | 0.420511649 | 3.09E-09 | 0.445866094 | 2.53E-10 | 0.406893393 | 2.77E-08 | 0.424423712 | 0.165562233 |
| SKYLWKHG | 0.406863808 | 1.09E-08 | 0.435962925 | 6.89E-10 | 0.417660186 | 1.08E-08 | 0.420162306 | 0.165538158 |

FIG. 62A

SLE vs. HC – 5121 Significant Peptides

| motif | n | n.lib | enrich | p | fdr | padj.holm | Pr_seqs.motif | PLR |
|---|---|---|---|---|---|---|---|---|
| PQNN | 5 | 5 | 10.55542941 | 9.67E-08 | 0.000236238 | 0.000472379 | 1 | Inf |
| PGGN | 7 | 8 | 9.236000735 | 1.17E-09 | 5.70E-06 | 5.70E-06 | 0.875 | 165.2442882 |
| PGD | 36 | 111 | 7.866665947 | 3.54E-23 | 3.14E-20 | 6.27E-20 | 0.324324324 | 11.33103691 |
| PGG | 38 | 119 | 7.745470814 | 4.21E-24 | 7.46E-21 | 7.46E-21 | 0.319327731 | 11.07457311 |
| PSEK | 6 | 9 | 7.036952941 | 2.90E-07 | 0.000471701 | 0.001414524 | 0.666666667 | 47.21265378 |
| PDD | 32 | 112 | 6.930158096 | 6.53E-19 | 2.89E-16 | 1.15E-15 | 0.285714286 | 9.442530756 |
| PPD | 35 | 127 | 6.684601314 | 5.63E-20 | 3.33E-17 | 9.97E-17 | 0.275590551 | 8.980667838 |
| PKDD | 5 | 8 | 6.597143382 | 4.90E-06 | 0.003403291 | 0.023915725 | 0.625 | 39.34387815 |
| PSKG | 5 | 8 | 6.597143382 | 4.90E-06 | 0.003403291 | 0.023915725 | 0.625 | 39.34387815 |
| P.....N | 193 | 791 | 6.333265119 | 5.98E-95 | 1.66E-93 | 4.85E-93 | 0.243994943 | 7.618764364 |
| PDS | 31 | 119 | 6.318673559 | 4.21E-17 | 1.49E-14 | 7.44E-14 | 0.260504202 | 8.315865154 |
| PGS | 31 | 121 | 6.214232673 | 7.06E-17 | 2.08E-14 | 1.25E-13 | 0.256198347 | 8.131068151 |
| PGE | 31 | 122 | 6.16329634 | 9.10E-17 | 2.30E-14 | 1.61E-13 | 0.254098361 | 8.041715753 |
| P.....Q | 225 | 954 | 6.12182607 | 3.21E-107 | 1.33E-105 | 2.64E-105 | 0.235849057 | 7.285903361 |
| PSK | 28 | 111 | 6.118517959 | 3.33E-15 | 5.36E-13 | 5.86E-12 | 0.252252252 | 7.963580155 |
| PGL | 25 | 100 | 6.063888334 | 1.22E-13 | 1.55E-11 | 2.15E-10 | 0.25 | 7.86877563 |
| PPP | 19 | 77 | 5.985136538 | 1.30E-10 | 6.25E-09 | 2.26E-07 | 0.246753247 | 7.733107084 |
| PPE | 31 | 127 | 5.920646878 | 3.11E-16 | 6.90E-14 | 5.50E-13 | 0.244094488 | 7.622876391 |
| P.....A | 182 | 798 | 5.91991321 | 2.02E-84 | 3.36E-83 | 1.60E-82 | 0.228070175 | 6.974596581 |
| PDN | 30 | 126 | 5.775131747 | 1.92E-15 | 3.41E-13 | 3.39E-12 | 0.238095238 | 7.376977153 |
| PDE | 29 | 124 | 5.672669732 | 9.27E-15 | 1.37E-12 | 1.63E-11 | 0.233870968 | 7.206141893 |
| PPG | 25 | 112 | 5.414186013 | 1.91E-12 | 1.69E-10 | 3.35E-09 | 0.223214286 | 6.783427267 |
| PGV | 24 | 109 | 5.340672295 | 7.16E-12 | 5.29E-10 | 1.25E-08 | 0.220183486 | 6.665315828 |
| PSL | 26 | 119 | 5.299532662 | 1.18E-12 | 1.10E-10 | 2.07E-09 | 0.218487395 | 6.59961827 |
| PEQ | 25 | 115 | 5.272946378 | 3.57E-12 | 2.88E-10 | 6.26E-09 | 0.217391304 | 6.557313025 |
| PSS | 27 | 125 | 5.239199521 | 5.89E-13 | 6.52E-11 | 1.04E-09 | 0.216 | 6.503783939 |
| P....N | 246 | 1231 | 5.12411985 | 4.91E-99 | 2.43E-97 | 4.81E-97 | 0.19983753 | 5.895590269 |
| PEN | 27 | 128 | 5.116405782 | 1.07E-12 | 1.06E-10 | 1.89E-09 | 0.2109375 | 6.310602238 |
| PPS | 26 | 124 | 5.085841829 | 3.23E-12 | 2.72E-10 | 5.65E-09 | 0.209677419 | 6.262903052 |
| P....Q | 262 | 1327 | 5.062588093 | 3.92E-104 | 3.88E-102 | 3.88E-102 | 0.19743783 | 5.80737807 |
| P.....P | 151 | 782 | 5.012068955 | 4.43E-60 | 4.60E-59 | 3.37E-58 | 0.193094629 | 5.649057623 |
| P....A | 243 | 1254 | 4.968793659 | 7.01E-95 | 2.31E-93 | 6.80E-93 | 0.193779904 | 5.673924267 |
| PER | 23 | 114 | 4.89366427 | 1.27E-10 | 6.25E-09 | 2.21E-07 | 0.201754386 | 5.966434269 |
| PDL | 25 | 124 | 4.890232528 | 2.07E-11 | 1.36E-09 | 3.61E-08 | 0.201612903 | 5.961193659 |
| PES | 24 | 122 | 4.771584263 | 8.86E-11 | 5.07E-09 | 1.54E-07 | 0.196721311 | 5.781141279 |
| PEE | 24 | 124 | 4.694623227 | 1.26E-10 | 6.25E-09 | 2.20E-07 | 0.193548387 | 5.665518453 |
| KGG | 22 | 114 | 4.680896258 | 7.76E-10 | 2.93E-08 | 1.34E-06 | 0.192982456 | 5.644991213 |
| PDK | 22 | 116 | 4.60019115 | 1.10E-09 | 3.89E-08 | 1.89E-06 | 0.189655172 | 5.524885017 |
| QKGA | 6 | 14 | 4.523755462 | 8.72E-06 | 0.003403291 | 0.042544303 | 0.428571429 | 17.70474517 |
| PEL | 22 | 118 | 4.522221809 | 1.54E-09 | 5.34E-08 | 2.65E-06 | 0.186440678 | 5.409783245 |
| PGR | 21 | 115 | 4.429274957 | 5.29E-09 | 1.64E-07 | 9.08E-06 | 0.182608696 | 5.27375388 |
| PEV | 23 | 126 | 4.427601006 | 1.02E-09 | 3.69E-08 | 1.76E-06 | 0.182539683 | 5.271315713 |
| PQQ | 23 | 126 | 4.427601006 | 1.02E-09 | 3.69E-08 | 1.76E-06 | 0.182539683 | 5.271315713 |
| PNN | 24 | 134 | 4.34427821 | 6.68E-10 | 2.63E-08 | 1.15E-06 | 0.179104478 | 5.150471321 |
| AGD | 22 | 123 | 4.338391654 | 3.46E-09 | 1.12E-07 | 5.95E-06 | 0.178861789 | 5.141972194 |
| PGQ | 26 | 146 | 4.319482101 | 1.51E-10 | 6.88E-09 | 2.63E-07 | 0.178082192 | 5.114704159 |
| AAD | 22 | 124 | 4.303404624 | 4.05E-09 | 1.28E-07 | 6.96E-06 | 0.177419355 | 5.091560702 |
| P...Q | 322 | 1916 | 4.273377156 | 1.37E-106 | 1.38E-104 | 1.38E-104 | 0.168058455 | 4.768655746 |
| PKN | 23 | 131 | 4.258608601 | 2.24E-09 | 7.51E-08 | 3.86E-06 | 0.175572519 | 5.027273319 |
| P.....K | 170 | 1037 | 4.255170907 | 8.63E-57 | 7.96E-56 | 6.47E-55 | 0.163934426 | 4.628691547 |

FIG. 62B

SLE vs. HC – 5121 Significant Peptides

| AA | n | n.lib | enrich | p | fdr | padj.holm | Pr_seqs.motif | PLR |
|---|---|---|---|---|---|---|---|---|
| P | 4922 | 56321 | 2.18973536 | 0 | 0 | 0 | 0.087391914 | 2.26055645 |
| K | 3302 | 62082 | 1.332698009 | 1.97E-83 | 5.92E-83 | 1.38E-82 | 0.053187719 | 1.326098867 |
| A | 2841 | 57451 | 1.239064803 | 1.35E-44 | 3.04E-44 | 8.11E-44 | 0.049450836 | 1.228082305 |
| G | 5422 | 111145 | 1.222334198 | 3.41E-106 | 1.53E-105 | 2.73E-105 | 0.048783121 | 1.210649569 |
| Q | 2904 | 60519 | 1.202334332 | 3.53E-37 | 6.36E-37 | 1.77E-36 | 0.04798493 | 1.189842459 |
| S | 3458 | 81297 | 1.065788055 | 2.36E-15 | 3.03E-15 | 7.07E-15 | 0.042535395 | 1.048711807 |
| D | 4129 | 98037 | 1.055298326 | 4.39E-19 | 6.58E-19 | 1.75E-18 | 0.042116752 | 1.037936318 |
| E | 3600 | 88289 | 1.021683271 | 4.93E-09 | 5.55E-09 | 9.86E-09 | 0.040775182 | 1.00346889 |
| N | 2396 | 59481 | 1.009320123 | 0.003082016 | 0.003082016 | 0.003082016 | 0.040281771 | 0.990816488 |

FIG. 63A

SLE vs. Other AI/non-AI mimic diseases - 684 Significant Peptides

| motif | n | n.lib | enrich | p | fdr | padj.holm | Pr_seqs.motif | PLR |
|---|---|---|---|---|---|---|---|---|
| PELL | 2 | 3 | 10.43898141 | 7.46E-05 | 0.001327717 | 0.012904216 | 0.666666667 | 366.4473684 |
| PHHN | 2 | 3 | 10.43898141 | 7.46E-05 | 0.001327717 | 0.012904216 | 0.666666667 | 366.4473684 |
| PLKP | 2 | 3 | 10.43898141 | 7.46E-05 | 0.001327717 | 0.012904216 | 0.666666667 | 366.4473684 |
| PVHQ | 2 | 3 | 10.43898141 | 7.46E-05 | 0.001327717 | 0.012904216 | 0.666666667 | 366.4473684 |
| PVHR | 2 | 3 | 10.43898141 | 7.46E-05 | 0.001327717 | 0.012904216 | 0.666666667 | 366.4473684 |
| PGG | 10 | 119 | 10.03388058 | 6.98E-10 | 2.91E-07 | 5.81E-07 | 0.084033613 | 16.80951231 |
| PSL | 10 | 119 | 10.03388058 | 6.98E-10 | 2.91E-07 | 5.81E-07 | 0.084033613 | 16.80951231 |
| PEL | 8 | 118 | 8.095130771 | 1.90E-07 | 5.27E-05 | 0.000157663 | 0.06779661 | 13.32535885 |
| YPP | 5 | 74 | 8.067782356 | 3.98E-05 | 0.001700068 | 0.032411914 | 0.067567568 | 13.27707857 |
| KNSL | 2 | 4 | 7.829236056 | 0.000148685 | 0.001450707 | 0.024681703 | 0.5 | 183.2236842 |
| PDVP | 2 | 4 | 7.829236056 | 0.000148685 | 0.001450707 | 0.024681703 | 0.5 | 183.2236842 |
| SPPG | 2 | 4 | 7.829236056 | 0.000148685 | 0.001450707 | 0.024681703 | 0.5 | 183.2236842 |
| YPGR | 2 | 4 | 7.829236056 | 0.000148685 | 0.001450707 | 0.024681703 | 0.5 | 183.2236842 |
| YPGS | 2 | 4 | 7.829236056 | 0.000148685 | 0.001450707 | 0.024681703 | 0.5 | 183.2236842 |
| YPNN | 2 | 4 | 7.829236056 | 0.000148685 | 0.001450707 | 0.024681703 | 0.5 | 183.2236842 |
| KQP | 6 | 92 | 7.787163839 | 8.19E-06 | 0.000524979 | 0.006726409 | 0.065217391 | 12.78304774 |
| PPG | 7 | 112 | 7.462698679 | 1.92E-06 | 0.000386712 | 0.001591784 | 0.0625 | 12.21491228 |
| VKA | 6 | 99 | 7.236556295 | 1.25E-05 | 0.000743279 | 0.010243509 | 0.060606061 | 11.82088285 |
| PDL | 7 | 124 | 6.740502033 | 3.78E-06 | 0.000422214 | 0.003129817 | 0.056451613 | 10.96210076 |
| P.....H | 38 | 1183 | 6.71482748 | 4.78E-20 | 4.02E-18 | 4.02E-18 | 0.032121724 | 6.080786026 |
| PSS | 7 | 125 | 6.686578017 | 3.99E-06 | 0.000422214 | 0.003296952 | 0.056 | 10.86920161 |
| PLK | 7 | 129 | 6.479242264 | 4.91E-06 | 0.000430373 | 0.004050653 | 0.054263566 | 10.51283434 |
| PLA | 7 | 130 | 6.429401939 | 5.17E-06 | 0.000430373 | 0.004257236 | 0.053846154 | 10.42736414 |
| GVKA | 2 | 5 | 6.263388845 | 0.000246983 | 0.001690887 | 0.039270373 | 0.4 | 122.1491228 |
| PEGE | 2 | 5 | 6.263388845 | 0.000246983 | 0.001690887 | 0.039270373 | 0.4 | 122.1491228 |
| PPGG | 2 | 5 | 6.263388845 | 0.000246983 | 0.001690887 | 0.039270373 | 0.4 | 122.1491228 |
| QQYG | 2 | 5 | 6.263388845 | 0.000246983 | 0.001690887 | 0.039270373 | 0.4 | 122.1491228 |
| VKAG | 2 | 5 | 6.263388845 | 0.000246983 | 0.001690887 | 0.039270373 | 0.4 | 122.1491228 |
| VPVQ | 2 | 5 | 6.263388845 | 0.000246983 | 0.001690887 | 0.039270373 | 0.4 | 122.1491228 |
| YPPS | 2 | 5 | 6.263388845 | 0.000246983 | 0.001690887 | 0.039270373 | 0.4 | 122.1491228 |
| PEQ | 6 | 115 | 6.229731071 | 2.93E-05 | 0.001524463 | 0.023952187 | 0.052173913 | 10.08570739 |
| PHN | 7 | 136 | 6.145751853 | 6.95E-06 | 0.000524979 | 0.005721627 | 0.051470588 | 9.942370461 |
| P.....Q | 28 | 954 | 6.135439299 | 3.34E-14 | 9.35E-13 | 2.74E-12 | 0.029350105 | 5.540240991 |
| P...Q | 58 | 1916 | 6.073718305 | 3.81E-27 | 3.47E-25 | 3.47E-25 | 0.030271399 | 5.719576795 |
| QAG | 6 | 118 | 6.071348078 | 3.39E-05 | 0.001658742 | 0.027656983 | 0.050847458 | 9.815554511 |
| P.....Y | 23 | 796 | 6.040192439 | 8.58E-12 | 1.20E-10 | 6.78E-10 | 0.028894472 | 5.451674951 |
| QYG | 7 | 139 | 6.013109727 | 8.02E-06 | 0.000524979 | 0.006593177 | 0.050359712 | 9.716407496 |
| P....N | 36 | 1231 | 5.993709099 | 2.44E-17 | 7.47E-16 | 2.19E-15 | 0.029244517 | 5.519709315 |
| YPG | 6 | 121 | 5.920818787 | 3.90E-05 | 0.001700068 | 0.031805758 | 0.049586777 | 9.559496568 |
| NPG | 6 | 122 | 5.872287485 | 4.08E-05 | 0.001700068 | 0.033225819 | 0.049180328 | 9.477087114 |
| P....Q | 36 | 1327 | 5.560102412 | 2.42E-16 | 5.57E-15 | 2.16E-14 | 0.027128862 | 5.109258429 |
| AAG | 6 | 130 | 5.510915948 | 5.82E-05 | 0.002203116 | 0.047304833 | 0.046153846 | 8.865662139 |
| PVV | 6 | 130 | 5.510915948 | 5.82E-05 | 0.002203116 | 0.047304833 | 0.046153846 | 8.865662139 |
| P.....A | 21 | 798 | 5.501136364 | 3.64E-10 | 4.36E-09 | 2.84E-08 | 0.026315789 | 4.951991465 |
| PGA | 8 | 177 | 5.396753847 | 4.05E-06 | 0.000422214 | 0.003349327 | 0.04519774 | 8.673310495 |
| P....H | 44 | 1680 | 5.367778764 | 4.44E-19 | 2.04E-17 | 4.04E-17 | 0.026190476 | 4.927776348 |
| P..Q | 63 | 2388 | 5.251889902 | 9.60E-26 | 9.80E-24 | 9.80E-24 | 0.02638191 | 4.964770798 |
| PG | 80 | 3107 | 5.045319163 | 6.67E-31 | 7.73E-29 | 7.73E-29 | 0.02574831 | 4.842383461 |
| P.....N | 19 | 791 | 5.021264797 | 1.06E-08 | 1.11E-07 | 8.13E-07 | 0.024020228 | 4.509391192 |
| P.....V | 33 | 1382 | 4.991624457 | 5.55E-14 | 1.17E-12 | 4.50E-12 | 0.023878437 | 4.482121259 |

FIG. 63B

SLE vs. Other AI/non-AI mimic diseases - 684 Significant Peptides

| AA | n | n.lib | enrich | p | fdr | padj.holm | Pr_seqs.motif | PLR |
|---|---|---|---|---|---|---|---|---|
| P | 683 | 56321 | 2.359573513 | 1.19E-101 | 7.15E-101 | 7.15E-101 | 0.012126915 | 2.24921414 |
| G | 866 | 111145 | 1.516041633 | 1.21E-48 | 3.62E-48 | 6.03E-48 | 0.007791624 | 1.438820723 |
| Q | 436 | 60519 | 1.401773715 | 2.79E-15 | 5.58E-15 | 1.12E-14 | 0.007204349 | 1.329586178 |
| A | 370 | 57451 | 1.253104523 | 1.81E-07 | 2.72E-07 | 5.43E-07 | 0.006440271 | 1.187658996 |
| V | 401 | 68411 | 1.140516572 | 0.000129288 | 0.000155145 | 0.000258575 | 0.00586163 | 1.080321973 |
| K | 358 | 62082 | 1.122019729 | 0.001383794 | 0.001383794 | 0.001383794 | 0.005766567 | 1.062699743 |

FIG. 64A

SLE v Not (Not SLE = Other AI/non-AI mimic diseases + HC) – 2042 Significant peptides

| motif | n | n.lib | enrich | p | fdr | padj.holm | Pr_seqs.motif | PLR |
|---|---|---|---|---|---|---|---|---|
| YPPV | 3 | 4 | 10.45673816 | 1.46E-05 | 0.00281211 | 0.016799742 | 0.75 | 182.125857 |
| PSL | 22 | 119 | 10.1613147 | 1.99E-17 | 2.94E-14 | 2.94E-14 | 0.18487395 | 13.76896513 |
| PGG | 19 | 119 | 8.775680878 | 4.88E-14 | 3.60E-11 | 7.20E-11 | 0.159663866 | 11.53463761 |
| PGD | 17 | 111 | 8.4178295 | 2.07E-12 | 1.02E-09 | 3.05E-09 | 0.153153153 | 10.97921833 |
| PEGE | 3 | 5 | 8.365390532 | 3.60E-05 | 0.002985 | 0.041404854 | 0.6 | 91.0629285 |
| PLAE | 3 | 5 | 8.365390532 | 3.60E-05 | 0.002985 | 0.041404854 | 0.6 | 91.0629285 |
| PPLN | 3 | 5 | 8.365390532 | 3.60E-05 | 0.002985 | 0.041404854 | 0.6 | 91.0629285 |
| PSLA | 3 | 5 | 8.365390532 | 3.60E-05 | 0.002985 | 0.041404854 | 0.6 | 91.0629285 |
| PSLK | 3 | 5 | 8.365390532 | 3.60E-05 | 0.002985 | 0.041404854 | 0.6 | 91.0629285 |
| ASFQ | 4 | 7 | 7.967038601 | 1.92E-06 | 0.001111484 | 0.002221047 | 0.571428571 | 80.94482533 |
| PER | 16 | 114 | 7.714171926 | 3.57E-11 | 1.21E-08 | 5.26E-08 | 0.140350877 | 9.911611265 |
| PEQ | 16 | 115 | 7.64709217 | 4.08E-11 | 1.21E-08 | 6.02E-08 | 0.139130435 | 9.81149398 |
| PEL | 16 | 118 | 7.452674572 | 6.08E-11 | 1.50E-08 | 8.94E-08 | 0.13559322 | 9.522920628 |
| PDL | 16 | 124 | 7.092061287 | 1.30E-10 | 2.40E-08 | 1.91E-07 | 0.129032258 | 8.993869482 |
| PGH | 16 | 124 | 7.092061287 | 1.30E-10 | 2.40E-08 | 1.91E-07 | 0.129032258 | 8.993869482 |
| P.....Q | 98 | 954 | 6.927537353 | 3.60E-50 | 1.35E-48 | 2.67E-48 | 0.102725367 | 6.95028582 |
| PPG | 14 | 112 | 6.870434371 | 2.79E-09 | 3.43E-07 | 4.09E-06 | 0.125 | 8.672659857 |
| PPV | 15 | 124 | 6.648807456 | 1.22E-09 | 2.00E-07 | 1.79E-06 | 0.120967742 | 8.35439711 |
| PGV | 13 | 109 | 6.555276831 | 1.81E-08 | 1.70E-06 | 2.65E-05 | 0.119266055 | 8.220958823 |
| P....Q | 129 | 1327 | 6.433764437 | 1.16E-61 | 1.09E-59 | 1.09E-59 | 0.097211756 | 6.537071662 |
| PLA | 15 | 130 | 6.34193942 | 2.36E-09 | 3.17E-07 | 3.47E-06 | 0.115384615 | 7.918515522 |
| PLQ | 15 | 130 | 6.34193942 | 2.36E-09 | 3.17E-07 | 3.47E-06 | 0.115384615 | 7.918515522 |
| PPL | 14 | 122 | 6.307284013 | 8.58E-09 | 9.05E-07 | 1.26E-05 | 0.114754098 | 7.869635796 |
| P.....A | 74 | 798 | 6.253598626 | 2.74E-35 | 3.42E-34 | 1.92E-33 | 0.09273183 | 6.205024594 |
| P.....N | 73 | 791 | 6.223684258 | 1.07E-34 | 1.14E-33 | 7.37E-33 | 0.092288243 | 6.172324773 |
| ADAD | 4 | 9 | 6.196585579 | 6.75E-06 | 0.002570048 | 0.007792904 | 0.444444444 | 48.5668952 |
| ADD | 13 | 120 | 5.954376455 | 5.79E-08 | 3.72E-06 | 8.42E-05 | 0.108333333 | 7.375813523 |
| YPP | 8 | 74 | 5.941997294 | 2.07E-05 | 0.000478237 | 0.029301653 | 0.108108108 | 7.358620485 |
| NPG | 13 | 122 | 5.856763726 | 7.05E-08 | 4.34E-06 | 0.000102536 | 0.106557377 | 7.240477496 |
| PPS | 13 | 124 | 5.762299795 | 8.56E-08 | 5.06E-06 | 0.000124355 | 0.10483871 | 7.110018442 |
| PFQ | 12 | 115 | 5.735319127 | 2.80E-07 | 1.22E-05 | 0.00040498 | 0.104347826 | 7.072848816 |
| RQA | 10 | 97 | 5.666337626 | 3.04E-06 | 0.000106887 | 0.004364649 | 0.103092784 | 6.978002184 |
| PHN | 14 | 136 | 5.658004776 | 3.48E-08 | 2.45E-06 | 5.07E-05 | 0.102941176 | 6.966562836 |
| PVH | 12 | 117 | 5.637279484 | 3.39E-07 | 1.43E-05 | 0.00048878 | 0.102564103 | 6.938127886 |
| PPE | 13 | 127 | 5.626182477 | 1.14E-07 | 6.22E-06 | 0.000164879 | 0.102362205 | 6.922912693 |
| P.....H | 98 | 1183 | 5.586534771 | 5.02E-42 | 1.25E-40 | 3.66E-40 | 0.082840237 | 5.483359136 |
| PSRE | 4 | 10 | 5.576927021 | 1.11E-05 | 0.002570048 | 0.012805813 | 0.4 | 40.47241267 |
| P...Q | 163 | 1916 | 5.545249333 | 3.36E-68 | 3.50E-66 | 3.50E-66 | 0.085073069 | 5.64489726 |
| PLK | 13 | 129 | 5.538954842 | 1.37E-07 | 6.73E-06 | 0.000197875 | 0.100775194 | 6.803552129 |
| PPH | 13 | 130 | 5.496347497 | 1.50E-07 | 7.13E-06 | 0.000216565 | 0.1 | 6.745402111 |
| PSH | 13 | 132 | 5.413069505 | 1.79E-07 | 8.01E-06 | 0.000258934 | 0.098484848 | 6.632034009 |
| PVQ | 13 | 132 | 5.413069505 | 1.79E-07 | 8.01E-06 | 0.000258934 | 0.098484848 | 6.632034009 |
| LQA | 12 | 123 | 5.362290241 | 5.83E-07 | 2.33E-05 | 0.000840642 | 0.097560976 | 6.563093946 |
| ADA | 15 | 156 | 5.284949516 | 2.88E-08 | 2.13E-06 | 4.20E-05 | 0.096153846 | 6.458363724 |
| PSS | 12 | 125 | 5.276493597 | 6.94E-07 | 2.70E-05 | 0.000999804 | 0.096 | 6.446932991 |
| PVN | 11 | 115 | 5.257375867 | 2.08E-06 | 7.67E-05 | 0.00298522 | 0.095652174 | 6.421103933 |
| PEV | 12 | 126 | 5.234616664 | 7.56E-07 | 2.86E-05 | 0.001088592 | 0.095238095 | 6.390380947 |
| ADS | 10 | 106 | 5.185233488 | 6.78E-06 | 0.000187473 | 0.009664857 | 0.094339623 | 6.323814479 |
| P....N | 93 | 1231 | 5.000014502 | 5.14E-36 | 1.21E-34 | 4.68E-34 | 0.075548335 | 4.96124918 |
| YPG | 11 | 121 | 4.996679543 | 3.42E-06 | 0.000114069 | 0.004905712 | 0.090909091 | 6.0708619 |

FIG. 64B

SLE v Not (Not SLE = Other AI/non-AI mimic diseases + HC) – 2042 Significant peptides

| motif | n | n.lib | enrich | p | fdr | padj.holm | Pr_seqs.motif | PLR |
|---|---|---|---|---|---|---|---|---|
| P | 2120 | 56321 | 2.397104155 | 0 | 0 | 0 | 0.037641377 | 2.374536859 |
| G | 2336 | 111145 | 1.338456648 | 1.40E-76 | 5.61E-76 | 9.81E-76 | 0.02101759 | 1.303341948 |
| Q | 1255 | 60519 | 1.320606357 | 1.57E-30 | 4.17E-30 | 9.39E-30 | 0.020737289 | 1.285591874 |
| A | 1111 | 57451 | 1.231509787 | 1.86E-17 | 3.72E-17 | 9.31E-17 | 0.019338219 | 1.197147244 |
| K | 1063 | 62082 | 1.090407842 | 4.34E-06 | 5.78E-06 | 1.30E-05 | 0.017122515 | 1.057592914 |
| S | 1365 | 81297 | 1.069250674 | 3.30E-07 | 5.28E-07 | 1.32E-06 | 0.016790287 | 1.036722025 |
| V | 1084 | 68411 | 1.009078016 | 0.02355836 | 0.026923839 | 0.047116719 | 0.015845405 | 0.977440596 |

FIG. 65A

SLE vs. RA – 201 Significant Peptides

| motif | n | n.lib | enrich | p | fdr | padj.holm | Pr_seqs.motif | PLR |
|---|---|---|---|---|---|---|---|---|
| P.....H | 23 | 1183 | 9.975758161 | 3.35E-19 | 2.41E-17 | 2.41E-17 | 0.019442096 | 12.41029336 |
| YVHH | 2 | 4 | 8.037634409 | 1.30E-05 | 0.000194504 | 0.000454736 | 0.5 | 625.9104478 |
| PPG | 5 | 112 | 7.935716998 | 8.59E-07 | 0.000188102 | 0.000188102 | 0.044642857 | 29.24815176 |
| KQP | 4 | 92 | 7.728698293 | 1.24E-05 | 0.000707237 | 0.002685739 | 0.043478261 | 28.4504749 |
| RQP | 4 | 93 | 7.64559401 | 1.29E-05 | 0.000707237 | 0.002790194 | 0.043010753 | 28.13080664 |
| PHN | 5 | 136 | 6.535296351 | 2.24E-06 | 0.000244946 | 0.000487655 | 0.036764706 | 23.88971175 |
| P..H | 29 | 2698 | 6.457119438 | 3.67E-16 | 3.31E-14 | 3.31E-14 | 0.010748703 | 6.800825397 |
| P.....Y | 10 | 796 | 6.445991864 | 2.32E-07 | 8.34E-06 | 1.64E-05 | 0.012562814 | 7.963237249 |
| PPGG | 2 | 5 | 6.430107527 | 2.16E-05 | 0.000194504 | 0.000735516 | 0.4 | 417.2736318 |
| PVHW | 2 | 5 | 6.430107527 | 2.16E-05 | 0.000194504 | 0.000735516 | 0.4 | 417.2736318 |
| P...Y | 17 | 1544 | 6.250324188 | 2.44E-10 | 8.97E-09 | 2.10E-08 | 0.011010363 | 6.968223714 |
| P...W | 13 | 1214 | 6.121891425 | 3.13E-08 | 1.28E-06 | 2.53E-06 | 0.010708402 | 6.775050642 |
| PVH | 4 | 117 | 6.077267034 | 3.19E-05 | 0.001396245 | 0.006853716 | 0.034188034 | 22.15612204 |
| P.....W | 10 | 862 | 5.952447243 | 4.75E-07 | 1.14E-05 | 3.33E-05 | 0.011600928 | 7.346366758 |
| P.H | 31 | 3422 | 5.55478797 | 4.91E-15 | 4.57E-13 | 4.57E-13 | 0.00905903 | 5.721976963 |
| P....Y | 11 | 1138 | 5.52600636 | 9.60E-07 | 1.57E-05 | 7.49E-05 | 0.009666081 | 6.109152551 |
| KPPG | 2 | 6 | 5.358422939 | 3.24E-05 | 0.000194504 | 0.001037354 | 0.333333333 | 312.9552239 |
| PRWY | 2 | 6 | 5.358422939 | 3.24E-05 | 0.000194504 | 0.001037354 | 0.333333333 | 312.9552239 |
| P...H | 20 | 2271 | 4.999352732 | 3.09E-10 | 8.97E-09 | 2.63E-08 | 0.008806693 | 5.56117679 |
| PQY | 4 | 147 | 4.837008456 | 7.75E-05 | 0.002423978 | 0.016502971 | 0.027210884 | 17.50798455 |
| P....H | 14 | 1680 | 4.764087302 | 1.94E-07 | 5.30E-06 | 1.55E-05 | 0.008333333 | 5.259751662 |
| H..Y | 15 | 1948 | 4.62578106 | 3.43E-07 | 6.17E-06 | 2.95E-05 | 0.007700205 | 4.85703917 |
| HH | 18 | 2453 | 4.602873951 | 6.74E-08 | 2.29E-06 | 6.74E-06 | 0.007337954 | 4.626853413 |
| PFAP | 2 | 7 | 4.592933948 | 4.53E-05 | 0.000204028 | 0.001360189 | 0.285714286 | 250.3641791 |
| QVAP | 2 | 7 | 4.592933948 | 4.53E-05 | 0.000204028 | 0.001360189 | 0.285714286 | 250.3641791 |
| P..W | 17 | 2285 | 4.469361505 | 9.33E-08 | 2.80E-06 | 8.21E-06 | 0.007439825 | 4.691568612 |
| P....P | 9 | 1155 | 4.454730983 | 4.91E-06 | 0.000574802 | 0.003729206 | 0.007792208 | 4.915527077 |
| P...W | 13 | 1694 | 4.356431249 | 1.75E-06 | 2.60E-05 | 0.000145238 | 0.007674144 | 4.840473421 |
| P...N | 13 | 1698 | 4.346168749 | 1.79E-06 | 2.60E-05 | 0.000147189 | 0.007656066 | 4.828982683 |
| Y.....H | 10 | 1186 | 4.326314944 | 7.84E-06 | 0.000112866 | 0.000532979 | 0.008431703 | 5.322367753 |
| P..Q | 17 | 2388 | 4.276587537 | 1.72E-07 | 3.87E-06 | 1.50E-05 | 0.007118928 | 4.487759431 |
| YP | 15 | 2252 | 4.178082372 | 2.63E-06 | 5.36E-05 | 0.000257466 | 0.006660746 | 4.196985568 |
| Y.H | 23 | 3400 | 4.147961499 | 3.98E-09 | 1.23E-07 | 3.63E-07 | 0.006764706 | 4.262937607 |
| P..P | 15 | 2184 | 4.125925598 | 1.39E-06 | 2.09E-05 | 0.000118167 | 0.006868132 | 4.328564646 |
| P.G | 36 | 5372 | 4.109152833 | 2.25E-13 | 1.05E-11 | 2.07E-11 | 0.006701415 | 4.22278413 |
| HG | 34 | 5251 | 4.061542704 | 3.48E-12 | 3.55E-10 | 3.55E-10 | 0.006474957 | 4.079155688 |
| PG | 20 | 3107 | 4.037781998 | 1.04E-07 | 2.64E-06 | 1.03E-05 | 0.006437078 | 4.055137336 |
| HWPQ | 2 | 8 | 4.018817204 | 6.04E-05 | 0.000214816 | 0.001691017 | 0.25 | 208.6368159 |
| PAGG | 2 | 8 | 4.018817204 | 6.04E-05 | 0.000214816 | 0.001691017 | 0.25 | 208.6368159 |
| HHG | 4 | 177 | 4.017176514 | 0.000158278 | 0.003695277 | 0.033396644 | 0.02259887 | 14.47191787 |
| P.N | 18 | 2749 | 4.014981633 | 3.03E-07 | 5.63E-06 | 2.70E-05 | 0.006547836 | 4.125370948 |
| P....G | 31 | 4531 | 3.911367195 | 1.23E-12 | 1.01E-10 | 1.01E-10 | 0.006841757 | 4.311827529 |
| PQ | 24 | 3855 | 3.905179352 | 1.06E-08 | 5.42E-07 | 1.07E-06 | 0.006225681 | 3.921130448 |
| P....Q | 9 | 1327 | 3.877328022 | 0.000138637 | 0.001154003 | 0.010259119 | 0.006782216 | 4.274047064 |
| P.....Q | 7 | 954 | 3.764891684 | 0.000414797 | 0.00497756 | 0.027791379 | 0.007337526 | 4.626581979 |
| P.Q | 18 | 2932 | 3.764387623 | 7.52E-07 | 1.16E-05 | 6.61E-05 | 0.006139154 | 3.86629652 |
| H....H | 11 | 1672 | 3.761121554 | 3.40E-05 | 0.000464314 | 0.002616016 | 0.006578947 | 4.145102303 |
| P....A | 8 | 1254 | 3.647148173 | 0.000481139 | 0.003034877 | 0.033679734 | 0.006379585 | 4.018686663 |
| FHG | 4 | 196 | 3.627756342 | 0.000233472 | 0.004433919 | 0.048795594 | 0.020408163 | 13.039801 |
| HQGY | 2 | 9 | 3.572281959 | 7.76E-05 | 0.000214816 | 0.002016883 | 0.222222222 | 178.8315565 |

FIG. 65B

SLE vs. RA – 201 Significant Peptides

| AA | n | n.lib | enrich | p | fdr | padj.holm | Pr_seqs.motif | PLR |
|---|---|---|---|---|---|---|---|---|
| P | 214 | 56321 | 2.509525227 | 6.74E-37 | 5.39E-36 | 5.39E-36 | 0.003799648 | 2.3873106 |
| H | 184 | 65939 | 1.842992705 | 2.14E-17 | 5.72E-17 | 1.29E-16 | 0.002790458 | 1.751464107 |
| G | 272 | 111145 | 1.616319169 | 5.31E-20 | 2.12E-19 | 3.71E-19 | 0.002447254 | 1.535519394 |
| Q | 115 | 60519 | 1.255030404 | 0.002905917 | 0.005811834 | 0.014529584 | 0.00190023 | 1.191637996 |
| Y | 105 | 56760 | 1.221785768 | 0.010677387 | 0.017083818 | 0.042709546 | 0.001849894 | 1.160014068 |

FIG. 66A

SLE vs. OA – 455 Significant Peptides

| motif | n | n.lib | enrich | p | fdr | padj.holm | Pr_seqs.motif | PLR |
|---|---|---|---|---|---|---|---|---|
| RQA | 8 | 97 | 11.15455536 | 1.71E-09 | 2.22E-07 | 8.82E-07 | 0.082474227 | 24.80385233 |
| PDES | 2 | 3 | 10.31424376 | 3.25E-05 | 0.000505757 | 0.002830108 | 0.666666667 | 551.8857143 |
| PDL | 9 | 124 | 9.816458497 | 5.16E-10 | 8.92E-08 | 2.67E-07 | 0.072580645 | 21.59552795 |
| PLAE | 3 | 5 | 9.282819383 | 3.56E-07 | 3.24E-05 | 3.24E-05 | 0.6 | 413.9142857 |
| P.....N | 25 | 791 | 8.89149673 | 1.10E-17 | 3.97E-16 | 7.82E-16 | 0.031605563 | 9.005967922 |
| PDE | 8 | 124 | 8.725740886 | 1.20E-08 | 1.25E-06 | 6.19E-06 | 0.064516129 | 19.03054187 |
| RQP | 6 | 93 | 8.725740886 | 8.24E-07 | 4.75E-05 | 0.000420899 | 0.064516129 | 19.03054187 |
| P.....Q | 28 | 954 | 8.256975663 | 8.33E-19 | 6.00E-17 | 6.00E-17 | 0.029350105 | 8.343844492 |
| QPK | 10 | 167 | 8.098741541 | 3.75E-10 | 8.92E-08 | 1.94E-07 | 0.05988024 | 17.57597816 |
| PEL | 7 | 118 | 8.023244798 | 1.76E-07 | 1.31E-05 | 9.04E-05 | 0.059322034 | 17.4018018 |
| PDDF | 2 | 4 | 7.735682819 | 6.49E-05 | 0.00053704 | 0.005388105 | 0.5 | 275.9428571 |
| QRRA | 2 | 4 | 7.735682819 | 6.49E-05 | 0.00053704 | 0.005388105 | 0.5 | 275.9428571 |
| RQAP | 2 | 4 | 7.735682819 | 6.49E-05 | 0.00053704 | 0.005388105 | 0.5 | 275.9428571 |
| P....Q | 34 | 1327 | 7.456141625 | 3.59E-20 | 3.05E-18 | 3.05E-18 | 0.025621703 | 7.256038007 |
| KQP | 5 | 92 | 7.350488247 | 1.60E-05 | 0.000609861 | 0.008133307 | 0.054347826 | 15.85878489 |
| RNP | 5 | 93 | 7.271450739 | 1.69E-05 | 0.000609861 | 0.008554746 | 0.053763441 | 15.67857143 |
| P....P | 28 | 1155 | 7.054759313 | 2.85E-16 | 8.09E-15 | 2.37E-14 | 0.024242424 | 6.855723159 |
| P....A | 30 | 1254 | 6.961933533 | 3.56E-17 | 1.51E-15 | 2.99E-15 | 0.023923445 | 6.763305322 |
| PLA | 6 | 130 | 6.242260788 | 5.80E-06 | 0.000250804 | 0.002945862 | 0.046153846 | 13.35207373 |
| DESA | 2 | 5 | 6.188546256 | 0.000107957 | 0.000818675 | 0.008636568 | 0.4 | 183.9619048 |
| P.....P | 16 | 782 | 5.756050261 | 4.07E-09 | 5.86E-08 | 2.77E-07 | 0.020460358 | 5.76381947 |
| PGG | 5 | 119 | 5.682730409 | 5.53E-05 | 0.001594187 | 0.027755449 | 0.042016807 | 12.10275689 |
| P.....A | 16 | 798 | 5.640640732 | 5.40E-09 | 6.48E-08 | 3.62E-07 | 0.020050125 | 5.64588966 |
| P.....V | 27 | 1382 | 5.496257472 | 6.12E-14 | 1.47E-12 | 4.29E-12 | 0.019536903 | 5.498492356 |
| P....N | 23 | 1231 | 5.437207879 | 2.30E-11 | 3.90E-10 | 1.86E-09 | 0.018683997 | 5.253878903 |
| AAG | 5 | 130 | 5.20188399 | 8.41E-05 | 0.002181391 | 0.042030662 | 0.038461538 | 11.03771429 |
| KNGG | 2 | 6 | 5.15712188 | 0.00016158 | 0.001027003 | 0.012764807 | 0.333333333 | 137.9714286 |
| RQPK | 2 | 6 | 5.15712188 | 0.00016158 | 0.001027003 | 0.012764807 | 0.333333333 | 137.9714286 |
| PYP | 6 | 158 | 5.136037357 | 1.76E-05 | 0.000609861 | 0.008901144 | 0.037974684 | 10.8924812 |
| PQD | 10 | 268 | 5.046603871 | 3.48E-08 | 3.01E-06 | 1.79E-05 | 0.037313433 | 10.69545958 |
| QNK | 8 | 220 | 4.918144863 | 9.84E-07 | 5.11E-05 | 0.000501817 | 0.036363636 | 10.41293801 |
| P..Q | 38 | 2388 | 4.648599089 | 6.52E-15 | 2.78E-13 | 6.19E-13 | 0.015912898 | 4.462054711 |
| PAD | 9 | 266 | 4.576093435 | 3.81E-07 | 2.47E-05 | 0.000194907 | 0.033834586 | 9.663368538 |
| QKG | 14 | 421 | 4.497590908 | 3.00E-10 | 8.92E-08 | 1.56E-07 | 0.033254157 | 9.491891892 |
| P...A | 24 | 1582 | 4.468141221 | 9.89E-10 | 3.63E-08 | 9.50E-08 | 0.01517067 | 4.250724372 |
| KWPN | 2 | 7 | 4.420390183 | 0.000225715 | 0.001027003 | 0.017380046 | 0.285714286 | 110.3771429 |
| PEQE | 2 | 7 | 4.420390183 | 0.000225715 | 0.001027003 | 0.017380046 | 0.285714286 | 110.3771429 |
| PQAD | 2 | 7 | 4.420390183 | 0.000225715 | 0.001027003 | 0.017380046 | 0.285714286 | 110.3771429 |
| QQNK | 2 | 7 | 4.420390183 | 0.000225715 | 0.001027003 | 0.017380046 | 0.285714286 | 110.3771429 |
| QRGL | 2 | 7 | 4.420390183 | 0.000225715 | 0.001027003 | 0.017380046 | 0.285714286 | 110.3771429 |
| RARA | 2 | 7 | 4.420390183 | 0.000225715 | 0.001027003 | 0.017380046 | 0.285714286 | 110.3771429 |
| Q....K | 21 | 1434 | 4.261635464 | 1.16E-08 | 1.64E-07 | 9.26E-07 | 0.014644351 | 4.101061571 |
| P...N | 24 | 1698 | 4.16289718 | 3.83E-09 | 7.43E-08 | 3.56E-07 | 0.014134276 | 3.956169995 |
| R...K | 26 | 1862 | 4.112593643 | 1.12E-09 | 3.63E-08 | 1.07E-07 | 0.01396348 | 3.907687519 |
| RQ | 34 | 2445 | 4.02120571 | 1.26E-11 | 6.80E-10 | 1.35E-09 | 0.01390593 | 3.891355099 |
| R.....K | 13 | 910 | 4.018956522 | 5.91E-06 | 4.26E-05 | 0.000372356 | 0.014285714 | 3.999171843 |
| P...Q | 26 | 1916 | 3.996685471 | 2.01E-09 | 4.87E-08 | 1.89E-07 | 0.013569937 | 3.796039305 |
| R..K | 33 | 2434 | 3.960647436 | 2.49E-11 | 4.78E-10 | 2.29E-09 | 0.013557929 | 3.792634022 |
| P..P | 29 | 2184 | 3.878985735 | 6.23E-10 | 8.55E-09 | 5.61E-08 | 0.013278388 | 3.713384156 |
| GKAG | 2 | 8 | 3.86784141 | 0.000300292 | 0.001062335 | 0.021320753 | 0.25 | 91.98095238 |

FIG. 66B

SLE vs. OA – 455 Significant Peptides

| AA | n | n.lib | enrich | p | fdr | padj.holm | Pr_seqs.motif | PLR |
|---|---|---|---|---|---|---|---|---|
| P | 464 | 56321 | 2.421917695 | 4.76E-73 | 3.33E-72 | 3.33E-72 | 0.00823849 | 2.292237065 |
| K | 327 | 62082 | 1.548437962 | 2.16E-17 | 5.04E-17 | 1.08E-16 | 0.005267227 | 1.461149936 |
| Q | 309 | 60519 | 1.5009924 | 1.12E-14 | 1.96E-14 | 4.48E-14 | 0.005105835 | 1.416149192 |
| G | 551 | 111145 | 1.457382082 | 2.24E-27 | 7.86E-27 | 1.35E-26 | 0.004957488 | 1.374798943 |
| A | 257 | 57451 | 1.315065208 | 3.58E-07 | 5.01E-07 | 1.07E-06 | 0.004473377 | 1.239943251 |
| N | 239 | 59481 | 1.181221645 | 0.000841749 | 0.000982041 | 0.001683499 | 0.00401809 | 1.113236266 |

FIG. 67A

SLE vs. Fibromyalgia – 464 Significant Peptides

| motif | n | n.lib | enrich | p | fdr | padj.holm | Pr_seqs.motif | PLR |
|---|---|---|---|---|---|---|---|---|
| PPD | 19 | 127 | 20.88522016 | 9.61E-25 | 5.70E-22 | 5.70E-22 | 0.149606299 | 47.60047494 |
| PLDE | 2 | 2 | 16.62579058 | 1.41E-05 | 0.000938846 | 0.001863574 | 1 | Inf |
| PGD | 11 | 111 | 13.83435399 | 6.75E-13 | 2.00E-10 | 4.00E-10 | 0.099099099 | 29.76282328 |
| P.....N | 42 | 791 | 13.13845236 | 1.26E-33 | 6.95E-32 | 6.95E-32 | 0.053097345 | 15.17221238 |
| PDD | 9 | 112 | 11.21795425 | 5.59E-10 | 6.63E-08 | 3.30E-07 | 0.080357143 | 23.64213676 |
| PPGD | 2 | 3 | 11.08386039 | 4.22E-05 | 0.001230018 | 0.005492214 | 0.666666667 | 541.1422414 |
| PDE | 9 | 124 | 10.13234578 | 1.39E-09 | 1.18E-07 | 8.14E-07 | 0.072580645 | 21.17513118 |
| P.....Q | 37 | 954 | 9.596762636 | 4.80E-25 | 1.32E-23 | 2.59E-23 | 0.038784067 | 10.91726441 |
| P....Q | 44 | 1327 | 8.526836153 | 7.51E-27 | 5.63E-25 | 5.63E-25 | 0.033157498 | 9.279134303 |
| P.....A | 27 | 798 | 8.37205893 | 3.33E-17 | 4.45E-16 | 1.73E-15 | 0.033834586 | 9.475253254 |
| PDDF | 2 | 4 | 8.312895292 | 8.43E-05 | 0.001230018 | 0.010872623 | 0.5 | 270.5711207 |
| PDEV | 2 | 4 | 8.312895292 | 8.43E-05 | 0.001230018 | 0.010872623 | 0.5 | 270.5711207 |
| PGGE | 2 | 4 | 8.312895292 | 8.43E-05 | 0.001230018 | 0.010872623 | 0.5 | 270.5711207 |
| PKEE | 2 | 4 | 8.312895292 | 8.43E-05 | 0.001230018 | 0.010872623 | 0.5 | 270.5711207 |
| P....P | 37 | 1155 | 8.238078085 | 2.59E-22 | 9.70E-21 | 1.91E-20 | 0.032034632 | 8.954500416 |
| P.D | 146 | 4787 | 8.087337243 | 1.29E-81 | 1.09E-79 | 1.09E-79 | 0.030499269 | 8.511825818 |
| P....N | 37 | 1231 | 7.729472126 | 2.14E-21 | 5.36E-20 | 1.56E-19 | 0.030056864 | 8.384532216 |
| PPE | 7 | 127 | 7.694554797 | 6.22E-07 | 3.69E-05 | 0.000363176 | 0.05511811 | 15.78331537 |
| P.....P | 24 | 782 | 7.59409267 | 1.54E-14 | 1.21E-13 | 7.56E-13 | 0.030690537 | 8.566895642 |
| PPG | 6 | 112 | 7.478636167 | 4.69E-06 | 0.000214117 | 0.002727192 | 0.053571429 | 15.31534645 |
| P....A | 36 | 1254 | 7.382630431 | 3.22E-20 | 6.03E-19 | 2.32E-18 | 0.028708134 | 7.997175981 |
| PP | 58 | 2171 | 7.08448628 | 3.01E-30 | 1.37E-28 | 2.71E-28 | 0.026715799 | 7.426940369 |
| PRD | 13 | 259 | 7.007010463 | 3.33E-11 | 4.93E-09 | 1.96E-08 | 0.05019305 | 14.29847386 |
| P..D | 130 | 4989 | 6.874721013 | 6.13E-65 | 4.72E-63 | 4.72E-63 | 0.026057326 | 7.238988617 |
| PHRD | 2 | 5 | 6.650316233 | 0.000140121 | 0.001230018 | 0.017375045 | 0.4 | 180.3807471 |
| PLAE | 2 | 5 | 6.650316233 | 0.000140121 | 0.001230018 | 0.017375045 | 0.4 | 180.3807471 |
| PPDE | 2 | 5 | 6.650316233 | 0.000140121 | 0.001230018 | 0.017375045 | 0.4 | 180.3807471 |
| PPDN | 2 | 5 | 6.650316233 | 0.000140121 | 0.001230018 | 0.017375045 | 0.4 | 180.3807471 |
| PPEE | 2 | 5 | 6.650316233 | 0.000140121 | 0.001230018 | 0.017375045 | 0.4 | 180.3807471 |
| PND | 14 | 299 | 6.536511433 | 1.49E-11 | 2.94E-09 | 8.78E-09 | 0.046822742 | 13.29121295 |
| PPR | 6 | 130 | 6.443132698 | 1.10E-05 | 0.000409431 | 0.006385188 | 0.046153846 | 13.092151 |
| PQD | 12 | 268 | 6.250800379 | 6.92E-10 | 6.84E-08 | 4.07E-07 | 0.044776119 | 12.68302128 |
| PD | 72 | 3098 | 6.162987352 | 2.04E-33 | 1.86E-31 | 1.86E-31 | 0.023240801 | 6.437911662 |
| P.....V | 34 | 1382 | 6.087546307 | 4.05E-17 | 4.45E-16 | 2.06E-15 | 0.024602026 | 6.824494142 |
| P.....K | 25 | 1037 | 5.965305034 | 8.83E-13 | 4.86E-12 | 4.06E-11 | 0.024108004 | 6.684069187 |
| P...D | 95 | 4191 | 5.9447121 | 9.44E-43 | 6.71E-41 | 6.71E-41 | 0.022667621 | 6.275453239 |
| P...N | 38 | 1698 | 5.869090321 | 9.49E-18 | 3.25E-16 | 6.64E-16 | 0.02237927 | 6.193796739 |
| PAP | 7 | 170 | 5.748285054 | 4.35E-06 | 0.000214117 | 0.002529282 | 0.041176471 | 11.61961868 |
| P.....H | 27 | 1183 | 5.647424367 | 3.87E-13 | 2.37E-12 | 1.82E-11 | 0.022823331 | 6.319567698 |
| PHDQ | 2 | 6 | 5.541930194 | 0.000209656 | 0.001230018 | 0.024949031 | 0.333333333 | 135.2855603 |
| PPDL | 2 | 6 | 5.541930194 | 0.000209656 | 0.001230018 | 0.024949031 | 0.333333333 | 135.2855603 |
| PPDR | 2 | 6 | 5.541930194 | 0.000209656 | 0.001230018 | 0.024949031 | 0.333333333 | 135.2855603 |
| PPRD | 2 | 6 | 5.541930194 | 0.000209656 | 0.001230018 | 0.024949031 | 0.333333333 | 135.2855603 |
| PRDV | 2 | 6 | 5.541930194 | 0.000209656 | 0.001230018 | 0.024949031 | 0.333333333 | 135.2855603 |
| PRQD | 2 | 6 | 5.541930194 | 0.000209656 | 0.001230018 | 0.024949031 | 0.333333333 | 135.2855603 |
| P...Q | 40 | 1916 | 5.475066127 | 1.37E-17 | 3.25E-16 | 9.46E-16 | 0.020876827 | 5.769107051 |
| P...P | 31 | 1486 | 5.471013252 | 5.86E-14 | 8.33E-13 | 3.93E-12 | 0.020861373 | 5.764745527 |
| P..N | 48 | 2317 | 5.465632583 | 1.03E-20 | 2.64E-19 | 7.71E-19 | 0.020716444 | 5.723849182 |
| PKD | 10 | 264 | 5.287924563 | 8.66E-08 | 6.42E-06 | 5.07E-05 | 0.037878788 | 10.65240633 |
| P....H | 33 | 1680 | 5.051389096 | 5.33E-14 | 5.00E-13 | 3.63E-12 | 0.019642857 | 5.421279285 |

FIG. 67B

SLE vs. Fibromyalgia – 464 Significant Peptides

| AA | n | n.lib | enrich | p | fdr | padj.holm | Pr_seqs.motif | PLR |
|---|---|---|---|---|---|---|---|---|
| P | 614 | 56321 | 2.920526074 | 1.66E-131 | 9.98E-131 | 9.98E-131 | 0.010901795 | 2.982222487 |
| D | 593 | 98037 | 1.620420595 | 3.66E-40 | 1.10E-39 | 1.83E-39 | 0.006048737 | 1.646573156 |
| G | 451 | 111145 | 1.087050414 | 0.000125052 | 0.000250103 | 0.000500206 | 0.004057762 | 1.102386538 |

FIG. 68A

SLE vs. Sjögren's – Top 500 peptides

| motif | n | n.lib | enrich | p | fdr | padj.holm | Pr_seqs.motif | PLR |
|---|---|---|---|---|---|---|---|---|
| ALHW | 2 | 4 | 8.235423381 | 0.000121098 | 0.00082934 | 0.023735274 | 0.5 | 251.018 |
| WSHW | 2 | 4 | 8.235423381 | 0.000121098 | 0.00082934 | 0.023735274 | 0.5 | 251.018 |
| YVHH | 2 | 4 | 8.235423381 | 0.000121098 | 0.00082934 | 0.023735274 | 0.5 | 251.018 |
| H.....H | 50 | 1157 | 8.11088305 | 4.65E-30 | 5.16E-28 | 5.16E-28 | 0.043215212 | 11.33775971 |
| H..H | 84 | 2652 | 6.961124155 | 9.89E-43 | 9.69E-41 | 9.69E-41 | 0.031674208 | 8.210869159 |
| H....H | 55 | 1672 | 6.723054398 | 3.71E-28 | 4.08E-26 | 4.08E-26 | 0.032894737 | 8.538027211 |
| HHF | 14 | 235 | 6.666661592 | 5.32E-12 | 4.01E-10 | 3.05E-09 | 0.059574468 | 15.90159276 |
| HQFQ | 2 | 5 | 6.588338705 | 0.000201224 | 0.00116607 | 0.038031419 | 0.4 | 167.3453333 |
| QYHY | 2 | 5 | 6.588338705 | 0.000201224 | 0.00116607 | 0.038031419 | 0.4 | 167.3453333 |
| HFH | 9 | 158 | 6.374317028 | 4.82E-08 | 1.75E-06 | 2.72E-05 | 0.056962025 | 15.16216107 |
| H.H | 83 | 2930 | 6.307002126 | 3.20E-39 | 1.50E-37 | 2.98E-37 | 0.028327645 | 7.318051985 |
| H...H | 59 | 2080 | 6.078459459 | 1.62E-27 | 8.41E-26 | 1.67E-25 | 0.028365385 | 7.328086096 |
| WHY | 9 | 167 | 6.030790961 | 7.76E-08 | 2.50E-06 | 4.37E-05 | 0.053892216 | 14.29849367 |
| HRH | 15 | 279 | 6.016380469 | 4.07E-12 | 3.93E-10 | 2.34E-09 | 0.053763441 | 14.26238636 |
| H...F | 76 | 2708 | 6.014088021 | 9.70E-35 | 1.01E-32 | 1.01E-32 | 0.028064993 | 7.248240122 |
| HF | 165 | 6250 | 5.992626513 | 3.46E-73 | 3.01E-71 | 3.01E-71 | 0.0264 | 6.806568611 |
| VHH | 5 | 95 | 5.889719827 | 7.08E-05 | 0.000830735 | 0.037658586 | 0.052631579 | 13.94544444 |
| H.....F | 56 | 1803 | 5.829399163 | 2.10E-26 | 1.17E-24 | 2.31E-24 | 0.031059346 | 8.046369777 |
| HFG | 44 | 846 | 5.82010139 | 5.15E-32 | 2.99E-29 | 2.99E-29 | 0.052009456 | 13.7715611 |
| AHH | 7 | 137 | 5.717757205 | 3.10E-06 | 7.24E-05 | 0.001725216 | 0.051094891 | 13.51635385 |
| HHH | 5 | 98 | 5.709422282 | 8.21E-05 | 0.000898028 | 0.043328322 | 0.051020408 | 13.4955914 |
| RHF | 35 | 696 | 5.627390352 | 2.63E-25 | 7.63E-23 | 1.52E-22 | 0.050287356 | 13.29142209 |
| H.F | 105 | 4184 | 5.587404697 | 1.43E-44 | 1.35E-42 | 1.35E-42 | 0.025095602 | 6.461605786 |
| HH | 60 | 2453 | 5.552224097 | 8.83E-26 | 1.28E-24 | 7.24E-24 | 0.024459845 | 6.293806937 |
| Y.....H | 35 | 1186 | 5.538789361 | 2.24E-16 | 8.30E-15 | 2.45E-14 | 0.029510961 | 7.633040834 |
| W...H | 55 | 2136 | 5.517804244 | 8.53E-24 | 2.96E-22 | 8.70E-22 | 0.025749064 | 6.634305622 |
| HFV | 8 | 167 | 5.360703076 | 9.98E-07 | 2.76E-05 | 0.000558635 | 0.047904192 | 12.62983648 |
| H.Y | 63 | 2633 | 5.327239176 | 3.22E-26 | 7.57E-25 | 2.93E-24 | 0.023927079 | 6.153359533 |
| H..F | 79 | 3271 | 5.307868569 | 2.47E-32 | 1.21E-30 | 2.40E-30 | 0.024151636 | 6.212538221 |
| H...Y | 40 | 1635 | 5.242604333 | 5.66E-17 | 1.18E-15 | 5.66E-15 | 0.024464832 | 6.295122257 |
| Y.H | 80 | 3400 | 5.238700561 | 2.05E-32 | 6.43E-31 | 1.89E-30 | 0.023529412 | 6.048626506 |
| HY | 65 | 2865 | 5.149938169 | 4.86E-26 | 8.46E-25 | 4.03E-24 | 0.022687609 | 5.827203571 |
| HLY | 11 | 246 | 5.003867658 | 1.95E-08 | 8.10E-07 | 1.11E-05 | 0.044715447 | 11.74977872 |
| VPH | 8 | 181 | 4.946063059 | 1.82E-06 | 4.80E-05 | 0.001018743 | 0.044198895 | 11.60776879 |
| Y..H | 59 | 2662 | 4.870993767 | 1.05E-22 | 3.41E-21 | 1.00E-20 | 0.022163787 | 5.689612755 |
| HHL | 11 | 259 | 4.752708278 | 3.31E-08 | 1.28E-06 | 1.87E-05 | 0.042471042 | 11.1338629 |
| YHY | 6 | 143 | 4.695301121 | 4.79E-05 | 0.000631079 | 0.02570884 | 0.041958042 | 10.99348905 |
| P...H | 49 | 2271 | 4.623637672 | 2.83E-18 | 7.36E-17 | 2.86E-16 | 0.021576398 | 5.53550045 |
| HYH | 7 | 172 | 4.554260099 | 1.37E-05 | 0.000234456 | 0.007517952 | 0.040697674 | 10.64924848 |
| HYG | 6 | 148 | 4.536676083 | 5.80E-05 | 0.000729624 | 0.031004811 | 0.040540541 | 10.60639437 |
| HVH | 7 | 173 | 4.527934896 | 1.43E-05 | 0.000236451 | 0.007790661 | 0.040462428 | 10.58509639 |
| H....F | 50 | 2291 | 4.460516231 | 2.92E-18 | 1.61E-16 | 3.18E-16 | 0.021824531 | 5.600580098 |
| YRH | 16 | 404 | 4.431868385 | 7.55E-11 | 3.98E-09 | 4.30E-08 | 0.03960396 | 10.35125773 |
| Y...H | 45 | 2192 | 4.399231453 | 3.96E-16 | 6.87E-15 | 3.92E-14 | 0.020529197 | 5.261206334 |
| FHRH | 4 | 15 | 4.392225803 | 5.40E-07 | 3.05E-05 | 0.000120472 | 0.266666667 | 91.27927273 |
| NRH | 20 | 513 | 4.362755428 | 4.54E-13 | 5.27E-11 | 2.62E-10 | 0.038986355 | 10.183286 |
| HLW | 8 | 207 | 4.324818424 | 4.92E-06 | 9.83E-05 | 0.002713126 | 0.038647343 | 10.09117588 |
| P....H | 35 | 1680 | 4.257934452 | 1.16E-12 | 4.27E-11 | 1.26E-10 | 0.020833333 | 5.340808511 |
| W....H | 33 | 1602 | 4.210092492 | 6.81E-12 | 1.50E-10 | 7.21E-10 | 0.020599251 | 5.279537285 |
| HAF | 6 | 160 | 4.196425377 | 8.91E-05 | 0.000957322 | 0.046971504 | 0.0375 | 9.779922078 |

FIG. 68B

SLE vs. Sjögren's

| motif | n | n.lib | enrich | p | fdr | padj.holm | Pr_seqs.motif | PLR |
|---|---|---|---|---|---|---|---|---|
| H | 850 | 65939 | 2.978885644 | 1.32E-191 | 9.27E-191 | 9.27E-191 | 0.012890702 | 3.278054664 |
| Y | 360 | 56760 | 1.465673975 | 3.09E-15 | 7.21E-15 | 1.54E-14 | 0.006342495 | 1.602242553 |
| F | 478 | 75858 | 1.456142141 | 9.83E-21 | 3.44E-20 | 5.90E-20 | 0.006301247 | 1.591756487 |
| W | 325 | 58364 | 1.286813399 | 8.90E-08 | 1.56E-07 | 3.56E-07 | 0.005568501 | 1.40562122 |
| P | 312 | 56321 | 1.280151882 | 2.90E-07 | 4.06E-07 | 8.71E-07 | 0.005539674 | 1.39830413 |

SLE vs. ...

FIG. 75A

SLE v Healthy
AKAP12|52~~11083.0
RBM34|41~~10272.0
H2AFY|14~~10182.0
TEX13D|65~~9915.0
ZFHX4|192~~9846.0
SRP72|65~~9814.14285714
SRPRA|16~~9727.0
BRD2|58~~9679.0
EIF5B|14~~9671.0
YY1|17~~9574.28571429
HMGN2|4~~9546.57142857
PCDH1|90~~9420.85714286
H2AFY2|13~~9346.85714286
RRBP1|62~~9322.0
HIST1H1D|19~~9290.0
MLLT1|29~~9273.0
ARHGAP30|0~~9252.0
TADA1|9~~9230.0
FAM193B|63~~9079.0
MSR1|34~~9063.0
FER1L6|122~~9030.0
MYBBP1A|127~~9015.0
ARSJ|57~~8993.0
LAMA4|142~~8951.14285714
CDCA2|56~~8934.0
HMGA2|5~~8854.0
TCF25|12~~8835.0
HIST1H1T|16~~8825.57142857
ZNF706|1~~8793.0
H2AFY|13~~8725.0
SMKR1|0~~8720.0
XPC|38~~8693.0
SPEF2|96~~8677.0
CXCL9|9~~8649.0
CCDC153|0~~8643.0
RPL4|38~~8638.0
EEF1D|13~~8624.0
COPS7A|25~~8619.0
SSB|34~~8559.0

FIG. 75B

SLE v Other AI/non-AI mimic diseases
ARFGAP2|21~~8604.0
MYBBP1A|127~~8307.0
PCDHGA2|91~~8268.0
NOLC1|50~~8225.0
C17orf49|9~~8121.0
AKAP12|52~~8119.0
HMGN2|4~~8068.0
SRPRA|16~~8047.42857143
TEX13D|65~~8018.0
ARFGAP2|22~~8005.0
HIST1H1D|19~~7982.0
TADA1|9~~7937.0
COL11A1|152~~7866.0
HIST1H1E|2~~7842.0
BRD2|58~~7805.0
SSB|34~~7793.0
PDCD4|10~~7772.85714286
H2AFY|14~~7771.0
PCDHGB6|91~~7760.0
HIST1H1C|17~~7750.0
CIC|207~~7740.0
EIF5B|14~~7740.0
PCDH1|90~~7721.85714286
HIST1H1C|2~~7717.0
MSR1|34~~7715.0
CKAP5|54~~7702.0
HMGA2|5~~7640.0
AMMECR1L|1~~7624.0
HIST1H1B|16~~7616.0
HMGN4|4~~7604.0
YY1|17~~7571.71428571
RPL4|37~~7535.0
ZFHX4|192~~7518.0
SOX11|17~~7504.28571429
RBBP5|47~~7493.57142857
RRBP1|62~~7452.42857143
CDYL2|11~~7443.0
RBM34|41~~7426.0
H1FOO|17~~7408.0

FIG. 75C

SLE v Not
H2AFY|14~~9340.0
ARFGAP2|21~~9194.0
SRPRA|16~~9151.42857143
HMGN2|4~~9034.0
TEX13D|65~~8977.0
AKAP12|52~~8942.0
RRBP1|62~~8895.42857143
PCDHGA12|91~~8838.0
EIF5B|14~~8793.0
H2AFY|13~~8714.0
HIST1H1E|2~~8708.0
HMGN4|4~~8698.0
HIST1H1D|19~~8695.0
MYBBP1A|127~~8670.0
ARFGAP2|22~~8618.0
COL11A1|152~~8587.0
RBM34|41~~8562.0
NOLC1|50~~8544.0
ZFHX4|192~~8542.0
MSR1|34~~8502.0
HMGA2|5~~8491.0
RPL4|37~~8458.0
BRD2|58~~8437.0
TADA1|9~~8433.0
SSB|34~~8367.0
HIST1H1C|2~~8336.0
PCDHGA1|91~~8314.0
PCDHGB2|91~~8314.0
PCDHGA5|91~~8314.0
COPS7A|25~~8275.0
RPL4|38~~8267.42857143
PCDHGB6|91~~8264.0
C17orf49|9~~8246.0
YY1|17~~8128.71428571
PDCD4|10~~8102.85714286
HIST1H1C|17~~8086.0
SPEF2|97~~8078.0
PIN4|2~~8074.0
ARHGAP30|0~~8067.0

FIG. 76A

RA vs. HC – 3062 significant peptides

| motif | n | n.lib | enrich | p | fdr | padj.holm | Pr_seqs.motif | PLR |
|---|---|---|---|---|---|---|---|---|
| HRW | 26 | 94 | 9.943726326 | 1.10E-19 | 1.44E-17 | 1.43E-16 | 0.276595745 | 15.35243209 |
| HLWG | 8 | 12 | 7.80314868 | 9.98E-11 | 3.19E-08 | 2.86E-07 | 0.666666667 | 80.30502939 |
| HRSW | 5 | 8 | 7.315451888 | 6.46E-07 | 5.63E-05 | 0.001836291 | 0.625 | 66.92085783 |
| HWG | 29 | 144 | 7.24001014 | 1.14E-17 | 1.07E-15 | 1.48E-14 | 0.201388889 | 10.12541675 |
| HWLG | 12 | 20 | 7.022833812 | 1.08E-14 | 1.55E-11 | 3.10E-11 | 0.6 | 60.22877204 |
| HWYK | 4 | 7 | 6.688413154 | 1.55E-05 | 0.00066316 | 0.043411004 | 0.571428571 | 53.53668626 |
| RWW | 19 | 107 | 6.383715032 | 4.39E-11 | 1.22E-09 | 5.55E-08 | 0.177570093 | 8.669292946 |
| HPW | 42 | 239 | 6.317642667 | 1.78E-22 | 2.92E-20 | 2.32E-19 | 0.175732218 | 8.560434605 |
| RHF | 120 | 696 | 6.198343996 | 3.62E-60 | 4.74E-57 | 4.74E-57 | 0.172413793 | 8.365107228 |
| WPW | 32 | 187 | 6.151939282 | 3.77E-17 | 3.08E-15 | 4.87E-14 | 0.171122995 | 8.289551421 |
| HWR | 34 | 208 | 5.876506904 | 1.73E-17 | 1.51E-15 | 2.24E-14 | 0.163461538 | 7.845893676 |
| HPWG | 9 | 18 | 5.85236151 | 2.28E-10 | 6.54E-08 | 6.52E-07 | 0.5 | 40.1525147 |
| PKFW | 5 | 10 | 5.85236151 | 2.78E-06 | 0.000173833 | 0.007871057 | 0.5 | 40.1525147 |
| QHW | 27 | 168 | 5.777742082 | 5.07E-14 | 2.66E-12 | 6.52E-11 | 0.160714286 | 7.68877941 |
| RWR | 33 | 206 | 5.759043888 | 9.44E-17 | 7.27E-15 | 1.22E-13 | 0.160194175 | 7.659150202 |
| HLW | 33 | 207 | 5.73122242 | 1.10E-16 | 7.96E-15 | 1.41E-13 | 0.15942029 | 7.615132098 |
| PWG | 41 | 259 | 5.690989198 | 3.12E-20 | 4.53E-18 | 4.05E-17 | 0.158301158 | 7.551619736 |
| HWY | 15 | 95 | 5.676378186 | 2.49E-08 | 3.58E-07 | 3.03E-05 | 0.157894737 | 7.528596506 |
| WWG | 22 | 140 | 5.649347814 | 1.67E-11 | 5.21E-10 | 2.12E-08 | 0.157142857 | 7.486062062 |
| HWP | 15 | 97 | 5.559339461 | 3.32E-08 | 4.62E-07 | 4.04E-05 | 0.154639175 | 7.344972201 |
| HPWR | 8 | 17 | 5.508104951 | 4.36E-09 | 8.34E-07 | 1.25E-05 | 0.470588235 | 35.69112417 |
| KHWR | 8 | 17 | 5.508104951 | 4.36E-09 | 8.34E-07 | 1.25E-05 | 0.470588235 | 35.69112417 |
| RHPW | 8 | 17 | 5.508104951 | 4.36E-09 | 8.34E-07 | 1.25E-05 | 0.470588235 | 35.69112417 |
| NRHF | 28 | 61 | 5.372659747 | 4.15E-28 | 1.19E-24 | 1.19E-24 | 0.459016393 | 34.06880035 |
| WQHR | 5 | 11 | 5.320328646 | 4.99E-06 | 0.000256087 | 0.014066333 | 0.454545455 | 33.46042891 |
| HFW | 27 | 186 | 5.218605752 | 6.30E-13 | 2.95E-11 | 8.08E-10 | 0.14516129 | 6.818351552 |
| HWW | 15 | 106 | 5.087320073 | 1.12E-07 | 1.43E-06 | 0.000134974 | 0.141509434 | 6.618546379 |
| VHW | 14 | 99 | 5.083894268 | 2.96E-07 | 3.46E-06 | 0.000354203 | 0.141414141 | 6.613355362 |
| RWH | 25 | 178 | 5.049212806 | 9.28E-12 | 3.04E-10 | 1.18E-08 | 0.140449438 | 6.560868414 |
| KHW | 26 | 186 | 5.025324057 | 4.03E-12 | 1.51E-10 | 5.14E-09 | 0.139784946 | 6.524783638 |
| WWP | 13 | 93 | 5.025324057 | 8.90E-07 | 9.47E-06 | 0.00105634 | 0.139784946 | 6.524783638 |
| WGWR | 6 | 14 | 5.016309866 | 8.09E-07 | 6.28E-05 | 0.002295123 | 0.428571429 | 30.11438602 |
| HWL | 24 | 173 | 4.98733806 | 3.11E-11 | 9.05E-10 | 3.94E-08 | 0.138728324 | 6.467519146 |
| WPH | 20 | 145 | 4.958675197 | 1.46E-09 | 2.94E-08 | 1.82E-06 | 0.137931034 | 6.424402351 |
| PWH | 42 | 309 | 4.886461481 | 3.60E-18 | 3.62E-16 | 4.66E-15 | 0.13592233 | 6.316125907 |
| NHLW | 5 | 12 | 4.876967925 | 8.37E-06 | 0.000394258 | 0.023547457 | 0.416666667 | 28.68036764 |
| WRH | 62 | 460 | 4.845488046 | 7.57E-26 | 2.48E-23 | 9.89E-23 | 0.134782609 | 6.25491435 |
| WVP | 23 | 171 | 4.83543327 | 1.49E-10 | 3.62E-09 | 1.87E-07 | 0.134502924 | 6.239917824 |
| RWG | 20 | 149 | 4.8255564 | 2.37E-09 | 4.49E-08 | 2.94E-06 | 0.134228188 | 6.225196077 |
| WHF | 56 | 418 | 4.816320885 | 2.24E-23 | 5.80E-21 | 2.92E-20 | 0.133971292 | 6.211438738 |
| RPW | 29 | 218 | 4.782392019 | 8.63E-13 | 3.72E-11 | 1.11E-09 | 0.133027523 | 6.160967863 |
| WRW | 19 | 143 | 4.776625933 | 6.98E-09 | 1.19E-07 | 8.60E-06 | 0.132867133 | 6.152401445 |
| WHW | 21 | 159 | 4.748165401 | 1.29E-09 | 2.69E-08 | 1.61E-06 | 0.132075472 | 6.11016528 |
| RHW | 25 | 190 | 4.730315155 | 3.95E-11 | 1.12E-09 | 4.99E-08 | 0.131578947 | 6.083714348 |
| WKWH | 6 | 15 | 4.681889208 | 1.32E-06 | 9.53E-05 | 0.003737006 | 0.4 | 26.76834313 |
| HFG | 110 | 846 | 4.674401264 | 4.80E-43 | 3.14E-40 | 6.28E-40 | 0.130023641 | 6.001055186 |
| WHP | 23 | 177 | 4.671520278 | 3.00E-10 | 6.89E-09 | 3.76E-07 | 0.129943503 | 5.996804143 |
| R....W | 150 | 1189 | 4.647873462 | 4.42E-54 | 2.41E-52 | 4.78E-52 | 0.126156434 | 5.796801929 |
| KWW | 12 | 93 | 4.638760668 | 5.45E-06 | 4.99E-05 | 0.006369851 | 0.129032258 | 5.948520696 |
| QWW | 12 | 93 | 4.638760668 | 5.45E-06 | 4.99E-05 | 0.006369851 | 0.129032258 | 5.948520696 |

FIG. 76B

RA vs. HC - 3062 significant peptides

| motif | n | n.lib | enrich | p | fdr | padj.holm | Pr_seqs.motif | PLR |
|---|---|---|---|---|---|---|---|---|
| W | 3303 | 58364 | 2.213682455 | 0 | 0 | 0 | 0.056593105 | 2.408669585 |
| H | 2971 | 65939 | 1.762430879 | 1.76E-228 | 4.39E-228 | 7.03E-228 | 0.045056795 | 1.894503893 |
| R | 2429 | 63785 | 1.489569437 | 3.70E-104 | 6.17E-104 | 1.11E-103 | 0.038081054 | 1.589583059 |
| P | 1763 | 56321 | 1.224429412 | 1.23E-25 | 1.54E-25 | 2.46E-25 | 0.031302711 | 1.297497771 |
| F | 2009 | 75858 | 1.035929848 | 5.47E-06 | 5.47E-06 | 5.47E-06 | 0.026483693 | 1.092315428 |

FIG. 77A

RA vs. Other rheumatic diseases – 328 significant peptides

| motif | n | n.lib | enrich | p | fdr | padj.holm | Pr_seqs.motif | PLR |
|---|---|---|---|---|---|---|---|---|
| HHWW | 2 | 3 | 10.46020023 | 2.15E-05 | 0.000195409 | 0.002281976 | 0.666666667 | 766.347561 |
| H.....H | 34 | 1157 | 8.483960889 | 8.21E-24 | 6.65E-22 | 6.65E-22 | 0.029386344 | 11.60098712 |
| H..W | 49 | 2061 | 8.037520327 | 6.33E-30 | 5.25E-28 | 5.25E-28 | 0.023774867 | 9.33176702 |
| PHH | 8 | 127 | 7.945098851 | 2.58E-09 | 1.94E-07 | 9.61E-07 | 0.062992126 | 25.75958188 |
| H...H | 49 | 2080 | 7.869057715 | 1.10E-29 | 9.86E-28 | 9.86E-28 | 0.023557692 | 9.244468362 |
| H.H | 60 | 2930 | 7.2385476 | 6.69E-33 | 6.02E-31 | 6.02E-31 | 0.020477816 | 8.010601683 |
| WWG | 8 | 140 | 7.207339672 | 5.58E-09 | 2.62E-07 | 2.06E-06 | 0.057142857 | 23.22265336 |
| HWG | 8 | 144 | 7.007135792 | 6.97E-09 | 2.91E-07 | 2.56E-06 | 0.055555556 | 22.53963415 |
| HH | 46 | 2453 | 6.732862595 | 4.71E-24 | 9.55E-23 | 3.68E-22 | 0.018752548 | 7.322805942 |
| WW | 44 | 2353 | 6.713828098 | 5.02E-23 | 8.13E-22 | 3.87E-21 | 0.018699533 | 7.301709113 |
| HPY | 13 | 249 | 6.585019178 | 3.13E-13 | 3.92E-11 | 1.17E-10 | 0.052208835 | 21.10703028 |
| H....H | 35 | 1672 | 6.488899522 | 6.20E-20 | 5.34E-18 | 5.34E-18 | 0.020933014 | 8.192475453 |
| W....W | 26 | 1246 | 6.468365971 | 3.79E-15 | 1.09E-13 | 3.18E-13 | 0.020866774 | 8.165998601 |
| HHH | 5 | 98 | 6.435124707 | 7.47E-06 | 0.000132837 | 0.002659839 | 0.051020408 | 20.60074089 |
| WWW | 4 | 79 | 6.386250342 | 6.50E-05 | 0.000660215 | 0.022089116 | 0.050632911 | 20.43593496 |
| W..H | 50 | 2670 | 6.330860427 | 6.50E-26 | 2.70E-24 | 5.33E-24 | 0.018726592 | 7.312476727 |
| HRH | 14 | 279 | 6.329025877 | 6.65E-14 | 1.25E-11 | 2.49E-11 | 0.050179211 | 20.24314312 |
| HWGV | 2 | 5 | 6.276120138 | 7.15E-05 | 0.000379991 | 0.007221887 | 0.4 | 255.449187 |
| WPHP | 2 | 5 | 6.276120138 | 7.15E-05 | 0.000379991 | 0.007221887 | 0.4 | 255.449187 |
| WPHR | 2 | 5 | 6.276120138 | 7.15E-05 | 0.000379991 | 0.007221887 | 0.4 | 255.449187 |
| WWWG | 2 | 5 | 6.276120138 | 7.15E-05 | 0.000379991 | 0.007221887 | 0.4 | 255.449187 |
| W...H | 39 | 2136 | 6.098925723 | 4.17E-20 | 1.88E-18 | 3.71E-18 | 0.018258427 | 7.126264873 |
| WPH | 7 | 145 | 6.088959378 | 1.61E-07 | 4.65E-06 | 5.85E-05 | 0.048275862 | 19.43635118 |
| WG | 59 | 3483 | 6.081882216 | 3.49E-28 | 9.41E-27 | 2.75E-26 | 0.01693942 | 6.602585587 |
| H..H | 47 | 2652 | 5.991400264 | 1.80E-23 | 4.98E-22 | 1.46E-21 | 0.017722474 | 6.913308132 |
| H...W | 29 | 1631 | 5.939283041 | 4.89E-15 | 8.81E-14 | 4.21E-13 | 0.017780503 | 6.936354328 |
| YHWG | 3 | 8 | 5.883862629 | 1.07E-06 | 1.57E-05 | 0.000118525 | 0.375 | 229.9042683 |
| H.W | 45 | 2741 | 5.803250037 | 2.70E-21 | 6.07E-20 | 2.35E-19 | 0.016417366 | 6.395704793 |
| W.H | 55 | 3359 | 5.787892953 | 1.19E-25 | 5.36E-24 | 1.06E-23 | 0.016373921 | 6.378498162 |
| W.....H | 24 | 1200 | 5.774083969 | 1.32E-13 | 2.67E-12 | 1.03E-11 | 0.02 | 7.819873071 |
| NHP | 9 | 197 | 5.762213189 | 4.43E-09 | 2.38E-07 | 1.64E-06 | 0.045685279 | 18.34542566 |
| HQF | 8 | 180 | 5.605708634 | 3.97E-08 | 1.49E-06 | 1.46E-05 | 0.044444444 | 17.8220363 |
| HW | 41 | 2637 | 5.58230029 | 9.60E-19 | 1.11E-17 | 7.20E-17 | 0.015547971 | 6.051666025 |
| WWP | 4 | 93 | 5.424879323 | 0.000122551 | 0.001047252 | 0.040809404 | 0.043010753 | 17.22129351 |
| Y.....H | 22 | 1186 | 5.355389854 | 5.79E-12 | 7.82E-11 | 4.40E-10 | 0.018549747 | 7.242116126 |
| VHH | 4 | 95 | 5.310671337 | 0.000133058 | 0.001111772 | 0.044175195 | 0.042105263 | 16.84280354 |
| HP | 43 | 2931 | 5.267349129 | 1.12E-18 | 1.13E-17 | 8.26E-17 | 0.014670761 | 5.705149779 |
| HG | 77 | 5251 | 5.264876338 | 2.68E-32 | 1.08E-30 | 2.14E-30 | 0.014663874 | 5.7024316 |
| HLWG | 4 | 12 | 5.230100115 | 2.51E-08 | 7.72E-07 | 2.91E-06 | 0.333333333 | 191.5868902 |
| HWHR | 2 | 6 | 5.230100115 | 0.000107064 | 0.000485906 | 0.010064017 | 0.333333333 | 191.5868902 |
| WWGA | 2 | 6 | 5.230100115 | 0.000107064 | 0.000485906 | 0.010064017 | 0.333333333 | 191.5868902 |
| H....W | 20 | 1189 | 5.214196804 | 2.35E-10 | 2.89E-09 | 1.88E-08 | 0.016820858 | 6.555582215 |
| HHP | 4 | 98 | 5.148099766 | 0.000150019 | 0.001226243 | 0.049656336 | 0.040816327 | 16.30526725 |
| HWH | 8 | 199 | 5.070490221 | 8.60E-08 | 2.94E-06 | 3.15E-05 | 0.040201005 | 16.04916358 |
| H...F | 41 | 2708 | 5.05737529 | 3.16E-18 | 9.47E-17 | 2.78E-16 | 0.015140325 | 5.890560555 |
| HHG | 7 | 177 | 4.988130564 | 6.19E-07 | 1.55E-05 | 0.00022393 | 0.039548023 | 15.7777439 |
| P.H | 48 | 3422 | 4.958257035 | 7.11E-20 | 1.28E-18 | 6.11E-18 | 0.014026885 | 5.451197826 |
| HLW | 8 | 207 | 4.874529247 | 1.16E-07 | 3.64E-06 | 4.25E-05 | 0.038647343 | 15.40397107 |
| W....H | 25 | 1602 | 4.837453184 | 6.78E-12 | 1.17E-10 | 5.56E-10 | 0.015605493 | 6.074409963 |
| WH | 56 | 4165 | 4.827391143 | 3.90E-22 | 5.27E-21 | 2.97E-20 | 0.013445378 | 5.222129887 |

FIG. 77B

RA vs. other rheumatic diseases – 328 peptides

| motif | n | n.lib | enrich | p | fdr | padj.holm | Pr_seqs.motif | PLR |
|---|---|---|---|---|---|---|---|---|
| H | 522 | 65939 | 2.981019771 | 2.22E-118 | 1.33E-117 | 1.33E-117 | 0.007916408 | 3.057564753 |
| W | 385 | 58364 | 2.484004571 | 4.07E-64 | 1.22E-63 | 2.04E-63 | 0.006596532 | 2.544402378 |
| P | 230 | 56321 | 1.537779931 | 3.53E-12 | 7.05E-12 | 1.41E-11 | 0.004083734 | 1.571196262 |
| Y | 195 | 56760 | 1.293686167 | 2.61E-05 | 3.14E-05 | 5.23E-05 | 0.003435518 | 1.320938517 |
| G | 352 | 111145 | 1.192585276 | 3.47E-07 | 5.21E-07 | 1.04E-06 | 0.003167034 | 1.217379895 |
| F | 217 | 75858 | 1.077196802 | 0.038372675 | 0.038372675 | 0.038372675 | 0.002860608 | 1.09925451 |

FIG. 78A

RA v NOT – 1564 significant peptide

| motif | n | n.lib | enrich | p | fdr | padj.holm | Pr_seqs.motif | PLR |
|---|---|---|---|---|---|---|---|---|
| HHWW | 3 | 3 | 12.65504103 | 2.47E-06 | 9.02E-05 | 0.003073385 | 1 | Inf |
| HWG | 20 | 144 | 7.769597458 | 1.00E-14 | 7.52E-13 | 1.04E-11 | 0.138888889 | 12.83361521 |
| HHPF | 3 | 5 | 7.593024619 | 2.42E-05 | 0.000491055 | 0.029436785 | 0.6 | 119.3526215 |
| WWG | 19 | 140 | 7.592006659 | 7.07E-14 | 3.91E-12 | 7.31E-11 | 0.135714286 | 12.49421382 |
| HHP | 13 | 98 | 7.420758388 | 8.00E-10 | 2.05E-08 | 8.09E-07 | 0.132653061 | 12.1692869 |
| HLWG | 7 | 12 | 7.382107268 | 6.14E-11 | 1.15E-08 | 7.82E-08 | 0.583333333 | 111.3957801 |
| WPH | 19 | 145 | 7.330213326 | 1.35E-13 | 6.78E-12 | 1.40E-10 | 0.131034483 | 11.99841168 |
| HFG | 110 | 846 | 7.273665705 | 8.90E-71 | 9.36E-68 | 9.36E-68 | 0.130023641 | 11.89201844 |
| HRW | 11 | 94 | 6.546299135 | 6.00E-08 | 1.05E-06 | 5.96E-05 | 0.117021277 | 10.54521154 |
| HWQW | 4 | 8 | 6.327520516 | 2.24E-06 | 8.94E-05 | 0.002790083 | 0.5 | 79.56841432 |
| HLW | 23 | 207 | 6.215677966 | 1.44E-14 | 1.01E-12 | 1.50E-11 | 0.111111111 | 9.94605179 |
| VHW | 11 | 99 | 6.215677966 | 1.03E-07 | 1.69E-06 | 0.00010189 | 0.111111111 | 9.94605179 |
| PHW | 13 | 122 | 5.960937066 | 1.21E-08 | 2.36E-07 | 1.21E-05 | 0.106557377 | 9.489810882 |
| HW | 207 | 2637 | 5.928641769 | 1.17E-90 | 4.92E-89 | 9.73E-89 | 0.078498294 | 6.778050109 |
| H.....H | 100 | 1157 | 5.914730805 | 7.29E-45 | 7.87E-43 | 7.87E-43 | 0.086430424 | 7.52775916 |
| HWH | 21 | 199 | 5.90333234 | 5.45E-13 | 2.39E-11 | 5.61E-10 | 0.105527638 | 9.387284836 |
| WVP | 18 | 171 | 5.888537021 | 2.51E-11 | 8.80E-10 | 2.57E-08 | 0.105263158 | 9.36098992 |
| W....H | 132 | 1602 | 5.857397583 | 4.34E-58 | 4.38E-56 | 4.38E-56 | 0.082397004 | 7.144918837 |
| HWL | 18 | 173 | 5.820461448 | 3.05E-11 | 1.03E-09 | 3.12E-08 | 0.104046243 | 9.240202954 |
| HWW | 11 | 106 | 5.805208666 | 2.09E-07 | 3.13E-06 | 0.000205042 | 0.103773585 | 9.213184816 |
| HWP | 10 | 97 | 5.767123886 | 7.87E-07 | 9.98E-06 | 0.000763513 | 0.103092784 | 9.14579475 |
| RWW | 11 | 107 | 5.75095438 | 2.30E-07 | 3.36E-06 | 0.000225303 | 0.102803738 | 9.117214141 |
| HHF | 24 | 235 | 5.71313379 | 2.59E-14 | 1.51E-12 | 2.68E-11 | 0.10212766 | 9.050435752 |
| HHW | 10 | 98 | 5.708275683 | 8.66E-07 | 1.07E-05 | 0.000839183 | 0.102040816 | 9.041865264 |
| HWA | 10 | 98 | 5.708275683 | 8.66E-07 | 1.07E-05 | 0.000839183 | 0.102040816 | 9.041865264 |
| RHF | 71 | 696 | 5.706635374 | 3.42E-39 | 1.80E-36 | 3.59E-36 | 0.102011494 | 9.038971867 |
| HWVP | 4 | 9 | 5.624462681 | 3.98E-06 | 0.000127246 | 0.004936093 | 0.444444444 | 63.65473146 |
| HWK | 23 | 229 | 5.618538598 | 1.26E-13 | 6.64E-12 | 1.30E-10 | 0.100436681 | 8.883852085 |
| W...H | 163 | 2136 | 5.519038738 | 5.38E-68 | 5.17E-66 | 5.17E-66 | 0.076310861 | 6.573568948 |
| H..W | 154 | 2061 | 5.499987486 | 6.46E-64 | 3.14E-62 | 6.21E-62 | 0.074721009 | 6.425556269 |
| H.W | 201 | 2741 | 5.465296131 | 2.31E-82 | 2.06E-80 | 2.06E-80 | 0.073330901 | 6.296555622 |
| W.....W | 63 | 795 | 5.423026958 | 9.14E-27 | 1.97E-25 | 9.51E-25 | 0.079245283 | 6.848101233 |
| HRH | 27 | 279 | 5.413655003 | 2.49E-15 | 2.02E-13 | 2.59E-12 | 0.096774194 | 8.525187249 |
| WWP | 9 | 93 | 5.413655003 | 4.73E-06 | 4.74E-05 | 0.004483243 | 0.096774194 | 8.525187249 |
| W.....H | 94 | 1200 | 5.360619108 | 8.87E-39 | 4.79E-37 | 9.49E-37 | 0.078333333 | 6.762595792 |
| H...H | 152 | 2080 | 5.285150263 | 4.76E-61 | 2.28E-59 | 4.52E-59 | 0.073076923 | 6.273028515 |
| WHW | 15 | 159 | 5.277462424 | 5.08E-09 | 1.07E-07 | 5.10E-06 | 0.094339623 | 8.288376492 |
| HSW | 18 | 191 | 5.271936285 | 1.58E-10 | 4.36E-09 | 1.60E-07 | 0.094240838 | 8.278794554 |
| W..H | 191 | 2670 | 5.265517715 | 7.21E-76 | 6.99E-74 | 6.99E-74 | 0.071535581 | 6.13052325 |
| H...W | 118 | 1631 | 5.232450549 | 2.81E-47 | 6.74E-46 | 2.61E-45 | 0.072348253 | 6.20560006 |
| WVR | 12 | 130 | 5.163794003 | 2.16E-07 | 3.19E-06 | 0.000211676 | 0.092307692 | 8.091703151 |
| H....W | 86 | 1189 | 5.141737262 | 3.50E-34 | 7.07E-33 | 3.40E-32 | 0.072329689 | 6.203883619 |
| W...W | 116 | 1639 | 5.118658101 | 1.45E-45 | 2.78E-44 | 1.33E-43 | 0.070774863 | 6.060365109 |
| WHF | 38 | 418 | 5.0855547 | 5.35E-20 | 9.38E-18 | 5.60E-17 | 0.090909091 | 7.956841432 |
| HNLP | 4 | 10 | 5.062016413 | 6.56E-06 | 0.000182479 | 0.008098683 | 0.4 | 53.04560955 |
| H....H | 118 | 1672 | 5.016941286 | 2.79E-45 | 1.41E-43 | 2.79E-43 | 0.070574163 | 6.041874447 |
| WGV | 11 | 123 | 5.002862753 | 9.40E-07 | 1.15E-05 | 0.000908728 | 0.089430894 | 7.814754978 |
| HFH | 14 | 158 | 4.956806479 | 3.63E-08 | 6.58E-07 | 3.61E-05 | 0.088607595 | 7.735818059 |
| HPY | 22 | 249 | 4.942587298 | 5.56E-12 | 2.09E-10 | 5.70E-09 | 0.088353414 | 7.711476278 |
| HYW | 22 | 249 | 4.942587298 | 5.56E-12 | 2.09E-10 | 5.70E-09 | 0.088353414 | 7.711476278 |

FIG. 78B

RA v NOT – 1564 significant peptides

| motif | n | n.lib | enrich | p | fdr | padj.holm | Pr_seqs.motif | PLR |
|---|---|---|---|---|---|---|---|---|
| W | 1918 | 58364 | 2.499343535 | 2.65044974171058e-318 | 7.95134922513173e-318 | 1.32522487085529e-317 | 0.032862724 | 2.703685269 |
| H | 2090 | 65939 | 2.410606535 | 0 | 0 | 0 | 0.031695961 | 2.604551143 |
| P | 893 | 56321 | 1.205878316 | 2.71E-12 | 4.06E-12 | 8.13E-12 | 0.015855542 | 1.281925994 |
| F | 1155 | 75858 | 1.157985166 | 5.62E-13 | 1.12E-12 | 2.25E-12 | 0.015225817 | 1.230225273 |
| Y | 797 | 56760 | 1.067919052 | 0.001083108 | 0.001083108 | 0.001287012 | 0.014041579 | 1.133177746 |
| R | 889 | 63785 | 1.059999355 | 0.000643506 | 0.000772207 | 0.001287012 | 0.013937446 | 1.124655309 |

FIG. 79A

RA v Other AI/non-AI mimic diseases – 742 peptides

| motif | n | n.lib | enrich | p | fdr | padj.holm | Pr_seqs.motif | PLR |
|---|---|---|---|---|---|---|---|---|
| HHP | 11 | 98 | 9.894641891 | 3.99E-11 | 2.73E-09 | 2.97E-08 | 0.112244898 | 21.3454937 |
| HHWW | 2 | 3 | 9.702561966 | 0.000120036 | 0.001072492 | 0.043933015 | 0.666666667 | 337.6469003 |
| HHPF | 3 | 5 | 8.73230577 | 2.52E-06 | 6.91E-05 | 0.001001287 | 0.6 | 253.2351752 |
| HWG | 13 | 144 | 7.958190511 | 1.13E-11 | 8.95E-10 | 8.42E-09 | 0.090277778 | 16.75347215 |
| H.....H | 60 | 1157 | 7.252908303 | 4.00E-33 | 3.88E-31 | 3.88E-31 | 0.051858254 | 9.233734738 |
| W...H | 98 | 2136 | 6.963801946 | 2.50E-50 | 2.30E-48 | 2.30E-48 | 0.04588015 | 8.11810506 |
| W.....H | 59 | 1200 | 6.876462215 | 2.24E-31 | 1.09E-29 | 2.15E-29 | 0.049166667 | 8.72969637 |
| W..H | 110 | 2670 | 6.322790118 | 2.62E-52 | 2.52E-50 | 2.52E-50 | 0.041198502 | 7.254132623 |
| WWG | 10 | 140 | 6.296590294 | 2.57E-08 | 8.05E-07 | 1.87E-05 | 0.071428571 | 12.98641924 |
| HLWG | 5 | 12 | 6.064101229 | 7.80E-09 | 1.07E-06 | 3.19E-06 | 0.416666667 | 120.5881787 |
| HRH | 19 | 279 | 6.003200782 | 3.78E-14 | 4.74E-12 | 2.82E-11 | 0.068100358 | 12.33709828 |
| H...H | 82 | 2080 | 5.983731546 | 1.26E-37 | 5.80E-36 | 1.15E-35 | 0.039423077 | 6.928690146 |
| H..W | 80 | 2061 | 5.957160995 | 1.21E-36 | 3.88E-35 | 1.14E-34 | 0.038816109 | 6.817706214 |
| H....H | 66 | 1672 | 5.827301144 | 3.75E-30 | 3.53E-28 | 3.53E-28 | 0.039473684 | 6.937950006 |
| W....H | 62 | 1602 | 5.713325633 | 5.86E-28 | 2.75E-26 | 5.45E-26 | 0.038701623 | 6.796788252 |
| WWP | 6 | 93 | 5.687242846 | 2.91E-05 | 0.000342393 | 0.02007978 | 0.064516129 | 11.64299656 |
| H.H | 106 | 2930 | 5.645826763 | 1.19E-45 | 1.09E-43 | 1.09E-43 | 0.036177474 | 6.336857548 |
| H..H | 97 | 2652 | 5.613394394 | 5.52E-42 | 2.65E-40 | 5.25E-40 | 0.036576169 | 6.409344291 |
| HVH | 11 | 173 | 5.605057256 | 1.74E-08 | 5.71E-07 | 1.27E-05 | 0.063583815 | 11.46332069 |
| HW | 93 | 2637 | 5.603692813 | 1.40E-39 | 2.80E-38 | 1.08E-37 | 0.035267349 | 6.171611974 |
| HH | 86 | 2453 | 5.570605506 | 1.57E-36 | 2.52E-35 | 1.19E-34 | 0.035059111 | 6.133847364 |
| HFG | 53 | 846 | 5.522541369 | 6.90E-35 | 5.19E-32 | 5.19E-32 | 0.062647754 | 11.28328229 |
| HWQW | 3 | 8 | 5.457691106 | 1.39E-05 | 0.0002201 | 0.005402351 | 0.375 | 101.2940701 |
| WYPA | 3 | 8 | 5.457691106 | 1.39E-05 | 0.0002201 | 0.005402351 | 0.375 | 101.2940701 |
| YHWG | 3 | 8 | 5.457691106 | 1.39E-05 | 0.0002201 | 0.005402351 | 0.375 | 101.2940701 |
| HWP | 6 | 97 | 5.452717368 | 3.69E-05 | 0.000408942 | 0.025333768 | 0.06185567 | 11.13121649 |
| VHW | 6 | 99 | 5.342561462 | 4.14E-05 | 0.000439409 | 0.028297796 | 0.060606061 | 10.89183549 |
| H....W | 43 | 1189 | 5.338833793 | 8.83E-19 | 1.66E-17 | 7.95E-17 | 0.036164844 | 6.334562265 |
| WHH | 9 | 149 | 5.324633403 | 5.31E-07 | 1.21E-05 | 0.000382604 | 0.060402685 | 10.85293608 |
| HWH | 12 | 199 | 5.315714419 | 7.16E-09 | 2.70E-07 | 5.26E-06 | 0.060301508 | 10.83359038 |
| HPY | 15 | 249 | 5.310377356 | 9.95E-11 | 5.77E-09 | 7.38E-08 | 0.060240964 | 10.82201603 |
| WHY | 10 | 167 | 5.27857869 | 1.36E-07 | 3.78E-06 | 9.86E-05 | 0.05988024 | 10.753086 |
| W.....W | 30 | 795 | 5.277745224 | 1.08E-13 | 1.31E-12 | 9.71E-12 | 0.037735849 | 6.620527456 |
| HPF | 10 | 169 | 5.216110303 | 1.52E-07 | 4.07E-06 | 0.000110005 | 0.059171598 | 10.61782705 |
| W....W | 43 | 1246 | 5.094601428 | 4.76E-18 | 7.46E-17 | 4.24E-16 | 0.034510433 | 6.034420911 |
| W.H | 109 | 3359 | 5.064141095 | 1.34E-42 | 4.11E-41 | 1.21E-40 | 0.032450134 | 5.662078789 |
| HFH | 9 | 158 | 5.0213315 | 8.68E-07 | 1.77E-05 | 0.000622064 | 0.056962025 | 10.19738961 |
| HHV | 16 | 281 | 5.019346 | 5.53E-11 | 3.47E-09 | 4.10E-08 | 0.056939502 | 10.19311397 |
| WGV | 7 | 123 | 5.016795519 | 1.44E-05 | 0.000196631 | 0.010039132 | 0.056910569 | 10.18762199 |
| W.W | 82 | 2564 | 4.990972015 | 5.55E-32 | 1.02E-30 | 4.89E-30 | 0.031981279 | 5.577567652 |
| HHY | 6 | 106 | 4.989750799 | 6.08E-05 | 0.000594233 | 0.041137835 | 0.056603774 | 10.12940701 |
| WHP | 10 | 177 | 4.980353905 | 2.33E-07 | 6.05E-06 | 0.000168809 | 0.056497175 | 10.10918863 |
| HF | 195 | 6250 | 4.957424344 | 5.48E-73 | 4.39E-71 | 4.39E-71 | 0.0312 | 5.436923662 |
| RWW | 6 | 107 | 4.943117614 | 6.40E-05 | 0.00061816 | 0.043285977 | 0.056074766 | 10.02911585 |
| HQF | 10 | 180 | 4.897348006 | 2.72E-07 | 6.83E-06 | 0.000196928 | 0.055555556 | 9.930791184 |
| PWY | 9 | 162 | 4.897348006 | 1.07E-06 | 2.01E-05 | 0.000762994 | 0.055555556 | 9.930791184 |
| WG | 107 | 3483 | 4.881258464 | 5.39E-40 | 1.44E-38 | 4.20E-38 | 0.030720643 | 5.350743236 |
| WPH | 8 | 145 | 4.863573193 | 4.44E-06 | 7.44E-05 | 0.003150496 | 0.055172414 | 9.858303658 |
| PHH | 7 | 127 | 4.858786211 | 1.77E-05 | 0.000229771 | 0.012322552 | 0.05511811 | 9.848034591 |
| H.W | 85 | 2741 | 4.839485504 | 3.65E-32 | 8.39E-31 | 3.25E-30 | 0.03101058 | 5.402858909 |

FIG. 79B

RA v Other AI/non-AI mimic diseases – 742 peptides

| H | 1100 | 65939  | 2.695283183 | 1.12E-211   | 6.72E-211   | 6.72E-211   | 0.016682085 | 2.864106404 |
|---|------|--------|-------------|-------------|-------------|-------------|-------------|-------------|
| W | 888  | 58364  | 2.458227031 | 6.44E-143   | 1.93E-142   | 3.22E-142   | 0.015214858 | 2.608309968 |
| F | 565  | 75858  | 1.203375409 | 3.01E-09    | 6.01E-09    | 1.20E-08    | 0.007448127 | 1.266854147 |
| P | 418  | 56321  | 1.199112685 | 3.21E-06    | 4.82E-06    | 9.64E-06    | 0.007421743 | 1.262333008 |
| Y | 396  | 56760  | 1.127215293 | 0.00074599  | 0.00074599  | 0.00074599  | 0.006976744 | 1.186113233 |
| G | 714  | 111145 | 1.037916353 | 0.000331221 | 0.000397466 | 0.000662443 | 0.006424041 | 1.091540812 |

FIG. 80A

RA vs. OA – 130 significant peptides

| motif | n | n.lib | enrich | p | fdr | padj.holm | Pr_seqs.motif | PLR |
|---|---|---|---|---|---|---|---|---|
| WW | 20 | 2353 | 6.655701866 | 7.05E-12 | 5.36E-10 | 5.36E-10 | 0.008499788 | 8.300900129 |
| H....W | 12 | 1189 | 6.552255468 | 3.73E-08 | 2.89E-06 | 3.24E-06 | 0.010092515 | 9.872217502 |
| NWLH | 2 | 6 | 6.298890165 | 1.98E-05 | 0.000202541 | 0.000434683 | 0.333333333 | 484.15 |
| H.W | 21 | 2741 | 5.842087136 | 1.70E-11 | 1.34E-09 | 1.34E-09 | 0.007661437 | 7.475845588 |
| HWW | 3 | 106 | 5.802254349 | 0.000256489 | 0.006509626 | 0.041038183 | 0.028301887 | 28.20291262 |
| RWW | 3 | 107 | 5.748027673 | 0.000263664 | 0.006509626 | 0.041922607 | 0.028037383 | 27.93173077 |
| H..W | 16 | 2061 | 5.694247384 | 4.30E-09 | 3.70E-07 | 3.70E-07 | 0.007763222 | 7.57594132 |
| W...P | 13 | 1549 | 5.679770763 | 6.15E-08 | 2.34E-06 | 4.61E-06 | 0.008392511 | 8.195247396 |
| H.....P | 6 | 627 | 5.431387958 | 0.000168341 | 0.002491441 | 0.011783843 | 0.009569378 | 9.355555556 |
| HSWP | 2 | 7 | 5.399048712 | 2.76E-05 | 0.000202541 | 0.000580449 | 0.285714286 | 387.32 |
| SWP | 3 | 114 | 5.395078606 | 0.000317543 | 0.006509626 | 0.049854208 | 0.026315789 | 26.17027027 |
| W.P | 18 | 2556 | 5.369939919 | 1.72E-09 | 4.76E-08 | 1.34E-07 | 0.007042254 | 6.867375887 |
| W.W | 18 | 2564 | 5.353185036 | 1.81E-09 | 4.76E-08 | 1.39E-07 | 0.007020281 | 6.845797329 |
| W..P | 14 | 2013 | 5.101273411 | 1.48E-07 | 3.19E-06 | 1.23E-05 | 0.006954794 | 6.781490745 |
| PPW | 4 | 166 | 4.940071976 | 4.32E-05 | 0.003372826 | 0.007040316 | 0.024096386 | 23.90864198 |
| R.....H | 10 | 1200 | 4.72983368 | 4.05E-06 | 0.000150012 | 0.000300025 | 0.008333333 | 8.13697479 |
| W.....H | 10 | 1200 | 4.72983368 | 4.05E-06 | 0.000150012 | 0.000300025 | 0.008333333 | 8.13697479 |
| WFRG | 2 | 8 | 4.724167623 | 3.68E-05 | 0.000202541 | 0.000699687 | 0.25 | 322.7666667 |
| W....W | 9 | 1246 | 4.689385083 | 2.65E-05 | 0.000460979 | 0.002198924 | 0.007223114 | 7.045028294 |
| W..H | 17 | 2670 | 4.670162584 | 2.49E-08 | 1.07E-06 | 2.12E-06 | 0.006367041 | 6.204711647 |
| H.....W | 6 | 735 | 4.633306462 | 0.000390585 | 0.003612915 | 0.026169223 | 0.008163265 | 7.969547325 |
| WP | 14 | 2410 | 4.548799395 | 9.26E-07 | 1.76E-05 | 6.76E-05 | 0.005809129 | 5.657846411 |
| W...L | 17 | 2572 | 4.473184696 | 1.90E-08 | 1.45E-06 | 1.45E-06 | 0.006609642 | 6.442700587 |
| HW | 15 | 2637 | 4.454171357 | 4.95E-07 | 1.25E-05 | 3.66E-05 | 0.005688282 | 5.539473684 |
| WAW | 5 | 232 | 4.418383341 | 8.01E-06 | 0.001313926 | 0.001313926 | 0.021551724 | 21.32819383 |
| H..P | 11 | 1860 | 4.337845512 | 1.41E-05 | 0.00020272 | 0.001145605 | 0.005913978 | 5.760573283 |
| W.....V | 10 | 1317 | 4.309643444 | 9.03E-06 | 0.000222761 | 0.000650223 | 0.007593014 | 7.408569243 |
| VKWN | 2 | 9 | 4.19926011 | 4.73E-05 | 0.000208168 | 0.000851597 | 0.222222222 | 276.6571429 |
| W..L | 18 | 3170 | 4.164928814 | 5.31E-08 | 1.52E-06 | 4.46E-06 | 0.005678233 | 5.52963198 |
| H...W | 10 | 1631 | 4.14939627 | 2.99E-05 | 0.000455127 | 0.002155865 | 0.006131208 | 5.973473165 |
| WH | 22 | 4165 | 4.136123203 | 4.33E-09 | 1.65E-07 | 3.25E-07 | 0.005282113 | 5.141829592 |
| W...H | 13 | 2136 | 4.118897431 | 2.16E-06 | 4.11E-05 | 0.000157728 | 0.006086142 | 5.929298163 |
| W.....K | 7 | 985 | 4.033563747 | 0.000297777 | 0.003612915 | 0.020546591 | 0.007106599 | 6.930572597 |
| R.W | 14 | 2681 | 3.981887564 | 3.51E-06 | 4.62E-05 | 0.000259663 | 0.005221932 | 5.082939633 |
| W....L | 12 | 1973 | 3.948622276 | 7.00E-06 | 0.000152317 | 0.000588257 | 0.006082108 | 5.925344212 |
| W.K | 15 | 2950 | 3.877278654 | 2.19E-06 | 3.45E-05 | 0.000163889 | 0.005084746 | 4.948722317 |
| W...A | 9 | 1571 | 3.877083886 | 0.000123105 | 0.001231072 | 0.008617381 | 0.005728835 | 5.579193342 |
| SWPW | 2 | 10 | 3.779334099 | 5.91E-05 | 0.000216675 | 0.001004586 | 0.2 | 242.075 |
| R..W | 11 | 2135 | 3.779106629 | 4.87E-05 | 0.000597922 | 0.003893447 | 0.005152225 | 5.014736347 |
| W....R | 9 | 1568 | 3.726386361 | 0.000149505 | 0.002167829 | 0.012259447 | 0.005739796 | 5.589929442 |
| H...P | 9 | 1650 | 3.691453809 | 0.000176604 | 0.001491322 | 0.012009071 | 0.005454545 | 5.310603291 |
| W....F | 13 | 2291 | 3.683915785 | 6.10E-06 | 0.000152317 | 0.000518204 | 0.005674378 | 5.525856014 |
| W...K | 10 | 1853 | 3.652274861 | 8.53E-05 | 0.001080434 | 0.006056114 | 0.005396654 | 5.253933804 |
| W.V | 17 | 3608 | 3.592858915 | 1.30E-06 | 2.56E-05 | 9.86E-05 | 0.004711752 | 4.583987747 |
| W...F | 15 | 2834 | 3.582038806 | 1.98E-06 | 4.11E-05 | 0.000146788 | 0.005292872 | 5.152358993 |
| W.A | 12 | 2562 | 3.571575965 | 4.85E-05 | 0.000438118 | 0.003495126 | 0.004683841 | 4.556705882 |
| HP | 13 | 2931 | 3.473068311 | 3.72E-05 | 0.000490781 | 0.002680216 | 0.004435346 | 4.313879369 |
| RWWV | 2 | 11 | 3.435758272 | 7.22E-05 | 0.000226819 | 0.001154716 | 0.181818182 | 215.1777778 |
| WA | 10 | 2370 | 3.303980272 | 0.000420518 | 0.002493085 | 0.027333647 | 0.004219409 | 4.102966102 |
| W..W | 10 | 2236 | 3.280367805 | 0.000324337 | 0.00309922 | 0.025298287 | 0.004472272 | 4.349955076 |

FIG. 80B

RA vs. OA – 130 significant peptides

| motif | n | n.lib | enrich | p | fdr | padj.holm | Pr_seqs.motif | PLR |
|---|---|---|---|---|---|---|---|---|
| W | 180 | 58364 | 2.776747543 | 4.33E-37 | 2.60E-36 | 2.60E-36 | 0.003084093 | 2.995565791 |
| H | 144 | 65939 | 1.966206264 | 2.95E-16 | 8.86E-16 | 1.48E-15 | 0.002183837 | 2.119237024 |
| P | 98 | 56321 | 1.566623577 | 2.86E-06 | 5.71E-06 | 1.14E-05 | 0.001740026 | 1.687803924 |

FIG. 81A

RA vs. Fibromyalgia – 753 peptides

| motif | n | n.lib | enrich | p | fdr | padj.holm | Pr_seqs.motif | PLR |
|---|---|---|---|---|---|---|---|---|
| HHKN | 2 | 3 | 10.95349936 | 0.000127021 | 0.001249608 | 0.042170834 | 0.666666667 | 332.685259 |
| HWPH | 2 | 3 | 10.95349936 | 0.000127021 | 0.001249608 | 0.042170834 | 0.666666667 | 332.685259 |
| HWYH | 2 | 3 | 10.95349936 | 0.000127021 | 0.001249608 | 0.042170834 | 0.666666667 | 332.685259 |
| KPWY | 2 | 3 | 10.95349936 | 0.000127021 | 0.001249608 | 0.042170834 | 0.666666667 | 332.685259 |
| QKWP | 2 | 3 | 10.95349936 | 0.000127021 | 0.001249608 | 0.042170834 | 0.666666667 | 332.685259 |
| WPH | 11 | 145 | 7.204404246 | 3.61E-09 | 3.29E-07 | 2.94E-06 | 0.075862069 | 13.65499197 |
| H.....H | 51 | 1157 | 6.193607695 | 2.00E-24 | 1.05E-22 | 2.08E-22 | 0.044079516 | 7.670410582 |
| HPF | 11 | 169 | 6.181293583 | 1.79E-08 | 1.47E-06 | 1.45E-05 | 0.065088757 | 11.58081598 |
| H....H | 70 | 1672 | 6.032866688 | 1.55E-32 | 1.62E-30 | 1.62E-30 | 0.041866029 | 7.268404534 |
| HWP | 6 | 97 | 5.874256508 | 4.27E-05 | 0.000835482 | 0.033337889 | 0.06185567 | 10.9676459 |
| HHV | 17 | 281 | 5.745343405 | 8.12E-12 | 1.11E-09 | 6.63E-09 | 0.060498221 | 10.7114572 |
| HLWG | 4 | 12 | 5.476749679 | 8.58E-07 | 7.81E-05 | 0.000309663 | 0.333333333 | 83.17131474 |
| HSW | 11 | 191 | 5.469312124 | 6.28E-08 | 3.68E-06 | 5.07E-05 | 0.057591623 | 10.16538291 |
| H.....F | 68 | 1803 | 5.299318989 | 3.59E-28 | 3.77E-26 | 3.77E-26 | 0.03771492 | 6.519480579 |
| VPH | 10 | 181 | 5.246803695 | 3.64E-07 | 1.52E-05 | 0.000292041 | 0.055248619 | 9.727639151 |
| W....H | 58 | 1602 | 5.217079364 | 4.17E-24 | 2.17E-22 | 4.29E-22 | 0.036204744 | 6.248622092 |
| H......P | 23 | 627 | 5.154270081 | 2.84E-10 | 4.58E-09 | 2.84E-08 | 0.036682616 | 6.334239202 |
| HHL | 14 | 259 | 5.13335929 | 2.36E-09 | 2.42E-07 | 1.92E-06 | 0.054054054 | 9.505293113 |
| WHY | 9 | 167 | 5.117989951 | 1.71E-06 | 5.66E-05 | 0.001360914 | 0.053892216 | 9.475213072 |
| H...H | 71 | 2080 | 5.085682587 | 3.12E-28 | 1.53E-26 | 3.02E-26 | 0.034134615 | 5.878709155 |
| YHR | 7 | 131 | 5.074580367 | 2.55E-05 | 0.000551946 | 0.020028712 | 0.053435115 | 9.390309729 |
| HPL | 9 | 169 | 5.057422023 | 1.88E-06 | 5.94E-05 | 0.001497678 | 0.053254438 | 9.356772908 |
| W...H | 71 | 2136 | 4.952350084 | 1.47E-27 | 4.81E-26 | 1.41E-25 | 0.0332397 | 5.719286534 |
| W..H | 87 | 2670 | 4.945334201 | 2.83E-33 | 2.77E-31 | 2.77E-31 | 0.03258427 | 5.60271342 |
| PYHR | 3 | 10 | 4.929074711 | 3.21E-05 | 0.000615845 | 0.011122438 | 0.3 | 71.28969835 |
| HRF | 11 | 213 | 4.904406646 | 1.89E-07 | 8.61E-06 | 0.000151785 | 0.051643192 | 9.058262001 |
| H...F | 86 | 2708 | 4.731556479 | 1.10E-31 | 1.08E-29 | 1.08E-29 | 0.031757755 | 5.455936741 |
| W.....H | 40 | 1200 | 4.683662812 | 2.10E-15 | 7.36E-14 | 2.17E-13 | 0.033333333 | 5.735952741 |
| HWG | 7 | 144 | 4.616458529 | 4.68E-05 | 0.000892925 | 0.036431569 | 0.048611111 | 8.499258441 |
| HFG | 41 | 846 | 4.60242674 | 9.56E-23 | 7.85E-20 | 7.85E-20 | 0.048463357 | 8.472109079 |
| H....L | 64 | 2014 | 4.579124688 | 1.79E-23 | 6.22E-22 | 1.83E-21 | 0.031777557 | 5.459450404 |
| HYW | 12 | 249 | 4.57672997 | 1.12E-07 | 5.79E-06 | 9.07E-05 | 0.048192771 | 8.422411619 |
| H.F | 123 | 4184 | 4.562103491 | 1.83E-42 | 1.81E-40 | 1.81E-40 | 0.029397706 | 5.038203257 |
| HWK | 11 | 229 | 4.561740679 | 3.88E-07 | 1.52E-05 | 0.000311126 | 0.048034934 | 8.393435433 |
| H.W | 80 | 2741 | 4.529316285 | 6.40E-28 | 1.58E-26 | 6.14E-26 | 0.029186428 | 5.000905809 |
| HH | 71 | 2453 | 4.465527716 | 6.02E-25 | 7.92E-24 | 4.45E-23 | 0.02894415 | 4.958155623 |
| H..H | 78 | 2652 | 4.463841216 | 3.51E-27 | 1.72E-25 | 3.40E-25 | 0.029411765 | 5.040685742 |
| HPLG | 5 | 19 | 4.323749747 | 1.27E-07 | 1.54E-05 | 4.59E-05 | 0.263157895 | 59.40808196 |
| HRL | 11 | 243 | 4.298924344 | 6.97E-07 | 2.60E-05 | 0.00055772 | 0.04526749 | 7.886935019 |
| W.H | 92 | 3359 | 4.25039724 | 7.04E-30 | 2.32E-28 | 6.82E-28 | 0.027389104 | 4.684273619 |
| HW | 72 | 2637 | 4.212446085 | 7.81E-24 | 8.81E-23 | 5.70E-22 | 0.027303754 | 4.669266792 |
| H..L | 82 | 2961 | 4.203035903 | 8.31E-27 | 2.72E-25 | 7.98E-25 | 0.027693347 | 4.737789377 |
| SWH | 10 | 227 | 4.183574752 | 2.82E-06 | 8.28E-05 | 0.002241077 | 0.044052863 | 7.665558962 |
| H.L | 95 | 3546 | 4.157541293 | 4.27E-30 | 2.11E-28 | 4.19E-28 | 0.02679075 | 4.579121936 |
| WVPH | 3 | 12 | 4.10756226 | 5.84E-05 | 0.000923612 | 0.019959155 | 0.25 | 55.44754316 |
| H.H | 77 | 2930 | 4.07825899 | 3.54E-24 | 7.01E-23 | 3.36E-22 | 0.026279863 | 4.489443558 |
| HAH | 8 | 188 | 4.041155186 | 3.53E-05 | 0.00070596 | 0.027534142 | 0.042553191 | 7.393005755 |
| H....F | 64 | 2291 | 4.025472336 | 1.22E-20 | 3.18E-19 | 1.24E-18 | 0.027935399 | 4.780389891 |
| HFP | 10 | 236 | 4.024031647 | 3.98E-06 | 0.000112753 | 0.00315833 | 0.042372881 | 7.36029334 |
| W.....L | 45 | 1588 | 3.981703272 | 1.25E-14 | 3.27E-13 | 1.27E-12 | 0.028337531 | 4.85121084 |

FIG. 81B

RA vs. Fibromyalgia

| motif | n | n.lib | enrich | p | fdr | padj.holm | Pr_seqs.motif | PLR |
|---|---|---|---|---|---|---|---|---|
| H | 1085 | 65939 | 2.595371706 | 6.04E-196 | 4.23E-195 | 4.23E-195 | 0.016454602 | 2.78289316 |
| W | 644 | 58364 | 1.740415742 | 3.56E-47 | 1.25E-46 | 2.14E-46 | 0.011034199 | 1.855936476 |
| F | 581 | 75858 | 1.208055615 | 1.03E-09 | 2.40E-09 | 5.14E-09 | 0.007659047 | 1.283859183 |
| V | 497 | 68411 | 1.145889221 | 1.40E-05 | 2.45E-05 | 5.61E-05 | 0.007264914 | 1.217308461 |
| R | 458 | 63785 | 1.13255448 | 0.000119272 | 0.000139151 | 0.000238545 | 0.007180372 | 1.203040161 |
| L | 509 | 71596 | 1.121350051 | 6.87E-05 | 9.61E-05 | 0.000205962 | 0.007109336 | 1.191053194 |

FIG. 82A

RA vs. SS – Top 500 peptides

| motif | n | n.lib | enrich | p | fdr | padj.holm | Pr_seqs.motif | PLR |
|---|---|---|---|---|---|---|---|---|
| ALHW | 2 | 4 | 8.235423381 | 0.000121098 | 0.00082934 | 0.023735274 | 0.5 | 251.018 |
| WSHW | 2 | 4 | 8.235423381 | 0.000121098 | 0.00082934 | 0.023735274 | 0.5 | 251.018 |
| YVHH | 2 | 4 | 8.235423381 | 0.000121098 | 0.00082934 | 0.023735274 | 0.5 | 251.018 |
| H.....H | 50 | 1157 | 8.11088305 | 4.65E-30 | 5.16E-28 | 5.16E-28 | 0.043215212 | 11.33775971 |
| H..H | 84 | 2652 | 6.961124155 | 9.89E-43 | 9.69E-41 | 9.69E-41 | 0.031674208 | 8.210869159 |
| H....H | 55 | 1672 | 6.723054398 | 3.71E-28 | 4.08E-26 | 4.08E-26 | 0.032894737 | 8.538027211 |
| HHF | 14 | 235 | 6.666661592 | 5.32E-12 | 4.01E-10 | 3.05E-09 | 0.059574468 | 15.90159276 |
| HQFQ | 2 | 5 | 6.588338705 | 0.000201224 | 0.00116607 | 0.038031419 | 0.4 | 167.3453333 |
| QYHY | 2 | 5 | 6.588338705 | 0.000201224 | 0.00116607 | 0.038031419 | 0.4 | 167.3453333 |
| HFH | 9 | 158 | 6.374317028 | 4.82E-08 | 1.75E-06 | 2.72E-05 | 0.056962025 | 15.16216107 |
| H.H | 83 | 2930 | 6.307002126 | 3.20E-39 | 1.50E-37 | 2.98E-37 | 0.028327645 | 7.318051985 |
| H...H | 59 | 2080 | 6.078459459 | 1.62E-27 | 8.41E-26 | 1.67E-25 | 0.028365385 | 7.328086096 |
| WHY | 9 | 167 | 6.030790961 | 7.76E-08 | 2.50E-06 | 4.37E-05 | 0.053892216 | 14.29849367 |
| HRH | 15 | 279 | 6.016380469 | 4.07E-12 | 3.93E-10 | 2.34E-09 | 0.053763441 | 14.26238636 |
| H...F | 76 | 2708 | 6.014088021 | 9.70E-35 | 1.01E-32 | 1.01E-32 | 0.028064993 | 7.248240122 |
| HF | 165 | 6250 | 5.992626513 | 3.46E-73 | 3.01E-71 | 3.01E-71 | 0.0264 | 6.806568611 |
| VHH | 5 | 95 | 5.889719827 | 7.08E-05 | 0.000830735 | 0.037658586 | 0.052631579 | 13.94544444 |
| H.....F | 56 | 1803 | 5.829399163 | 2.10E-26 | 1.17E-24 | 2.31E-24 | 0.031059346 | 8.046369777 |
| HFG | 44 | 846 | 5.82010139 | 5.15E-32 | 2.99E-29 | 2.99E-29 | 0.052009456 | 13.7715611 |
| AHH | 7 | 137 | 5.717757205 | 3.10E-06 | 7.24E-05 | 0.001725216 | 0.051094891 | 13.51635385 |
| HHH | 5 | 98 | 5.709422282 | 8.21E-05 | 0.000898028 | 0.043328322 | 0.051020408 | 13.4955914 |
| RHF | 35 | 696 | 5.627390352 | 2.63E-25 | 7.63E-23 | 1.52E-22 | 0.050287356 | 13.29142209 |
| H.F | 105 | 4184 | 5.587404697 | 1.43E-44 | 1.35E-42 | 1.35E-42 | 0.025095602 | 6.461605786 |
| HH | 60 | 2453 | 5.552224097 | 8.83E-26 | 1.28E-24 | 7.24E-24 | 0.024459845 | 6.293806937 |
| Y.....H | 35 | 1186 | 5.538789361 | 2.24E-16 | 8.30E-15 | 2.45E-14 | 0.029510961 | 7.633040834 |
| W...H | 55 | 2136 | 5.517804244 | 8.53E-24 | 2.96E-22 | 8.70E-22 | 0.025749064 | 6.634305622 |
| HFV | 8 | 167 | 5.360703076 | 9.98E-07 | 2.76E-05 | 0.000558635 | 0.047904192 | 12.62983648 |
| H.Y | 63 | 2633 | 5.327239176 | 3.22E-26 | 7.57E-25 | 2.93E-24 | 0.023927079 | 6.153359533 |
| H..F | 79 | 3271 | 5.307868569 | 2.47E-32 | 1.21E-30 | 2.40E-30 | 0.024151636 | 6.212538221 |
| H...Y | 40 | 1635 | 5.242604333 | 5.66E-17 | 1.18E-15 | 5.66E-15 | 0.024464832 | 6.295122257 |
| Y.H | 80 | 3400 | 5.238700561 | 2.05E-32 | 6.43E-31 | 1.89E-30 | 0.023529412 | 6.048626506 |
| HY | 65 | 2865 | 5.149938169 | 4.86E-26 | 8.46E-25 | 4.03E-24 | 0.022687609 | 5.827203571 |
| HLY | 11 | 246 | 5.003867658 | 1.95E-08 | 8.10E-07 | 1.11E-05 | 0.044715447 | 11.74977872 |
| VPH | 8 | 181 | 4.946063059 | 1.82E-06 | 4.80E-05 | 0.001018743 | 0.044198895 | 11.60776879 |
| Y..H | 59 | 2662 | 4.870993767 | 1.05E-22 | 3.41E-21 | 1.00E-20 | 0.022163787 | 5.689612755 |
| HHL | 11 | 259 | 4.752708278 | 3.31E-08 | 1.28E-06 | 1.87E-05 | 0.042471042 | 11.1338629 |
| YHY | 6 | 143 | 4.695301121 | 4.79E-05 | 0.000631079 | 0.02570884 | 0.041958042 | 10.99348905 |
| P...H | 49 | 2271 | 4.623637672 | 2.83E-18 | 7.36E-17 | 2.86E-16 | 0.021576398 | 5.53550045 |
| HYH | 7 | 172 | 4.554260099 | 1.37E-05 | 0.000234456 | 0.007517952 | 0.040697674 | 10.64924848 |
| HYG | 6 | 148 | 4.536676083 | 5.80E-05 | 0.000729624 | 0.031004811 | 0.040540541 | 10.60639437 |
| HVH | 7 | 173 | 4.527934896 | 1.43E-05 | 0.000236451 | 0.007790661 | 0.040462428 | 10.58509639 |
| H....F | 50 | 2291 | 4.460516231 | 2.92E-18 | 1.61E-16 | 3.18E-16 | 0.021824531 | 5.600580098 |
| YRH | 16 | 404 | 4.431868385 | 7.55E-11 | 3.98E-09 | 4.30E-08 | 0.03960396 | 10.35125773 |
| Y...H | 45 | 2192 | 4.399231453 | 3.96E-16 | 6.87E-15 | 3.92E-14 | 0.020529197 | 5.261206334 |
| FHRH | 4 | 15 | 4.392225803 | 5.40E-07 | 3.05E-05 | 0.000120472 | 0.266666667 | 91.27927273 |
| NRH | 20 | 513 | 4.362755428 | 4.54E-13 | 5.27E-11 | 2.62E-10 | 0.038986355 | 10.183286 |
| HLW | 8 | 207 | 4.324818424 | 4.92E-06 | 9.83E-05 | 0.002713126 | 0.038647343 | 10.09117588 |
| P....H | 35 | 1680 | 4.257934452 | 1.16E-12 | 4.27E-11 | 1.26E-10 | 0.020833333 | 5.340808511 |
| W....H | 33 | 1602 | 4.210092492 | 6.81E-12 | 1.50E-10 | 7.21E-10 | 0.020599251 | 5.279537285 |
| HAF | 6 | 160 | 4.196425377 | 8.91E-05 | 0.000957322 | 0.046971504 | 0.0375 | 9.779922078 |

FIG. 82B

RA vs. SS – Top 500 peptides

| motif | n | n.lib | enrich | p | fdr | padj.holm | Pr_seqs.motif | PLR |
|---|---|---|---|---|---|---|---|---|
| H | 850 | 65939 | 2.978885644 | 1.32E-191 | 9.27E-191 | 9.27E-191 | 0.012890702 | 3.278054664 |
| Y | 360 | 56760 | 1.465673975 | 3.09E-15 | 7.21E-15 | 1.54E-14 | 0.006342495 | 1.602242553 |
| F | 478 | 75858 | 1.456142141 | 9.83E-21 | 3.44E-20 | 5.90E-20 | 0.006301247 | 1.591756487 |
| W | 325 | 58364 | 1.286813399 | 8.90E-08 | 1.56E-07 | 3.56E-07 | 0.005568501 | 1.40562122 |
| P | 312 | 56321 | 1.280151882 | 2.90E-07 | 4.06E-07 | 8.71E-07 | 0.005539674 | 1.39830413 |

RA v Healthy

ADAM30|7~~6775.0
DNAJC30|0~~6734.0
ST8SIA3|28~~6731.0
VIPR1|40~~6217.0
HYAL2|19~~6208.57142857
GIMAP1|25~~6039.0
INVS|92~~5952.0
SLC17A9|22~~5887.0
PDF|4~~5874.0
STARD10|29~~5864.0
NOXA1|18~~5857.0
MRPS18A|19~~5835.0
RNF20|28~~5802.0
ZNF579|8~~5792.0
KRBA1|89~~5782.0
GGT2|14~~5778.0
GGT1|14~~5778.0
CCDC88B|8~~5770.14285714
TTI2|23~~5736.0
CCDC142|72~~5617.0
ABHD11|1~~5545.0
EMILIN2|0~~5524.0
CCSER2|59~~5507.0
MGAT4B|11~~5476.0
PKN3|9~~5465.0
ANXA2R|14~~5461.0
CARNS1|29~~5443.0
LRRC41|75~~5408.0
OBSCN|687~~5389.0
AKIRIN1|8~~5382.0
ACTRT2|8~~5363.0
NUTM2E|33~~5356.0
NUTM2A|33~~5356.0
NUTM2B|33~~5356.0
NUTM2D|33~~5355.0
ADAM8|3~~5346.0
ZNF697|14~~5341.0
SNAPC4|72~~5341.0
IL17RE|47~~5339.0

FIG. 87B

RA v Other AI/non-AI mimic diseases

MN1|10~~7405.0
KRBA1|89~~6360.0
AGTRAP|10~~6259.0
SIK3|92~~6235.0
MGAT4B|11~~6199.0
SZT2|305~~6078.0
BCAM|52~~6074.0
SLC25A16|6~~6048.0
OBSCN|687~~6012.0
HELZ|153~~5998.0
TIE1|63~~5973.0
NHS|107~~5941.0
PACS1|94~~5935.0
SEPP1|20~~5928.0
MGAT4B|12~~5915.0
CEACAM3|5~~5912.14285714
CEACAM5|5~~5912.14285714
STRADA|34~~5901.0
MBOAT4|33~~5844.79220779
IQSEC2|131~~5843.0
EPN2|22~~5802.0
PRR26|18~~5776.0
FN3KRP|28~~5721.0
RBM27|69~~5710.0
STARD10|29~~5683.0
CLCN2|87~~5669.0
CACNA1H|52~~5621.0
USP13|28~~5608.0
CCDC185|17~~5586.0
NLK|4~~5570.0
HIVEP2|122~~5559.0
RPL3L|0~~5511.0
DNHD1|258~~5505.0
ZNF865|15~~5489.0
PARP16|19~~5463.0
PPM1N|11~~5441.0
PRR7|9~~5439.0
TBX5|42~~5436.0
IQSEC1|100~~5415.0

FIG. 87C
RA v Not

MN1|10~~6590.0
MGAT4B|11~~6369.0
KRBA1|89~~6329.0
OBSCN|687~~6265.0
SIK3|92~~6198.0
ADAM30|7~~6167.0
CEACAM3|5~~6094.14285714
CEACAM5|5~~6094.14285714
BCAM|52~~6094.0
TIE1|63~~6084.0
ZNF579|8~~5919.0
AGTRAP|10~~5916.0
NHS|107~~5902.0
SZT2|305~~5887.0
SLC25A16|6~~5844.0
HSPB11|13~~5787.0
STRADA|34~~5754.0
ST8SIA3|28~~5749.0
PPM1N|11~~5747.0
STARD10|29~~5747.0
EPN2|22~~5728.0
MGAT4B|12~~5714.0
B4GALT5|17~~5665.0
HELZ|153~~5661.0
PRR26|18~~5623.0
B3GNT6|23~~5622.0
CHD2|162~~5606.0
ZNF697|14~~5601.0
ZNF697|13~~5595.0
IQSEC2|131~~5591.0
CLCN2|87~~5580.0
HIVEP2|122~~5566.0
POLE|167~~5561.0
CCDC185|17~~5554.0
PKD1L2|197~~5536.0
HELZ|135~~5525.0
SCNN1D|1~~5508.0
CCR3|33~~5483.0
TBX5|42~~5467.0

FIG. 88A
SLE, RA, FM, OA, SS and HC multiclassifier – top 3175 significant peptides

| motif | n | n.lib | enrich | p | fdr | padj.holm | Pr_seqs. motif | PLR |
|---|---|---|---|---|---|---|---|---|
| PGDS | 3 | 3 | 12.94112164 | 1.66E-05 | 0.004387632 | 0.039356061 | 1 | Inf |
| PLAE | 4 | 5 | 10.35289731 | 2.07E-06 | 0.000968388 | 0.004927116 | 0.8 | 154.7514961 |
| PQNN | 4 | 5 | 10.35289731 | 2.07E-06 | 0.000968388 | 0.004927116 | 0.8 | 154.7514961 |
| PSRQ | 4 | 5 | 10.35289731 | 2.07E-06 | 0.000968388 | 0.004927116 | 0.8 | 154.7514961 |
| PPD | 31 | 127 | 9.140744792 | 1.26E-21 | 2.10E-18 | 2.10E-18 | 0.244094488 | 12.49295932 |
| PGD | 27 | 111 | 9.10886774 | 5.41E-19 | 4.53E-16 | 9.06E-16 | 0.243243243 | 12.43538808 |
| PGGN | 5 | 8 | 8.088201025 | 5.66E-07 | 0.000968388 | 0.001347733 | 0.625 | 64.47979003 |
| PDD | 24 | 112 | 8.024478723 | 1.06E-15 | 5.19E-13 | 1.77E-12 | 0.214285714 | 10.55123837 |
| PDS | 24 | 119 | 7.552450563 | 4.51E-15 | 1.51E-12 | 7.54E-12 | 0.201680672 | 9.773778699 |
| PDE | 25 | 124 | 7.549912777 | 1.24E-15 | 5.19E-13 | 2.07E-12 | 0.201612903 | 9.769665155 |
| PGQE | 4 | 7 | 7.394926652 | 1.39E-05 | 0.004140819 | 0.033029203 | 0.571428571 | 51.58383202 |
| PDL | 24 | 124 | 7.247916266 | 1.19E-14 | 3.33E-12 | 1.99E-11 | 0.193548387 | 9.285089764 |
| PSEK | 5 | 9 | 7.189512023 | 1.25E-06 | 0.000968388 | 0.002966832 | 0.555555556 | 48.35984252 |
| PEQ | 21 | 115 | 6.838251434 | 1.73E-12 | 4.13E-10 | 2.88E-09 | 0.182608696 | 8.643035684 |
| P.....N | 137 | 791 | 6.704738664 | 4.03E-69 | 1.77E-67 | 3.51E-67 | 0.173198483 | 8.104340581 |
| PGS | 21 | 121 | 6.499164586 | 4.81E-12 | 1.01E-09 | 8.02E-09 | 0.173553719 | 8.124453543 |
| NEPD | 5 | 10 | 6.47056082 | 2.44E-06 | 0.000968388 | 0.005798129 | 0.5 | 38.68787402 |
| P.....Q | 157 | 954 | 6.370727788 | 1.01E-75 | 8.86E-74 | 8.86E-74 | 0.164570231 | 7.621074304 |
| PEE | 21 | 124 | 6.341926733 | 7.84E-12 | 1.31E-09 | 1.31E-08 | 0.169354839 | 7.887818974 |
| PGG | 20 | 119 | 6.293708803 | 2.82E-11 | 3.63E-09 | 4.69E-08 | 0.168067227 | 7.815732124 |
| PEN | 21 | 128 | 6.143741523 | 1.47E-11 | 2.24E-09 | 2.45E-08 | 0.1640625 | 7.592947237 |
| PGE | 20 | 122 | 6.138945471 | 4.51E-11 | 5.39E-09 | 7.49E-08 | 0.163934426 | 7.58585765 |
| P.....A | 125 | 798 | 6.063800334 | 4.24E-58 | 7.46E-57 | 3.56E-56 | 0.156641604 | 7.185712113 |
| P....N | 180 | 1231 | 5.700548499 | 1.96E-78 | 1.75E-76 | 1.75E-76 | 0.146222583 | 6.625896596 |
| PDN | 19 | 126 | 5.646855398 | 5.95E-10 | 5.54E-08 | 9.88E-07 | 0.150793651 | 6.869809405 |
| PEV | 19 | 126 | 5.646855398 | 5.95E-10 | 5.54E-08 | 9.88E-07 | 0.150793651 | 6.869809405 |
| PGL | 15 | 100 | 5.617135106 | 3.99E-08 | 2.23E-06 | 6.57E-05 | 0.15 | 6.827271885 |
| P.....P | 113 | 782 | 5.593832546 | 4.61E-49 | 5.79E-48 | 3.78E-47 | 0.144501279 | 6.534723115 |
| PEL | 17 | 118 | 5.39498852 | 9.51E-09 | 6.93E-07 | 1.57E-05 | 0.144067797 | 6.511820379 |
| PSL | 17 | 119 | 5.349652482 | 1.08E-08 | 7.56E-07 | 1.79E-05 | 0.142857143 | 6.447979003 |
| PPG | 16 | 112 | 5.349652482 | 2.90E-08 | 1.74E-06 | 4.78E-05 | 0.142857143 | 6.447979003 |
| PPE | 18 | 127 | 5.307529234 | 4.61E-09 | 3.68E-07 | 7.63E-06 | 0.141732283 | 6.388823232 |
| PDA | 23 | 167 | 5.157449399 | 6.45E-11 | 7.20E-09 | 1.07E-07 | 0.137724551 | 6.179313211 |
| PPS | 17 | 124 | 5.133940689 | 2.03E-08 | 1.31E-06 | 3.36E-05 | 0.137096774 | 6.146671573 |
| PDV | 15 | 111 | 5.060482078 | 1.65E-07 | 7.88E-06 | 0.000270199 | 0.135135135 | 6.044980315 |
| PSK | 15 | 111 | 5.060482078 | 1.65E-07 | 7.88E-06 | 0.000270199 | 0.135135135 | 6.044980315 |
| P....A | 160 | 1254 | 4.974215986 | 1.74E-61 | 5.15E-60 | 1.51E-59 | 0.127591707 | 5.658189984 |
| PES | 16 | 122 | 4.911156377 | 9.87E-08 | 5.01E-06 | 0.000162139 | 0.131147541 | 5.839679097 |
| P....Q | 167 | 1327 | 4.906228162 | 3.01E-63 | 1.34E-61 | 2.65E-61 | 0.125847777 | 5.569719794 |
| PGQ | 19 | 146 | 4.873313563 | 7.39E-09 | 5.63E-07 | 1.22E-05 | 0.130136986 | 5.787949656 |
| PDK | 15 | 116 | 4.84235785 | 2.96E-07 | 1.24E-05 | 0.000483744 | 0.129310345 | 5.745723864 |
| PVH | 15 | 117 | 4.800970176 | 3.31E-07 | 1.35E-05 | 0.000541457 | 0.128205128 | 5.689393238 |
| EPD | 28 | 223 | 4.701936711 | 5.68E-12 | 1.06E-09 | 9.48E-09 | 0.125560538 | 5.55518191 |
| PLA | 16 | 130 | 4.608931369 | 2.40E-07 | 1.06E-05 | 0.000394241 | 0.123076923 | 5.429877055 |
| PLQ | 16 | 130 | 4.608931369 | 2.40E-07 | 1.06E-05 | 0.000394241 | 0.123076923 | 5.429877055 |
| PPR | 16 | 130 | 4.608931369 | 2.40E-07 | 1.06E-05 | 0.000394241 | 0.123076923 | 5.429877055 |
| PSS | 15 | 125 | 4.493708085 | 7.85E-07 | 3.06E-05 | 0.001282634 | 0.12 | 5.275619184 |
| PGV | 13 | 109 | 4.466223632 | 4.49E-06 | 0.000141793 | 0.007281721 | 0.119266055 | 5.23898294 |
| P...Q | 217 | 1916 | 4.431017296 | 1.82E-73 | 1.73E-71 | 1.73E-71 | 0.113256785 | 4.941299977 |
| PER | 13 | 114 | 4.270336631 | 7.39E-06 | 0.000217176 | 0.011965175 | 0.114035088 | 4.979627349 |

FIG. 88B

SLE, RA, FM, OA, SS and HC multiclassifier – top 3175 significant peptides

| motif | n | n.lib | enrich | p | fdr | padj.holm | Pr_seqs. motif | PLR |
|---|---|---|---|---|---|---|---|---|
| P | 3280 | 56321 | 2.292938973 | 0 | 0 | 0 | 0.058237602 | 2.392417691 |
| Q | 1728 | 60519 | 1.124193331 | 1.70E 12 | 3.40E-12 | 6.81E 12 | 0.028553016 | 1.137123817 |
| G | 3164 | 111145 | 1.12081918 | 1.62E-32 | 4.86E-32 | 8.10E-32 | 0.028467317 | 1.133610852 |
| A | 1538 | 57451 | 1.054017333 | 5.45E-05 | 6.54E-05 | 0.00010892 | 0.026770639 | 1.064188118 |
| K | 1596 | 62082 | 1.012176377 | 0.008450706 | 0.008450706 | 0.008450706 | 0.025707935 | 1.020828736 |
| D | 2505 | 98037 | 1.006020259 | 6.07E-06 | 9.11E-06 | 1.82E-05 | 0.025551577 | 1.014457191 |

FIG. 90

| SLE vs Healthy Controls | | | | | |
|---|---|---|---|---|---|
| PEPTIDE | STATISTIC | P.VALUE | P.BON | MEAN1 | MEAN2 |
| RASPPG | 80.02502368 | 1.59E-15 | 2.01E-10 | 3.140725483 | 3.37005126 |
| GPQQNKVG | 78.42385608 | 2.70E-15 | 3.40E-10 | 3.128783457 | 3.366162573 |
| PLGEDELSG | 77.15629123 | 4.31E-15 | 5.44E-10 | 3.907318071 | 3.479600346 |
| LPVNRELG | 73.98185389 | 1.43E-14 | 1.80E-09 | 3.664375393 | 3.331425783 |
| KVPVQKGAQVL | 73.15803336 | 1.55E-14 | 1.95E-09 | 3.231724814 | 3.453319232 |
| GVKGG | 72.86921984 | 1.82E-14 | 2.29E-09 | 3.139898367 | 3.370851139 |
| PNLHNNRD | 72.53847096 | 3.58E-14 | 4.51E-09 | 3.592315041 | 3.347526843 |
| GLLKG | 70.6915306 | 3.60E-14 | 4.54E-09 | 3.272841844 | 3.463511741 |
| KQPSSG | 69.83004949 | 4.87E-14 | 6.13E-09 | 3.04454852 | 3.276948768 |
| VQGRGVG | 69.74698122 | 4.94E-14 | 6.22E-09 | 3.095511258 | 3.286715551 |
| QQKQLGKLS | 69.33896429 | 5.78E-14 | 7.29E-09 | 3.201501665 | 3.408589859 |
| PLAEEDQL | 68.44132388 | 7.73E-14 | 9.73E-09 | 3.906061924 | 3.462320914 |
| PEQEEGKFD | 68.72286864 | 7.77E-14 | 9.79E-09 | 3.761135671 | 3.323591124 |
| GLAAKSG | 68.30755339 | 8.98E-14 | 1.13E-08 | 3.151308427 | 3.392354447 |
| GRKADG | 68.20456756 | 9.09E-14 | 1.15E-08 | 3.102685058 | 3.361413897 |
| PRADDEG | 68.31414311 | 9.33E-14 | 1.18E-08 | 4.116393173 | 3.629327878 |
| PPGKHQEG | 67.63780522 | 1.06E-13 | 1.34E-08 | 3.877614632 | 3.473127128 |
| RLQAGG | 67.46850555 | 1.11E-13 | 1.40E-08 | 3.116989399 | 3.353616555 |
| PSLKEPQFE | 67.03385728 | 1.26E-13 | 1.58E-08 | 3.988000931 | 3.604510015 |
| PDLGDNVDG | 67.0281395 | 1.49E-13 | 1.88E-08 | 3.736414835 | 3.337984749 |
| QLQAVKSG | 66.86563897 | 1.49E-13 | 1.88E-08 | 3.065664423 | 3.265200395 |
| QKGGNKNVG | 66.44222856 | 1.62E-13 | 2.04E-08 | 3.157922368 | 3.379440453 |
| GGPQNKG | 66.19081615 | 1.71E-13 | 2.15E-08 | 3.210496987 | 3.412915814 |
| PVKEEAWEG | 66.17876696 | 1.74E-13 | 2.20E-08 | 3.983178291 | 3.58226341 |
| EPEYKERSG | 66.86644869 | 1.81E-13 | 2.28E-08 | 3.509935131 | 3.209284709 |
| PEGDDGNQKHF | 66.78935684 | 1.97E-13 | 2.49E-08 | 3.69321671 | 3.309490201 |
| ADRDDPKRE | 66.55744356 | 2.26E-13 | 2.85E-08 | 3.356249829 | 3.079587299 |
| PPEREGHG | 65.62345972 | 2.35E-13 | 2.96E-08 | 4.153229795 | 3.745684702 |
| PFAGDHSG | 65.10396367 | 2.46E-13 | 3.10E-08 | 3.91674583 | 3.586716216 |
| QGAPKVGVSG | 64.69419755 | 2.94E-13 | 3.71E-08 | 3.055551822 | 3.289522242 |
| PLGSDSEPRE | 64.69335416 | 3.04E-13 | 3.83E-08 | 3.821404382 | 3.45293089 |
| PDGDQKPWFG | 64.46516559 | 3.08E-13 | 3.88E-08 | 3.996569515 | 3.567012766 |
| PGQAEYQE | 64.48431816 | 3.12E-13 | 3.94E-08 | 4.008370204 | 3.601385643 |
| PGVHDDG | 64.76672459 | 3.36E-13 | 4.23E-08 | 3.840834956 | 3.539166435 |
| PLQKNEFEG | 64.03004348 | 3.61E-13 | 4.55E-08 | 3.862015105 | 3.474123955 |
| KAGPGAKFE | 63.99119909 | 3.71E-13 | 4.67E-08 | 3.133829965 | 3.347565264 |

FIG. 90, Continued

| | | | | | |
|---|---|---|---|---|---|
| GKNQGG | 63.97594031 | 3.72E-13 | 4.69E-08 | 3.060261944 | 3.283514444 |
| PGLNEPDG | 64.03813088 | 4.06E-13 | 5.12E-08 | 4.067740544 | 3.633795371 |
| PSLADEG | 63.66200494 | 4.17E-13 | 5.26E-08 | 3.959911912 | 3.528230248 |
| PDRNQQFE | 63.73414052 | 4.45E-13 | 5.60E-08 | 3.737408938 | 3.351525035 |
| PDLDAGAEG | 64.17897977 | 4.55E-13 | 5.74E-08 | 3.821662788 | 3.364937732 |
| EPGSRFEG | 64.37148503 | 4.83E-13 | 6.08E-08 | 3.596404751 | 3.281413809 |
| QGRGWKKVE | 63.24554188 | 4.91E-13 | 6.18E-08 | 3.151030903 | 3.341936413 |
| PASSEASLSD | 63.07538155 | 5.25E-13 | 6.62E-08 | 3.814668341 | 3.412022163 |
| EPEFGPSG | 65.64753077 | 5.27E-13 | 6.64E-08 | 3.675179936 | 3.286400153 |
| LPSERGSE | 63.08649882 | 5.49E-13 | 6.92E-08 | 3.665914112 | 3.328132421 |
| PGFEGYNRQG | 62.88982011 | 5.65E-13 | 7.11E-08 | 4.239068546 | 3.859950401 |
| RPKGEQSG | 62.85388022 | 5.72E-13 | 7.20E-08 | 3.123508688 | 3.352460337 |
| PYAVHRDA | 63.48031012 | 5.82E-13 | 7.33E-08 | 3.753696373 | 3.442763342 |
| PLKFNQENDG | 63.43008886 | 6.16E-13 | 7.77E-08 | 3.644637454 | 3.312283965 |

FIG. 91

| SLE vs Other Autoimmune Diseases and Non-Autoimmune Mimic Diseases | | | | | |
|---|---|---|---|---|---|
| PEPTIDE | STATISTIC | P.VALUE | P.BON | MEAN1 | MEAN2 |
| PVHQYQFG | 62.42905331 | 2.31E-13 | 2.91E-08 | 3.515176404 | 3.380871994 |
| PGNWYWSG | 57.93415572 | 1.16E-12 | 1.46E-07 | 3.737056123 | 3.624770336 |
| PGSFSEHVL | 57.46061615 | 1.81E-12 | 2.28E-07 | 3.542619873 | 3.421281624 |
| APRGVKSD | 56.56721632 | 5.91E-12 | 7.45E-07 | 3.208465133 | 3.387399924 |
| PYKGESAHLF | 51.47926377 | 1.24E-11 | 1.56E-06 | 3.520844106 | 3.422091342 |
| GPQQNKVG | 53.01679864 | 1.81E-11 | 2.28E-06 | 3.190160007 | 3.366162573 |
| VKPGG | 52.88027674 | 2.55E-11 | 3.22E-06 | 3.144825835 | 3.337903392 |
| PFGHGYNNFS | 48.04794284 | 5.79E-11 | 7.30E-06 | 3.576219201 | 3.421524581 |
| RPLAGPG | 48.80606562 | 7.11E-11 | 8.96E-06 | 3.302245658 | 3.482745693 |
| PYHPQFLS | 45.85901321 | 1.48E-10 | 1.86E-05 | 3.584834736 | 3.466975092 |
| PLSRAFDHG | 45.21501487 | 1.56E-10 | 1.96E-05 | 3.543896525 | 3.403135574 |
| YPEQPSED | 44.81438185 | 1.60E-10 | 2.02E-05 | 3.556978482 | 3.341178309 |
| RPPGG | 46.93107555 | 1.62E-10 | 2.05E-05 | 3.311085691 | 3.494759756 |
| PKNAEYWHFS | 46.09092752 | 1.93E-10 | 2.43E-05 | 3.715945171 | 3.598530629 |
| KQPSSG | 46.21859945 | 2.33E-10 | 2.93E-05 | 3.111061642 | 3.276948768 |
| GAAVKG | 46.36437867 | 2.43E-10 | 3.06E-05 | 3.195751262 | 3.36171806 |
| GPNLQKQLG | 46.58384766 | 2.96E-10 | 3.73E-05 | 3.200054443 | 3.379086156 |
| GKPAQQLG | 46.13619268 | 3.56E-10 | 4.49E-05 | 3.144213404 | 3.321117884 |
| PYQGKFELNHLS | 44.19070595 | 3.59E-10 | 4.52E-05 | 3.622227096 | 3.507190339 |
| NPSQRYADG | 43.01403771 | 3.62E-10 | 4.56E-05 | 3.374597563 | 3.200531763 |
| APLKPQSG | 44.77897216 | 3.93E-10 | 4.96E-05 | 3.280067348 | 3.439548214 |
| DPRKSVSG | 44.9375453 | 4.40E-10 | 5.55E-05 | 3.223903248 | 3.389297257 |
| PKGVQHYHG | 43.98008055 | 4.55E-10 | 5.74E-05 | 3.667490536 | 3.507923413 |
| RQGPSDKG | 45.34011085 | 4.69E-10 | 5.91E-05 | 3.170853377 | 3.345855105 |
| RGEKLPG | 45.47815714 | 5.08E-10 | 6.41E-05 | 3.158630005 | 3.312401847 |
| GSVGNKLSG | 43.84656511 | 5.91E-10 | 7.44E-05 | 3.188822778 | 3.345915627 |
| RASPPG | 43.08595591 | 6.36E-10 | 8.02E-05 | 3.21491063 | 3.37005126 |
| GRQPLG | 44.02236903 | 6.76E-10 | 8.52E-05 | 3.279625967 | 3.448342976 |
| QPFHGG | 41.70044832 | 6.81E-10 | 8.58E-05 | 3.496695881 | 3.374669269 |
| PSKVHLERHS | 42.49402499 | 6.96E-10 | 8.77E-05 | 3.522435265 | 3.372260337 |
| KAGPGAKFE | 43.77634108 | 7.00E-10 | 8.82E-05 | 3.187565418 | 3.347565264 |
| PSQWNRWG | 42.43462207 | 7.33E-10 | 9.24E-05 | 3.75087224 | 3.628311206 |
| GWKNGSG | 43.60881465 | 8.09E-10 | 1.02E-04 | 3.307982879 | 3.464263677 |
| GKNQGG | 42.90756378 | 9.00E-10 | 1.13E-04 | 3.124745401 | 3.283514444 |
| PNVPVGREVFS | 41.42431851 | 9.56E-10 | 1.20E-04 | 3.489523288 | 3.36103854 |
| PVLQSERGKDG | 41.08896146 | 9.67E-10 | 1.22E-04 | 3.48557497 | 3.272324727 |
| SKAGG | 42.71101811 | 9.68E-10 | 1.22E-04 | 3.063053259 | 3.218631776 |

FIG. 91, Continued

| | | | | | |
|---|---|---|---|---|---|
| LPVNRELG | 42.43064555 | 9.77E-10 | 1.23E-04 | 3.541033524 | 3.331425783 |
| KQPPG | 42.63204087 | 9.82E-10 | 1.24E-04 | 3.095032284 | 3.268675569 |
| PNVEGDYSAWRVL | 40.85453217 | 1.07E-09 | 1.34E-04 | 3.452569894 | 3.364596956 |
| PNLHNNRD | 41.6591216 | 1.09E-09 | 1.38E-04 | 3.493833272 | 3.347526843 |
| VRNPKDG | 42.05506127 | 1.18E-09 | 1.49E-04 | 3.132226172 | 3.279551811 |
| GRKADG | 42.65424918 | 1.27E-09 | 1.60E-04 | 3.175137449 | 3.361413897 |
| GLAAKSG | 43.05537503 | 1.30E-09 | 1.63E-04 | 3.220362847 | 3.392354447 |
| PKHRERVYANRD | 39.64477209 | 1.33E-09 | 1.68E-04 | 3.550044969 | 3.413299517 |
| VPDKVKG | 41.79827352 | 1.42E-09 | 1.79E-04 | 3.184015466 | 3.368206747 |
| PLPHENYQRG | 41.10609968 | 1.44E-09 | 1.81E-04 | 3.76371606 | 3.573064974 |
| VQGRGVG | 41.31064859 | 1.51E-09 | 1.90E-04 | 3.153884402 | 3.286715551 |
| GGPQNKG | 42.2405289 | 1.52E-09 | 1.91E-04 | 3.270265437 | 3.412915814 |
| RPSPAGG | 41.4944688 | 1.58E-09 | 1.99E-04 | 3.276249077 | 3.449463335 |

FIG. 92

| SLE vs Not-SLE Diseases | | | | | |
|---|---|---|---|---|---|
| PEPTIDE | STATISTIC | P.VALUE | P.BON | MEAN1 | MEAN2 |
| PVHQYQFG | 69.11638612 | 2.88E-14 | 3.63E-09 | 3.517329701 | 3.380871994 |
| PGSFSEHVL | 65.30055132 | 1.44E-13 | 1.82E-08 | 3.546136872 | 3.421281624 |
| APRGVKSD | 65.55751114 | 3.79E-13 | 4.78E-08 | 3.199741588 | 3.387399924 |
| GPQQNKVG | 64.40872273 | 4.84E-13 | 6.10E-08 | 3.178553544 | 3.366162573 |
| PLSRAFDHG | 59.04891761 | 8.12E-13 | 1.02E-07 | 3.555579829 | 3.403135574 |
| PYKGESAHLF | 57.22857961 | 1.71E-12 | 2.16E-07 | 3.521561654 | 3.422091342 |
| PGNWYWSG | 56.88511472 | 2.63E-12 | 3.32E-07 | 3.731031356 | 3.624770336 |
| PFGHGYNNFS | 56.80995255 | 2.66E-12 | 3.35E-07 | 3.581482992 | 3.421524581 |
| NPSQRYADG | 54.38706551 | 3.89E-12 | 4.90E-07 | 3.387700652 | 3.200531763 |
| PVLQSERGKDG | 55.23552579 | 3.93E-12 | 4.96E-07 | 3.508201497 | 3.272324727 |
| AVEVGEAVLG | 54.76245133 | 4.19E-12 | 5.27E-07 | 3.226127991 | 3.011805542 |
| PNLHNNRD | 56.55755764 | 4.24E-12 | 5.35E-07 | 3.512456427 | 3.347526843 |
| KQPSSG | 57.15184651 | 5.61E-12 | 7.06E-07 | 3.09848384 | 3.276948768 |
| RASPPG | 55.73972368 | 6.97E-12 | 8.78E-07 | 3.200882028 | 3.37005126 |
| VKPGG | 57.31060468 | 6.99E-12 | 8.81E-07 | 3.141299143 | 3.337903392 |
| LPVNRELG | 55.6730272 | 8.25E-12 | 1.04E-06 | 3.564357788 | 3.331425783 |
| PDVPEGDG | 53.46823612 | 8.63E-12 | 1.09E-06 | 3.415619559 | 3.181984408 |
| PSKVHLERHS | 53.83949718 | 1.01E-11 | 1.28E-06 | 3.535141551 | 3.372260337 |
| PKGVQHYHG | 53.25098958 | 1.58E-11 | 1.99E-06 | 3.678390307 | 3.507923413 |
| RPLAGPG | 53.61803647 | 1.63E-11 | 2.06E-06 | 3.300358158 | 3.482745693 |
| GAAVKG | 54.41531336 | 1.64E-11 | 2.07E-06 | 3.187038792 | 3.36171806 |
| PYSHQRQVE | 53.16529751 | 1.69E-11 | 2.13E-06 | 3.560765496 | 3.324954599 |
| YPEQPSED | 50.64342587 | 1.81E-11 | 2.28E-06 | 3.557776331 | 3.341178309 |
| GPNLQKQLG | 54.60021341 | 2.17E-11 | 2.74E-06 | 3.189962673 | 3.379086156 |
| PDLPDLED | 51.6796655 | 2.37E-11 | 2.99E-06 | 3.537777861 | 3.299454031 |
| APLKPQSG | 52.62917152 | 2.57E-11 | 3.23E-06 | 3.271524349 | 3.439548214 |
| GKNQGG | 52.94832969 | 2.70E-11 | 3.40E-06 | 3.112551414 | 3.283514444 |
| VQGRGVG | 52.15633933 | 3.16E-11 | 3.98E-06 | 3.14284589 | 3.286715551 |
| NSREPKDALF | 48.7956618 | 3.18E-11 | 4.00E-06 | 3.124851587 | 2.941586452 |
| DPRKSVSG | 52.79556311 | 3.21E-11 | 4.05E-06 | 3.215459224 | 3.389297257 |
| PVKVGEAED | 50.86880839 | 3.32E-11 | 4.18E-06 | 3.371890398 | 3.128586339 |
| KAGPGAKFE | 52.6760359 | 3.42E-11 | 4.31E-06 | 3.177403906 | 3.347565264 |
| PLPHENYQRG | 51.27146853 | 3.50E-11 | 4.41E-06 | 3.778327533 | 3.573064974 |
| PVVVHDG | 51.00577863 | 3.52E-11 | 4.44E-06 | 3.525849761 | 3.345442806 |
| PHYRVQQEG | 50.25375736 | 3.79E-11 | 4.77E-06 | 3.424724071 | 3.234111296 |
| ELPDDG | 48.95521401 | 3.87E-11 | 4.87E-06 | 3.101779852 | 2.935128147 |
| YPHKYQHG | 50.06402578 | 4.15E-11 | 5.23E-06 | 3.431697562 | 3.298932694 |

FIG. 92, Continued

| RQGPSDKG | 52.74125172 | 4.19E-11 | 5.28E-06 | 3.161904583 | 3.345855105 |
|---|---|---|---|---|---|
| RPPGG | 51.07196643 | 4.32E-11 | 5.45E-06 | 3.308505569 | 3.494759756 |
| GLLKG | 51.62805792 | 4.69E-11 | 5.91E-06 | 3.325699041 | 3.463511741 |
| KVQAPSG | 51.46689546 | 4.96E-11 | 6.26E-06 | 3.145822831 | 3.326961383 |
| PHHGSLG | 50.25834324 | 5.09E-11 | 6.42E-06 | 3.514130612 | 3.325287131 |
| PNVPVGREVFS | 49.09038494 | 5.24E-11 | 6.60E-06 | 3.495585179 | 3.36103854 |
| GRQPLG | 51.48499413 | 5.34E-11 | 6.73E-06 | 3.270412001 | 3.448342976 |
| PYHPQFLS | 48.86022088 | 5.56E-11 | 7.00E-06 | 3.584073792 | 3.466975092 |
| PELHLNVG | 50.3082056 | 5.56E-11 | 7.01E-06 | 3.614911699 | 3.383399504 |
| GRKADG | 51.80289259 | 5.59E-11 | 7.04E-06 | 3.161436516 | 3.361413897 |
| GVQYG | 48.58930495 | 5.68E-11 | 7.15E-06 | 3.413536642 | 3.231250777 |
| GGPQNKG | 51.61366763 | 5.97E-11 | 7.52E-06 | 3.25896307 | 3.412915814 |
| VRNPKDG | 50.59780151 | 6.09E-11 | 7.68E-06 | 3.123623807 | 3.279551811 |

FIG. 93

| RA vs Healthy Controls | | | | | |
|---|---|---|---|---|---|
| PEPTIDE | STATISTIC | P.VALUE | P.BON | MEAN1 | MEAN2 |
| RSEGKWHLPWHF | 62.75905752 | 3.43E-13 | 4.32E-08 | 3.593421351 | 3.745416449 |
| KFKVWEWHFS | 59.90823715 | 9.93E-13 | 1.25E-07 | 3.543481975 | 3.690847796 |
| NRFRFSPHWG | 58.43652289 | 1.66E-12 | 2.09E-07 | 3.533790612 | 3.704313561 |
| QFSPRHSWPALS | 56.84508957 | 3.04E-12 | 3.83E-07 | 3.475183108 | 3.63243175 |
| RRQHRVFD | 56.858949 | 3.10E-12 | 3.90E-07 | 3.441986013 | 3.588069455 |
| QSRKVPWLD | 55.98439088 | 4.29E-12 | 5.41E-07 | 3.526022383 | 3.73589035 |
| RWELWKRVD | 55.63405337 | 4.76E-12 | 6.00E-07 | 3.468212061 | 3.617522965 |
| KFRSEWQPHFG | 55.54116762 | 4.91E-12 | 6.18E-07 | 3.478671064 | 3.629351333 |
| KRWENHFYNHV | 55.76669369 | 4.93E-12 | 6.21E-07 | 3.537437212 | 3.68003729 |
| NWLHGPNFG | 55.40038464 | 5.25E-12 | 6.61E-07 | 3.444909136 | 3.598956256 |
| NRYWQKLPGYHVE | 55.20172819 | 5.56E-12 | 7.01E-07 | 3.411418088 | 3.552091101 |
| HWKESRFG | 55.71401411 | 5.69E-12 | 7.17E-07 | 3.354367895 | 3.504816107 |
| RFGWGPAPHLG | 53.96979955 | 9.03E-12 | 1.14E-06 | 3.629961649 | 3.782897897 |
| FEKHGHWG | 53.7750849 | 9.86E-12 | 1.24E-06 | 3.604277496 | 3.753734349 |
| QYKLRHWHLG | 53.76545983 | 1.01E-11 | 1.27E-06 | 3.434307807 | 3.593106862 |
| RQYNKHFRD | 54.01020893 | 1.13E-11 | 1.42E-06 | 3.328495072 | 3.460028537 |
| FWNSRLENRHL | 53.16384804 | 1.23E-11 | 1.55E-06 | 3.423165185 | 3.574905601 |
| KYEHWKFD | 53.15496469 | 1.25E-11 | 1.57E-06 | 3.540311354 | 3.690057696 |
| QYKERHWLG | 52.97286279 | 1.31E-11 | 1.65E-06 | 3.515638499 | 3.669757841 |
| RNWAWHLG | 52.85362124 | 1.40E-11 | 1.76E-06 | 3.543423322 | 3.696160648 |
| RDPQRLFHAWG | 52.93310097 | 1.41E-11 | 1.78E-06 | 3.593808811 | 3.737216723 |
| QWVSQRHAFE | 53.35852713 | 1.45E-11 | 1.82E-06 | 3.47821029 | 3.630983391 |
| WNVGAKHNHPYHL | 52.49066025 | 1.61E-11 | 2.03E-06 | 3.61811818 | 3.774408116 |
| RNSWPWLEG | 52.40937708 | 1.63E-11 | 2.05E-06 | 3.788184447 | 3.970648431 |
| RERHKHWHLG | 52.17949456 | 1.85E-11 | 2.33E-06 | 3.473986601 | 3.633365928 |
| QRDVQHQHVF | 52.13833636 | 1.86E-11 | 2.34E-06 | 3.350858668 | 3.488825263 |
| RGPWYRPYEG | 52.14945326 | 1.89E-11 | 2.38E-06 | 3.544590117 | 3.696721205 |
| WERGARDNHVL | 52.15118297 | 2.14E-11 | 2.70E-06 | 3.427749713 | 3.570425087 |
| RHQWQAHFG | 51.29079223 | 2.53E-11 | 3.19E-06 | 3.461310438 | 3.603493843 |
| RKWDAWLG | 50.98581869 | 2.83E-11 | 3.57E-06 | 3.59852912 | 3.743885117 |
| QHLRVSWRPYNHL | 51.06012935 | 2.88E-11 | 3.63E-06 | 3.43593097 | 3.573069404 |
| NHSYRLGWGWHS | 51.21636278 | 2.97E-11 | 3.74E-06 | 3.384832925 | 3.541081334 |
| SWYLPNRHL | 50.62888364 | 3.28E-11 | 4.14E-06 | 3.428210716 | 3.572239473 |
| RVNQWRHRFE | 50.55265981 | 3.46E-11 | 4.36E-06 | 3.434893959 | 3.580452942 |
| QSQWGYWKHF | 50.43565675 | 3.50E-11 | 4.41E-06 | 3.487889281 | 3.615321847 |
| RQDAPWRHF | 50.44369218 | 3.50E-11 | 4.41E-06 | 3.535048659 | 3.685042727 |
| RDQHLPFYNRHL | 50.33937382 | 3.64E-11 | 4.59E-06 | 3.462977285 | 3.618201572 |

FIG. 93, Continued

| | | | | | |
|---|---|---|---|---|---|
| RVGYAHLNGRFE | 50.34854235 | 3.73E-11 | 4.69E-06 | 3.39289995 | 3.518455324 |
| KSEDHQFNRHF | 50.41589573 | 3.74E-11 | 4.71E-06 | 3.428357141 | 3.584449954 |
| RGHSWNRRLD | 50.37782589 | 3.80E-11 | 4.79E-06 | 3.308214368 | 3.458288715 |
| NVVWWNRHL | 50.18168179 | 3.98E-11 | 5.01E-06 | 3.505553414 | 3.658553541 |
| WPHRHLFWKE | 50.00320857 | 4.17E-11 | 5.25E-06 | 3.48758606 | 3.643495735 |
| GKYRVFFEG | 49.78353656 | 4.52E-11 | 5.70E-06 | 3.39354563 | 3.517058026 |
| HVRAQRPWSE | 49.79441508 | 4.68E-11 | 5.90E-06 | 3.580666325 | 3.749220004 |
| KNSPRLPHFD | 49.99457953 | 4.77E-11 | 6.01E-06 | 3.486465121 | 3.629116446 |
| RFWKGHFPRE | 49.97652836 | 4.86E-11 | 6.12E-06 | 3.306583226 | 3.47248046 |
| RWHQQRFE | 49.71787565 | 4.87E-11 | 6.14E-06 | 3.482399381 | 3.629155115 |
| QSREWHSQLFS | 49.58135484 | 4.90E-11 | 6.17E-06 | 3.302839279 | 3.427496076 |
| WYNRPWHLHG | 49.60417766 | 5.01E-11 | 6.31E-06 | 3.599037143 | 3.764697821 |
| NQRYAWAWPHVS | 49.54824461 | 5.03E-11 | 6.33E-06 | 3.439676565 | 3.585626323 |

FIG. 94

| RA vs Other Autoimmune Diseases and Non-Autoimmune Mimic Diseases | | | | | |
|---|---|---|---|---|---|
| PEPTIDE | STATISTIC | P.VALUE | P.BON | MEAN1 | MEAN2 |
| WYEHGKVFG | 43.94643024 | 6.86E-10 | 8.64E-05 | 3.486797722 | 3.594761761 |
| SWYLPNRHL | 43.07756805 | 7.87E-10 | 9.92E-05 | 3.457981402 | 3.572239473 |
| WNVGAKHNHPYHL | 42.95230225 | 9.79E-10 | 1.23E-04 | 3.648030229 | 3.774408116 |
| HWLGFPAHG | 42.85452396 | 1.03E-09 | 1.30E-04 | 3.471012466 | 3.60345322 |
| FHPHQFSG | 42.56856422 | 1.07E-09 | 1.34E-04 | 3.390920763 | 3.513267667 |
| HWRWYNG | 41.36770065 | 1.82E-09 | 2.29E-04 | 3.351888688 | 3.48801237 |
| YVHHQRHFG | 41.52452694 | 1.96E-09 | 2.47E-04 | 3.377977026 | 3.49740469 |
| NWLHGPNFG | 40.15688539 | 2.09E-09 | 2.63E-04 | 3.483058209 | 3.598956256 |
| WWVSGPNPHFS | 40.09270036 | 2.43E-09 | 3.06E-04 | 3.859488442 | 3.976191751 |
| HHGYWNKWG | 40.96727254 | 2.43E-09 | 3.07E-04 | 3.461055288 | 3.589151154 |
| WYPGRLG | 39.83231267 | 3.00E-09 | 3.78E-04 | 3.66338746 | 3.781660734 |
| LPWHWQGKHFS | 39.80815072 | 3.04E-09 | 3.82E-04 | 3.399351356 | 3.506810054 |
| PVHWARHFG | 40.26198181 | 3.04E-09 | 3.83E-04 | 3.481875982 | 3.591911403 |
| SWFGDNKRHL | 40.00509043 | 3.08E-09 | 3.89E-04 | 3.408033489 | 3.512062565 |
| WYRGGWG | 39.93122543 | 3.12E-09 | 3.93E-04 | 3.660166384 | 3.780771882 |
| WPWWHGYRG | 39.50549922 | 3.50E-09 | 4.41E-04 | 3.333458102 | 3.444241048 |
| SYPQHHVF | 39.21213838 | 3.65E-09 | 4.60E-04 | 3.557079873 | 3.650814894 |
| WDHFYVQRHV | 39.46131219 | 4.09E-09 | 5.15E-04 | 3.476912811 | 3.596000188 |
| WVWHPWRAG | 38.7037715 | 4.11E-09 | 5.17E-04 | 3.6669977 | 3.818431782 |
| KVYWHFGHHG | 39.50316288 | 4.23E-09 | 5.34E-04 | 3.396632754 | 3.516082312 |
| WVQYVPG | 38.84148956 | 4.50E-09 | 5.67E-04 | 3.532161389 | 3.64604056 |
| YHYADYHLPKG | 39.14371762 | 4.66E-09 | 5.87E-04 | 3.324241227 | 3.429833029 |
| WQGDYWRPRFS | 38.41031503 | 4.75E-09 | 5.98E-04 | 3.702029105 | 3.851605006 |
| QWHYVVSG | 38.39309218 | 4.94E-09 | 6.22E-04 | 3.386707581 | 3.471482638 |
| AHWLAHPLG | 38.59880793 | 4.98E-09 | 6.27E-04 | 3.604463687 | 3.73062135 |
| WVLNPWYWNHG | 38.46722856 | 5.41E-09 | 6.81E-04 | 3.698722698 | 3.818109412 |
| HFVHARHVL | 38.6113179 | 5.63E-09 | 7.10E-04 | 3.345702826 | 3.458376553 |
| WSEWYLKV | 37.61607856 | 5.78E-09 | 7.28E-04 | 3.856378231 | 3.965355299 |
| HLWFAAHLG | 37.90374594 | 5.98E-09 | 7.53E-04 | 3.323970675 | 3.433572264 |
| WNVVNGARHF | 38.21681565 | 5.98E-09 | 7.53E-04 | 3.535626639 | 3.638449341 |
| HWFHFSPG | 38.25753665 | 6.53E-09 | 8.23E-04 | 3.269776643 | 3.387228667 |
| WSPAGYHYNFS | 37.19048316 | 6.64E-09 | 8.37E-04 | 3.563319023 | 3.654282001 |
| HAHFRWG | 38.11720363 | 7.00E-09 | 8.81E-04 | 3.459966669 | 3.591094964 |
| NEPFHFRHFG | 37.69564678 | 7.08E-09 | 8.92E-04 | 3.48692298 | 3.599332758 |
| WGRQWG | 37.32159164 | 7.35E-09 | 9.27E-04 | 3.773040535 | 3.897082409 |
| PYVNFGWPHG | 37.25242074 | 7.40E-09 | 9.32E-04 | 3.607576678 | 3.711691445 |
| WVSQYNGWG | 36.87579488 | 8.15E-09 | 1.03E-03 | 3.675821498 | 3.780326232 |

FIG. 94, Continued

| WYNRPWHLHG | 37.34676695 | 8.48E-09 | 1.07E-03 | 3.63382636 | 3.764697821 |
| --- | --- | --- | --- | --- | --- |
| WSHPRLHVG | 37.38018859 | 8.50E-09 | 1.07E-03 | 3.457672468 | 3.583320216 |
| RHGEWRSPHFS | 37.14445952 | 8.71E-09 | 1.10E-03 | 3.520230977 | 3.650838943 |
| KHHGWHPYFS | 37.26698323 | 8.82E-09 | 1.11E-03 | 3.674003621 | 3.792636204 |
| HYVWYWHSG | 37.13141594 | 8.96E-09 | 1.13E-03 | 3.315503649 | 3.417105965 |
| WYPANKQHVF | 36.8099545 | 9.13E-09 | 1.15E-03 | 3.722376155 | 3.83178386 |
| SWVHLFQG | 36.94397366 | 9.30E-09 | 1.17E-03 | 3.277550417 | 3.386452172 |
| WQYSLGHFS | 36.25843521 | 9.31E-09 | 1.17E-03 | 3.526359257 | 3.608421637 |
| KAHFPHWKD | 37.05925758 | 9.61E-09 | 1.21E-03 | 3.555810119 | 3.669687245 |
| YQFAPPWRHL | 36.6209159 | 1.01E-08 | 1.27E-03 | 3.546542599 | 3.658060452 |
| SHYWAQVLS | 36.57631842 | 1.04E-08 | 1.31E-03 | 3.348932385 | 3.440510619 |
| HVAHFPPKLD | 36.34694647 | 1.09E-08 | 1.38E-03 | 3.434743159 | 3.557206885 |
| WRWSQAHFG | 36.1585032 | 1.12E-08 | 1.41E-03 | 3.586364558 | 3.70216231 |

FIG. 95

| RA vs Not-RA Diseases | | | | | |
|---|---|---|---|---|---|
| PEPTIDE | STATISTIC | P.VALUE | P.BON | MEAN1 | MEAN2 |
| SWYLPNRHL | 49.63847953 | 7.43E-11 | 9.36E-06 | 3.451966092 | 3.572239473 |
| NWLHGPNFG | 48.35872894 | 9.81E-11 | 1.24E-05 | 3.475350006 | 3.598956256 |
| WNVGAKHNHPYHL | 48.71045335 | 1.27E-10 | 1.60E-05 | 3.641986356 | 3.774408116 |
| HWLGFPAHG | 47.34833685 | 2.13E-10 | 2.68E-05 | 3.466356625 | 3.60345322 |
| WQGDYWRPRFS | 45.63635943 | 2.65E-10 | 3.34E-05 | 3.689436181 | 3.851605006 |
| WVWHPWRAG | 44.65676992 | 4.00E-10 | 5.04E-05 | 3.657693244 | 3.818431782 |
| WYEHGKVFG | 44.92298446 | 4.37E-10 | 5.50E-05 | 3.484831678 | 3.594761761 |
| WGRQWG | 44.12287124 | 5.00E-10 | 6.30E-05 | 3.763767829 | 3.897082409 |
| WRWSQAHFG | 43.96612641 | 5.22E-10 | 6.58E-05 | 3.577184438 | 3.70216231 |
| FHPHQFSG | 44.56418377 | 5.66E-10 | 7.13E-05 | 3.390131083 | 3.513267667 |
| YVHHQRHFG | 44.9342872 | 5.93E-10 | 7.47E-05 | 3.374638496 | 3.49740469 |
| SYPQHHVF | 43.95196674 | 6.28E-10 | 7.92E-05 | 3.553327958 | 3.650814894 |
| HHGYWNKWG | 44.52617958 | 6.55E-10 | 8.25E-05 | 3.456496968 | 3.589151154 |
| NEPFHFRHFG | 43.85226319 | 6.92E-10 | 8.72E-05 | 3.480213668 | 3.599332758 |
| HLWFAAHLG | 43.46901534 | 6.97E-10 | 8.79E-05 | 3.317903011 | 3.433572264 |
| WPWWHGYRG | 43.90681841 | 7.11E-10 | 8.96E-05 | 3.329544072 | 3.444241048 |
| WYRGGWG | 44.02332935 | 7.16E-10 | 9.03E-05 | 3.656164332 | 3.780771882 |
| AHWLAHPLG | 43.64424043 | 7.60E-10 | 9.57E-05 | 3.598671622 | 3.73062135 |
| WYPGRLG | 43.59606467 | 7.87E-10 | 9.92E-05 | 3.660304643 | 3.781660734 |
| WWVSGPNPHFS | 43.19243334 | 8.08E-10 | 1.02E-04 | 3.857393841 | 3.976191751 |
| RHGEWRSPHFS | 43.34685843 | 8.52E-10 | 1.07E-04 | 3.512786728 | 3.650838943 |
| WVLNPWYWNHG | 43.44603196 | 8.60E-10 | 1.08E-04 | 3.693424821 | 3.818109412 |
| WSEWYLKV | 42.3458936 | 8.98E-10 | 1.13E-04 | 3.851573007 | 3.965355299 |
| HFVHARHVL | 43.55795774 | 9.06E-10 | 1.14E-04 | 3.340345914 | 3.458376553 |
| PVHWARHFG | 43.49407062 | 9.63E-10 | 1.21E-04 | 3.478963333 | 3.591911403 |
| WYNRPWHLHG | 43.17553468 | 9.72E-10 | 1.22E-04 | 3.626797032 | 3.764697821 |
| WQYSLGHFS | 41.84397562 | 1.03E-09 | 1.29E-04 | 3.522462073 | 3.608421637 |
| NFHVAWHPFSG | 42.86764331 | 1.03E-09 | 1.30E-04 | 3.588409436 | 3.711006117 |
| HYHWGVG | 42.07271829 | 1.06E-09 | 1.34E-04 | 3.563633021 | 3.702528692 |
| SWFGDNKRHL | 42.89587399 | 1.10E-09 | 1.39E-04 | 3.405763282 | 3.512062565 |
| HAHFRWG | 43.06874152 | 1.11E-09 | 1.40E-04 | 3.453506182 | 3.591094964 |
| HVLQHVRHYHFG | 42.53564065 | 1.16E-09 | 1.46E-04 | 3.396528716 | 3.504790304 |
| KHHGWHPYFS | 42.30038672 | 1.32E-09 | 1.66E-04 | 3.668124079 | 3.792636204 |
| HWRWYNG | 41.91827064 | 1.35E-09 | 1.70E-04 | 3.349680625 | 3.48801237 |
| WDHFYVQRHV | 42.38505999 | 1.35E-09 | 1.71E-04 | 3.473304189 | 3.596000188 |
| WVQYVPG | 42.22143015 | 1.37E-09 | 1.73E-04 | 3.529777604 | 3.64604056 |
| WGWNSRDRVLG | 41.73049765 | 1.40E-09 | 1.77E-04 | 3.530928163 | 3.64767335 |

FIG. 95, Continued

| | | | | | |
|---|---|---|---|---|---|
| WSHPRLHVG | 42.18279219 | 1.42E-09 | 1.79E-04 | 3.452084281 | 3.583320216 |
| WWPKVFPNHS | 41.92643282 | 1.43E-09 | 1.80E-04 | 3.69911294 | 3.821329748 |
| KFKVWEWHFS | 41.69260301 | 1.48E-09 | 1.87E-04 | 3.588273049 | 3.690847796 |
| HWFHFSPG | 42.33847801 | 1.49E-09 | 1.88E-04 | 3.265600726 | 3.387228667 |
| WWAVKHFG | 41.87178289 | 1.50E-09 | 1.90E-04 | 3.52803194 | 3.644554584 |
| WQWQNRAHFG | 41.45952566 | 1.65E-09 | 2.08E-04 | 3.558514948 | 3.677303143 |
| GWVWANRHFG | 41.62908094 | 1.67E-09 | 2.11E-04 | 3.513600286 | 3.620767223 |
| QWHYVVSG | 41.30817528 | 1.68E-09 | 2.12E-04 | 3.384901077 | 3.471482638 |
| NWSPFEWKG | 41.12700835 | 1.69E-09 | 2.13E-04 | 3.689181812 | 3.8117486 |
| WNVVNGARHF | 41.69556683 | 1.69E-09 | 2.13E-04 | 3.532825194 | 3.638449341 |
| WVSQYNGWG | 41.04193377 | 1.76E-09 | 2.22E-04 | 3.673273334 | 3.780326232 |
| KWWVHFG | 41.56616887 | 1.82E-09 | 2.29E-04 | 3.578196887 | 3.689630847 |
| SHYWAQVLS | 41.0114256 | 1.94E-09 | 2.44E-04 | 3.345421631 | 3.440510619 |

SEQUENCE LISTING

```
<160> NUMBER OF SEQ ID NOS: 1266

<210> SEQ ID NO 1
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 1

Phe Ala Gly Glu
1

<210> SEQ ID NO 2
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 2

Lys Lys Arg Trp
1

<210> SEQ ID NO 3
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 3

Lys Arg Phe Phe
1

<210> SEQ ID NO 4
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 4

Ala Ser Asp Asp
1

<210> SEQ ID NO 5
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 5
```

```
Leu Lys Ser Phe
1

<210> SEQ ID NO 6
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 6

Pro Lys Ala Arg
1

<210> SEQ ID NO 7
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 7

Trp Trp Tyr Trp
1

<210> SEQ ID NO 8
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 8

Val Lys Lys Arg
1

<210> SEQ ID NO 9
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 9

Gly Pro Arg Pro Gln Tyr His Glu Asp
1               5

<210> SEQ ID NO 10
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 10

Gly Pro Arg Pro Ser Gly Asn Leu Asp
1               5

<210> SEQ ID NO 11
<211> LENGTH: 11
<212> TYPE: PRT
<213> ORGANISM: Unknown
```

```
<220> FEATURE:
<223> OTHER INFORMATION: Description of Unknown:
      Marker peptide

<400> SEQUENCE: 11

Ala Lys Gly Arg Ser Ala Trp Phe Val Ser Gly
1               5                   10

<210> SEQ ID NO 12
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 12

Gly Pro Arg Glu Asn Glu Tyr Gln His Phe
1               5                   10

<210> SEQ ID NO 13
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 13

Gln Val Lys Ser Phe Pro Tyr Val Gly
1               5

<210> SEQ ID NO 14
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 14

Arg Leu Lys Lys Leu Phe Ala Gly
1               5

<210> SEQ ID NO 15
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 15

Ala Asn Pro Lys Arg Leu Val Pro Phe Gly
1               5                   10

<210> SEQ ID NO 16
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 16

Gly Gln Arg Arg Trp Leu Gly
1               5
```

<210> SEQ ID NO 17
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 17

Ala Val Lys Lys Leu Phe Gly Leu Asp
1               5

<210> SEQ ID NO 18
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 18

Ser Pro Val Ala Lys Arg Val His Phe Ser
1               5                   10

<210> SEQ ID NO 19
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 19

Lys Arg Gly Lys Arg Leu Leu Ser Trp Gln Gly
1               5                   10

<210> SEQ ID NO 20
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 20

Arg Pro Arg Ser Leu Ala Gln Phe Gly
1               5

<210> SEQ ID NO 21
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 21

Gln Arg Lys Arg Gly Val Leu Pro Phe Asp
1               5                   10

<210> SEQ ID NO 22
<211> LENGTH: 8
<212> TYPE: PRT
<213> ORGANISM: Unknown
<220> FEATURE:
<223> OTHER INFORMATION: Description of Unknown:
      Marker peptide

```
<400> SEQUENCE: 22

Lys Ala Tyr Glu Asp Pro Asp Gly
1               5

<210> SEQ ID NO 23
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 23

Val Lys Lys Arg Ala Trp Arg Val Phe Glu
1               5                   10

<210> SEQ ID NO 24
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 24

Glu His Ser Val Lys Arg Leu Phe Ser
1               5

<210> SEQ ID NO 25
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 25

Phe Asn Gln Ser Asp Pro Ser Pro Leu Asp
1               5                   10

<210> SEQ ID NO 26
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 26

Lys Ser Ala Tyr Lys Ser Gly Leu Phe Gly
1               5                   10

<210> SEQ ID NO 27
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 27

Gly Arg Arg Ser Val Phe Ser Gly
1               5

<210> SEQ ID NO 28
<211> LENGTH: 9
<212> TYPE: PRT
```

```
<213> ORGANISM: Unknown
<220> FEATURE:
<223> OTHER INFORMATION: Description of Unknown:
      Marker peptide

<400> SEQUENCE: 28

Phe Ser His Gly Val Ser Glu Glu Gly
1               5

<210> SEQ ID NO 29
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 29

Pro Arg Ala Arg Ser Ala Trp Pro Gln Asp Gly
1               5                   10

<210> SEQ ID NO 30
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 30

Val Lys Arg Gly His Pro Leu Phe Ser
1               5

<210> SEQ ID NO 31
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 31

Asn Lys Pro Leu Lys Arg Tyr Leu Asp
1               5

<210> SEQ ID NO 32
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 32

Lys Arg Val Ala Lys Arg Ser Ala Pro Trp Phe Gly
1               5                   10

<210> SEQ ID NO 33
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 33

Lys Gly Arg Ser Leu Leu Phe Glu
1               5
```

```
<210> SEQ ID NO 34
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 34

Ser Lys Arg Trp Pro Trp Val Gly
1               5

<210> SEQ ID NO 35
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 35

Ser Ser Gly Leu Lys Arg Phe Gly
1               5

<210> SEQ ID NO 36
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 36

Ser Lys Arg Arg Trp Phe Ser Gly
1               5

<210> SEQ ID NO 37
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 37

Phe Gly Glu Gln Asp Ala Asp Gly
1               5

<210> SEQ ID NO 38
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 38

Gln Ser Arg Lys Val Pro Trp Leu Asp
1               5

<210> SEQ ID NO 39
<211> LENGTH: 9
<212> TYPE: PRT
<213> ORGANISM: Unknown
<220> FEATURE:
<223> OTHER INFORMATION: Description of Unknown:
      Marker peptide
```

<400> SEQUENCE: 39

Lys Gln Arg Gly Arg Ser Val Phe Gly
1               5

<210> SEQ ID NO 40
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 40

Ala Gly Phe Arg Lys Arg Leu Phe Gly
1               5

<210> SEQ ID NO 41
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 41

Ala Lys Arg Arg Tyr Val Ala Arg Phe Asp
1               5                   10

<210> SEQ ID NO 42
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 42

Pro Lys Arg Phe Leu Ser His Trp Gly
1               5

<210> SEQ ID NO 43
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 43

Tyr Ser Gly Glu Ser Glu Gln Asp Gly
1               5

<210> SEQ ID NO 44
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 44

His Pro Phe Lys Lys His Phe Gly
1               5

<210> SEQ ID NO 45
<211> LENGTH: 9

```
<212> TYPE: PRT
<213> ORGANISM: Unknown
<220> FEATURE:
<223> OTHER INFORMATION: Description of Unknown:
      Marker peptide

<400> SEQUENCE: 45

Leu Asp Gln Ala Lys Arg Phe Phe Gly
1               5

<210> SEQ ID NO 46
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 46

Tyr Gly Pro Arg Arg His Pro Tyr Ala Asn Gly
1               5                   10

<210> SEQ ID NO 47
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 47

Gln His Ser Gln Lys Arg Ser Asn Phe Phe Ser
1               5                   10

<210> SEQ ID NO 48
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 48

Lys Ser Gly Tyr Glu Glu Pro Glu Gly
1               5

<210> SEQ ID NO 49
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 49

Pro Lys Lys Arg Ser Trp Asn Tyr Arg Leu Asp
1               5                   10

<210> SEQ ID NO 50
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 50

Lys Lys Arg Tyr Phe Gln Leu Gly
```

```
1               5

<210> SEQ ID NO 51
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 51

Phe Gly Asp Asp Ser Asp Gly
1               5

<210> SEQ ID NO 52
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 52

Gly Ala Gln Lys Arg Val Ser Arg Trp Val Ser Gly
1               5                   10

<210> SEQ ID NO 53
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 53

Ala Leu Lys Ser Phe Arg Asp
1               5

<210> SEQ ID NO 54
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 54

Pro Ser Arg Lys Arg Phe Phe Asp
1               5

<210> SEQ ID NO 55
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 55

Val Gly Glu Leu Lys Arg Val Phe Ser
1               5

<210> SEQ ID NO 56
<211> LENGTH: 7
<212> TYPE: PRT
<213> ORGANISM: Unknown
<220> FEATURE:
<223> OTHER INFORMATION: Description of Unknown:
```

```
                    Marker peptide

<400> SEQUENCE: 56

Phe Gly His Asp Asp Glu Gly
1               5

<210> SEQ ID NO 57
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 57

Lys Val Ala Arg Leu Tyr Gly Asp Gly
1               5

<210> SEQ ID NO 58
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 58

Val Gly Val Lys Arg Ser Arg Leu Glu
1               5

<210> SEQ ID NO 59
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 59

Tyr Asp Glu Lys
1

<210> SEQ ID NO 60
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 60

Pro Val Arg Arg
1

<210> SEQ ID NO 61
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 61

Ser Asn Pro Val
1

<210> SEQ ID NO 62
```

```
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 62

Asp Lys Tyr Glu
1

<210> SEQ ID NO 63
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 63

Asp Val His Tyr
1

<210> SEQ ID NO 64
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 64

Asn Pro Asp Gln
1

<210> SEQ ID NO 65
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 65

Gln Glu Glu Phe
1

<210> SEQ ID NO 66
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 66

Glu Asp Trp Pro
1

<210> SEQ ID NO 67
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 67
```

Glu Asp Phe Pro
1

<210> SEQ ID NO 68
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 68

Pro Leu Val Asp
1

<210> SEQ ID NO 69
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 69

Leu Arg Asp Pro
1

<210> SEQ ID NO 70
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 70

Pro Ala Arg Arg
1

<210> SEQ ID NO 71
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 71

Pro Glu Leu Glu
1

<210> SEQ ID NO 72
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 72

Pro Glu Tyr Lys
1

<210> SEQ ID NO 73
<211> LENGTH: 4
<212> TYPE: PRT
<213> ORGANISM: Unknown
<220> FEATURE:

<223> OTHER INFORMATION: Description of Unknown:
    Motif sequence

<400> SEQUENCE: 73

Val Val Val Ser
1

<210> SEQ ID NO 74
<211> LENGTH: 4
<212> TYPE: PRT
<213> ORGANISM: Unknown
<220> FEATURE:
<223> OTHER INFORMATION: Description of Unknown:
    Motif sequence

<400> SEQUENCE: 74

Tyr Asp Pro Val
1

<210> SEQ ID NO 75
<211> LENGTH: 4
<212> TYPE: PRT
<213> ORGANISM: Unknown
<220> FEATURE:
<223> OTHER INFORMATION: Description of Unknown:
    Motif sequence

<400> SEQUENCE: 75

Asp Gly Leu His
1

<210> SEQ ID NO 76
<211> LENGTH: 4
<212> TYPE: PRT
<213> ORGANISM: Unknown
<220> FEATURE:
<223> OTHER INFORMATION: Description of Unknown:
    Motif sequence

<400> SEQUENCE: 76

Asn Pro Gly Ser
1

<210> SEQ ID NO 77
<211> LENGTH: 4
<212> TYPE: PRT
<213> ORGANISM: Unknown
<220> FEATURE:
<223> OTHER INFORMATION: Description of Unknown:
    Motif sequence

<400> SEQUENCE: 77

Asn Pro His Pro
1

<210> SEQ ID NO 78
<211> LENGTH: 4
<212> TYPE: PRT
<213> ORGANISM: Unknown
<220> FEATURE:
<223> OTHER INFORMATION: Description of Unknown:
    Motif sequence

<400> SEQUENCE: 78

Pro Glu Ser Gln
1

```
<210> SEQ ID NO 79
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 79

Pro Phe His Pro
1

<210> SEQ ID NO 80
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 80

Pro Phe Leu Pro
1

<210> SEQ ID NO 81
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 81

Val Glu Ser Val
1

<210> SEQ ID NO 82
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 82

Pro Val Glu Ser
1

<210> SEQ ID NO 83
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 83

Pro Glu Val Ala
1

<210> SEQ ID NO 84
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 84
```

Pro Gln Asp Lys
1

<210> SEQ ID NO 85
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 85

Pro Trp Asp Gln
1

<210> SEQ ID NO 86
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 86

Pro Tyr Glu Val
1

<210> SEQ ID NO 87
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 87

Trp Glu Leu Pro
1

<210> SEQ ID NO 88
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 88

Tyr His Asp Ser
1

<210> SEQ ID NO 89
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 89

Ala Asn Tyr Pro
1

<210> SEQ ID NO 90
<211> LENGTH: 4
<212> TYPE: PRT
<213> ORGANISM: Unknown

```
<220> FEATURE:
<223> OTHER INFORMATION: Description of Unknown:
      Motif sequence

<400> SEQUENCE: 90

Glu Val Tyr His
1

<210> SEQ ID NO 91
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 91

Pro Asp Ala Glu
1

<210> SEQ ID NO 92
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 92

Pro Asp Arg Asp
1

<210> SEQ ID NO 93
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 93

Pro Leu Asn Glu
1

<210> SEQ ID NO 94
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 94

Tyr Arg Asn Asp
1

<210> SEQ ID NO 95
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 95

His His Ala Pro
1
```

```
<210> SEQ ID NO 96
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 96

Arg Val Trp Trp
1

<210> SEQ ID NO 97
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 97

Leu Gly Asn Trp
1

<210> SEQ ID NO 98
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 98

Pro Tyr Tyr Tyr
1

<210> SEQ ID NO 99
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 99

Gly His Arg Tyr
1

<210> SEQ ID NO 100
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 100

Arg Arg Leu Val
1

<210> SEQ ID NO 101
<211> LENGTH: 4
<212> TYPE: PRT
<213> ORGANISM: Unknown
<220> FEATURE:
<223> OTHER INFORMATION: Description of Unknown:
      Motif sequence
```

```
<400> SEQUENCE: 101

Arg Tyr Arg Trp
1

<210> SEQ ID NO 102
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 102

Arg Tyr Ser Trp
1

<210> SEQ ID NO 103
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 103

Val Arg Tyr Arg
1

<210> SEQ ID NO 104
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 104

Tyr Arg Arg Asn
1

<210> SEQ ID NO 105
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 105

Arg Tyr His Tyr
1

<210> SEQ ID NO 106
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 106

Gly Phe Val Gln
1

<210> SEQ ID NO 107
<211> LENGTH: 4
<212> TYPE: PRT
```

```
<213> ORGANISM: Unknown
<220> FEATURE:
<223> OTHER INFORMATION: Description of Unknown:
      Motif sequence

<400> SEQUENCE: 107

Pro Pro Phe Arg
1

<210> SEQ ID NO 108
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 108

Leu Arg Tyr Gly
1

<210> SEQ ID NO 109
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 109

Pro Pro Arg Asn
1

<210> SEQ ID NO 110
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 110

Pro Val Arg Arg
1

<210> SEQ ID NO 111
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 111

Tyr Tyr Tyr Asp
1

<210> SEQ ID NO 112
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 112

Tyr Asp Glu Tyr
1
```

```
<210> SEQ ID NO 113
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 113

Ser Tyr Glu Glu
1

<210> SEQ ID NO 114
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 114

Pro Ala Arg Arg
1

<210> SEQ ID NO 115
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 115

Glu Lys Lys Asp
1

<210> SEQ ID NO 116
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 116

Arg Asn Tyr Ala
1

<210> SEQ ID NO 117
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 117

Ala Arg Ser Gln
1

<210> SEQ ID NO 118
<211> LENGTH: 4
<212> TYPE: PRT
<213> ORGANISM: Unknown
<220> FEATURE:
<223> OTHER INFORMATION: Description of Unknown:
      Motif sequence
```

```
<400> SEQUENCE: 118

Asn Glu Val Asp
1

<210> SEQ ID NO 119
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 119

Ser Gly Leu Phe
1

<210> SEQ ID NO 120
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 120

Asp Glu His His
1

<210> SEQ ID NO 121
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 121

Pro Pro Phe Arg
1

<210> SEQ ID NO 122
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 122

Val Asp Asp His
1

<210> SEQ ID NO 123
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 123

Pro Val Arg Gln
1

<210> SEQ ID NO 124
<211> LENGTH: 4
```

```
<212> TYPE: PRT
<213> ORGANISM: Unknown
<220> FEATURE:
<223> OTHER INFORMATION: Description of Unknown:
      Motif sequence

<400> SEQUENCE: 124

Pro Leu Arg Arg
1

<210> SEQ ID NO 125
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 125

Asp Tyr Tyr Gly
1

<210> SEQ ID NO 126
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 126

His Pro Asp Glu
1

<210> SEQ ID NO 127
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 127

Pro Pro Arg Lys
1

<210> SEQ ID NO 128
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 128

Lys His Val Arg
1

<210> SEQ ID NO 129
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 129

Glu Glu His Ser
```

-continued

```
<210> SEQ ID NO 130
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 130

Pro Arg Asn Arg
1

<210> SEQ ID NO 131
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 131

Arg Ala Tyr Lys
1

<210> SEQ ID NO 132
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 132

Arg Trp Tyr Tyr
1

<210> SEQ ID NO 133
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 133

Val Trp Trp Trp
1

<210> SEQ ID NO 134
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 134

Lys Lys Arg Trp
1

<210> SEQ ID NO 135
<211> LENGTH: 4
<212> TYPE: PRT
<213> ORGANISM: Unknown
<220> FEATURE:
<223> OTHER INFORMATION: Description of Unknown:
```

```
            Motif sequence

<400> SEQUENCE: 135

Ala Ser Asp Asp
1

<210> SEQ ID NO 136
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 136

Tyr Trp Gly Asn
1

<210> SEQ ID NO 137
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 137

Lys Arg Phe Phe
1

<210> SEQ ID NO 138
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 138

Ala Ser Glu Glu
1

<210> SEQ ID NO 139
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 139

Ser Asp Ser Tyr
1

<210> SEQ ID NO 140
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 140

Gln Arg Ser Gln
1

<210> SEQ ID NO 141
```

```
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 141

Trp Phe Pro His
1

<210> SEQ ID NO 142
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 142

Arg Gln Tyr Gln
1

<210> SEQ ID NO 143
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 143

Ser Ala Tyr Glu
1

<210> SEQ ID NO 144
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 144

His Val Glu Val
1

<210> SEQ ID NO 145
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 145

Asn His Asn Val
1

<210> SEQ ID NO 146
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 146
```

Asp Tyr Trp Lys
1

<210> SEQ ID NO 147
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 147

Asp Lys Ser Gly
1

<210> SEQ ID NO 148
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 148

Pro Asp Leu Gln
1

<210> SEQ ID NO 149
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 149

Pro Asp Ser Val
1

<210> SEQ ID NO 150
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 150

Pro Asp Val Val
1

<210> SEQ ID NO 151
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 151

Pro Glu Arg Ala
1

<210> SEQ ID NO 152
<211> LENGTH: 4
<212> TYPE: PRT
<213> ORGANISM: Unknown
<220> FEATURE:

```
<223> OTHER INFORMATION: Description of Unknown:
      Motif sequence

<400> SEQUENCE: 152

Pro Gly Ser Leu
1

<210> SEQ ID NO 153
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 153

Pro Gln Glu Ser
1

<210> SEQ ID NO 154
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 154

Pro Asp His Gln
1

<210> SEQ ID NO 155
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 155

Gln Ala Phe Asp Ser His
1               5

<210> SEQ ID NO 156
<211> LENGTH: 5
<212> TYPE: PRT
<213> ORGANISM: Unknown
<220> FEATURE:
<223> OTHER INFORMATION: Description of Unknown:
      Marker peptide

<400> SEQUENCE: 156

Arg His Ser Val Val
1               5

<210> SEQ ID NO 157
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 157

Ser Asp Leu Trp Lys Leu
1               5
```

```
<210> SEQ ID NO 158
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 158

Pro Leu Glu Glu Val Leu Asn
1               5

<210> SEQ ID NO 159
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 159

Arg Gln Val Asp
1

<210> SEQ ID NO 160
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 160

Arg Glu Phe Asp
1

<210> SEQ ID NO 161
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 161

Arg Gln Leu Asp
1

<210> SEQ ID NO 162
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 162

Pro Arg Arg Asp
1

<210> SEQ ID NO 163
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 163
```

Arg Asn Tyr Asp
1

<210> SEQ ID NO 164
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 164

Arg Glu Val Asp
1

<210> SEQ ID NO 165
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 165

Arg Tyr Val Asp
1

<210> SEQ ID NO 166
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 166

Arg Leu Val Asp
1

<210> SEQ ID NO 167
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 167

Arg Ser Val Asp
1

<210> SEQ ID NO 168
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 168

Arg Lys Arg Asp
1

<210> SEQ ID NO 169
<211> LENGTH: 4
<212> TYPE: PRT
<213> ORGANISM: Unknown

```
<220> FEATURE:
<223> OTHER INFORMATION: Description of Unknown:
      Motif sequence

<400> SEQUENCE: 169

Asp Tyr Ala Asp
1

<210> SEQ ID NO 170
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 170

Arg Glu Leu Glu
1

<210> SEQ ID NO 171
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 171

Arg Gln Phe Asp
1

<210> SEQ ID NO 172
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 172

His Arg Ser Val
1

<210> SEQ ID NO 173
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 173

Leu Arg Lys Phe
1

<210> SEQ ID NO 174
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 174

Leu Arg Tyr Val
1
```

```
<210> SEQ ID NO 175
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 175

Arg Val Val Arg
1

<210> SEQ ID NO 176
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 176

Val Arg Arg Leu
1

<210> SEQ ID NO 177
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 177

Glu Val Asp Gly
1

<210> SEQ ID NO 178
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 178

Leu Arg Glu Val
1

<210> SEQ ID NO 179
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 179

Arg Lys Gln Asp
1

<210> SEQ ID NO 180
<211> LENGTH: 4
<212> TYPE: PRT
<213> ORGANISM: Unknown
<220> FEATURE:
<223> OTHER INFORMATION: Description of Unknown:
      Motif sequence
```

```
<400> SEQUENCE: 180

Leu Arg Glu Phe
1

<210> SEQ ID NO 181
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 181

Leu Arg Val Val
1

<210> SEQ ID NO 182
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 182

Phe Arg Leu Val
1

<210> SEQ ID NO 183
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 183

Gly Val Glu Gln
1

<210> SEQ ID NO 184
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 184

Phe Asp Asp Asp
1

<210> SEQ ID NO 185
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 185

Gly Lys Ala Val
1

<210> SEQ ID NO 186
<211> LENGTH: 4
<212> TYPE: PRT
```

```
<213> ORGANISM: Unknown
<220> FEATURE:
<223> OTHER INFORMATION: Description of Unknown:
      Motif sequence

<400> SEQUENCE: 186

Leu Asp Phe Tyr
1

<210> SEQ ID NO 187
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 187

Val Val Arg Leu
1

<210> SEQ ID NO 188
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 188

Leu Arg Lys Val
1

<210> SEQ ID NO 189
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 189

Leu Arg Gln Val
1

<210> SEQ ID NO 190
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 190

Tyr Arg Gln Leu
1

<210> SEQ ID NO 191
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 191

Arg Asp Lys Asp
1
```

<210> SEQ ID NO 192
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 192

Arg Asp Tyr Asp
1

<210> SEQ ID NO 193
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 193

Arg Ser Ala Asp
1

<210> SEQ ID NO 194
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 194

Ala Arg Asp Tyr
1

<210> SEQ ID NO 195
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 195

Gly Val Glu Asn
1

<210> SEQ ID NO 196
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 196

Lys Tyr His Asp
1

<210> SEQ ID NO 197
<211> LENGTH: 4
<212> TYPE: PRT
<213> ORGANISM: Unknown
<220> FEATURE:
<223> OTHER INFORMATION: Description of Unknown:
      Motif sequence

```
<400> SEQUENCE: 197

Arg Ala His Asp
1

<210> SEQ ID NO 198
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 198

Arg Ser His Ser
1

<210> SEQ ID NO 199
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 199

Arg Val Leu Lys
1

<210> SEQ ID NO 200
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 200

Tyr Arg Tyr Trp
1

<210> SEQ ID NO 201
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 201

Gly Gln Pro Ala
1

<210> SEQ ID NO 202
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 202

Leu Asp Tyr Asp
1

<210> SEQ ID NO 203
<211> LENGTH: 4
```

```
<212> TYPE: PRT
<213> ORGANISM: Unknown
<220> FEATURE:
<223> OTHER INFORMATION: Description of Unknown:
      Motif sequence

<400> SEQUENCE: 203

Val Phe Tyr Asp
1

<210> SEQ ID NO 204
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 204

Phe Arg Lys Arg
1

<210> SEQ ID NO 205
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 205

Arg Ala Val Asp
1

<210> SEQ ID NO 206
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 206

Val Asp Ala Asp
1

<210> SEQ ID NO 207
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 207

Tyr Leu Asp Tyr
1

<210> SEQ ID NO 208
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 208

Gln Pro Ala Glu
```

1

<210> SEQ ID NO 209
<211> LENGTH: 4
<212> TYPE: PRT
<213> ORGANISM: Unknown
<220> FEATURE:
<223> OTHER INFORMATION: Description of Unknown:
    Motif sequence

<400> SEQUENCE: 209

Gln Val Asp Ala
1

<210> SEQ ID NO 210
<211> LENGTH: 4
<212> TYPE: PRT
<213> ORGANISM: Unknown
<220> FEATURE:
<223> OTHER INFORMATION: Description of Unknown:
    Motif sequence

<400> SEQUENCE: 210

Arg Asp Leu Asp
1

<210> SEQ ID NO 211
<211> LENGTH: 4
<212> TYPE: PRT
<213> ORGANISM: Unknown
<220> FEATURE:
<223> OTHER INFORMATION: Description of Unknown:
    Motif sequence

<400> SEQUENCE: 211

Arg Gly Val Glu
1

<210> SEQ ID NO 212
<211> LENGTH: 4
<212> TYPE: PRT
<213> ORGANISM: Unknown
<220> FEATURE:
<223> OTHER INFORMATION: Description of Unknown:
    Motif sequence

<400> SEQUENCE: 212

Phe Asp Val Phe
1

<210> SEQ ID NO 213
<211> LENGTH: 4
<212> TYPE: PRT
<213> ORGANISM: Unknown
<220> FEATURE:
<223> OTHER INFORMATION: Description of Unknown:
    Motif sequence

<400> SEQUENCE: 213

Phe Glu Tyr Ser
1

<210> SEQ ID NO 214
<211> LENGTH: 4
<212> TYPE: PRT
<213> ORGANISM: Unknown
<220> FEATURE:
<223> OTHER INFORMATION: Description of Unknown:

```
                  Motif sequence

<400> SEQUENCE: 214

His Leu Val Asp
1

<210> SEQ ID NO 215
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 215

His Gln Lys Ser
1

<210> SEQ ID NO 216
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 216

Arg Leu Leu Asp
1

<210> SEQ ID NO 217
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 217

Arg Tyr Val Glu
1

<210> SEQ ID NO 218
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 218

Val Asp Gly Tyr
1

<210> SEQ ID NO 219
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 219

Val Glu Val Asp
1

<210> SEQ ID NO 220
```

```
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 220

His Leu Gln Arg
1

<210> SEQ ID NO 221
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 221

Val Asp Pro Ala
1

<210> SEQ ID NO 222
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 222

Tyr Asp Tyr Ala
1

<210> SEQ ID NO 223
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 223

Phe Asp Tyr Phe
1

<210> SEQ ID NO 224
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 224

Lys His Lys His
1

<210> SEQ ID NO 225
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 225
```

Arg Tyr Phe Asp
1

<210> SEQ ID NO 226
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 226

Asp Gly His Glu
1

<210> SEQ ID NO 227
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 227

Phe Asp Tyr Ala
1

<210> SEQ ID NO 228
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 228

Lys Tyr Asn Lys
1

<210> SEQ ID NO 229
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 229

Arg Tyr Leu Glu
1

<210> SEQ ID NO 230
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 230

Leu Asp Phe Asp
1

<210> SEQ ID NO 231
<211> LENGTH: 4
<212> TYPE: PRT
<213> ORGANISM: Unknown
<220> FEATURE:

```
<223> OTHER INFORMATION: Description of Unknown:
      Motif sequence

<400> SEQUENCE: 231

Arg Gln Lys Glu
1

<210> SEQ ID NO 232
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 232

Arg Phe Leu Asp
1

<210> SEQ ID NO 233
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 233

Ser Ala Gln Lys
1

<210> SEQ ID NO 234
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 234

Asp Trp Val Asp
1

<210> SEQ ID NO 235
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 235

Arg Phe Phe Asp
1

<210> SEQ ID NO 236
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 236

Arg Gln Leu Glu
1
```

```
<210> SEQ ID NO 237
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 237

Arg Lys Val Glu
1

<210> SEQ ID NO 238
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 238

Lys Lys Arg Asp
1

<210> SEQ ID NO 239
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 239

Arg Gln Val Glu
1

<210> SEQ ID NO 240
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 240

Asp Pro Val Ser
1

<210> SEQ ID NO 241
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 241

Asp Tyr Phe Gly
1

<210> SEQ ID NO 242
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 242
```

Asp Tyr Phe Asp
1

<210> SEQ ID NO 243
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 243

Phe Arg Leu Gly
1

<210> SEQ ID NO 244
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 244

Arg Arg Val Asp
1

<210> SEQ ID NO 245
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 245

Lys Lys Arg His
1

<210> SEQ ID NO 246
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 246

Arg Arg Leu Glu
1

<210> SEQ ID NO 247
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 247

Arg Arg Leu Asp
1

<210> SEQ ID NO 248
<211> LENGTH: 4
<212> TYPE: PRT
<213> ORGANISM: Unknown

```
<220> FEATURE:
<223> OTHER INFORMATION: Description of Unknown:
      Motif sequence

<400> SEQUENCE: 248

Asp Pro Leu Ser
1

<210> SEQ ID NO 249
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 249

Asp Val Phe Gly
1

<210> SEQ ID NO 250
<211> LENGTH: 5
<212> TYPE: PRT
<213> ORGANISM: Unknown
<220> FEATURE:
<223> OTHER INFORMATION: Description of Unknown:
      Motif sequence

<400> SEQUENCE: 250

Phe Asp Val Phe Gly
1               5

<210> SEQ ID NO 251
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 251

His Arg Ser Val
1

<210> SEQ ID NO 252
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 252

Leu Arg Tyr Val
1

<210> SEQ ID NO 253
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 253

Val Arg Tyr Arg
1
```

<210> SEQ ID NO 254
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 254

Ala Leu Arg Tyr
1

<210> SEQ ID NO 255
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 255

Leu Arg Gly Tyr
1

<210> SEQ ID NO 256
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 256

Arg Glu Val Asp
1

<210> SEQ ID NO 257
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 257

Arg Arg His Tyr
1

<210> SEQ ID NO 258
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 258

Arg Ala Ser Tyr
1

<210> SEQ ID NO 259
<211> LENGTH: 4
<212> TYPE: PRT
<213> ORGANISM: Unknown
<220> FEATURE:
<223> OTHER INFORMATION: Description of Unknown:
      Motif sequence

```
<400> SEQUENCE: 259

Arg Pro Tyr Pro
1

<210> SEQ ID NO 260
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 260

Arg Arg Tyr Arg
1

<210> SEQ ID NO 261
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 261

Val Ser Arg Tyr
1

<210> SEQ ID NO 262
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 262

Leu Trp Val Ala
1

<210> SEQ ID NO 263
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 263

Trp Lys Ala Trp
1

<210> SEQ ID NO 264
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 264

Glu Trp Lys Trp
1

<210> SEQ ID NO 265
<211> LENGTH: 4
<212> TYPE: PRT
```

```
<213> ORGANISM: Unknown
<220> FEATURE:
<223> OTHER INFORMATION: Description of Unknown:
      Motif sequence

<400> SEQUENCE: 265

Trp Lys Trp Leu
1

<210> SEQ ID NO 266
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 266

Trp Val Lys Leu
1

<210> SEQ ID NO 267
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 267

Leu Arg Glu Glu
1

<210> SEQ ID NO 268
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 268

Tyr Ser Ser Arg
1

<210> SEQ ID NO 269
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 269

Gly Asp Lys Trp
1

<210> SEQ ID NO 270
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 270

Leu Arg Arg Lys
1
```

```
<210> SEQ ID NO 271
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 271

Pro Gly Lys Gln
1

<210> SEQ ID NO 272
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 272

Arg Tyr Pro Asn
1

<210> SEQ ID NO 273
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 273

Arg Tyr Ser Phe
1

<210> SEQ ID NO 274
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 274

Phe Asp Asp Lys
1

<210> SEQ ID NO 275
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 275

Leu Leu Pro Arg
1

<210> SEQ ID NO 276
<211> LENGTH: 4
<212> TYPE: PRT
<213> ORGANISM: Unknown
<220> FEATURE:
<223> OTHER INFORMATION: Description of Unknown:
      Motif sequence
```

<400> SEQUENCE: 276

Leu Leu Arg Tyr
1

<210> SEQ ID NO 277
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 277

Leu Pro Arg Arg
1

<210> SEQ ID NO 278
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 278

Leu Arg Tyr Val
1

<210> SEQ ID NO 279
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 279

Ser Ala Asp Asp
1

<210> SEQ ID NO 280
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 280

Val Ala Ala Asp
1

<210> SEQ ID NO 281
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 281

His Lys Trp Trp
1

<210> SEQ ID NO 282
<211> LENGTH: 4

```
<212> TYPE: PRT
<213> ORGANISM: Unknown
<220> FEATURE:
<223> OTHER INFORMATION: Description of Unknown:
      Motif sequence

<400> SEQUENCE: 282

Trp Glu Lys Lys
1

<210> SEQ ID NO 283
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 283

Pro Gln Trp Trp
1

<210> SEQ ID NO 284
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 284

Trp Lys Trp Asp
1

<210> SEQ ID NO 285
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 285

Lys Glu Trp Ala
1

<210> SEQ ID NO 286
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 286

Leu Arg Tyr Val
1

<210> SEQ ID NO 287
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 287

Ala Leu Arg Tyr
```

```
<210> SEQ ID NO 288
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 288

Gln Gln Tyr Arg
1

<210> SEQ ID NO 289
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 289

Arg Ala Tyr Ser
1

<210> SEQ ID NO 290
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 290

Arg Pro Tyr Pro
1

<210> SEQ ID NO 291
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 291

Val Ser Arg Tyr
1

<210> SEQ ID NO 292
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 292

Arg Glu Val Asp
1

<210> SEQ ID NO 293
<211> LENGTH: 4
<212> TYPE: PRT
<213> ORGANISM: Unknown
<220> FEATURE:
<223> OTHER INFORMATION: Description of Unknown:
```

-continued

```
      Motif sequence

<400> SEQUENCE: 293

Leu Arg Gly Tyr
1

<210> SEQ ID NO 294
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 294

Gly Pro Arg Arg
1

<210> SEQ ID NO 295
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 295

Asn Pro Arg Tyr
1

<210> SEQ ID NO 296
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 296

Arg Tyr Val Asp
1

<210> SEQ ID NO 297
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 297

His Arg Ser Val
1

<210> SEQ ID NO 298
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 298

Leu Arg Tyr Val
1

<210> SEQ ID NO 299
```

```
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 299

Val Arg Tyr Arg
1

<210> SEQ ID NO 300
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 300

Tyr Ser Ser Arg
1

<210> SEQ ID NO 301
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 301

Arg Ala Ser Tyr
1

<210> SEQ ID NO 302
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 302

Leu Arg Gly Tyr
1

<210> SEQ ID NO 303
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 303

Arg Glu Val Asp
1

<210> SEQ ID NO 304
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 304
```

Arg Arg His Tyr
1

<210> SEQ ID NO 305
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 305

Glu Asn Gly Asp
1

<210> SEQ ID NO 306
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 306

Asn Gly Asp Ser
1

<210> SEQ ID NO 307
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 307

Arg Asn Gly Glu
1

<210> SEQ ID NO 308
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 308

Ala Asn Gly Asp
1

<210> SEQ ID NO 309
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 309

Asp Arg Asn Gly
1

<210> SEQ ID NO 310
<211> LENGTH: 4
<212> TYPE: PRT
<213> ORGANISM: Unknown
<220> FEATURE:

```
<223> OTHER INFORMATION: Description of Unknown:
      Motif sequence

<400> SEQUENCE: 310

Lys Glu Trp Pro
1

<210> SEQ ID NO 311
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 311

Asn Gly Asp Asp
1

<210> SEQ ID NO 312
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 312

Asn Gly Asp Val
1

<210> SEQ ID NO 313
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 313

Trp Glu Lys Lys
1

<210> SEQ ID NO 314
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 314

Arg Glu Val Asp
1

<210> SEQ ID NO 315
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 315

Asp Asn Gly Asp
1
```

```
<210> SEQ ID NO 316
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 316

Leu Arg Asp Val
1

<210> SEQ ID NO 317
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 317

Val Asn Gly Asp
1

<210> SEQ ID NO 318
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 318

Val Leu Leu Lys
1

<210> SEQ ID NO 319
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 319

Trp Trp Leu Ala
1

<210> SEQ ID NO 320
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 320

Leu Trp Val Ala
1

<210> SEQ ID NO 321
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 321
```

Phe His Phe Ala
1

<210> SEQ ID NO 322
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 322

Phe His Phe Val
1

<210> SEQ ID NO 323
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 323

Phe Val Asn Leu
1

<210> SEQ ID NO 324
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 324

His Phe Phe Ala
1

<210> SEQ ID NO 325
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 325

Asn Trp Ala Val
1

<210> SEQ ID NO 326
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 326

Phe Trp Phe Ala
1

<210> SEQ ID NO 327
<211> LENGTH: 4
<212> TYPE: PRT
<213> ORGANISM: Unknown

```
<220> FEATURE:
<223> OTHER INFORMATION: Description of Unknown:
      Motif sequence

<400> SEQUENCE: 327

Phe Ala Trp Phe
1

<210> SEQ ID NO 328
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 328

Pro Gln Trp Trp
1

<210> SEQ ID NO 329
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 329

Lys Phe Trp Phe
1

<210> SEQ ID NO 330
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 330

Phe Trp Val Lys
1

<210> SEQ ID NO 331
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 331

Trp Lys Val Lys
1

<210> SEQ ID NO 332
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 332

Asn Lys Trp His
1
```

```
<210> SEQ ID NO 333
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 333

Trp Glu Lys Lys
1

<210> SEQ ID NO 334
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 334

Tyr Ser Ala Arg
1

<210> SEQ ID NO 335
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 335

Asp Gly Arg Trp
1

<210> SEQ ID NO 336
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 336

His Pro Lys Trp
1

<210> SEQ ID NO 337
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 337

Lys Glu Leu Trp
1

<210> SEQ ID NO 338
<211> LENGTH: 4
<212> TYPE: PRT
<213> ORGANISM: Unknown
<220> FEATURE:
<223> OTHER INFORMATION: Description of Unknown:
      Motif sequence
```

```
<400> SEQUENCE: 338

Gly Pro Arg Arg
1

<210> SEQ ID NO 339
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 339

Asn Lys Glu Phe
1

<210> SEQ ID NO 340
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 340

Trp Lys Lys Glu
1

<210> SEQ ID NO 341
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 341

His Lys Asp Trp
1

<210> SEQ ID NO 342
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 342

Lys Lys Pro Trp
1

<210> SEQ ID NO 343
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 343

Leu Arg Tyr Val
1

<210> SEQ ID NO 344
<211> LENGTH: 4
<212> TYPE: PRT
```

```
<213> ORGANISM: Unknown
<220> FEATURE:
<223> OTHER INFORMATION: Description of Unknown:
      Motif sequence

<400> SEQUENCE: 344

Trp Glu Lys Lys
1

<210> SEQ ID NO 345
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 345

Arg Glu Val Asp
1

<210> SEQ ID NO 346
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 346

Tyr Leu Leu Pro
1

<210> SEQ ID NO 347
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 347

Lys Phe Trp Phe
1

<210> SEQ ID NO 348
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 348

Lys Trp Trp Lys
1

<210> SEQ ID NO 349
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 349

Gly Pro Arg Arg
1
```

<210> SEQ ID NO 350
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 350

Tyr Gly Pro Arg
1

<210> SEQ ID NO 351
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 351

Arg Ala Val Tyr
1

<210> SEQ ID NO 352
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 352

Ser Arg Tyr Gly
1

<210> SEQ ID NO 353
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 353

Leu Arg Lys Val
1

<210> SEQ ID NO 354
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 354

Pro Lys Trp Lys
1

<210> SEQ ID NO 355
<211> LENGTH: 9
<212> TYPE: PRT
<213> ORGANISM: Unknown
<220> FEATURE:
<223> OTHER INFORMATION: Description of Unknown:
      Marker peptide

```
<400> SEQUENCE: 355

Lys Arg His Arg His Gln Pro Glu Gly
1               5

<210> SEQ ID NO 356
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 356

Arg Ser His Arg Ala Ser Asp
1               5

<210> SEQ ID NO 357
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 357

Asn Ser His Ser Gly Lys His Leu Gln Arg Leu Phe
1               5                   10

<210> SEQ ID NO 358
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 358

Gly Arg His Ser Arg Arg Glu Gly
1               5

<210> SEQ ID NO 359
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 359

Lys Ala Gln Tyr Lys Gln Arg Asp
1               5

<210> SEQ ID NO 360
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 360

Arg Asn Arg Asp Arg Phe Gly Gln Lys Ser Glu
1               5                   10

<210> SEQ ID NO 361
<211> LENGTH: 9
```

```
<212> TYPE: PRT
<213> ORGANISM: Unknown
<220> FEATURE:
<223> OTHER INFORMATION: Description of Unknown:
      Marker peptide

<400> SEQUENCE: 361

Lys Tyr Ser Tyr Leu Asp Tyr Lys Gly
1               5

<210> SEQ ID NO 362
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 362

Arg Asn Gln His Gln Lys Ser Pro Glu Gly
1               5                   10

<210> SEQ ID NO 363
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 363

Glu Asn Arg Gly Arg Lys Arg Asp
1               5

<210> SEQ ID NO 364
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 364

Lys Ser Gly Ser His Gln Lys Arg Glu
1               5

<210> SEQ ID NO 365
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 365

Lys Gln Val Asp Ala His Lys Arg Phe Gly
1               5                   10

<210> SEQ ID NO 366
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 366

Ser Ala Phe Arg Lys Arg Asp Gly
```

<210> SEQ ID NO 367
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 367

Val Leu Gly Arg Glu Lys Gln His Gly
1               5

<210> SEQ ID NO 368
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 368

Ser Phe Arg Lys Arg His Glu Gly
1               5

<210> SEQ ID NO 369
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 369

Arg Phe Arg Arg Asn Asp Gly
1               5

<210> SEQ ID NO 370
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 370

Lys Lys His Tyr Arg Ser Asp Asp Gly
1               5

<210> SEQ ID NO 371
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 371

Lys Phe His Gln Asn Lys Val Ser Asp
1               5

<210> SEQ ID NO 372
<211> LENGTH: 9
<212> TYPE: PRT
<213> ORGANISM: Unknown
<220> FEATURE:
<223> OTHER INFORMATION: Description of Unknown:

```
                        Marker peptide

<400> SEQUENCE: 372

Asn Lys Asp Arg Ala Arg Arg Asp Gly
1               5

<210> SEQ ID NO 373
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 373

Asn Gly Gln His Lys Arg Ser Arg Asp Gly
1               5                   10

<210> SEQ ID NO 374
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 374

Ser Ser Tyr Lys Gly Ala His Gly
1               5

<210> SEQ ID NO 375
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 375

Val Asp Lys Ala Arg His Gln His Ser
1               5

<210> SEQ ID NO 376
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 376

Arg Ser His Ser Asn Ser Gly Lys Leu Glu
1               5                   10

<210> SEQ ID NO 377
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 377

Ser Asn His Arg His Lys Phe Asp Gly
1               5

<210> SEQ ID NO 378
```

```
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 378

Lys Lys Arg Glu Arg Trp Gln Glu Gly
1               5

<210> SEQ ID NO 379
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 379

His Lys His Ala Lys Arg Gly Asp Gly
1               5

<210> SEQ ID NO 380
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 380

Lys Asn His Lys Lys Arg His Ser Glu
1               5

<210> SEQ ID NO 381
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 381

Lys Ser Lys Trp Ala Asn Lys Glu Gly
1               5

<210> SEQ ID NO 382
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 382

Lys Lys Lys Lys Arg His Glu Asp
1               5

<210> SEQ ID NO 383
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 383
```

Lys Leu His Lys His Lys Ser Glu
1               5

<210> SEQ ID NO 384
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 384

Lys Tyr Ser Lys Ser Lys His Glu
1               5

<210> SEQ ID NO 385
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 385

Lys Ser Lys Arg Asp Ala Trp Gly Tyr Glu Gly
1               5                   10

<210> SEQ ID NO 386
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 386

Gly Ala Asn Lys Tyr Asn Lys Tyr Asp Gly
1               5                   10

<210> SEQ ID NO 387
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 387

Lys Phe Ser Asn Tyr Gln Asp Lys Gly
1               5

<210> SEQ ID NO 388
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 388

Lys Lys Glu Tyr Gly Tyr Lys Asp Gly
1               5

<210> SEQ ID NO 389
<211> LENGTH: 8
<212> TYPE: PRT
<213> ORGANISM: Unknown
<220> FEATURE:

```
<223> OTHER INFORMATION: Description of Unknown:
      Marker peptide

<400> SEQUENCE: 389

His Lys Tyr Lys Ser Arg Ser Glu
1               5

<210> SEQ ID NO 390
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 390

Lys Ser Val Gly Pro Gln His Val Tyr Lys Glu
1               5                   10

<210> SEQ ID NO 391
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 391

Lys Ser Ser His Phe Asn Lys Glu Gly
1               5

<210> SEQ ID NO 392
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 392

Phe Ser Arg Glu Lys Asn Lys Gly
1               5

<210> SEQ ID NO 393
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 393

Gln Ser Leu Lys Lys Arg Asp
1               5

<210> SEQ ID NO 394
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 394

Leu Asn Glu Gly Lys Arg Arg Gly
1               5
```

-continued

```
<210> SEQ ID NO 395
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 395

Tyr Asp Tyr Lys Lys Tyr Trp Lys Gly
1               5

<210> SEQ ID NO 396
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 396

Lys Ala Ala Arg Lys Asp Gly
1               5

<210> SEQ ID NO 397
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 397

Ser Arg Lys Gln Asp Gly
1               5

<210> SEQ ID NO 398
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 398

Arg Ser Lys Lys Asp Asp Gly
1               5

<210> SEQ ID NO 399
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 399

Lys Asn Gly Lys Lys Phe Ser Glu
1               5

<210> SEQ ID NO 400
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 400
```

-continued

Val Ala Gln Ser Lys Arg Glu Lys Arg Phe Gly
1               5                   10

<210> SEQ ID NO 401
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 401

Lys Ala Gly Ser Ser Gly
1               5

<210> SEQ ID NO 402
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 402

Ser Asn Asp Arg Lys Arg Phe Gly
1               5

<210> SEQ ID NO 403
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 403

Asn Ala Lys Pro Ser Tyr Gly
1               5

<210> SEQ ID NO 404
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 404

Gly Ser Lys His Asn Gln Arg Ser Glu
1               5

<210> SEQ ID NO 405
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 405

Lys Gln Gly Ser Arg Ser Asp Gly
1               5

<210> SEQ ID NO 406
<211> LENGTH: 9
<212> TYPE: PRT
<213> ORGANISM: Unknown

<220> FEATURE:
<223> OTHER INFORMATION: Description of Unknown:
      Marker peptide

<400> SEQUENCE: 406

Lys Ala Gly Phe Glu Lys His Ser Gly
1               5

<210> SEQ ID NO 407
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 407

Lys Leu His His Lys Val Leu Asp
1               5

<210> SEQ ID NO 408
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 408

Lys Leu Ala Glu Asn His Val Lys Leu Gly
1               5                   10

<210> SEQ ID NO 409
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 409

Lys Leu Glu Lys Lys His Pro Lys Asp Gly
1               5                   10

<210> SEQ ID NO 410
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 410

Glu Lys Asn His Phe Lys His Leu Phe
1               5

<210> SEQ ID NO 411
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 411

Ser Arg Lys Lys Arg Ser Glu Asp
1               5

<210> SEQ ID NO 412
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 412

Gly Asp Lys His Lys His Val Leu Ser
1               5

<210> SEQ ID NO 413
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 413

Lys Ala Glu Gly Lys His Tyr Lys Gly
1               5

<210> SEQ ID NO 414
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 414

Lys Asn Asp His Gln Arg Gly
1               5

<210> SEQ ID NO 415
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 415

Glu Gln Glu Asp Lys Phe Asp Arg Ser Gly
1               5                   10

<210> SEQ ID NO 416
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 416

Ser Asn Asp Val Ser Pro Val Leu Ser Glu
1               5                   10

<210> SEQ ID NO 417
<211> LENGTH: 9
<212> TYPE: PRT
<213> ORGANISM: Unknown
<220> FEATURE:
<223> OTHER INFORMATION: Description of Unknown:
      Marker peptide

```
<400> SEQUENCE: 417

Phe Arg Trp His Tyr Lys Arg Glu Asp
1               5

<210> SEQ ID NO 418
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 418

Phe Arg His His Ala Arg Ser Glu Asp
1               5

<210> SEQ ID NO 419
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 419

Phe Phe Asn His Gln Ser Asp Gly
1               5

<210> SEQ ID NO 420
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 420

Leu Trp Leu Tyr Pro Asn Lys Arg Gly
1               5

<210> SEQ ID NO 421
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 421

Phe Lys Asn Tyr Lys Arg His Asp Gly
1               5

<210> SEQ ID NO 422
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 422

Ala Trp Phe His Lys Arg Gln Asp Gly
1               5

<210> SEQ ID NO 423
<211> LENGTH: 8
<212> TYPE: PRT
```

<213> ORGANISM: Unknown
<220> FEATURE:
<223> OTHER INFORMATION: Description of Unknown:
      Marker peptide

<400> SEQUENCE: 423

Leu Phe Phe His Gln Lys Ser Gly
1               5

<210> SEQ ID NO 424
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 424

Phe Trp Lys His Lys His Gly Ala Val Asp
1               5                   10

<210> SEQ ID NO 425
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 425

Leu Phe His Leu Gln Arg Pro Gly
1               5

<210> SEQ ID NO 426
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 426

Ser His Phe Lys Arg Ser His Ser Glu
1               5

<210> SEQ ID NO 427
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 427

Phe Gln His Leu Tyr Lys Arg Ala Gly
1               5

<210> SEQ ID NO 428
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 428

Val Tyr His Arg Lys Arg Asp
1               5

```
<210> SEQ ID NO 429
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 429

Tyr Arg Tyr Trp Lys Arg Gly Gln Pro Ala Asp
1               5                   10

<210> SEQ ID NO 430
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 430

Ala Ala Leu Lys Asn Arg Asp Gly
1               5

<210> SEQ ID NO 431
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 431

Ser Phe Asn Lys Lys Arg Asp Gly
1               5

<210> SEQ ID NO 432
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 432

Ser Tyr His Phe Gln Lys Pro Gly
1               5

<210> SEQ ID NO 433
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 433

Val Lys His Lys Tyr Trp Arg Glu Gly
1               5

<210> SEQ ID NO 434
<211> LENGTH: 8
<212> TYPE: PRT
<213> ORGANISM: Unknown
<220> FEATURE:
<223> OTHER INFORMATION: Description of Unknown:
      Marker peptide
```

```
<400> SEQUENCE: 434

Leu Asn His Asn Gly Arg Ser Gly
1               5

<210> SEQ ID NO 435
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 435

Val Arg His Arg Lys Val Glu Gly
1               5

<210> SEQ ID NO 436
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 436

Leu Ala His Arg Gln His Ser Gly
1               5

<210> SEQ ID NO 437
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 437

Arg Phe His Lys His Arg Asp Gly
1               5

<210> SEQ ID NO 438
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 438

Lys Gln Tyr Ser Ala Gln Lys Asp
1               5

<210> SEQ ID NO 439
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 439

Lys Lys Tyr Arg Gln Lys Glu Gly
1               5

<210> SEQ ID NO 440
<211> LENGTH: 7
```

```
<212> TYPE: PRT
<213> ORGANISM: Unknown
<220> FEATURE:
<223> OTHER INFORMATION: Description of Unknown:
      Marker peptide

<400> SEQUENCE: 440

Arg Tyr Tyr Arg Lys Asp Gly
1               5

<210> SEQ ID NO 441
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 441

Arg Leu Tyr Ser Arg Lys Arg Glu
1               5

<210> SEQ ID NO 442
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 442

Lys Gly Tyr Phe Gln Trp Asn Lys Ser Asp
1               5                   10

<210> SEQ ID NO 443
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 443

Ser Arg Tyr Arg Tyr Ala Asn Asp Gly
1               5

<210> SEQ ID NO 444
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 444

Lys Leu Tyr Ala Tyr Ala Gln Gln Gly
1               5

<210> SEQ ID NO 445
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 445

Ala Val Glu Asp Leu Val Pro Ala Val Glu
```

1               5                    10

<210> SEQ ID NO 446
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 446

Gly Val Glu Asn Leu Phe Asp Glu Gly
1               5

<210> SEQ ID NO 447
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 447

Gly Leu Glu His Leu Val Asp Gly
1               5

<210> SEQ ID NO 448
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 448

Gly Val Glu His Leu Ala Trp Gly
1               5

<210> SEQ ID NO 449
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 449

Gly Val Glu Gln Leu Gly Lys His Ser Asp
1               5                    10

<210> SEQ ID NO 450
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 450

Gly Ala Asp Glu Leu Phe Gly
1               5

<210> SEQ ID NO 451
<211> LENGTH: 9
<212> TYPE: PRT
<213> ORGANISM: Unknown
<220> FEATURE:
<223> OTHER INFORMATION: Description of Unknown:

Marker peptide

<400> SEQUENCE: 451

Gly Val Glu Asn Trp Val Ser Asp Gly
1               5

<210> SEQ ID NO 452
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 452

Gly Phe Glu Asp Leu Pro Gln Glu Gly
1               5

<210> SEQ ID NO 453
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 453

Glu Pro His Tyr His Val Asn Lys Val Asp
1               5                   10

<210> SEQ ID NO 454
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 454

Asp Tyr Ser Ser Asp Gln Val Ser Gly
1               5

<210> SEQ ID NO 455
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 455

Gln Arg Gly Phe Val Ser Gly Lys Glu Asp
1               5                   10

<210> SEQ ID NO 456
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 456

Gly Trp Gly His Leu Ser Glu Gln Ser Gly
1               5                   10

<210> SEQ ID NO 457

```
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 457

Tyr Asn Lys Leu Pro Glu Asp Tyr Glu Trp Val Gly
1               5                   10

<210> SEQ ID NO 458
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 458

Trp His Val Lys Gly Val Leu Pro Glu Asp
1               5                   10

<210> SEQ ID NO 459
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 459

Ala Ser Pro Tyr Asn Gln Val Lys Pro Tyr Glu Asp
1               5                   10

<210> SEQ ID NO 460
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 460

Ala Ser Pro Arg Ser Pro Phe Glu Val Glu
1               5                   10

<210> SEQ ID NO 461
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 461

Ala Arg Pro Pro Tyr Gln Pro Ala Glu Asp
1               5                   10

<210> SEQ ID NO 462
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 462
```

```
Ala Trp Gly Ser Ala Val Glu Val Asp
1               5
```

<210> SEQ ID NO 463
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 463

```
Ala Arg Pro Glu Gln Asp Tyr Phe Gly
1               5
```

<210> SEQ ID NO 464
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 464

```
Ala Lys Pro Gln Trp Ala Phe Glu Asp
1               5
```

<210> SEQ ID NO 465
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 465

```
Ala Arg Pro Asn Glu Trp Gly Tyr Phe Asp
1               5                   10
```

<210> SEQ ID NO 466
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 466

```
Ala Arg Gly Asp Tyr Tyr Leu Glu Gly
1               5
```

<210> SEQ ID NO 467
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 467

```
Ala Asp Pro Tyr Ser Tyr Ala Ala Leu Ser Asp
1               5                   10
```

<210> SEQ ID NO 468
<211> LENGTH: 11
<212> TYPE: PRT
<213> ORGANISM: Unknown
<220> FEATURE:

<223> OTHER INFORMATION: Description of Unknown:
      Marker peptide

<400> SEQUENCE: 468

Ala Glu Pro Tyr Arg Tyr Trp Gln Asn Leu Glu
1               5                   10

<210> SEQ ID NO 469
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 469

Ala Lys Trp Tyr Glu Asn Phe Ser Asp
1               5

<210> SEQ ID NO 470
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 470

Ala Tyr Pro Ser Tyr Ala Val Glu Asp
1               5

<210> SEQ ID NO 471
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 471

Ala Gln Gly Trp Asp Gly Ser Gly Val Phe Glu
1               5                   10

<210> SEQ ID NO 472
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 472

Ala Ala Asp Val Tyr Trp His Ser Asp
1               5

<210> SEQ ID NO 473
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 473

Asp Arg Tyr Tyr Ala Asp Gly
1               5

```
<210> SEQ ID NO 474
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 474

Asp Arg Tyr Trp Ser Asp Tyr Gln Gly
1               5

<210> SEQ ID NO 475
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 475

Asp Arg Trp Tyr Ala Leu Asp Gly
1               5

<210> SEQ ID NO 476
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 476

Asp Arg Ser Phe Pro Tyr Trp Asp Gly
1               5

<210> SEQ ID NO 477
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 477

Val Pro Arg Arg Phe Asp Gln Arg Glu Asp
1               5                   10

<210> SEQ ID NO 478
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 478

Gln Arg Gly Gly Ala Phe Asp Trp Val Asp
1               5                   10

<210> SEQ ID NO 479
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 479
```

```
Ser Arg Gly Phe Glu Leu Ser Glu
1               5

<210> SEQ ID NO 480
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 480

Gly Gln Arg Ala Phe Glu Tyr Ser Asp
1               5

<210> SEQ ID NO 481
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 481

Glu Pro Arg Arg Leu Asp Tyr Asp Gly
1               5

<210> SEQ ID NO 482
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 482

Arg Arg Asp Leu Asp Phe Ser Asp
1               5

<210> SEQ ID NO 483
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 483

Gly Arg Glu Leu Glu Trp Gln Phe Ser
1               5

<210> SEQ ID NO 484
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 484

Val Val Arg Leu Gln Leu Ser Glu
1               5

<210> SEQ ID NO 485
<211> LENGTH: 9
<212> TYPE: PRT
<213> ORGANISM: Unknown
```

```
<220> FEATURE:
<223> OTHER INFORMATION: Description of Unknown:
      Marker peptide

<400> SEQUENCE: 485

Gly Pro Phe Val Arg Val Leu Phe Ser
1               5

<210> SEQ ID NO 486
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 486

Pro Ser Gln Leu Trp Val Lys Phe Gly
1               5

<210> SEQ ID NO 487
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 487

Arg Gln Val Leu Arg Phe Val Ser Glu
1               5

<210> SEQ ID NO 488
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 488

Arg Val Asn Phe Arg Val Leu Lys Val Glu
1               5                   10

<210> SEQ ID NO 489
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 489

Asp Arg Arg Leu Arg Val Leu Ser Gly
1               5

<210> SEQ ID NO 490
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 490

Pro Leu Val Leu Arg Val Pro Lys Gly
1               5
```

```
<210> SEQ ID NO 491
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 491

Pro Leu Asn Phe Lys Arg Leu Ala Val Phe Ser
1               5                   10

<210> SEQ ID NO 492
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 492

Gln Phe Arg Leu Gly Phe Ala Gly
1               5

<210> SEQ ID NO 493
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 493

Lys Leu Val His Leu Arg Val Gly
1               5

<210> SEQ ID NO 494
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 494

Val Arg Val Val Arg Leu Gly
1               5

<210> SEQ ID NO 495
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 495

Arg Leu Asn Phe Arg Leu Val Gly
1               5

<210> SEQ ID NO 496
<211> LENGTH: 7
<212> TYPE: PRT
<213> ORGANISM: Unknown
<220> FEATURE:
<223> OTHER INFORMATION: Description of Unknown:
      Marker peptide
```

-continued

```
<400> SEQUENCE: 496

Tyr Gln Leu Leu Leu Lys Gly
1               5

<210> SEQ ID NO 497
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 497

Ala Val Leu Lys Ala Arg Phe Asn Lys His Phe
1               5                   10

<210> SEQ ID NO 498
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 498

Pro Ser Ala Val Lys Leu Phe Arg Leu Gly
1               5                   10

<210> SEQ ID NO 499
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 499

Tyr Arg Val Leu Lys Leu Ser Ala Asp Pro Val Ser
1               5                   10

<210> SEQ ID NO 500
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 500

Leu Pro Arg Pro Pro Lys Leu Phe Gly
1               5

<210> SEQ ID NO 501
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 501

Pro Pro Lys Tyr Val Ser Ala Arg Phe Ser
1               5                   10

<210> SEQ ID NO 502
<211> LENGTH: 11
<212> TYPE: PRT
```

```
<213> ORGANISM: Unknown
<220> FEATURE:
<223> OTHER INFORMATION: Description of Unknown:
      Marker peptide

<400> SEQUENCE: 502

Pro Ala Arg Phe Arg Val Ala Leu Leu Ser Asp
1               5                   10

<210> SEQ ID NO 503
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 503

Ala Leu Arg Val Val Leu Lys Asp
1               5

<210> SEQ ID NO 504
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 504

Ala Leu Arg Ala Val Val Leu Ser
1               5

<210> SEQ ID NO 505
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 505

Val Arg Phe Leu Val Leu Gly
1               5

<210> SEQ ID NO 506
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 506

Val Pro Trp Lys Ala Leu Arg Leu Phe
1               5

<210> SEQ ID NO 507
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 507

Ala Val Arg Leu Lys Phe Arg Glu Gly
1               5
```

<210> SEQ ID NO 508
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 508

Leu Arg Val Val Arg Phe Gly
1               5

<210> SEQ ID NO 509
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 509

Ala Tyr Leu Trp Asp Tyr Phe Asp Gly
1               5

<210> SEQ ID NO 510
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 510

Val Trp Ser Lys Phe Glu Tyr Glu Asp
1               5

<210> SEQ ID NO 511
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 511

Phe Val Ser Tyr Ser Asp Tyr Glu Asp
1               5

<210> SEQ ID NO 512
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 512

Leu Tyr Glu Asn Arg Phe Glu Tyr Ser Asp
1               5                   10

<210> SEQ ID NO 513
<211> LENGTH: 7
<212> TYPE: PRT
<213> ORGANISM: Unknown
<220> FEATURE:
<223> OTHER INFORMATION: Description of Unknown:
      Marker peptide

```
<400> SEQUENCE: 513

Phe Tyr Asp Trp Asp Glu Asp
1               5

<210> SEQ ID NO 514
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 514

Ser Phe Asp Tyr Phe Asp Ala Phe Asp
1               5

<210> SEQ ID NO 515
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 515

Tyr Lys Ser Leu Asp Phe Tyr Asp
1               5

<210> SEQ ID NO 516
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 516

Gly Tyr Ser Ser Ala Trp Val Ser Glu
1               5

<210> SEQ ID NO 517
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 517

Tyr Trp Leu Asp Tyr Asp Ser Ala Leu Ser
1               5                   10

<210> SEQ ID NO 518
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 518

Ala Ala Tyr Leu Asp Tyr Ser Asp
1               5

<210> SEQ ID NO 519
<211> LENGTH: 8
```

```
<212> TYPE: PRT
<213> ORGANISM: Unknown
<220> FEATURE:
<223> OTHER INFORMATION: Description of Unknown:
      Marker peptide

<400> SEQUENCE: 519

Tyr Val Tyr Glu Phe Asp Ser Gly
1               5

<210> SEQ ID NO 520
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 520

Tyr Asn Ser Tyr Gln Trp Leu Glu Tyr Glu Asp
1               5                   10

<210> SEQ ID NO 521
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 521

Asn Val Phe Tyr Asp Tyr Ala Asp Val Glu Asp
1               5                   10

<210> SEQ ID NO 522
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 522

Ala Gly Trp Tyr Ser Asp Trp Phe Ser Asp
1               5                   10

<210> SEQ ID NO 523
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 523

Trp Leu Asp Ser Ala Trp Phe Pro Ser Glu
1               5                   10

<210> SEQ ID NO 524
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 524

Tyr Tyr Glu Ser Tyr Ala Glu Asp
```

```
1               5

<210> SEQ ID NO 525
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 525

Phe Gln Glu Pro Tyr Pro Tyr Gln Glu Asp
1               5                   10

<210> SEQ ID NO 526
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 526

Tyr Asp Trp Val Asn Ala Lys Phe Asp
1               5

<210> SEQ ID NO 527
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 527

Gln Lys Arg Trp Leu Asp Ala Pro Phe Asp
1               5                   10

<210> SEQ ID NO 528
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 528

Asp Trp Gly Ser Trp Phe Gly
1               5

<210> SEQ ID NO 529
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 529

Phe Arg Ser Gly Leu Asp Phe Asp Gly
1               5

<210> SEQ ID NO 530
<211> LENGTH: 9
<212> TYPE: PRT
<213> ORGANISM: Unknown
<220> FEATURE:
<223> OTHER INFORMATION: Description of Unknown:
```

Marker peptide

<400> SEQUENCE: 530

Tyr Val Asp Lys Asp Phe Arg Phe Gly
1               5

<210> SEQ ID NO 531
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 531

Tyr Ser Gly Val Asp Trp Phe Pro Asn Ser Asp
1               5                   10

<210> SEQ ID NO 532
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 532

Arg Tyr Gln Phe Glu Asp Asn Tyr Phe Gly
1               5                   10

<210> SEQ ID NO 533
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 533

Val Arg Gln Val Asp Gly His Glu Gly
1               5

<210> SEQ ID NO 534
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 534

Phe Arg Gln Val Glu Gly Pro Val Asp
1               5

<210> SEQ ID NO 535
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 535

Leu Arg Ala Leu Glu Pro His Ser Glu
1               5

<210> SEQ ID NO 536

```
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 536

Phe Arg Gln Leu Glu Lys His Asp
1               5

<210> SEQ ID NO 537
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 537

Leu Arg Glu Val Asp Gln Val Asp Gly
1               5

<210> SEQ ID NO 538
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 538

Phe Arg Leu Val Asp Glu Gly
1               5

<210> SEQ ID NO 539
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 539

Leu Arg Glu Val Glu Pro Trp Lys Glu
1               5

<210> SEQ ID NO 540
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 540

Val Arg Leu Val Asp Pro Glu Asp
1               5

<210> SEQ ID NO 541
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 541
```

```
Leu Arg Tyr Leu Glu Pro Ala Asp Gly
1               5
```

<210> SEQ ID NO 542
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 542

```
Leu Arg Tyr Val Asp Pro Ala Gln Lys Arg Asp
1               5                   10
```

<210> SEQ ID NO 543
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 543

```
Val Arg Arg Val Asp Pro Tyr Phe Asp
1               5
```

<210> SEQ ID NO 544
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 544

```
Leu Arg Glu Phe Asp Tyr Phe Ser Glu
1               5
```

<210> SEQ ID NO 545
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 545

```
Ser Arg Gln Val Asp Pro Leu Ser Glu
1               5
```

<210> SEQ ID NO 546
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 546

```
Phe Arg Glu Ala Asp Leu Glu Asp
1               5
```

<210> SEQ ID NO 547
<211> LENGTH: 9
<212> TYPE: PRT
<213> ORGANISM: Unknown
<220> FEATURE:

```
<223> OTHER INFORMATION: Description of Unknown:
      Marker peptide

<400> SEQUENCE: 547

Leu Arg Lys Val Glu Ala His Ser Gly
1               5

<210> SEQ ID NO 548
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 548

Val Arg Arg Leu Asp Lys Glu Asp
1               5

<210> SEQ ID NO 549
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 549

Phe Arg Lys Leu Glu Asn Asp Gly
1               5

<210> SEQ ID NO 550
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 550

Val Arg Lys Val Asp Trp Glu Gly
1               5

<210> SEQ ID NO 551
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 551

Asn Arg Ala Leu Asp Phe Asp Ala His Gly
1               5                   10

<210> SEQ ID NO 552
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 552

Leu Arg Leu Asn Asp Pro Ser Asp Gly
1               5
```

```
<210> SEQ ID NO 553
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 553

Gly Arg Gln Leu Asp Pro Glu Gly
1               5

<210> SEQ ID NO 554
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 554

Gln Arg Gln Phe Asp Ala Gln Leu Ala Lys Leu Glu
1               5                   10

<210> SEQ ID NO 555
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 555

Arg Arg Ser Phe Asp Gly Asp Gly
1               5

<210> SEQ ID NO 556
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 556

Gly Arg Asn Phe Asp Lys Arg Glu Gly
1               5

<210> SEQ ID NO 557
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 557

Tyr Arg Gln Ala Asp Phe Ser Gly
1               5

<210> SEQ ID NO 558
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 558
```

-continued

Tyr Arg Leu Val Asp Tyr Gln Ala Leu Glu Asp
1               5                   10

<210> SEQ ID NO 559
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 559

Leu Arg Lys Phe Asn His Val Glu Asp
1               5

<210> SEQ ID NO 560
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 560

Phe Arg Leu Leu Asp Leu Ser Gly
1               5

<210> SEQ ID NO 561
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 561

Leu Arg Glu Phe His Val Glu Gly
1               5

<210> SEQ ID NO 562
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 562

Tyr Arg Lys Tyr Asp Tyr Ala Leu Glu
1               5

<210> SEQ ID NO 563
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 563

Asn Arg Arg Val Asp Gly Trp Trp Glu Gly
1               5                   10

<210> SEQ ID NO 564
<211> LENGTH: 9
<212> TYPE: PRT
<213> ORGANISM: Unknown

```
<220> FEATURE:
<223> OTHER INFORMATION: Description of Unknown:
      Marker peptide

<400> SEQUENCE: 564

Asn Arg Glu Phe Asp Asp Tyr His Gly
1               5

<210> SEQ ID NO 565
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 565

Gln Arg Leu Phe Glu Ser Asp His Arg Glu Gly
1               5                   10

<210> SEQ ID NO 566
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 566

Phe Pro Gln Arg Glu Gly Tyr Lys Tyr Asp
1               5                   10

<210> SEQ ID NO 567
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 567

Phe Val Lys Arg Asp Glu Asp
1               5

<210> SEQ ID NO 568
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 568

Phe Arg Ala His Asp Asn Val Glu Asp
1               5

<210> SEQ ID NO 569
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 569

Ala Arg Glu Phe Asp Phe Tyr Gly
1               5
```

```
<210> SEQ ID NO 570
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 570

Gln Arg Glu Leu Asp Phe Tyr Ala Leu Ser
1               5                   10

<210> SEQ ID NO 571
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 571

Leu Arg Glu Tyr Glu Asn His Asp Gly
1               5

<210> SEQ ID NO 572
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 572

His Arg Glu Val Asp Gly Ala His Phe Asp
1               5                   10

<210> SEQ ID NO 573
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 573

Ala Arg Asp Leu Asp His Ser Trp His Ser Asp
1               5                   10

<210> SEQ ID NO 574
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 574

Glu Arg Tyr Val Asp Gly Tyr His Asp
1               5

<210> SEQ ID NO 575
<211> LENGTH: 7
<212> TYPE: PRT
<213> ORGANISM: Unknown
<220> FEATURE:
<223> OTHER INFORMATION: Description of Unknown:
      Marker peptide
```

```
<400> SEQUENCE: 575

Glu Arg Leu Leu Asp Tyr Gly
1               5

<210> SEQ ID NO 576
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 576

Glu Arg Gln Phe Asp Val Phe Gly
1               5

<210> SEQ ID NO 577
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 577

Gly Arg Ser Ala Asp Tyr Gln Phe Asp
1               5

<210> SEQ ID NO 578
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 578

Asn Arg Asp Phe Asp Gly Pro Val Val Asp
1               5                   10

<210> SEQ ID NO 579
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 579

Gly Arg Asp Tyr Asp Ala Trp Val Ser
1               5

<210> SEQ ID NO 580
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 580

Gly Arg Ser Leu Asp Asp Gly
1               5

<210> SEQ ID NO 581
<211> LENGTH: 10
<212> TYPE: PRT
```

<213> ORGANISM: Unknown
<220> FEATURE:
<223> OTHER INFORMATION: Description of Unknown:
     Marker peptide

<400> SEQUENCE: 581

His Arg Gln Leu Asp Gly Trp Asn Phe Asp
1               5                   10

<210> SEQ ID NO 582
<211> LENGTH: 9
<212> TYPE: PRT
<213> ORGANISM: Unknown
<220> FEATURE:
<223> OTHER INFORMATION: Description of Unknown:
     Marker peptide

<400> SEQUENCE: 582

Gly Arg Arg Leu Glu Asp Leu Asp Gly
1               5

<210> SEQ ID NO 583
<211> LENGTH: 11
<212> TYPE: PRT
<213> ORGANISM: Unknown
<220> FEATURE:
<223> OTHER INFORMATION: Description of Unknown:
     Marker peptide

<400> SEQUENCE: 583

Gly Arg His Leu Asp Tyr Glu Tyr Lys Ser Glu
1               5                   10

<210> SEQ ID NO 584
<211> LENGTH: 8
<212> TYPE: PRT
<213> ORGANISM: Unknown
<220> FEATURE:
<223> OTHER INFORMATION: Description of Unknown:
     Marker peptide

<400> SEQUENCE: 584

Ser Arg Phe Leu Asp His Glu Asp
1               5

<210> SEQ ID NO 585
<211> LENGTH: 8
<212> TYPE: PRT
<213> ORGANISM: Unknown
<220> FEATURE:
<223> OTHER INFORMATION: Description of Unknown:
     Marker peptide

<400> SEQUENCE: 585

Leu Arg Pro Leu Glu Val Asp Gly
1               5

<210> SEQ ID NO 586
<211> LENGTH: 8
<212> TYPE: PRT
<213> ORGANISM: Unknown
<220> FEATURE:
<223> OTHER INFORMATION: Description of Unknown:
     Marker peptide

<400> SEQUENCE: 586

Val Arg Pro Val Glu Arg Asp Gly
1               5

<210> SEQ ID NO 587
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 587

Arg Arg Tyr Val Asp Ser Asp Gly
1               5

<210> SEQ ID NO 588
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 588

Gly Arg Ala Val Asp Lys Val Leu Asp
1               5

<210> SEQ ID NO 589
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 589

Ser Arg Leu Val Glu Glu Gly
1               5

<210> SEQ ID NO 590
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 590

Ser Arg Ser Val Asp Pro Ala His Val Asp
1               5                   10

<210> SEQ ID NO 591
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 591

His Arg Ser Val Asp Ala Glu Gly
1               5

<210> SEQ ID NO 592
<211> LENGTH: 12
<212> TYPE: PRT
<213> ORGANISM: Unknown
<220> FEATURE:
<223> OTHER INFORMATION: Description of Unknown:
      Marker peptide -continued

```
<400> SEQUENCE: 592

His Arg His Val Asp Asn Asp Pro Asn Gln Leu Glu
1               5                   10

<210> SEQ ID NO 593
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 593

Leu Arg Ala His Asp Glu Asp
1               5

<210> SEQ ID NO 594
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 594

Gln Arg Phe Ala Val Asp Ala Asp Asn Ser Asp
1               5                   10

<210> SEQ ID NO 595
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 595

Gln Arg Asn Tyr Asp Phe Gly
1               5

<210> SEQ ID NO 596
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 596

Gln Arg His Val Asp Gly Phe Asn Lys Ala Gly
1               5                   10

<210> SEQ ID NO 597
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 597

Gln Arg His Val Glu Gly Val Tyr Gln Leu Trp Gly
1               5                   10

<210> SEQ ID NO 598
<211> LENGTH: 8
```

-continued

```
<212> TYPE: PRT
<213> ORGANISM: Unknown
<220> FEATURE:
<223> OTHER INFORMATION: Description of Unknown:
      Marker peptide

<400> SEQUENCE: 598

Leu Arg Lys Phe Asp Val Phe Gly
1               5

<210> SEQ ID NO 599
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 599

Glu Arg Leu Phe Asp Phe Glu Asn Val Gly
1               5                   10

<210> SEQ ID NO 600
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 600

Gly Arg Leu Phe Asp Trp Gln Gly Glu Asp
1               5                   10

<210> SEQ ID NO 601
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 601

Lys Arg Leu Phe Asp Tyr Ala Pro Phe Pro Glu Asp
1               5                   10

<210> SEQ ID NO 602
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 602

Gln Arg Leu Tyr Asp Trp Gln Pro Arg Asp
1               5                   10

<210> SEQ ID NO 603
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 603

Leu Pro Arg Arg Glu Asp Tyr Asn Gln Phe Glu
```

1               5                   10

<210> SEQ ID NO 604
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 604

Phe Pro Arg Arg Asp Phe Glu Asp
1               5

<210> SEQ ID NO 605
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 605

Phe Pro Ser Arg Asp Gly Ala Leu Glu
1               5

<210> SEQ ID NO 606
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 606

Leu Pro Asn Arg Asp Ser Leu Gly
1               5

<210> SEQ ID NO 607
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 607

Leu Pro Leu Arg Glu Asn Gln Gly
1               5

<210> SEQ ID NO 608
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 608

Leu Arg Lys Ser Asp Leu Ser Asp
1               5

<210> SEQ ID NO 609
<211> LENGTH: 9
<212> TYPE: PRT
<213> ORGANISM: Unknown
<220> FEATURE:
<223> OTHER INFORMATION: Description of Unknown:

-continued

Marker peptide

<400> SEQUENCE: 609

Leu Arg Asp Lys Asp Arg Val Ser Asp
1               5

<210> SEQ ID NO 610
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 610

Val Arg Arg Leu Tyr Glu Asp
1               5

<210> SEQ ID NO 611
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 611

Leu Arg Arg Val Leu Ser Glu Asn Glu
1               5

<210> SEQ ID NO 612
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 612

Leu Arg Lys Leu Ser Leu Glu Asp
1               5

<210> SEQ ID NO 613
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 613

Leu Arg Lys Val Pro Val Glu Gly
1               5

<210> SEQ ID NO 614
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 614

Pro Gly Val Gly His Lys His Phe Gly
1               5

<210> SEQ ID NO 615

```
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 615

Pro Gly Lys Phe Gln Arg Pro Arg Asp
1               5

<210> SEQ ID NO 616
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 616

Pro Ala Val Gly Lys Gln Val Leu Lys Arg Val Ser
1               5                   10

<210> SEQ ID NO 617
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 617

Pro Gly Lys Trp Phe Lys Ser Gly
1               5

<210> SEQ ID NO 618
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 618

Pro Gly Arg His Ala Lys Tyr Asn Lys Val Ser
1               5                   10

<210> SEQ ID NO 619
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 619

Ala Gln Ala Val Ala Arg Asp Lys Asp Gly
1               5                   10

<210> SEQ ID NO 620
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 620
```

Pro Gly His Asp Asn Lys Gly Gln Val Ser
1               5                   10

<210> SEQ ID NO 621
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 621

Pro Gly Lys Glu Arg His Leu Val Asp
1               5

<210> SEQ ID NO 622
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 622

Pro Gly Ser Ala Gln Lys Glu Tyr Asn His Leu
1               5                   10

<210> SEQ ID NO 623
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 623

Pro Gly Ser Gly Ala Lys Glu Phe Ser Gly
1               5                   10

<210> SEQ ID NO 624
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 624

Pro Gly Phe Glu Gln Lys Pro Ala Gln Gly
1               5                   10

<210> SEQ ID NO 625
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 625

Pro Gly Trp Glu Pro Lys Tyr Ala Ser Gly
1               5                   10

<210> SEQ ID NO 626
<211> LENGTH: 12
<212> TYPE: PRT
<213> ORGANISM: Unknown
<220> FEATURE:

```
<223> OTHER INFORMATION: Description of Unknown:
     Marker peptide

<400> SEQUENCE: 626

Pro Ala Lys Glu Ala Lys Glu Pro His Ala Asp Gly
1               5                   10

<210> SEQ ID NO 627
<211> LENGTH: 9
<212> TYPE: PRT
<213> ORGANISM: Unknown
<220> FEATURE:
<223> OTHER INFORMATION: Description of Unknown:
     Marker peptide

<400> SEQUENCE: 627

Pro Gly Arg Gly Ala Lys Gln His Asp
1               5

<210> SEQ ID NO 628
<211> LENGTH: 9
<212> TYPE: PRT
<213> ORGANISM: Unknown
<220> FEATURE:
<223> OTHER INFORMATION: Description of Unknown:
     Marker peptide

<400> SEQUENCE: 628

Pro Gly Val Glu Gln Arg Arg Leu Gly
1               5

<210> SEQ ID NO 629
<211> LENGTH: 10
<212> TYPE: PRT
<213> ORGANISM: Unknown
<220> FEATURE:
<223> OTHER INFORMATION: Description of Unknown:
     Marker peptide

<400> SEQUENCE: 629

Pro Gly Lys Ala Val Tyr Ala Val Ser Asp
1               5                   10

<210> SEQ ID NO 630
<211> LENGTH: 10
<212> TYPE: PRT
<213> ORGANISM: Unknown
<220> FEATURE:
<223> OTHER INFORMATION: Description of Unknown:
     Marker peptide

<400> SEQUENCE: 630

Pro Gly Lys Ser Val Leu Asn Arg Glu Gly
1               5                   10

<210> SEQ ID NO 631
<211> LENGTH: 8
<212> TYPE: PRT
<213> ORGANISM: Unknown
<220> FEATURE:
<223> OTHER INFORMATION: Description of Unknown:
     Marker peptide

<400> SEQUENCE: 631

Val Gly Lys Ala Val Lys His Asp
1               5
```

-continued

```
<210> SEQ ID NO 632
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 632

Pro Gly Arg Ala Gln Arg His Asn Asp Gly
1               5                   10

<210> SEQ ID NO 633
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 633

Val Gly Arg Gln Val Asp Tyr Lys Phe Asp
1               5                   10

<210> SEQ ID NO 634
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 634

Val Leu Arg Arg Leu Glu Arg Glu Gly
1               5

<210> SEQ ID NO 635
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 635

Leu Arg Ser Trp Asp Tyr Asn Glu Gly
1               5

<210> SEQ ID NO 636
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 636

His Trp Leu Arg Gln Val Glu Asp
1               5

<210> SEQ ID NO 637
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 637
```

Leu Leu Arg Tyr Val Glu Asp Gly
1               5

<210> SEQ ID NO 638
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 638

Tyr Arg Lys Gln Asp Ala Trp Asp
1               5

<210> SEQ ID NO 639
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 639

Leu Arg Lys Trp Glu Asp Gly
1               5

<210> SEQ ID NO 640
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 640

Tyr Arg Gly Gln Phe Asp Lys Asp Tyr Leu Gly
1               5                   10

<210> SEQ ID NO 641
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 641

Leu Arg Arg Tyr Leu Glu Asp Gly
1               5

<210> SEQ ID NO 642
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 642

Val Arg Gly Val Glu Ala Trp Phe Asp
1               5

<210> SEQ ID NO 643
<211> LENGTH: 11
<212> TYPE: PRT
<213> ORGANISM: Unknown

```
<220> FEATURE:
<223> OTHER INFORMATION: Description of Unknown:
      Marker peptide

<400> SEQUENCE: 643

Ala Arg Leu Leu Glu Phe Glu Trp Gln Lys Asp
1               5                   10

<210> SEQ ID NO 644
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 644

Tyr Arg Gly Val Glu Leu Asn Phe Asp
1               5

<210> SEQ ID NO 645
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 645

Leu Arg Asp Phe His Phe Asp
1               5

<210> SEQ ID NO 646
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 646

Tyr Arg Ser Ala Asp Val Phe Tyr Asp
1               5

<210> SEQ ID NO 647
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 647

Leu Pro Arg Tyr Asp Glu Asp
1               5

<210> SEQ ID NO 648
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 648

Leu Pro Tyr His Asp Arg Leu Asp Gln His Leu Asp
1               5                   10
```

<210> SEQ ID NO 649
<211> LENGTH: 9
<212> TYPE: PRT
<213> ORGANISM: Unknown
<220> FEATURE:
<223> OTHER INFORMATION: Description of Unknown:
    Marker peptide

<400> SEQUENCE: 649

Val Arg Tyr Phe Glu Gln Leu Glu Gly
1               5

<210> SEQ ID NO 650
<211> LENGTH: 9
<212> TYPE: PRT
<213> ORGANISM: Unknown
<220> FEATURE:
<223> OTHER INFORMATION: Description of Unknown:
    Marker peptide

<400> SEQUENCE: 650

Val Arg Val Ala Asp Gly Trp Arg Asp
1               5

<210> SEQ ID NO 651
<211> LENGTH: 9
<212> TYPE: PRT
<213> ORGANISM: Unknown
<220> FEATURE:
<223> OTHER INFORMATION: Description of Unknown:
    Marker peptide

<400> SEQUENCE: 651

Lys Gln Arg Trp Val Glu Val Asp Gly
1               5

<210> SEQ ID NO 652
<211> LENGTH: 7
<212> TYPE: PRT
<213> ORGANISM: Unknown
<220> FEATURE:
<223> OTHER INFORMATION: Description of Unknown:
    Marker peptide

<400> SEQUENCE: 652

Leu Arg Phe Ala Glu Val Gly
1               5

<210> SEQ ID NO 653
<211> LENGTH: 7
<212> TYPE: PRT
<213> ORGANISM: Unknown
<220> FEATURE:
<223> OTHER INFORMATION: Description of Unknown:
    Marker peptide

<400> SEQUENCE: 653

Leu Pro Phe Arg Asp Pro Gly
1               5

<210> SEQ ID NO 654
<211> LENGTH: 11
<212> TYPE: PRT
<213> ORGANISM: Unknown
<220> FEATURE:
<223> OTHER INFORMATION: Description of Unknown:
    Marker peptide

```
<400> SEQUENCE: 654

Asn Arg Gln Phe Asp Trp Leu Pro Trp Ser Gly
1               5                   10

<210> SEQ ID NO 655
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 655

Arg Ala Asn Phe Asp Tyr Ala Asp His Glu Gly
1               5                   10

<210> SEQ ID NO 656
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 656

Arg Ser Ser Phe Asp Glu Asp Gly
1               5

<210> SEQ ID NO 657
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 657

Pro Lys Leu Tyr Asp Gly His Glu Asn Val Glu
1               5                   10

<210> SEQ ID NO 658
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 658

Pro Arg Gln Val Asp Asn Lys Glu Tyr Glu Gly
1               5                   10

<210> SEQ ID NO 659
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 659

Pro Pro Arg Arg Asp Val Ser Glu
1               5

<210> SEQ ID NO 660
<211> LENGTH: 11
<212> TYPE: PRT
```

```
<213> ORGANISM: Unknown
<220> FEATURE:
<223> OTHER INFORMATION: Description of Unknown:
      Marker peptide

<400> SEQUENCE: 660

Ala Arg Asp Tyr Asp Gly Asn Pro Phe Ser Gly
1               5                   10

<210> SEQ ID NO 661
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 661

Glu Arg Tyr Tyr Asp Gly
1               5

<210> SEQ ID NO 662
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 662

Trp Arg Asn Tyr Asp Pro Tyr Val Glu
1               5

<210> SEQ ID NO 663
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 663

Trp Arg Gln Ser Asp Gly Tyr Val Pro Asp Gly
1               5                   10

<210> SEQ ID NO 664
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 664

Ala Arg Pro Tyr Asp Trp Glu Asn Lys Val Asp
1               5                   10

<210> SEQ ID NO 665
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 665

Ala Arg Pro Ala Asp Val Asp Tyr Phe Gly
1               5                   10
```

<210> SEQ ID NO 666
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 666

Gln Val Trp Arg Gln Val Asp Ala Asp
1               5

<210> SEQ ID NO 667
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 667

Phe Arg Glu Val Ala Asn Val Glu Asp
1               5

<210> SEQ ID NO 668
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 668

Tyr Arg Gln Val His Glu Ala Trp Asp
1               5

<210> SEQ ID NO 669
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 669

Asn Arg Pro Val Asp Gly Tyr Pro Phe Gly
1               5                   10

<210> SEQ ID NO 670
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 670

Tyr Arg Ser Ser Asp Pro Val Ser Asn Val Ser Asp
1               5                   10

<210> SEQ ID NO 671
<211> LENGTH: 10
<212> TYPE: PRT
<213> ORGANISM: Unknown
<220> FEATURE:
<223> OTHER INFORMATION: Description of Unknown:
      Marker peptide <210> SEQ ID NO 671
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 671

Ala Lys Ala Arg Asp Tyr Gly Val Glu Asp
1               5                   10

<210> SEQ ID NO 672
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 672

Leu Arg Asn Gly His Phe Glu Asp
1               5

<210> SEQ ID NO 673
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 673

His Pro Gln Arg Asp Asn Pro Tyr His Val Glu
1               5                   10

<210> SEQ ID NO 674
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 674

Tyr Pro Arg Arg Asp Arg Glu Asp
1               5

<210> SEQ ID NO 675
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 675

Gln Tyr Arg Gln Leu Asp His Asp Gly
1               5

<210> SEQ ID NO 676
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 676

Ala Phe Arg Glu Leu Glu Ala Ser Gly
1               5

<210> SEQ ID NO 677
<211> LENGTH: 8

```
<212> TYPE: PRT
<213> ORGANISM: Unknown
<220> FEATURE:
<223> OTHER INFORMATION: Description of Unknown:
      Marker peptide

<400> SEQUENCE: 677

Ser Lys Tyr His Asp Leu Phe Asp
1               5

<210> SEQ ID NO 678
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 678

Phe Arg Asn His Glu Val Phe Asp
1               5

<210> SEQ ID NO 679
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 679

Leu Lys Tyr His Asp Ala Phe Ser Asp
1               5

<210> SEQ ID NO 680
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 680

Asn Arg Asn Tyr Asp Lys Phe Glu Gly
1               5

<210> SEQ ID NO 681
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 681

Lys Arg Trp Tyr Asp Ala Asn Asp
1               5

<210> SEQ ID NO 682
<211> LENGTH: 13
<212> TYPE: PRT
<213> ORGANISM: Unknown
<220> FEATURE:
<223> OTHER INFORMATION: Description of Unknown:
      Marker peptide

<400> SEQUENCE: 682

Gln Arg His Phe Asp Pro Asp Ala Val Glu Lys Arg Val
```

<210> SEQ ID NO 683
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 683

Phe Gln Arg Ala Val Asp Asn His Glu
1               5

<210> SEQ ID NO 684
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 684

Tyr Arg Tyr Val Glu Asp Trp Pro Ser Asp
1               5                   10

<210> SEQ ID NO 685
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 685

Leu Arg Asn Ser Asp Pro Gln Val Glu Asp
1               5                   10

<210> SEQ ID NO 686
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 686

Phe Arg Gln Ala Glu Asp
1               5

<210> SEQ ID NO 687
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 687

Tyr Arg Glu Tyr Asp Gly Gln Pro Ala Glu Asp
1               5                   10

<210> SEQ ID NO 688
<211> LENGTH: 11
<212> TYPE: PRT
<213> ORGANISM: Unknown
<220> FEATURE:
<223> OTHER INFORMATION: Description of Unknown:

Marker peptide

<400> SEQUENCE: 688

Tyr Arg Arg Val Glu Asp Ala Glu Ala Lys Asp
1               5                   10

<210> SEQ ID NO 689
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 689

Leu Ala Glu Arg Asp Tyr Ala Asp Gly
1               5

<210> SEQ ID NO 690
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 690

Phe Pro Glu Arg Asp Lys Arg Leu Gly
1               5

<210> SEQ ID NO 691
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 691

Phe Arg Leu Glu Asp Gly Ala Gly Leu Glu Asp
1               5                   10

<210> SEQ ID NO 692
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 692

Leu Arg Phe Phe Asp Pro Ala Glu Gly
1               5

<210> SEQ ID NO 693
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 693

Phe Arg Pro Phe Asp Asn Asp Gly
1               5

<210> SEQ ID NO 694

```
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 694

Leu Arg Tyr Phe Asp Tyr Leu Asp
1               5

<210> SEQ ID NO 695
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 695

Phe Arg Tyr Phe Asp Pro Leu Ser Asp
1               5

<210> SEQ ID NO 696
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 696

Pro Arg Phe Phe Asp Asp Asp Gly
1               5

<210> SEQ ID NO 697
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 697

Tyr Arg Gln Leu Glu Leu Asp Trp Ser Gly
1               5                   10

<210> SEQ ID NO 698
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 698

Glu Arg Trp Val Asp Pro Asn Arg Phe Glu
1               5                   10

<210> SEQ ID NO 699
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 699
```

```
Leu Ala Arg Gln Leu Asp Trp Val Asp
1               5

<210> SEQ ID NO 700
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 700

Leu Arg Val Ala Glu Phe Glu Gly
1               5

<210> SEQ ID NO 701
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 701

Ser Pro Leu Arg Asp Gly Pro Phe Glu
1               5

<210> SEQ ID NO 702
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 702

Gln Arg Val Val Glu Tyr Gln Asn Phe Asp
1               5                   10

<210> SEQ ID NO 703
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 703

Leu Arg Asp Tyr Glu Leu Phe Asp
1               5

<210> SEQ ID NO 704
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 704

His Arg Glu Leu Glu Val Phe Ser Gly
1               5

<210> SEQ ID NO 705
<211> LENGTH: 10
<212> TYPE: PRT
<213> ORGANISM: Unknown
<220> FEATURE:
```

```
<223> OTHER INFORMATION: Description of Unknown:
      Marker peptide

<400> SEQUENCE: 705

Leu Arg Glu Trp Glu Gly Ala Gln Phe Glu
1               5                   10

<210> SEQ ID NO 706
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 706

Leu Arg Asn Phe Gln Glu Asp
1               5

<210> SEQ ID NO 707
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 707

Leu Arg Val Gln Asp Pro Ser Asp
1               5

<210> SEQ ID NO 708
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 708

His Arg Gly Val Asp Gly Arg Val Asp
1               5

<210> SEQ ID NO 709
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 709

Ser Arg Ser Phe Glu His Asp Gly
1               5

<210> SEQ ID NO 710
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 710

Val Arg Val Phe Asp Asp Asp Gly
1               5
```

```
<210> SEQ ID NO 711
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 711

Arg Arg Glu Phe Asp Gly Tyr Leu Ser
1               5

<210> SEQ ID NO 712
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 712

Arg Arg Ser Val Asp Tyr Asn Val Ser Glu
1               5                   10

<210> SEQ ID NO 713
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 713

His Arg Val Val Asp Asp Gly
1               5

<210> SEQ ID NO 714
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 714

Val Val Arg Glu Val Asp Gly
1               5

<210> SEQ ID NO 715
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 715

Phe Gln Gln Arg Glu Gln Leu Ser Glu
1               5

<210> SEQ ID NO 716
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 716
```

Val Arg Gln Tyr Glu Asp Gly
1               5

<210> SEQ ID NO 717
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 717

Gly Pro Ser Arg Glu Pro Glu Gly
1               5

<210> SEQ ID NO 718
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 718

Val Arg Leu Ala Asp Ser Glu Asp
1               5

<210> SEQ ID NO 719
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 719

His Arg Ser Val Glu Pro Ser Glu
1               5

<210> SEQ ID NO 720
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 720

Leu Arg Ala Ala Glu Asp Gly
1               5

<210> SEQ ID NO 721
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 721

Leu Arg Gln Val Gln Leu Ser Glu
1               5

<210> SEQ ID NO 722
<211> LENGTH: 8
<212> TYPE: PRT
<213> ORGANISM: Unknown

```
<220> FEATURE:
<223> OTHER INFORMATION: Description of Unknown:
      Marker peptide

<400> SEQUENCE: 722

Leu Arg Gln Lys Glu Phe Asp Gly
1               5

<210> SEQ ID NO 723
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 723

Gly Arg Phe Leu Asp Pro Ala Lys Asp
1               5

<210> SEQ ID NO 724
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 724

Tyr Arg Lys Leu His Glu Pro Asp
1               5

<210> SEQ ID NO 725
<211> LENGTH: 78
<212> TYPE: PRT
<213> ORGANISM: Unknown
<220> FEATURE:
<223> OTHER INFORMATION: Description of Unknown:
      NGRN sequence

<400> SEQUENCE: 725

Met Asp Cys Cys Thr Glu Asn Ala Cys Ser Lys Pro Asp Asp Ile
1               5                   10                  15

Leu Asp Ile Pro Leu Asp Asp Pro Gly Ala Asn Ala Ala Ala Lys
                20                  25                  30

Ile Gln Ala Ser Phe Arg Gly His Met Ala Arg Lys Ile Lys Ser
            35                  40                  45

Gly Glu Arg Gly Arg Lys Gly Pro Gly Pro Gly Pro Gly Gly Ala
        50                  55                  60

Gly Val Ala Arg Gly Gly Ala Gly Gly Pro Ser Gly Asp
65                  70                  75

<210> SEQ ID NO 726
<211> LENGTH: 7
<212> TYPE: PRT
<213> ORGANISM: Unknown
<220> FEATURE:
<223> OTHER INFORMATION: Description of Unknown:
      Marker peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
```

```
<400> SEQUENCE: 726

Arg Xaa Gly Xaa Gly Gly Gly
1               5

<210> SEQ ID NO 727
<211> LENGTH: 7
<212> TYPE: PRT
<213> ORGANISM: Unknown
<220> FEATURE:
<223> OTHER INFORMATION: Description of Unknown:
      Marker peptide
<220> FEATURE:
<221> NAME/KEY: MOD_RES
<222> LOCATION: (4)..(5)
<223> OTHER INFORMATION: Any amino acid

<400> SEQUENCE: 727

Arg Lys Lys Xaa Xaa Ser Gly
1               5

<210> SEQ ID NO 728
<211> LENGTH: 8
<212> TYPE: PRT
<213> ORGANISM: Unknown
<220> FEATURE:
<223> OTHER INFORMATION: Description of Unknown:
      Marker peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid

<400> SEQUENCE: 728

Ala Arg Xaa Gly Xaa Xaa Gly Gly
1               5

<210> SEQ ID NO 729
<211> LENGTH: 8
<212> TYPE: PRT
<213> ORGANISM: Unknown
<220> FEATURE:
<223> OTHER INFORMATION: Description of Unknown:
      Marker peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(6)
<223> OTHER INFORMATION: Any amino acid

<400> SEQUENCE: 729

Val Xaa Arg Gly Xaa Xaa Gly Gly
1               5

<210> SEQ ID NO 730
<211> LENGTH: 5
<212> TYPE: PRT
<213> ORGANISM: Unknown
<220> FEATURE:
<223> OTHER INFORMATION: Description of Unknown:
      Marker peptide
<220> FEATURE:
<221> NAME/KEY: MOD_RES
<222> LOCATION: (2)..(2)
```

```
<223> OTHER INFORMATION: Any amino acid

<400> SEQUENCE: 730

Lys Xaa Gly Glu Arg
1               5

<210> SEQ ID NO 731
<211> LENGTH: 9
<212> TYPE: PRT
<213> ORGANISM: Unknown
<220> FEATURE:
<223> OTHER INFORMATION: Description of Unknown:
      Marker peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(8)
<223> OTHER INFORMATION: Any amino acid

<400> SEQUENCE: 731

Lys Ser Xaa Glu Arg Xaa Xaa Xaa Gly
1               5

<210> SEQ ID NO 732
<211> LENGTH: 6
<212> TYPE: PRT
<213> ORGANISM: Unknown
<220> FEATURE:
<223> OTHER INFORMATION: Description of Unknown:
      Marker peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 732

Lys Xaa Gly Xaa Arg Gly
1               5

<210> SEQ ID NO 733
<211> LENGTH: 6
<212> TYPE: PRT
<213> ORGANISM: Unknown
<220> FEATURE:
<223> OTHER INFORMATION: Description of Unknown:
      Marker peptide
<220> FEATURE:
<221> NAME/KEY: MOD_RES
<222> LOCATION: (3)..(4)
<223> OTHER INFORMATION: Any amino acid

<400> SEQUENCE: 733

Lys Lys Xaa Xaa Ser Gly
1               5

<210> SEQ ID NO 734
<211> LENGTH: 10
<212> TYPE: PRT
<213> ORGANISM: Unknown
<220> FEATURE:
<223> OTHER INFORMATION: Description of Unknown:
      Marker peptide
<220> FEATURE:
<221> NAME/KEY: MOD_RES
```

```
<222> LOCATION: (2)..(2)
<223> OTHER INFORMATION: Any amino acid
<220> FEATURE:
<221> NAME/KEY: MOD_RES
<222> LOCATION: (6)..(9)
<223> OTHER INFORMATION: Any amino acid

<400> SEQUENCE: 734

His Xaa Ala Arg Lys Xaa Xaa Xaa Xaa Gly
1               5                   10

<210> SEQ ID NO 735
<211> LENGTH: 11
<212> TYPE: PRT
<213> ORGANISM: Unknown
<220> FEATURE:
<223> OTHER INFORMATION: Description of Unknown:
      Marker peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 735

Lys Xaa Xaa Glu Xaa Xaa Xaa Lys Gly Xaa Gly
1               5                   10

<210> SEQ ID NO 736
<211> LENGTH: 7
<212> TYPE: PRT
<213> ORGANISM: Unknown
<220> FEATURE:
<223> OTHER INFORMATION: Description of Unknown:
      Marker peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 736

Gly Xaa Gly Pro Ser Xaa Asp
1               5

<210> SEQ ID NO 737
<211> LENGTH: 5
<212> TYPE: PRT
<213> ORGANISM: Unknown
<220> FEATURE:
<223> OTHER INFORMATION: Description of Unknown:
      Marker peptide
<220> FEATURE:
<221> NAME/KEY: MOD_RES
<222> LOCATION: (4)..(4)
<223> OTHER INFORMATION: Any amino acid

<400> SEQUENCE: 737

Arg Gly Arg Xaa Gly
1               5
```

```
<210> SEQ ID NO 738
<211> LENGTH: 7
<212> TYPE: PRT
<213> ORGANISM: Unknown
<220> FEATURE:
<223> OTHER INFORMATION: Description of Unknown:
      Marker peptide
<220> FEATURE:
<221> NAME/KEY: MOD_RES
<222> LOCATION: (4)..(6)
<223> OTHER INFORMATION: Any amino acid

<400> SEQUENCE: 738

Ala Ala Lys Xaa Xaa Xaa Ser
1               5

<210> SEQ ID NO 739
<211> LENGTH: 9
<212> TYPE: PRT
<213> ORGANISM: Unknown
<220> FEATURE:
<223> OTHER INFORMATION: Description of Unknown:
      Marker peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 739

Lys Xaa Xaa Glu Xaa Xaa Arg Xaa Gly
1               5

<210> SEQ ID NO 740
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 740

Gln Arg Lys Lys
1

<210> SEQ ID NO 741
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 741

Arg Arg Gly Ser
1

<210> SEQ ID NO 742
<211> LENGTH: 4
<212> TYPE: PRT
<213> ORGANISM: Unknown
<220> FEATURE:
<223> OTHER INFORMATION: Description of Unknown:
      Motif sequence
```

<400> SEQUENCE: 742

His Lys Arg Arg
1

<210> SEQ ID NO 743
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 743

His Arg Leu Asn
1

<210> SEQ ID NO 744
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 744

Lys Val His Arg
1

<210> SEQ ID NO 745
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 745

Lys Lys Trp Arg
1

<210> SEQ ID NO 746
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 746

Arg His Arg Gly
1

<210> SEQ ID NO 747
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 747

Arg Arg His Tyr
1

<210> SEQ ID NO 748
<211> LENGTH: 5

```
<212> TYPE: PRT
<213> ORGANISM: Unknown
<220> FEATURE:
<223> OTHER INFORMATION: Description of Unknown:
      Motif sequence

<400> SEQUENCE: 748

Lys Arg Trp His Phe
1               5

<210> SEQ ID NO 749
<211> LENGTH: 5
<212> TYPE: PRT
<213> ORGANISM: Unknown
<220> FEATURE:
<223> OTHER INFORMATION: Description of Unknown:
      Motif sequence

<400> SEQUENCE: 749

Leu Trp Lys His Gly
1               5

<210> SEQ ID NO 750
<211> LENGTH: 5
<212> TYPE: PRT
<213> ORGANISM: Unknown
<220> FEATURE:
<223> OTHER INFORMATION: Description of Unknown:
      Motif sequence

<400> SEQUENCE: 750

Trp Lys His Arg Gly
1               5

<210> SEQ ID NO 751
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 751

Ala Lys Ala Lys
1

<210> SEQ ID NO 752
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 752

Arg His Lys Leu
1

<210> SEQ ID NO 753
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 753

Asn Lys Tyr Lys
```

```
<210> SEQ ID NO 754
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 754

Lys Phe Ser Gly
1

<210> SEQ ID NO 755
<211> LENGTH: 5
<212> TYPE: PRT
<213> ORGANISM: Unknown
<220> FEATURE:
<223> OTHER INFORMATION: Description of Unknown:
      Motif sequence

<400> SEQUENCE: 755

Arg Trp His Phe Asp
1               5

<210> SEQ ID NO 756
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 756

Phe His His Lys
1

<210> SEQ ID NO 757
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 757

Lys Lys Pro His
1

<210> SEQ ID NO 758
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 758

Leu His His Asn
1

<210> SEQ ID NO 759
<211> LENGTH: 4
<212> TYPE: PRT
<213> ORGANISM: Unknown
<220> FEATURE:
<223> OTHER INFORMATION: Description of Unknown:
```

```
                    Motif sequence

<400> SEQUENCE: 759

Lys Arg Arg His
1

<210> SEQ ID NO 760
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 760

Asn Lys Lys His
1

<210> SEQ ID NO 761
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 761

Ser Pro Asn Leu
1

<210> SEQ ID NO 762
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 762

His Arg Glu Gly
1

<210> SEQ ID NO 763
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 763

Arg His Lys Arg
1

<210> SEQ ID NO 764
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 764

Arg Trp Lys Gly
1

<210> SEQ ID NO 765
```

```
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 765

His Phe Arg Asn
1

<210> SEQ ID NO 766
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 766

Lys Ala Ala Tyr
1

<210> SEQ ID NO 767
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 767

Lys Gly Gly Gln
1

<210> SEQ ID NO 768
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 768

Lys His Tyr Pro
1

<210> SEQ ID NO 769
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 769

Lys Pro His Pro
1

<210> SEQ ID NO 770
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 770
```

```
His Lys Arg Gly
1

<210> SEQ ID NO 771
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 771

Arg Trp His Phe
1

<210> SEQ ID NO 772
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 772

Arg His Lys Tyr Tyr Gly
1               5

<210> SEQ ID NO 773
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 773

Arg Arg Leu Arg Ser Trp Lys Gly
1               5

<210> SEQ ID NO 774
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 774

Arg Gly Tyr His Leu Tyr His Glu Lys Gly
1               5                   10

<210> SEQ ID NO 775
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 775

Lys His Arg Trp Ser Gly Arg Leu Gly
1               5

<210> SEQ ID NO 776
<211> LENGTH: 8
<212> TYPE: PRT
<213> ORGANISM: Unknown
<220> FEATURE:
```

```
<223> OTHER INFORMATION: Description of Unknown:
      Marker peptide

<400> SEQUENCE: 776

His His Asp Trp Lys His Arg Gly
1               5

<210> SEQ ID NO 777
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 777

Arg Lys Ala Phe Gly Arg Gly
1               5

<210> SEQ ID NO 778
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 778

Arg Arg Leu His Arg His Ser Gly
1               5

<210> SEQ ID NO 779
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 779

His Ser Gln Lys Ala Arg Ala Val Gly
1               5

<210> SEQ ID NO 780
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 780

Ala His Arg Pro Arg Lys Arg Gly
1               5

<210> SEQ ID NO 781
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 781

Ser Lys Arg His Lys Tyr Val Gly
1               5
```

<210> SEQ ID NO 782
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 782

Asn His Arg Asn Asp Trp Gln Arg His Leu
1               5                   10

<210> SEQ ID NO 783
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 783

Arg Lys Lys His Tyr Lys Arg Gly
1               5

<210> SEQ ID NO 784
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 784

Arg Ser Arg His Arg Gln Arg Leu Ser
1               5

<210> SEQ ID NO 785
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 785

Arg Leu His Gly Arg Gly Arg Asp Gly
1               5

<210> SEQ ID NO 786
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 786

His Phe Arg Gln Arg Gln Arg Asp
1               5

<210> SEQ ID NO 787
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 787

His Leu Asn Arg Trp Arg Tyr Lys Asp
1               5

<210> SEQ ID NO 788
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 788

Tyr His Glu Gly Arg Asn Ser Arg Gly
1               5

<210> SEQ ID NO 789
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 789

Arg Arg Pro Arg Ala Arg Gly
1               5

<210> SEQ ID NO 790
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 790

Lys His Pro Tyr Tyr Ala Tyr Lys Gly
1               5

<210> SEQ ID NO 791
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 791

His Arg Trp His Arg Glu Gly
1               5

<210> SEQ ID NO 792
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 792

Gln His Arg His Lys Lys Asp Gly
1               5

<210> SEQ ID NO 793
<211> LENGTH: 10
<212> TYPE: PRT
<213> ORGANISM: Unknown

```
<220> FEATURE:
<223> OTHER INFORMATION: Description of Unknown:
      Marker peptide

<400> SEQUENCE: 793

Gln His Val Asn Ala Lys Ala Lys Val Glu
1               5                   10

<210> SEQ ID NO 794
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 794

Arg His Phe Arg Tyr Gln Leu Lys Asp Gly
1               5                   10

<210> SEQ ID NO 795
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 795

Lys Arg Arg Gly His Ser Asn Leu Phe Ser
1               5                   10

<210> SEQ ID NO 796
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 796

Trp Tyr Ala Arg Lys Asp Arg Gly
1               5

<210> SEQ ID NO 797
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 797

Arg His Phe Arg Asn Lys Glu Phe Gly
1               5

<210> SEQ ID NO 798
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 798

Lys Ser Arg Phe Ala Asn Arg Tyr Gly
1               5
```

```
<210> SEQ ID NO 799
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 799

Arg His Gly Lys Ala Ala Lys Asp
1               5

<210> SEQ ID NO 800
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 800

His Ser Ala Arg Lys Arg Lys Val Gly
1               5

<210> SEQ ID NO 801
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 801

Val Arg Lys Ser Gln Lys Arg Gly
1               5

<210> SEQ ID NO 802
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 802

His Asp Lys Lys His Phe Pro Arg Asp Gly
1               5                   10

<210> SEQ ID NO 803
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 803

Arg Gly Asp Lys Val Leu Ser Phe Asp
1               5

<210> SEQ ID NO 804
<211> LENGTH: 11
<212> TYPE: PRT
<213> ORGANISM: Unknown
<220> FEATURE:
<223> OTHER INFORMATION: Description of Unknown:
      Marker peptide
```

```
<400> SEQUENCE: 804

Gln His Leu Glu Lys Phe Pro Arg Trp Lys Gly
1               5                   10

<210> SEQ ID NO 805
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 805

Tyr His Arg Arg Gly Asn Arg Leu Glu
1               5

<210> SEQ ID NO 806
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 806

Arg Arg Arg Phe Phe Gly
1               5

<210> SEQ ID NO 807
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 807

Arg Arg Lys Glu Trp Arg Phe Ser Asp
1               5

<210> SEQ ID NO 808
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 808

Phe Tyr Glu Arg His Lys Leu Gly
1               5

<210> SEQ ID NO 809
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 809

His Lys Gly Tyr Gly Gly
1               5

<210> SEQ ID NO 810
<211> LENGTH: 10
<212> TYPE: PRT
```

<213> ORGANISM: Unknown
<220> FEATURE:
<223> OTHER INFORMATION: Description of Unknown:
      Marker peptide

<400> SEQUENCE: 810

Ala Lys Gln Ala His Val Ala Lys Val Glu
1               5                   10

<210> SEQ ID NO 811
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 811

Arg Tyr Arg Tyr His Tyr Lys Phe Glu
1               5

<210> SEQ ID NO 812
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 812

Gly Lys Lys Pro His Leu Ser Gly
1               5

<210> SEQ ID NO 813
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 813

Ser Pro His Lys Arg Leu Ala Lys Val Ser
1               5                   10

<210> SEQ ID NO 814
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 814

Pro Arg Gly Arg His Ser Tyr Arg Trp Arg Asp
1               5                   10

<210> SEQ ID NO 815
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 815

Arg Ser Lys Ala Ala Asn Val Ser Asp
1               5

```
<210> SEQ ID NO 816
<211> LENGTH: 8
<212> TYPE: PRT
<213> ORGANISM: Unknown
<220> FEATURE:
<223> OTHER INFORMATION: Description of Unknown:
     Marker peptide

<400> SEQUENCE: 816

Lys Tyr Arg Arg Trp His Phe Asp
1               5

<210> SEQ ID NO 817
<211> LENGTH: 8
<212> TYPE: PRT
<213> ORGANISM: Unknown
<220> FEATURE:
<223> OTHER INFORMATION: Description of Unknown:
     Marker peptide

<400> SEQUENCE: 817

His Arg Lys Leu Pro Leu Phe Asp
1               5

<210> SEQ ID NO 818
<211> LENGTH: 9
<212> TYPE: PRT
<213> ORGANISM: Unknown
<220> FEATURE:
<223> OTHER INFORMATION: Description of Unknown:
     Marker peptide

<400> SEQUENCE: 818

Arg Arg His Tyr Pro Ala Phe Glu Gly
1               5

<210> SEQ ID NO 819
<211> LENGTH: 7
<212> TYPE: PRT
<213> ORGANISM: Unknown
<220> FEATURE:
<223> OTHER INFORMATION: Description of Unknown:
     Marker peptide

<400> SEQUENCE: 819

Val Lys Lys Lys Arg Ser Gly
1               5

<210> SEQ ID NO 820
<211> LENGTH: 7
<212> TYPE: PRT
<213> ORGANISM: Unknown
<220> FEATURE:
<223> OTHER INFORMATION: Description of Unknown:
     Marker peptide

<400> SEQUENCE: 820

Lys Phe Arg Trp Trp Asp Gly
1               5

<210> SEQ ID NO 821
<211> LENGTH: 8
<212> TYPE: PRT
<213> ORGANISM: Unknown
<220> FEATURE:
<223> OTHER INFORMATION: Description of Unknown:
     Marker peptide
```

```
<400> SEQUENCE: 821

Ser Lys Tyr Leu Trp Lys His Gly
1               5

<210> SEQ ID NO 822
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 822

Pro Gln Asn Asn
1

<210> SEQ ID NO 823
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 823

Pro Gly Gly Asn
1

<210> SEQ ID NO 824
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 824

Pro Ser Glu Lys
1

<210> SEQ ID NO 825
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 825

Pro Lys Asp Asp
1

<210> SEQ ID NO 826
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 826

Pro Ser Lys Gly
1

<210> SEQ ID NO 827
<211> LENGTH: 4
```

```
<212> TYPE: PRT
<213> ORGANISM: Unknown
<220> FEATURE:
<223> OTHER INFORMATION: Description of Unknown:
      Motif sequence

<400> SEQUENCE: 827

Gln Lys Gly Ala
1

<210> SEQ ID NO 828
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 828

Pro Glu Leu Leu
1

<210> SEQ ID NO 829
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 829

Pro His His Asn
1

<210> SEQ ID NO 830
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 830

Pro Leu Lys Pro
1

<210> SEQ ID NO 831
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 831

Pro Val His Gln
1

<210> SEQ ID NO 832
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 832

Pro Val His Arg
```

```
<210> SEQ ID NO 833
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 833

Lys Asn Ser Leu
1

<210> SEQ ID NO 834
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 834

Pro Asp Val Pro
1

<210> SEQ ID NO 835
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 835

Ser Pro Pro Gly
1

<210> SEQ ID NO 836
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 836

Tyr Pro Gly Arg
1

<210> SEQ ID NO 837
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 837

Tyr Pro Gly Ser
1

<210> SEQ ID NO 838
<211> LENGTH: 4
<212> TYPE: PRT
<213> ORGANISM: Unknown
<220> FEATURE:
<223> OTHER INFORMATION: Description of Unknown:
```

```
                Motif sequence

<400> SEQUENCE: 838

Tyr Pro Asn Asn
1

<210> SEQ ID NO 839
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 839

Gly Val Lys Ala
1

<210> SEQ ID NO 840
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 840

Pro Glu Gly Glu
1

<210> SEQ ID NO 841
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 841

Pro Pro Gly Gly
1

<210> SEQ ID NO 842
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 842

Gln Gln Tyr Gly
1

<210> SEQ ID NO 843
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 843

Val Lys Ala Gly
1

<210> SEQ ID NO 844
```

<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 844

Val Pro Val Gln
1

<210> SEQ ID NO 845
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 845

Tyr Pro Pro Ser
1

<210> SEQ ID NO 846
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 846

Tyr Pro Pro Val
1

<210> SEQ ID NO 847
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 847

Pro Glu Gly Glu
1

<210> SEQ ID NO 848
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 848

Pro Leu Ala Glu
1

<210> SEQ ID NO 849
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 849

Pro Pro Leu Asn
1

<210> SEQ ID NO 850
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 850

Pro Ser Leu Ala
1

<210> SEQ ID NO 851
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 851

Pro Ser Leu Lys
1

<210> SEQ ID NO 852
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 852

Ala Ser Phe Gln
1

<210> SEQ ID NO 853
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 853

Ala Asp Ala Asp
1

<210> SEQ ID NO 854
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 854

Pro Ser Arg Glu
1

<210> SEQ ID NO 855
<211> LENGTH: 4
<212> TYPE: PRT
<213> ORGANISM: Unknown
<220> FEATURE:

<223> OTHER INFORMATION: Description of Unknown:
      Motif sequence

<400> SEQUENCE: 855

Tyr Val His His
1

<210> SEQ ID NO 856
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 856

Pro Pro Gly Gly
1

<210> SEQ ID NO 857
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 857

Pro Val His Trp
1

<210> SEQ ID NO 858
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 858

Lys Pro Pro Gly
1

<210> SEQ ID NO 859
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 859

Pro Arg Trp Tyr
1

<210> SEQ ID NO 860
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 860

Pro Phe Ala Pro
1

```
<210> SEQ ID NO 861
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 861

Gln Val Ala Pro
1

<210> SEQ ID NO 862
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 862

His Trp Pro Gln
1

<210> SEQ ID NO 863
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 863

Pro Ala Gly Gly
1

<210> SEQ ID NO 864
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 864

His Gln Gly Tyr
1

<210> SEQ ID NO 865
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 865

Pro Asp Glu Ser
1

<210> SEQ ID NO 866
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 866
```

Pro Leu Ala Glu
1

<210> SEQ ID NO 867
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 867

Pro Asp Asp Phe
1

<210> SEQ ID NO 868
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 868

Gln Arg Arg Ala
1

<210> SEQ ID NO 869
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 869

Arg Gln Ala Pro
1

<210> SEQ ID NO 870
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 870

Asp Glu Ser Ala
1

<210> SEQ ID NO 871
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 871

Lys Asn Gly Gly
1

<210> SEQ ID NO 872
<211> LENGTH: 4
<212> TYPE: PRT
<213> ORGANISM: Unknown

```
<220> FEATURE:
<223> OTHER INFORMATION: Description of Unknown:
      Motif sequence

<400> SEQUENCE: 872

Arg Gln Pro Lys
1

<210> SEQ ID NO 873
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 873

Lys Trp Pro Asn
1

<210> SEQ ID NO 874
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 874

Pro Glu Gln Glu
1

<210> SEQ ID NO 875
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 875

Pro Gln Ala Asp
1

<210> SEQ ID NO 876
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 876

Gln Gln Asn Lys
1

<210> SEQ ID NO 877
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 877

Gln Arg Gly Leu
1
```

```
<210> SEQ ID NO 878
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 878

Arg Ala Arg Ala
1

<210> SEQ ID NO 879
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 879

Gly Lys Ala Gly
1

<210> SEQ ID NO 880
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 880

Pro Leu Asp Glu
1

<210> SEQ ID NO 881
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 881

Pro Pro Gly Asp
1

<210> SEQ ID NO 882
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 882

Pro Asp Asp Phe
1

<210> SEQ ID NO 883
<211> LENGTH: 4
<212> TYPE: PRT
<213> ORGANISM: Unknown
<220> FEATURE:
<223> OTHER INFORMATION: Description of Unknown:
      Motif sequence
```

```
<400> SEQUENCE: 883

Pro Asp Glu Val
1

<210> SEQ ID NO 884
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 884

Pro Gly Gly Glu
1

<210> SEQ ID NO 885
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 885

Pro Lys Glu Glu
1

<210> SEQ ID NO 886
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 886

Pro His Arg Asp
1

<210> SEQ ID NO 887
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 887

Pro Leu Ala Glu
1

<210> SEQ ID NO 888
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 888

Pro Pro Asp Glu
1

<210> SEQ ID NO 889
<211> LENGTH: 4
<212> TYPE: PRT
```

-continued

```
<213> ORGANISM: Unknown
<220> FEATURE:
<223> OTHER INFORMATION: Description of Unknown:
      Motif sequence

<400> SEQUENCE: 889

Pro Pro Asp Asn
1

<210> SEQ ID NO 890
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 890

Pro Pro Glu Glu
1

<210> SEQ ID NO 891
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 891

Pro His Asp Gln
1

<210> SEQ ID NO 892
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 892

Pro Pro Asp Leu
1

<210> SEQ ID NO 893
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 893

Pro Pro Asp Arg
1

<210> SEQ ID NO 894
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 894

Pro Pro Arg Asp
1
```

```
<210> SEQ ID NO 895
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 895

Pro Arg Asp Val
1

<210> SEQ ID NO 896
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 896

Pro Arg Gln Asp
1

<210> SEQ ID NO 897
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 897

Ala Leu His Trp
1

<210> SEQ ID NO 898
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 898

Trp Ser His Trp
1

<210> SEQ ID NO 899
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 899

Tyr Val His His
1

<210> SEQ ID NO 900
<211> LENGTH: 4
<212> TYPE: PRT
<213> ORGANISM: Unknown
<220> FEATURE:
<223> OTHER INFORMATION: Description of Unknown:
      Motif sequence
```

<400> SEQUENCE: 900

His Gln Phe Gln
1

<210> SEQ ID NO 901
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 901

Gln Tyr His Tyr
1

<210> SEQ ID NO 902
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 902

Phe His Arg His
1

<210> SEQ ID NO 903
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 903

His Leu Trp Gly
1

<210> SEQ ID NO 904
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 904

His Arg Ser Trp
1

<210> SEQ ID NO 905
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 905

His Trp Leu Gly
1

<210> SEQ ID NO 906
<211> LENGTH: 4

```
<212> TYPE: PRT
<213> ORGANISM: Unknown
<220> FEATURE:
<223> OTHER INFORMATION: Description of Unknown:
      Motif sequence

<400> SEQUENCE: 906

His Trp Tyr Lys
1

<210> SEQ ID NO 907
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 907

His Pro Trp Gly
1

<210> SEQ ID NO 908
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 908

Pro Lys Phe Trp
1

<210> SEQ ID NO 909
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 909

His Pro Trp Arg
1

<210> SEQ ID NO 910
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 910

Lys His Trp Arg
1

<210> SEQ ID NO 911
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 911

Arg His Pro Trp
```

<210> SEQ ID NO 912
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 912

Asn Arg His Phe
1

<210> SEQ ID NO 913
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 913

Trp Gln His Arg
1

<210> SEQ ID NO 914
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 914

Trp Gly Trp Arg
1

<210> SEQ ID NO 915
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 915

Asn His Leu Trp
1

<210> SEQ ID NO 916
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 916

Trp Lys Trp His
1

<210> SEQ ID NO 917
<211> LENGTH: 4
<212> TYPE: PRT
<213> ORGANISM: Unknown
<220> FEATURE:
<223> OTHER INFORMATION: Description of Unknown:

```
         Motif sequence

<400> SEQUENCE: 917

His His Trp Trp
1

<210> SEQ ID NO 918
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 918

His Trp Gly Val
1

<210> SEQ ID NO 919
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 919

Trp Pro His Pro
1

<210> SEQ ID NO 920
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 920

Trp Pro His Arg
1

<210> SEQ ID NO 921
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 921

Trp Trp Trp Gly
1

<210> SEQ ID NO 922
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 922

Tyr His Trp Gly
1

<210> SEQ ID NO 923
```

-continued

```
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 923

His Leu Trp Gly
1

<210> SEQ ID NO 924
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 924

His Trp His Arg
1

<210> SEQ ID NO 925
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 925

Trp Trp Gly Ala
1

<210> SEQ ID NO 926
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 926

His His Trp Trp
1

<210> SEQ ID NO 927
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 927

His His Pro Phe
1

<210> SEQ ID NO 928
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 928
```

His Leu Trp Gly
1

<210> SEQ ID NO 929
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 929

His Trp Gln Trp
1

<210> SEQ ID NO 930
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 930

His Trp Val Pro
1

<210> SEQ ID NO 931
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 931

His Asn Leu Pro
1

<210> SEQ ID NO 932
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 932

His His Trp Trp
1

<210> SEQ ID NO 933
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 933

His His Pro Phe
1

<210> SEQ ID NO 934
<211> LENGTH: 4
<212> TYPE: PRT
<213> ORGANISM: Unknown
<220> FEATURE:

```
<223> OTHER INFORMATION: Description of Unknown:
      Motif sequence

<400> SEQUENCE: 934

His Leu Trp Gly
1

<210> SEQ ID NO 935
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 935

His Trp Gln Trp
1

<210> SEQ ID NO 936
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 936

Trp Tyr Pro Ala
1

<210> SEQ ID NO 937
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 937

Tyr His Trp Gly
1

<210> SEQ ID NO 938
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 938

Asn Trp Leu His
1

<210> SEQ ID NO 939
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 939

His Ser Trp Pro
1
```

```
<210> SEQ ID NO 940
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 940

Trp Phe Arg Gly
1

<210> SEQ ID NO 941
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 941

Val Lys Trp Asn
1

<210> SEQ ID NO 942
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 942

Ser Trp Pro Trp
1

<210> SEQ ID NO 943
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 943

Arg Trp Trp Val
1

<210> SEQ ID NO 944
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 944

His His Lys Asn
1

<210> SEQ ID NO 945
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 945
```

His Trp Pro His
1

<210> SEQ ID NO 946
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 946

His Trp Tyr His
1

<210> SEQ ID NO 947
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 947

Lys Pro Trp Tyr
1

<210> SEQ ID NO 948
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 948

Gln Lys Trp Pro
1

<210> SEQ ID NO 949
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 949

His Leu Trp Gly
1

<210> SEQ ID NO 950
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 950

Pro Tyr His Arg
1

<210> SEQ ID NO 951
<211> LENGTH: 4
<212> TYPE: PRT
<213> ORGANISM: Unknown

```
<220> FEATURE:
<223> OTHER INFORMATION: Description of Unknown:
      Motif sequence

<400> SEQUENCE: 951

His Pro Leu Gly
1

<210> SEQ ID NO 952
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 952

Trp Val Pro His
1

<210> SEQ ID NO 953
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 953

Ala Leu His Trp
1

<210> SEQ ID NO 954
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 954

Trp Ser His Trp
1

<210> SEQ ID NO 955
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 955

Tyr Val His His
1

<210> SEQ ID NO 956
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 956

His Gln Phe Gln
1
```

```
<210> SEQ ID NO 957
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 957

Gln Tyr His Tyr
1

<210> SEQ ID NO 958
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 958

Phe His Arg His
1

<210> SEQ ID NO 959
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 959

Pro Gly Asp Ser
1

<210> SEQ ID NO 960
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 960

Pro Leu Ala Glu
1

<210> SEQ ID NO 961
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 961

Pro Gln Asn Asn
1

<210> SEQ ID NO 962
<211> LENGTH: 4
<212> TYPE: PRT
<213> ORGANISM: Unknown
<220> FEATURE:
<223> OTHER INFORMATION: Description of Unknown:
      Motif sequence
```

```
<400> SEQUENCE: 962

Pro Ser Arg Gln
1

<210> SEQ ID NO 963
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 963

Pro Gly Gly Asn
1

<210> SEQ ID NO 964
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 964

Pro Gly Gln Glu
1

<210> SEQ ID NO 965
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 965

Pro Ser Glu Lys
1

<210> SEQ ID NO 966
<211> LENGTH: 4
<212> TYPE: PRT
<213> ORGANISM: Unknown
<220> FEATURE:
<223> OTHER INFORMATION: Description of Unknown:
      Motif sequence

<400> SEQUENCE: 966

Asn Glu Pro Asp
1

<210> SEQ ID NO 967
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 967

Arg Ala Ser Pro Pro Gly
1               5

<210> SEQ ID NO 968
<211> LENGTH: 8
<212> TYPE: PRT
```

```
<213> ORGANISM: Unknown
<220> FEATURE:
<223> OTHER INFORMATION: Description of Unknown:
      Marker peptide

<400> SEQUENCE: 968

Gly Pro Gln Gln Asn Lys Val Gly
1               5

<210> SEQ ID NO 969
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 969

Pro Leu Gly Glu Asp Glu Leu Ser Gly
1               5

<210> SEQ ID NO 970
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 970

Leu Pro Val Asn Arg Glu Leu Gly
1               5

<210> SEQ ID NO 971
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 971

Lys Val Pro Val Gln Lys Gly Ala Gln Val Leu
1               5                   10

<210> SEQ ID NO 972
<211> LENGTH: 5
<212> TYPE: PRT
<213> ORGANISM: Unknown
<220> FEATURE:
<223> OTHER INFORMATION: Description of Unknown:
      Marker peptide

<400> SEQUENCE: 972

Gly Val Lys Gly Gly
1               5

<210> SEQ ID NO 973
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 973

Pro Asn Leu His Asn Asn Arg Asp
1               5
```

```
<210> SEQ ID NO 974
<211> LENGTH: 5
<212> TYPE: PRT
<213> ORGANISM: Unknown
<220> FEATURE:
<223> OTHER INFORMATION: Description of Unknown:
      Marker peptide

<400> SEQUENCE: 974

Gly Leu Leu Lys Gly
1               5

<210> SEQ ID NO 975
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 975

Lys Gln Pro Ser Ser Gly
1               5

<210> SEQ ID NO 976
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 976

Val Gln Gly Arg Gly Val Gly
1               5

<210> SEQ ID NO 977
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 977

Gln Gln Lys Gln Leu Gly Lys Leu Ser
1               5

<210> SEQ ID NO 978
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 978

Pro Leu Ala Glu Glu Asp Gln Leu
1               5

<210> SEQ ID NO 979
<211> LENGTH: 9
<212> TYPE: PRT
<213> ORGANISM: Unknown
<220> FEATURE:
<223> OTHER INFORMATION: Description of Unknown:
      Marker peptide
```

-continued

<400> SEQUENCE: 979

Pro Glu Gln Glu Glu Gly Lys Phe Asp
1               5

<210> SEQ ID NO 980
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 980

Gly Leu Ala Ala Lys Ser Gly
1               5

<210> SEQ ID NO 981
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 981

Gly Arg Lys Ala Asp Gly
1               5

<210> SEQ ID NO 982
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 982

Pro Arg Ala Asp Asp Glu Gly
1               5

<210> SEQ ID NO 983
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 983

Pro Pro Gly Lys His Gln Glu Gly
1               5

<210> SEQ ID NO 984
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 984

Arg Leu Gln Ala Gly Gly
1               5

<210> SEQ ID NO 985
<211> LENGTH: 9

```
<212> TYPE: PRT
<213> ORGANISM: Unknown
<220> FEATURE:
<223> OTHER INFORMATION: Description of Unknown:
      Marker peptide

<400> SEQUENCE: 985

Pro Ser Leu Lys Glu Pro Gln Phe Glu
1               5

<210> SEQ ID NO 986
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 986

Pro Asp Leu Gly Asp Asn Val Asp Gly
1               5

<210> SEQ ID NO 987
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 987

Gln Leu Gln Ala Val Lys Ser Gly
1               5

<210> SEQ ID NO 988
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 988

Gln Lys Gly Gly Asn Lys Asn Val Gly
1               5

<210> SEQ ID NO 989
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 989

Gly Gly Pro Gln Asn Lys Gly
1               5

<210> SEQ ID NO 990
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 990

Pro Val Lys Glu Glu Ala Trp Glu Gly
```

<210> SEQ ID NO 991
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 991

Glu Pro Glu Tyr Lys Glu Arg Ser Gly
1               5

<210> SEQ ID NO 992
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 992

Pro Glu Gly Asp Asp Gly Asn Gln Lys His Phe
1               5                   10

<210> SEQ ID NO 993
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 993

Ala Asp Arg Asp Asp Pro Lys Arg Glu
1               5

<210> SEQ ID NO 994
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 994

Pro Pro Glu Arg Glu Gly His Gly
1               5

<210> SEQ ID NO 995
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 995

Pro Phe Ala Gly Asp His Ser Gly
1               5

<210> SEQ ID NO 996
<211> LENGTH: 10
<212> TYPE: PRT
<213> ORGANISM: Unknown
<220> FEATURE:
<223> OTHER INFORMATION: Description of Unknown:

Marker peptide

<400> SEQUENCE: 996

Gln Gly Ala Pro Lys Val Gly Val Ser Gly
1               5                   10

<210> SEQ ID NO 997
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 997

Pro Leu Gly Ser Asp Ser Glu Pro Arg Glu
1               5                   10

<210> SEQ ID NO 998
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 998

Pro Asp Gly Asp Gln Lys Pro Trp Phe Gly
1               5                   10

<210> SEQ ID NO 999
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 999

Pro Gly Gln Ala Glu Tyr Gln Glu
1               5

<210> SEQ ID NO 1000
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1000

Pro Gly Val His Asp Asp Gly
1               5

<210> SEQ ID NO 1001
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1001

Pro Leu Gln Lys Asn Glu Phe Glu Gly
1               5

<210> SEQ ID NO 1002

```
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1002

Lys Ala Gly Pro Gly Ala Lys Phe Glu
1               5

<210> SEQ ID NO 1003
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1003

Gly Lys Asn Gln Gly Gly
1               5

<210> SEQ ID NO 1004
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1004

Pro Gly Leu Asn Glu Pro Asp Gly
1               5

<210> SEQ ID NO 1005
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1005

Pro Ser Leu Ala Asp Glu Gly
1               5

<210> SEQ ID NO 1006
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1006

Pro Asp Arg Asn Gln Gln Phe Glu
1               5

<210> SEQ ID NO 1007
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1007
```

```
Pro Asp Leu Asp Ala Gly Ala Glu Gly
1               5

<210> SEQ ID NO 1008
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1008

Glu Pro Gly Ser Arg Phe Glu Gly
1               5

<210> SEQ ID NO 1009
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1009

Gln Gly Arg Gly Trp Lys Lys Val Glu
1               5

<210> SEQ ID NO 1010
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1010

Pro Ala Ser Ser Glu Ala Ser Leu Ser Asp
1               5                   10

<210> SEQ ID NO 1011
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1011

Glu Pro Glu Phe Gly Pro Ser Gly
1               5

<210> SEQ ID NO 1012
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1012

Leu Pro Ser Glu Arg Gly Ser Glu
1               5

<210> SEQ ID NO 1013
<211> LENGTH: 10
<212> TYPE: PRT
<213> ORGANISM: Unknown
<220> FEATURE:
```

```
<223> OTHER INFORMATION: Description of Unknown:
      Marker peptide

<400> SEQUENCE: 1013

Pro Gly Phe Glu Gly Tyr Asn Arg Gln Gly
1               5                   10

<210> SEQ ID NO 1014
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1014

Arg Pro Lys Gly Glu Gln Ser Gly
1               5

<210> SEQ ID NO 1015
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1015

Pro Tyr Ala Val His Arg Asp Ala
1               5

<210> SEQ ID NO 1016
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1016

Pro Leu Lys Phe Asn Gln Glu Asn Asp Gly
1               5                   10

<210> SEQ ID NO 1017
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1017

Pro Val His Gln Tyr Gln Phe Gly
1               5

<210> SEQ ID NO 1018
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1018

Pro Gly Asn Trp Tyr Trp Ser Gly
1               5
```

-continued

```
<210> SEQ ID NO 1019
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1019

Pro Gly Ser Phe Ser Glu His Val Leu
1               5

<210> SEQ ID NO 1020
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1020

Ala Pro Arg Gly Val Lys Ser Asp
1               5

<210> SEQ ID NO 1021
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1021

Pro Tyr Lys Gly Glu Ser Ala His Leu Phe
1               5                   10

<210> SEQ ID NO 1022
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1022

Gly Pro Gln Gln Asn Lys Val Gly
1               5

<210> SEQ ID NO 1023
<211> LENGTH: 5
<212> TYPE: PRT
<213> ORGANISM: Unknown
<220> FEATURE:
<223> OTHER INFORMATION: Description of Unknown:
      Marker peptide

<400> SEQUENCE: 1023

Val Lys Pro Gly Gly
1               5

<210> SEQ ID NO 1024
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1024
```

```
Pro Phe Gly His Gly Tyr Asn Asn Phe Ser
1               5                   10
```

<210> SEQ ID NO 1025
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1025

```
Arg Pro Leu Ala Gly Pro Gly
1               5
```

<210> SEQ ID NO 1026
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1026

```
Pro Tyr His Pro Gln Phe Leu Ser
1               5
```

<210> SEQ ID NO 1027
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1027

```
Pro Leu Ser Arg Ala Phe Asp His Gly
1               5
```

<210> SEQ ID NO 1028
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1028

```
Tyr Pro Glu Gln Pro Ser Glu Asp
1               5
```

<210> SEQ ID NO 1029
<211> LENGTH: 5
<212> TYPE: PRT
<213> ORGANISM: Unknown
<220> FEATURE:
<223> OTHER INFORMATION: Description of Unknown:
      Marker peptide

<400> SEQUENCE: 1029

```
Arg Pro Pro Gly Gly
1               5
```

<210> SEQ ID NO 1030
<211> LENGTH: 10
<212> TYPE: PRT
<213> ORGANISM: Unknown

```
<220> FEATURE:
<223> OTHER INFORMATION: Description of Unknown:
      Marker peptide

<400> SEQUENCE: 1030

Pro Lys Asn Ala Glu Tyr Trp His Phe Ser
1               5                   10

<210> SEQ ID NO 1031
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1031

Lys Gln Pro Ser Ser Gly
1               5

<210> SEQ ID NO 1032
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1032

Gly Ala Ala Val Lys Gly
1               5

<210> SEQ ID NO 1033
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1033

Gly Pro Asn Leu Gln Lys Gln Leu Gly
1               5

<210> SEQ ID NO 1034
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1034

Gly Lys Pro Ala Gln Gln Leu Gly
1               5

<210> SEQ ID NO 1035
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 1035

Pro Tyr Gln Gly Lys Phe Glu Leu Asn His Leu Ser
1               5                   10
```

```
<210> SEQ ID NO 1036
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1036

Asn Pro Ser Gln Arg Tyr Ala Asp Gly
1               5

<210> SEQ ID NO 1037
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1037

Ala Pro Leu Lys Pro Gln Ser Gly
1               5

<210> SEQ ID NO 1038
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1038

Asp Pro Arg Lys Ser Val Ser Gly
1               5

<210> SEQ ID NO 1039
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1039

Pro Lys Gly Val Gln His Tyr His Gly
1               5

<210> SEQ ID NO 1040
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1040

Arg Gln Gly Pro Ser Asp Lys Gly
1               5

<210> SEQ ID NO 1041
<211> LENGTH: 7
<212> TYPE: PRT
<213> ORGANISM: Unknown
<220> FEATURE:
<223> OTHER INFORMATION: Description of Unknown:
      Marker peptide
```

```
<400> SEQUENCE: 1041

Arg Gly Glu Lys Leu Pro Gly
1               5

<210> SEQ ID NO 1042
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1042

Gly Ser Val Gly Asn Lys Leu Ser Gly
1               5

<210> SEQ ID NO 1043
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1043

Arg Ala Ser Pro Pro Gly
1               5

<210> SEQ ID NO 1044
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1044

Gly Arg Gln Pro Leu Gly
1               5

<210> SEQ ID NO 1045
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1045

Gln Pro Phe His Gly Gly
1               5

<210> SEQ ID NO 1046
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1046

Pro Ser Lys Val His Leu Glu Arg His Ser
1               5                   10

<210> SEQ ID NO 1047
<211> LENGTH: 9
<212> TYPE: PRT
```

```
<213> ORGANISM: Unknown
<220> FEATURE:
<223> OTHER INFORMATION: Description of Unknown:
      Marker peptide

<400> SEQUENCE: 1047

Lys Ala Gly Pro Gly Ala Lys Phe Glu
1               5

<210> SEQ ID NO 1048
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1048

Pro Ser Gln Trp Asn Arg Trp Gly
1               5

<210> SEQ ID NO 1049
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1049

Gly Trp Lys Asn Gly Ser Gly
1               5

<210> SEQ ID NO 1050
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1050

Gly Lys Asn Gln Gly Gly
1               5

<210> SEQ ID NO 1051
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1051

Pro Asn Val Pro Val Gly Arg Glu Val Phe Ser
1               5                   10

<210> SEQ ID NO 1052
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1052

Pro Val Leu Gln Ser Glu Arg Gly Lys Asp Gly
1               5                   10
```

```
<210> SEQ ID NO 1053
<211> LENGTH: 5
<212> TYPE: PRT
<213> ORGANISM: Unknown
<220> FEATURE:
<223> OTHER INFORMATION: Description of Unknown:
      Marker peptide

<400> SEQUENCE: 1053

Ser Lys Ala Gly Gly
1               5

<210> SEQ ID NO 1054
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1054

Leu Pro Val Asn Arg Glu Leu Gly
1               5

<210> SEQ ID NO 1055
<211> LENGTH: 5
<212> TYPE: PRT
<213> ORGANISM: Unknown
<220> FEATURE:
<223> OTHER INFORMATION: Description of Unknown:
      Marker peptide

<400> SEQUENCE: 1055

Lys Gln Pro Pro Gly
1               5

<210> SEQ ID NO 1056
<211> LENGTH: 13
<212> TYPE: PRT
<213> ORGANISM: Unknown
<220> FEATURE:
<223> OTHER INFORMATION: Description of Unknown:
      Marker peptide

<400> SEQUENCE: 1056

Pro Asn Val Glu Gly Asp Tyr Ser Ala Trp Arg Val Leu
1               5                   10

<210> SEQ ID NO 1057
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1057

Pro Asn Leu His Asn Asn Arg Asp
1               5

<210> SEQ ID NO 1058
<211> LENGTH: 7
<212> TYPE: PRT
<213> ORGANISM: Unknown
<220> FEATURE:
<223> OTHER INFORMATION: Description of Unknown:
      Marker peptide
```

```
<400> SEQUENCE: 1058

Val Arg Asn Pro Lys Asp Gly
1               5

<210> SEQ ID NO 1059
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1059

Gly Arg Lys Ala Asp Gly
1               5

<210> SEQ ID NO 1060
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1060

Gly Leu Ala Ala Lys Ser Gly
1               5

<210> SEQ ID NO 1061
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 1061

Pro Lys His Arg Glu Arg Val Tyr Ala Asn Arg Asp
1               5                   10

<210> SEQ ID NO 1062
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1062

Val Pro Asp Lys Val Lys Gly
1               5

<210> SEQ ID NO 1063
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1063

Pro Leu Pro His Glu Asn Tyr Gln Arg Gly
1               5                   10

<210> SEQ ID NO 1064
<211> LENGTH: 7
```

-continued

```
<212> TYPE: PRT
<213> ORGANISM: Unknown
<220> FEATURE:
<223> OTHER INFORMATION: Description of Unknown:
      Marker peptide

<400> SEQUENCE: 1064

Val Gln Gly Arg Gly Val Gly
1               5

<210> SEQ ID NO 1065
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1065

Gly Gly Pro Gln Asn Lys Gly
1               5

<210> SEQ ID NO 1066
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1066

Arg Pro Ser Pro Ala Gly Gly
1               5

<210> SEQ ID NO 1067
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1067

Pro Val His Gln Tyr Gln Phe Gly
1               5

<210> SEQ ID NO 1068
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1068

Pro Gly Ser Phe Ser Glu His Val Leu
1               5

<210> SEQ ID NO 1069
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1069

Ala Pro Arg Gly Val Lys Ser Asp
```

```
<210> SEQ ID NO 1070
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1070

Gly Pro Gln Gln Asn Lys Val Gly
1               5

<210> SEQ ID NO 1071
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1071

Pro Leu Ser Arg Ala Phe Asp His Gly
1               5

<210> SEQ ID NO 1072
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1072

Pro Tyr Lys Gly Glu Ser Ala His Leu Phe
1               5                   10

<210> SEQ ID NO 1073
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1073

Pro Gly Asn Trp Tyr Trp Ser Gly
1               5

<210> SEQ ID NO 1074
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1074

Pro Phe Gly His Gly Tyr Asn Asn Phe Ser
1               5                   10

<210> SEQ ID NO 1075
<211> LENGTH: 9
<212> TYPE: PRT
<213> ORGANISM: Unknown
<220> FEATURE:
<223> OTHER INFORMATION: Description of Unknown:
```

Marker peptide

<400> SEQUENCE: 1075

Asn Pro Ser Gln Arg Tyr Ala Asp Gly
1               5

<210> SEQ ID NO 1076
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1076

Pro Val Leu Gln Ser Glu Arg Gly Lys Asp Gly
1               5                   10

<210> SEQ ID NO 1077
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1077

Ala Val Glu Val Gly Glu Ala Val Leu Gly
1               5                   10

<210> SEQ ID NO 1078
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1078

Pro Asn Leu His Asn Asn Arg Asp
1               5

<210> SEQ ID NO 1079
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1079

Lys Gln Pro Ser Ser Gly
1               5

<210> SEQ ID NO 1080
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1080

Arg Ala Ser Pro Pro Gly
1               5

<210> SEQ ID NO 1081

```
<211> LENGTH: 5
<212> TYPE: PRT
<213> ORGANISM: Unknown
<220> FEATURE:
<223> OTHER INFORMATION: Description of Unknown:
      Marker peptide

<400> SEQUENCE: 1081

Val Lys Pro Gly Gly
1               5

<210> SEQ ID NO 1082
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1082

Leu Pro Val Asn Arg Glu Leu Gly
1               5

<210> SEQ ID NO 1083
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1083

Pro Asp Val Pro Glu Gly Asp Gly
1               5

<210> SEQ ID NO 1084
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1084

Pro Ser Lys Val His Leu Glu Arg His Ser
1               5                   10

<210> SEQ ID NO 1085
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1085

Pro Lys Gly Val Gln His Tyr His Gly
1               5

<210> SEQ ID NO 1086
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1086
```

Arg Pro Leu Ala Gly Pro Gly
1               5

<210> SEQ ID NO 1087
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1087

Gly Ala Ala Val Lys Gly
1               5

<210> SEQ ID NO 1088
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1088

Pro Tyr Ser His Gln Arg Gln Val Glu
1               5

<210> SEQ ID NO 1089
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1089

Tyr Pro Glu Gln Pro Ser Glu Asp
1               5

<210> SEQ ID NO 1090
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1090

Gly Pro Asn Leu Gln Lys Gln Leu Gly
1               5

<210> SEQ ID NO 1091
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1091

Pro Asp Leu Pro Asp Leu Glu Asp
1               5

<210> SEQ ID NO 1092
<211> LENGTH: 8
<212> TYPE: PRT
<213> ORGANISM: Unknown
<220> FEATURE:

```
<223> OTHER INFORMATION: Description of Unknown:
      Marker peptide

<400> SEQUENCE: 1092

Ala Pro Leu Lys Pro Gln Ser Gly
1               5

<210> SEQ ID NO 1093
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1093

Gly Lys Asn Gln Gly Gly
1               5

<210> SEQ ID NO 1094
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1094

Val Gln Gly Arg Gly Val Gly
1               5

<210> SEQ ID NO 1095
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1095

Asn Ser Arg Glu Pro Lys Asp Ala Leu Phe
1               5                   10

<210> SEQ ID NO 1096
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1096

Asp Pro Arg Lys Ser Val Ser Gly
1               5

<210> SEQ ID NO 1097
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1097

Pro Val Lys Val Gly Glu Ala Glu Asp
1               5
```

```
<210> SEQ ID NO 1098
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1098

Lys Ala Gly Pro Gly Ala Lys Phe Glu
1               5

<210> SEQ ID NO 1099
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1099

Pro Leu Pro His Glu Asn Tyr Gln Arg Gly
1               5                   10

<210> SEQ ID NO 1100
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1100

Pro Val Val Val His Asp Gly
1               5

<210> SEQ ID NO 1101
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1101

Pro His Tyr Arg Val Gln Gln Glu Gly
1               5

<210> SEQ ID NO 1102
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1102

Glu Leu Pro Asp Asp Gly
1               5

<210> SEQ ID NO 1103
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1103
```

```
Tyr Pro His Lys Tyr Gln His Gly
1               5

<210> SEQ ID NO 1104
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1104

Arg Gln Gly Pro Ser Asp Lys Gly
1               5

<210> SEQ ID NO 1105
<211> LENGTH: 5
<212> TYPE: PRT
<213> ORGANISM: Unknown
<220> FEATURE:
<223> OTHER INFORMATION: Description of Unknown:
      Marker peptide

<400> SEQUENCE: 1105

Arg Pro Pro Gly Gly
1               5

<210> SEQ ID NO 1106
<211> LENGTH: 5
<212> TYPE: PRT
<213> ORGANISM: Unknown
<220> FEATURE:
<223> OTHER INFORMATION: Description of Unknown:
      Marker peptide

<400> SEQUENCE: 1106

Gly Leu Leu Lys Gly
1               5

<210> SEQ ID NO 1107
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1107

Lys Val Gln Ala Pro Ser Gly
1               5

<210> SEQ ID NO 1108
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1108

Pro His His Gly Ser Leu Gly
1               5

<210> SEQ ID NO 1109
<211> LENGTH: 11
<212> TYPE: PRT
<213> ORGANISM: Unknown
```

```
<220> FEATURE:
<223> OTHER INFORMATION: Description of Unknown:
      Marker peptide

<400> SEQUENCE: 1109

Pro Asn Val Pro Val Gly Arg Glu Val Phe Ser
1               5                   10

<210> SEQ ID NO 1110
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1110

Gly Arg Gln Pro Leu Gly
1               5

<210> SEQ ID NO 1111
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1111

Pro Tyr His Pro Gln Phe Leu Ser
1               5

<210> SEQ ID NO 1112
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1112

Pro Glu Leu His Leu Asn Val Gly
1               5

<210> SEQ ID NO 1113
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1113

Gly Arg Lys Ala Asp Gly
1               5

<210> SEQ ID NO 1114
<211> LENGTH: 5
<212> TYPE: PRT
<213> ORGANISM: Unknown
<220> FEATURE:
<223> OTHER INFORMATION: Description of Unknown:
      Marker peptide

<400> SEQUENCE: 1114

Gly Val Gln Tyr Gly
1               5
```

```
<210> SEQ ID NO 1115
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1115

Gly Gly Pro Gln Asn Lys Gly
1               5

<210> SEQ ID NO 1116
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1116

Val Arg Asn Pro Lys Asp Gly
1               5

<210> SEQ ID NO 1117
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 1117

Arg Ser Glu Gly Lys Trp His Leu Pro Trp His Phe
1               5                   10

<210> SEQ ID NO 1118
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1118

Lys Phe Lys Val Trp Glu Trp His Phe Ser
1               5                   10

<210> SEQ ID NO 1119
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1119

Asn Arg Phe Arg Phe Ser Pro His Trp Gly
1               5                   10

<210> SEQ ID NO 1120
<211> LENGTH: 12
<212> TYPE: PRT
<213> ORGANISM: Unknown
<220> FEATURE:
<223> OTHER INFORMATION: Description of Unknown:
      Marker peptide
```

```
<400> SEQUENCE: 1120

Gln Phe Ser Pro Arg His Ser Trp Pro Ala Leu Ser
1               5                   10

<210> SEQ ID NO 1121
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1121

Arg Arg Gln His Arg Val Phe Asp
1               5

<210> SEQ ID NO 1122
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1122

Gln Ser Arg Lys Val Pro Trp Leu Asp
1               5

<210> SEQ ID NO 1123
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1123

Arg Trp Glu Leu Trp Lys Arg Val Asp
1               5

<210> SEQ ID NO 1124
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1124

Lys Phe Arg Ser Glu Trp Gln Pro His Phe Gly
1               5                   10

<210> SEQ ID NO 1125
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1125

Lys Arg Trp Glu Asn His Phe Tyr Asn His Val
1               5                   10

<210> SEQ ID NO 1126
<211> LENGTH: 9
<212> TYPE: PRT
```

```
<213> ORGANISM: Unknown
<220> FEATURE:
<223> OTHER INFORMATION: Description of Unknown:
      Marker peptide

<400> SEQUENCE: 1126

Asn Trp Leu His Gly Pro Asn Phe Gly
1               5

<210> SEQ ID NO 1127
<211> LENGTH: 13
<212> TYPE: PRT
<213> ORGANISM: Unknown
<220> FEATURE:
<223> OTHER INFORMATION: Description of Unknown:
      Marker peptide

<400> SEQUENCE: 1127

Asn Arg Tyr Trp Gln Lys Leu Pro Gly Tyr His Val Glu
1               5                   10

<210> SEQ ID NO 1128
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1128

His Trp Lys Glu Ser Arg Phe Gly
1               5

<210> SEQ ID NO 1129
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1129

Arg Phe Gly Trp Gly Pro Ala Pro His Leu Gly
1               5                   10

<210> SEQ ID NO 1130
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1130

Phe Glu Lys His Gly His Trp Gly
1               5

<210> SEQ ID NO 1131
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1131

Gln Tyr Lys Leu Arg His Trp His Leu Gly
1               5                   10
```

<210> SEQ ID NO 1132
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1132

Arg Gln Tyr Asn Lys His Phe Arg Asp
1               5

<210> SEQ ID NO 1133
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1133

Phe Trp Asn Ser Arg Leu Glu Asn Arg His Leu
1               5                   10

<210> SEQ ID NO 1134
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1134

Lys Tyr Glu His Trp Lys Phe Asp
1               5

<210> SEQ ID NO 1135
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1135

Gln Tyr Lys Glu Arg His Trp Leu Gly
1               5

<210> SEQ ID NO 1136
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1136

Arg Asn Trp Ala Trp His Leu Gly
1               5

<210> SEQ ID NO 1137
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1137

Arg Asp Pro Gln Arg Leu Phe His Ala Trp Gly
1               5                   10

<210> SEQ ID NO 1138
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1138

Gln Trp Val Ser Gln Arg His Ala Phe Glu
1               5                   10

<210> SEQ ID NO 1139
<211> LENGTH: 13
<212> TYPE: PRT
<213> ORGANISM: Unknown
<220> FEATURE:
<223> OTHER INFORMATION: Description of Unknown:
      Marker peptide

<400> SEQUENCE: 1139

Trp Asn Val Gly Ala Lys His Asn His Pro Tyr His Leu
1               5                   10

<210> SEQ ID NO 1140
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1140

Arg Asn Ser Trp Pro Trp Leu Glu Gly
1               5

<210> SEQ ID NO 1141
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1141

Arg Glu Arg His Lys His Trp His Leu Gly
1               5                   10

<210> SEQ ID NO 1142
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1142

Gln Arg Asp Val Gln His Gln His Val Phe
1               5                   10

<210> SEQ ID NO 1143
<211> LENGTH: 10

```
<212> TYPE: PRT
<213> ORGANISM: Unknown
<220> FEATURE:
<223> OTHER INFORMATION: Description of Unknown:
      Marker peptide

<400> SEQUENCE: 1143

Arg Gly Pro Trp Tyr Arg Pro Tyr Glu Gly
1               5                   10

<210> SEQ ID NO 1144
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1144

Trp Glu Arg Gly Ala Arg Asp Asn His Val Leu
1               5                   10

<210> SEQ ID NO 1145
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1145

Arg His Gln Trp Gln Ala His Phe Gly
1               5

<210> SEQ ID NO 1146
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1146

Arg Lys Trp Asp Ala Trp Leu Gly
1               5

<210> SEQ ID NO 1147
<211> LENGTH: 13
<212> TYPE: PRT
<213> ORGANISM: Unknown
<220> FEATURE:
<223> OTHER INFORMATION: Description of Unknown:
      Marker peptide

<400> SEQUENCE: 1147

Gln His Leu Arg Val Ser Trp Arg Pro Tyr Asn His Leu
1               5                   10

<210> SEQ ID NO 1148
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 1148

Asn His Ser Tyr Arg Leu Gly Trp Gly Trp His Ser
```

```
1               5                   10

<210> SEQ ID NO 1149
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1149

Ser Trp Tyr Leu Pro Asn Arg His Leu
1               5

<210> SEQ ID NO 1150
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1150

Arg Val Asn Gln Trp Arg His Arg Phe Glu
1               5                   10

<210> SEQ ID NO 1151
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1151

Gln Ser Gln Trp Gly Tyr Trp Lys His Phe
1               5                   10

<210> SEQ ID NO 1152
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1152

Arg Gln Asp Ala Pro Trp Arg His Phe
1               5

<210> SEQ ID NO 1153
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 1153

Arg Asp Gln His Leu Pro Phe Tyr Asn Arg His Leu
1               5                   10

<210> SEQ ID NO 1154
<211> LENGTH: 12
<212> TYPE: PRT
<213> ORGANISM: Unknown
<220> FEATURE:
<223> OTHER INFORMATION: Description of Unknown:
```

Marker peptide

<400> SEQUENCE: 1154

Arg Val Gly Tyr Ala His Leu Asn Gly Arg Phe Glu
1               5                   10

<210> SEQ ID NO 1155
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1155

Lys Ser Glu Asp His Gln Phe Asn Arg His Phe
1               5                   10

<210> SEQ ID NO 1156
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1156

Arg Gly His Ser Trp Asn Arg Arg Leu Asp
1               5                   10

<210> SEQ ID NO 1157
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1157

Asn Val Val Trp Trp Asn Arg His Leu
1               5

<210> SEQ ID NO 1158
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1158

Trp Pro His Arg His Leu Phe Trp Lys Glu
1               5                   10

<210> SEQ ID NO 1159
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1159

Gly Lys Tyr Arg Val Phe Phe Glu Gly
1               5

<210> SEQ ID NO 1160

```
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1160

His Val Arg Ala Gln Arg Pro Trp Ser Glu
1               5                   10

<210> SEQ ID NO 1161
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1161

Lys Asn Ser Pro Arg Leu Pro His Phe Asp
1               5                   10

<210> SEQ ID NO 1162
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1162

Arg Phe Trp Lys Gly His Phe Pro Arg Glu
1               5                   10

<210> SEQ ID NO 1163
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1163

Arg Trp His Gln Gln Arg Phe Glu
1               5

<210> SEQ ID NO 1164
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1164

Gln Ser Arg Glu Trp His Ser Gln Leu Phe Ser
1               5                   10

<210> SEQ ID NO 1165
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1165
```

Trp Tyr Asn Arg Pro Trp His Leu His Gly
1               5                   10

<210> SEQ ID NO 1166
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 1166

Asn Gln Arg Tyr Ala Trp Ala Trp Pro His Val Ser
1               5                   10

<210> SEQ ID NO 1167
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1167

Trp Tyr Glu His Gly Lys Val Phe Gly
1               5

<210> SEQ ID NO 1168
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1168

Ser Trp Tyr Leu Pro Asn Arg His Leu
1               5

<210> SEQ ID NO 1169
<211> LENGTH: 13
<212> TYPE: PRT
<213> ORGANISM: Unknown
<220> FEATURE:
<223> OTHER INFORMATION: Description of Unknown:
      Marker peptide

<400> SEQUENCE: 1169

Trp Asn Val Gly Ala Lys His Asn His Pro Tyr His Leu
1               5                   10

<210> SEQ ID NO 1170
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1170

His Trp Leu Gly Phe Pro Ala His Gly
1               5

<210> SEQ ID NO 1171
<211> LENGTH: 8
<212> TYPE: PRT
<213> ORGANISM: Unknown
<220> FEATURE:

<223> OTHER INFORMATION: Description of Unknown:
      Marker peptide

<400> SEQUENCE: 1171

Phe His Pro His Gln Phe Ser Gly
1               5

<210> SEQ ID NO 1172
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1172

His Trp Arg Trp Tyr Asn Gly
1               5

<210> SEQ ID NO 1173
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1173

Tyr Val His His Gln Arg His Phe Gly
1               5

<210> SEQ ID NO 1174
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1174

Asn Trp Leu His Gly Pro Asn Phe Gly
1               5

<210> SEQ ID NO 1175
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1175

Trp Trp Val Ser Gly Pro Asn Pro His Phe Ser
1               5                   10

<210> SEQ ID NO 1176
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1176

His His Gly Tyr Trp Asn Lys Trp Gly
1               5

```
<210> SEQ ID NO 1177
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1177

Trp Tyr Pro Gly Arg Leu Gly
1               5

<210> SEQ ID NO 1178
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1178

Leu Pro Trp His Trp Gln Gly Lys His Phe Ser
1               5                   10

<210> SEQ ID NO 1179
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1179

Pro Val His Trp Ala Arg His Phe Gly
1               5

<210> SEQ ID NO 1180
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1180

Ser Trp Phe Gly Asp Asn Lys Arg His Leu
1               5                   10

<210> SEQ ID NO 1181
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1181

Trp Tyr Arg Gly Gly Trp Gly
1               5

<210> SEQ ID NO 1182
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1182
```

Trp Pro Trp Trp His Gly Tyr Arg Gly
1               5

<210> SEQ ID NO 1183
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1183

Ser Tyr Pro Gln His His Val Phe
1               5

<210> SEQ ID NO 1184
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1184

Trp Asp His Phe Tyr Val Gln Arg His Val
1               5                   10

<210> SEQ ID NO 1185
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1185

Trp Val Trp His Pro Trp Arg Ala Gly
1               5

<210> SEQ ID NO 1186
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1186

Lys Val Tyr Trp His Phe Gly His His Gly
1               5                   10

<210> SEQ ID NO 1187
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1187

Trp Val Gln Tyr Val Pro Gly
1               5

<210> SEQ ID NO 1188
<211> LENGTH: 11
<212> TYPE: PRT
<213> ORGANISM: Unknown

```
<220> FEATURE:
<223> OTHER INFORMATION: Description of Unknown:
      Marker peptide

<400> SEQUENCE: 1188

Tyr His Tyr Ala Asp Tyr His Leu Pro Lys Gly
1               5                   10

<210> SEQ ID NO 1189
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1189

Trp Gln Gly Asp Tyr Trp Arg Pro Arg Phe Ser
1               5                   10

<210> SEQ ID NO 1190
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1190

Gln Trp His Tyr Val Val Ser Gly
1               5

<210> SEQ ID NO 1191
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1191

Ala His Trp Leu Ala His Pro Leu Gly
1               5

<210> SEQ ID NO 1192
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1192

Trp Val Leu Asn Pro Trp Tyr Trp Asn His Gly
1               5                   10

<210> SEQ ID NO 1193
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1193

His Phe Val His Ala Arg His Val Leu
1               5
```

```
<210> SEQ ID NO 1194
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1194

Trp Ser Glu Trp Tyr Leu Lys Val
1               5

<210> SEQ ID NO 1195
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1195

His Leu Trp Phe Ala Ala His Leu Gly
1               5

<210> SEQ ID NO 1196
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1196

Trp Asn Val Val Asn Gly Ala Arg His Phe
1               5                   10

<210> SEQ ID NO 1197
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1197

His Trp Phe His Phe Ser Pro Gly
1               5

<210> SEQ ID NO 1198
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1198

Trp Ser Pro Ala Gly Tyr His Tyr Asn Phe Ser
1               5                   10

<210> SEQ ID NO 1199
<211> LENGTH: 7
<212> TYPE: PRT
<213> ORGANISM: Unknown
<220> FEATURE:
<223> OTHER INFORMATION: Description of Unknown:
      Marker peptide
```

```
<400> SEQUENCE: 1199

His Ala His Phe Arg Trp Gly
1               5

<210> SEQ ID NO 1200
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1200

Asn Glu Pro Phe His Phe Arg His Phe Gly
1               5                   10

<210> SEQ ID NO 1201
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1201

Trp Gly Arg Gln Trp Gly
1               5

<210> SEQ ID NO 1202
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1202

Pro Tyr Val Asn Phe Gly Trp Pro His Gly
1               5                   10

<210> SEQ ID NO 1203
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1203

Trp Val Ser Gln Tyr Asn Gly Trp Gly
1               5

<210> SEQ ID NO 1204
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1204

Trp Tyr Asn Arg Pro Trp His Leu His Gly
1               5                   10

<210> SEQ ID NO 1205
<211> LENGTH: 9
<212> TYPE: PRT
```

```
<213> ORGANISM: Unknown
<220> FEATURE:
<223> OTHER INFORMATION: Description of Unknown:
      Marker peptide

<400> SEQUENCE: 1205

Trp Ser His Pro Arg Leu His Val Gly
1               5

<210> SEQ ID NO 1206
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1206

Arg His Gly Glu Trp Arg Ser Pro His Phe Ser
1               5                   10

<210> SEQ ID NO 1207
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1207

Lys His His Gly Trp His Pro Tyr Phe Ser
1               5                   10

<210> SEQ ID NO 1208
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1208

His Tyr Val Trp Tyr Trp His Ser Gly
1               5

<210> SEQ ID NO 1209
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1209

Trp Tyr Pro Ala Asn Lys Gln His Val Phe
1               5                   10

<210> SEQ ID NO 1210
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1210

Ser Trp Val His Leu Phe Gln Gly
1               5
```

```
<210> SEQ ID NO 1211
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1211

Trp Gln Tyr Ser Leu Gly His Phe Ser
1               5

<210> SEQ ID NO 1212
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1212

Lys Ala His Phe Pro His Trp Lys Asp
1               5

<210> SEQ ID NO 1213
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1213

Tyr Gln Phe Ala Pro Pro Trp Arg His Leu
1               5                   10

<210> SEQ ID NO 1214
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1214

Ser His Tyr Trp Ala Gln Val Leu Ser
1               5

<210> SEQ ID NO 1215
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1215

His Val Ala His Phe Pro Pro Lys Leu Asp
1               5                   10

<210> SEQ ID NO 1216
<211> LENGTH: 9
<212> TYPE: PRT
<213> ORGANISM: Unknown
<220> FEATURE:
<223> OTHER INFORMATION: Description of Unknown:
      Marker peptide
```

<400> SEQUENCE: 1216

Trp Arg Trp Ser Gln Ala His Phe Gly
1               5

<210> SEQ ID NO 1217
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1217

Ser Trp Tyr Leu Pro Asn Arg His Leu
1               5

<210> SEQ ID NO 1218
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1218

Asn Trp Leu His Gly Pro Asn Phe Gly
1               5

<210> SEQ ID NO 1219
<211> LENGTH: 13
<212> TYPE: PRT
<213> ORGANISM: Unknown
<220> FEATURE:
<223> OTHER INFORMATION: Description of Unknown:
      Marker peptide

<400> SEQUENCE: 1219

Trp Asn Val Gly Ala Lys His Asn His Pro Tyr His Leu
1               5                   10

<210> SEQ ID NO 1220
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1220

His Trp Leu Gly Phe Pro Ala His Gly
1               5

<210> SEQ ID NO 1221
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1221

Trp Gln Gly Asp Tyr Trp Arg Pro Arg Phe Ser
1               5                   10

<210> SEQ ID NO 1222
<211> LENGTH: 9

```
<212> TYPE: PRT
<213> ORGANISM: Unknown
<220> FEATURE:
<223> OTHER INFORMATION: Description of Unknown:
      Marker peptide

<400> SEQUENCE: 1222

Trp Val Trp His Pro Trp Arg Ala Gly
1               5

<210> SEQ ID NO 1223
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1223

Trp Tyr Glu His Gly Lys Val Phe Gly
1               5

<210> SEQ ID NO 1224
<211> LENGTH: 6
<212> TYPE: PRT
<213> ORGANISM: Unknown
<220> FEATURE:
<223> OTHER INFORMATION: Description of Unknown:
      Marker peptide

<400> SEQUENCE: 1224

Trp Gly Arg Gln Trp Gly
1               5

<210> SEQ ID NO 1225
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1225

Trp Arg Trp Ser Gln Ala His Phe Gly
1               5

<210> SEQ ID NO 1226
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1226

Phe His Pro His Gln Phe Ser Gly
1               5

<210> SEQ ID NO 1227
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1227

Tyr Val His His Gln Arg His Phe Gly
```

<210> SEQ ID NO 1228
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1228

Ser Tyr Pro Gln His His Val Phe
1               5

<210> SEQ ID NO 1229
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1229

His His Gly Tyr Trp Asn Lys Trp Gly
1               5

<210> SEQ ID NO 1230
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1230

Asn Glu Pro Phe His Phe Arg His Phe Gly
1               5                   10

<210> SEQ ID NO 1231
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1231

His Leu Trp Phe Ala Ala His Leu Gly
1               5

<210> SEQ ID NO 1232
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1232

Trp Pro Trp Trp His Gly Tyr Arg Gly
1               5

<210> SEQ ID NO 1233
<211> LENGTH: 7
<212> TYPE: PRT
<213> ORGANISM: Unknown
<220> FEATURE:
<223> OTHER INFORMATION: Description of Unknown:

```
            Marker peptide

<400> SEQUENCE: 1233

Trp Tyr Arg Gly Gly Trp Gly
1               5

<210> SEQ ID NO 1234
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1234

Ala His Trp Leu Ala His Pro Leu Gly
1               5

<210> SEQ ID NO 1235
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1235

Trp Tyr Pro Gly Arg Leu Gly
1               5

<210> SEQ ID NO 1236
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1236

Trp Trp Val Ser Gly Pro Asn Pro His Phe Ser
1               5                   10

<210> SEQ ID NO 1237
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1237

Arg His Gly Glu Trp Arg Ser Pro His Phe Ser
1               5                   10

<210> SEQ ID NO 1238
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1238

Trp Val Leu Asn Pro Trp Tyr Trp Asn His Gly
1               5                   10

<210> SEQ ID NO 1239
```

```
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1239

Trp Ser Glu Trp Tyr Leu Lys Val
1               5

<210> SEQ ID NO 1240
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1240

His Phe Val His Ala Arg His Val Leu
1               5

<210> SEQ ID NO 1241
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1241

Pro Val His Trp Ala Arg His Phe Gly
1               5

<210> SEQ ID NO 1242
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1242

Trp Tyr Asn Arg Pro Trp His Leu His Gly
1               5                   10

<210> SEQ ID NO 1243
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1243

Trp Gln Tyr Ser Leu Gly His Phe Ser
1               5

<210> SEQ ID NO 1244
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1244
```

```
Asn Phe His Val Ala Trp His Pro Phe Ser Gly
1               5                   10
```

<210> SEQ ID NO 1245
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1245

```
His Tyr His Trp Gly Val Gly
1               5
```

<210> SEQ ID NO 1246
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1246

```
Ser Trp Phe Gly Asp Asn Lys Arg His Leu
1               5                   10
```

<210> SEQ ID NO 1247
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1247

```
His Ala His Phe Arg Trp Gly
1               5
```

<210> SEQ ID NO 1248
<211> LENGTH: 12
<212> TYPE: PRT
<213> ORGANISM: Unknown
<220> FEATURE:
<223> OTHER INFORMATION: Description of Unknown:
      Marker peptide

<400> SEQUENCE: 1248

```
His Val Leu Gln His Val Arg His Tyr His Phe Gly
1               5                   10
```

<210> SEQ ID NO 1249
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1249

```
Lys His His Gly Trp His Pro Tyr Phe Ser
1               5                   10
```

<210> SEQ ID NO 1250
<211> LENGTH: 7
<212> TYPE: PRT
<213> ORGANISM: Unknown
<220> FEATURE:

```
-continued

<223> OTHER INFORMATION: Description of Unknown:
      Marker peptide

<400> SEQUENCE: 1250

His Trp Arg Trp Tyr Asn Gly
1               5

<210> SEQ ID NO 1251
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1251

Trp Asp His Phe Tyr Val Gln Arg His Val
1               5                   10

<210> SEQ ID NO 1252
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1252

Trp Val Gln Tyr Val Pro Gly
1               5

<210> SEQ ID NO 1253
<211> LENGTH: 11
<212> TYPE: PRT
<213> ORGANISM: Unknown
<220> FEATURE:
<223> OTHER INFORMATION: Description of Unknown:
      Marker peptide

<400> SEQUENCE: 1253

Trp Gly Trp Asn Ser Arg Asp Arg Val Leu Gly
1               5                   10

<210> SEQ ID NO 1254
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1254

Trp Ser His Pro Arg Leu His Val Gly
1               5

<210> SEQ ID NO 1255
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1255

Trp Trp Pro Lys Val Phe Pro Asn His Ser
1               5                   10
```

```
<210> SEQ ID NO 1256
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1256

Lys Phe Lys Val Trp Glu Trp His Phe Ser
1               5                   10

<210> SEQ ID NO 1257
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1257

His Trp Phe His Phe Ser Pro Gly
1               5

<210> SEQ ID NO 1258
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1258

Trp Trp Ala Val Lys His Phe Gly
1               5

<210> SEQ ID NO 1259
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1259

Trp Gln Trp Gln Asn Arg Ala His Phe Gly
1               5                   10

<210> SEQ ID NO 1260
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1260

Gly Trp Val Trp Ala Asn Arg His Phe Gly
1               5                   10

<210> SEQ ID NO 1261
<211> LENGTH: 8
<212> TYPE: PRT
<213> ORGANISM: Unknown
<220> FEATURE:
<223> OTHER INFORMATION: Description of Unknown:
      Marker peptide

<400> SEQUENCE: 1261
```

```
Gln Trp His Tyr Val Val Ser Gly
1               5

<210> SEQ ID NO 1262
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1262

Asn Trp Ser Pro Phe Glu Trp Lys Gly
1               5

<210> SEQ ID NO 1263
<211> LENGTH: 10
<212> TYPE: PRT
<213> ORGANISM: Unknown
<220> FEATURE:
<223> OTHER INFORMATION: Description of Unknown:
      Marker peptide

<400> SEQUENCE: 1263

Trp Asn Val Val Asn Gly Ala Arg His Phe
1               5                   10

<210> SEQ ID NO 1264
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1264

Trp Val Ser Gln Tyr Asn Gly Trp Gly
1               5

<210> SEQ ID NO 1265
<211> LENGTH: 7
<212> TYPE: PRT
<213> ORGANISM: Unknown
<220> FEATURE:
<223> OTHER INFORMATION: Description of Unknown:
      Marker peptide

<400> SEQUENCE: 1265

Lys Trp Trp Val His Phe Gly
1               5

<210> SEQ ID NO 1266
<211> LENGTH: 9
<212> TYPE: PRT
<213> ORGANISM: Unknown
<220> FEATURE:
<223> OTHER INFORMATION: Description of Unknown:
      Marker peptide

<400> SEQUENCE: 1266

Ser His Tyr Trp Ala Gln Val Leu Ser
1               5
```

US 11,371,990 B2

METHODS FOR IDENTIFYING CANDIDATE BIOMARKERS

CROSS-REFERENCE

This application is a U.S. National Phase of International Application No. PCT/US2017/061194, filed on Nov. 10, 2017, which claims the benefit of U.S. Provisional Application No. 62/421,182, filed Nov. 11, 2016; U.S. Provisional Application No. 62/462,320, filed Feb. 22, 2017, U.S. Provisional Application No. 62/522,052, filed Jun. 19, 2017; U.S. Provisional Application No. 62/522,636, filed Jun. 20, 2017; and U.S. Provisional Application No. 62/581,581, filed Nov. 3, 2017, each of which is incorporated herein by reference in its entirety.

SEQUENCE LISTING

The instant application contains a Sequence Listing which has been filed electronically in ASCII format and is hereby incorporated by reference in its entirety. Said ASCII copy, created on Jul. 11, 2019, is named 43638-721_831_SL.txt and is 238,858 bytes in size.

BACKGROUND OF THE INVENTION

Progression from health to disease is accompanied by complex changes in protein expression in both the circulation and affected tissues. Large-scale comparative interrogation of the human proteome can offer insights into disease biology as well as lead to the discovery of new biomarkers for diagnostics, new targets for therapeutics, and can identify patients most likely to benefit from treatment.

SUMMARY OF THE INVENTION

Provided herein are methods, devices and assays for identifying candidate biomarkers using discriminating peptides of immunosignatures. In one aspect, a method is provided for identifying at least one candidate protein biomarker for a condition. In some aspects, the methods, devices and assays provide for identifying at least one candidate biomarker for an autoimmune disease comprising: (a) providing a peptide array and contacting a biological sample from a plurality of subjects known to have the autoimmune disease to the peptide array; (b) identifying a set of discriminating peptides bound to antibodies in the biological sample from the plurality of subjects that differentiate the autoimmune disease from at least one different health condition; (c) aligning each of the peptides in the set of discriminating peptides to one or more proteins in a proteome; and (d) obtaining a protein score and ranking for each of the identified proteins according to a statistical significance, thereby identifying at least one candidate biomarker for the autoimmune disease.

In some aspects, the methods, devices and assays further comprise obtaining an overlap score, wherein said score corrects for composition of the peptides on the peptide array. In other aspects, the ranking for each of the identified proteins is made relative to the ranking of proteins identified from aligning non-discriminating peptides. In yet other aspects, the identified candidate biomarkers are ranked according to a p-value of less than $10^{-3}$.

In other aspects, the step of identifying the set of discriminating peptides comprises: (i) detecting binding of antibodies present in the biological sample from the plurality of subjects having the autoimmune disease to obtain a first combination of binding signals; (ii) detecting binding of antibodies present in samples from one or more reference groups of subjects to the same peptide array, each reference group having a different health condition to obtain a second combination of binding signals; (iii) comparing the first combination of binding signals to the second combination of binding signals to obtain a set of differentiating binding signals; and (iv) identifying peptides on the array that are differentially bound by antibodies in samples from subjects having the autoimmune disease and the antibodies in the samples from the one or more reference groups of subjects, thereby identifying said discriminating peptides.

In some aspects, the discriminating peptides comprise an enrichment of one or more sequence motifs of at least 100% as compared to the remaining peptides on the array. In other aspects, the first combination of binding signals comprises signals that are lower than signals from the second combination of binding signals. In some aspects, the set of differentiating binding signals is obtained by detecting the binding of antibodies present in samples from subjects with the autoimmune disease and the antibodies in the samples from the one or more reference group of subjects to at least 25 peptides on an array of peptides comprising at least 10,000 different peptides. In other aspects, the number of discriminating peptides corresponds to at least a portion of the total number of peptides on the array. In some aspects, the method performance for differentiating the autoimmune disease from the at least one different health condition is characterized by an area under the receiver operator characteristic (ROC) curve (AUC) ranging from 0.60 to 0.70, 0.70 to 0.79, 0.80 to 0.89, or 0.90 to 1.00.

In some instances, the autoimmune disease targeted in the methods, devices and assays disclosed herein is scleroderma (SSc) and the reference group of subjects are healthy subjects and the discriminating peptides that differentiate the first combination of binding signals from the second combination of binding signals are enriched by at least 100% in one or more sequence motifs listed in FIG. 8A. In some instances, the autoimmune disease is scleroderma and the reference group of subjects are healthy subjects and the discriminating peptides that differentiate the first combination of binding signals from the second combination of binding signals are enriched by at least 100% in one or more amino acids listed in FIG. 8B. In other instances, the autoimmune disease is SSc and the reference group of subjects are healthy subjects and the discriminating peptides that differentiate the first combination of binding signals from the second combination of binding signals comprise at least one peptide of the list provided in Table 3.

In yet other instances, the discriminating peptides identified in the methods, assays and devices disclosed herein comprise one or more sequence motifs provided in FIG. 8A, wherein the discriminating peptides differentiate the binding of antibodies from samples from subjects with SSc from healthy subjects. In other instances, the peptides are selected from the list provided in FIG. 8C.

In some instances, the methods, devices and assays provide a candidate biomarker for SSc selected from the list provided in Table 3, wherein the candidate biomarker predicts the occurrence of SSc relative to a population of healthy subjects.

In yet other instances, the autoimmune disease targeted for the methods, devices and assays disclosed herein is SLE and the reference group of subjects are healthy subjects, and the discriminating peptides that differentiate the first combination of binding signals from the second combination of binding signals are enriched by at least 100% in one or more sequence motifs listed in FIG. 62A. In some instances, the autoimmune disease is SLE and the reference group of subjects are healthy subjects, and the discriminating peptides that differentiate the first combination of binding signals from the second combination of binding signals are enriched by at least 100% in one or more amino acids listed in FIG. 62B. In other instances, the autoimmune disease is SLE and the reference group of subjects are healthy subjects and the discriminating peptides that differentiate the first combination of binding signals from the second combination of binding signals are selected comprise at least one peptide of the list provided in FIG. 90. In yet other instances, the autoimmune disease is SLE and the reference group of subjects are healthy subjects, and wherein the at least one candidate biomarker is selected from the list provided in FIG. 75A.

In one aspect, the methods, devices and assays provide a set of discriminating peptides, wherein the discriminating peptides comprise one or more sequence motifs provided in FIG. 62A, wherein the discriminating peptides differentiate the binding of antibodies from samples from subjects with SLE from healthy subjects. In some instances, the peptides are selected from the list provided in FIG. 90.

In other aspects, the methods, devices and assays provide a candidate biomarker for SLE selected from the list provided in FIG. 75A, wherein the candidate biomarker predicts the occurrence of SLE relative to a population of healthy subjects.

In some instances, the autoimmune disease targeted in the methods, devices and systems disclosed herein is SLE and the reference group of subjects are subjects with other autoimmune and non-autoimmune mimic diseases, and the discriminating peptides that differentiate the first combination of binding signals from the second combination of binding signals are enriched by at least 100% in one or more sequence motifs listed in FIG. 63A. In some aspects, the autoimmune disease is SLE and the reference group of subjects are subjects with other autoimmune and non-autoimmune mimic diseases, and the discriminating peptides that differentiate the first combination of binding signals from the second combination of binding signals are enriched by at least 100% in one or more amino acids listed in FIG. 63B. In other aspects, the autoimmune disease is SLE and the reference group of subjects are subjects with other autoimmune and non-autoimmune mimic diseases, and discriminating peptides that differentiate the first combination of binding signals from the second combination of binding signals are selected comprise at least one peptide of the list provided in FIG. 91. In yet other aspects, the autoimmune disease is SLE and the reference group of subjects are subjects with other autoimmune and non-autoimmune mimic diseases, and wherein the at least one candidate biomarker is selected from the list provided in FIG. 75B.

In some aspects, the methods, devices and assays disclosed herein provide a set of discriminating peptides, wherein the discriminating peptides comprise one or more sequence motifs provided in FIG. 63A, wherein the discriminating peptides differentiate the binding of antibodies from samples from subjects with SLE from subjects with other autoimmune and non-autoimmune mimic diseases. In some instances, the peptides are selected from the list provided in FIG. 91.

In yet other instances, the methods, devices and assays disclosed herein provide a candidate biomarker for SLE selected from the list provided in FIG. 75B, wherein the candidate biomarker predicts the occurrence of SLE relative to a population of subjects with other autoimmune and non-autoimmune mimic diseases.

In some aspects, the autoimmune disease targeted in the methods, devices and assays disclosed herein is SLE and the reference group of subjects are subjects with other autoimmune, non-autoimmune mimic diseases, and healthy subjects, and the discriminating peptides that differentiate the first combination of binding signals from the second combination of binding signals are enriched by at least 100% in one or more sequence motifs listed in FIG. 64A. In some instances, the autoimmune disease is SLE and the reference group of subjects are subjects with other autoimmune, non-autoimmune mimic diseases, and healthy subjects, and the discriminating peptides that differentiate the first combination of binding signals from the second combination of binding signals are enriched by at least 100% in one or more amino acids listed in FIG. 64B. In other instances, the autoimmune disease is SLE and the reference group of subjects are other autoimmune, non-autoimmune mimic diseases, and healthy subjects comprising and the discriminating peptides that differentiate the first combination of binding signals from the second combination of binding signals are selected comprise at least one peptide of the list provided in FIG. 92. In yet other instances, the autoimmune disease is SLE and the reference group of subjects are other autoimmune, non-autoimmune mimic diseases, and healthy subjects comprising, and wherein the at least one candidate biomarker is selected from the list provided in FIG. 75C.

In still other aspects, the methods, devices and assays disclosed herein provide a set of discriminating peptides, wherein the discriminating peptides comprise one or more sequence motifs provided in FIG. 64A, wherein the discriminating peptides differentiate the binding of antibodies from samples from subjects with SLE from other autoimmune, non-autoimmune mimic diseases, and healthy subjects. In some instances, the peptides are selected from the list provided in FIG. 92.

In one aspect, the methods, devices and assays disclosed herein provide a candidate biomarker for SLE selected from the list provided in FIG. 75C, wherein the candidate biomarker predicts the occurrence of SLE relative to a population of other autoimmune, non-autoimmune mimic diseases, and healthy subjects.

In still other instances, the autoimmune disease targeted in the methods, devices and assays disclosed herein is RA and the reference group of subjects are healthy subjects, and the discriminating peptides that differentiate the first combination of binding signals from the second combination of binding signals are enriched by at least 100% in one or more sequence motifs listed in FIG. 76A. In some instances, the autoimmune disease is RA and the reference group of subjects are healthy subjects, and the discriminating peptides that differentiate the first combination of binding signals from the second combination of binding signals are enriched by at least 100% in one or more amino acids listed in FIG. 76B. In other instances, the autoimmune disease is SLE and the reference group of subjects are healthy subjects and the discriminating peptides that differentiate the first combination of binding signals from the second combination of binding signals are selected comprise at least one peptide of the list provided in FIG. 93. In some aspects, the autoimmune disease is RA and the reference group of subjects are healthy subjects, and wherein the at least one candidate biomarker is selected from the list provided in FIG. 87A.

In one aspect, the methods, devices and assays disclosed herein provide a set of discriminating peptides, wherein the discriminating peptides comprise one or more sequence motifs provided in FIG. 76A, wherein the discriminating peptides differentiate the binding of antibodies from samples from subjects with RA from healthy subjects. In some embodiments, the peptides are selected from the list provided in FIG. 93.

In other aspects, the methods, devices and assays disclosed herein provide a candidate biomarker for RA selected from the list provided in FIG. 87A, wherein the candidate biomarker predicts the occurrence of RA relative to a population of healthy subjects.

In some aspects, the autoimmune disease targeted in the methods, devices and assays disclosed herein is RA and the reference group of subjects are subjects with other autoimmune, non-autoimmune mimic diseases, and healthy subjects comprising, and the discriminating peptides that differentiate the first combination of binding signals from the second combination of binding signals are enriched by at least 100% in one or motifs listed in FIG. 78A. In some instances, the autoimmune disease is RA and the reference group of subjects are subjects with other autoimmune, non-autoimmune mimic diseases, and healthy subjects, and the discriminating peptides that differentiate the first combination of binding signals from the second combination of binding signals are enriched by at least 100% in one or amino acids listed in FIG. 78B. In other instances, the autoimmune disease is RA and the reference group of subjects are subjects with other autoimmune, non-autoimmune mimic diseases, and healthy subjects, and the discriminating peptides that differentiate the first combination of binding signals from the second combination of binding signals are selected comprise at least one peptide of the list provided in FIG. 95. In yet other instances, the autoimmune disease is RA and the reference group of subjects are subjects with other autoimmune, non-autoimmune mimic diseases, and healthy subjects, and wherein the at least one candidate biomarker is selected from the list provided in FIG. 87C.

In some aspects, the methods, devices and assays disclosed herein provide a set of discriminating peptides, wherein the discriminating peptides comprise one or more sequence motifs provided in FIG. 78A, wherein the discriminating peptides differentiate the binding of antibodies from samples from subjects with RA from subjects with other autoimmune, non-autoimmune mimic diseases, and healthy subjects. In some instances, the peptides are selected from the list provided in FIG. 95.

In other aspects, the methods, devices and assays disclosed herein provide a candidate biomarker for RA selected from the list provided in FIG. 87C, wherein the candidate biomarker predicts the occurrence of RA relative to a population of subjects with other autoimmune, non-autoimmune mimic diseases, and healthy subjects.

In other instances, the autoimmune disease targeted by the methods, devices and assays disclosed herein is RA and the reference group of subjects are subjects with other autoimmune and non-autoimmune mimic diseases, and the discriminating peptides that differentiate the first combination of binding signals from the second combination of binding signals are enriched by at least 100% in one or more amino acids listed in FIG. 79A. In yet other instances, the autoimmune disease is RA and the reference group of subjects are subjects with other autoimmune and non-autoimmune mimic diseases, and the discriminating peptides that differentiate the first combination of binding signals from the second combination of binding signals are enriched by at least 100% in one or more amino acids listed in FIG. 79B.

In still other instances, the autoimmune disease is RA and the reference group of subjects are subjects with other autoimmune and non-autoimmune mimic diseases, and wherein the at least one candidate biomarker is selected from the list provided in FIG. 87B. In yet other instances, the autoimmune disease is RA and the reference group of subjects are subjects with other autoimmune and non-autoimmune mimic diseases, and the discriminating peptides that differentiate the first combination of binding signals from the second combination of binding signals are selected comprise at least one peptide of the list provided in FIG. 94. In still other instances, the autoimmune disease is RA and the reference group of subjects are subjects with other autoimmune and non-autoimmune mimic diseases, and wherein the at least one candidate biomarker is selected from the list provided in FIG. 87B.

In one aspect, the methods, systems and assays disclosed herein provide a set of discriminating peptides, wherein the discriminating peptides comprise one or more sequence motifs provided in FIG. 79A, wherein the discriminating peptides differentiate the binding of antibodies from samples from subjects with RA from subjects with other autoimmune and non-autoimmune mimic diseases. In some instances, the peptides are selected from the list provided in FIG. 94.

In other aspects, the methods, systems and assays disclosed herein provide a candidate biomarker for RA selected from the list provided in FIG. 87B, wherein the candidate biomarker predicts the occurrence of RA relative to a population of subjects with other autoimmune and non-autoimmune mimic diseases.

Also disclosed herein are methods, systems and assays for identifying at least one candidate biomarker for an infection comprising: (a) providing a peptide array and contacting a biological sample from a plurality of subjects known to have or suspected of having an infection to the peptide array; (b) identifying a set of discriminating peptides bound to antibodies in the biological sample from said subject, the set of discriminating peptides displaying binding signals capable of differentiating samples that are seropositive for said infectious disease from samples that are seronegative for said infectious disease; (c) aligning each of the peptides in the set of discriminating peptides to one or more proteins in a proteome; and (d) obtaining a protein score and ranking for each of the identified proteins according to a statistical significance, thereby identifying at least one candidate biomarker for the autoimmune disease. In some aspects, the methods, systems and assays further comprise obtaining an overlap score, wherein said score corrects for the peptide composition of the peptide library. In some instances, the ranking for each of the identified proteins is made relative to the ranking of proteins identified from aligning randomly chosen non-discriminating peptides. In other instances, the identified candidate biomarkers are ranked according to a p-value of less than $10^{-3}$.

In some instances, the step of identifying the set of discriminating peptides comprises: (i) detecting the binding of antibodies present in the samples from the plurality of subjects known to have or suspected of having the infection to obtain a first combination of binding signals; (ii) detecting the binding of antibodies to a same peptide array of peptides, said antibodies being present in samples from one or more reference groups of subjects, identifying a set of discriminating peptides bound to antibodies in the biological sample from said subject, the set of discriminating peptides displaying binding signals capable of differentiating samples that are seropositive for said infectious disease from samples that are seronegative for said infectious disease; (iii) comparing the first to the second combination of binding signals to obtain a set of differentiating binding signals; and (iv) identifying the peptides on the array that are differentially bound by antibodies in samples from subjects having the autoimmune disease and the antibodies in the samples from the one or more reference groups of subjects, thereby identifying said discriminating peptides.

In some instances, the discriminating peptides comprise an enrichment of one or more sequence motifs of at least 100% as compared to the remaining peptides on the array. In other instances, the discriminating peptides comprise an enrichment of one or more amino acids of at least 100% as compared to the remaining peptides on the array. In yet other instances, the first combination of binding signals comprises signals that are lower than signals from the second combination of binding signals. In still other embodiments, the set of differentiating binding signals is obtained by detecting the binding of antibodies present in samples from subjects having or suspected of having the infection and the antibodies in the samples from the one or more reference group of subjects to at least 25 peptides on an array of peptides comprising at least 10,000 different peptides. In one aspect, the number of discriminating peptides corresponds to at least a portion of the total number of peptides on the array. In other aspects, the method performance for differentiating the autoimmune disease from the at least one different health condition is characterized by an area under the receiver operator characteristic (ROC) curve (AUC) ranging from 0.60 to 0.70, 0.70 to 0.79, 0.80 to 0.89, or 0.90 to 1.00.

In some aspects, the infection is selected from a parasitic infection. In some instances, the infection is a *T. cruzi* infection, and the method differentiates subjects that are seropositive from subjects that are seronegative for *T. cruzi*. In one aspect, the subjects having or suspected of having said infection are asymptomatic for the *T. cruzi* infection. In another aspects, the subjects having or suspected of having said infection are symptomatic for the *T. cruzi* infection. In still other instances, the subjects having or suspected of having the *T. cruzi* infection and the reference subjects are asymptomatic for any infectious disease. In one aspect, the discriminating peptides that differentiate the first combination of binding signals from the second combination of binding signals are enriched by at least 100% in one or more motifs listed in FIGS. 36B-36F. In another aspect, the discriminating peptides that differentiate the first combination of binding signals from the second combination of binding signals are enriched by at least 100% in one or more amino acids listed in FIG. 36A. In still other aspects, discriminating peptides that differentiate the first combination of binding signals from the second combination of binding signals are selected comprise at least one peptide of the list provided in FIGS. 48A-48N. In still other aspects, the at least one candidate biomarker is selected from the list provided in Tables 6 and 7.

In some instances, the methods, systems and assays disclosed herein provide a set of discriminating peptides that differentiate the binding of antibodies in samples from subjects that are seropositive for *T. cruzi* from subjects that are seronegative for *T. cruzi*, wherein the discriminating peptides comprise one or more sequence motifs provided in FIGS. 36B-36F. In some instances, the peptides are selected from the list provided in FIGS. 48A-48N. In other aspects, the peptides comprise peptides that correlate with the activity of the *T. cruzi* infection.

In one aspect, the methods, devices and assays disclosed herein provide a candidate biomarker for a *T. cruzi* infection, wherein the biomarker is selected from the biomarkers provided in Tables 6 and 7, and wherein the candidate biomarker identifies subjects that are seropositive for *T. cruzi*.

Also disclosed herein are methods, assays and devices for identifying at least one candidate biomarker indicative of autoimmune disease activity comprising: (a) providing a peptide array and contacting a plurality of biological samples from a plurality of subjects known to have the autoimmune disease to the peptide array; (b) identifying a set of discriminating peptides bound to antibodies in the biological samples, wherein the binding to the discriminating peptides correlates with a known disease score, and wherein binding to the discriminating peptides further correlates a change in antibody binding with a change in known disease score; (c) aligning each of the peptides in the set of discriminating peptides to one or more proteins in a proteome; and (d) obtaining a protein score and ranking for each of the identified proteins according to a statistical significance, thereby identifying at least one candidate biomarker indicative of autoimmune disease activity.

In one aspect, the step of identifying the set of correlating peptides comprises: (i) detecting the binding of antibodies present in the samples from the plurality of subjects having the autoimmune disease at a corresponding known first disease score to obtain a first combination of binding signals; (ii) detecting the binding of antibodies in samples collected from the same plurality of subjects at a later time and corresponding known at least second disease score to a same peptide array of peptides, to obtain at least a second combination of binding signals for each of the subjects; (iii) comparing the first combination of binding signals and first known disease score to the second combination of binding signals and at least second disease score; and (iv) identifying the peptides that display a correlation between (i) the change between the first and at least second combination of binding signals, and (ii) the corresponding change in known disease score for each subject; thereby identifying the set of correlating peptides.

In other aspects, the first combination of binding signals correlates with the first known disease score, and wherein the second combination of binding signals correlates with the second disease score. In still other aspects, the autoimmune disease comprises systemic lupus erythematosus (SLE), rheumatoid arthritis, Sjogren's disease, multiple sclerosis, ulcerative colitis, psoriatic arthritis, scleroderma and/or type I diabetes. In still other aspects, the autoimmune disease is systemic lupus erythematosus (SLE). In still other instances, discriminating peptides correlate with SLE disease activity score and/or a change in lupus disease activity score as defined by the SLEDAI score. In one aspect, the set of discriminating peptides are enriched by greater than 100% in one or more sequence motifs or amino acids listed in FIGS. 60A-60G. In other instances, the set of discriminating peptides comprise one or more of the peptides provided in FIG. 61. In yet other aspects, the candidate biomarker is selected from the set of biomarkers provided in Table 11. In still other aspects, the first combination of binding signals comprises signals that are lower than signals from the second combination of binding signals. In still other aspects, the set of discriminating peptides is obtained by detecting the binding of antibodies present in samples from subjects to at least 25 peptides on an array of peptides comprising at least 10,000 different peptides. In some instances, the number of discriminating peptides corresponds to at least a portion of the total number of peptides on the array.

In some aspects, the methods, assays and devices disclosed herein provide a set of discriminating peptides, wherein the discriminating peptides comprise one or more sequence motifs provided in FIGS. 60A-60G, wherein the discriminating peptides correlate with SLE disease activity score and/or a change in SLE disease activity score as defined by the SLEDAI score. In some instances, the peptides are selected from the list provided in FIG. 61.

In one aspect, the methods, assays and devices disclosed herein provide a candidate biomarker for predicting the presence and/or SLE disease activity, wherein said candidate biomarker is a protein or a fragment thereof selected from the list in Table 11.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings in the following.

FIG. 5 is a list of clinical manifestations and physiological symptoms of SSc.

FIG. 6 is an example of a list of clinical symptoms used to assess SSc diagnosis and assessment.

FIG. 7 shows a list of clinical manifestations and symptoms for polymyositis and dermatomyositis, and clinical differentiation criteria for both.

FIGS. 8A-8C shows a listing of the top submotifs (SEQ ID NOS 1-8, respectively, in order of appearance) (FIG. 8A) and the amino acids (FIG. 8B) most enriched in the top 1000 discriminating peptides obtained when comparing patients with SSc and healthy subjects; and a list of the top 50 discriminating peptides obtained from the comparison of samples from SSc patients and samples from healthy subjects (SEQ ID NOS 9-58, respectively, in order of appearance) (FIG. 8C).

FIG. 9A is Volcano Plot depicting the differentiation of subjects with Scleroderma (SSc) from healthy controls by peptide binding intensities. The ratio of mean intensity among samples from patients with Scleroderma to mean intensity in control patients is plotted vs. the p-value for the difference in means from a t-test.

FIG. 9B shows ROC curves for an ImmunoSignature model of Scleroderma for identifying patients with Scleroderma from healthy controls. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

FIG. 9C shows ROC estimates as a function of input size—Five fold cross validated area under the ROC curve (+/−95% CI) are provided for models of different input peptide sizes. Peptides were selected based on a t-test and the top k features were used in a support vector machine to build a classifier of Scleroderma vs. healthy controls. Feature selection and model construction were performed within the cross-validation loop to prevent bias.

FIGS. 10A-10B shows a listing of the top submotifs (SEQ ID NOS 59-74, respectively, in order of appearance) (FIG. 10A) and the amino acids (FIG. 10B) that are most enriched in the top 1000 discriminating peptides identified obtained when comparing patients diagnosed with SSc and other autoimmune disorders.

FIG. 11A is a Volcano Plot depicting the differentiation of subjects with Scleroderma (SSc) from other autoimmune mimic diseases ("Other AI") by peptide binding intensities. The ratio of mean intensity among samples from patients with Scleroderma to mean intensity in patients with other autoimmune disorders is plotted vs. the p-value for the difference in means from a t-test.

FIG. 11B shows ROC curves for an ImmunoSignature model of Scleroderma for identifying patients with Scleroderma from other autoimmune diseases. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

FIG. 11C shows ROC estimates as a function of input size—Four fold cross validated area under the ROC curve (+/−95% CI) are provided for models of different input peptide sizes. Peptides were selected based on a t-test and the top k features were used in a support vector machine to build a classifier of Scleroderma vs. other autoimmune disorders. Feature selection and model construction were performed within the cross-validation loop to prevent bias.

FIGS. 12A-12B shows a listing of the top submotifs (SEQ ID NOS 75-94, respectively, in order of appearance) (FIG. 12A) and amino acids (FIG. 12B) most enriched in the 1000 top discriminating peptides identified in an immunosignature obtained when comparing patients diagnosed with SSc and patients in a renal crisis.

FIG. 13A shows a Volcano Plot depicting the differentiation of subjects with Scleroderma (SSc) having renal crisis from subjects with SSc without renal crisis by peptide binding intensities. The ratio of mean intensity among samples from patients with Scleroderma having renal crisis to mean intensity in patients with SSc without renal crisis is plotted vs. the p-value for the difference in means from a t-test.

FIG. 13B shows ROC curves for an ImmunoSignature model of Scleroderma for identifying patients with Scleroderma with renal crisis from subjects with SSc without renal crisis. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

FIG. 13C are ROC estimates as a function of input size—Four fold cross validated area under the ROC curve (+/−95% CI) are provided for models of different input peptide sizes. Peptides were selected based on a t-test and the top k features were used in a support vector machine to build a classifier of Scleroderma with renal crisis vs. SSc without renal crisis. Feature selection and model construction were performed within the cross-validation loop to prevent bias.

FIGS. 14A-14B shows a listing of the top submotifs (SEQ ID NOS 95-105, respectively, in order of appearance) (FIG. 14A) and amino acids (FIG. 14B) most enriched in the 1000 top discriminating peptides identified in an immunosignature when comparing a table depicting the top discriminating peptides in an immunosignature obtained when comparing patients diagnosed with SSc and gastric antral vascular ectasia (GAVE).

FIG. 15A shows a Volcano Plot depicting the differentiation of subjects with Scleroderma (SSc) having Gastric Antral Vascular Ectasia (GAVE) from subjects with SSc without GAVE by peptide binding intensities. The ratio of mean intensity among samples from patients with Scleroderma having GAVE to mean intensity in patients with SSc without GAVE is plotted vs. the p-value for the difference in means from a t-test.

FIG. 15B shows ROC curves for an ImmunoSignature model of Scleroderma for identifying patients with Scleroderma with GAVE from subjects with SSc without GAVE. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

FIG. 15C shows ROC estimates as a function of input size—Four-fold cross validated area under the ROC curve (+/−95% CI) are provided for models of different input peptide sizes. Peptides were selected based on a t-test and the top k features were used in a support vector machine to build a classifier of Scleroderma with GAVE vs. SSc without GAVE. Feature selection and model construction were performed within the cross-validation loop to prevent bias.

FIGS. 16A-16B shows a listing of the top submotifs (SEQ ID NOS 106-119, respectively, in order of appearance) (FIG. 16A) and amino acids (FIG. 16B) most enriched in the 1000 top discriminating peptides identified in an immunosignature obtained when comparing patients diagnosed with SSc and DM.

FIG. 17A shows a Volcano Plot depicting the differentiation of subjects with Scleroderma (SSc) from subjects with Dermatomyositis (DM) by peptide binding intensities. The ratio of mean intensity among samples from patients with DM to mean intensity in patients with DM is plotted vs. the p-value for the difference in means from a t-test.

FIG. 17B shows ROC curves for an ImmunoSignature model of Scleroderma for identifying patients with Scleroderma from DM. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

FIG. 17C shows ROC estimates as a function of input size—Four fold cross validated area under the ROC curve (+/−95% CI) are provided for models of different input peptide sizes. Peptides were selected based on a t-test and the top k features were used in a support vector machine to build a classifier of Scleroderma vs. DM. Feature selection and model construction were performed within the cross-validation loop to prevent bias.

FIGS. 18A-18B show a listing of the top submotifs (SEQ ID NOS 120-131, respectively, in order of appearance) (FIG. 18A) and amino acids (FIG. 18B) most enriched in the 1000 top discriminating peptides identified in an immunosignature obtained when comparing patients diagnosed with SSc with interstitial lung disease (ILD+) and SSc without interstitial lung disease (ILD−).

FIG. 19A shows a Volcano plot visualizing the differentiation of subjects with Scleroderma (SSc) having Interstitial Lung Disease (ILD) (ILD+) from subjects with SSC without ILD (ILD−) by peptide binding intensities. The ratio of mean intensity among samples from patients with Scleroderma-ILD+ to mean intensity in patients with SSC ILD− is plotted vs. the p-value for the difference in means from a t-test.

FIG. 19B shows ROC curves for an ImmunoSignature model of Scleroderma for identifying patients with Scleroderma ILD+ from subjects with SSc ILD−. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

FIGS. 20A-20B shows a listing of the top submotifs (SEQ ID NOS 132-141, respectively, in order of appearance) (FIG. 20A) and amino acids (FIG. 20B) most enriched in the 1000 top discriminating peptides identified in an immunosignature obtained when comparing patients diagnosed with DM and healthy subjects.

FIG. 21A shows a Volcano Plot depicting the differentiation of subjects with Dermatomyositis (DM) from healthy controls by peptide binding intensities. The ratio of mean intensity among samples from patients with DM to mean intensity in control patients is plotted vs. the p-value for the difference in means from a t-test.

FIG. 21B shows ROC curves for an ImmunoSignature model of DM for identifying patients with DM from healthy controls. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

FIG. 21C shows ROC estimates as a function of input size—Four fold cross validated area under the ROC curve (+/−95% CI) are provided for models of different input peptide sizes. Peptides were selected based on a t-test and the top k features were used in a support vector machine to build a classifier of DM vs. healthy controls. Feature selection and model construction were performed within the cross-validation loop to prevent bias.

FIGS. 22A-22B show a listing of the top submotifs (SEQ ID NOS 142-147, respectively, in order of appearance) (FIG. 22A) and amino acids (FIG. 22B) most enriched in the 1000 top discriminating peptides identified in an immunosignature obtained when comparing patients diagnosed with DM and other autoimmune disorders.

FIG. 23A shows a Volcano Plot depicting the differentiation of subjects with Dermatomyositis (DM) from other autoimmune mimic diseases (Other AI) by peptide binding intensities. The ratio of mean intensity among samples from patients with Scleroderma to mean intensity in patients with other autoimmune disorders is plotted vs. the p-value for the difference in means from a t-test.

FIG. 23B shows ROC curves for an ImmunoSignature model of DM for identifying Subjects with Dermatomyositis (DM) from other autoimmune mimic diseases (Other AI). The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

FIG. 23C shows ROC estimates as a function of input size—Four fold cross validated area under the ROC curve (+/−95% CI) are provided for models of different input peptide sizes. Peptides were selected based on a t-test and the top k features were used in a support vector machine to build a classifier of DM vs. other autoimmune disorders. Feature selection and model construction were performed within the cross-validation loop to prevent bias.

FIGS. 24A-24B show a listing of the top submotifs (SEQ ID NOS 148-154, respectively, in order of appearance) (FIG. 24A) and amino acids (FIG. 24B) most enriched in the 1000 top discriminating peptides identified in an immunosignature obtained when comparing patients diagnosed with DM and Interstitial lung disease (ILD+) and DM without interstitial lung disease (ILD−).

FIG. 25A shows a Volcano Plot depicting the differentiation of subjects with Dermatomyositis (DM) having Interstitial Lung Disease (ILD) (ILD+) from subjects with DM without ILD (ILD−) by peptide binding intensities. The ratio of mean intensity among samples from patients with DM ILD+ to mean intensity in patients with DM ILD− is plotted vs. the p-value for the difference in means from a t-test.

FIG. 25B shows ROC curves for an ImmunoSignature model of DM for identifying patients with DM with ILD from subjects with DM without ILD. The green line (top) indicates the upper 95% confidence interval of the classifier (middle) and the red line (bottom) the lower 95% confidence interval. Sensitivity estimates are provided for a test with 90% Specificity and Specificity estimates are provided for a test with 90% Sensitivity. Accuracy is estimated at a threshold that matches sensitivity and specificity.

FIG. 25C shows ROC estimates as a function of input size—Five fold cross validated area under the ROC curve (+/−95% CI) are provided for models of different input peptide sizes. Peptides were selected based on a t-test and the top k features were used in a support vector machine to build a classifier of DM ILD+vs. DM ILD−. Feature selection and model construction were performed within the cross-validation loop to prevent bias.

FIGS. 31A-31B show performance of immunosignature assay (IST) in distinguishing Chagas seropositive from seronegative donors. (FIG. 31A) Receiver Operating Characteristic (ROC) curve for the 2015 training cohort. The blue curve was generated by calculating the median of out-of-bag predictions in 100 four-fold cross-validation trials. (FIG. 31B) ROC curve for the 2016 verification cohort. The blue curve was generated by applying the training set-derived algorithm to predict the 2016 samples. Confidence intervals (CI), shown in gray, were estimated by bootstrap resampling of the donors in the training cohort, and estimated by the DeLong method (DeLong E R, et al. *Biometrics* 44:837-845 [1988]) in the verification cohort.

FIGS. 36A-36F show the top amino acids (FIG. 36A) and submotifs (SEQ ID NOS 159-250, respectively, in order of appearance) (FIG. 36B-36F) that are most enriched in the top 1000 discriminating peptides that distinguish samples of seropositive subjects infected with Chagas from sample from subjects that are seronegative (healthy) for Chagas.

FIGS. 37A-37B show the top submotifs (SEQ ID NOS 251-261, respectively, in order of appearance) (FIG. 37A) and amino acids (FIG. 37B) that are most enriched in the top 1000 discriminating peptides that distinguish samples of subjects infected with Chagas from sample from a group of subjects infected with HBV, HCV, and WNV.

FIGS. 38A-38B show the top submotifs (SEQ ID NOS 262-266, respectively, in order of appearance) (FIG. 38A) and amino acids (FIG. 38B) that are most enriched in the top 1000 discriminating peptides that distinguish samples of subjects infected with HBV from sample from a group of subjects infected with Chagas, HCV, and WNV.

FIGS. 39A-39B show the submotifs (SEQ ID NOS 267-280, respectively, in order of appearance) (FIG. 39A) and amino acids (FIG. 39B) that are most enriched in the top 1000 discriminating peptides that distinguish samples of subjects infected with HCV from sample from a group of subjects infected with HBV, Chagas, and WNV.

FIGS. 40A-40B show the top submotifs (SEQ ID NOS 281-285, respectively, in order of appearance) (FIG. 40A) and amino acids (FIG. 40B) that are most enriched in the top 1000 discriminating peptides that distinguish samples of subjects infected with WNV from sample from a group of subjects infected with HBV, HCV, and Chagas.

FIGS. 41A-41B show the top submotifs (SEQ ID NOS 286-296, respectively, in order of appearance) (FIG. 41A) and amino acids (FIG. 41B) that are most enriched in the top 1000 discriminating peptides that distinguish samples of subjects infected with Chagas from samples from subjects infected with HBV.

FIGS. 42A-42B shows the top submotifs (SEQ ID NOS 297-304, respectively, in order of appearance) (FIG. 42A) and amino acids (FIG. 42B) that are most enriched in the top 1000 discriminating peptides that distinguish samples of subjects infected with Chagas from samples from subjects infected with HCV.

FIGS. 43A-43B show the submotifs (SEQ ID NOS 305-317, respectively, in order of appearance) (FIG. 43A) and amino acids (FIG. 43B) that are most enriched in the top 1000 discriminating peptides that distinguish samples of subjects infected with Chagas from samples from subjects infected with WNV.

FIGS. 44A-44B show the submotifs (SEQ ID NOS 318-327, respectively, in order of appearance) (FIG. 44A) and amino acids (FIG. 44B) that are enriched in the top 500 discriminating peptides that distinguish samples of subjects infected with HBV from samples from subjects infected with HCV.

FIGS. 45A-45B show the submotifs (SEQ ID NOS 328-332, respectively, in order of appearance) (FIG. 45A) and amino acids (FIG. 45B) that are enriched in the top 1000 discriminating peptides that distinguish samples of subjects infected with HBV from samples from subjects infected with WNV.

FIGS. 46A-46B show the submotifs (SEQ ID NOS 333-342, respectively, in order of appearance) (FIG. 46A) and amino acids (FIG. 46B) that are most enriched in the top 500 discriminating peptides that distinguish samples of subjects infected with HCV from samples from subjects infected with WNV.

FIGS. 47A-47B show the submotifs (SEQ ID NOS 343-354, respectively, in order of appearance) (FIG. 47A) and amino acids (FIG. 47B) that are most enriched in the top 1000 discriminating peptides that distinguish samples from subjects infected with Chagas, HCV, HBV, and WNV from each other determined by a multiclass classifier.

FIGS. 48A-48N show the sequences of the discriminating peptides that distinguish seropositive Chagas samples from seronegative Chagas samples (SEQ ID NOS 355-724, respectively, in order of appearance).

FIGS. 49A-49B show a SLEDAI Score Sheet of clinical and laboratory manifestations used to assess systemic lupus erythematosus diagnosis and assessment.

FIG. 54A shows the distribution of overlap scores; FIG. 54B shows the alignment of peptides mapped to known protein NGRN (SEQ ID NOS 725-739, respectively, in order of appearance); and FIG. 54C shows examples of known and candidate biomarkers identified by peptide alignments and their cellular location.

FIGS. 60A-60G show the peptide submotifs and amino acids that are enriched in the peptides that correlate to a diagnosis from a SLEDAI score.

FIG. 61 shows a table listing the top 50 of the 702 significant peptides that correlate with SLEDAI scores (SEQ ID NOS 772-821, respectively, in order of appearance).

FIGS. 62A-62B show peptide submotifs (SEQ ID NOS 822-827, respectively, in order of appearance) (FIG. 62A) and amino acids (FIG. 62B) that are enriched in the peptides that discriminate between the systemic lupus erythematosus (SLE) samples from the healthy donor (HC) samples.

FIGS. 63A-63B show peptide submotifs (SEQ ID NOS 828-845, respectively, in order of appearance) (FIG. 63A) and amino acids (FIG. 63B) that are enriched in the peptides that discriminate between the SLE samples from a group of other diseases that are autoimmune and non-autoimmune-mimic diseases (Other AI+non-AI mimic).

FIGS. 64A-64B show peptide submotifs (SEQ ID NOS 846-854, respectively, in order of appearance) (FIG. 64A) and amino acids (FIG. 64B) that are enriched in the peptides that discriminate between the SLE samples from the "Not SLE" samples, which are samples of other autoimmune diseases, non-autoimmune mimic diseases and healthy controls.

FIGS. 65A-65B show peptide submotifs (SEQ ID NOS 855-864, respectively, in order of appearance) (FIG. 65A)

and amino acids (FIG. 65B) that are enriched in the peptides that discriminate between the SLE samples from the rheumatoid arthritis (RA) group of samples.

FIGS. 66A-66B show peptide submotifs (SEQ ID NOS 865-879, respectively, in order of appearance) (FIG. 66A) and amino acids (FIG. 66B) that are enriched in the peptides that discriminate between the SLE samples from the osteoarthritis (OA) group of samples.

FIGS. 67A-67B show peptide submotifs (SEQ ID NOS 880-896, respectively, in order of appearance) (FIG. 67A) and amino acids (FIG. 67B) that are enriched in the peptides that discriminate between the SLE samples from the fibromyalgia (FM) group of samples.

FIGS. 68A-68B show the peptide submotifs (SEQ ID NOS 897-902, respectively, in order of appearance) (FIG. 68A) and amino acids (FIG. 68B) that are enriched in the peptides that discriminate between the SLE samples from the Sjogren's (SS) group of samples.

Figure 69B:
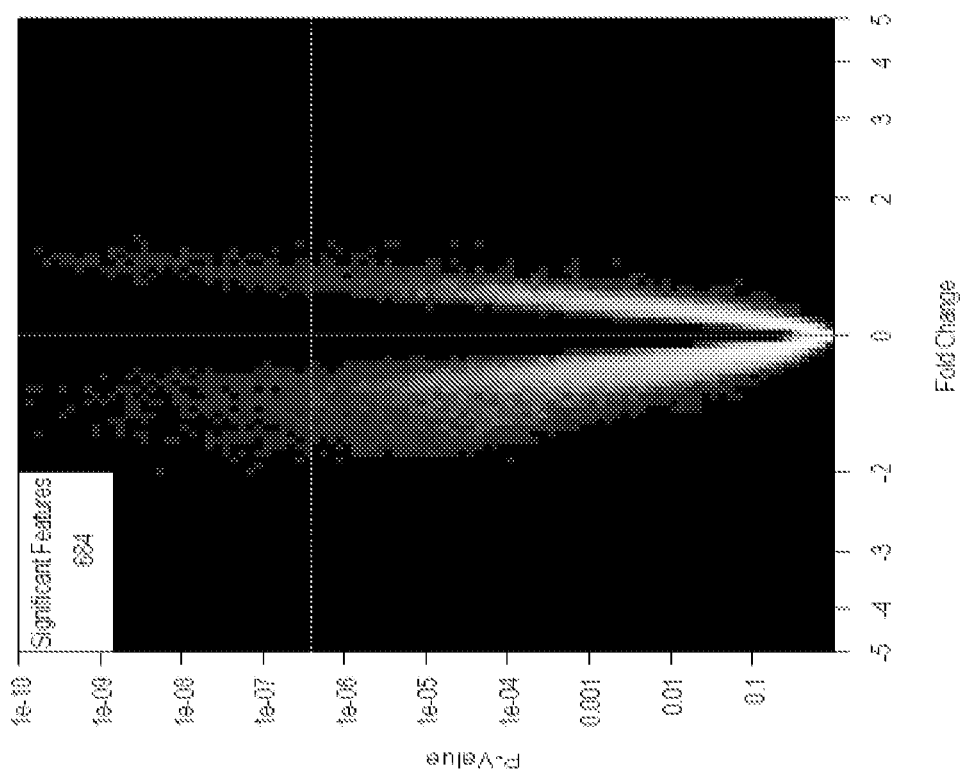
Figure 69A:
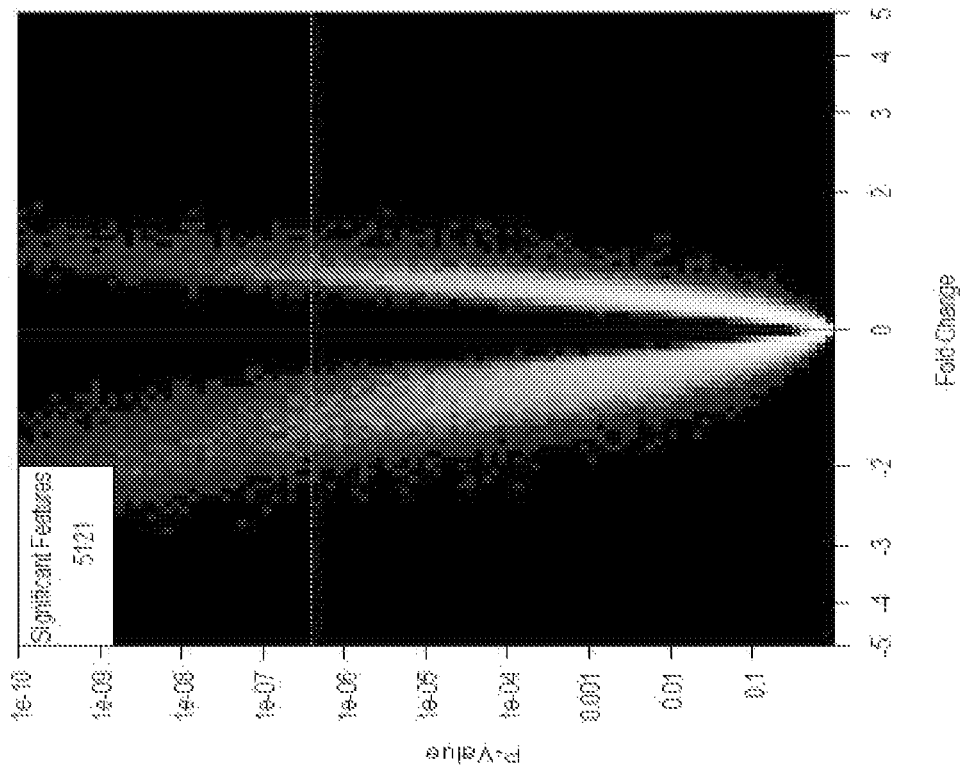
Figure 69C:
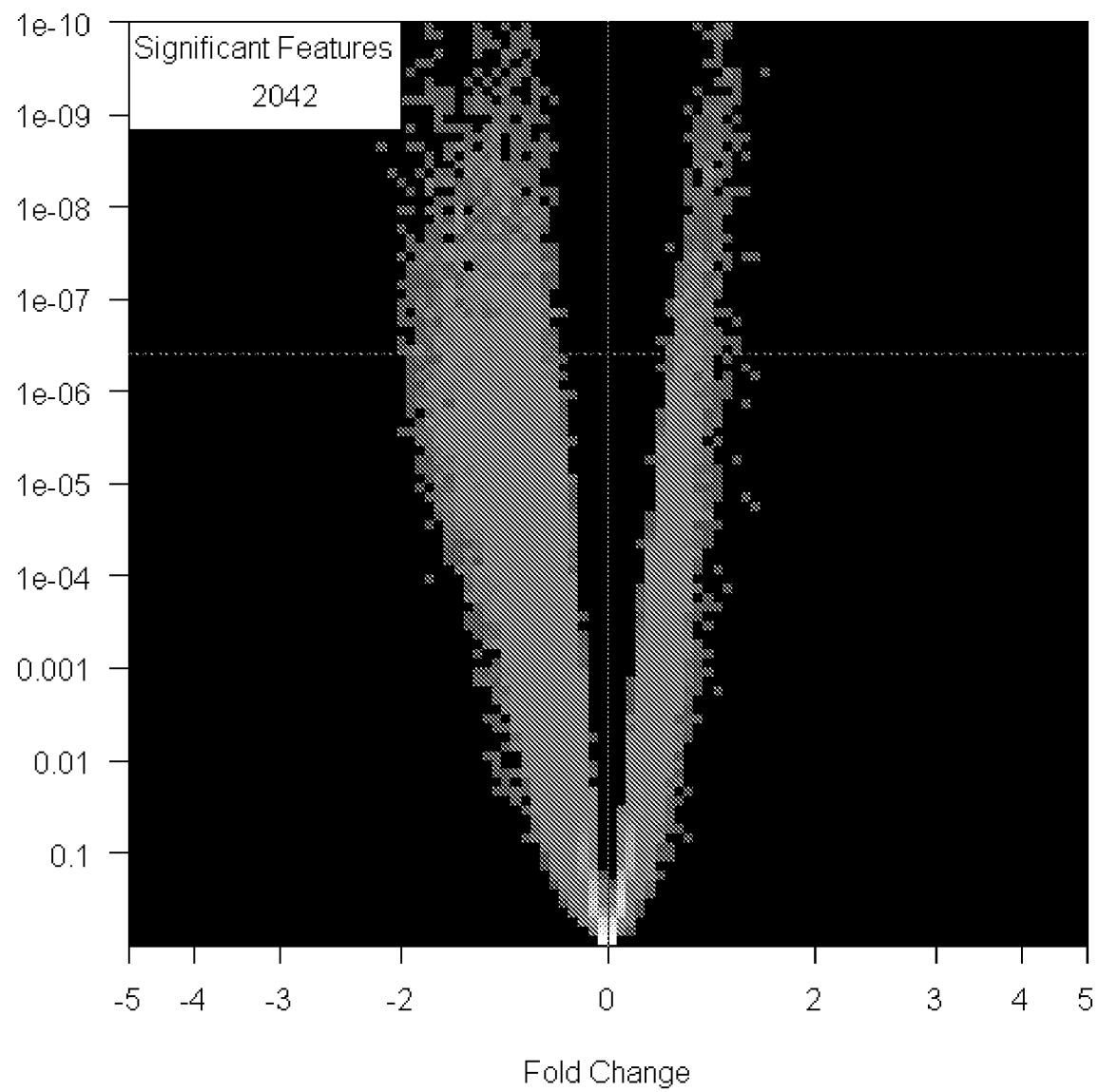

FIGS. 69A-69C show a Volcano plot visualizing library peptides displaying antibody-binding signals that significantly differentiate SLE samples from samples from Healthy Donors (FIG. 69A); a Volcano plot visualizing library peptides displaying antibody-binding signals that significantly differentiate SLE samples from samples of subjects of the "Other AI+non-AI mimic" group (FIG. 69B); and shows a Volcano plot visualizing library peptides displaying antibody-binding signals that significantly differentiate SLE samples from samples of subjects of the "Not SLE" group (FIG. 69C).

Figure 70:
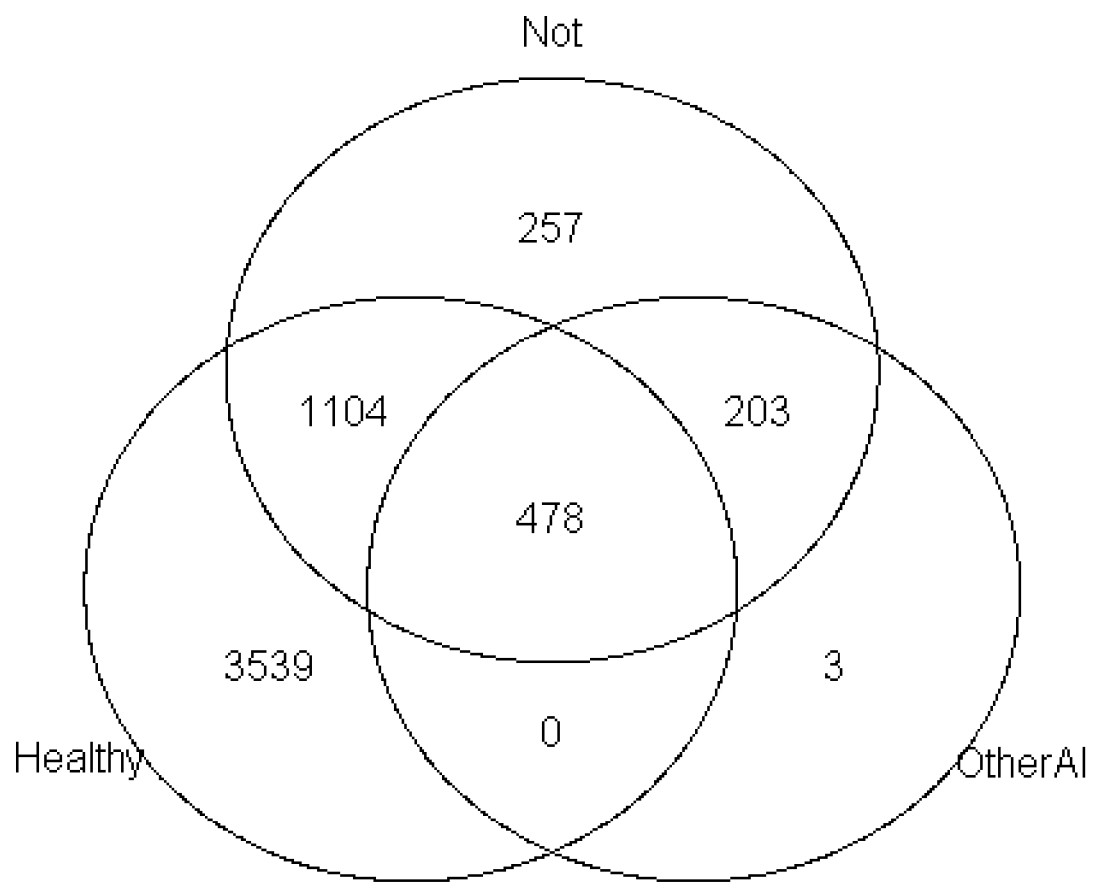

FIG. 70 shows a Venn diagram showing the distribution of peptides that passed the Bonferroni cutoff for each of contrasts and the 478 peptides that are common to all contrasts.

Figure 71:
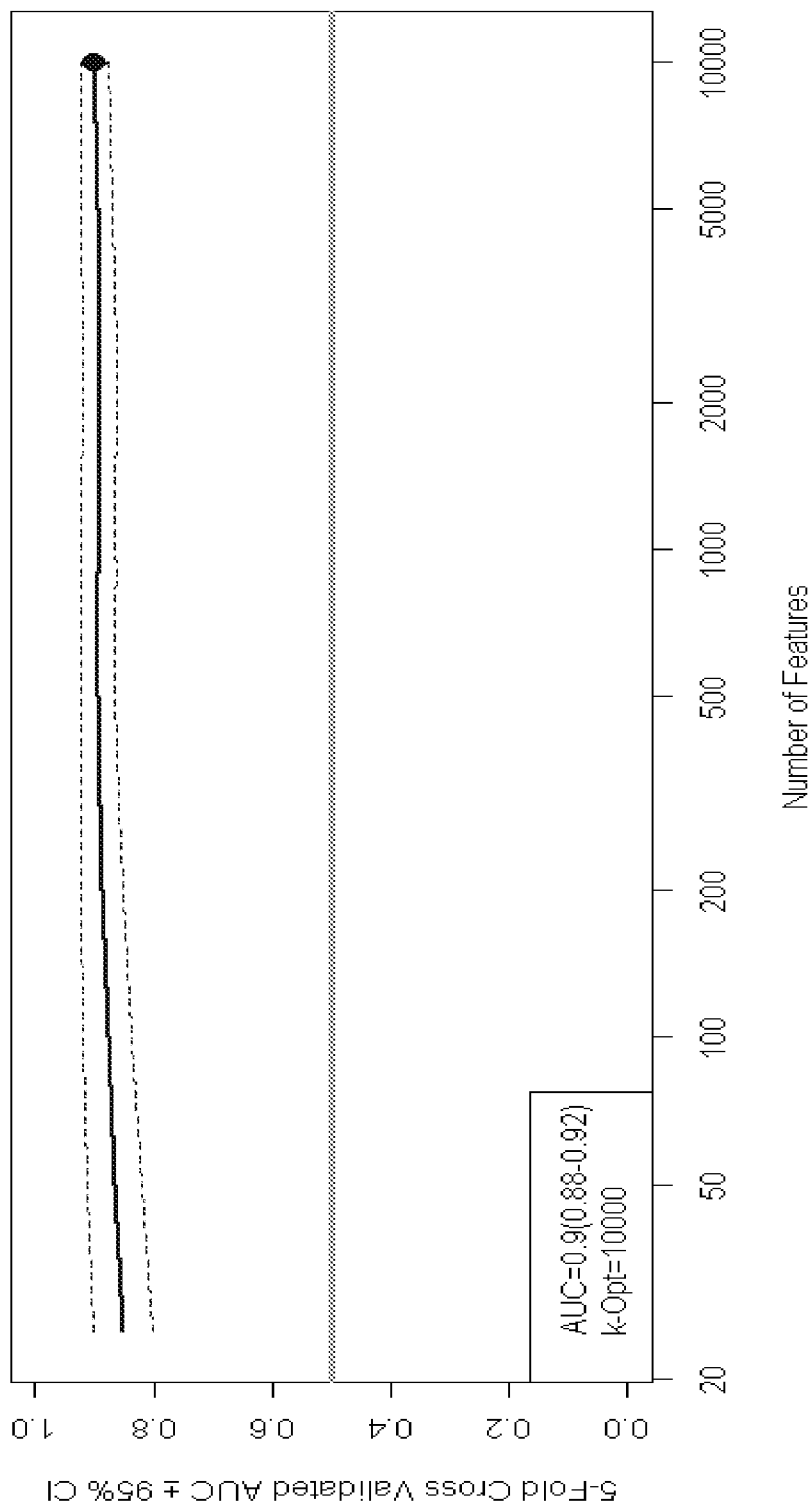

FIG. 71 shows graphs of the 5-fold cross validated performance at a 95% confidence level (Y-axis) as a function of the number of input discriminating peptides (Number of Features i.e. peptides; x-axis) in a SLE Healthy Donor assay.

Figure 72:
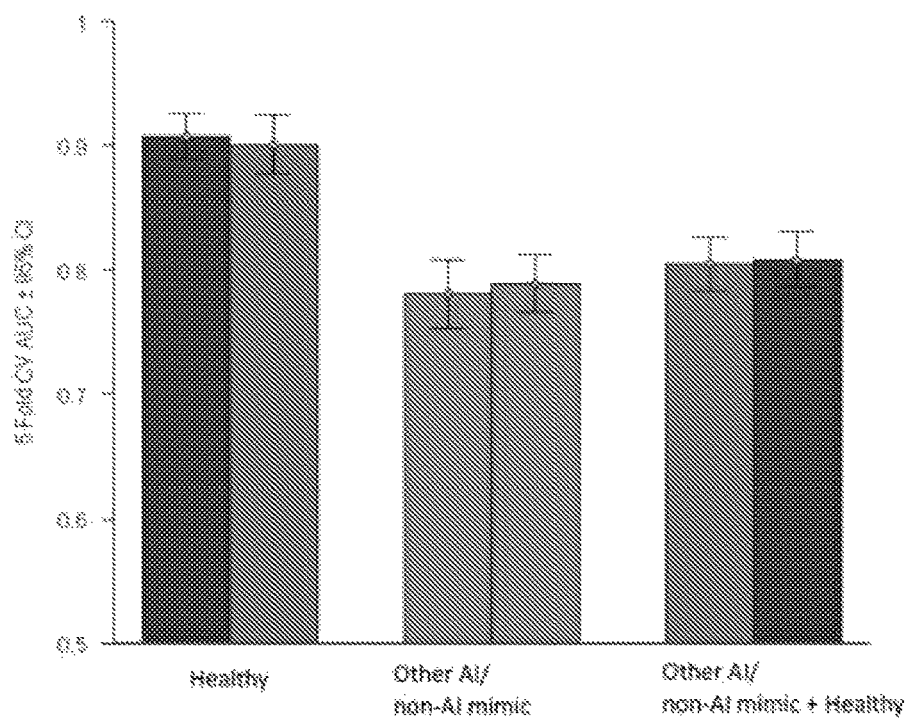

FIG. 72 shows the area under the receiver operating characteristic curve (AUC) as assay performance in discriminating SLE samples from HC, from Other AI+non-AI mimic diseases, and from the "Not SLE" group i.e. Other AI+non-AI mimic+HC. In each group, the bar on the left represents performance in discriminating SLE alone from the indicated condition, and the bar on the right represents performance in discriminating a mixture of Mixed SLE and Other AI samples.

Figure 73:
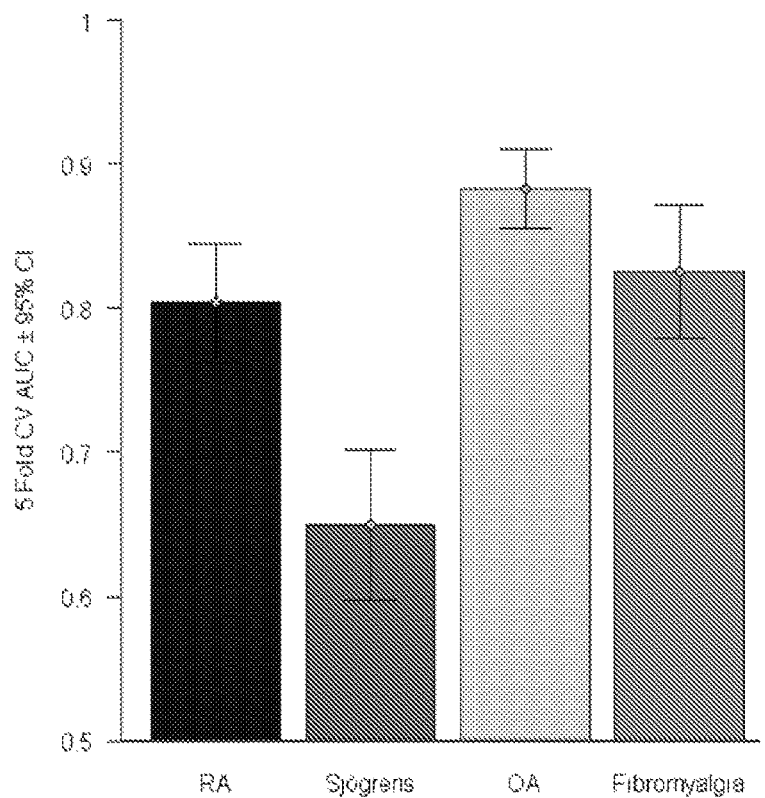

FIG. 73 shows assay performance for differential diagnosis of SLE from RA, Sjogrens, OA, and Fibromyalgia.

Figure 74:
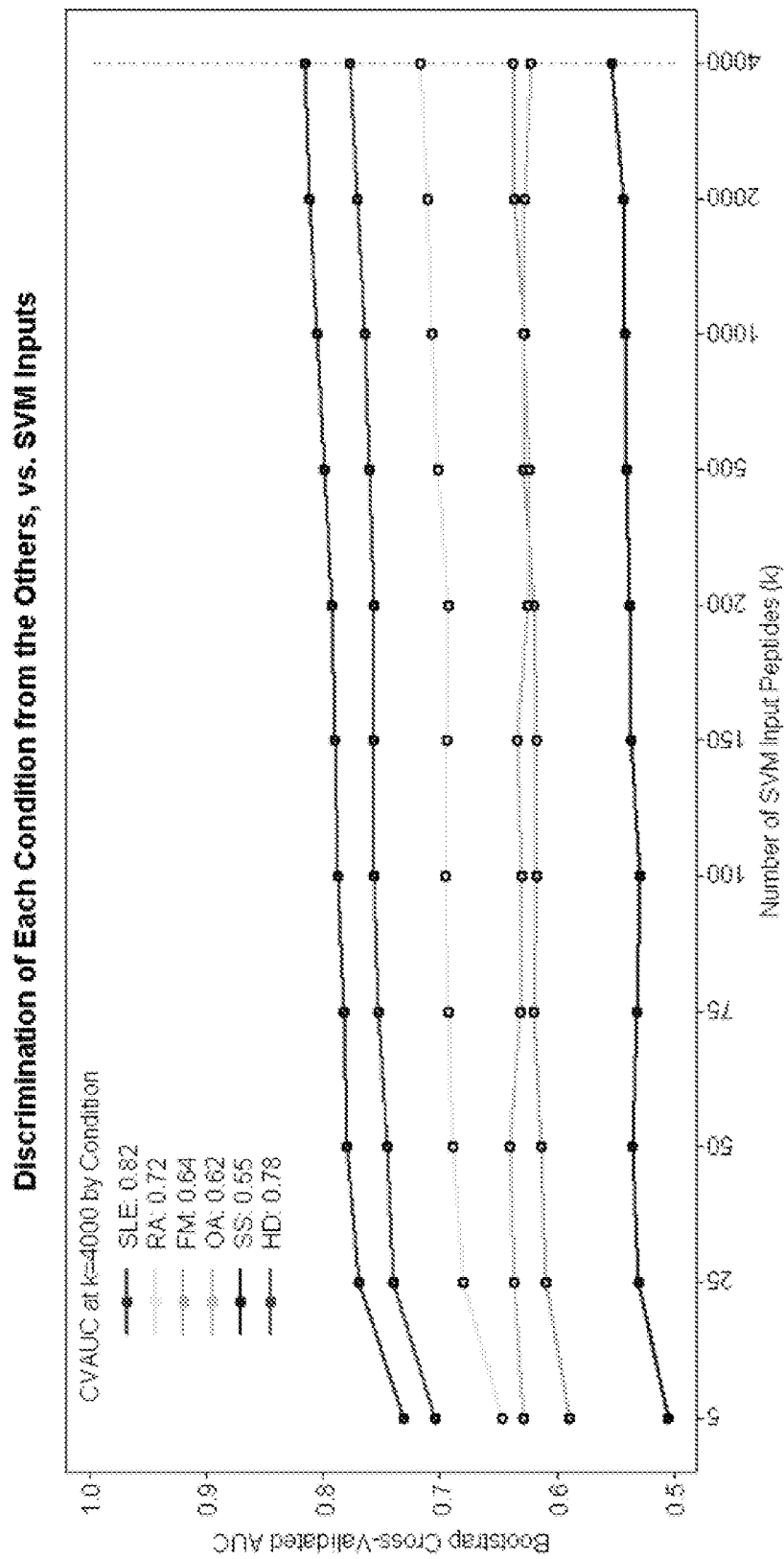

FIG. 74 shows the assay performance using a multiclassifier that simultaneously discriminates each disease from a mixture of the remaining others.

FIGS. 75A-75C show the top candidate biomarkers identified by peptides discriminating SLE from healthy subjects (FIG. 75A), from a group of subjects with other autoimmune disease or autoimmune-mimic diseases (Other AI+non-AI mimic) (FIG. 75B), and from the "Not SLE" group represented (FIG. 75C).

FIGS. 76A-76B show peptide submotifs (SEQ ID NOS 903-916, respectively, in order of appearance) (FIG. 76A) and amino acids (FIG. 76B) that are enriched in the peptides that discriminate between the RA samples from the healthy donor (HC) samples.

FIGS. 77A-77B show peptide submotifs (SEQ ID NOS 917-925, respectively, in order of appearance) (FIG. 77A) and amino acids (FIG. 77B) that are enriched in the peptides that discriminate between the RA samples from the samples from other rheumatic diseases.

FIGS. 78A-78B show peptide submotifs (SEQ ID NOS 926-931, respectively, in order of appearance) (FIG. 78A) and amino acids (FIG. 78B) that are enriched in the peptides that discriminate between the RA samples from the "Not RA" group represented by samples from Other AI+non-AI mimic and HC (C).

FIGS. 79A-79B show peptide submotifs (SEQ ID NOS 932-937, respectively, in order of appearance) (FIG. 79A) and amino acids (FIG. 79B) that are enriched in the peptides that discriminate between the RA samples from Other AI+non-AI mimic group.

FIGS. 80A-80B show peptide submotifs (SEQ ID NOS 938-943, respectively, in order of appearance) (FIG. 80A) and amino acids (FIG. 80B) that are enriched in the peptides that discriminate between the RA samples from the OA group of samples.

FIGS. 81A-81B show peptide submotifs (SEQ ID NOS 944-952, respectively, in order of appearance) (FIG. 81A) and amino acids (FIG. 81B) that are enriched in the peptides that discriminate between the RA samples from the FM group of samples.

FIGS. 82A-82B show peptide submotifs (SEQ ID NOS 953-958, respectively, in order of appearance) (FIG. 82A) and amino acids (FIG. 82B) that are enriched in the peptides that discriminate between the RA samples from the SS group of samples.

Figure 83B:
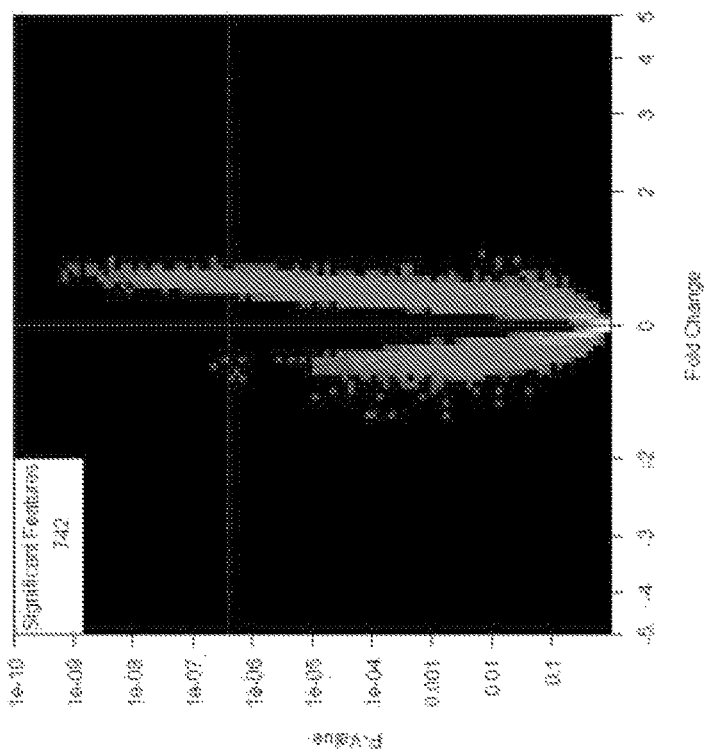
Figure 83A:
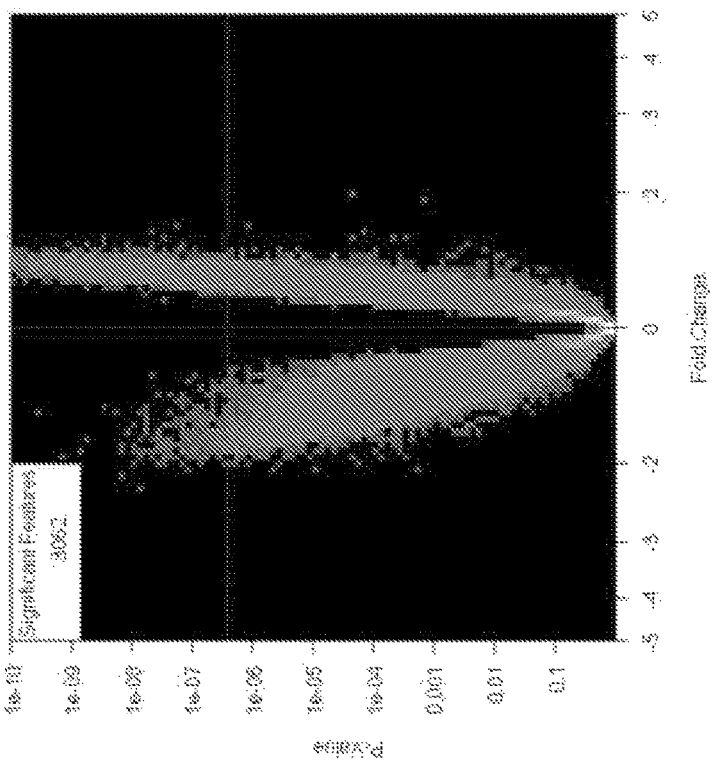

FIG. 83A shows a Volcano plot visualizing library peptides displaying antibody-binding signals that significantly differentiate RA samples from samples from Healthy Donors.

FIG. 83B shows a Volcano plot visualizing library peptides displaying antibody-binding signals that significantly differentiate RA samples from samples of subjects of the "Other AI+non-AI mimic" group.

Figure 83C:
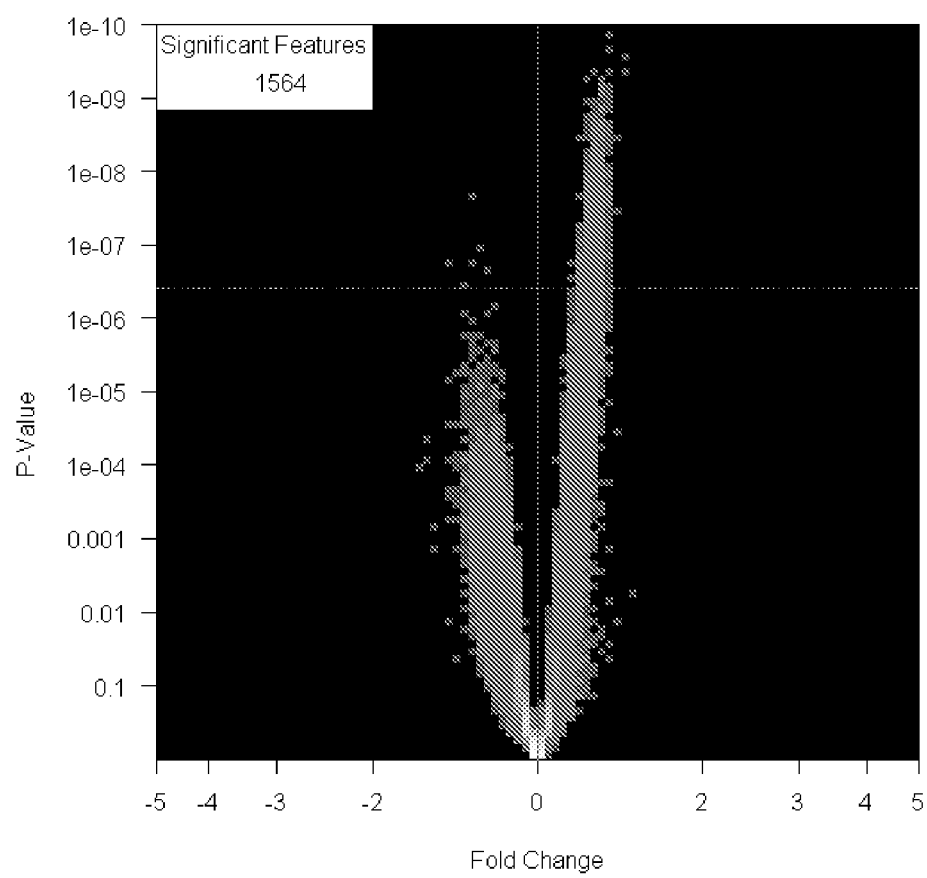

FIG. 83C shows a Volcano plot visualizing library peptides displaying antibody-binding signals that significantly differentiate RA samples from samples of subjects of the "Not RA" group.

Figure 84:
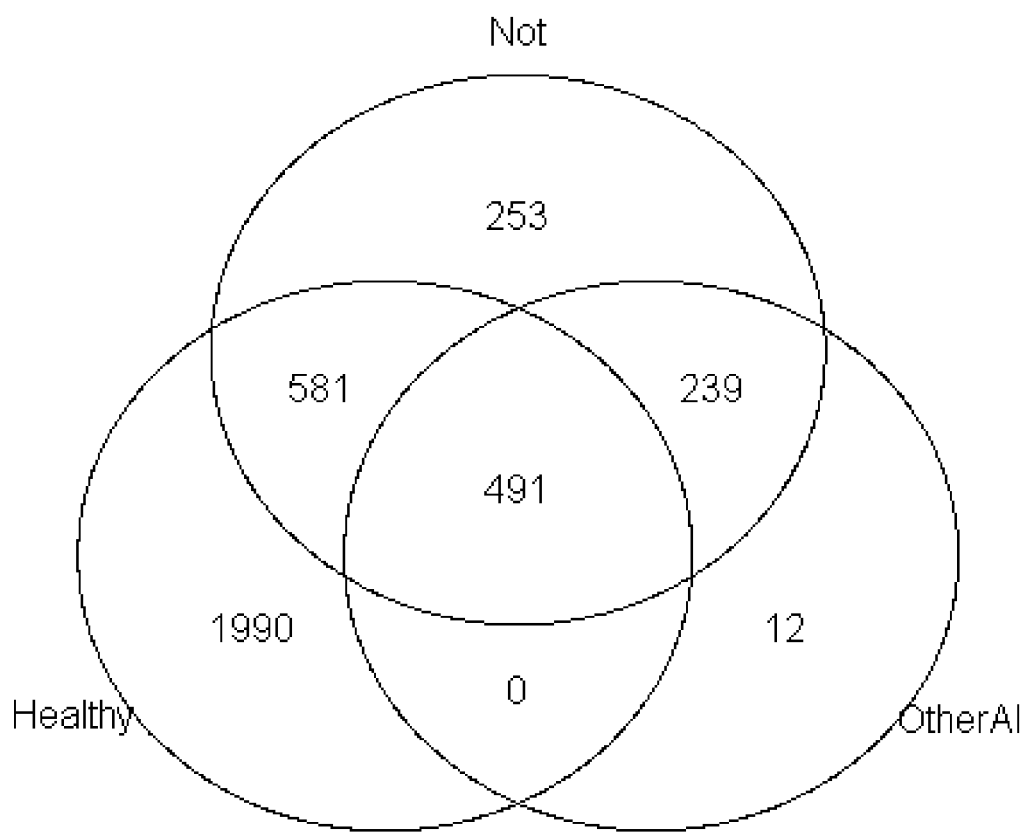

FIG. 84 shows a Venn diagram showing the distribution of peptides that passed the Bonferroni cutoff for each of contrasts and the 491 peptides that are common to all contrasts.

Figure 85:
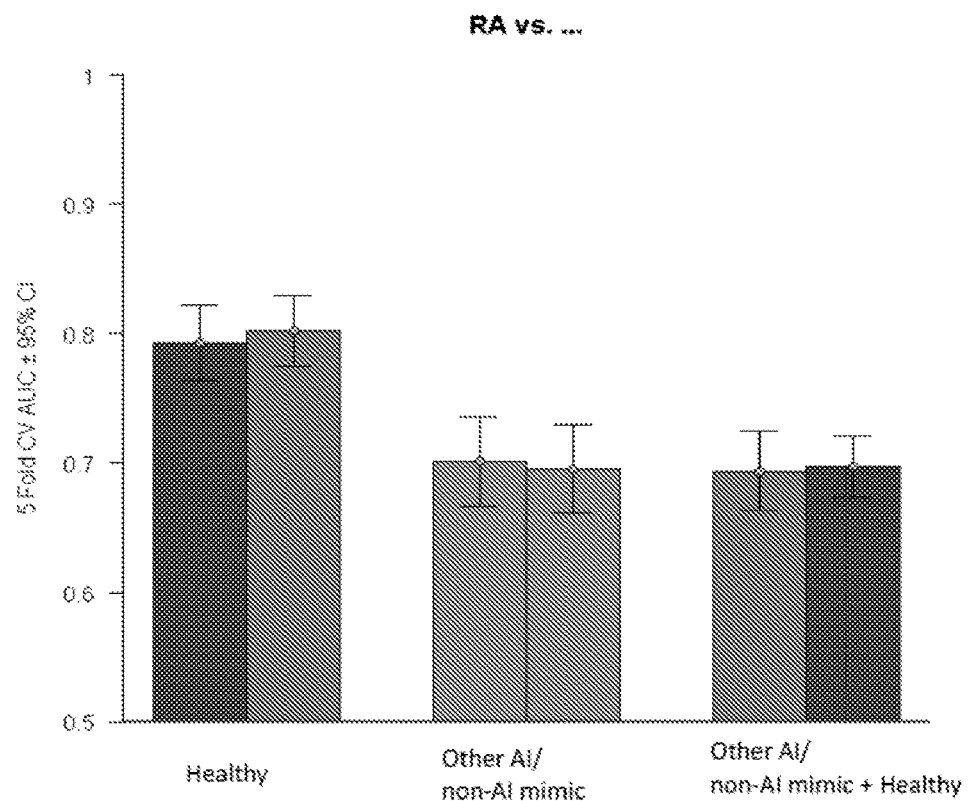

FIG. 85 shows the area under the receiver operating characteristic curve (AUC) as assay performance in discriminating RA samples from HC, from Other AI+non-AI mimic diseases, and from "Not RA" i.e. Other AI+non-AI mimic+HC. In each group, the bar on the left represents performance in discriminating RA alone from the indicated condition, and the bar on the right represents performance in discriminating a mixture of Mixed RA and Other AI+non-AI mimic samples.

Figure 86:
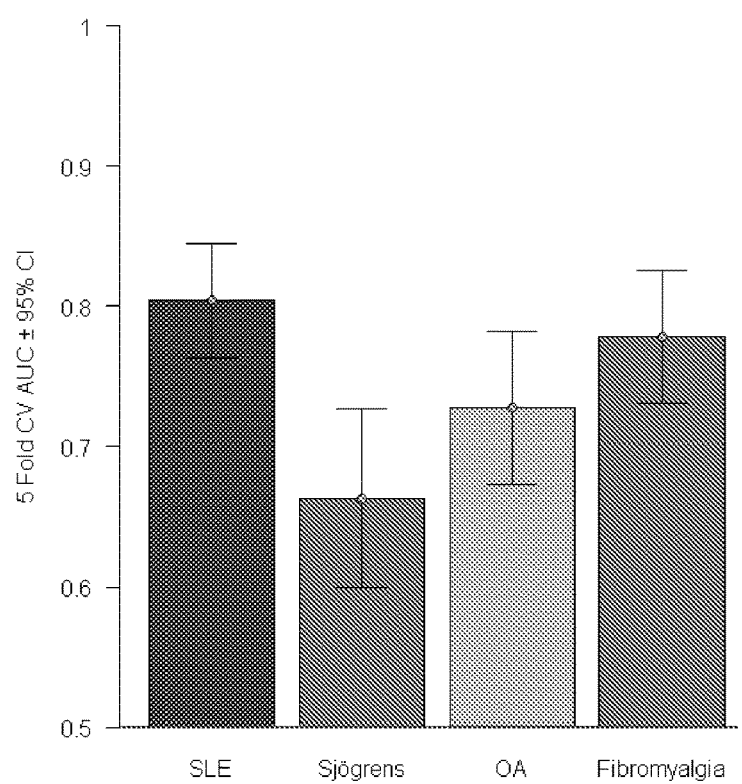

FIG. 86 shows assay performance for differential diagnosis of RA from SLE, Sjogrens, OA, and Fibromyoalgia.

FIGS. 87A-87C show candidate biomarkers identified by peptides discriminating RA from healthy subjects (FIG. 87A), RA from a group of subjects with other autoimmune disease (Other AI+non-AI mimic diseases) (FIG. 87B), and RA from the "Not RA" group represented by samples from Other AI+non-AI mimic and HC (FIG. 87C).

FIGS. 88A-88B show peptide submotifs (SEQ ID NOS 959-966, respectively, in order of appearance) (FIG. 88A) and amino acids (FIG. 88B) that are enriched in the peptides that simultaneously discriminate SLE, RA, FM, OA, SS, and HC from each other.

Figure 89:
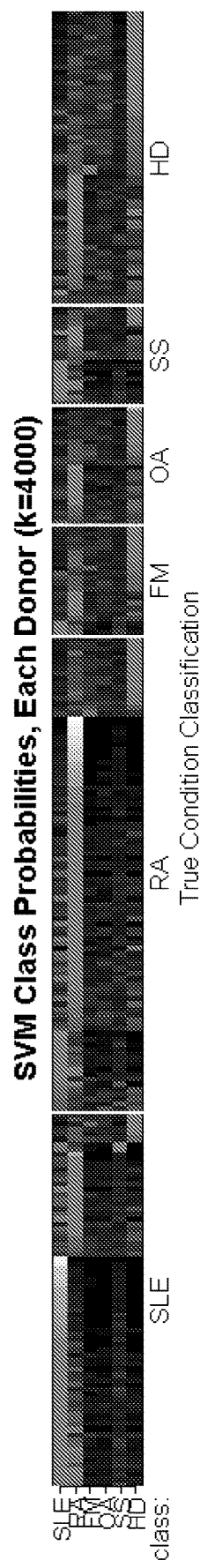

FIG. 89 shows a heat map visualizing the probabilities of SLE, RA, FM, OA, SS, and HC class assignments. Each sample has a predicted class membership for each disease class ranging from 0 (black) to 100% (white).

FIG. 90 shows the top significant peptides (SEQ ID NOS 967-1016, respectively, in order of appearance) that discriminate between the SLE samples from the healthy (HC) group of samples.

FIG. 91 shows the top significant peptides (SEQ ID NOS 1017-1066, respectively, in order of appearance) that discriminate between the SLE samples from the Other Autoimmune and non-Autoimmune mimic diseases (Other AI+non-AI) group of samples.

FIG. 92 shows the top significant peptides (SEQ ID NOS 1067-1116, respectively, in order of appearance) that discriminate between the SLE samples from the Not SLE (Not SLE—Other AI+non-AI+HC) group of samples.

FIG. 93 shows the top significant peptides (SEQ ID NOS 1117-1166, respectively, in order of appearance) that discriminate between the RA samples from the healthy (HC) group of samples.

FIG. 94 shows the top significant peptides (SEQ ID NOS 1167-1216, respectively, in order of appearance) that discriminate between the RA samples from the Other Autoimmune and non-Autoimmune mimic diseases (Other AI+non-AI) group of samples.

FIG. 95 shows the top significant peptides (SEQ ID NOS 1217-1266, respectively, in order of appearance) that discriminate between the RA samples from the Not RA (Not RA—Other AI+non-AI+HC) group of samples.

DETAILED DESCRIPTION OF THE INVENTION

The disclosed embodiments concern methods, apparatus, and systems for identifying candidate biomarkers, particularly protein biomarkers, useful for the diagnosis, prognosis, monitoring disease activity and screening, and/or as a targets for the treatment of diseases and conditions in subjects, in particular cancer, autoimmune and infectious diseases. The identification of candidate biomarkers is predicated on discovering discriminating peptides present on a peptide array, which can distinguish samples from different subjects having different health conditions by the binding patterns of antibodies present in the samples.

Unless defined otherwise herein, all technical and scientific terms used herein have the same meaning as commonly understood by one of ordinary skill in the art to which this invention belongs. Various scientific dictionaries that include the terms included herein are well known and available to those in the art. Although any methods and materials similar or equivalent to those described herein find use in the practice or testing of the present invention, some preferred methods and materials are described.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the specification as a whole.

The terms defined immediately below are more fully described by reference to the Specification as a whole. It is to be understood that this invention is not limited to the particular methodology, protocols, and reagents described, as these may vary, depending upon the context they are used by those of skill in the art.

Definitions

The terms "condition" and "health condition" are used herein interchangeably to refer to a healthy state, and all illnesses including diseases and disorders, but can include injuries and normal health situations, such as pregnancy, that might affect a person's health, benefit from medical assistance, or have implications for medical treatments.

The term "immunosignature" (IS, IST or IMS) herein refers to a combination of binding signals produced by the differential binding of antibodies in a sample from a subject to an array of peptides relative to the binding of antibodies in reference sample(s) to the array of peptides.

The term "subject" herein refers to a human subject as well as a non-human subject such as a non-human mammal Thus, various veterinary applications are contemplated in which case the subject may be a non-human mammal (e.g., a feline, a porcine, an equine, a bovine, and the like). The concepts described herein are also applicable to plants.

The term "relevance" is used herein to refer to a score that is obtained for a biomarker identified according to the method for querying a proteome.

The term "patient sample" and "subject sample" are used interchangeably herein to refer to a sample e.g. a biological fluid sample, obtained from a patient i.e. a recipient of medical attention, care or treatment. The subject sample can be any of the samples described herein. In certain embodiments, the subject sample is obtained by non-invasive procedures e.g. peripheral blood sample.

As used herein the term "microarray system" refers to a system usually comprised of array peptides formatted on a solid planar surface like glass, plastic or silicon chip and any one or more of instruments needed to handle samples (automated robotics), instruments to read the reporter molecules (scanners), and analyze the data (bioinformatic tools).

The term "array peptide" herein refers to a peptide immobilized on a microarray.

The term "discriminating" and "differentiating" are used herein interchangeably in reference to peptides in an antibody binding profile/pattern that differentially bind antibodies in a sample from a subject or subjects e.g. a test subject, relative to a reference subject or subjects to determine the health condition of the test subject.

The term "accuracy" herein refers to the proportion of correct outcomes classified by the method.

The term "sensitivity" herein refers to the proportion of samples to be correctly identified as being positive for the condition being tested.

The term "specificity" herein refers to the proportion of samples to be correctly identified as being negative for the condition being tested.

The term "amino acid" herein refers to naturally occurring carboxy-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (tip, W), tyrosine (tyr, Y), and valine (val, V).

Description

The human plasma proteome is likely to contain most, if not all, human proteins, as well as proteins derived from some viruses, bacteria, and fungi. Almost all cells in the body communicate with plasma directly or through extracellular or cerebrospinal fluids, and many release at least part of their contents into plasma upon damage or death. It is likely that any disease state would produce some specific pattern of protein change in the body's biofluids reflective of various states of the cells at real time and at given conditions.

Despite the importance of biomarkers to our understanding of immunology, the field of biomarker discovery has progressed slowly. To successfully target therapies towards the specific patient population in which they will have the most benefit requires a huge leap in the speed of biomarker discovery.

The methods, apparatus, and systems provided identify discriminating peptides that differentially bind antibodies from samples of subjects having different health conditions. Subsequently, the discriminating peptides are used to identify proteins as candidate biomarkers specific for the health condition differentiated by the antibody binding to the peptide array. In addition to discriminating health conditions, discriminating peptides can also correlate with the activity of a disease.

Figure 1:
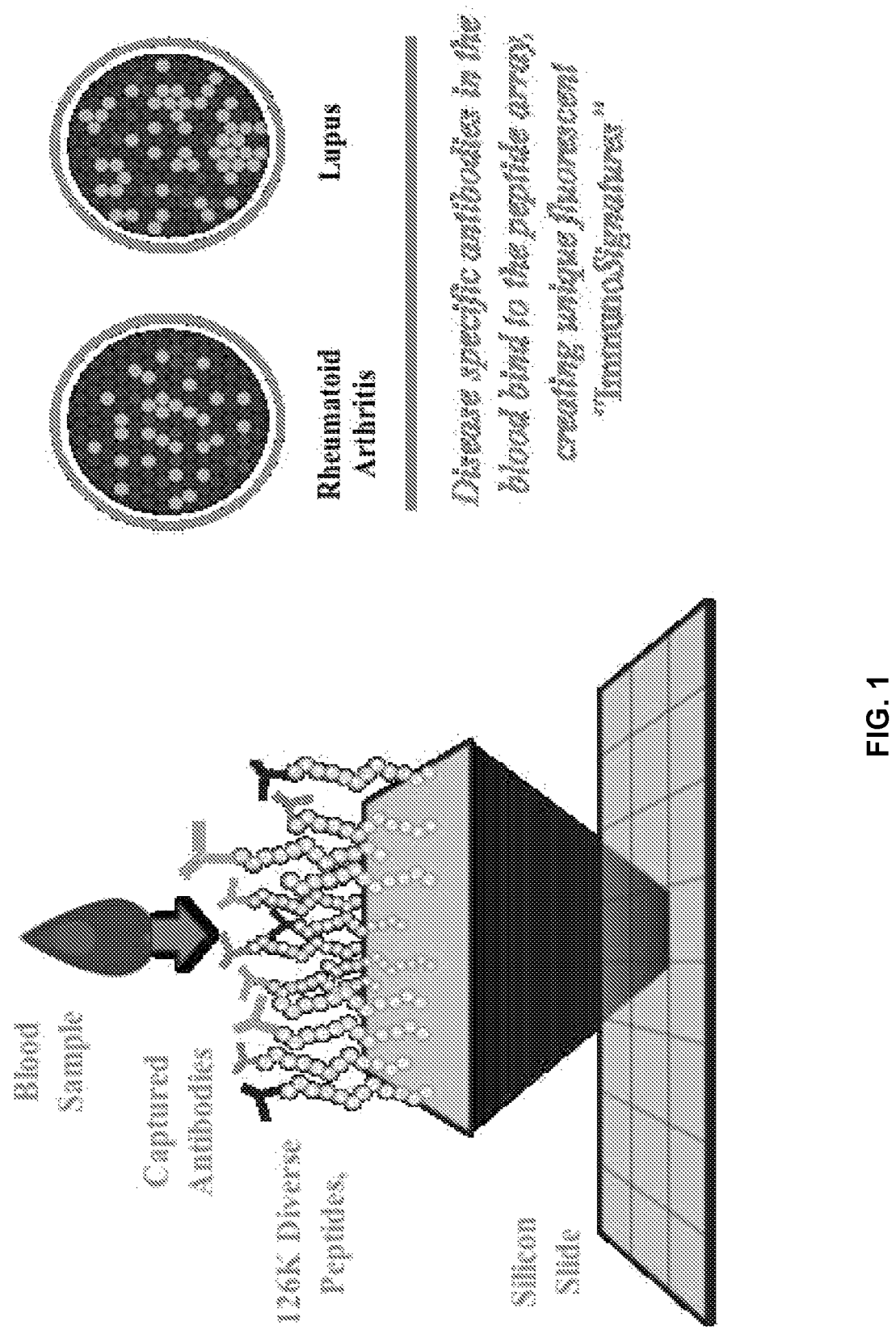
FIG. 1 shows the detection of antibody-bound array peptides of immunosignatures.
Figure 2:
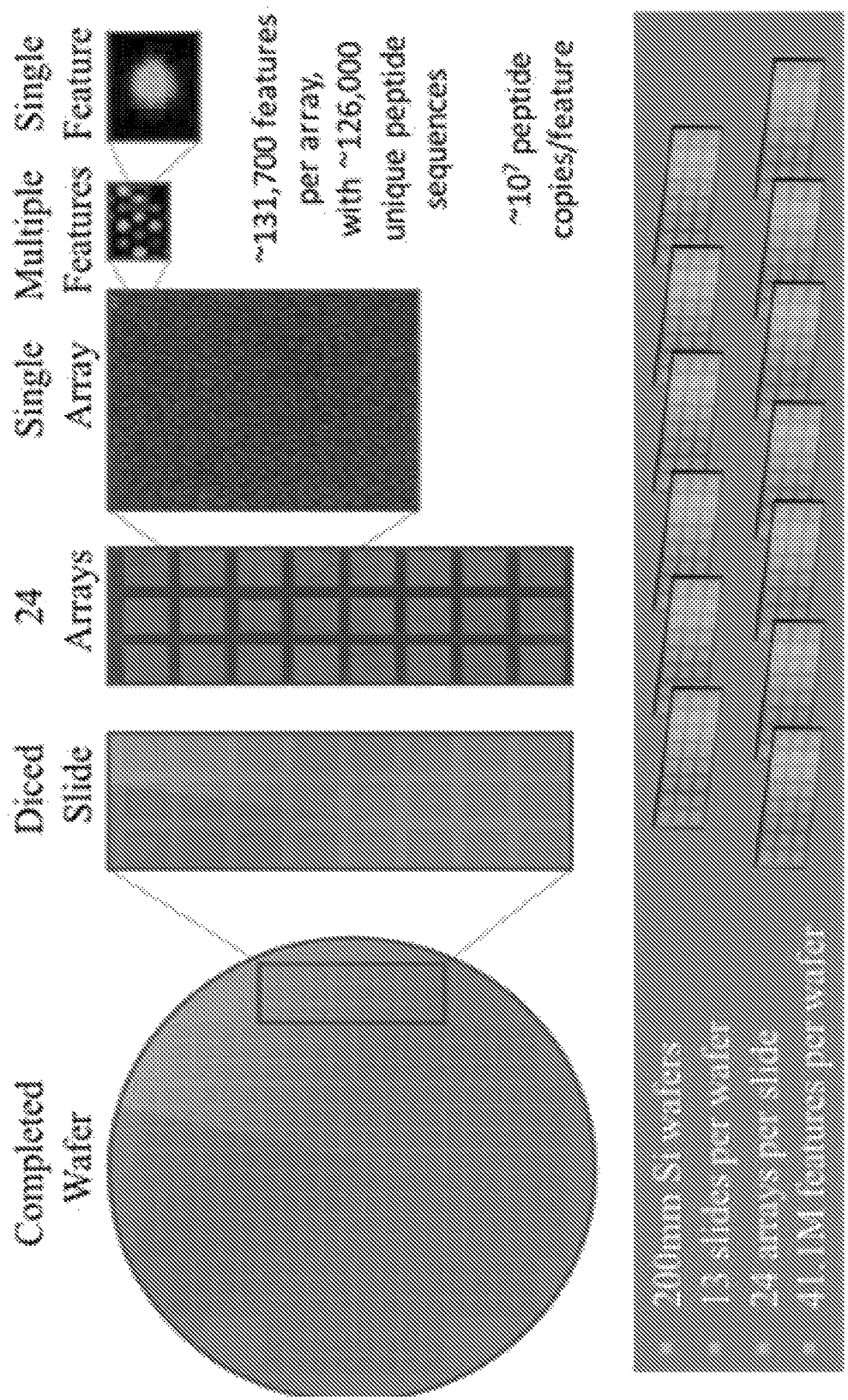
FIG. 2 shows a schematic of an exemplary peptide array for use in the disclosed embodiments.

Differential binding of antibodies in patient samples to the array results in specific binding patterns or signatures indicative of a health condition. For example, as is shown in FIG. 1, antibodies in samples from subjects with rheumatoid arthritis or lupus bind to peptide arrays and are detected to provide combinations of binding patterns that are unique to the health conditions. In some instances, these binding patterns, known as immunosignatures, can accurately differentiate combinations of binding signals corresponding to a disease from the combination of binding signals corresponding to a different disease, which in some instances can be a closely related disease. In other instances, combinations of binding signals corresponding to any one disease can also be discerned from binding signals from healthy subjects.

Comparing two or more combinations of binding signals identifies the peptides that are bound differentially. These differentially bound peptides are known as discriminating peptides, which are used to query a proteome to identify proteins that can be targeted as biomarkers for any one health condition.

Methods, apparatus and systems are presented for identifying candidate biomarkers for conditions including autoimmune diseases, and infections. Candidate biomarkers are identified for autoimmune disease, mimic conditions that are not classified as autoimmune, but that present with symptoms that are often associated with certain autoimmune diseases. Non-limiting examples of mimic disease conditions include osteoarthritis and fibromyalgia, which overlap in symptomology with autoimmune diseases such as systemic lupus erythematosus (SLE) and rheumatoid arthritis (RA). Other candidate biomarkers are also identified for infectious diseases including infections by protozoan organisms e.g. *T. cruzi*. Candidate biomarkers are also identified for their correlation to disease activity corresponding to evaluation according to known disease scoring systems e.g. SLEDAI, and to disease progression according to clinical manifestations indicative of the progress of a disease e.g. organ involvement in scleroderma.

In one aspect, disclosed herein are methods and devices for identifying at least one candidate biomarker for an autoimmune disease, the method comprising: (a) providing a peptide array and contacting a biological sample from a plurality of subjects known to have the autoimmune disease to the peptide array; (b) identifying a set of discriminating peptides bound to antibodies in the biological sample from the plurality of subjects that differentiate the autoimmune disease from at least one different health condition; (c) aligning each of the peptides in the set of discriminating peptides to one or more proteins in a proteome; and (d) obtaining a protein score and ranking for each of the identified proteins according to a statistical significance, thereby identifying at least one candidate biomarker for the autoimmune disease.

Immunosignatures—Binding Assay

The method is predicated on the binding of the complex mixture of antibodies in a sample e.g. blood sample, to an array of peptides. The technology disclosed herein uses arrays of at least thousands of unique peptides designed from chemical sequence space to enable broad surveys of individuals' antibody binding repertoires from samples of small volume. Samples from subjects known to have a first condition comprise different mixtures of antibodies that bind different sets or combinations of array peptides to provide antibody binding patterns or profiles, also known as IS. The different combinations of binding patterns can be detected to provide combinations of binding signal data. Typically, an immunosignature characteristic of a condition is determined relative to one or more reference immunosignatures, which are obtained from one or more different sets of reference samples obtained from one or more groups of reference subjects, each group having a different condition. For example, immunosignatures obtained from a group of subjects known to have a first condition are compared to immunosignatures of reference subjects known to have a second different condition. Accordingly, comparison of the two immunosignatures can identify discriminating peptides, which are the array peptides that are differentially bound by the antibodies from the two groups of subjects. A reference group can be a group of healthy subjects, and the condition is referred to herein as a healthy condition. In some instances, the 'healthy' subjects are subjects that are in remission for the disease. In some embodiments, the discriminating peptides may be downregulated as compared to the immunosignatures of reference subjects having the second different condition. In other instances, the discriminating peptides may be upregulated as compared to the immunosignatures of reference subjects having the second different condition.

Thus, the step of identifying the discriminating peptides comprises: (i) detecting binding of antibodies present in the biological sample from the plurality of subjects having the autoimmune disease to obtain a first combination of binding signals; (ii) detecting binding of antibodies present in samples from one or more reference groups of subjects to the same peptide array, each reference group having a different health condition to obtain a second combination of binding signals; (iii) comparing the first combination of binding signals to the second combination of binding signals to obtain a set of differentiating binding signals; and (iv) identifying peptides on the array that are differentially bound by antibodies in samples from subjects having the autoimmune disease and the antibodies in the samples from the one or more reference groups of subjects, thereby identifying said discriminating peptides.

Array peptides that differentially bind antibodies from samples of subjects having different conditions are capable of distinguishing the conditions or disease state, and serve to query corresponding proteomes for the identification of protein biomarkers specific for the differentiated disease.

The immunosignature (IS) of a plurality of subjects with a first health condition is identified as a pattern of binding of antibodies that are bound to the array peptides. The peptide array can be contacted with the sample under any suitable conditions to promote binding of antibodies in the sample to peptides immobilized on the array. Thus, the methods of the invention are not limited by any specific type of binding conditions employed. Such conditions will vary depending on the array being used, the type of substrate, the density of the peptides arrayed on the substrate, desired stringency of the binding interaction, and nature of the competing materials in the binding solution. In a preferred embodiment, the conditions comprise a step to remove unbound antibodies from the addressable array. Determining the need for such a step, and appropriate conditions for such a step, are well within the level of skill in the art.

Any suitable detection technique can be used in the methods of the invention detecting binding of antibodies in the sera to peptides on the array to generate a health condition immune profile. Bound antibodies can be detected, for example, using a detectably labeled secondary antibody. Alternatively, any type of detectable label can be used to label peptides on the array, including but not limited to radioisotope labels, fluorescent labels, luminescent labels, and electrochemical labels (i.e.: ligand labels with different electrode mid-point potential, where detection comprises detecting electric potential of the label). In other instances, binding interactions between antibodies in samples and the peptides on an array can be detected in a competition format. A difference in the binding profile of an array to a sample in the presence versus absence of a competitive inhibitor of binding can be useful in characterizing the sample.

Detection of signal from detectable labels is well within the level of skill in the art. For example, fluorescent array readers are well known in the art, as are instruments to record electric potentials on a substrate (For electrochemical detection see, for example, J. Wang (2000) Analytical Electrochemistry, Vol., 2nd ed., Wiley—VCH, New York). Binding interactions can also be detected using other label-free methods such a s SPR and mass spectrometry. SPR can provide a measure if dissociation constants and dissociation rates. The A-100 Biocore/GE instrument, for example, is suitable for this type of analysis. FLEX chips can be used to up to 400 binding reactions on the same support.

Classification Algorithms

Analyses of the antibody binding signal data, i.e. immunosignaturing (IMS), and the identification discriminating peptides derived therefrom are typically performed using various computer algorithms and programs. The antibody binding pattern produced by the labeled secondary antibody is scanned using, for example, a laser scanner. The images of the binding signals acquired by the scanner can be imported and processed using software such as the GenePix Pro 8 software (Molecular Devices, Santa Clara, Calif.), to provide tabular information for each peptide, for example, in a continuous value ranging from 0-65,000. Tabular data can be imported and statistical analysis performed using, for example, into Agilent's Gene Spring 7.3.1 (Agilent, Santa Clara, Calif.), or into the R language and environment for statistical computing (R Foundation for Statistical Computing, Vienna, Austria. URL https://www.R-project.org/).

Peptides displaying differential signaling patterns between samples obtained from subjects with different health conditions can be identified using known statistical tests such as a Welch-corrected T—test or ANOVA. For example, patterns of antibody binding to array peptides can be obtained for a set of samples comprising samples from a group of test patients e.g. subjects having a disease, and samples form a group of reference subjects e.g. healthy patients. Binding signal information is compared, and the statistical analyses are applied to select the discriminating peptides that distinguish the two conditions i.e. the test and reference groups at predetermined stringency levels. In some embodiments, a list of the most discriminating peptides can be obtained by ranking the peptides according to their p-value. For example, discriminating peptides can be ranked and identified as having p-values of between zero and one. The cutoff for the p-value can be further adjusted to account for instances when several dependent or independent statistical tests are being performed simultaneously on a single data set. For example, a Bonferroni correction can be used to reduce the chances of obtaining false positives when multiple pairwise tests are performed on a single set of data. The correction is dependent on the size of the array library. In some embodiments, the cut-off p value for determining the discriminating peptides can be adjusted to less than $10^{-30}$, less than $10^{-29}$, less than $10^{-28}$, less than $10^{-27}$, less than $10^{-26}$, less than $10^{-25}$, less than $10^{-24}$, less than $10^{-23}$, less than $10^{-22}$, less than $10^{-21}$, less than $10^{-20}$, less than $10^{-19}$, less than $10^{-18}$, less than $10^{-17}$, less than $10^{-16}$, less than $10^{-15}$, less than $10^{-14}$, less than $10^{-13}$, less than $10^{-12}$, less than $10^{-11}$, less than $10^{-10}$, less than $10^{-9}$, less than $10^{-8}$, less than $10^{-7}$, less than $10^{-6}$, or less than $10^{-5}$, less than $10^{-4}$, less than $10^{-3}$, or less than $10^{-2}$. The adjustment is dependent on the size of the array library. Alternatively, discriminating peptides are not ranked, and the binding signal information displayed up to all of the identified discriminating peptides is used to classify a condition e.g. the serological state of a sample.

Binding signal information of the discriminating peptides selected following statistical analysis can be imported into a machine learning algorithm to obtain a statistical or mathematical model i.e. a classifier that classifies the antibody profile data with the desired accuracy, sensitivity and specificity, and determine presence or absence of disease, severity of disease, disease progression, and other applications described elsewhere herein. A basic classification algorithm, Linear Discriminant Analysis (LDA) is widely used in analyzing biomedical data in order to classify two or more disease classes. LDA can be, for example, a classification algorithm. A more complex classification method, Support Vector Machines (SVM), uses mathematical kernels to separate classes by a hyperplane, projecting the original predictors to higher-dimensional spaces. Some common kernels include linear, polynomial, sigmoid or radial basis functions. A comparative study of common classifiers described in the art is described in (Kukreja et al, BMC Bioinformatics. 2012; 13: 139). Other algorithms for data analysis and predictive modeling based on data of antibody binding profiles include Bayes Net, Logistic Regression, Simple Logistic, Multilayer Perceptron, KNearest neighbor, K Star, Attribute Selected Classifier (ACS), Classification via clustering, Classification via Regression, Hyper Pipes, Voting Feature Interval Classifier, J48 (Java implementation of C4.5 algorithm), Random Trees, and Random Forest.

In some embodiments, antibody binding profiles are obtained from a training set of samples, which are used to identify the most discriminative combination of peptides by applying an elimination algorithm based on SVM analysis. The accuracy of the algorithm at various levels of significance can be determined by cross-validation. To generate and evaluate antibody binding profiles of a feasible number of discriminating peptides, multiple models can be built, using a plurality of discriminating peptides to identify the best performing model. In some embodiments, at least 25, at least 50, at least 75, at least 100, at least 200, at least 300, at least 400, at least 500, at least 750, at least 1000, at least 1500, at least 2000, at least 3000, at least 4000, at least 5000, at least 6000, at least 7000, at least 8000, at least 9000, at least 10,000, at least 11,000 at least 12,000 at least 13,000 at least 14,000 at least 15,000 at least 16,000 at least 17,000 at least 18,000 at least 19,000 at least 20,000 or more discriminating peptides are used to train a specific disease-classifying model. In some embodiments at least 0.00001%, at least 0.0001%, at least 0.0005%, at least 0.001%, at least 0.005%, at least 0.01%, at least 0.05%, at least 0.1%, at least 0.5%, at least 1.0%, at least 2%, at least 3%, at least 4%, at least 5%, at least 10%, at least 20%, at least 30%, at least 40%, at least 50%, at least 60%, at least 70%, at least 80%, at least 90%, at least 95%, or at least 99% of the total number of peptides on the array are discriminating peptides, and the corresponding binding signal information is used to train a specific condition-classifying model. In some embodiments, the signal information obtained for all of the peptides on the array is used to train the condition-specific model.

Multiple models comprising different numbers of discriminating peptides can be generated, and the performance of each model can be evaluated by a cross-validation process. An SVM classifier can be trained and cross-validated by assigning each sample of a training set of samples to one of a plurality of cross-validation groups. For example, for a four-fold cross-validation, each sample is assigned to one of four cross-validation groups such that each group comprises test and control i.e. reference samples; one of the cross-validation groups e.g. group 1, is held-out, and an SVM classifier model is trained using the samples in groups 2-4. Peptides that discriminate test cases and reference samples in the training group are analyzed and ranked by p value; the top k peptides are then used as predictors for the SVM model. To elucidate the relationship between the number of input predictors and model performance, and to guard against overfitting, the sub=loop is repeated for a range of k, e.g. 25, 50, 100, 250, 1000, 200, 3000 top peptides or more. Predictions i.e. classification of samples in group 1 are made suing the model generated using groups 2-4. Models for each of the four groups are generated, and the performance (AUC, sensitivity and/or specificity) is calculated using all the predictions from the 4 models using signal binding data from true disease samples. The cross-validation steps are repeated at least 100 times, and the average performance is calculated relative to a confidence interval e.g. 95%. Diagnostic visualization can be generated using e.g. volcano plots, ROC (receiver operating characteristic) curves, and model performance relative to the number of input peptides.

An optimal model based on antibody binding information to a set of discriminating input peptides is selected and used to differentiate health conditions. The performance of different classifiers is determined using a validation set, and using a test set of samples, performance characteristics such as accuracy, sensitivity, specificity, and F-measure are obtained from the model having the greatest performance. Different sets of discriminating peptides are identified to distinguish different conditions. Accordingly, an optimal model based on a set of the most discriminating input peptides is established for each of the health conditions.

In some embodiments, the resulting classification performance can be provided as a Radio Operator Characteristic curve (ROC). Specificity, sensitivity, and accuracy metrics of the classification can be determined by the area under the ROC (AUC). In some embodiments, the method determines/classifies a health condition of a plurality of subjects with a method performance or accuracy characterized by an area under the receiver operator characteristic (ROC) curve (AUC) being greater than 0.60. In other embodiments, the method performance characterized by an area under the receiver operator characteristic (ROC) curve (AUC) being greater 0.70, greater than 0.80, greater than 0.90, greater than 0.95, method performance characterized by an area under the receiver operator characteristic (ROC) curve (AUC) being greater than 0.97, method performance characterized by an area under the receiver operator characteristic (ROC) curve (AUC) being greater than 0.99. In other embodiments, the method performance is characterized by an area under the receiver operator characteristic (ROC) curve (AUC) ranging from 0.60 to 0.70, 0.70 to 0.79, 0.80 to 0.89, or 0.90 to 1.0. In yet other embodiments, method performance is expressed in terms of sensitivity, specificity, predictive values or likelihood ratios (LRs).

In some embodiments, the method has a sensitivity of at least 60%, for example 65%, 70%, 75%, 80%, 85%, 90%, 91%, 92%, 93%, 94%, 95%, 96%, 97%, 98%, 99% or 100% sensitivity.

In other embodiments, the method has a specificity of at least 60%, for example 65%, 70%, 75%, 80%, 85%, 90%, 91%, 92%, 93%, 94%, 95%, 96%, 97%, 98%, 99% or 100% specificity.

In some embodiments, the step of identifying discriminating peptides comprises: (i) detecting the binding of antibodies present in samples form a plurality of subjects having said disease to an array of different peptides to obtain a first combination of binding signals; (ii) detecting the binding of antibodies to a same array of peptides, said antibodies being present in samples from one or more reference groups of subjects, each group having a different health condition; (iii) comparing said first to said second combination of binding signals; and (iv) identifying peptides on said array that are differentially bound by antibodies in samples from subjects having said disease and the antibodies in said samples from one or more reference groups of subjects, thereby identifying said discriminating peptides. In some embodiments, the number of discriminating peptides corresponds to at least a portion of the total number of peptides on said array. In some embodiments, at least 0.1%, at least 1%, at least 10%, at least 25%, at least 50%, at least 75%, at least 80%, or at least 90%, of the total number of peptides on an array are discriminating peptides. In other embodiments, at least 0.00005%, at least 0.0001%, at least 0.0005%, at least 0.0001%, at least 0.001%, at least 0.003%, at least 0.005%, at least 0.01%, at least 0.05%, at least 0.1%, at least 0.5%, at least 1.0%, at least 1.5%, at least 2%, at least 3%, at least 4%, at least 5% or at least 10% of the total number of peptides on an array. In some embodiments, discriminating peptides are identified from differential antibody binding to peptide arrays comprising a library of at least 5,000, at least 10,000, at least 15,000, at least 20,000, at least 25,000, at least 50,000, at least 100,000, at least 200,000, at least 300,000, at least 400,000, at least 500,00, at least 1,000,000, at least 100,000,000 or more different peptides on the array substrate. In some embodiments, antibody binding comprises a combination of binding signals to at least 1, at least 2, at least 5, at least 10, at least 15, at least 20, at least 25, at least 30, at least 35, at least 40, at least 45, at least 50, at least 60, at least 70, at least 80, at least 90, at least 100, at least 125, at least 150, at least 175, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10000, at least 20000, or more discriminating peptides on an array. For example, at least 25 peptides on an array of 10,000 peptides are identified as discriminating peptides for a given condition.

Discriminating peptides can be characterized by enrichment of one or more particular amino acids, and/or by enrichment of one or more sequence motifs. Enrichment of amino acid and motif content is relative to the corresponding total amino acid and motif content of all the peptides in the array library. Enriched motifs can be identified from a list of significant peptides unless that list was less than 100 peptides long, in which case the top 500 peptides based on the p-value associated with a Welch's t-test were used. The different n-mers in this list of peptides is compared to the same sized n-mers in the total library to determine if any were enriched. Fold enrichment is calculated by determining the number of times a motif (e.g. ABCD) occurs in the list divided by the number of times the motif (ABCD) occurs in the library. This value is further divided by the relative number of times the motif type (e.g., tetramers) appears in the library (i.e., total number of all tetramers in the list divided by the total number of tetramers in the library). This Fold Enrichment (E) calculation can be represented by:

$E=(m/M)/(t/T)$ where m is the number of times the motif occurs as part of the discriminating peptide list; M is the total number of times the motif occurs in the library; t is the number of times the motif type appears in the list; and T is the number of times the motif occurs in the library. Fold enrichment can also be reported as Percent enrichment, i.e., "Enrichment value" multiplied by 100. In some embodiments, the discriminating peptides that distinguish a first from a second health condition obtained with the methods and arrays disclosed herein are enriched by one or more different protein sequence motifs.

The result of an antibody profiling experiment provides a list of peptides where the intensities of the peptides in a study is related to other covariates of interest of the samples included in the study. Examples of such covariates include categorical variables, such as a disease or treatment response classification for donor in a study, or continuous numerical variables, such as a biomarker or disease activity index. This list is drawn from the larger list or "library" of peptides that were measured in the study.

The method for identifying enriched motifs or submotifs within a list of peptides identifies common patterns of amino acids within the list of peptides that occur at a higher frequency within the list than their occurrences within the library. Such patterns can help infer the in vivo targets of the antibodies that are binding to the peptides, by comparing the amino acid patterns to known amino acid sequences of proteins. They can also form the basis for predicting what other peptides, not included in the library that was measured, would also show a relationship to the covariate of interest, generalizing the results of the study.

A peptide may be represented as a sequence of letters that symbolizes the sequence of amino acids from the free amine ("N") terminus to the free carboxyl ("C") terminus of a peptide. There is a standard set of letters that are commonly used by those skilled in the art for this purpose, for example, "V" for valine, "R" for arginine and "K" for lysine.

To implement the method, each peptide in the list is segmented into all possible contiguous subsequences of a specified length k. For example, a hypothetical peptide sequence ABCDEFG would be segmented into subsequences of length k=4 (sometime referred to as "tetramers" or "4-mers") as: ABCD, BCDE, CDEF, DEFG. One would then count the total number of occurrences of each unique k-mer in all of the unique peptides within the list. Next one would repeat this approach for all the peptides in the library and tabulate the number of occurrences of each unique k-mer in the library peptides.

Typically, only k-mers in the list that occur a minimum number of times, such as two, would be considered. For each unique k-mer remaining in the list an enrichment ratio is calculated as the number of times the unique k-mer occurs within the list over the sum of all k-mer occurrences in the list, divided by the total number of times it occurs in the library over the sum of all k-mer occurrences in the library. To estimate the likelihood (p-value) that a particular k-mer's enrichment ratio could have arisen by chance, one may apply Fisher's exact test using the four quantities used in the calculation of the enrichment ratio as inputs. One would typically require a p-value of <0.05 after adjusting for multiple hypothesis testing, for example using the procedure proscribed by Benjamini and Hochberg (1995) or Holm (1979).

This procedure may be repeated where the length of the subsequences k is incremented from one to seven and the enriched sub-motifs are identified for each length. One may also identify enriched "gapped" subsequences of length k>2, where only the amino acids at the N- and C-termini are considered regardless of the intervening sequence. This is achieved by substituting an arbitrary character, such as a period, for the letters in positions 2 through k−1. For example, a hypothetical peptide sequence ABCDEFG would be segmented into subsequences of length k=4 (sometimes referred to as "gapped tetramers" or "gapped 4-mers") as: A . . . D, B . . . E, C . . . F, D . . . G. The entire procedure described above is then repeated to identify enriched gapped k-mers of a range of lengths k, such as 3 to 7. All enriched sub-motifs, that is k-mers and gapped k-mers, may be combined in a single table, and ordered by increasing p-values, then by decreasing enrichment ratio in the case of ties. The resulting table contains subsequences that were found to occur more commonly in the list of peptides than would be expected by chance if a list of the same size were randomly selected from the library of peptides, with 95% confidence for each peptide after accounting for multiplicity.

In some embodiments, the immunosignature binding patterns identify one or more discriminating peptides for a disease or condition obtained with the methods and arrays disclosed herein that comprise at least 1, at least 2, at least 3, at least 4, at least 5, at least 6, at least 7, at least 8, at least 9 or at least 10 different enriched peptide motifs. In some embodiments, the motifs are at least 25% identical, at least 30% identical, at least 40% identical, at least 50% identical, at least 60% identical, at least 70% identical, at least 80% identical, at least 90% identical, at least 95% identical or at least 99% identical to peptides on the peptide array. In other embodiments, the motifs are at least 25% similar, at least 30% similar, at least 40% similar, at least 50% similar, at least 60% similar, at least 70% similar, at least 80% similar, at least 90% similar, at least 95% similar or at least 99% similar to peptides on the peptide array.

Any one of the discriminating peptides can be enriched by at least 100%, at least 125%, at least 150%, at least 175%, at least 200%, at least 225%, at least 250%, at least 275%, at least 300%, at least 350%, at least 400%, at least 450%, or at least 500% in at least one protein sequence submotif or motif identified for the discriminating set.

In other embodiments, the discriminating peptides can be enriched by at least 100%, at least 125%, at least 150%, at least 175%, at least 200%, at least 225%, at least 250%, at least 275%, at least 300%, at least 350%, at least 400%, at least 450%, or at least 500% in at least one amino acid.

Identifying Candidate Target Proteins

The discriminating peptides obtained can then be used for identifying candidate therapeutic targets and developing treatments for individual subjects against an identified disorder or condition. In other aspects, the differential binding of antibodies in samples from groups of subjects having two or more different health conditions identifies discriminating peptides on the array can be analyzed, for example, by comparing the sequence of one or more discriminating peptides that distinguish between two or more health conditions in the array sequences in a protein database to identify a candidate target protein. In some embodiments, splaying the antibody repertoire out on an array of peptides (immunosignaturing, IMS) and comparing samples from subjects with a first condition to samples from subjects with a second condition, for example, healthy reference subjects or subjects with a different condition, can identify discriminating peptides useful for identifying candidate biomarkers for a condition relative to two or more different conditions.

In cases where the informatics cannot identify a putative match, such as in the case of discontinuous epitopes, the informative peptide can be used as an affinity reagent to purify reactive antibody. Purified antibody can then be used in standard immunological techniques to identify the target.

Having identified a set of discriminating peptides for a health condition, the appropriate reference proteome can be queried to relate the sequences of the discriminating peptides bound by the antibodies in a sample. Reference proteomes have been selected among all proteomes (manually and algorithmically, according to a number of criteria) to provide broad coverage of the tree of life. Reference proteomes constitute a representative cross-section of the taxonomic diversity to be found within UniProtKB at http://www.uniprot.org/proteomes/?query=reference:yes Reference proteomes include the proteomes of well-studied model organisms and other proteomes of interest for biomedical and biotechnological research. Species of particular importance may be represented by numerous reference proteomes for specific ecotypes or strains of interest. Examples of proteomes that can be queried include without limitation the human proteome, and proteomes from other mammals, non-mammal animals, viruses, bacteria and protozoan parasites. Additionally, other compilations of proteins that can be queried include without limitation lists of disease-relevant proteins, lists of proteins containing known or unknown mutations (including single nucleotide polymorphisms, insertions, substitutions and deletions), lists of proteins consisting of known and unknown splice variants, or lists of peptides or proteins from a combinatorial library (including natural and unnatural amino acids). In some embodiments, the proteome that can be queried using discriminating peptides include without limitation the human proteome RefSeq release 84, corresponding to human genome build GrCh38 (https://www.ncbi.nlm.nih.gov/refseq/), compiled Mar. 10, 2016, using the longest transcript variant for each unique gene ID. In other embodiments, the proteome that can be queried is the proteome of *T. cruzi* (Sodré C L et al., Arch Microbiol. [2009] February; 191 (2):177-84. Epub 2008 Nov. 11. Proteomic map of *Trypanosoma cruzi* CL Brener: the reference strain of the genome project).

Software for aligning single and multiple proteins to a proteome or protein list include without limitation BLAST, CS-BLAST, CUDAWS++, DIAMOND, FASTA, GGSEARCH (GG or GL), Genoogle, HMMER, H-suite, IDF, KLAST, MMseqs2, USEARCH, OSWALD, Parasail, PSI-BLAST, PSI Protein, Sequilab, SAM, SSEARCH, SWAPHI, SWIMM, and SWIPE.

Alternatively, sequence motifs that are enriched in the discriminating peptides relative to the motifs found in the entire peptide library on the array can be aligned to a proteome to identify target proteins that can be validated as possible therapeutic targets for the treatment of the condition. Discriminating peptides are aligned to the longest available transcript in the proteome database. Online databases and search tools for identifying protein domains, families and functional sites are available e.g. Prosite at ExPASy, Motif Scan (MyHits, SIB, Switzerland), Interpro 5, MOTIF (GenomeNet, Japan), and Pfam (EMBL-EBI).

In some embodiments, the alignment method can be any method for mapping amino acids of a query sequence onto a longer protein sequence, including BLAST (Altschul, S. F. & Gish, W. [1996] "Local alignment statistics." Meth. Enzymol. 266:460-480), the use of compositional substitution and scoring matrices, exact matching with and without gaps, epitope prediction, antigenicity prediction, hydrophobicity prediction, surface accessibility prediction. For each approach, a canonical or modified scoring system can be used, with the modified scoring system optimized to correct for biases in the peptide library composition. In some embodiments, a modified BLAST alignment is used, requiring a seed of 3 amino acids with a gap penalty of 4, with a scoring matrix of BLOSUM62 (Henikoff, J. G. Amino acid substitution matrices from protein blocks. Proc. Natl. Acad. Sci. USA 89, 10915-10919 [1992]) modified to reflect the amino composition of the array (States, D. J., Gish, W., Altschul, S. F. [1991] "Improved sensitivity of nucleic acid database searches using application-specific scoring matrices." Methods 3:66-70.) The number of seed amino acids and gap penalties are easily discerned by one of skill in the art. These modifications can include increasing the score of degenerate substitutions, remove penalties for amino acids absent from the array and score all exact matches equally.

The discriminating peptides that can be used to identify candidate biomarker proteins according to the method provided, are chosen according to their ability to distinguish between two or more different health conditions. Accordingly, discriminating peptides can be chosen at a predetermined statistical stringency, e.g. by p-value, for the probability of discriminating between two or more conditions; by differences in the relative binding signal intensity changes between two or more conditions; by their intensity rank in a single condition; by their coefficients in a machine learning model trained against two or more conditions e.g. AUC, or by their correlation with one or more study parameters. In some embodiments, the discriminating peptides selected for identifying one or more candidate biomarkers are chosen as having a p-value of p<1E–03, p<1E–04, or p<1E–05.

The method provided for identifying candidate protein biomarkers utilizes the homology between the discriminating peptides and the proteins of a proteome or other protein list, while correcting for the potential oversampling from lists comprising larger peptides relative to lists The query peptides are the discriminating peptides capable of distinguishing two or more different health conditions to be aligned can be chosen based on their p-value for discrimination between two or more conditions, their relative signal intensity changes between two or more conditions, by their intensity rank in a single condition, by their coefficients in a machine learning model trained against two or more conditions, or by their correlation with one or more study parameters.

Having identified the set of discriminating peptides and the proteome or protein list to be queried, all the discriminating peptides are aligned, and peptides having a positive BLAST score are identified. For each of the proteins to which discriminating peptides are aligned, the scores for the BLAST-positive peptides in the alignment are assembled into a matrix e.g. modified BLOSUM62. These modifications can include increasing the score of degenerate substitutions, remove penalties for amino acids absent from the array and score all exact matches equally.

Each row of the matrix corresponds to an aligned peptide and each column corresponds to one of the consecutive amino acids that comprise this protein, with gaps and deletions allowed within the peptide rows to allow for alignment to the protein.

Using the modified BLAST scoring matrix described above, each position in the matrix receives the score for paired amino acids of the peptide and protein in that column. Then, for each amino acid in the protein, the corresponding column is summed to create an "overlap score" that represents coverage of that amino acid by the ImmunoSignature discriminating peptides.

The amino acid overlap score, s, is a corrected score of the representation of amino acids in the discriminating peptides that accounts for the composition of the library. For example, peptides on an array can exclude one or more of the 20 natural amino acids. Therefore, the overlap score accounts for the amino acid content in the library. To correct this score for library composition, an overlap score is calculated by the same method for a list of all array peptides. This allows for the calculation of an overlap score, s, at each amino acid via the equation $$s = a - (b/d) * c$$

where a is the overlap score from the ImmunoSignature peptides, b is the number of ImmunoSignature peptides, c is the overlap score for the full array of peptide and d is the number of peptides on the full array. The overlap score "s" for the discriminating peptides can be represented by "$s_d$."

Next, the amino acid overlap score obtained from the alignment of the discriminating peptides is converted to a protein score, 'S' i.e. '$S_d$'. To convert these scores at the amino acid level, $s_d$, to a full-protein statistic, $S_d$, the sum of scores for every possible tiling n-mer epitope within a protein is calculated, and the final score is the maximum along windows of e.g., 20 mer. In some embodiments, the scores can be obtained for tiling 10-mer epitopes, 15-mer-epitopes, 20-mer epitopes, 25-mer epitopes, 30 mer-epitopes, 35-mer-epitopes, 40-mer-epitopes, 45-mer epitopes, or 50-mer epitopes. Protein score $S_d$ is the maximum score obtained along the rolling window. In some embodiments, the n-mer correlates to the entire length of the protein i.e. the discriminating peptides are aligned to the entire sequence of the protein. Alternatively, the scores can be obtained by aligning the peptide sequences to the entire protein sequences.

Ranking of the identified candidate biomarkers is made subsequently relative to the ranking of randomly chosen non-discriminating peptides. Accordingly, an overlap score for non-discriminating peptides (non-discriminating 's' score '$s_r$') that align to each of one or more proteins of a same proteome or protein list is obtained as described for discriminating peptides. The non-discriminating 's' score is then converted to a non-discriminating protein 'S' score i.e. '$S_r$' for each of a plurality of randomly chosen non-discriminating peptides. For example, non-discriminating protein 'S' scores can be obtained for at least 25, at least 50, at least 100, or more randomly-chosen non-discriminating peptides.

The protein biomarkers identified are then ranked relative to the proteins identified by alignment of non-discriminating peptides. In some embodiments, the final protein score, $S_r$ score—for the randomly chosen non-discriminating peptides can be calculated using the equivalent number of discriminating peptides used to obtain protein score $S_d$. In other embodiments, at least 20%, at least 30%, at least 40%, at least 50%, at least 60%, at least 70%, at least 80%, at least 85%, at least 90%, at least 95%, at least 98%, at least 99% of the number of discriminating peptides used to determine $S_d$ are used to determine the non-discriminating protein 'S,' score.

In some embodiments, the candidate protein biomarkers are ranked by their $S_d$ score relative to the $S_r$ score of the proteins identified by alignment of non-discriminating peptides. In some embodiments, ranking can be determined according to a p-value. Top candidate biomarkers can be chosen as having a p-value less than $10^{-3}$, less than $10^{-4}$, less than $10^{-5}$, less than $10^{-6}$, less than $10^{-7}$, less than $10^{-8}$, less than $10^{-9}$, less than $10^{-19}$, less than $10^{-12}$, less than $10^{-15}$, less than $10^{-18}$, less than $10^{-20}$, or less. In some embodiments, at least 5, at least 10, at least 15, at least 20, at least 30, at least 40, at least 50, at least 60, at least 70, at least 80, at least 90, at least 100, at least 120, at least 150, at least 180, at least 200, at least 250, at least 300, at least 350, at least 400, at least 450, at least 500, or more candidate biomarkers are identified according to the method.

In other embodiments, candidate biomarkers are chosen according to the $S_d$ score obtained by tiling a plurality of discriminating peptides to n-mer epitopes as described in the preceding paragraphs, and selecting the number of candidate biomarkers as a percent of proteins having the greatest $S_d$ score for the pathogen's proteome. In some embodiments, candidate biomarkers are proteins having the highest ranking $S_d$ scores and comprising at least 0.01% of the total number of proteins of the pathogens' proteome. In other embodiments, candidate biomarkers are proteins having the highest ranking $S_d$ scores and comprising at least 0.02%, at least 0.03%, at least 0.04%, at least 0.05%, at least 0.1%, at least 0.15%, at least 0.2%, at least 0.25%, at least 0.3%, at least 0.35%, at least 0.4%, at least 0.45%, at least 0.5%, at least 0.55%, at least 0.6%, at least 0.65%, at least 0.7%, at least 0.75%, at least 0.8%, at least 0.85%, at least 0.9%, at least 1%, at least 2%, at least 3%, at least 4%, at least 5%, at least 10%, at least 20%, or more of the total number of proteins of the pathogens' proteome.

In some embodiments, a method is provided for identifying a candidate target protein for the treatment of an autoimmune disease in a human subject, the method comprising: (a) identifying a set of discriminating peptides that differentiate the autoimmune disease from one or more different autoimmune diseases; (b) aligning the set of peptides to proteins in a human proteome; (c) identifying regions of homology between each peptide in the set to a region of an immunogenic protein; and (d) identifying the protein as a candidate target protein for treating said autoimmune disease. The method can further comprise identifying a set of discriminating peptides that differentiate the autoimmune disease from a healthy condition.

In some embodiments, a method is provided for identifying at least one candidate protein biomarker for a disease in a subject, the method comprising: (a) providing a peptide array and incubating a biological sample from said subject to the peptide array; (b) identifying a set of discriminating peptides bound to an antibody in the biological sample from said subject, the set of peptides capable of differentiating the disease from at least one different condition; (c) querying a proteome database with each of the peptides in the set of peptides; (d) aligning each of the peptides in the set of peptides to one or more proteins in the proteome database; and (e) obtaining a relevance score and/or ranking for each of the identified proteins from the proteome database; wherein each of the identified proteins is a candidate biomarker for the disease in the subject. In some embodiments, the method further comprises obtaining an overlap score, wherein said score corrects for the peptide composition of the peptide library. The discriminating peptides can be identified by statistical means e.g. t-test, as having p-values of less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$. In some embodiments, the resulting candidate biomarkers can be ranked according to a p-value of less than less than $10^{-3}$, less than less than $10^{-4}$, less than less than $10^{-5}$, or less than less than $10^{-6}$ when compared to proteins identified according to the method but using randomly chosen non-discriminating peptides.

The candidate biomarkers identified according to the methods provided herein can be subsequently validated and used for diagnosis, prognosis, monitoring and screening of a disease or condition, including but not limited to autoimmune diseases, infections, and/or as a therapeutic target for treatment of a variety of diseases or conditions, including autoimmune diseases or infection, and thus serve as basis the development of therapeutics for the treatment and prevention of diseases.

Candidate Biomarkers of Autoimmune Disease

Detecting and diagnosing immune-mediated disorders, such as autoimmune disorders, is challenging, with patients having a difficult time receiving an accurate or correct diagnosis. In many instances, patients are often misdiagnosed with other autoimmune conditions because of the closely related nature of these diseases. There are currently no reliable bio-markers available for the detection and assessment of autoimmune diseases or disorders.

For example, Systemic Sclerosis or Scleroderma (SSc) is a multisystem autoimmune disease in which there is increased fibroblast activity resulting in abnormal growth of connective tissue. SSc is difficult to diagnose or obtain a prognosis of the disease condition because of its close relationship to other similar diseases. SSc causes vascular damage and fibrosis in the skin, the gastrointestinal (GI) tract and other internal organs, and is suspected in patients with skin thickening, puffy or swollen fingers, hand stiffness, and painful distal finger ulcers. Symptoms of Raynaud's phenomenon (RP; disorder which affects blood vessels, mostly in the extremities (fingers and toes); cause blood vessels to narrow in cold and stress, resulting in numb feeling in the affected extremities) and gastroesophageal reflux are often present. FIG. 5 depicts a list of clinical manifestations of systemic sclerosis, which are heterogenous and vary as a result of the type of disease (limited or diffuse) and organ involvement.

The diagnosis of systemic scleroderma may be made on the basis of characteristic findings of cutaneous skin thickening, which may be in association with Raynaud's phenomenon and varying degrees of internal organ involvement. In early stages of the disease, Raynaud's phenomenon may be the only clinical manifestation of the disease. Nailfold capillarscopy may be helpful in these cases for determining whether Raynaud's phenomenon is primary or secondary to SSc. Diagnostic criteria for SSc as proposed by the American College of Rheumatology are listed in FIG. 6, however experts differ regarding the usefulness of these criteria, and disease manifestations are often advanced by the time patients fulfill these criteria. Additionally, the heterogeneity of clinical presentation, range of internal organ involvement, and differences in rates of disease progression make counseling and management of each individual patient's disease challenging.

Scleroderma may occur alone or in overlap syndromes with other diseases of connective tissue (such as systemic lupus erythematosus, dermatomyositis, and rheumatoid arthritis). Depending on which other diseases it is associated with, the disease state may be referred to as an "overlap syndrome". Overlap diseases associated with scleroderma may also be a mimic disease, i.e., different diseases that present with, for example, scleroderma, but cannot be readily distinguished from scleroderma symptoms.

Example 1 illustrates a method for identifying candidate target proteins using discriminating peptides that distinguish samples form healthy subjects from samples from subjects having SSc.

In one embodiment, a method is provided for identifying a candidate biomarker of SSc. The method comprises (a) providing a peptide array and contacting a biological sample from a plurality of subjects known to have SSc to the peptide array; (b) identifying a set of discriminating peptides bound to antibodies in the biological sample from the plurality of subjects that differentiate SSc from at least one different health condition; (c) aligning each of the peptides in the set of discriminating peptides to one or more proteins in a proteome; and (d) obtaining a protein score and ranking for each of the identified proteins according to a statistical significance, thereby identifying at least one candidate biomarker for SSc.

In some embodiments, the step of identifying discriminating peptides comprises the step of identifying the set of discriminating peptides comprises: (i) detecting binding of antibodies present in the biological sample from the plurality of subjects having SSc to obtain a first combination of binding signals; (ii) detecting binding of antibodies present in samples from one or more reference groups of subjects to the same peptide array, each reference group having a different health condition to obtain a second combination of binding signals; (iii) comparing the first combination of binding signals to the second combination of binding signals to obtain a set of differentiating binding signals; and (iv) identifying peptides on the array that are differentially bound by antibodies in samples from subjects having SSc and the antibodies in the samples from the one or more reference groups of subjects, thereby identifying said discriminating peptides.

In some embodiments, candidate biomarkers of SSc can be identified using any one or more of the discriminating peptides listed in FIG. 8C. The discriminating peptides were found to be enriched in sequence motifs listed in FIG. 8A. In some embodiments, the discriminating peptides for identifying a candidate biomarker of SSc with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the motifs listed in FIG. 8A. The same discriminating peptides were found to be enriched in amino acids listed in FIG. 8B.

Accordingly, in other embodiments, the discriminating peptides for identifying a candidate biomarker of SSc with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the amino acids listed in FIG. 8B.

An exemplary list of discriminating peptides that can be used for identifying candidate biomarkers of SSc is provided in FIG. 8C. The list provides the top 50 discriminating peptides, which are peptides that discriminate the combination of antibody binding signals obtained using samples from subjects with SSc from the combination of binding signals obtained using samples from healthy subjects. In some embodiments, the method for identifying a candidate biomarker for SSc comprises identifying a set of discriminating peptides that comprise one or more of the discriminating peptides listed in FIG. 8C.

Candidate biomarkers for SSc are subsequently identified by aligning a set of discriminating peptides to a human proteome. As described elsewhere herein, an overlap score is determined from the alignment of the discriminating peptides to the proteome; and proteins so identified are scored and ranked relative to proteins that are identified using randomly chosen non-discriminating peptides to identify candidate biomarkers for SSc. In one embodiment, a candidate biomarker for SSc is selected from the list of candidate biomarkers listed in Table 3. In some embodiments, the candidate biomarker proteins identified according to the method are ranked according to a p-value of less than less than $10^{-3}$, less than less than $10^{-4}$, less than less than $10^{-5}$, or less than less than $10^{-6}$.

Alternatively, discriminating peptides identified according to the methods provided, can identify candidate target proteins i.e. candidate biomarkers, using sequence motifs that are enriched in the most discriminating peptides that distinguish two different conditions. In one embodiment, the method for identifying a candidate target for the treatment of an autoimmune disease in a human subject comprises (a) obtaining a set of discriminating peptides that differentiate the autoimmune disease from one or more different autoimmune diseases; (b) identifying a set of motifs for said discriminating peptides; (c) aligning the set of motifs to a human proteome; (d) identifying regions of homology between each motif in the set to a region of an immunogenic protein; and (e) identifying the protein as a candidate target said autoimmune disease.

Similarly, in another embodiment, a method is provided for identifying candidate target proteins using discriminating peptides that distinguish samples form healthy subjects from samples from subjects having DM. In some embodiments, candidate biomarkers of DM can be identified using any one or more discriminating peptides were found to be enriched in sequence motifs listed in FIG. 20A. In some embodiments, the discriminating peptides for identifying a candidate biomarker of DM with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the motifs listed in FIG. 20A. The same discriminating peptides were found to be enriched in amino acids listed in FIG. 20B. Accordingly, in other embodiments, the discriminating peptides for identifying a candidate biomarker of DM with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the amino acids listed in FIG. 20B.

Discriminating peptides identified according to the methods provided, can identify candidate target proteins i.e. candidate biomarkers, for DM using sequence motifs that are enriched in the most discriminating peptides that distinguish two different conditions. In one embodiment, the method for identifying a candidate target for the treatment of an autoimmune disease in a human subject comprises (a) obtaining a set of discriminating peptides that differentiate the autoimmune disease from one or more different autoimmune diseases; (b) identifying a set of motifs for said discriminating peptides; (c) aligning the set of motifs to a human proteome; (d) identifying regions of homology between each motif in the set to a region of an immunogenic protein; and (e) identifying the protein as a candidate target said autoimmune disease.

Candidate biomarkers can be identified using discriminating peptides that distinguish samples from subjects having other autoimmune diseases, and samples from subjects having mimic diseases, which may or may not be autoimmune.

In some aspects, the methods and devices disclosed herein are used for identifying at least one candidate biomarker for SSc and differentiating against dermatomyositis (DM), the method comprising: (a) providing a peptide array and contacting a biological sample from a plurality of subjects known to have SSc to the peptide array; (b) identifying a set of discriminating peptides bound to antibodies in the biological sample from the plurality of subjects that differentiate SSc from DM; (c) aligning each of the peptides in the set of discriminating peptides to one or more proteins in a proteome; and (d) obtaining a protein score and ranking for each of the identified proteins according to a statistical significance, thereby identifying at least one candidate biomarker for SSc. In some embodiments, the step of identifying the set of discriminating peptides comprises: (i) detecting binding of antibodies present in the biological sample from the plurality of subjects having SSc to obtain a first combination of binding signals; (ii) detecting binding of antibodies present in samples from one or more reference groups of subjects to the same peptide array, each reference group having a different health condition, including DM, to obtain a second combination of binding signals; (iii) comparing the first combination of binding signals to the second combination of binding signals to obtain a set of differentiating binding signals; and (iv) identifying peptides on the array that are differentially bound by antibodies in samples from subjects having SSc and the antibodies in the samples from the one or more reference groups of subjects, thereby identifying said discriminating peptides.

In some embodiments, the discriminating peptides of the immunosignature binding patterns for differentiating autoimmune diseases with the methods and arrays disclosed herein are enriched in at least one, at least two, at least three, at least four, at least five, at least six, at least seven, at least eight, at least nine, or at least ten different amino acids. Enrichment of the amino acids can be by at least 100%, at least 125%, at least 150%, at least 175%, at least 200%, at least 225%, at least 250%, at least 275%, at least 300%, at least 350%, at least 400%, at least 450%, or at least 500% in at least one amino acid for the peptides comprising the immunosignature for the autoimmune disease. In preferred embodiments, the differential diagnosis is made between SSc and DM. In some embodiments, discriminating peptides that distinguish SSc from DM reference subjects are enriched in one or more of serine, glycine, tyrosine, arginine, alanine, glutamine and valine (FIG. 16B).

In some embodiments, the discriminating peptides of the immunosignature binding patterns for providing a differential diagnosis of autoimmune disease in a subject with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one motif for the peptides comprising the immunosignature for the autoimmune disease. In preferred embodiments, the autoimmune disease is SSc or DM. In some embodiments, discriminating peptides that distinguish SSc from DM subjects are enriched in one or more of motifs provided in FIG. 16A.

In some embodiments, methods and devices are provided for identifying at least one candidate biomarker for an autoimmune disease, the method comprising: (a) providing a peptide array and contacting a biological sample from a plurality of subjects known to have the autoimmune disease to the peptide array; (b) identifying a set of discriminating peptides bound to antibodies in the biological sample from the plurality of subjects that differentiate the autoimmune disease from at least one different health condition; (c) aligning each of the peptides in the set of discriminating peptides to one or more proteins in a proteome; and (d) obtaining a protein score and ranking for each of the identified proteins according to a statistical significance, thereby identifying at least one candidate biomarker for the autoimmune disease.

In some embodiments, the autoimmune disease is scleroderma v other autoimmune diseases, and candidate biomarkers are identified for discerning SSc from any one or more other autoimmune diseases.

In some embodiments, candidate biomarkers can be identified for a group of subjects relative to a different group of reference subjects each reference subject having one of a plurality of different autoimmune diseases. In some embodiments, the differential diagnosis is made relative to a group of subjects having other autoimmune diseases comprising Mixed Connective Tissue Disease (MCTD), Undifferentiated Connective Tissue Disease (UCTD), myositis, polymyositis, systemic lupus erythomatosus, and morphea. The discriminating peptides of the immunosignature binding patterns for making a differential diagnosis of an autoimmune disease in a subject with the methods and arrays disclosed herein are enriched in at least one, at least two, at least three, at least four, at least five, at least six, at least seven, at least eight, at least nine, or at least ten different amino acids. Enrichment of the amino acids can be by at least 100%, at least 125%, at least 150%, at least 175%, at least 200%, at least 225%, at least 250%, at least 275%, at least 300%, at least 350%, at least 400%, at least 450%, or at least 500% in at least one amino acid for the discriminating peptides that identify the autoimmune disease. In preferred embodiments, the autoimmune disease is SSc or DM. Exemplary discriminating peptides that distinguish a subject with SSc from reference subjects each having one of a plurality of different diseases are enriched in one or more of aspartic acid, glutamic acid, proline, valine, glycine, and serine (FIG. 10B).

Discriminating peptides that distinguish a subject with DM from reference subjects each having one of a plurality of different diseases are enriched in one or more of lysine, histidine, serine, arginine, glutamic acid, alanine, and glycine (FIG. 22B).

In some embodiments, the discriminating peptides of the immunosignature binding patterns for providing a differential diagnosis of autoimmune disease in a subject with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one motif for the peptides comprising the immunosignature for the autoimmune disease. In preferred embodiments, the autoimmune disease is SSc or DM. In some embodiments, discriminating peptides that distinguish SSc from the group of reference subjects each having one of a plurality of different autoimmune diseases are enriched in one or more of motifs provided in FIG. 10A. In some embodiments, discriminating peptides that distinguish DM from the group of reference subjects each having one of a plurality of different autoimmune diseases are enriched in one or more of motifs provided in FIG. 22A.

Other autoimmune diseases including SLE and RA also require careful evaluation by a rheumatologist. Difficulties in accurately quantifying disease and response to treatment can make patient care subjective and inconsistent. Accordingly, differential antibody binding to array peptides was assessed to identify discriminating peptides to provide candidate biomarkers for these diseases.

In some instances, methods, apparatus, and systems are presented for identifying candidate biomarkers of other autoimmune diseases including, Systemic Lupus Erythematosus (SLE), Rheumatoid Arthritis (RA), Sjogrens' disease (SS), Scleroderma, Osteoarthritis (OA), and Fibromyalgia (FM). The disclosed embodiments provide for identifying discriminating peptides that differentiate autoimmune diseases from each other, and from mimic disease conditions that are not classified as autoimmune, but that present with symptoms that are often associated with certain autoimmune diseases. Non-limiting examples of mimic disease conditions include osteoarthritis and fibromyalgia, which overlap in symptomology with autoimmune diseases such as SLE and RA. Additionally, methods, apparatus, and systems are presented for providing discriminating peptides and candidate biomarkers derived therefrom of autoimmune diseases including SLE and RA from samples obtained from a mixed population of conditions including other autoimmune diseases and non-autoimmune diseases.

In some instances, the mixed population also includes samples from healthy subjects. Examples 13-16 illustrate a method for identifying candidate target proteins using discriminating peptides that distinguish samples form healthy subjects from samples from subjects having SLE.

In some embodiments, a method is provided for identifying at least one candidate protein biomarker for systemic lupus erythematosus (SLE), the method comprising: (a) providing a peptide array and incubating a biological sample from a plurality of reference subjects known to have systemic lupus erythematosus to the peptide array; (b) identifying a set of discriminating peptides bound to antibodies in the biological sample from said subject, the set of discriminating peptides displaying binding signals capable of differentiating systemic lupus erythematosus from samples from healthy subjects; (c) querying a proteome database with each of the peptides in the set of discriminating peptides; (d) aligning each of the peptides in the set of discriminating peptides to one or more proteins in the human proteome database; and (e) obtaining a relevance score and ranking for each of the identified proteins from the proteome database; wherein each of the identified proteins is a candidate biomarker for systemic lupus erythematosus. The discriminating peptides can be identified by statistical means e.g. t-test, as having p-values of less than $10^{-3}$, less than $10^{-4}$, less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$. In some embodiments, the resulting candidate biomarkers can be ranked according to a p-value of less than less than $10^{-3}$, less than less than $10^{-4}$, less than less than $10^{-5}$, or less than less than $10^{-6}$ when compared to proteins identified according to the method but using non-discriminating peptides.

In some embodiments, candidate biomarkers of SLE can be identified using any one or more of the discriminating peptides listed in FIG. 90. The discriminating peptides were found to be enriched in sequence motifs listed in FIG. 62A. In some embodiments, the discriminating peptides for identifying a candidate biomarker of SSc with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the motifs listed in FIG. 62A. The same discriminating peptides were found to be enriched in amino acids listed in FIG. 62B. Accordingly, in other embodiments, the discriminating peptides for identifying a candidate biomarker of SLE with the methods and arrays disclosed herein are enriched in at least one, at least two, at least three, at least four, at least five, at least six, at least seven, at least eight, at least nine, or at least ten different amino acids. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the amino acids listed in FIG. 62B.

In some embodiments, the discriminating peptides used in the method are identified, for example by differences in binding signals, by statistical means e.g. t-test, as having p-values of less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$ comparing the relative binding signals of the antibody-bound peptides in the two different conditions.

An exemplary list of discriminating peptides that can be used for identifying candidate biomarkers of SLE is provided in FIG. 90. The list provides the top 50 discriminating peptides, which are peptides that discriminate with greatest significance the combination of antibody binding signals obtained using samples from subjects with SSc from the combination of binding signals obtained using samples from healthy subjects. In some embodiments, the method for identifying a candidate biomarker for SSc comprises identifying a set of discriminating peptides that comprise one or more of the discriminating peptides listed in FIG. 62A.

Candidate biomarkers for SLE are subsequently identified by aligning a set of discriminating peptides to a human proteome. As described elsewhere herein, an overlap score is determined from the alignment of the discriminating peptides to the proteome; and proteins so identified are scored and ranked relative to proteins that are identified using randomly chosen non-discriminating peptides to identify candidate biomarkers for SLE. In one embodiment, a candidate biomarker for SLE is selected from the list of candidate biomarkers listed in FIG. 75A. In some embodiments, the candidate biomarker proteins identified according to the method are ranked according to a p-value of less than less than $10^{-3}$, less than less than $10^{-4}$, less than less than $10^{-5}$, or less than less than $10^{-6}$.

In other embodiments, a method is provided for identifying at least one candidate protein biomarker for systemic lupus erythematosus (SLE), the method comprising: (a) providing a peptide array and incubating a biological sample from a plurality of reference subjects known to have systemic lupus erythematosus to the peptide array; (b) identifying a set of discriminating peptides bound to antibodies in the biological sample from said subject, the set of discriminating peptides displaying binding signals capable of differentiating systemic lupus erythematosus from samples from groups of subjects having other autoimmune diseases or non-autoimmune mimic diseases; (c) querying a proteome database with each of the peptides in the set of discriminating peptides; (d) aligning each of the peptides in the set of discriminating peptides to one or more proteins in the human proteome database; and (e) obtaining a relevance score and ranking for each of the identified proteins from the proteome database; wherein each of the identified proteins is a candidate biomarker for systemic lupus erythematosus. The discriminating peptides can be identified by statistical means e.g. t-test, as having p-values of less than $10^{-3}$, less than $10^{-4}$, less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$. In some embodiments, the resulting candidate biomarkers can be ranked according to a p-value of less than less than $10^{-3}$, less than less than $10^{-4}$, less than less than $10^{-5}$, or less than less than $10^{-6}$ when compared to proteins identified according to the method but using non-discriminating peptides.

In some embodiments, methods and devices are disclosed herein for identifying at least one candidate biomarker for SLE, the method comprising: (a) providing a peptide array and contacting a biological sample from a plurality of subjects known to have SLE to the peptide array; (b) identifying a set of discriminating peptides bound to antibodies in the biological sample from the plurality of subjects that differentiate SLE from at least one different health condition; (c) aligning each of the peptides in the set of discriminating peptides to one or more proteins in a proteome; and (d) obtaining a protein score and ranking for each of the identified proteins according to a statistical significance, thereby identifying at least one candidate biomarker for SLE.

In some embodiments, the step of identifying discriminating peptides comprises (i) detecting binding of antibodies present in the biological sample from the plurality of subjects having SLE to obtain a first combination of binding signals; (ii) detecting binding of antibodies present in samples from one or more reference groups of subjects to the same peptide array, each reference group having a different health condition to obtain a second combination of binding signals; (iii) comparing the first combination of binding signals to the second combination of binding signals to obtain a set of differentiating binding signals; and (iv) identifying peptides on the array that are differentially bound by antibodies in samples from subjects having SLE and the antibodies in the samples from the one or more reference groups of subjects, thereby identifying said discriminating peptides.

Examples 14-16 illustrate a method for identifying candidate target proteins for SLE using discriminating peptides that distinguish samples from subjects with SLE from samples from subjects having other auotoimmune or non-autoimmune mimic diseases.

In some embodiments, candidate biomarkers of SLE can be identified using any one or more of the discriminating peptides listed in FIG. 91. The discriminating peptides were found to be enriched in sequence motifs listed in FIG. 63A. In some embodiments, the discriminating peptides for identifying a candidate biomarker of SLE with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the motifs listed in FIG. 63A. The same discriminating peptides were found to be enriched in amino acids listed in FIG. 63B. Accordingly, in other embodiments, the discriminating peptides for identifying a candidate biomarker of SLE with the methods and arrays disclosed herein are enriched in at least one, at least two, at least three, at least four, at least five, at least six, at least seven, at least eight, at least nine, or at least ten different amino acids. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the amino acids listed in FIG. 63B. In some embodiments, discriminating peptides that distinguish SLE from healthy reference subjects are enriched in one or more amino acids.

In some embodiments, the discriminating peptides used in the method are identified, for example by differences in binding signals, by statistical means e.g. t-test, as having p-values of less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$ comparing the relative binding signals of the antibody-bound peptides in the two different conditions.

An exemplary list of discriminating peptides that can be used for identifying candidate biomarkers of SLE is provided in FIG. 75B. The list provides the top 50 discriminating peptides, which are peptides that discriminate with greatest significance the combination of antibody binding signals obtained using samples from subjects with SLE from the combination of binding signals obtained using samples from groups of subjects having other autoimmune diseases or non-autoimmune mimic diseases. In some embodiments, the method for identifying a candidate biomarker for SLE comprises identifying a set of discriminating peptides that comprise one or more of the discriminating peptides listed in FIG. 91.

Candidate biomarkers for SLE are subsequently identified by aligning a set of discriminating peptides to a human proteome. As described elsewhere herein, an overlap score is determined from the alignment of the discriminating peptides to the proteome; and proteins so identified are scored and ranked relative to proteins that are identified using randomly chosen non-discriminating peptides to identify candidate biomarkers for SLE. In one embodiment, a candidate biomarker for SLE is selected from the list of candidate biomarkers listed in FIG. 75B. In some embodiments, the candidate biomarker proteins identified according to the method are ranked according to a p-value of less than less than $10^{-3}$, less than less than $10^{-4}$, less than less than $10^{-5}$, or less than less than $10^{-6}$ In other embodiments, a method is provided for identifying at least one candidate protein biomarker for systemic lupus erythematosus (SLE), the method comprising: (a) providing a peptide array and incubating a biological sample from a plurality of reference subjects known to have systemic lupus erythematosus to the peptide array; (b) identifying a set of discriminating peptides bound to antibodies in the biological sample from said subject, the set of discriminating peptides displaying binding signals capable of differentiating systemic lupus erythematosus from samples from groups of subjects not having SLE who are healthy, have other autoimmune diseases or non-autoimmune mimic diseases; (c) querying a proteome database with each of the peptides in the set of discriminating peptides; (d) aligning each of the peptides in the set of discriminating peptides to one or more proteins in the human proteome database; and (e) obtaining a relevance score and ranking for each of the identified proteins from the proteome database; wherein each of the identified proteins is a candidate biomarker for systemic lupus erythematosus. The discriminating peptides can be identified by statistical means e.g. t-test, as having p-values of less than $10^{-3}$, less than $10^{-4}$, less than $10^{-5}$, less than $10^{-6}$, less than $10^{-7}$, less than $10^{-8}$, less than 10, less than $10^{-10}$, less than $10^{-11}$, less than $10^{-12}$, less than $10^{-13}$, less than $10^{-14}$, or less than $10^{-15}$. In some embodiments, the resulting candidate biomarkers can be ranked according to a p-value of less than less than $10^{-3}$, less than less than $10^{-4}$, less than less than $10^{-5}$, or less than less than $10^{-6}$ when compared to proteins identified according to the method but using non-discriminating peptides.

A method for identifying at least one candidate biomarker for SLE and discriminating against other autoimmune or non-autoimmune mimic diseases, the method comprising: (a) providing a peptide array and contacting a biological sample from a plurality of subjects known to have SLE to the peptide array; (b) identifying a set of discriminating peptides bound to antibodies in the biological sample from the plurality of subjects that differentiate SLE from at least one different health condition, including other autoimmune diseases or non-autoimmune mimic diseases; (c) aligning each of the peptides in the set of discriminating peptides to one or more proteins in a proteome; and (d) obtaining a protein score and ranking for each of the identified proteins according to a statistical significance, thereby identifying at least one candidate biomarker for SLE.

In some embodiments, the step of identifying discriminating peptides comprises (i) detecting binding of antibodies present in the biological sample from the plurality of subjects having SLE to obtain a first combination of binding signals; (ii) detecting binding of antibodies present in samples from one or more reference groups of subjects to the same peptide array, each reference group having a different health condition to obtain a second combination of binding signals, including other autoimmune diseases and non-autoimmune mimic diseases; (iii) comparing the first combination of binding signals to the second combination of binding signals to obtain a set of differentiating binding signals; and (iv) identifying peptides on the array that are differentially bound by antibodies in samples from subjects having the autoimmune disease and the antibodies in the samples from the one or more reference groups of subjects, thereby identifying said discriminating peptides.

Examples 14-16 illustrate a method for identifying candidate target proteins for SLE using discriminating peptides that distinguish samples from subjects with SLE from samples from subjects who are healthy, have other autoimmune or non-autoimmune mimic diseases ("Not SLE").

In some embodiments, candidate biomarkers of SLE can be identified using any one or more of the discriminating peptides listed in FIG. 92. The discriminating peptides were found to be enriched in sequence motifs listed in FIG. 64A. In some embodiments, the discriminating peptides for identifying a candidate biomarker of SLE with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the motifs listed in FIG. 64A. The same discriminating peptides were found to be enriched in amino acids listed in FIG. 64B. Accordingly, in other embodiments, the discriminating peptides for identifying a candidate biomarker of SLE with the methods and arrays disclosed herein are enriched in at least one, at least two, at least three, at least four, at least five, at least six, at least seven, at least eight, at least nine, or at least ten different amino acids. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the amino acids listed in FIG. 64B. In some embodiments, discriminating peptides that distinguish SLE from healthy reference subjects are enriched in one or more of amino acids.

In some embodiments, the discriminating peptides used in the method are identified, for example by differences in binding signals, by statistical means e.g. t-test, as having p-values of less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$ comparing the relative binding signals of the antibody-bound peptides in the two different conditions.

An exemplary list of discriminating peptides that can be used for identifying candidate biomarkers of SLE is provided in FIG. 92. The list provides the top 50 discriminating peptides, which are peptides that discriminate with greatest significance the combination of antibody binding signals obtained using samples from subjects with SLE from the combination of binding signals obtained using samples from groups of subjects having other autoimmune diseases or non-autoimmune mimic diseases. In some embodiments, the method for identifying a candidate biomarker for SLE comprises identifying a set of discriminating peptides that comprise one or more of the discriminating peptides listed in FIG. 92.

Candidate biomarkers for SLE are subsequently identified by aligning a set of discriminating peptides to a human proteome. As described elsewhere herein, an overlap score is determined from the alignment of the discriminating peptides to the proteome; and proteins so identified are scored and ranked relative to proteins that are identified using randomly chosen non-discriminating peptides to identify candidate biomarkers for SLE. In one embodiment, a candidate biomarker for SLE is selected from the list of candidate biomarkers listed in FIG. 75C. In some embodiments, the candidate biomarker proteins identified according to the method are ranked according to a p-value of less than less than $10^{-3}$, less than less than $10^{-4}$, less than less than $10^{-5}$, or less than less than $10^{-6}$ The methods provided can also identify candidate biomarkers for other autoimmune diseases. In some embodiments, candidate biomarkers are identified for RA. Examples 14, 17-18 illustrate a method for identifying candidate target proteins using discriminating peptides that distinguish samples form healthy subjects from samples from subjects having RA.

In some embodiments, a method is provided for identifying at least one candidate protein biomarker for rheumatoid arthritis (RA), the method comprising: (a) providing a peptide array and incubating a biological sample from a plurality of reference subjects known to have systemic lupus erythematosus to the peptide array; (b) identifying a set of discriminating peptides bound to antibodies in the biological sample from said subject, the set of discriminating peptides displaying binding signals capable of differentiating systemic lupus erythematosus from samples from healthy subjects; (c) querying a proteome database with each of the peptides in the set of discriminating peptides; (d) aligning each of the peptides in the set of discriminating peptides to one or more proteins in the human proteome database; and (e) obtaining a relevance score and ranking for each of the identified proteins from the proteome database; wherein each of the identified proteins is a candidate biomarker for systemic lupus erythematosus. The discriminating peptides can be identified by statistical means e.g. t-test, as having p-values of less than $10^{-3}$, less than $10^{-4}$, less than $10^{-5}$, less than $10^{-6}$, less than $10^{-7}$, less than $10^{-8}$, less than 10, less than $10^{-10}$, less than $10^{-11}$, less than $10^{-12}$, less than $10^{-13}$, less than $10^{-14}$, or less than $10^{-15}$. In some embodiments, the resulting candidate biomarkers can be ranked according to a p-value of less than less than $10^{-3}$, less than less than $10^{-4}$, less than less than $10^{-5}$, or less than less than $10^{-6}$ when compared to proteins identified according to the method but using non-discriminating peptides.

In some aspects, methods and devices for identifying at least one candidate biomarker RA, the method comprising: (a) providing a peptide array and contacting a biological sample from a plurality of subjects known to have RA to the peptide array; (b) identifying a set of discriminating peptides bound to antibodies in the biological sample from the plurality of subjects that differentiate RA from healthy controls; (c) aligning each of the peptides in the set of discriminating peptides to one or more proteins in a proteome; and (d) obtaining a protein score and ranking for each of the identified proteins according to a statistical significance, thereby identifying at least one candidate biomarker for RA.

In some embodiments, the step of identifying discriminating peptides comprises: (i) detecting binding of antibodies present in the biological sample from the plurality of subjects having RA to obtain a first combination of binding signals; (ii) detecting binding of antibodies present in samples from one or more reference groups of subjects to the same peptide array, each reference group having a different health condition to obtain a second combination of binding signals; (iii) comparing the first combination of binding signals to the second combination of binding signals to obtain a set of differentiating binding signals; and (iv) identifying peptides on the array that are differentially bound by antibodies in samples from subjects having RA and the antibodies in the samples from the one or more reference groups of subjects, including healthy controls, thereby identifying said discriminating peptides.

In some embodiments, candidate biomarkers of RA can be identified using any one or more of the discriminating peptides listed in FIG. 93. The discriminating peptides were found to be enriched in sequence motifs listed in FIG. 76A. In some embodiments, the discriminating peptides for identifying a candidate biomarker of SSc with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the motifs listed in FIG. 76A. The same discriminating peptides were found to be enriched in amino acids listed in FIG. 76B. Accordingly, in other embodiments, the discriminating peptides for identifying a candidate biomarker of RA with the methods and arrays disclosed herein are enriched in at least one, at least two, at least three, at least four, at least five, at least six, at least seven, at least eight, at least nine, or at least ten different amino acids. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the amino acids listed in FIG. 76B. In some embodiments, discriminating peptides that distinguish RA from healthy reference subjects are enriched in one or more of amino acids.

In some embodiments, the discriminating peptides used in the method are identified, for example by differences in binding signals, by statistical means e.g. t-test, as having p-values of less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$ comparing the relative binding signals of the antibody-bound peptides in the two different conditions.

An exemplary list of discriminating peptides that can be used for identifying candidate biomarkers of RA is provided in FIG. 93. The list provides the top 50 discriminating peptides, which are peptides that discriminate with greatest significance the combination of antibody binding signals obtained using samples from subjects with SSc from the combination of binding signals obtained using samples from healthy subjects. In some embodiments, the method for identifying a candidate biomarker for SSc comprises identifying a set of discriminating peptides that comprise one or more of the discriminating peptides listed in FIG. 93.

Candidate biomarkers for RA are subsequently identified by aligning a set of discriminating peptides to a human proteome. As described elsewhere herein, an overlap score is determined from the alignment of the discriminating peptides to the proteome; and proteins so identified are scored and ranked relative to proteins that are identified using randomly chosen non-discriminating peptides to identify candidate biomarkers for RA. In one embodiment, a candidate biomarker for RA is selected from the list of candidate biomarkers listed in FIG. 87A. In some embodiments, the candidate biomarker proteins identified according to the method are ranked according to a p-value of less than less than $10^{-3}$, less than less than $10^{-4}$, less than less than $10^{-5}$, or less than less than $10^{-6}$.

In other embodiments, a method is provided for identifying at least one candidate protein biomarker for systemic lupus erythematosus (RA), the method comprising: (a) providing a peptide array and incubating a biological sample from a plurality of reference subjects known to have systemic lupus erythematosus to the peptide array; (b) identifying a set of discriminating peptides bound to antibodies in the biological sample from said subject, the set of discriminating peptides displaying binding signals capable of differentiating systemic lupus erythematosus from samples from groups of subjects having other auotoimmune diseases or non-autoimmune mimic diseases; (c) querying a proteome database with each of the peptides in the set of discriminating peptides; (d) aligning each of the peptides in the set of discriminating peptides to one or more proteins in the human proteome database; and (e) obtaining a relevance score and ranking for each of the identified proteins from the proteome database; wherein each of the identified proteins is a candidate biomarker for systemic lupus erythematosus. The discriminating peptides can be identified by statistical means e.g. t-test, as having p-values of less than $10^{-3}$, less than $10^{-4}$, less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$. In some embodiments, the resulting candidate biomarkers can be ranked according to a p-value of less than less than $10^{-3}$, less than less than $10^{-4}$, less than less than $10^{-5}$, or less than less than $10^{-6}$ when compared to proteins identified according to the method but using non-discriminating peptides.

In some embodiments, the step of identifying discriminating peptides comprises . . . .

Examples 14 and 17-18 illustrate a method for identifying candidate target proteins for RA using discriminating peptides that distinguish samples from subjects with RA from samples from subjects having other auotoimmune or non-autoimmune mimic diseases.

In some embodiments, candidate biomarkers of RA can be identified using any one or more of the discriminating peptides listed in FIG. 87B. The discriminating peptides were found to be enriched in sequence motifs listed in FIG. 94. In some embodiments, the discriminating peptides for identifying a candidate biomarker of RA with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the motifs listed in FIG. 79A. The same discriminating peptides were found to be enriched in amino acids listed in FIG. 79B. Accordingly, in other embodiments, the discriminating peptides for identifying a candidate biomarker of RA with the methods and arrays disclosed herein are enriched in at least one, at least two, at least three, at least four, at least five, at least six, at least seven, at least eight, at least nine, or at least ten different amino acids. Enrichment of the amino acids can be by at least 100%, at least 125%, at least 150%, at least 175%, at least 200%, at least 225%, at least 250%, at least 275%, at least 300%, at least 350%, at least 400%, at least 450%, or at least 500% in at least one of the amino acids listed in FIG. 79B. In some embodiments, discriminating peptides that distinguish RA from healthy reference subjects are enriched in one or more of amino acids.

In some embodiments, the discriminating peptides used in the method are identified, for example by differences in binding signals, by statistical means e.g. t-test, as having p-values of less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$ comparing the relative binding signals of the antibody-bound peptides in the two different conditions.

An exemplary list of discriminating peptides that can be used for identifying candidate biomarkers of RA is provided in FIG. 94. The list provides the top 50 discriminating peptides, which are peptides that discriminate with greatest significance the combination of antibody binding signals obtained using samples from subjects with RA from the combination of binding signals obtained using samples from groups of subjects having other autoimmune diseases or non-autoimmune mimic diseases. In some embodiments, the method for identifying a candidate biomarker for RA comprises identifying a set of discriminating peptides that comprise one or more of the discriminating peptides listed in FIG. 94.

Candidate biomarkers for RA are subsequently identified by aligning a set of discriminating peptides to a human proteome. As described elsewhere herein, an overlap score is determined from the alignment of the discriminating peptides to the proteome; and proteins so identified are scored and ranked relative to proteins that are identified using randomly chosen non-discriminating peptides to identify candidate biomarkers for RA. In one embodiment, a candidate biomarker for RA is selected from the list of candidate biomarkers listed in FIG. 86B. In some embodiments, the candidate biomarker proteins identified according to the method are ranked according to a p-value of less than less than $10^{-3}$, less than less than $10^{-4}$, less than less than $10^{-5}$, or less than less than $10^{-6}$ In other embodiments, a method is provided for identifying at least one candidate protein biomarker for systemic lupus erythematosus (RA), the method comprising: (a) providing a peptide array and incubating a biological sample from a plurality of reference subjects known to have systemic lupus erythematosus to the peptide array; (b) identifying a set of discriminating peptides bound to antibodies in the biological sample from said subject, the set of discriminating peptides displaying binding signals capable of differentiating systemic lupus erythematosus from samples from groups of subjects not having RA who are healthy, have other autoimmune diseases or non-autoimmune mimic diseases; (c) querying a proteome database with each of the peptides in the set of discriminating peptides; (d) aligning each of the peptides in the set of discriminating peptides to one or more proteins in the human proteome database; and (e) obtaining a relevance score and ranking for each of the identified proteins from the proteome database; wherein each of the identified proteins is a candidate biomarker for systemic lupus erythematosus. The discriminating peptides can be identified by statistical means e.g. t-test, as having p-values of less than $10^{-3}$, less than $10^{-4}$, less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$. In some embodiments, the resulting candidate biomarkers can be ranked according to a p-value of less than less than $10^{-3}$, less than less than $10^{-4}$, less than less than $10^{-5}$, or less than less than $10^{-6}$ when compared to proteins identified according to the method but using non-discriminating peptides.

In some embodiments, the step of identifying discriminating peptides comprises (i) detecting binding of antibodies present in the biological sample from the plurality of subjects having RA to obtain a first combination of binding signals; (ii) detecting binding of antibodies present in samples from one or more reference groups of subjects having other autoimmune diseases or non-autoimmune mimic diseases to the same peptide array, each reference group having a different health condition to obtain a second combination of binding signals; (iii) comparing the first combination of binding signals to the second combination of binding signals to obtain a set of differentiating binding signals; and (iv) identifying peptides on the array that are differentially bound by antibodies in samples from subjects having RA and the antibodies in the samples from the one or more reference groups of subjects, thereby identifying said discriminating peptides.

Examples 14 and 17-18 illustrate a method for identifying candidate target proteins for RA using discriminating peptides that distinguish samples from subjects with RA from samples from subjects who are healthy, have other autoimmune or non-autoimmune mimic diseases ("Not RA").

In some embodiments, candidate biomarkers of RA can be identified using any one or more of the discriminating peptides listed in FIG. 95. The discriminating peptides were found to be enriched in sequence motifs listed in FIG. 78A. In some embodiments, the discriminating peptides for identifying a candidate biomarker of RA with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the motifs listed in FIG. 78A. The same discriminating peptides were found to be enriched in amino acids listed in FIG. 78B. Accordingly, in other embodiments, the discriminating peptides for identifying a candidate biomarker of RA with the methods and arrays disclosed herein are enriched in at least one, at least two, at least three, at least four, at least five, at least six, at least seven, at least eight, at least nine, or at least ten different amino acids. Enrichment of the amino acids can be by at least 100%, at least 125%, at least 150%, at least 175%, at least 200%, at least 225%, at least 250%, at least 275%, at least 300%, at least 350%, at least 400%, at least 450%, or at least 500% in at least one of the amino acids listed in FIG. 78B.

In some embodiments, the discriminating peptides used in the method are identified, for example by differences in binding signals, by statistical means e.g. t-test, as having p-values of less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$ comparing the relative binding signals of the antibody-bound peptides in the two different conditions.

An exemplary list of discriminating peptides that can be used for identifying candidate biomarkers of RA is provided in FIG. 95. The list provides the top 50 discriminating peptides, which are peptides that discriminate with greatest significance the combination of antibody binding signals obtained using samples from subjects with RA from the combination of binding signals obtained using samples from groups of subjects having other autoimmune diseases or non-autoimmune mimic diseases. In some embodiments, the method for identifying a candidate biomarker for RA comprises identifying a set of discriminating peptides that comprise one or more of the discriminating peptides listed in FIG. 95.

Candidate biomarkers for RA are subsequently identified by aligning a set of discriminating peptides to a human proteome. As described elsewhere herein, an overlap score is determined from the alignment of the discriminating peptides to the proteome; and proteins so identified are scored and ranked relative to proteins that are identified using randomly chosen non-discriminating peptides to identify candidate biomarkers for RA. In one embodiment, a candidate biomarker for RA is selected from the list of candidate biomarkers listed in FIG. 87C. In some embodiments, the candidate biomarker proteins identified according to the method are ranked according to a p-value of less than less than $10^{-3}$, less than less than $10^{-4}$, less than less than $10^{-5}$, or less than less than $10^{-6}$ Discriminating peptides that distinguish SLE from any one of RA, OA, FM, and SS can be identified, and enrichment of these peptides for sequence motifs can determined as described in elsewhere herein. Example 14-16 illustrate the method for identifying discriminating peptides that distinguish SLE from each of RA, OA, FM, and SS, and the enriched sequence motifs and amino acids are provided respectively in FIGS. 65A-68B. Similarly, discriminating peptides that distinguish samples from patients with RA from samples from each of groups of subjects with OA, FM, and SS are provided as described in Examples 14 and 17-18, and the corresponding sequence motifs and amino acids enriched in the discriminating peptides are provided in FIGS. 66A-68B, respectively. Additionally, comparison of binding signals obtained from a group of subjects with RA and subjects with other rheumatic diseases revealed a set of discriminating peptides that are enriched in motifs and amino acids listed in FIGS. 77A-77B.

The discriminating peptides identified can be used to identify candidate target proteins i.e. candidate biomarkers, using sequence the motifs that are enriched in the discriminating peptides that distinguish the different conditions. In one embodiment, the method for identifying a candidate target for the treatment of an autoimmune disease in a human subject comprises (a) obtaining a set of discriminating peptides that differentiate the autoimmune disease from one or more different autoimmune diseases; (b) identifying a set of motifs for said discriminating peptides; (c) aligning the set of motifs to a human proteome; (d) identifying regions of homology between each motif in the set to a region of an immunogenic protein; and (e) identifying the protein as a candidate target said autoimmune disease.

Additionally, candidate biomarkers can be identified using discriminating peptides that simultaneously distinguish SLE, RA, FM, OA, and healthy subjects from each other. Sequences of submotifs and amino acids that are enriched in the multiclassification of the diseases are listed in FIG. 89. The motifs can be used to identify candidate biomarkers as described elsewhere herein.

Biomarkers of Disease Progression

Binding signal information of the discriminating peptides selected following statistical analysis can be subsequently imported into a machine learning algorithm to obtain a model that classifies the antibody profile data with the desired accuracy, sensitivity and specificity, and identifies candidate biomarkers for disease progression. In some embodiments, candidate biomarkers can be identified for disease progression of autoimmune diseases including, but not limited to, SSc and DM. In some cases, disease progression is identified by organ involvement.

The milder form of scleroderma is generally limited to areas of skin are thick; usually just the fingers and/or face. Every person with scleroderma can have a different pattern of symptoms including calcinosis, which is the deposit of calcium under the ski and tissues, Raynaud's phenomenon, esophageal dysmotility, sclerodactily, and telangiectasias. However, scleroderma can progress to a diffuse disease which involves more areas and thickening of the skin, and can include the skin of the arms, legs, and trunk. The tightened skin makes it difficult to bend fingers, hands, and other joints. There is sometimes inflammation of the joints, tendons and muscles. Tight skin on the face can reduce the size of a person's mouth and make good dental care very important. The skin can lose or gain pigment; making areas of light or dark skin. Some people lose hair on the limbs, sweat less, and develop dry skin because of skin damage. More importantly, diffuse scleroderma can have associated involvement of internal organs such as the gastrointestinal tract, heart, lungs, or kidneys. The degree of organ involvement is highly variable—some get none at all and other patients organs may be badly affected. Discriminating peptides can also distinguish different states reflective of the progression of a disease e.g. an autoimmune disease. For example, progression of SSc can manifest in interstitial lung disease (ILD). In some case, SSc can progress to manifest in gastric antral vascular ectasia (GAVE). In other cases, SSc can progress to involve the kidneys. Complications relating to ILD and GAVE can also occur in other mimic autoimmune disease e.g. DM.

In some embodiments, the discriminating peptides distinguish from subjects having SSc and organ involvement from subjects having SSc without organ involvement. In other embodiments, the discriminating peptides distinguish from subjects having DM and organ involvement from subjects having DM without organ involvement. Thus, the candidate biomarkers can serve to diagnose a disease, to identifying a stage of disease progression. The biomarkers can also be used in the monitoring of disease. In some embodiments, the candidate biomarker proteins identified according to the method are ranked according to a p-value of less than less than $10^{-3}$, less than less than $10^{-4}$, less than less than $10^{-5}$, or less than less than $10^{-6}$.

In one aspect, a method is provided for identifying candidate biomarkers for a disease state or progression of an autoimmune disorder in a subject, the method comprising: a. contacting a peptide array with first biological samples from subjects with a known autoimmune disorder without a clinical manifestation that can occur with progression of the AI disease; b. detecting binding of antibodies in the first biological samples with same peptide arrays to obtain first immunosignature profile; c. contacting same peptide arrays with control samples derived from individuals with a known stage of the autoimmune disorder having a clinical manifestation associated with the AI; d. detecting binding of antibodies in the reference samples with same peptide arrays to obtain a second immunosignature profile; e. comparing the first immunosignature profile to the second immunosignature profile to identify discriminating peptides indicative of the clinical manifestation. Subsequently, the discriminating peptides are used to identify the candidate biomarkers indicative of disease stage or progression.

In some embodiments, the assays, methods and devices provided can determine disease progression in a subject known to have an autoimmune disease. The method comprising: (a) contacting a sample from a subject to an array of peptides comprising at least 10,000 different peptides synthesized in situ; (b) detecting the binding of antibodies present in the sample to at least 25 peptides on said array to obtain a first combination of binding signals; and (c) comparing the first combination of binding signals to at least a second combination of reference binding signals, wherein the second combination of reference binding signals comprises a combination of binding signals obtained from a reference group comprising a plurality of subjects having a clinical manifestation indicative of progression of said autoimmune disease, thereby making said differential diagnosis, wherein the method performance is characterized by an area under the receiver operator characteristic (ROC) curve (AUC) being greater than 0.6. In some embodiments, disease progression is determined in a subject having SSC accompanied by ILD. In other embodiments, progression is determined in a subject having SSC accompanied by GAVE. In yet other embodiments, progression is determined in a subject having DM accompanied by ILD.

In some embodiments, the discriminating peptides of the immunosignature binding patterns for determining the progression of an autoimmune disease in a subject with the methods and arrays disclosed herein are enriched in at least one, at least two, at least three, at least four, at least five, at least six, at least seven, at least eight, at least nine, or at least ten different amino acids. Enrichment of the amino acids can be by at least 100%, at least 125%, at least 150%, at least 175%, at least 200%, at least 225%, at least 250%, at least 275%, at least 300%, at least 350%, at least 400%, at least 450%, or at least 500% in at least one amino acid for the peptides comprising the immunosignature for the autoimmune disease. In some embodiments, determination of disease progression is made between in subjects with SSc, and the progression is determined in subjects with ILD and/or GAVE. In some embodiments, discriminating peptides that determine disease progression in subjects with SSc and ILD relative to subjects with SSC without ILD are enriched in one or more of proline, arginine, lysine, histidine, and aspartic acid (FIG. 18B). In other embodiments, discriminating peptides that determine disease progression in subjects with SSc and GAVE relative to subjects with SSC without GAVE are enriched in one or more of arginine, tyrosine, serine, histidine, lysine, and phenylalanine (FIG. 14B).

In some embodiments, the discriminating peptides of the immunosignature binding patterns for determining the progression of an autoimmune disease in a subject with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one motif for the peptides comprising the immunosignature for the autoimmune disease. In preferred embodiments, the autoimmune disease is SSc or DM. In preferred embodiments, determination of disease progression is made between in subjects with SSc, and the progression is determined in subjects with ILD and/or GAVE. In some embodiments, discriminating peptides that determine disease progression in subjects with SSc and ILD relative to subjects with SSC without ILD are enriched in one or more of motifs provided in FIG. 18A. In other embodiments, discriminating peptides that determine disease progression in subjects with SSc and GAVE relative to subjects with SSC without GAVE are enriched in one or more of motifs provided in FIG. 14A.

In some embodiments, the discriminating peptides of the immunosignature binding patterns for determining the progression of an autoimmune disease in a subject with the methods and arrays disclosed herein are enriched in at least one, at least two, at least three, at least four, at least five, at least six, at least seven, at least eight, at least nine, or at least ten different amino acids. Enrichment of the amino acids can be by at least 100%, at least 125%, at least 150%, at least 175%, at least 200%, at least 225%, at least 250%, at least 275%, at least 300%, at least 350%, at least 400%, at least 450%, or at least 500% in at least one amino acid for the peptides comprising the immunosignature for the autoimmune disease. In preferred embodiments, determination of disease progression is made between in subjects with SSc without renal crisis, and the progression is determined in subjects with SSc having renal crisis. In some embodiments, discriminating peptides that determine disease progression in subjects with SSc without renal crisis relative to subjects with SSC without renal crisis are enriched in one or more of proline, aspartic acid and glutamic acid (FIG. 14B).

In some embodiments, the discriminating peptides of the immunosignature binding patterns for determining the progression of an autoimmune disease in a subject with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one motif for the peptides comprising the immunosignature for the autoimmune disease. In preferred embodiments, determination of disease progression is made between in subjects with SSc without renal crisis, and the progression is determined in subjects with SSc having renal crisis. In some embodiments, discriminating peptides that determine disease progression in subjects with SSc and renal crisis relative to subjects with SSC without renal crisis are enriched in one or more of motifs provided in FIG. 12A.

In some embodiments, the discriminating peptides of the immunosignature binding patterns for determining the progression of an autoimmune disease in a subject with the methods and arrays disclosed herein are enriched in at least one, at least two, at least three, at least four, at least five, at least six, at least seven, at least eight, at least nine, or at least ten different amino acids. Enrichment of the amino acids can be by at least 100%, at least 125%, at least 150%, at least 175%, at least 200%, at least 225%, at least 250%, at least 275%, at least 300%, at least 350%, at least 400%, at least 450%, or at least 500% in at least one amino acid for the peptides comprising the immunosignature for the autoimmune disease. In preferred embodiments, determination of disease progression is made between in subjects with DM, and the progression is determined in subjects with ILD and/or GAVE. In some embodiments, discriminating peptides that determine disease progression in subjects with DM and ILD relative to subjects with DM without ILD are enriched in one or more of proline, aspartic acid, glutamic acid, serine, glycine, and glutamine (FIG. 24B).

In some embodiments, the discriminating peptides of the immunosignature binding patterns for determining the progression of an autoimmune disease in a subject with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one motif for the peptides comprising the immunosignature for the autoimmune disease. In preferred embodiments, determination of disease progression is made between in subjects with DM, and the progression is determined in subjects with ILD and/or GAVE. In some embodiments, discriminating peptides that determine disease progression in subjects with DM and ILD relative to subjects with DM without ILD are enriched in one or more of motifs provided in FIG. 24A.

As described for the method of identifying candidate biomarkers for an autoimmune disease, comparison of the disease immune profile/combination of binding signals to a reference combination of binding signals that reflects a progression of the disease e.g. disease immune profile of subjects having organ involvement, and identifying differentially bound peptides can reveal that at least some discriminating peptides bind more antibody in the disease immune profile compared to the reference; and/or peptides that at least some discriminating peptides bind less antibody in the disease immune profile compared to the reference. In some embodiments, a method is provided for identifying candidate biomarkers for progression of an autoimmune disorder, the method comprising: (a) providing a peptide array and contacting a plurality of biological samples from a plurality of subjects known to have the autoimmune disease to the peptide array; (b) identifying a set of discriminating peptides bound to antibodies in the biological samples, wherein the binding to the discriminating peptides correlates with a known disease score, and wherein binding to the discriminating peptides further correlates a change in antibody binding with a change in known disease score; (c) aligning each of the peptides in the set of discriminating peptides to one or more proteins in a proteome; and (d) obtaining a protein score and ranking for each of the identified proteins according to a statistical significance, thereby identifying at least one candidate biomarker indicative of autoimmune disease activity.

In some instances, the step of identifying the set of correlating peptides comprises: (i) detecting the binding of antibodies present in the samples from the plurality of subjects having the autoimmune disease at a corresponding known first disease score to obtain a first combination of binding signals; (ii) detecting the binding of antibodies in samples collected from the same plurality of subjects at a later time and corresponding known at least second disease score to a same peptide array of peptides, to obtain at least a second combination of binding signals for each of the subjects; (iii) comparing the first combination of binding signals and first known disease score to the second combination of binding signals and at least second disease score; and (iv) identifying the peptides that display a correlation between (i) the change between the first and at least second combination of binding signals, and (ii) the corresponding change in known disease score for each subject; thereby identifying the set of correlating peptides.

Candidate Biomarkers for Disease Activity

Autoimmune disease patients can experience chronically active disease, fluctuating rounds of remission and flare, or long quiescence. Accurately detecting and determining the status of a patient is central to prescribing appropriate drug regimens, evaluating treatment outcomes, defining patient subgroups, and early detection of flare onsets in order to improve therapeutic outcomes of patients afflicted with an autoimmune disease. Prompt treatment, for example of flares related to systemic lupus erytrematosus, not results in better immediate outcomes, but will prevent cumulative chronic organ damage. Accordingly, sensitive and specific diagnosis of disease activity remains an important unmet clinical need. See Oglesby et al, Impact of early versus late systemic lupus erythematosus diagnosis on clinical and economic outcomes. Applied Health Economics & Health Policy. 12(2):179-90, 2014; Lisnevskaia et al, Systemic lupus erythematosus. Lancet. 384(9957):1878-88, 2014.

A common approach instead for clinical studies is the use of scoring systems to evaluate physiological and biochemical manifestations of the autoimmune condition in subjects. For example, the most commonly used study of lupus activity for clinical subjects is the Systemic Lupus Erythematosus Disease Activity Index (SLEDAI). SLEDAI is a list of 24 clinical manifestations and laboratory tests, such as seizure, psychosis, organic brain syndrome, visual disturbance, other neurological problems, hair loss, new rash, muscle weakness, arthritis, blood vessel inflammation, mouth sores, chest pain worsening with deep breathing and manifestations of pleurisy and/or pericarditis and fever. The laboratory results analyzed include urinalysis testing, blood complement levels, increased anti-DNA antibody levels, low platelets and low white blood cell count. Each item is scored based on whether these manifestations have been present or absent in the patient in the previous 10 days. See FIGS. 49A and 49B.

The SLEDAI index requires weighting of the different clinical and laboratory test categories, including organ involvement. For example, joint pain and kidney disease are each multiplied by four, but central nervous system neurological manifestations are multiplied by eight. The assigned weighted assessment is then summed up into a final score, which ranges from zero to 105, with scores greater than 20 being unusual or rare. However, while there is no consensus on how to classify these scores, a SLEDAI score of 6 or more has been shown to be consistent with active disease requiring therapy, while a score below 3 is generally considered to be inactive. Scores of 4 to 15 are indicative of mild or moderate disease, and those greater than 15 are considered to be severe. A clinically meaningful difference has been reported to be an improvement of 6 points or worsening of 8 points.

The SLEDAI assessment was modified in the Safety of Estrogens in Lupus Erythematosus National Assessment (SELENA) trial, also known as the SELENA-SLEDAI flare index. While the SELENA-SLEDAI offers some clarification with regards to the definitions of clinical activity in each item, the basic premise and scoring system developed and characterized in the SLEDAI analysis has not changed significantly.

Yet other clinical assessment instruments for assessing systemic lupus erythematosus includes the BILAG (British Isles Lupus Activity Group), which is an 86 question physician's assessment of specific organ function, including a compilation of multiple manifestations and laboratory tests combined into a single score for a given organ system. In addition, other diseases or disorders have similar correlative assays which can also be used to establish or grade disease activity, including DAS28 (Disease Activity Score) for rheumatoid arthritis, TNM (Tumor, Node, Metastasis) staging system for cancer disorders, the Nottingham grading system (also known as the Elston-Ellis modification of the Scarff-Bloom-Richardson grading system), the Gleason scoring system for the prognosis and diagnosis of prostate cancer, amongst others.

Because of its complexity, disease scoring systems, such as SLEDAI, BILAG, and other correlative tests, are most commonly applied in research or clinical trials to evaluate the effectiveness of new drugs. It is, however, impractical for routine use by clinicians (for example, Rheumatologists). A simple, accurate, molecular test is needed to improve patient care.

Differential binding of patient samples to the array results in specific binding patterns or signatures indicative of the disease state of the patient. These binding signatures can accurately determine or diagnose a disease activity, including but not limited to autoimmune disease activity, infectious disease activity, cancer activity, and diabetes disease activity. For example, the methods and devices disclosed herein can identify or determine an SLE activity, correlating with clinical assessment outcomes, such as SLEDAI or BILAG.

Peptides with signal intensities that correlate with disease score, and that correlate with changes in peptide intensity and changes in disease score can be identified from samples from each of a plurality of subjects to obtain combinations of binding signals that correlate with disease score and with changes in diseases score e.g. SLEDAI, over time. Significant peptides that correlate with disease score can be identified by comparing combinations of antibody binding signals to a peptide array obtained from samples with a known disease score, and from combinations of antibody binding signals to a same peptide array obtained in pairs of samples each pair being from a same subject, wherein the second of the pair of samples is obtained at a time later than when the first sample was obtained. A correlation between combinations of binding signals at each time a sample is tested and the known disease score, and a correlation between changes in combinations of binding signals with changes in diseases score identifies array peptides that correlate with the disease score. The correlating peptides are akin to the discriminating peptides described for embodiments relating to the identification of biomarkers of disease described elsewhere herein, and are herein termed "discriminating peptides". The discriminating peptides of disease activity can be subsequently aligned to a proteome, and at least one candidate biomarker of disease activity can be identified as described elsewhere herein.

In one aspect, disclosed herein are methods and devices for identifying at least one candidate biomarker for an autoimmune disease, the method comprising: (a) providing a peptide array and contacting a biological sample from a plurality of subjects known to have the autoimmune disease to the peptide array; (b) identifying a set of discriminating peptides bound to antibodies in the biological sample from the plurality of subjects that differentiate the autoimmune disease from at least one different health condition; (c) aligning each of the peptides in the set of discriminating peptides to one or more proteins in a proteome; and (d) obtaining a protein score and ranking for each of the identified proteins according to a statistical significance, thereby identifying at least one candidate biomarker for the autoimmune disease.

In one embodiment, the autoimmune disease is SLE, and the discriminating peptides having signal intensities that correlate with SLE activity are identified. Examples 12-13 illustrate a method for identifying candidate target proteins for SLE activity using discriminating peptides that correlate combinations of binding signals corresponding to known SLEDAI score, and changes in signal intensities in the combinations of binding signals related to changes in corresponding SLEDAI score.

A set of 702 discriminating peptides that correlate to SLEDAI score is provided in FIG. 61. The discriminating peptides are enriched in peptide motifs and amino acids, relative to the motif and amino acid content in the library peptides. Motifs and amino acids that are enriched in the SLEDAI correlating peptides are provided in FIGS. 60A-60G.

The SLEDAI-correlating peptides can be enriched in at least one, at least two, at least three, at least four, at least five, at least six, at least seven, at least eight, at least nine, or at least ten different sequence motifs and/or amino acids. Enrichment of the sequence motifs and/or amino acids can be by at least 100%, at least 125%, at least 150%, at least 175%, at least 200%, at least 225%, at least 250%, at least 275%, at least 300%, at least 350%, at least 400%, at least 450%, or at least 500%, relative to the motif and/or amino acid content of the peptide library.

Discriminating peptides were aligned to a human proteome, and overlap scores were obtained from aligning the peptides to 20mer portions of proteome sequences that were set to overlap by 10mer. Proteins to which the peptides were aligned were identified and ranked by statistical relevance of protein score relative to the score of proteins identified using randomly chosen non-discriminating peptides. A set of discriminating peptides that correlate with SLEDAI score is provided in Table 11.

Candidate Biomarkers of Infectious Disease

Infectious diseases are disorders usually caused by microorganisms such as bacteria, viruses, fungi or parasites. Diagnosis of infection typically requires laboratory tests of body fluids such as blood, urine, throat swabs, stool samples, and in some cases, spinal taps. Imaging scan and biopsies may also be used to identify the infectious source. A variety of individual tests are available to diagnose an infection and include immunoassays, polymerase chain reaction, fluorescence in situ hybridization, and genetic testing for the pathogen. Present methods are time-consuming, complicated and labor-intensive and may require varying degrees of expertise. Additionally, the available diagnostic tools are often unreliable to detect early stages of infections, and often, more than one method is needed to positively diagnose an infection. In many instances, an infected person may not display any symptoms of infection until severe complications erupt.

An example is the infection by *Trypanosoma cruzi* (*T. cruzi*), which causes Chagas disease. Chagas disease is one of the leading cause of death and morbidity in Latin America and the Caribbean [Perez C J et al., Lymbery A J, Thompson R C (2014) Trends Parasitol 30: 176-182], and is a significant contributor to the global burden of cardiovascular disease [Chatelain E (2017) Comput Struct Biotechnol J 15: 98-103]. Chagas disease is considered the most neglected parasitic disease in these geographical regions, and epidemiologist are tracking its further spread into nonendemic countries including the US and Europe [Bern C (2015) Chagas' Disease. N Engl J Med 373: 1882; Bern C, and Montgomery S P (2009) Clin Infect Dis 49: e52-54; Rassi Jr A et al., (2010) The Lancet 375: 1388-1402]. The etiologic agent, *T. cruzi*, is a flagellated protozoan that is transmitted predominantly by blood-feeding triatomine insects to mammalian hosts, where it can multiply in any nucleated cell.

Other modes of dissemination include blood transfusion or congenital and oral routes [Steverding D (2014) Parasit Vectors 7: 317].

Methods, diagnostic tools and additional biomarkers are needed to identify infections, preferably detect infections at early stages, and in the absence of symptoms.

The disclosed embodiments concern methods, apparatus, and systems for identifying candidate biomarkers for infections. The methods are predicated on identifying discriminating peptides present on a peptide array, which are differentially bound by biological samples from subjects consequent to an infection, as compared to binding of samples from reference subjects. The identified candidate biomarkers are useful for the diagnosis, prognosis, monitoring and screening of infections, and/or as a therapeutic target for treatment of an infection.

The identification of any one infection and of the candidate biomarkers for the infection is founded on the presence of an immunosignature (IST), which exhibit the binding of antibodies from a subject to a library of peptides on an array as a pattern of binding signals i.e. a combination of binding signals, that reflect the immune status of the subject. IST is a combination of discriminating peptides that differentially bind antibodies present in a sample of a subject relative to a combination of peptides that are bound by antibodies present in reference samples. The patterns of binding signals comprise binding information that can be indicative of a state e.g. seropositive or seronegative, of a symptomatic, and/or of an asymptomatic state consequent to an infection.

The methods described herein provide several advantages over existing methods. In one aspect, the methods described can detect infections in both symptomatic and asymptomatic subjects. The methods are highly efficient in that a single testing event i.e. a single microarray signature can assess for the presence of any one of a plurality of infections, and the diagnosis of multiple infections can be determined simultaneously. The identification of any one infection is only limited by the number of different infections for which discriminating peptides have been identified. The methods, apparatus, and systems described herein are suitable for identifying infections caused by a wide variety of pathogens including bacteria, viruses, fungi, protozoans, worms, and infestations, and have applications in the fields of research, medical and veterinary diagnostics, and health surveillance, such as tracking the spread of an outbreak caused by a pathogen.

Methods, apparatus and systems are provided herein that enable detection and diagnosis of infections using a single noninvasive screening method that identifies differential patterns of peripheral-blood antibody binding to peptide arrays. Differential binding of patient samples to peptide arrays results in specific binding patterns i.e. immunosignatures (IST) that are indicative of the health condition, e.g. infection, of the patient. Additionally, the apparatus and systems provided herein allow for the identification of antigens or binding partners to antibodies of the biological sample, which can be assessed as candidate biomarkers for targeted therapeutic interventions.

Typically, an immunosignature characteristic of a condition is determined relative to one or more reference immunosignatures, which are obtained from one or more different sets of reference samples, each set being obtained from one or more groups of reference subjects, each group having a different condition e.g. a different infection. For example, an immunosignature obtained from a test subject identifies the infection of the test subject when compared to immunosignatures of reference subjects without infection and/or with different infections induced by different pathogens. Accordingly, comparison of immunosignatures from a test subject with those of reference subjects can determine the condition e.g. infection, of the test subject. A reference group can be a group of healthy subjects, and the condition is referred to herein as a healthy condition. Healthy subjects are typically those who do not have the infection that is being tested, or known to be seronegative for the infection that is being tested.

The methods provided can detect a number of different infections in samples e.g. blood, from different individuals within a population of symptomatic or asymptomatic subjects that are seropositive for the different infections with high performance, sensitivity and specificity. The infections that can be detected according to the methods provided include without limitation infections caused by microorganisms, including bacteria, viruses, fungi, protozoans, parasitic organisms and worms.

In some embodiments, the IST is based on diverse yet reproducible patterns of antibody binding to an array of peptides that are selected to provide an unbiased sampling of at least a portion of amino acid combinations less than 20 amino acids rather than represent known proteomic sequences. A peptide bound by an antibody in a sample from a subject may not be the natural target sequence, but may instead mimic the sequence or structure of the cognate natural epitope. For example, none of the peptides in the IST library described in Example 1 are identical matches to any 9 mer sequence in known proteome databases. This is not surprising since the number of possible 9 mer peptide sequences is several orders of magnitude greater than the number of contiguous 9 mer sequences in the proteome databases. Accordingly, the probability of any mimetic-peptide corresponding exactly to a natural sequence is low. Each IST peptide sequence that is selectively bound by an antibody could be a functional surrogate of the epitope that the antibody recognized in vivo. Consequently, the sequences of proteins comprising part or all of the antibody-bound array peptide sequence can serve to identify candidate protein biomarkers, which can be assessed as therapeutic targets.

In one aspect, a method is provided for identifying the serological state of a subject having or suspected of having at least one infection comprising: (a) contacting a sample from the subject to an array of peptides comprising at least 10,000 different peptides; (b) detecting the binding of antibodies present in the sample to at least 25 peptides on the array to obtain a combination of binding signals; and (c) comparing the combination of binding signals of the sample from the subject to one or more groups of combinations of reference binding signals, wherein at least one of each of the groups of combinations of reference binding signals are obtained from a plurality of reference subjects known to be seropositive for an infection, and wherein at least one of each of the groups of combinations of reference binding signals are obtained from a plurality of subjects known to be seronegative for an infection, thereby determining the serological state of the subject. In some embodiments, reference subjects that are seronegative for one infection can be seropositive for a different infection. The array peptides can be deposited or can be synthesized in situ on a solid surface. In some embodiments, the method performance can be characterized by an area under the receiver operator characteristic (ROC) curve (AUC) being greater than 0.6. In some embodiments, the reproducibility of classification from an AUC ranges from 0.60 to 0.69, 0.70 to 0.79, 0.80 to 0.89, or 0.90 to 1.0.

In some embodiments, the method further comprises identifying a combination of differentiating reference binding signals that distinguish samples from reference subjects known to be seropositive for the infection from samples from reference subjects known to be seronegative for the same infection, and identifying the combination of the array peptides that display the combination of differentiating binding signals. The combination of differentiating binding signals can comprise signals that are increased or decreased, newly added signals, and/or signals that are lost in the presence of an infection relative to the corresponding binding signals obtained from reference samples. The array peptides that display the combination of differentiating binding signals are known as discriminating peptides. The term "discriminating" when used in reference to array peptides is used herein interchangeably with "classifying". In some embodiments, a combination of differentiating reference binding signals comprises a combination of binding signals to at least 1, at least 2, at least 5, at least 10, at least 15, at least 20, at least 25, at least 30, at least 35, at least 40, at least 45, at least 50, at least 60, at least 70, at least 80, at least 90, at least 100, at least 125, at least 150, at least 175, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10000, at least 20000, or more discriminating peptides on an array. For example, at least 25 peptides on an array of 10,000 peptides are identified as discriminating peptides for a given condition. In some embodiments, each combination of differentiating binding signals is obtained by detecting the binding of antibodies present in a reference sample from each of a plurality of reference subjects to at least 25 peptides on same arrays of peptides comprising at least 10,000 different peptides. In some embodiments, the peptides are synthesized in situ. In some embodiments, discriminating peptides are identified from antibodies binding differentially to peptide arrays comprising a library of at least 5,000, at least 10,000, at least 15,000, at least 20,000, at least 25,000, at least 50,000, at least 100,000, at least 200,000, at least 300,000, at least 400,000, at least 500,00, at least 1,000,000, at least 2,000,000, at least 3,000,000, at least 4,000,000, at least 5,000,000 or at least 100,000,000 or more different peptides on the array substrate.

In some embodiments, at least 0.00005%, at least 0.0001%, at least 0.0005%, at least 0.0001%, at least 0.001%, at least 0.003%, at least 0.005%, at least 0.01%, at least 0.05%, at least 0.1%, at least 0.5%, at least 1%, at least 0.5%, at least 1.5%, at least 2%, at least 3%, at least 4%, at least 5%, at least 10%, at least 25%, at least 50%, at least 75%, at least 80%, or at least 90%, of the total number of peptides on an array are discriminating peptides. In other embodiments, all of the peptides on an array are discriminating peptides.

The characteristics of the combination of the discriminating peptides include the prevalence of one or more amino acids, and/or the prevalence of specific sequence motifs present in the identified discriminating peptides. Enrichment of amino acid and motif content is relative to the corresponding total amino acid and motif content of all the peptides in the array library. In some embodiments, the discriminating peptides of the immunosignature binding patterns that distinguish a subject that is seropositive consequent to an infection from reference subjects that are seronegative for the same infection can be enriched in at least one, at least two, at least three, at least four, at least five, at least six, at least seven, at least eight, at least nine, or at least ten different amino acids. In some embodiments, enrichment of the amino acids in discriminating peptides can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% relative to the total content of each of the amino acids present in all the library peptides.

Similarly, in some embodiments, the discriminating peptides of the immunosignature binding patterns that distinguish a subject that is seropositive consequent to an infection from reference subjects that are seronegative for the same infection can be enriched in at least one, at least two, at least three, at least four, at least five, at least six, at least seven, at least eight, at least nine, or at least ten different sequence motifs. Enrichment of the sequence motifs can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% in at least one motif relative to the total content of each of the motifs present in all library peptides.

Candidate biomarkers can be identified for the medical intervention of infectious diseases. In some embodiments, the infectious disease is caused by a parasitic infection by the protozoan *T. cruzi*.

Examples 6-11 illustrate a method for identifying candidate target proteins using discriminating peptides that identify the serological state of subjects that have or may be suspected of having been infected with *T. cruzi* (Chagas disease). In some embodiments, the discriminating peptides differentiate subjects that are seropositive from subjects that are seronegative for *T. cruzi*. Candidate protein targets are provided in Tables 6 and 7. Similarly, candidate protein targets can be identified using discriminating peptides that distinguish samples from subjects having other infectious diseases from samples from healthy subjects, samples from subjects having other infectious diseases, and samples from subjects having mimic diseases, which may or may not be infectious.

Disclosed herein are methods and devices for identifying at least one candidate biomarker for an infection, the method comprising: (a) providing a peptide array and contacting a biological sample from a plurality of subjects known to have the infection to the peptide array; (b) identifying a set of discriminating peptides bound to antibodies in the biological sample from the plurality of subjects that differentiate the infectious disease from at least one different health condition; (c) aligning each of the peptides in the set of discriminating peptides to one or more proteins in a proteome; and (d) obtaining a protein score and ranking for each of the identified proteins according to a statistical significance, thereby identifying at least one candidate biomarker for the infection.

In some embodiments, the step of identifying the set of discriminating peptides comprises: (i) detecting binding of antibodies present in the biological sample from the plurality of subjects having infectious disease to obtain a first combination of binding signals; (ii) detecting binding of antibodies present in samples from one or more reference groups of subjects to the same peptide array, each reference group having a different health condition to obtain a second combination of binding signals; (iii) comparing the first combination of binding signals to the second combination of binding signals to obtain a set of differentiating binding signals; and (iv) identifying peptides on the array that are differentially bound by antibodies in samples from subjects having the infectious disease and the antibodies in the samples from the one or more reference groups of subjects, thereby identifying said discriminating peptides.

In some embodiments, the discriminating peptides were found to be enriched in sequence motifs listed in FIG. 48A-N. In some embodiments, the discriminating peptides for identifying a candidate biomarker for a *T. cruzi* infection with the methods and arrays disclosed herein are enriched in at least one, at least two, at least three, at least four, at least five, at least six, at least seven, at least eight, at least nine, or at least ten different sequence motifs. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the motifs listed in FIG. 36A relative to the corresponding total motif content of all the peptides in the array library.

The same discriminating peptides were found to be enriched in amino acids listed in FIG. 37B. Accordingly, in other embodiments, the discriminating peptides for identifying a candidate biomarker for a *T. cruzi* infection with the methods and arrays disclosed herein are enriched in at least one, at least two, at least three, at least four, at least five, at least six, at least seven, at least eight, at least nine, or at least ten different amino acids. Enrichment of the sequence motifs can be by at least 100%, at least 125%, at least 150%, at least 175%, at least 200%, at least 225%, at least 250%, at least 275%, at least 300%, at least 350%, at least 400%, at least 450%, or at least 500% in at least one of the amino acids listed in FIG. 36B relative to the corresponding total amino acid content of all the peptides in the array library.

In some embodiments, the discriminating peptides used in the method are identified, for example by differences in binding signals, by statistical means e.g. t-test, as having p-values of less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$ comparing the relative binding signals of the antibody-bound peptides in the two different conditions.

An exemplary list of discriminating peptides that can be used for identifying candidate biomarkers of *T. cruzi* infection is provided in FIGS. 48A-48N. The list provides the top discriminating peptides, which are peptides that discriminate with greatest significance the combination of antibody binding signals obtained using samples from subjects that are seropositive for *T. cruzi* from the combination of binding signals obtained using samples from subjects that are seronegative for *T. cruzi*. In some embodiments, the method for identifying a candidate biomarker for *T. cruzi* comprises identifying a set of discriminating peptides that comprise one or more of the discriminating peptides listed in FIGS. 48A-48N.

Candidate biomarkers for *T. cruzi* are subsequently identified by aligning a set of discriminating peptides to a human proteome. As described elsewhere herein, an overlap score is determined from the alignment of the discriminating peptides to the proteome; and proteins so identified are scored and ranked relative to proteins that are identified using randomly chosen non-discriminating peptides to identify candidate biomarkers for *T. cruzi*. In one embodiment, a candidate biomarker for *T. cruzi* is selected from the list of candidate biomarkers listed in Tables 6 and 7. In some embodiments, the candidate biomarker proteins identified according to the method are ranked according to a p-value of less than less than $10^{-3}$, less than less than $10^{-4}$, less than less than $10^{-5}$, or less than less than $10^{-6}$.

Alternatively, discriminating peptides identified according to the methods provided, can identify candidate target proteins i.e. candidate biomarkers, using sequence motifs that are enriched in the most discriminating peptides that distinguish two different conditions. In one embodiment, the method for identifying a candidate target for the treatment of an autoimmune disease in a human subject comprises (a) obtaining a set of discriminating peptides that differentiate the autoimmune disease from one or more different autoimmune diseases; (b) identifying a set of motifs for said discriminating peptides; (c) aligning the set of motifs to a human proteome; (d) identifying regions of homology between each motif in the set to a region of an immunogenic protein; and (e) identifying the protein as a candidate target said autoimmune disease.

In preferred embodiments, the infectious disease is Chagas disease and the discriminating peptides that distinguish Chagas disease in seropositive subjects from reference subjects that are seropositive for HBV, are enriched in one or more of arginine, tryptophan, serine, alanine, valine, glutamine, and glycine (FIG. 41B). Enrichment of the one or more amino acids can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total amino acid content of all the peptides in the array library. In some embodiments, discriminating peptides that distinguish Chagas disease from HBV reference subjects are enriched in one or more of motifs provided in FIG. 41A. Enrichment of the one or more amino motifs can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total motif content of all the peptides in the array library.

In preferred embodiments, the infectious disease is Chagas disease and the discriminating peptides that distinguish Chagas disease in seropositive subjects from reference subjects that are seropositive for HCV, are enriched in one or more of arginine, tryptophan, serine, valine, and glycine (FIG. 42B). Enrichment of the one or more amino acids can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total amino acid content of all the peptides in the array library. In some embodiments, discriminating peptides that distinguish Chagas disease from healthy reference subjects are enriched in one or more of motifs provided in FIG. 42A. Enrichment of the one or more amino motifs can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total motif content of all the peptides in the array library.

In preferred embodiments, the infectious disease is Chagas disease and the discriminating peptides that distinguish Chagas disease in seropositive subjects from reference subjects that are seropositive for WNV, are enriched in one or more of lysine, tryptophan, aspartic acid, histidine, arginine, glutamic acid, and glycine (FIG. 43B). Enrichment of the one or more amino acids can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total amino acid content of all the peptides in the array library. In some embodiments, discriminating peptides that distinguish Chagas disease from WNV reference subjects are enriched in one or more of motifs provided in FIG. 43A. Enrichment of the one or more amino motifs can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total motif content of all the peptides in the array library.

In preferred embodiments, the infectious disease is HBV disease and the discriminating peptides that distinguish HCV disease in seropositive subjects from reference subjects that are seropositive for WNV, are enriched in one or more of phenylalanine, tryptophan, valine, leucine, alanine, and histidine (FIG. 44B). Enrichment of the one or more amino acids can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total amino acid content of all the peptides in the array library. In some embodiments, discriminating peptides that distinguish HBV disease from HCV reference subjects are enriched in one or more of motifs provided in FIG. 44A. Enrichment of the one or more amino motifs can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total motif content of all the peptides in the array library.

In preferred embodiments, the infectious disease is HBV disease and the discriminating peptides that distinguish WNV disease in seropositive subjects from reference subjects that are seropositive for WNV, are enriched in one or more of tryptophan, lysine, phenylalanine, histidine, and valine (FIG. 45B). Enrichment of the one or more amino acids can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total amino acid content of all the peptides in the array library. In some embodiments, discriminating peptides that distinguish HBV disease from WNV reference subjects are enriched in one or more of motifs provided in FIG. 45A. Enrichment of the one or more amino motifs can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total motif content of all the peptides in the array library.

In preferred embodiments, the infectious disease is HCV disease and the discriminating peptides that distinguish HCV disease in seropositive subjects from reference subjects that are seropositive for WNV, are enriched in one or more of lysine, tryptophan, arginine, tyrosine, and proline (FIG. 46B). Enrichment of the one or more amino acids can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total amino acid content of all the peptides in the array library. In some embodiments, discriminating peptides that distinguish HCV disease from WNV reference subjects are enriched in one or more of motifs provided in FIG. 46A. Enrichment of the one or more amino motifs can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total motif content of all the peptides in the array library.

In other embodiments, an individual classifier can be obtained to identify an infection relative to a combined group of two or more different infections, and a combination of discriminating peptides utilized by the classifier is provided. The characteristics of the combination of the discriminating peptides include the prevalence of one or more amino acids, and/or the prevalence of specific sequence motifs present in the identified discriminating peptides. For example, as shown in the examples, a first binary classifier was created based on discriminating peptides to distinguish subjects that were seropositive for *T. cruzii* from a group of subjects that were a combination of subjects each being seropositive for HPV, HCV, or WNV. A second binary classifier was created based on discriminating peptides to distinguish subjects that were seropositive for HBV from a group of subjects that were a combination of subjects each being seropositive for Chagas, HCV, or WNV. A third classifier was created based on discriminating peptides to distinguish subjects that were seropositive for HCV from a group of subjects that were a combination of subjects each being seropositive for HPV, Chagas, or WNV. A fourth classifier was created based on discriminating peptides to distinguish subjects that were seropositive for WVN from a group of subjects that were a combination of subjects each being seropositive for HPV, HCV, or Chagas.

Enrichment of amino acid and motif content is relative to the corresponding total amino acid and motif content of all the peptides in the array library. In some embodiments, the discriminating peptides of the immunosignature binding patterns that distinguish a subject with an infectious disease from a group of subjects each subject having one of two or more different infections in diagnosing or detecting an infectious disease in a subject with the methods and arrays disclosed herein are enriched in at least one, at least two, at least three, at least four, at least five, at least six, at least seven, at least eight, at least nine, or at least ten different amino acids. Enrichment of the amino acids can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% in by greater than one amino acid for the peptides comprising the immunosignature for the infectious disease.

Similarly, in some embodiments, the discriminating peptides of the immunosignature binding patterns for diagnosing or detecting an infectious disease in a subject relative to a group of subjects each having one of two or more different infections with the methods and arrays disclosed herein are enriched in at least one, at least two, at least three, at least four, at least five, at least six, at least seven, at least eight, at least nine, or at least ten different sequence motifs. Enrichment of the sequence motifs can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% in by greater than one motif for the peptides comprising the immunosignature for the infectious disease.

In some embodiments, the infectious disease is Chagas and the discriminating peptides that distinguish Chagas disease in seropositive subjects from a group of reference subjects that are seropositive for one of HBV, HCV and WNV, are enriched in one or more of one or more of arginine, tyrosine, serine and valine (FIG. 37B). Enrichment of the one or more amino acids can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total amino acid content of all the peptides in the array library. In some embodiments, discriminating peptides that distinguish Chagas disease from HBV, HCV and WNV reference subjects are enriched in one or more of motifs provided in FIG. 37A. Enrichment of the one or more amino motifs can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total motif content of all the peptides in the array library.

In some embodiments, the infectious disease is HBV and the discriminating peptides that distinguish HBV disease in seropositive subjects from a group of reference subjects that are seropositive for one of Chagas, HCV and WNV, are enriched in one or more of one or more of tryptophan, phenylalanine, lysine, valine, leucine, arginine, and histidine. (FIG. 38B). Enrichment of the one or more amino acids can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total amino acid content of all the peptides in the array library. In some embodiments, discriminating peptides that distinguish HBV disease from Chagas, HCV and WNV reference subjects are enriched in one or more of motifs provided in FIG. 38A. Enrichment of the one or more amino motifs can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total motif content of all the peptides in the array library.

In some embodiments, the infectious disease is HCV and the discriminating peptides that distinguish HCV disease in seropositive subjects from a group of reference subjects that are seropositive for one of Chagas, HBV and WNV, are enriched in one or more of one or more of arginine, tyrosine, aspartic acid, and glycine (FIG. 39B). Enrichment of the one or more amino acids can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total amino acid content of all the peptides in the array library. In some embodiments, discriminating peptides that distinguish HBV disease from Chagas, HBV and WNV reference subjects are enriched in one or more of motifs provided in FIG. 39A. Enrichment of the one or more amino motifs can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total motif content of all the peptides in the array library.

In some embodiments, the infectious disease is WNV and the discriminating peptides that distinguish WNV disease in seropositive subjects from a group of reference subjects that are seropositive for one of Chagas, HBV and HCV, are enriched in one or more of one or more of lysine, tryptophan, histidine, and proline (FIG. 40B). Enrichment of the one or more amino acids can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total amino acid content of all the peptides in the array library. In some embodiments, discriminating peptides that distinguish HBV disease from WNV reference subjects are enriched in one or more of motifs provided in FIG. 40A. Enrichment of the one or more amino motifs can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% or more, relative to the corresponding total motif content of all the peptides in the array library.

In yet other embodiments, individual classifiers that are independent of each other are obtained based on antibody binding to different sets of discriminating peptides, and combined into a multiclassifer to potentially achieve a best possible classification while increasing the efficiency and accuracy of classification. For example, a first individual classifier based on discriminating peptides that distinguish *T. cruzii* infection from a reference group of infections HBV, HCV, and WNV, can be combined with a second individual classifier based on discriminating peptides that distinguish HBV from a reference group of infections Chagas, HCV, and WNV, with a third individual classifier based on discriminating peptides that distinguish HCV from a reference group of infections Chagas, HBV and WNV, and with a fourth individual classifier based on discriminating peptides that distinguish WNV from a reference group of infections Chagas, HBV and HCV, to obtain a multiclassifier. Based on the discriminating peptides of each of the individual classifiers, an optimal combination of peptides can emerge to provide a multiclassifier that can simultaneously distinguish two or more different infections from each other. Example 7 demonstrates that the combination of discriminating peptides of the individual classifiers results in a multiclassifier based on a combination of discriminating peptides that can simultaneously distinguish a *T. cruzii* infection, an HPV infection, an HCV infection, and a WNV infection from each other.

In some embodiments, the discriminating peptides of the immunosignature binding patterns for providing a simultaneous identification of two or more infections in a subject with the methods and arrays disclosed herein are enriched in at least one, at least two, at least three, at least four, at least five, at least six, at least seven, at least eight, at least nine, or at least ten different amino acids. Enrichment of the amino acids can be by greater than 100%, by greater than 125%, by greater than 150%, by greater than 175%, by greater than 200%, by greater than 225%, by greater than 250%, by greater than 275%, by greater than 300%, by greater than 350%, by greater than 400%, by greater than 450%, or by greater than 500% in at least one amino acid for the peptides comprising the immunosignature for the infectious disease. In some embodiments, the simultaneous differentiation is made between Chagas, HBV, HCV, and WNV, wherein discriminating peptides simultaneously distinguish each of these infections from one another. In some embodiments, discriminating peptides that simultaneously distinguish Chagas from each of HBV, HCV, and WNV infections are enriched in one or more of arginine, tyrosine, lysine, tryptophan, valine and alanine (FIG. 47B). In some embodiments, discriminating peptides that simultaneously distinguish HBV from each of Chagas, HCV, and WNV infections are enriched in one or more motifs listed in (FIG. 47A).

Applications for Candidate Biomarkers

In other embodiments, the methods, apparatus and systems provided identify discriminating peptides that correlate with disease activity, and/or correlate with changes in disease activity over time. For example, discriminating peptides can determine disease activity and correlate it with the activity defined by known markers of an existing scoring system. Example 3 describes that several discriminating peptides correlate to the S/CO activity score for Chagas. These discriminating peptides have been used to identify proteins according to the method provided. Therefore, some of these proteins may be novel candidate biomarkers that can be used in tests and monitoring of Chagas disease activity.

The discriminating peptides can also serve as a basis for the design of drugs that inhibit or activate the target protein—protein interactions. In another aspect, therapeutic and diagnostic uses for the novel discriminating peptides identified by the methods of the invention are provided. Aspects and embodiments thus include formulations, medicaments and pharmaceutical compositions comprising the peptides and derivatives thereof according to the invention. In some embodiments, a novel discriminating peptide or its derivative is provided for use in medicine. More specifically, for use in antagonising or agonising the function of a target ligand, such as a cell-surface receptor. The discriminating peptides of the invention may be used in the treatment of various diseases and conditions of the human or animal body, such as cancer, and degenerative diseases. Treatment may also include preventative as well as therapeutic treatments and alleviation of a disease or condition.

Accordingly, the methods, systems and array devices disclosed herein are capable of identifying discriminating peptides, which serve to identify candidate biomarkers, identify vaccine targets, which in turn are useful for medical interventions for treating a disease and/or condition at an early stage of the disease and/or condition. For example, the methods, systems and array devices disclosed herein are capable of detecting, diagnosing and monitoring a disease and/or condition days or weeks before traditional biomarker-based assays. Moreover, only one array, i.e., one immunosignature assay, is needed to detect, diagnose and monitor a side spectra of diseases and conditions caused by infectious agents, including inflammatory conditions, autoimmune diseases, cancer and pathogenic infections. The candidate biomarkers can be identified for validation and subsequent development of therapeutics.

Diseases

The assays, methods and devices provided can be utilized to identify candidate biomarkers for medical intervention of any disease, which includes diagnosing a disease, providing a differential diagnosis of a disease relative to other a diseases, and mimic diseases, determining the progression of the disease, scoring the activity of the disease, serving as candidate target for evaluation as therapeutics for the treatment of the disease, and stratifying patients in clinical trials based on predicted responses to therapy.

The candidate biomarkers can be utilized in the medical intervention of any disease, including infectious diseases, blood disorders, cancer, cardiovascular disease, digestive diseases, endocrine diseases, nutritional disease, metabolic disease, genitourinary system diseases, immune system disorders, musculoskeletal disorders, neurological disorders, and respiratory disorders.

In some embodiments, the disease is autoimmune disease or disorder for which candidate biomarkers can be identified according to the methods provided. Non-limiting examples of autoimmune diseases include systemic lupus erythematosus (SLE) (e.g., systemic lupus erythematosus, discoid lupus, drug-induced lupus, neonatal lupus), rheumatoid arthritis, Sjogren's disease, multiple sclerosis (MS), inflammatory bowel disease (IBD) e.g., Crohn's disease, ulcerative colitis, collagenous colitis, lymphocytic colitis, ischemic colitis, diversion colitis, Behcet's syndrome, infective colitis, indeterminate colitisinterstitial cystitis, psoriatic arthritis, scleroderma (SSc), type I diabetes, Addison's disease, Agammaglobulinemia, Alopecia areata, Amyloidosis, Ankylosing spondylitis, Anti-GBM/Anti-TBM nephritis, Antiphospholipid syndrome (APS), Autoimmune hepatitis, Autoimmune inner ear disease (AIED), Axonal & neuronal neuropathy (AMAN), Behcet's disease, Bullous pemphigoid, Castleman disease (CD), Celiac disease, Chagas disease, Chronic inflammatory demyelinating polyneuropathy (CIDP), Chronic recurrent multifocal osteomyelitis (CRMO), chronic obstructive pulmonary disease (COPD), Churg-Strauss, Cicatricial pemphigoid/benign mucosal pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Graft Versus Host Disease (GVHD) e.g. rejection of kidney, lung, liver or heart transplant, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammalglobulinemia, IgA Nephropathy, IgG4-related sclerosing disease, Inclusion body myositis (IBM), Interstitial cystitis (IC), Juvenile arthritis, Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lyme disease chronic, Meniere's disease, Microscopic polyangiitis (MPA), Mixed connective tissue disease (MCTD), Mooren's ulcer, Mucha-Habermann disease, Myasthenia gravis, Myositis, Narcolepsy, Neuromyelitis optica, Neutropenia, Ocular cicatricial pemphigoid, Optic neuritis, Palindromic rheumatism (PR), PANDAS (Pediatric Autoimmune Neuropsychiatric Disorders Associated with *Streptococcus*), Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome (polyneuropathy, organomegaly, endocrinopathy, monoclonal gammopathy, skin changes), Polyarteritis nodosa, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Pure red cell aplasia (PRCA), Pyoderma angrenosum, Raynaud's phenomenon, Reactive Arthritis, Reflex sympathetic dystrophy, Reiter's syndrome, Relapsing polychondritis, Restless legs syndrome (RLS), Retroperitoneal fibrosis, Rheumatic fever, Rheumatoid arthritis (RA), Sarcoidosis, Schmidt syndrome, Scleritis, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Ulcerative colitis (UC), Undifferentiated connective tissue disease (UCTD), Uveitis, Vasculitis, Vitiligo, and/or Wegener's granulomatosis (now termed Granulomatosis with Polyangiitis (GPA).

In some embodiments, the disease is an infectious disease or disorder for which candidate biomarkers can be identified according to the methods provided. Non-limiting examples of infectious diseases include infectious diseases caused by a pathogen. A pathogen can be a pathogenic virus, a pathogenic bacteria, or a protozoan infection. An infection with a pathogenic viruses and/or a pathogenic bacteria can cause a condition, for example, an inflammation. Non-limiting examples of pathogenic bacteria can be found in the: a) *Bordetella* genus, such as *Bordetella pertussis* species; b) *Borrelia* genus, such *Borrelia burgdorferi* species; c) Brucelia genus, such as *Brucella abortus, Brucella canis, Brucela meliterisis*, and/or *Brucella suis* species; d) *Campylobacter* genus, such as *Campylobacter jejuni* species; e) *Chlamydia* and *Chlamydophila* genuses, such as *Chlamydia* pneumonia, *Chlamydia trachomatis*, and/or *Chlamydophila psittaci* species; f) *Clostridium* genus, such as *Clostridium botulinum, Clostridium difficile, Clostridium perfringens, Clostridium tetani* species; g) *Corynebacterium* genus, such as *Corynebacterium diphtheria* species; h) *Enterococcus* genus, such as *Enterococcus faecalis*, and/or *Enterococcus faecium* species; i) *Escherichia* genus, such as *Escherichia coli* species; j) *Francisella* genus, such as *Francisella tularensis* species; k) *Haemophilus* genus, such as *Haemophilus* influenza species; l) *Helicobacter* genus, such as *Helicobacter pylori* species; m) *Legionella* genus, such as *Legionella pneumophila* species; n) *Leptospira* genus, such as *Leptospira interrogans* species; o) *Listeria* genus, such as *Listeria monocytogenes* species; p) *Mycobacterium* genus, such as *Mycobacterium leprae, Mycobacterium tuberculosis*, and/or *mycobacterium ulcerans* species; q) *Mycoplasma* genus, such as *Mycoplasma* pneumonia species; r) *Neisseria* genus, such as *Neisseria gonorrhoeae* and/or *Neisseria meningitidia* species; s) *Pseudomonas* genus, such as *Pseudomonas aeruginosa* species; t) *Rickettsia* genus, such as *Rickettsia rickettsii* species; u) *Salmonella* genus, such as *Salmonella typhi* and/or *Salmonella typhimurium* species; v) *Shigella* genus, such as *Shigella sonnei* species; w) *Staphylococcus* genus, such as *Staphylococcus aureus, Staphylococcus epidermidis*, and/or *Staphylococcus saprophyticus* species; x) *Streptococcus* genus, such as *Streptococcus agalactiae, Streptococcus pneumonia*, and/or *Streptococcus pyogenes* species; y) *Treponema* genus, such as *Treponema pallidum* species; z) *Vibrio* genus, such as *Vibrio cholera*; and/or aa) *Yersinia* genus, such as *Yersinia pestis* species.

In some embodiments, the disease is an infectious disease or disorder caused by a pathogenic viral infection for which candidate biomarkers can be identified according to the methods provided. Non-limiting examples of pathogenic viral infections for which candidate biomarkers can be identified according to the methods provided include infections caused viruses that can be found in the following families of viruses and are illustrated with exemplary species: a) Adenoviridae family, such as Adenovirus species; b) Herpesviridae family, such as Herpes simplex type 1, Herpes simplex type 2, Varicella-zoster virus, Epstein-barr virus, Human cytomegalovirus, Human herpesvirus type 8 species; c) Papillomaviridae family, such as Human papillomavirus species; d) Polyomaviridae family, such as BK virus, JC virus species; e) Poxviridae family, such as Smallpox species; f) Hepadnaviridae family, such as Hepatitis B virus species; g) Parvoviridae family, such as Human bocavirus, Parvovirus B19 species; h) Astroviridae family, such as Human astrovirus species; i) Caliciviridae family, such as Norwalk virus species; j) Flaviviridae family, such as Hepatitis C virus, yellow fever virus, dengue virus, West Nile virus species; k) Togaviridae family, such as Rubella virus species; l) Hepeviridae family, such as Hepatitis E virus species; m) Retroviridae family, such as Human immunodeficiency virus (HIV) species; n) Orthomyxoviridaw family, such as Influenza virus species; o) Arenaviridae family, such as Guanarito virus, Junin virus, Lassa virus, Machupo virus, and/or Sabiá virus species; p) Bunyaviridae family, such as Crimean-Congo hemorrhagic fever virus species; q) Filoviridae family, such as Ebola virus and/or Marburg virus species; Paramyxoviridae family, such as Measles virus, Mumps virus, Parainfluenza virus, Respiratory syncytial virus, Human metapneumovirus, Hendra virus and/or Nipah virus species; r) Rhabdoviridae genus, such as Rabies virus species; s) Reoviridae family, such as Rotavirus, Orbivirus, Coltivirus and/or Banna virus species; t) Flaviviridae family, such as Zika Virus. In some embodiments, a virus is unassigned to a viral family, such as Hepatitis D.

In some embodiments, the subject suffers from a parasitic infection e.g. Chagas disease. Non-limiting examples of protozoa can be found in the following families of prototozoa and are illustrated with exemplary species: a) *Trypanosoma cruzi* species; *Trypanosoma brucei* species; *Toxoplasma gondii* species; *Plasmodium falciparum* species; *Entamoeba histolytica* species, and *Giardia lamblia* species. The capability of the method provided to identify candidate biomarkers for an infectious disease is demonstrated in the Examples, which show that discriminating peptides can identify candidate biomarkers in samples from subjects infected with the protozoan *Trypanosoma cruzi*, which causes Chagas disease, also known as American trypanosomiasis.

In some embodiments, the disease is a cancer for which candidate biomarkers can be identified according to the methods provided. Non-limiting examples of cancers include: acute and chronic leukemias, lymphomas, numerous solid tumors of mesenchymal or epithelial tissue, brain, breast, liver, stomach, colon cancer, B cell lymphoma, lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, a adrenal gland cancer, an osteosarcoma, a chondrosarcoma, a liposarcoma, a testes cancer, and a malignant fibrous histiocytoma, and other cancers.

In some embodiments, the disease is a metabolic disease or for which candidate biomarkers can be identified according to the methods provided. Non-limiting examples of metabolic diseases include: Acid-base imbalance; Metabolic brain diseases; Calcium metabolism disorders; DNA repair-deficiency disorders; Glucose metabolism disorders; Hyperlactatemia; Iron metabolism disorders; Lipid metabolism disorders; Malabsorption syndromes; Metabolic syndrome X; Inborn error of metabolism; Mitochondrial diseases; Phosphorus metabolism disorders; porphyria; and proteostasis deficiency.

Samples

The samples that are utilized according to the methods provided can be any biological samples. For example, the biological sample can be a biological liquid sample that comprises antibodies. Suitable biological liquid samples include, but are not limited to blood, plasma, serum, sweat, tears, sputum, urine, stool water, ear flow, lymph, saliva, cerebrospinal fluid, ravages, bone marrow suspension, vaginal flow, transcervical lavage, synovial fluid, aqueous humor, amniotic fluid, cerumen, breast milk, broncheoalveolar lavage fluid, brain fluid, cyst fluid, pleural and peritoneal fluid, pericardial fluid, ascites, milk, pancreatic juice, secretions of the respiratory, intestinal and genitourinary tracts, amniotic fluid, milk, and leukophoresis samples. A biological sample may also include the blastocyl cavity, umbilical cord blood, or maternal circulation which may be of fetal or maternal origin. In some embodiments, the sample is a sample that is easily obtainable by non-invasive procedures e.g. blood, plasma, serum, sweat, tears, sputum, urine, sputum, ear flow, or saliva. In certain embodiments the sample is a peripheral blood sample, or the plasma or serum fractions of a peripheral blood sample. As used herein, the terms "blood," "plasma" and "serum" expressly encompass fractions or processed portions thereof.

Because of its minimally invasive accessibility and its ready availability, blood is the most preferred and used human body fluid to be measured in routine clinical practice. Moreover, blood perfuses all body tissues and its composition is therefore relevant as an indicator of the over-all physiology of an individual. In some embodiments, the biological sample that is used to obtain an immunosignature/antibody binding profile is a blood sample. In other embodiments, the biological sample is a plasma sample. In yet other embodiments, the biological sample is a serum sample. In yet other embodiments, the biological sample is a dried blood sample. The biological sample may be obtained through a third party, such as a party not performing the analysis of the antibody binding profiles, and/or the party performing the binding assay to the peptide array. For example, the sample may be obtained through a clinician, physician, or other health care manager of a subject from which the sample is derived. Alternatively, the biological sample may be obtained by the party performing the binding assay of the sample to a peptide array, and/or the same party analyzing the antibody binding profile/IS. Biological samples that are to be assayed, can be archived (e.g., frozen) or otherwise stored in under preservative conditions.

The term "patient sample" and "subject sample" are used interchangeably herein to refer to a sample e.g. a biological fluid sample, obtained from a patient i.e. a recipient of medical attention, care or treatment. The subject sample can be any of the samples described herein. In certain embodiments, the subject sample is obtained by non-invasive procedures e.g. peripheral blood sample.

An antibody binding profile of circulating antibodies in a biofluid sample can be obtained according to the methods provided using limited quantities of sample. For example, peptides on the array can be contacted with a fraction of a milliliter of blood to obtain an antibody binding profile comprising a sufficient number of informative peptide-protein complexes to identify the health condition of the subject.

In some embodiments, the volume of biological sample that is needed to obtain an antibody binding profile is less than 10 ml, less than 5 ml, less than 3 ml, less than 2 ml, less than 1 ml, less than 900 ul, less than 800 ul, less than 700 ul, less than 600 ul, less than 500 ul, less than 400 ul, less than 300 ul, less than 200 ul, less than 100 ul, less than 50 ul, less than 40 ul, less than 30 ul, less than 20 ul, less than 10 ul, less than 1 ul, less than 900 nl, less than 800 nl, less than 700 nl, less than 600 nl, less than 500 nl, less than 400 nl, less than 300 nl, less than 200 nl, less than 100 nl, less than 50 nl, less than 40 nl, less than 30 nl, less than 20 nl, less than 10 nl, or less than 1 nl. In some embodiments, the biological fluid sample can be diluted several fold to obtain an antibody binding profile. For example, a biological sample obtained from a subject can be diluted at least by 2-fold, at least by 4-fold, at least by 8-fold, at least by 10-fold, at least by 15-fold, at least by 20-fold, at least by 30-fold, at least by 40-fold, at least by 50-fold, at least by 100-fold, at least by 200-fold, at least by 300-fold, at least by 400-fold, at least by 500-fold, at least by 600-fold, at least by 700-fold, at least by 800-fold, at least by 900-fold, at least by 1000-fold, at least by 5000-fold, or at least by 10,000-fold. Antibodies present in the diluted serum sample, and are considered significant to the health of the subject, because if antibodies remain present even in the diluted serum sample, they must reasonably have been present at relatively high amounts in the blood of the patient.

An example of detecting a disease in a subject according to the methods described herein is given in the Examples. The examples demonstrate that correct diagnosis of scleroderma was provided using a mere 100 microliters of serum or of plasma.

Treatments and Conditions

The methods and arrays of the invention provide methods, assays and devices for the identification of candidate biomarkers for a disease. The methods and arrays of the embodiments disclosed herein can be used, for example, for identifying one or more candidate biomarkers for a disease in a subject. A subject can be a human, a guinea pig, a dog, a cat, a horse, a mouse, a rabbit, and various other animals A subject can be of any age, for example, a subject can be an infant, a toddler, a child, a pre-adolescent, an adolescent, an adult, or an elderly individual.

The arrays and methods of the invention can be used by a user. A plurality of users can use a method of the invention to identify and/or provide a treatment of a condition. A user can be, for example, a human who wishes to monitor one's own health. A user can be, for example, a health care provider. A health care provider can be, for example, a physician. In some embodiments, the user is a health care provider attending the subject. Non-limiting examples of physicians and health care providers that can be users of the invention can include, an anesthesiologist, a bariatric surgery specialist, a blood banking transfusion medicine specialist, a cardiac electrophysiologist, a cardiac surgeon, a cardiologist, a certified nursing assistant, a clinical cardiac electrophysiology specialist, a clinical neurophysiology specialist, a clinical nurse specialist, a colorectal surgeon, a critical care medicine specialist, a critical care surgery specialist, a dental hygienist, a dentist, a dermatologist, an emergency medical technician, an emergency medicine physician, a gastrointestinal surgeon, a hematologist, a hospice care and palliative medicine specialist, a homeopathic specialist, an infectious disease specialist, an internist, a maxillofacial surgeon, a medical assistant, a medical examiner, a medical geneticist, a medical oncologist, a midwife, a neonatal-perinatal specialist, a nephrologist, a neurologist, a neurosurgeon, a nuclear medicine specialist, a nurse, a nurse practitioner, an obstetrician, an oncologist, an oral surgeon, an orthodontist, an orthopedic specialist, a pain management specialist, a pathologist, a pediatrician, a perfusionist, a periodontist, a plastic surgeon, a podiatrist, a proctologist, a prosthetic specialist, a psychiatrist, a pulmonologist, a radiologist, a surgeon, a thoracic specialist, a transplant specialist, a vascular specialist, a vascular surgeon, and a veterinarian. A diagnosis identified with an array and a method of the invention can be incorporated into a subject's medical record.

Array Platform

In some embodiments, disclosed herein are methods and process that provide for array platforms that allow for increased diversity and fidelity of chemical library synthesis. The array platforms comprise a plurality of individual features on the surface of the array. Each feature typically comprises a plurality of individual molecules synthesized in situ on the surface of the array, wherein the molecules are identical within a feature, but the sequence or identity of the molecules differ between features. The array molecules include, but are not limited to nucleic acids (including DNA, RNA, nucleosides, nucleotides, structure analogs or combinations thereof), peptides, peptide-mimetics, and combinations thereof and the like, wherein the array molecules may comprise natural or non-natural monomers within the molecules. Such array molecules include the synthesis of large synthetic peptide arrays. In some embodiments, a molecule in an array is a mimotope, a molecule that mimics the structure of an epitope and is able to bind an epitope-elicited antibody. In some embodiments, a molecule in the array is a paratope or a paratope mimetic, comprising a site in the variable region of an antibody (or T cell receptor) that binds to an epitope an antigen. In some embodiments, an array of the invention is a peptide array comprising random, pseudo-random or maximally diverse peptide sequences.

The peptide arrays can include control sequences that match epitopes of well characterized monoclonal antibodies (mAbs). Binding patterns to control sequences and to library peptides can be measured to qualify the arrays and the immunosignaturing assay process. mAbs with known epitopes e.g. 4C1, p53Ab1, p53Ab8 and LnKB2, can be assayed at different doses. Additionally, inter wafer signal precision can be determined by testing sample replicates e.g. plasma samples, on arrays from different wafers and calculating the coefficients of variation (CV) for all library peptides. Precision of the measurements of binding signals can be determined as an aggregate of the inter-array, inter-slide, inter-wafer and inter-day variations made on arrays synthesized on wafers of the same batch (within wafer batches). Additionally, precision of measurements can be determined for arrays on wafers of different batches (between wafer batches). In some embodiments, measurements of binding signals can be made within and/or between wafer batches with a precision varying less than 5%, less than 10%, less than 15%, less than 20%, less than 25%, or less than 30%.

The technologies disclosed herein include a photolithographic array synthesis platform that merges semiconductor manufacturing processes and combinatorial chemical synthesis to produce array-based libraries on silicon wafers. By utilizing the tremendous advancements in photolithographic feature patterning, the array synthesis platform is highly-scalable and capable of producing combinatorial chemical libraries with 40 million features on an 8-inch wafer. Photolithographic array synthesis is performed using semiconductor wafer production equipment in a class 10,000 cleanroom to achieve high reproducibility. When the wafer is diced into standard microscope slide dimensions, each slide contains more than 3 million distinct chemical entities.

In some embodiments, arrays with chemical libraries produced by photolithographic technologies disclosed herein are used for immune-based diagnostic assays, for example called immunosignature assays. Using a patient's antibody repertoire from a drop of blood bound to the arrays, a fluorescence binding profile image of the bound array provides sufficient information to classify disease vs. healthy.

In some embodiments, immunosignature assays are being developed for clinical application to diagnose/monitor autoimmune diseases and to assess response to autoimmune treatments. Exemplary embodiments of immunosignature assays is described in detail in US Pre-Grant Publication No. 2012/0190574, entitled "Compound Arrays for Sample Profiling" and US Pre-Grant Publication No. 2014/0087963, entitled "Immunosignaturing: A Path to Early Diagnosis and Health Monitoring", both of which are incorporated by reference herein for such disclosure. The arrays developed herein incorporate analytical measurement capability within each synthesized array using orthogonal analytical methods including ellipsometry, mass spectrometry and fluorescence. These measurements enable longitudinal qualitative and quantitative assessment of array synthesis performance.

In some embodiments, the array is a wafer-based, photolithographic, in situ peptide array produced using reusable masks and automation to obtain arrays of scalable numbers of combinatorial sequence peptides. In some embodiments, the peptide array comprises at least 5,000, at least 10,000, at least 15,000, at least 20,000, at least 30,000, at least 40,000, at least 50,000, at least 100,000, at least 200,000, at least 300,000, at least 400,000, at least 500,000, at least 1,000, 000, at least 2,000,000, at least 3,000,000, at least 4,000,000, at least 5,000,000, at least 10,000,000, at least 100,000,000 or more peptides having different sequences. Multiple copies of each of the different sequence peptides can be situated on the wafer at addressable locations known as features.

In some embodiments, detection of antibody binding on a peptide array poses some challenges that can be addressed by the technologies disclosed herein. Accordingly, in some embodiments, the arrays and methods disclosed herein utilize specific coatings and functional group densities on the surface of the array that can tune the desired properties necessary for performing immunosignature assays. For example, non-specific antibody binding on a peptide array may be minimized by coating the silicon surface with a moderately hydrophilic monolayer polyethylene glycol (PEG), polyvinyl alcohol, carboxymethyl dextran, and combinations thereof. In some embodiments, the hydrophilic monolayer is homogeneous. Second, synthesized peptides are linked to the silicon surface using a spacer that moves the peptide away from the surface so that the peptide is presented to the antibody in an unhindered orientation.

The in situ synthesized peptide libraries are disease agnostic and can be synthesized without a priori awareness of a disease they are intended to diagnose. Identical arrays can be used to determine any health condition.

The term "peptide" as used herein refers to a plurality of amino acids joined together in a linear or circular chain. For purposes of the present invention, the term peptide is not limited to any particular number of amino acids. Preferably, however, they contain up to about 400 amino acids, up to about 300 amino acids, up to about 250 amino acids, up to about 150 amino acids, up to about 70 amino acids, up to about 50 amino acids, up to about 40 amino acids, up to 30 amino acids, up to 20 amino acids, up to 15 amino acids, up to 10 amino acids, or up to 5 amino acids. In some embodiments, the peptides of the array are between 5 and 30 amino acids, between 5 and 20 amino acids, or between 5 and 15 amino acids. The amino acids forming all or a part of a peptide molecule may be any of the twenty conventional, naturally occurring amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y). Any of the amino acids in the peptides forming the present arrays may be replaced by a non-conventional amino acid. In general, conservative replacements are preferred. In some embodiments, the peptides on the array are synthesized from less of the 20 amino acids. In some embodiments, one or more of amino acids methionine, cysteine, isoleucine and threonine are excluded during synthesis of the peptides.

Digital Processing Device

In some embodiments, the systems, platforms, software, networks, and methods described herein include a digital processing device, or use of the same. In further embodiments, the digital processing device includes one or more hardware central processing units (CPUs), i.e., processors that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, a digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, a digital processing device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, a digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, a digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, a digital processing device includes a digital camera. In some embodiments, a digital camera captures digital images. In some embodiments, the digital camera is an autofocus camera. In some embodiments, a digital camera is a charge-coupled device (CCD) camera. In further embodiments, a digital camera is a CCD video camera. In other embodiments, a digital camera is a complementary metal-oxide-semiconductor (CMOS) camera. In some embodiments, a digital camera captures still images. In other embodiments, a digital camera captures video images. In various embodiments, suitable digital cameras include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and higher megapixel cameras, including increments therein. In some embodiments, a digital camera is a standard definition camera. In other embodiments, a digital camera is an HD video camera. In further embodiments, an HD video camera captures images with at least about 1280×about 720 pixels or at least about 1920×about 1080 pixels. In some embodiments, a digital camera captures color digital images. In other embodiments, a digital camera captures grayscale digital images. In various embodiments, digital images are stored in any suitable digital image format. Suitable digital image formats include, by way of non-limiting examples, Joint Photographic Experts Group (JPEG), JPEG 2000, Exchangeable image file format (Exif), Tagged Image File Format (TIFF), RAW, Portable Network Graphics (PNG), Graphics Interchange Format (GIF), Windows® bitmap (BMP), portable pixmap (PPM), portable graymap (PGM), portable bitmap file format (PBM), and WebP. In various embodiments, digital images are stored in any suitable digital video format. Suitable digital video formats include, by way of non-limiting examples, AVI, MPEG, Apple® QuickTime®, MP4, AVCHD®, Windows Media®, DivX™, Flash Video, Ogg Theora, WebM, and RealMedia.

Non-Transitory Computer Readable Storage Medium

In some embodiments, the systems, platforms, software, networks, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the systems, platforms, software, networks, and methods disclosed herein include at least one computer program. A computer program includes a sequence of instructions, executable in the digital processing device's CPU, written to perform a specified task. In light of the disclosure provided herein, those of skill in the art will recognize that a computer program may be written in various versions of various languages. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. A web application for providing a career development network for artists that allows artists to upload information and media files, in some embodiments, includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™ Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, Airplay SDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

The systems, platforms, software, networks, and methods disclosed herein include, in various embodiments, software, server, and database modules. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

The present invention is described in further detail in the following Examples which are not in any way intended to limit the scope of the invention as claimed. The attached Figures are meant to be considered as integral parts of the specification and description of the invention. The following examples are offered to illustrate, but not to limit the claimed invention.

EXAMPLES

Example 1—Diagnostic and Prognostic Assays for Scleroderma and Systemic Sclerosis Background: Scleroderma and Systemic Sclerosis (SSc) is a disease of the connective tissue featuring skin thickening that can involve scarring, blood vessel problems, and varying degrees of inflammation not only of skin but also internal organs. Diagnosis of SSc is difficult due to the complexity of manifestations and overlap with other autoimmune diseases. Major clinical manifestations of SSc are shown in FIG. 5. Diagnosis typically requires a combination of medical history review, physical examination, lab tests and X-Rays. No single biomarker is available but serologic testing has identified ANA and anticentromere antibodies (ACA) in 60%-80% of patients, and ScL 70 antibodies in 30%. However, these antibodies can also be found in some healthy individuals or patients with other autoimmune diseases e.g. dermatomyositis (DM). In addition to a better diagnostic, there is need for a better prognostic test. Raynaud's syndrome is the first manifestation of SSc in about 75% of patients, but does not serve as a prognostic. Patients with diffuse rather than limited skin involvement tend to develop more serious conditions such as ILD, PAH, GAVE, and renal complications. However, this observation is also not reliable enough to be prognostic.

Methods: A study population of 719 plasma samples was evaluated; it was comprised of SSC (n=301), DM (205), a group of other autoimmune diseases (95) including MCTD, UCTD, lupus, myositis & polymyositis, morphea, and a group of healthy samples (118). A panel of 84 control samples were used to facilitate assay qualifications.

All patients met ACR classification criteria at diagnosis. An IS assay was used to detect plasma antibodies bound to a microarray of ~126,000 unique peptides. Peptide sequences were designed (using 16 of the 20 amino acids) to broadly sample combinatorial space thus providing a library of diverse epitope mimetics for antibodies to selectively and competitively bind. Features most discriminating SSc contrasts were identified using a t-test. Support vector machines (SVM) classifiers were trained and assessed by 100 iterations of 5-fold cross validation analysis. Models ranging from 25 to 10,000 peptide inputs were evaluated.

Results: A classifier trained on 10,000 differentially bound peptides distinguished SSc patients from healthy donors with strong performance characteristics. Other algorithms with similar model sizes were built that differentiated SSc from other autoimmune diseases such as DM. Finally, SSc patients that ever progressed to one of several more severe conditions: ILD, renal crisis, and GAVE, could be distinguished from those SSc patients who never did progress. These cross-validated estimates of classification performance are provided in Table 1.

Figure 9A:
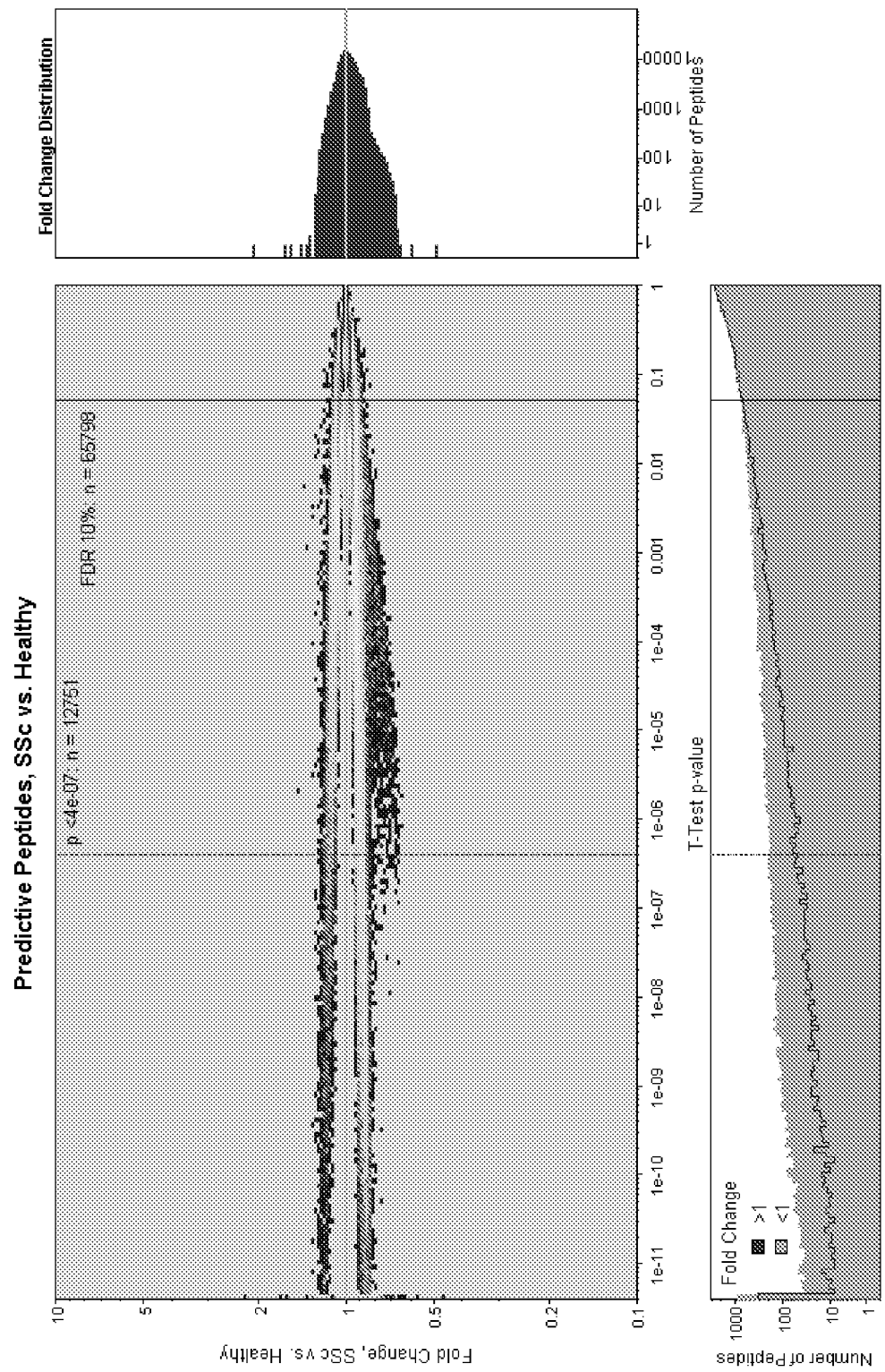
FIGS. 9A-9C are graphical representations of the results seen in FIGS. 8A-8C.
Figure 9B:
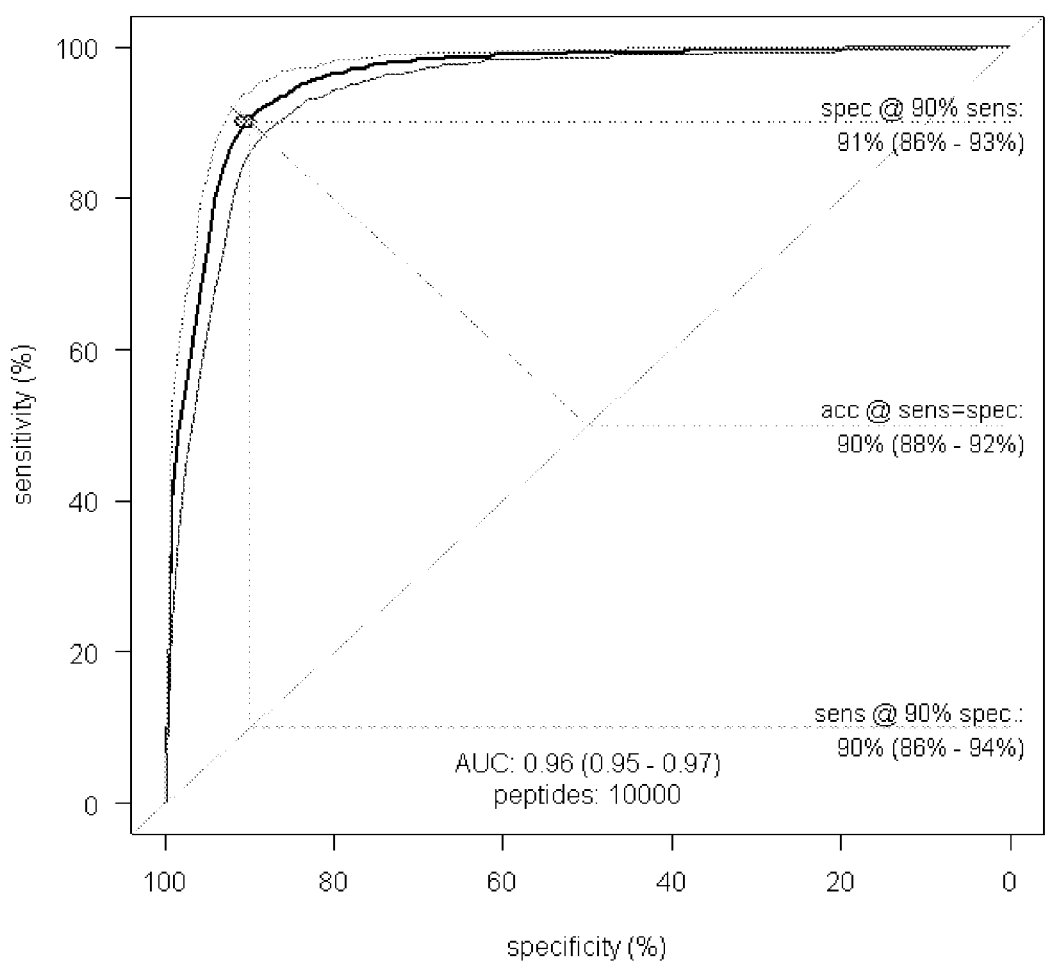
Figure 9C:
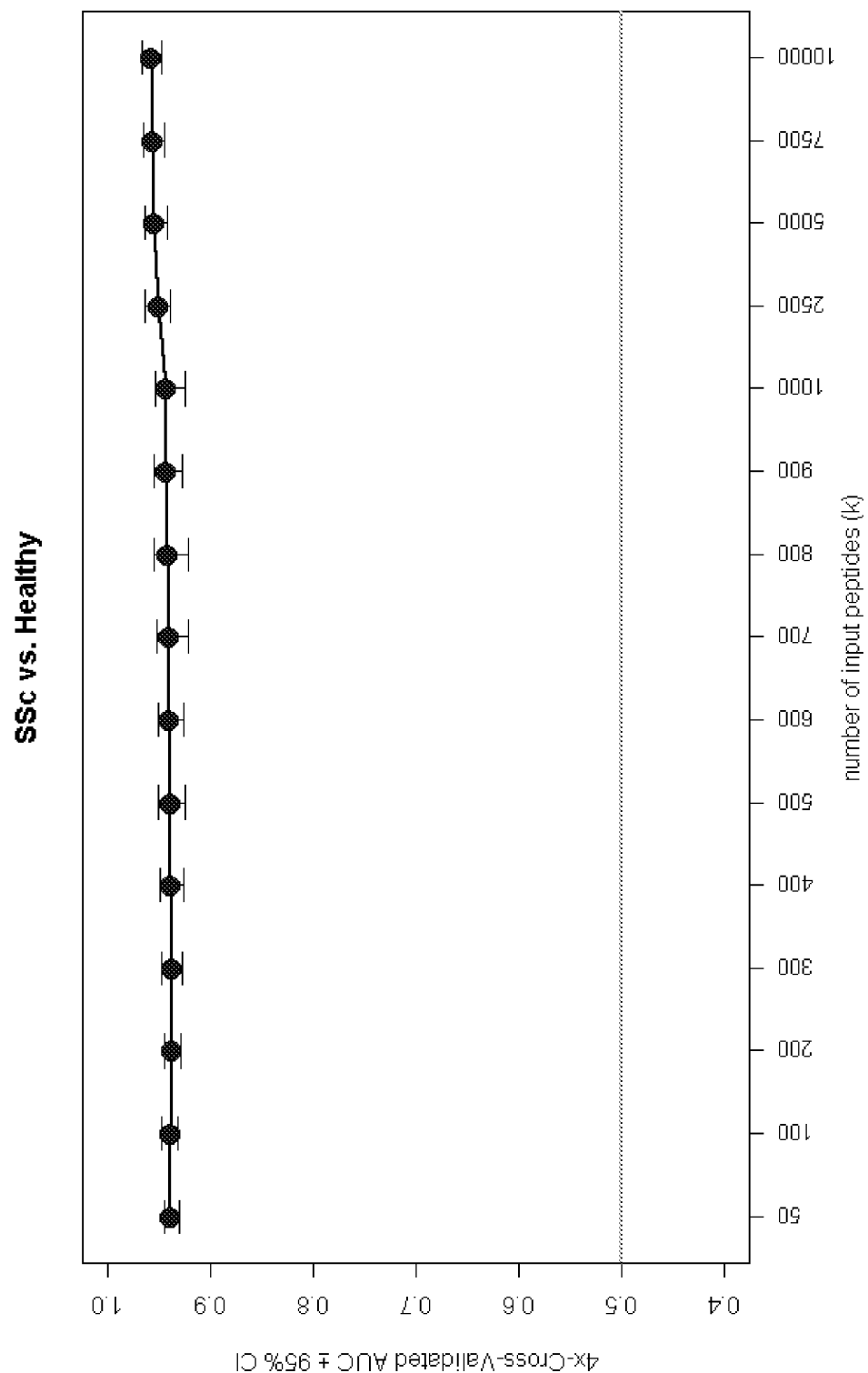

FIGS. 8A-8C shows a table depicting the top discriminating peptides in an immunosignature when comparing patients with SSc and healthy subjects. FIG. 8A depicts the top sub-motifs. FIG. 8B depicts the enriched peptides in the top 1000 discriminating peptides. FIG. 8C depicts the top 50 discriminating peptides. FIGS. 9A-9C is a graphical representation of the results in FIGS. 8A-8C. The headings apply to the list of motifs in (FIG. 8A) and to the amino acids list in (FIG. 8B) of this and all tables of discriminating peptides provided herein, where "n" is the number of times the motif appeared in the sequences of the top discriminating peptides; "n. lib" is the number of times the motif appeared in the library; "enrich" is the enrichment factor of the motif in the discriminating peptides relative to all of the motifs found in all sequences in the library; "padj. holm" is the p-adjusted value to control for multiple testing errors.

Figure 11A:
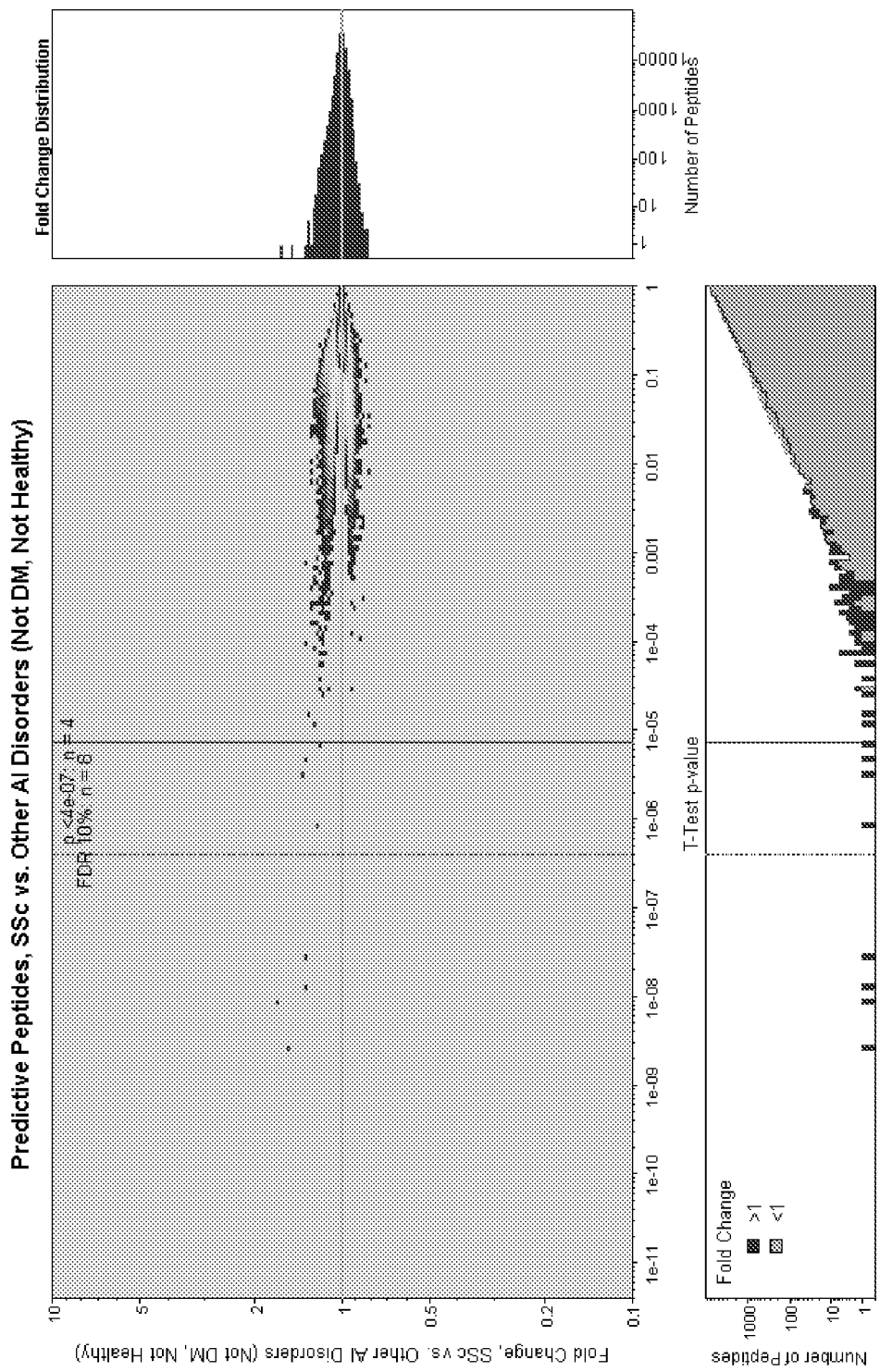
FIGS. 11A-11C are a graphical representation of the results seen in FIGS. 10A-10B.
Figure 11B:
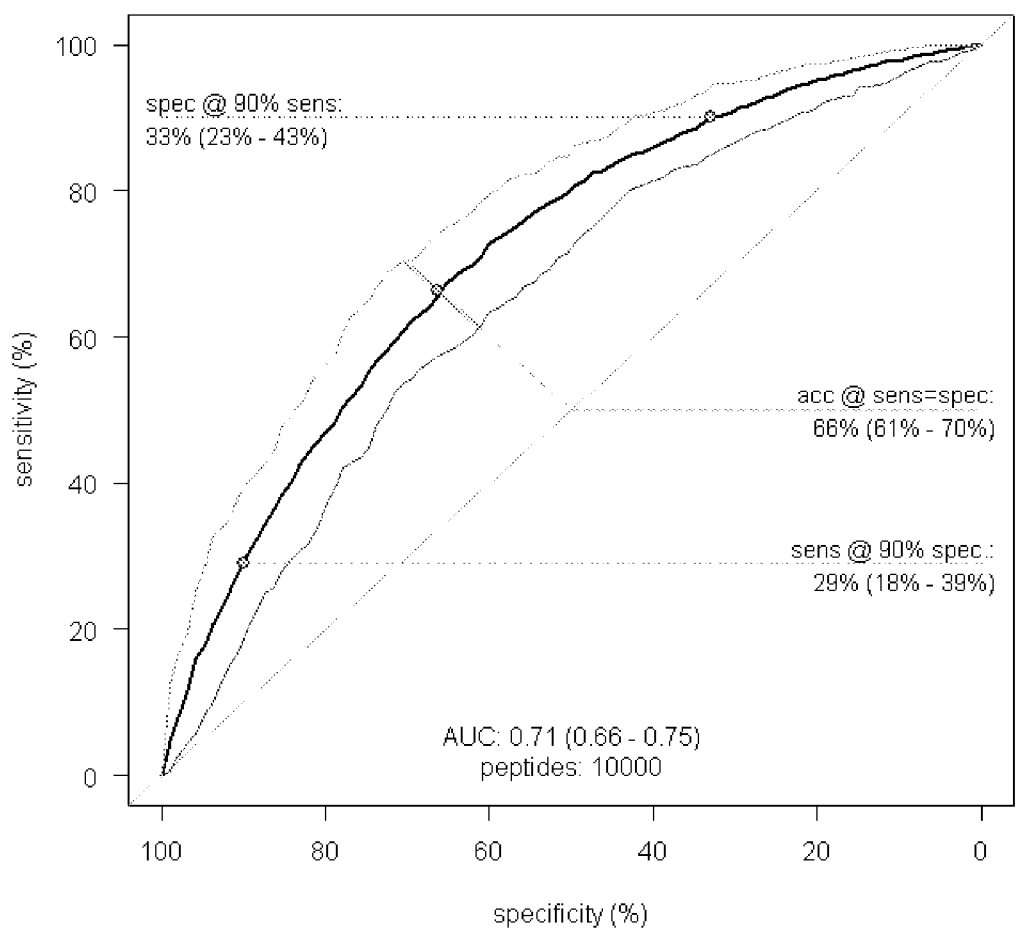
Figure 11C:
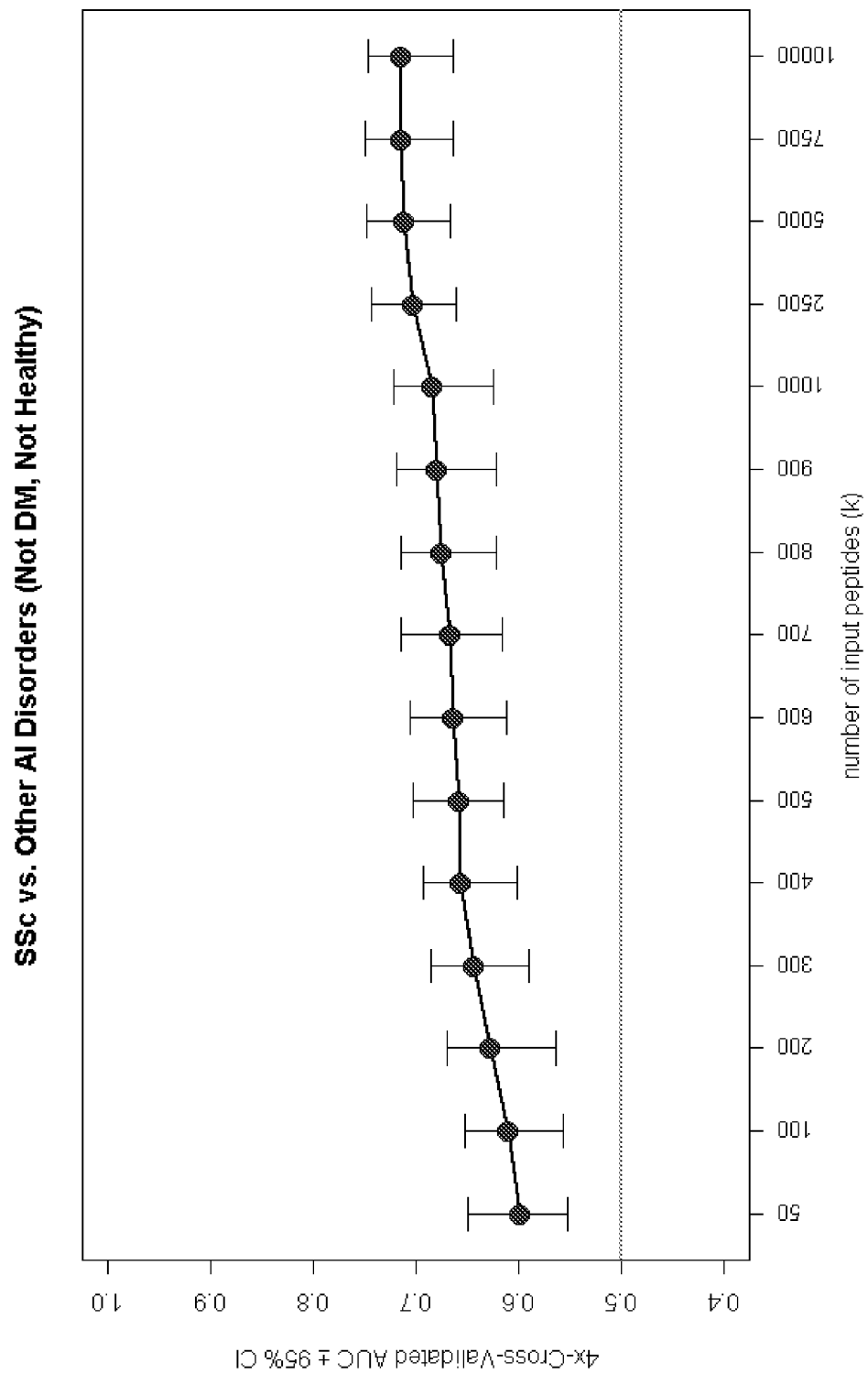

FIGS. 10A-10B show a table depicting the top submotifs (FIG. 10A) and the amino acids (FIG. 10B) that were found to be most enriched in the discriminating peptides identified in an immunosignature when comparing patients diagnosed with SSc and other autoimmune disorders. The submotifs and amino acids were determined in the top 1000 discriminating peptides. "Other autoimmune disorders" (Other AI) include Atypical myositis, acne rosacea, anti-PL7 with ILD and myositis, atypical myositis, Behcet's, Crohn's with atypical, rash, cutaneous lupus, Discoid lupus, DM, DM rash but negative antibodies, DM versus lupus, DM vs UCTD, drug eruption, eosinophilic fasciitis, Graft Versus Host Disease (GVHD), Hodgkins disease, lichen planus, 1SSc, lupus panniculitis, Mixed Connective Tissue Disease (MCTD), Morphea, myositis possibly drug induced, myositis with Jo-1 antibodies, nephrogenic systemic fibrosis, polymyalgia rheumatic, Polymyositis, possible DM—awaiting serotyping, possible drug eruption, Psoriasis, pulmonary fibrosis, pulmonary fibrosis with anti-J01, Raynauds only, Rhabdomyolysis, Sle, SLE/mixed, SSc, SSc/DM overlap, SSc/SLE, Undifferentiated Connective Tissue Disease (UCTD), UCTD with rash, Unknown, unknown with features of urticarial, and weakness no diagnosis. The analysis of the binding signals that differentiate SSc from Other AI is visualized in eth Volcano plot shown in FIG. 11A. The performance of the assay is characterized by the area under the receiver operator characteristic (ROC) curve (AUC) (FIG. 11B).

Figure 13A:
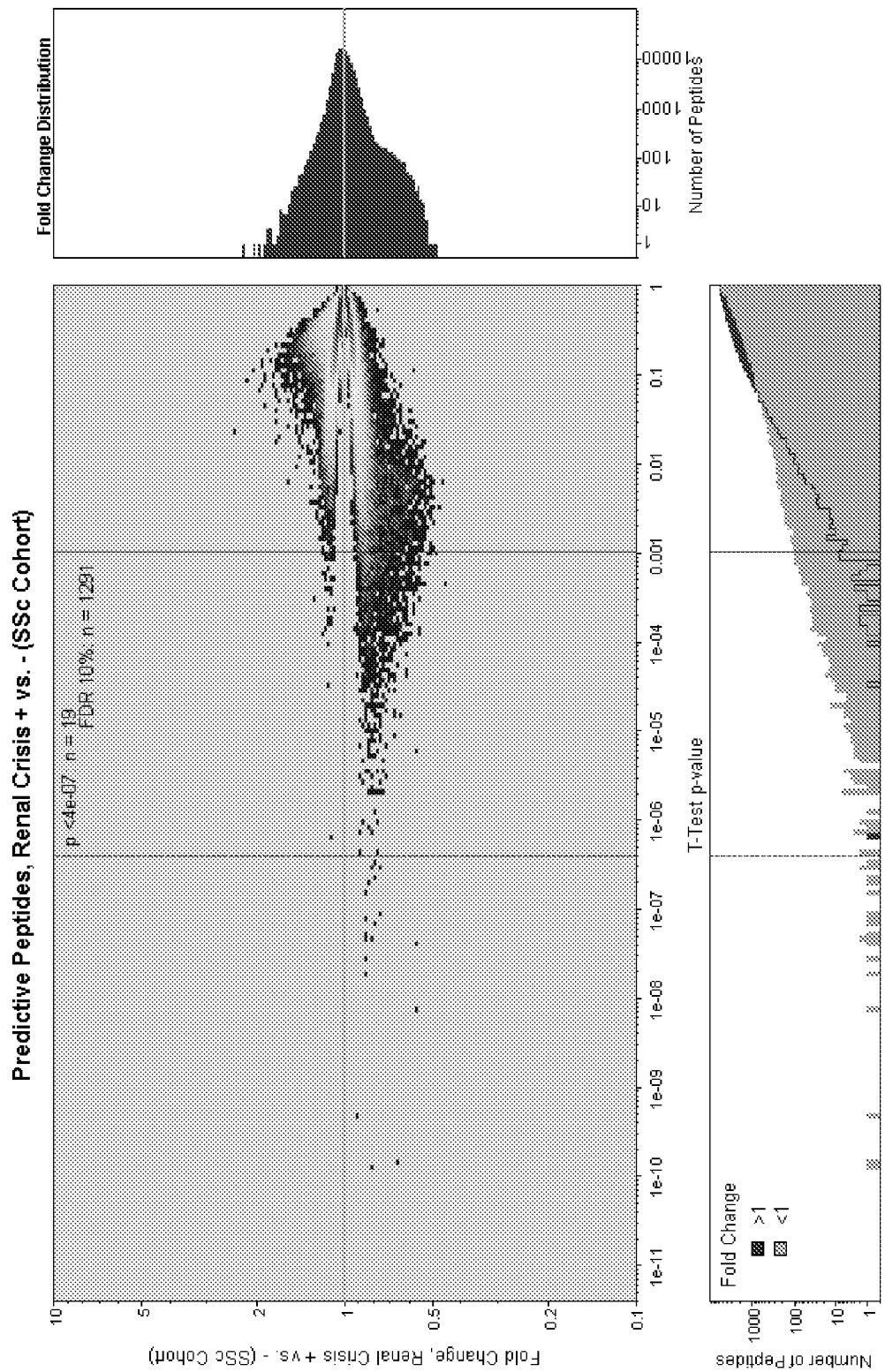
FIGS. 13A-13C are graphical representations of the results seen in FIGS. 12A-12C.
Figure 13B:
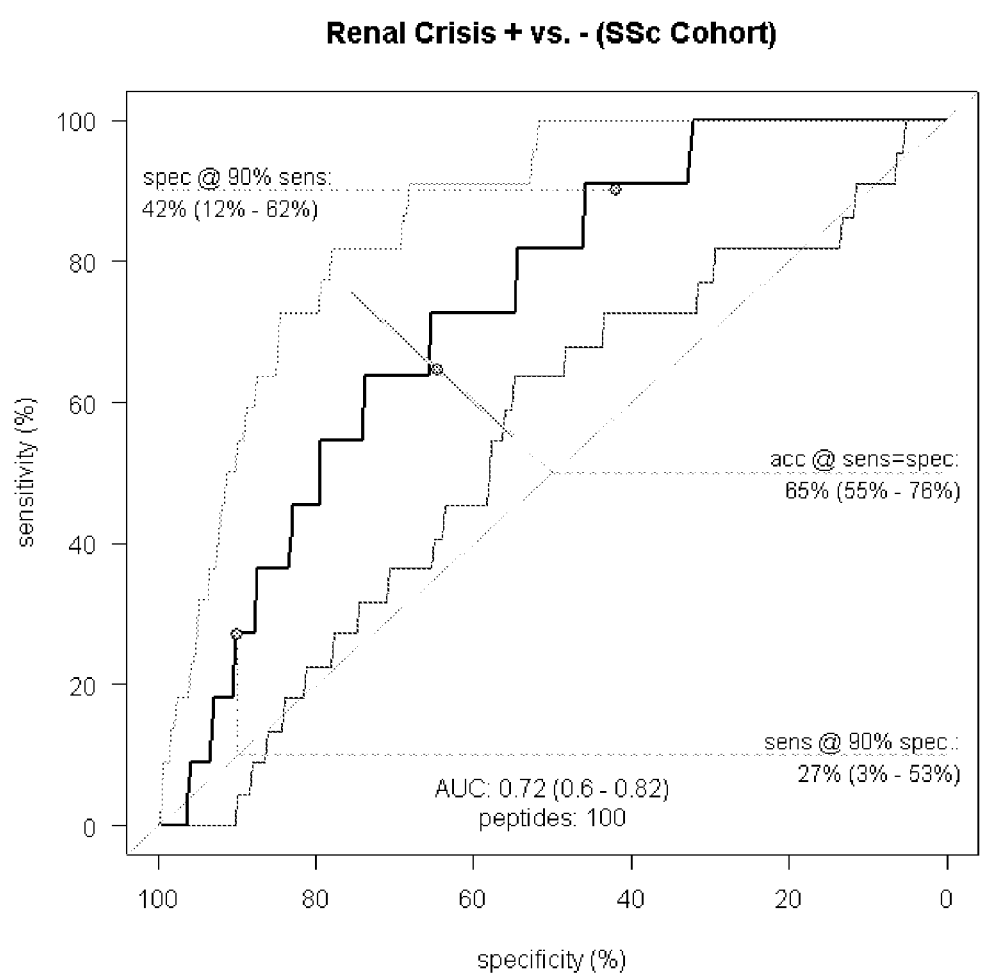
Figure 13C:
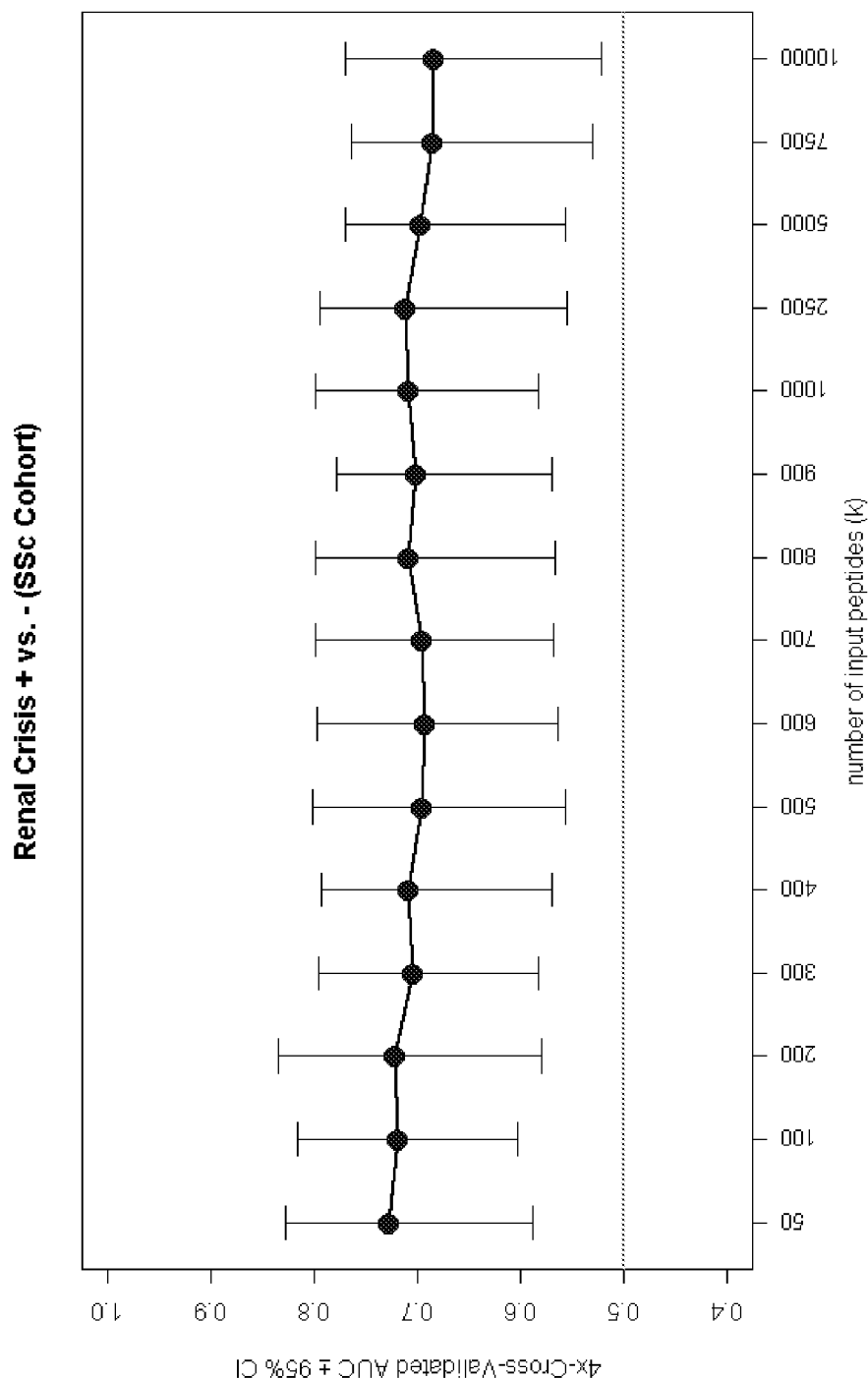

FIGS. 12A-12B show a table depicting the top submotifs (FIG. 12A) and amino acids (FIG. 12B) that were found to be most enriched in the discriminating peptides identified in an immunosignature when comparing patients diagnosed with SSc and patients in a renal crisis. FIGS. 13A-13B are graphical representations of the results seen in FIGS. 12A-12B. The analysis of the binding signals that differentiate SSc patients in renal crisis from SSc patients without renal crisis is visualized in eth Volcano plot shown in FIG. 13A. The performance of the assay is characterized by the area under the receiver operator characteristic (ROC) curve (AUC) (FIG. 13B).

Figure 15A:
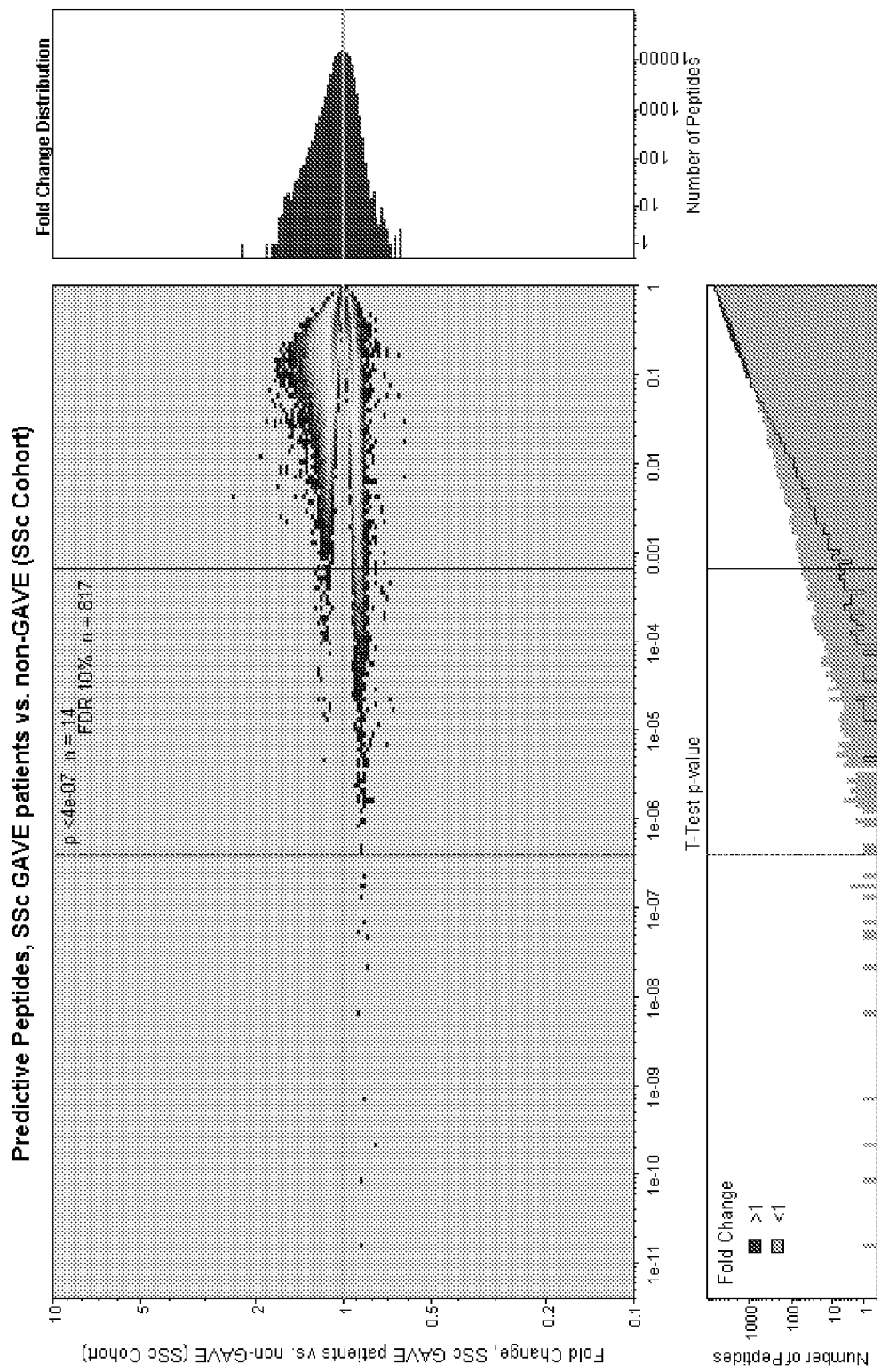
FIGS. 15A-15C are graphical representations of the results seen in FIGS. 14A-14C.
Figure 15B:
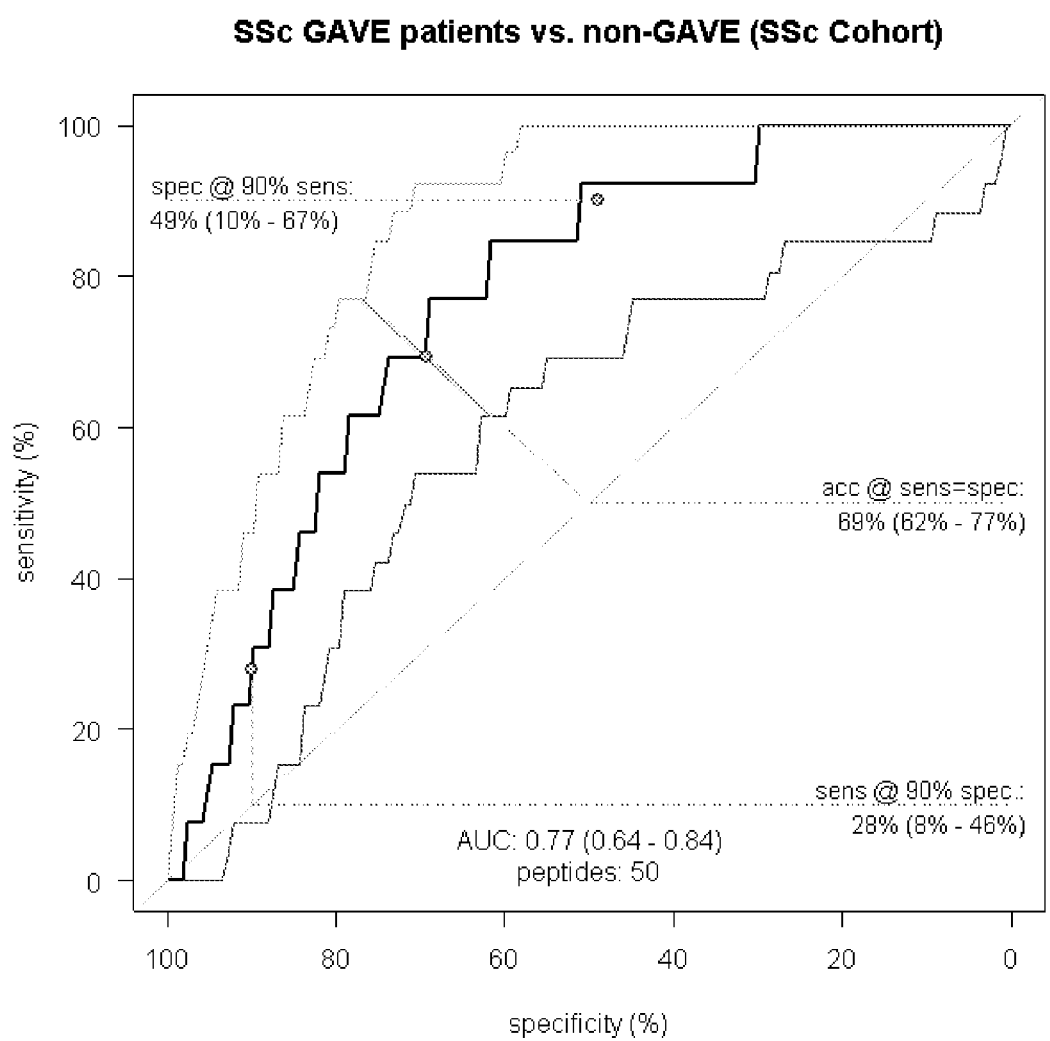
Figure 15C:
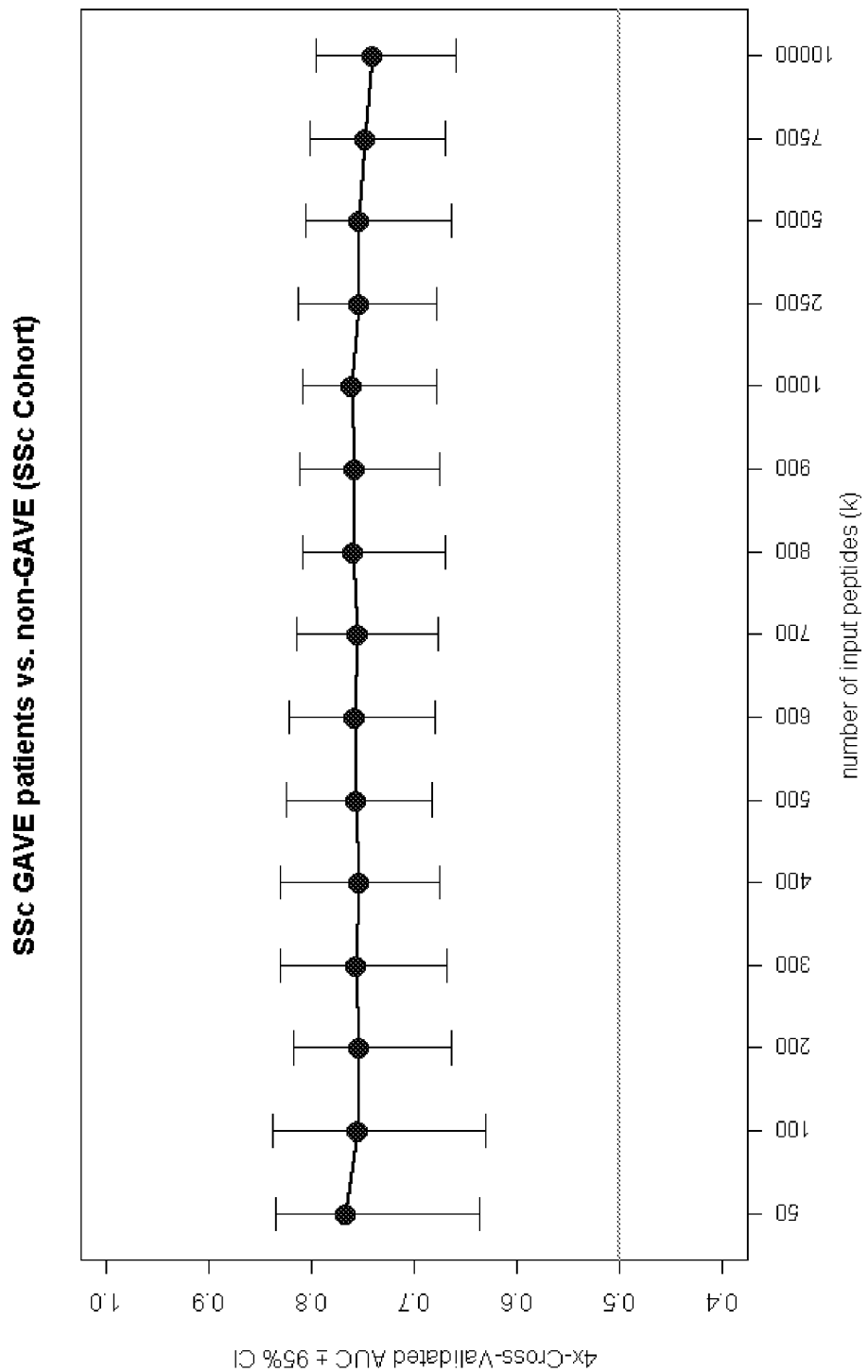

FIGS. 14A-14B show a table depicting the top submotifs (FIG. 14A) and amino acids (FIG. 14B) most enriched in the top discriminating peptides identified by immunosignature when comparing patients diagnosed with SSc and gastric antral vascular ectasia (GAVE) and patients with SSc without GAVE. FIGS. 15A-15C are graphical representations of the results seen in FIGS. 14A-14B. The analysis of the binding signals that differentiate SSc patients with GAVE from patients without GAVE is visualized in the Volcano plot shown in FIG. 15A. The performance of the assay is characterized by the area under the receiver operator characteristic (ROC) curve (AUC) (FIG. 15B).

Figure 17A:
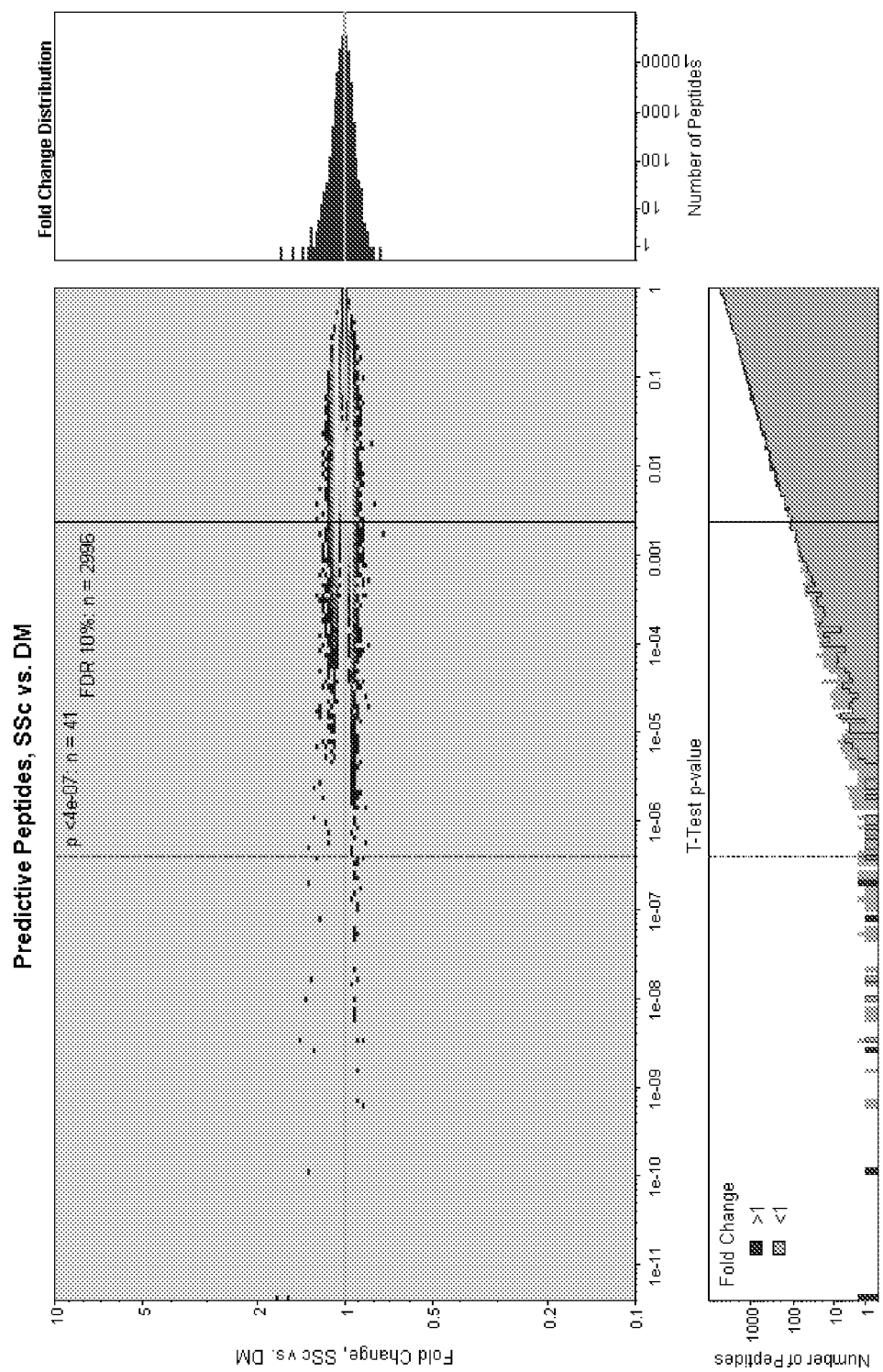
FIGS. 17A-17C are graphical representations of the results seen in FIGS. 16A-16B.
Figure 17B:
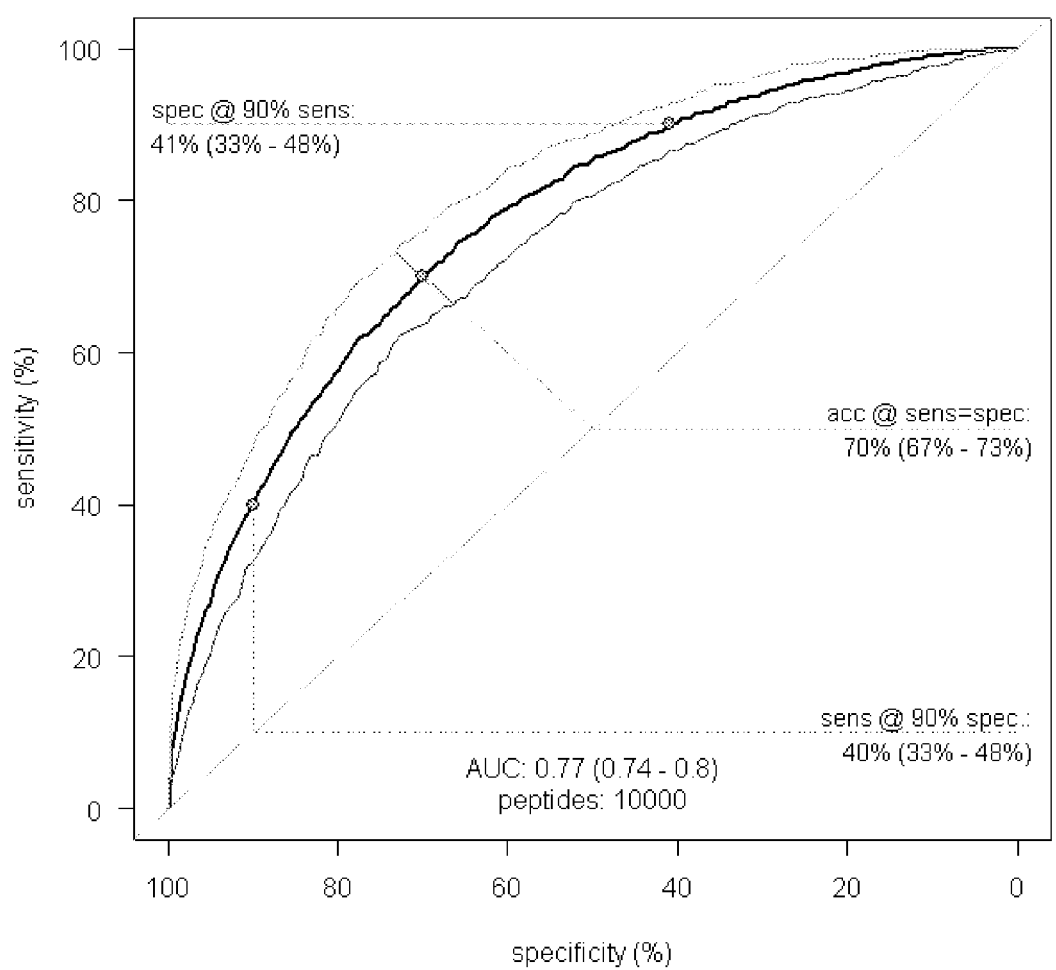
Figure 17C:
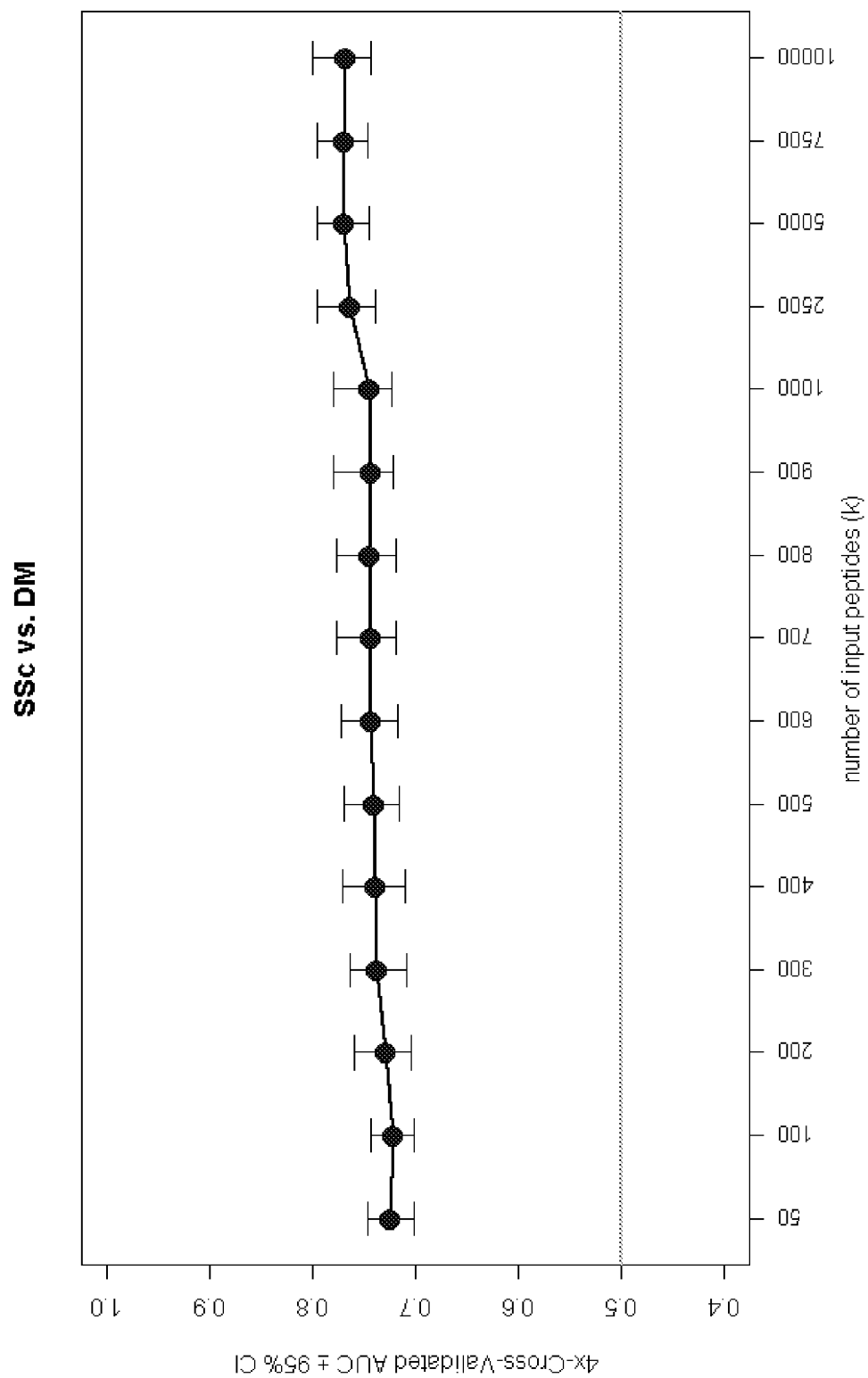

FIGS. 16A-16B shows a table depicting the top submotifs (FIG. 16A) and amino acids (FIG. 16B) most enriched in the discriminating peptides identified in an immunosignature when comparing patients diagnosed with SSc to patients with DM. FIGS. 17A-17B is a graphical representation of the results seen in FIGS. 16A-16B. The analysis of the binding signals that differentiate SSc patients from DM patients is visualized in the Volcano plot shown in FIG. 17A. The performance of the assay is characterized by the area under the receiver operator characteristic (ROC) curve (AUC) (FIG. 17B).

Figure 19A:
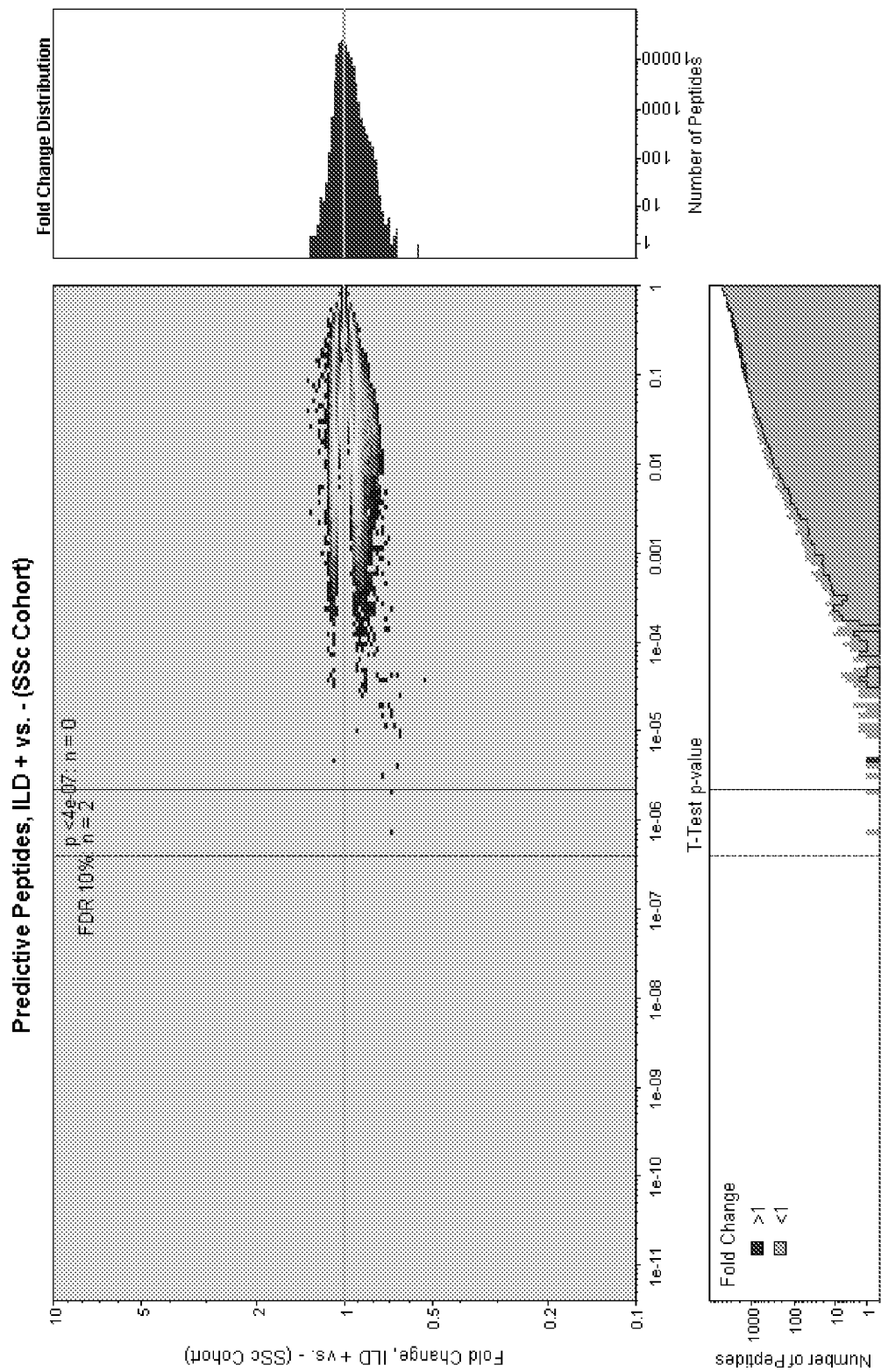
FIGS. 19A-19B are graphical representations of the results seen in FIGS. 18A-18B.
Figure 19B:
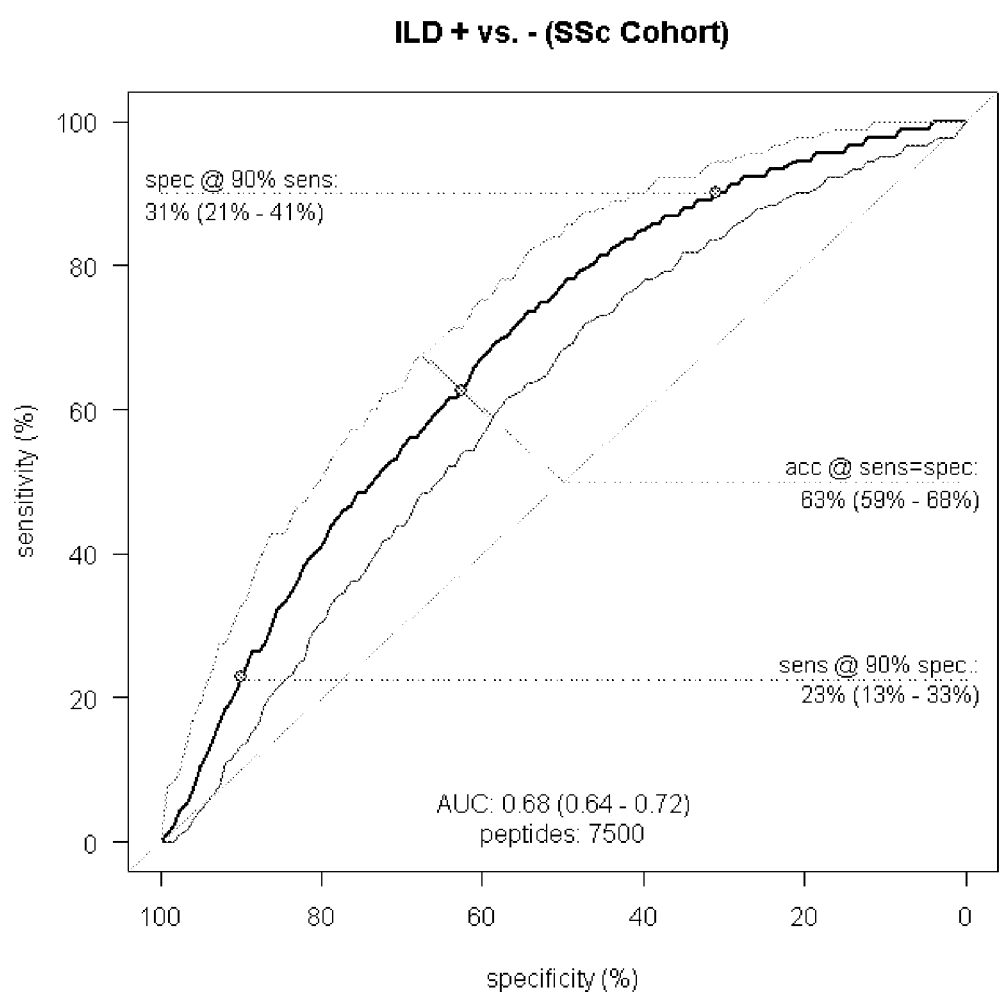
Figure 19C:
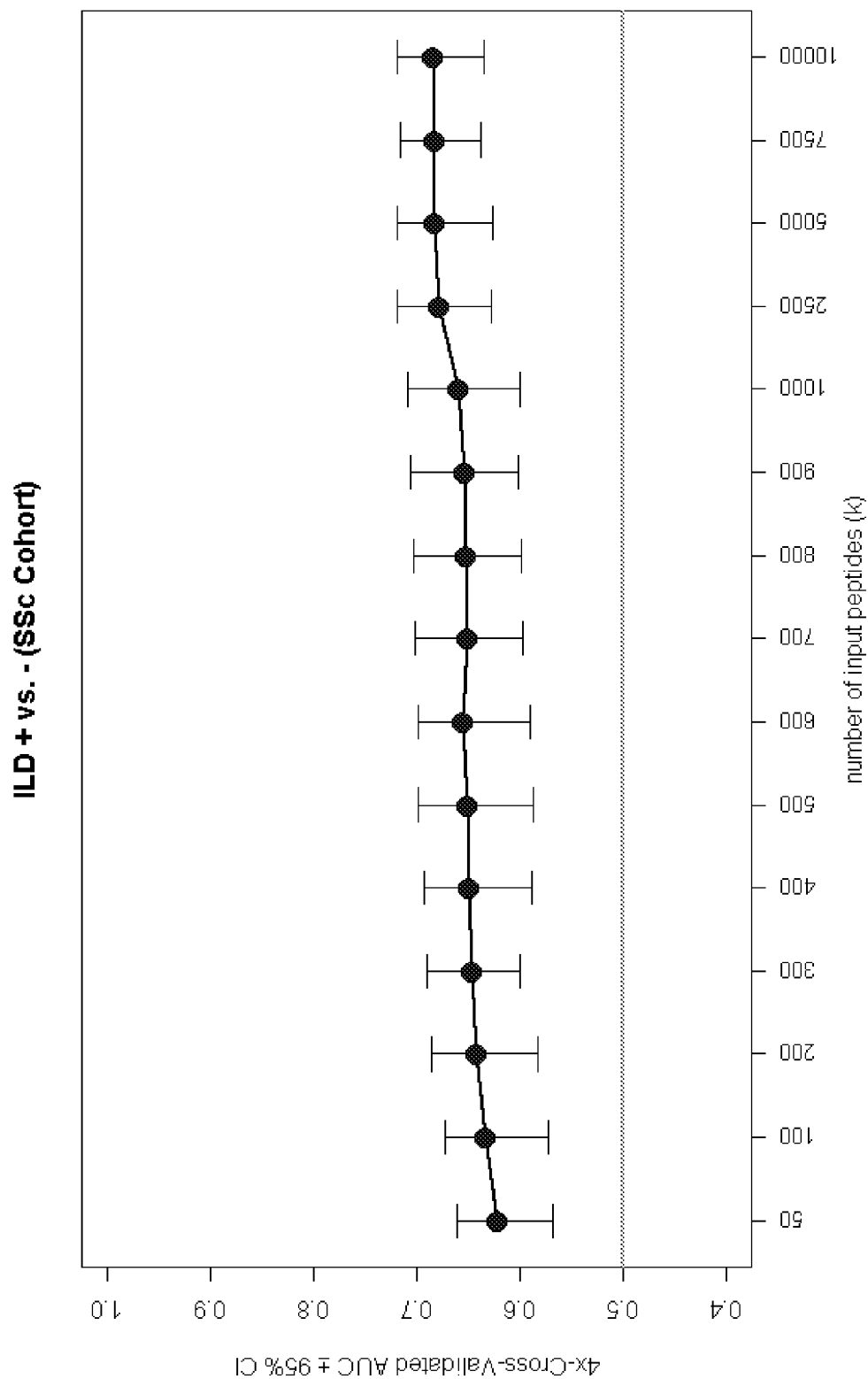
FIG. 19C shows ROC estimates as a function of input size—Four fold cross validated area under the ROC curve (+/−95% CI) are provided for models of different input peptide sizes. Peptides were selected based on a t-test and the top k features were used in a support vector machine to build a classifier of SSc ILD+vs. SSc ILD−. Feature selection and model construction were performed within the cross-validation loop to prevent bias.

FIGS. 18A-18B shows a table depicting the top submotifs (FIG. 18A) and amino acids (FIG. 18B) most enriched in the discriminating peptides identified in an immunosignature when comparing patients diagnosed with SSc with interstitial lung disease (ILD+) to patients with SSc without interstitial lung disease (ILD−). FIGS. 19A-19C are graphical representations of the results seen in FIGS. 18A-18B. The analysis of the binding signals that differentiate patients with SSc and ILD from patients with SSc without ILD is visualized in the Volcano plot shown in FIG. 19A. The performance of the assay is characterized by the area under the receiver operator characteristic (ROC) curve (AUC) (FIG. 19B).

Conclusions: Reproducible binding patterns produced by peripheral-blood antibody repertoires on a mimetic-peptide microarray can differentiate SSc from healthy donors and from other autoimmune diseases. In addition, distinctive immunosignatures were established for SSc patients that ever progressed to more serious disease manifestations. This suggests that the IS technology might be instrumental in the development of both new diagnostic and prognostic tests for SSc.

TABLE 1

Classification Performance Estimates of IS for SSc Diagnosis and Prognosis

| Contrast | AUC | Sens. @ 90% Spec. | Spec. @ 90% Sens. | Accuracy @ Sens. = Spec. |
|---|---|---|---|---|
| SSc vs Healthy | 0.96(0.95-0.97) | 90%(86-94%) | 91%(86-93%) | 90%(88-92%) |
| SSc vs Other AI | 0.71(0.66-0.75) | 29% (18%-39%) | 33% (23%-43%) | 66% (61%-70%) |
| SSc vs DM | 0.77(0.74-0.8) | 40%(33-48%) | 41%(33-48%) | 70%(67-73%) |
| SSc ILD+ vs ILD− | 0.68(0.64-0.72) | 23%(13-33%) | 31%(21-41%) | 63%(59-68%) |
| SSc Renal Crisis+ vs Crisis− | 0.72(0.6-0.82) | 27%(3-53%) | 42%(12-62%) | 65%(55-76%) |
| SSc GAVE+ vs GAVE− | 0.77(0.64-0.84) | 28%(8-46%) | 49%(10-67%) | 69%(62-77%) |

Example 2: Distinguishing Dermatomyositis and Systemic Sclerosis from Patients with Interstitial Lung Disease Background: Dermatomyositis (DM) is an inflammatory autoimmune disease with heterogeneous manifestations affecting skin, muscles, and lungs. The complexities of presentation make clinical diagnosis and prognosis challenging. Histologic findings also vary, confounding their utility. Several DM-specific antigens have been identified suggesting serologic diagnosis may be possible. However, alternative antigens would be required since many DM patients do not possess antibodies to these antigens. Interstitial lung disease (ILD) develops in 20-40% of patients, displaying a spectrum from mild to rapidly progressive, and possibly fatal, lung disease. Some DM-serotypes are at higher risk than others for ILD progression, but serotyping alone is not sufficiently sensitive or specific to guide clinical care.

A simple test to differentiate DM from other inflammatory autoimmune disease and to predict those that will progress to ILD would improve patient care. In addition, a discovery method for new DM-antigens would facilitate diagnostic and therapeutic efforts. The immunosignature (IS) platform was investigated to determine if it could address both clinical and discovery goals.

Methods: A study population of 719 plasma samples was evaluated; it was comprised of SSC (n=301), DM (205), a group of other autoimmune diseases (95) including MCTD, UCTD, lupus, myositis & polymyositis, morphea, and healthy samples (118). A panel of 84 control samples were used to facilitate assay qualifications. All patients met ACR classification criteria at diagnosis. An IS assay was used to detect plasma antibodies bound to a microarray of ~126,000 unique peptides. Peptide sequences were designed to broadly sample combinatorial space thus providing a library of diverse epitope mimetics for antibodies to selectively bind. Features most discriminating DM contrasts were identified using a t-test. Classification efficacy was determined in a support vector machine using 100 iterations of 5-fold cross validation.

Results: Cross-validated estimates of classification performance are provided in Table 2. Algorithms trained on differentially bound peptides distinguished DM from healthy donors and other AI, such as SSc. Both DM and SSc patients that ever progressed to ILD could be distinguished from those that never did. Up to 10,000 peptides whose antibody-binding characteristics differentiated disease groups were identified and used as inputs to these classifiers. Notably, the models for DM:ILD+/− and for SSc:ILD+/− were similarly predictive; however, the significantly distinguishing peptides used in these 2 classifiers showed no overlap.

TABLE 2

Classification performance estimates of IS for DM contrasts

| Contrast | AUC | Sens. @ 90% Spec. | Spec. @ 90% Sens. | Accuracy @ Sens. = Spec. |
|---|---|---|---|---|
| DM vs Healthy | 0.94 (0.93-0.96) | 83% (75-88%) | 85% (79-89%) | 87% (85-89%) |
| DM vs Other AI | 0.66 (0.61-0.70) | 17% (9%-25%) | 31% (23%-39%) | 62% (58%-66%) |
| DM vs SSc | 0.77 (0.74-0.8) | 40% (33-48%) | 41% (33-48%) | 70% (67-73%) |
| DM: ILD+ vs ILD− | 0.69 (0.63-0.72) | 22% (12-33%) | 30% (16-45%) | 65% (60-70%) |
| SSc: ILD+ vs ILD− | 0.68 (0.64-0.72) | 23% (13-33%) | 31% (21-41%) | 63% (59-68%) |

Figure 21A:
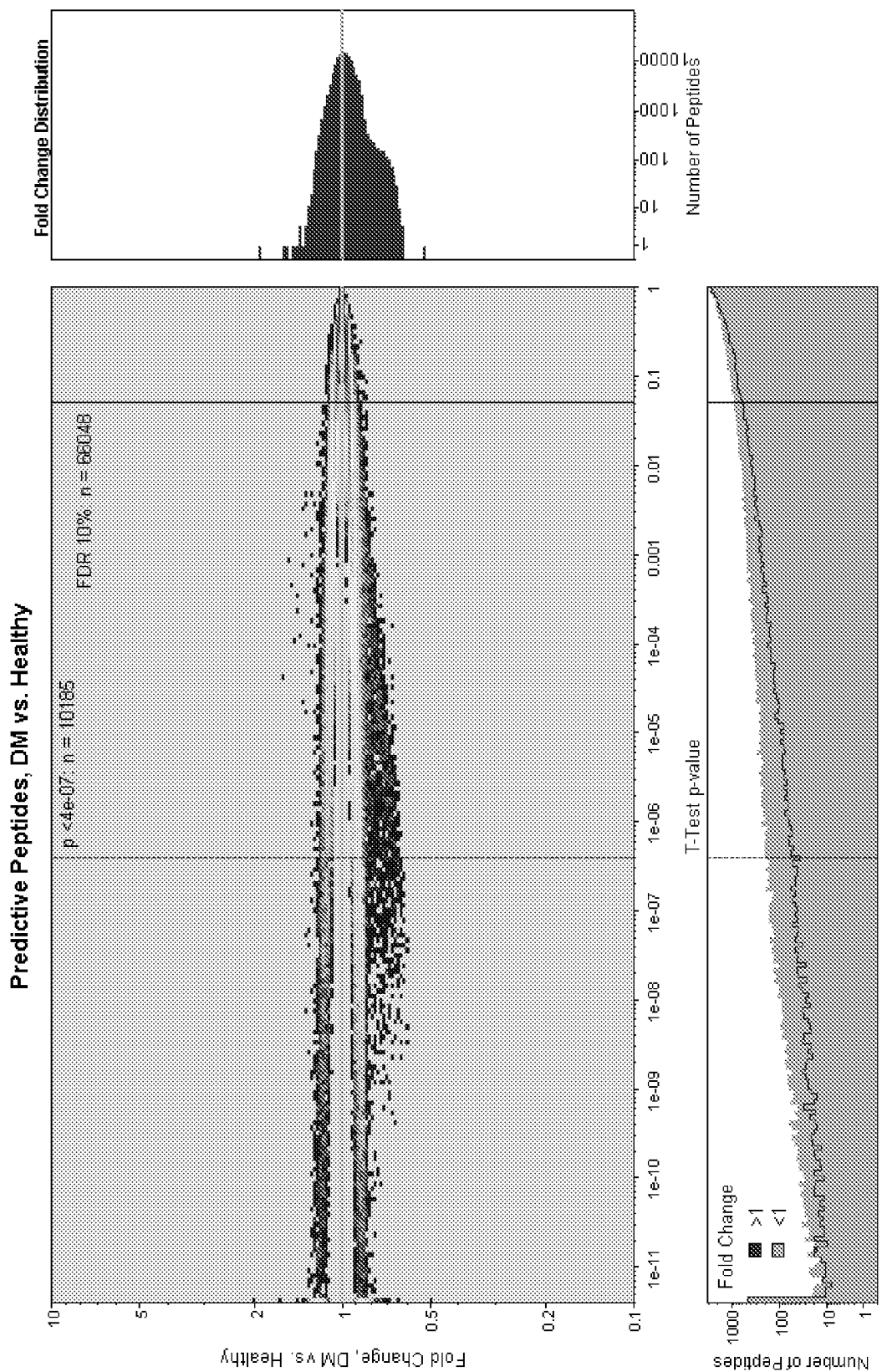
FIGS. 21A-21C are a graphical representations of FIG. 20A-20B.
Figure 21B:
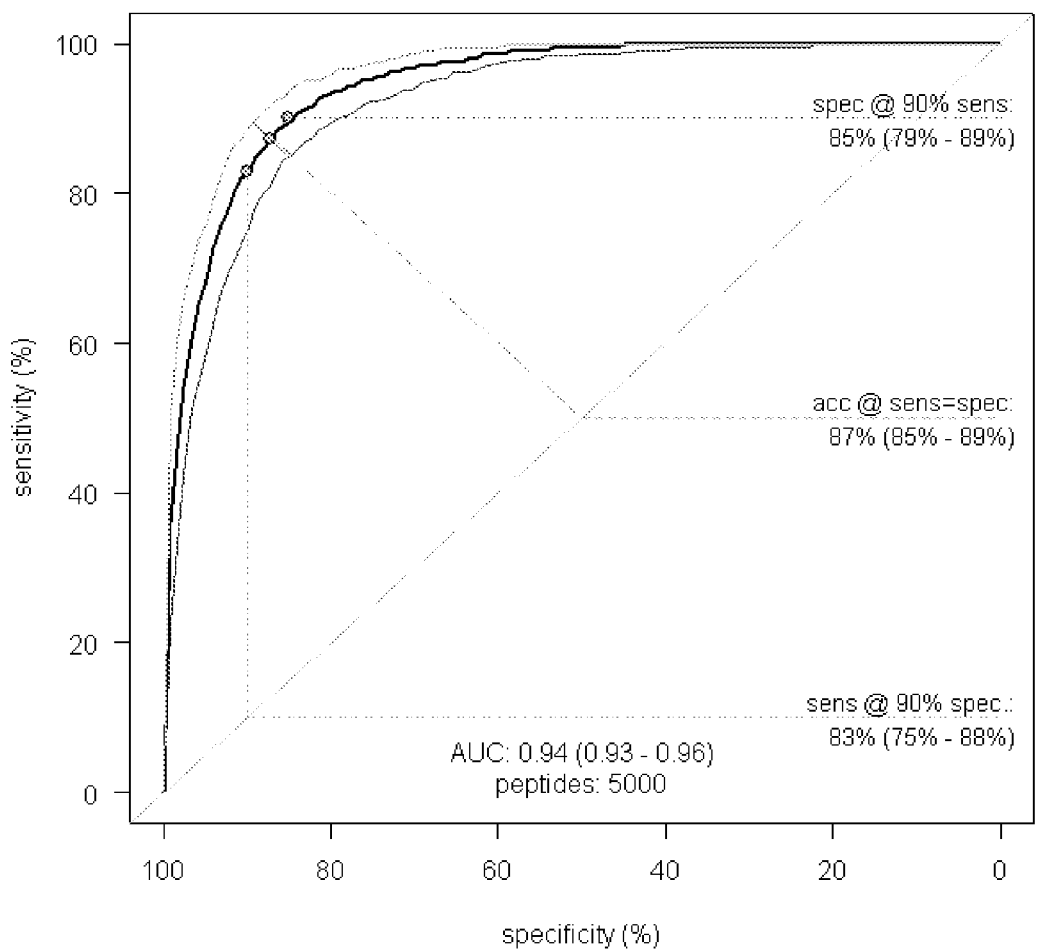
Figure 21C:
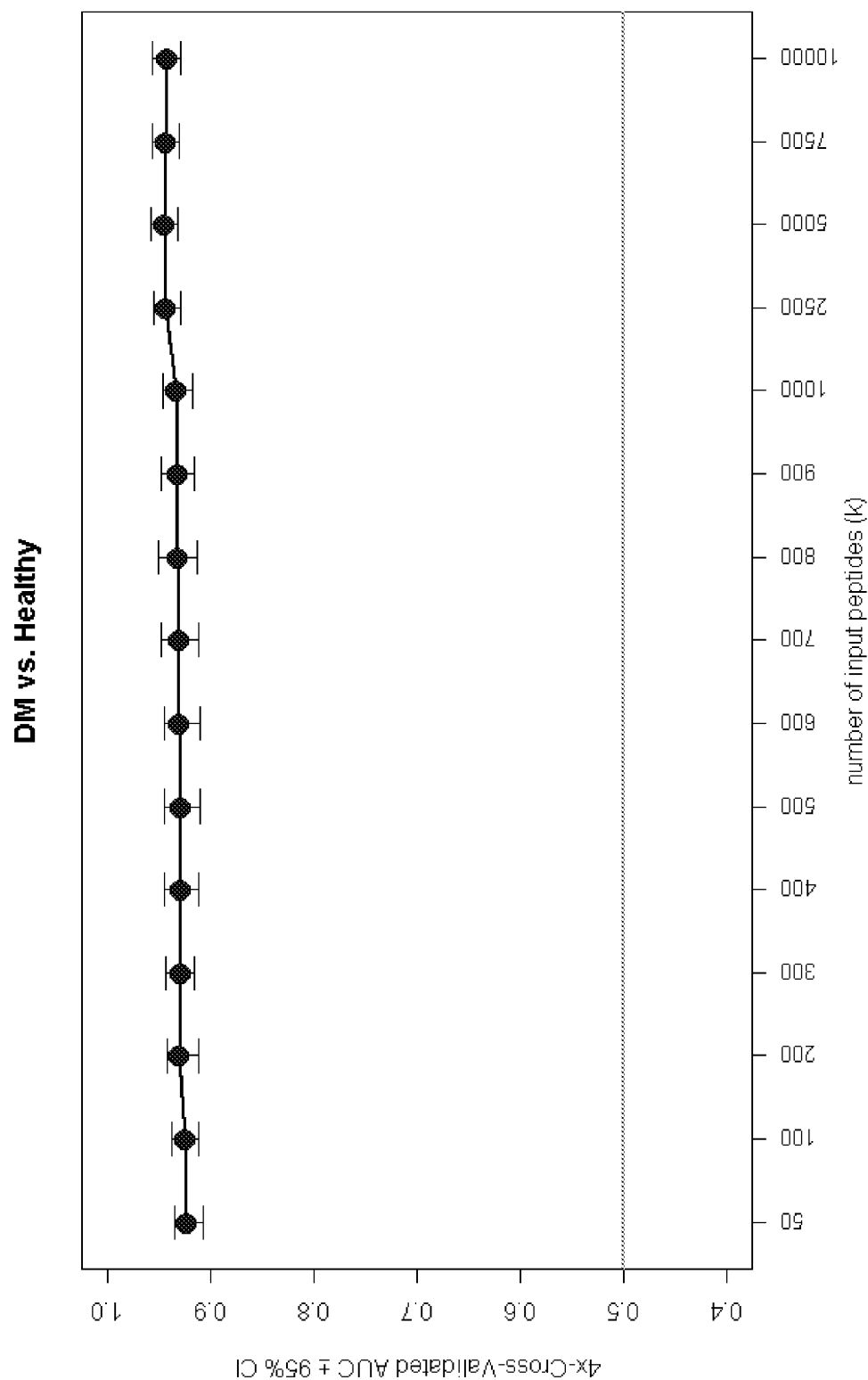

FIGS. 20A-20B show a table depicting the top submotifs (FIG. 20A) and amino acids (FIG. 20B) most enriched in the discriminating peptides identified in an immunosignature when comparing patients diagnosed with DM to healthy patients. FIGS. 21A-20B are graphical representations of the results seen in FIGS. 20A-20B. The analysis of the binding signals that differentiate patients with DMc from healthy patients is visualized in the Volcano plot shown in FIG. 21A. The performance of the assay is characterized by the area under the receiver operator characteristic (ROC) curve (AUC) (FIG. 21B).

Figure 23A:
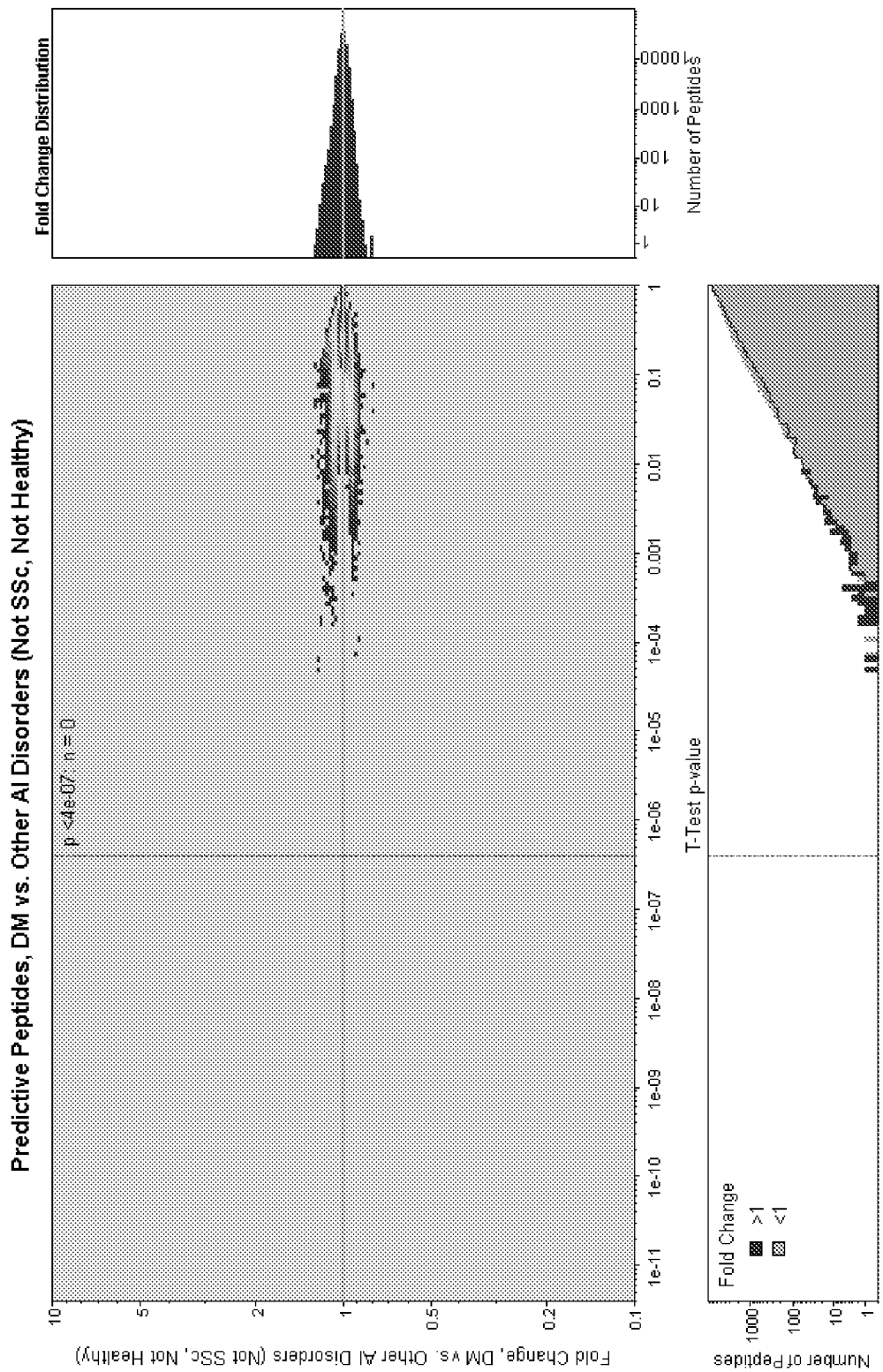
FIGS. 23A-23C are graphical representations of FIGS. 22A-22B.
Figure 23B:
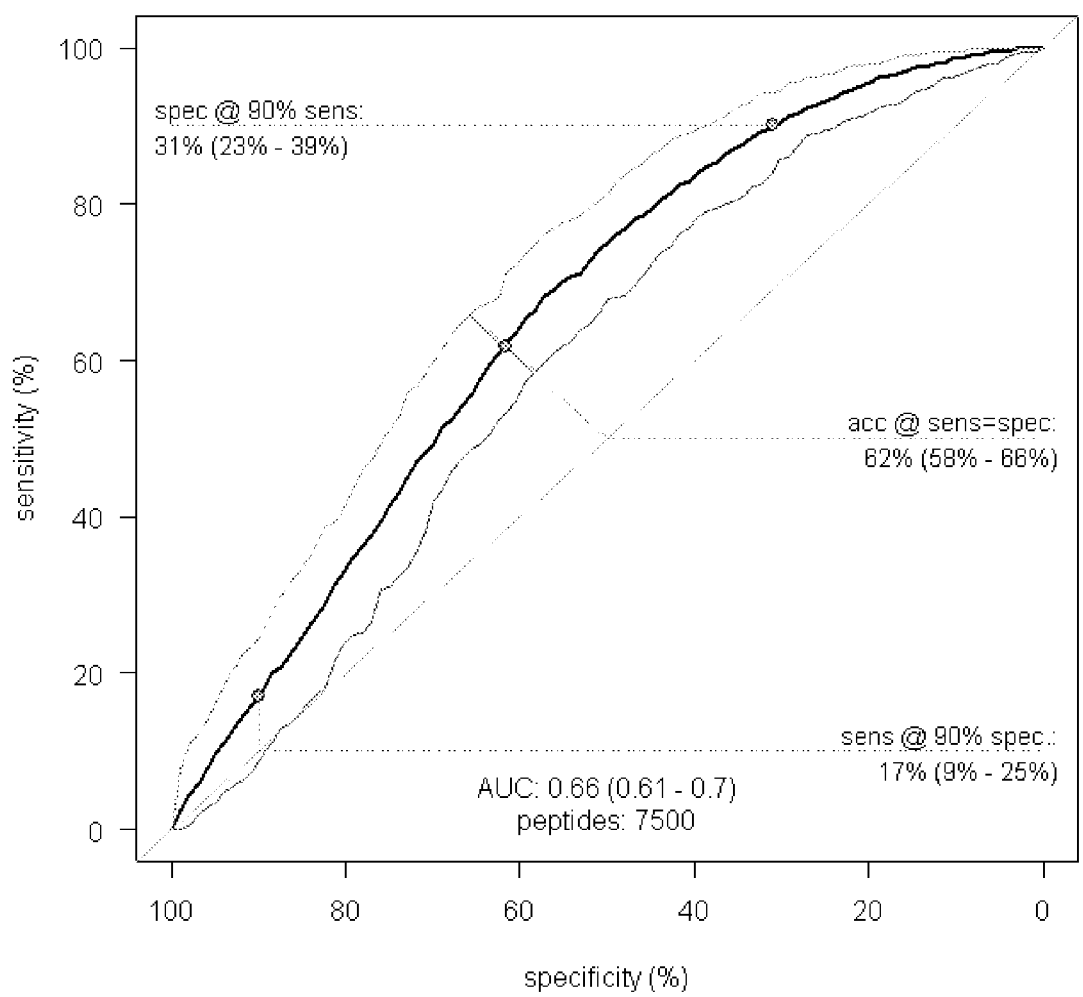
Figure 23C:
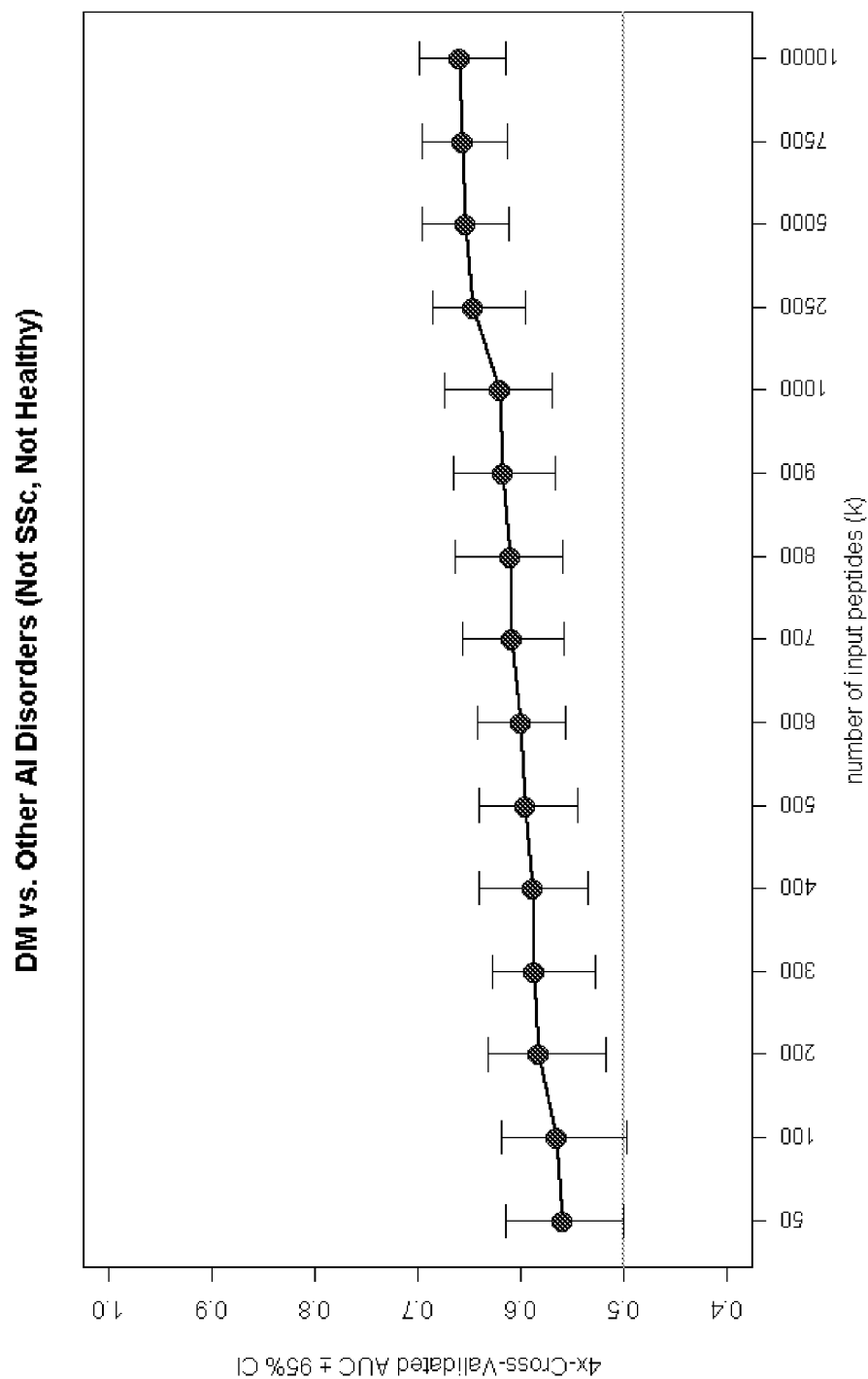

FIGS. 22A-22B shows a table depicting the top submotifs (FIG. 22A) and the amino acids (FIG. 22B) that were found to be most enriched in the discriminating peptides identified in an immunosignature when comparing patients diagnosed with SSc and other autoimmune disorders. The submotifs and amino acids were determined in the top 1000 discriminating peptides. "Other autoimmune disorders" (Other AI) include Atypical myositis, acne rosacea, anti-PL7 with ILD and myositis, atypical myositis, Behcet's, Crohn's with atypical, rash, cutaneous lupus, Discoid lupus, DM, DM rash but negative antibodies, DM versus lupus, DM vs UCTD, drug eruption, eosinophilic fasciitis, Graft Versus Host Disease (GVHD), Hodgkins disease, lichen planus, 1SSc, lupus panniculitis, Mixed Connective Tissue Disease (MCTD), Morphea, myositis possibly drug induced, myositis with Jo-1 antibodies, nephrogenic systemic fibrosis, polymyalgia rheumatic, Polymyositis, possible DM—awaiting serotyping, possible drug eruption, Psoriasis, pulmonary fibrosis, pulmonary fibrosis with anti-J01, Raynauds only, Rhabdomyolysis, Sle, SLE/mixed, SSc, SSc/DM overlap, SSc/SLE, Undifferentiated Connective Tissue Disease (UCTD), UCTD with rash, Unknown, unknown with features of urticarial, and weakness no diagnosis. The analysis of the binding signals that differentiate SSc from Other AI is visualized in eth Volcano plot shown in FIG. 23A. The performance of the assay is characterized by the area under the receiver operator characteristic (ROC) curve (AUC) (FIG. 23B).

Figure 25A:
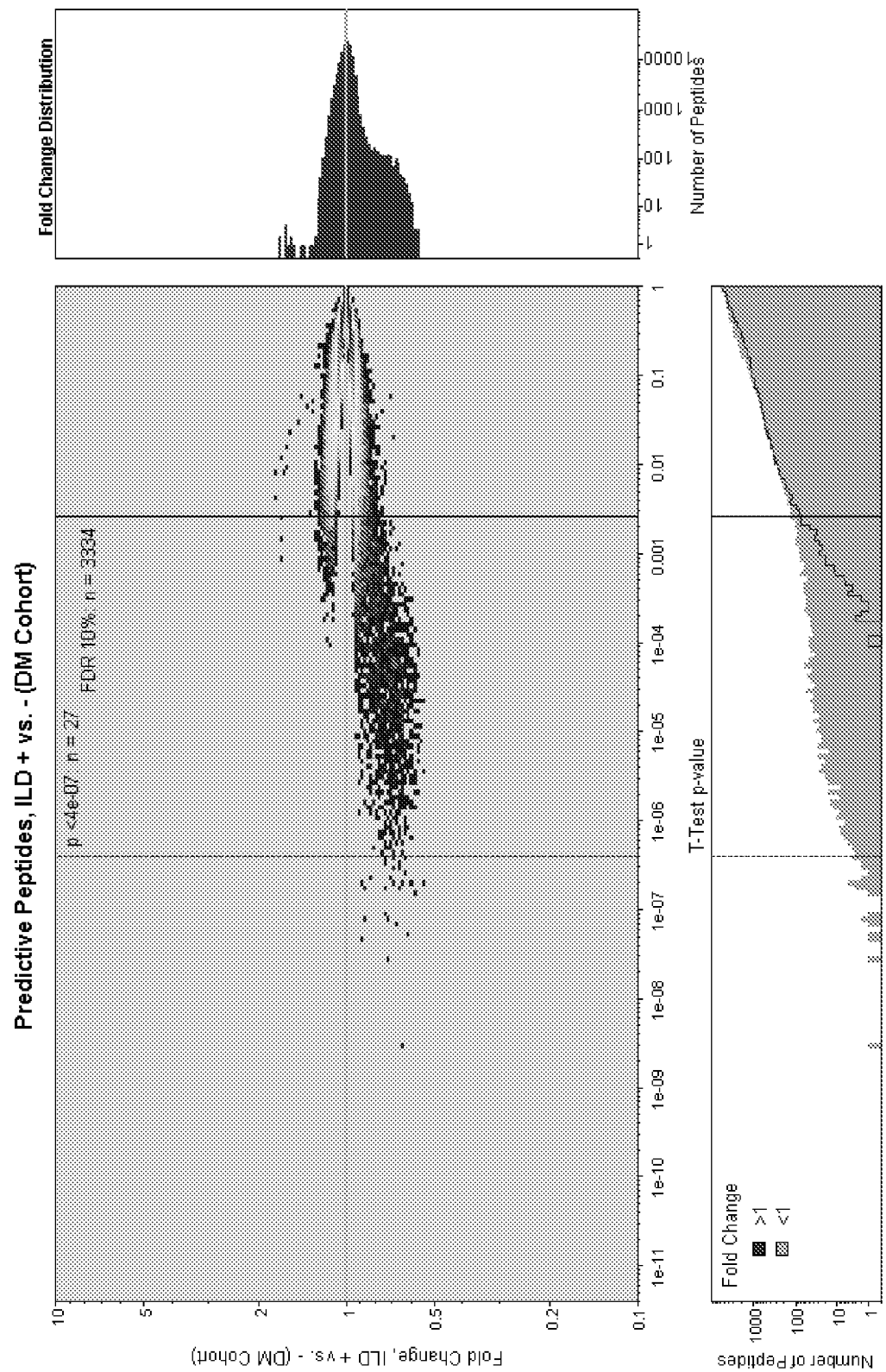
FIGS. 25A-25C are graphical representations of FIGS. 24A-24B.
Figure 25B:
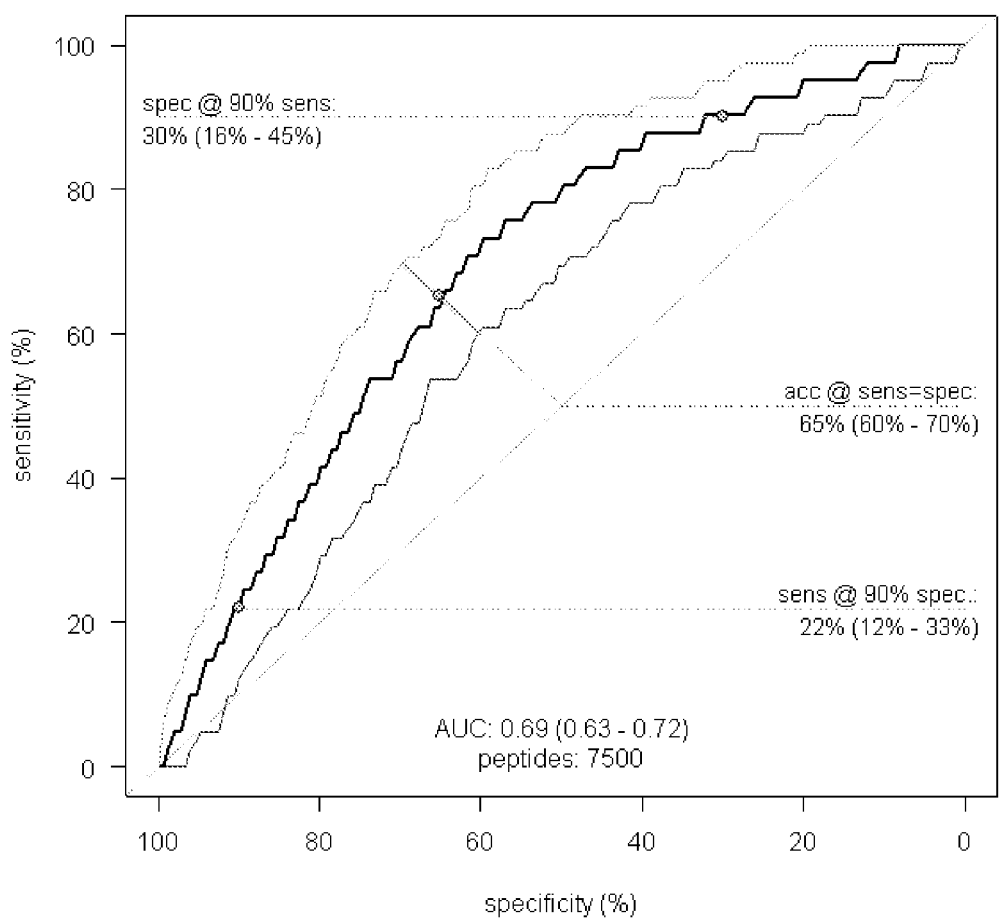
Figure 25C:
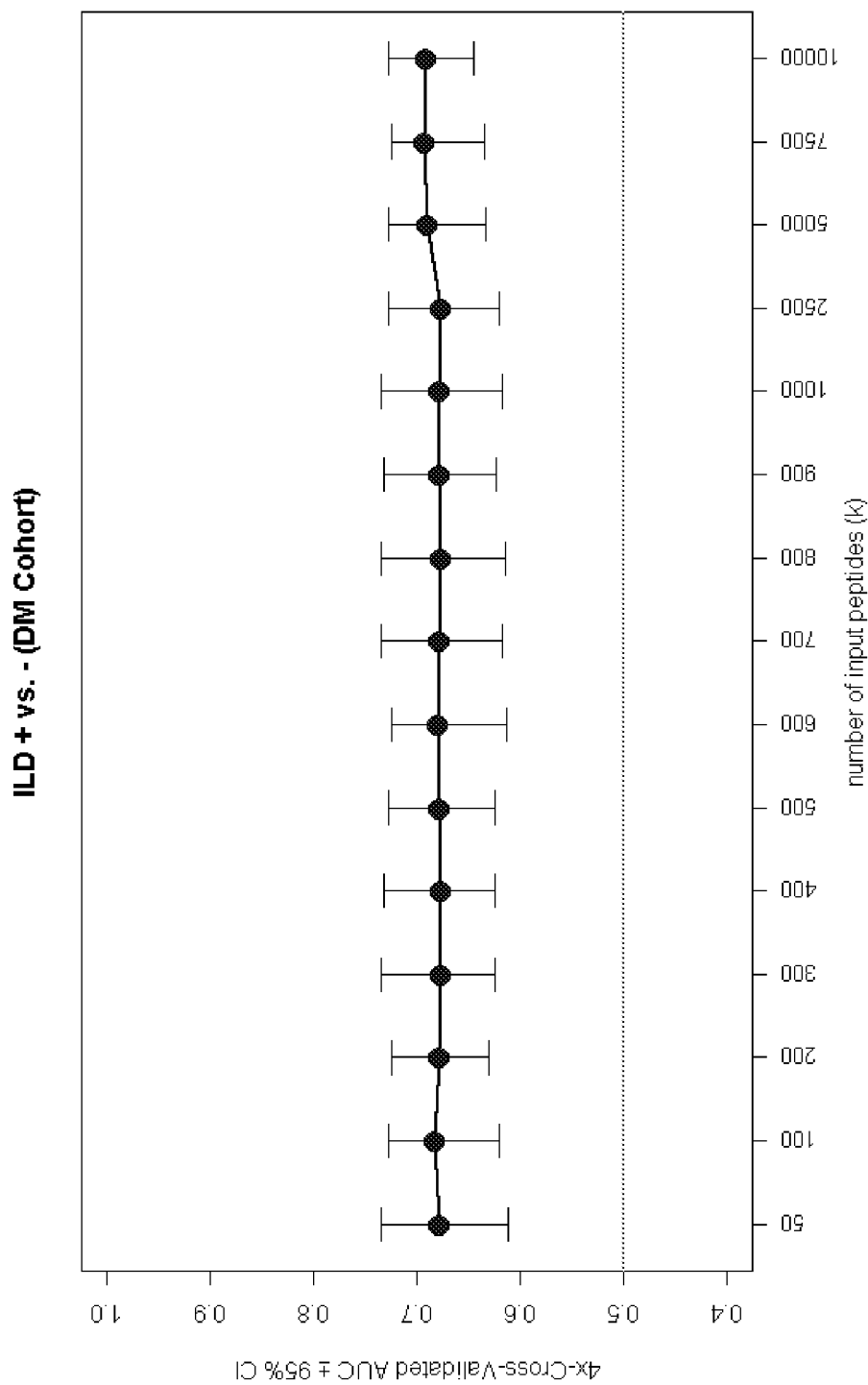

FIGS. 24A-24B shows a table depicting the top submotifs (FIG. 24A) and amino acids (FIG. 24B) most enriched in the discriminating peptides identified in an immunosignature when comparing patients diagnosed with SSc with interstitial lung disease (ILD+) to patients with SSc without interstitial lung disease (ILD−). FIGS. 25A-25B are graphical representations of the results seen in FIGS. 24A-24B. The analysis of the binding signals that differentiate patients with SSc and ILD from patients with SSc without ILD is visualized in the Volcano plot shown in FIG. 25A. The performance of the assay is characterized by the area under the receiver operator characteristic (ROC) curve (AUC) (FIG. 25B).

Mimotope binding patterns identified DM patients from non-DM patients. Deciphering the antigens that these peptides mimic may reveal new DM-specific antigens. Classifiers for DM versus other AI, and for patients that progressed to ILD were also evaluated. The lack of any overlap between the ILD predicting peptides for DM vs. SSc patients supports a conclusion that these are unique diseases, despite common clinical manifestations and treatment regimens.

Example 3—Identification of Immunogenic Autoantigen Targets

Discriminating peptides that differentiate healthy subjects from subjects with SSc were analyzed relative to the human proteome to indicate the originally immunogenic autoantigen targets. A portion of the top discriminating peptides of the comparison between SSc and healthy subjects is shown in FIG. 8C.

Proteome alignment: Array peptides were aligned to human proteome RefSeq release 84, corresponding to human genome build GrCh38 (https://www.ncbi.nlm.nih.gov/refseq/), compiled Mar. 10, 2016, using the longest transcript variant for each unique gene ID. The alignment algorithm uses a modified BLAST strategy (Altschul, S. F. & Gish, W. (1996) "Local alignment statistics." Meth. Enzymol. 266:460-480), requiring a seed of 3 amino acids with a gap penalty of 4, with a scoring matrix of BLOSUM62 (Henikoff, J. G. Amino acid substitution matrices from protein blocks. Proc. Natl. Acad. Sci. USA 89:10915-10919 [1992]) modified to reflect the amino composition of the array (States, D. J., Gish, W., Altschul, S. F. (1991) "Improved sensitivity of nucleic acid database searches using application-specific scoring matrices." Methods 3:66-70). These modifications increase the score of degenerate substitutions, remove penalties for amino acids absent from the array and score all exact matches equally.

To generate a p-value for alignment of a set of ImmunoSignature peptides to a protein, all peptides that yield a positive BLAST score to the protein were assembled into a matrix, with each row of the matrix corresponding to an aligned peptide and each column corresponding to one of the consecutive amino acids that comprise this protein, with gaps and deletions allowed within the peptide rows to allow for alignment to the protein. Each position within the matrix is the score, from the same scoring matrix as for the proteome alignments, of the paired peptide and protein amino acid in that position. Then, for each amino acid in the protein, the corresponding column is summed to create an "overlap score" that represents coverage of that amino acid by the ImmunoSignature peptides.

To correct this score for library composition, an overlap score is calculated using an identical method for a list of all array peptides. Finally, a Fischer Exact Test is used to calculate a p-value for the ImmunoSignaure overlap score versus the full library overlap score. To convert these p-values at the amino acid level to a full-protein statistic, the sum of the negative log of the p-value for every possible 20-mer epitope within a protein is calculated, and the final score is the maximum along this rolling window of 20 for each protein.

Table 3 provides a list of the top scoring target proteins that were identified according to the method. One hundred and sixty nine candidate biomarkers were identified. The discriminating peptides were chosen for having a p-value of less than p<2.53E−06 by Welch's t-test.

RNA Pol II subunit L is an example of the immunogenic autoantigens identified by the method by discriminating peptides that distinguish healthy subjects from subjects having SSc (FIGS. 8A and 8B).

TABLE 3

Candidate target proteins identified from alignments of discriminating peptides that distinguish samples from subjects having SSc from samples from healthy subjects

| | | | | | | | | |
|---|---|---|---|---|---|---|---|---|
| PF4 | GNGT1 | MAP1LC3A | GAGE12I | RGCC | IGLV2-11 | DYNLT1 | OCN3 | BGLAP |
| CAMK2N2 | SMAGP | SMIM2 | PRAC1 | ARPC5 | RPL22 | SERF1A | LEAP2 | ANAPC15 |
| GHRL | RIPPLY2 | ATPIF1 | BAD | SPANXN3 | PKIB | SERF1B | RPLP2 | GPIHBP1 |
| C1orf210 | ACBD7 | STATH | PPP1R11 | UQCRHL | UCMA | TMEM233 | SREK1IP1 | EVA1B |
| PF4V1 | SMIM17 | CLEC2B | TRBV10-3 | PAIP2B | POLR2D | VPREB1 | TIMM13 | OTOR |
| RPL22L1 | C4orf32 | MT1F | SPANXN2 | DEFA5 | APLN | IGLV1-40 | SAP30L | GABARAPL2 |
| IGLV1-50 | GAGE2E | IGLV5-37 | PYY | JCHAIN | FAM9C | PPP1R148 | IGLV2-14 | TAF13 |
| C9orf16 | IGKV2-40 | GAGE12C | C7orf49 | IGLV2-23 | PPP1R1B | PTMA | FAM174B | NHLH1 |
| LYRM9 | IGLV5-45 | GAGE12E | PLGLB2 | DEFA4 | MAP1LC3C | GAGE10 | RIPPLY1 | HINT1 |
| CDC26 | IGKV2D-40 | GAGE12D | PLGLB1 | GAGE12H | IGLV9-49 | PCP4L1 | COA4 | |
| TUSC2 | IGLV1-36 | FXYD2 | UBE2V1 | PAIP2 | SCX | ERICH4 | IGFL4 | |
| MAP1LC38 | RPLP1 | SDHAF4 | VAMP8 | IGLV3-32 | SCGB2A1 | FDCSP | BORC57 | |
| NPFF | DPH3 | HOPX | RPRM | UBL5 | PKIA | LINC00116 | SMIM7 | |
| SMIM13 | CTNN8IP1 | PRCD | GAGE13 | RD3L | PKIG | S100G | ISCA1 | |

TABLE 3-continued

Candidate target proteins identified from alignments of discriminating peptides
that distinguish samples from subjects having SSc from samples from healthy subjects

| IGLV1-44 | GNG11 | OTOS | NUPR1 | PIGY | ERICH2 | SMIM19 | EIF1AD |
|---|---|---|---|---|---|---|---|
| MAP1LC3B2 | POLR2L | C2orf76 | LINC00493 | APOC1 | DEFB131 | FAM1018 | THRSP |
| HIGD1C | IGLV3-22 | HMGA1 | PIGBOS1 | PPP1R1A | TRBV10-1 | CNPY1 | IGKV5-2 |
| SNN | C14orf142 | C1orf54 | PRAC2 | CENPM | LCE6A | SUMO4 | TGIF2-C20orf24 |
| DEXI | GAGE12G | LST1 | RNF7 | PRLH | CEND1 | HMGN1 | UBE2V2 |
| EVA1A | GAGE12F | DEFB114 | SMIM1 | C12orf57 | LAMTOR1 | PCP4 | BIK |

Figure 26A:
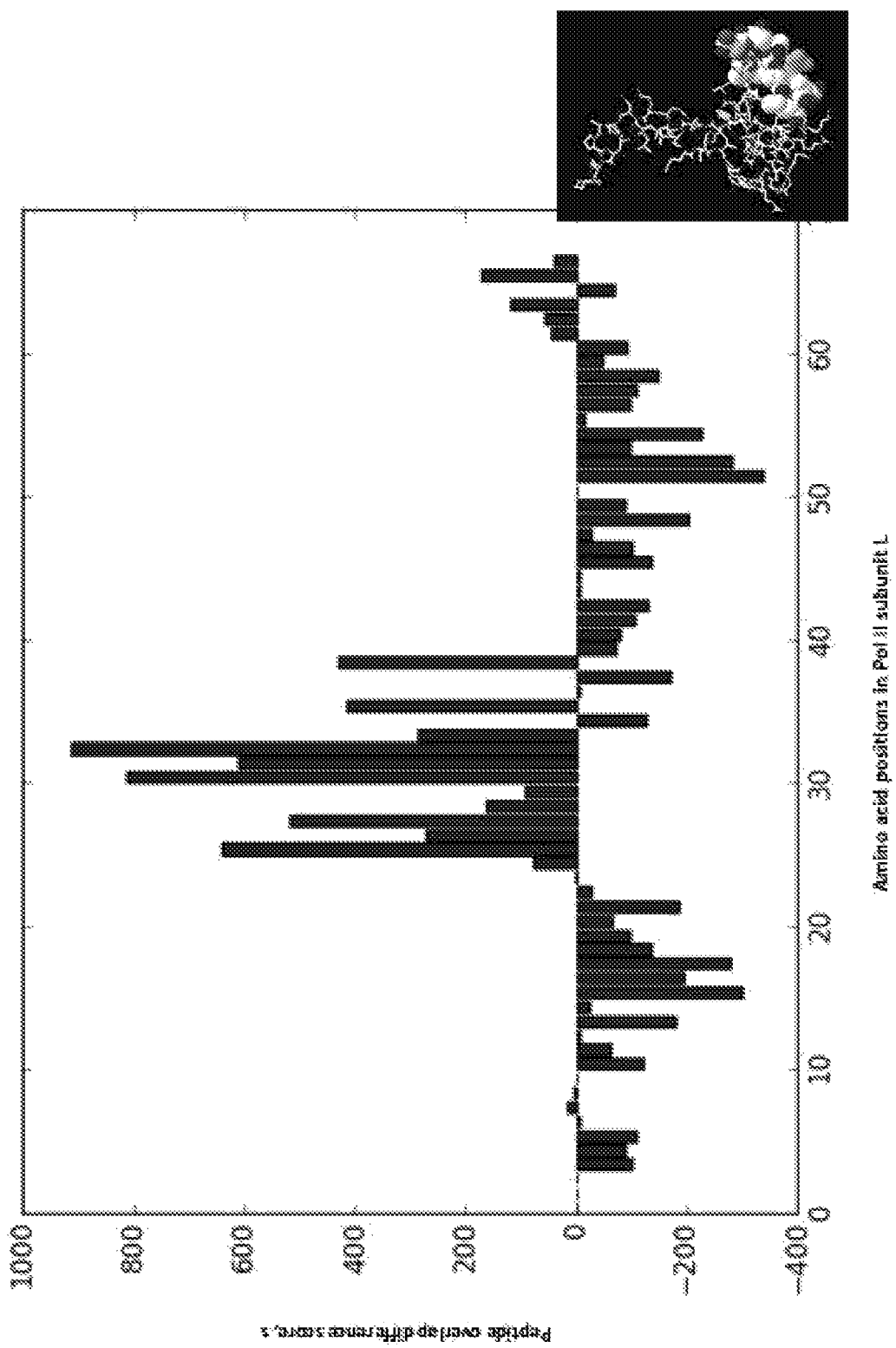
FIGS. 26A-26B shows the peptide overlap difference scores, s, calculated for the alignments of IMS peptide-submotifs plotted alongside the RNA Pol II subunit L aa positions (FIG. 26A), and a histogram displaying the distribution of protein epitope scores, S, for each protein in the human proteome vs the SSc vs healthy classifying peptides (FIG. 26B).
Figure 26B:
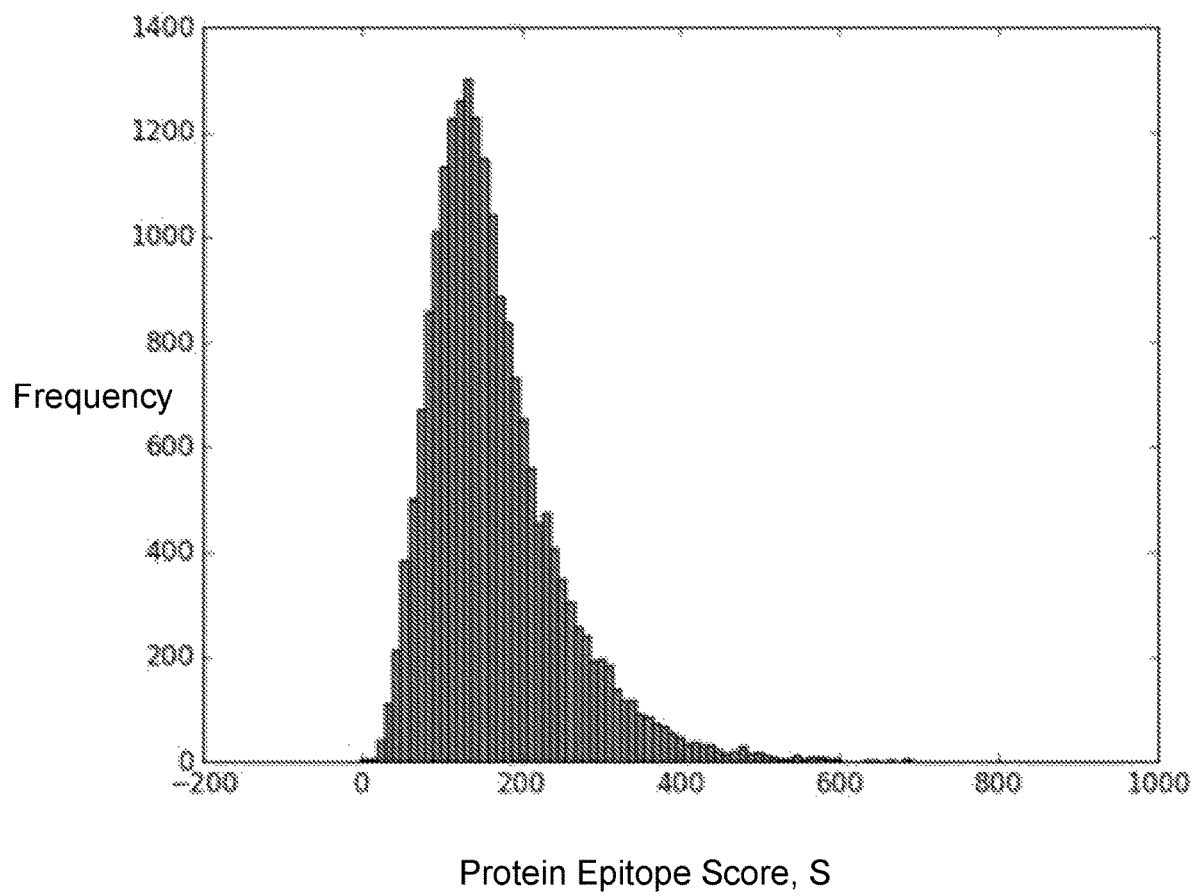

FIG. 26A shows the peptide overlap difference scores, s, calculated for the alignments of IMS peptide-motifs plotted alongside the RNA Pol II subunit L aa positions. Peptides from the SSc vs. healthy contrast showed significant alignment with RNA pol II subunit L, ranking it 35 out of 20,378 of the human proteins in the proteome. The ball and stick model to the right shows the structure of RNA pol II subunit L. The region displayed in balls corresponds to the aa positions marked with a red box within the graph. The highest scoring aa is aspartic acid, D, in the center of the RNA pol cluster; it is shown in the ball structure as orange. We note that a threonine (T) near the center of the cluster scored poorly; there is no T in the IMS array sequences. FIG. 26B shows a histogram displaying the distribution of protein epitope scores, S, for each protein in the human proteome vs the SSc vs healthy classifying peptides. POL R2L's score is 583.

RNA pol II, is a known autoantigen that has been characterized in patients with scleroderma.

Figure 27:
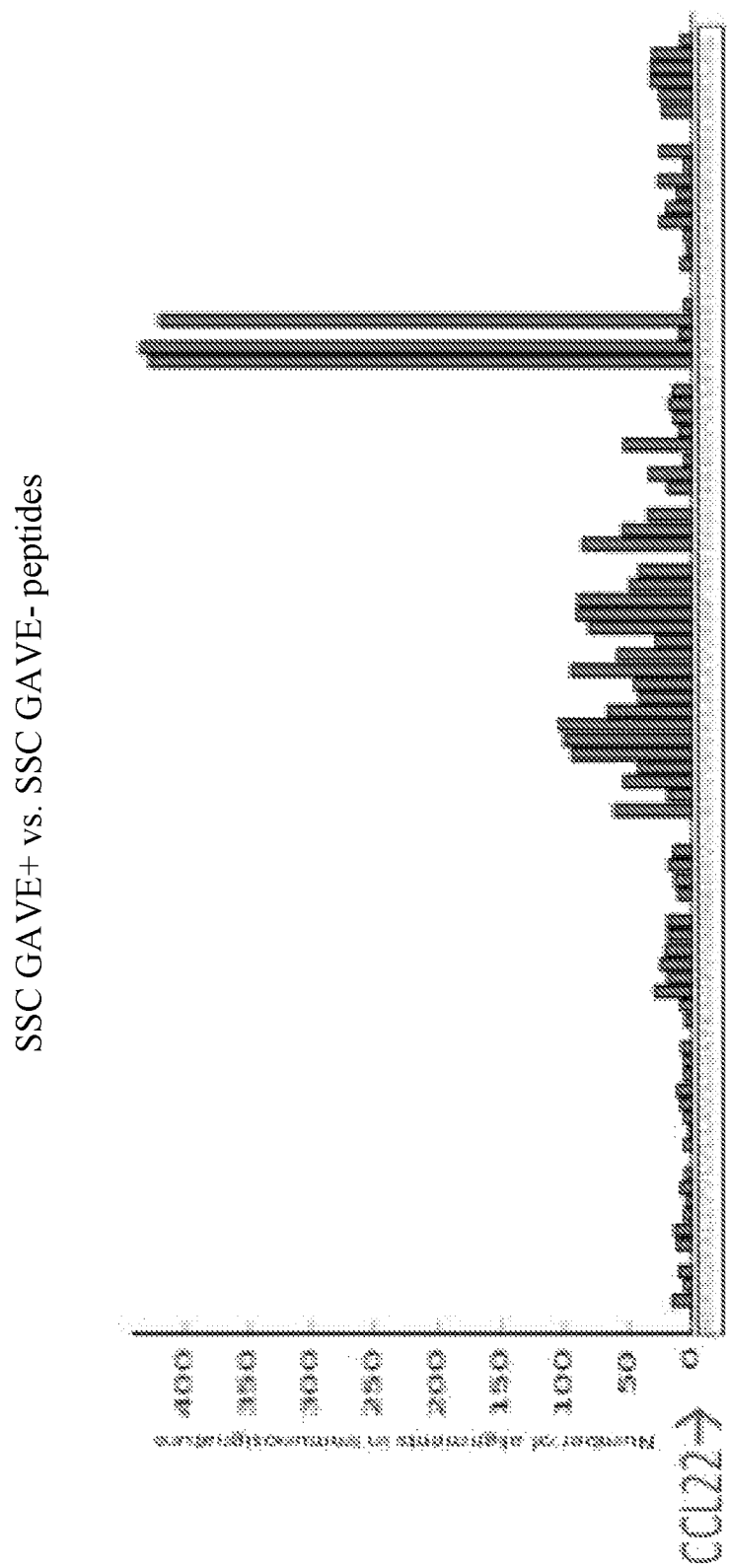
FIG. 27 shows a histogram representing the frequency of alignments of IS discriminating peptides distinguishing subjects with SSc having GAVE from subjects with SSc without GAVE along the protein sequence of CCL22.
Figure 28A:
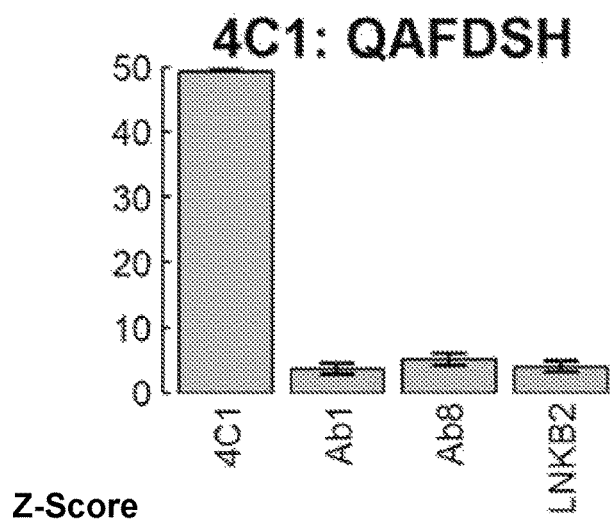
FIGS. 28A-28D shows bar graphs representing the binding of monoclonal antibody (mAb) standards (4C1 (FIG. 28A), p53Ab1 (FIG. 28B), p53Ab8 (FIG. 28C) and LnkB2 (FIG. 28D) to cognate epitope control features on the array (SEQ ID NOS 155-158, respectively, in order of appearance). A standard set of monoclonal antibodies was applied to arrays at 2.0 nM in triplicate. For each monoclonal antibody, the mean log 10 RFI of the cognate control features was used to calculate the Z-score. Z-scores are plotted separately for each control feature with the individual monoclonals plotted as individual bars. Error bars represent the standard deviation of the individual control feature Z-scores. The known epitope for each mAb is provided above each bar graph.
Figure 28B:
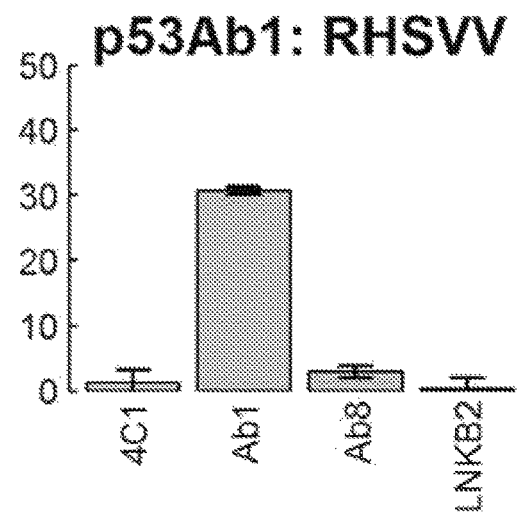
Figure 28C:
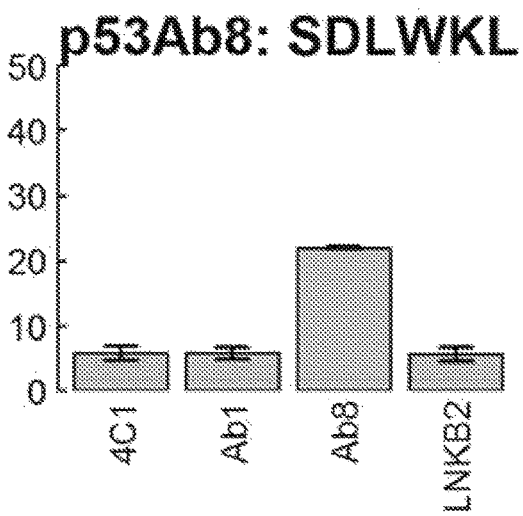
Figure 28D:
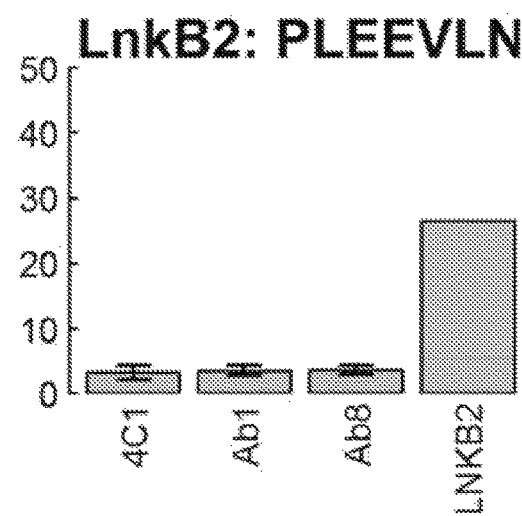

FIG. 27 shows an exemplary autoantigen, CCL22, that was determined as a candidate protein biomarker that was identified by the discriminating peptides comparing subjects having SSc with organ involvement (GAVE+) with subjects having SSc without organ involvement (GAVE −). CCL2 has been suggested to play an important role in scleroderma (Yamamoto T. Front Biosci. 2008 Jan. 1; 13:2686-95).

These data show that discriminating peptides that distinguish different disease states can be used to identify candidate antigen or autoantigen target that can be investigated for use in developing therapeutics. Additionally, the presence of specific antigen or autoantigen targets can be used to determine the severity of a disease, and potentially predict disease progression.

Discriminating peptides comprising peptides having sub-motifs provided in FIGS. 10A-10B (SSc v Other AI), can be aligned to the human proteome to identify candidate biomarkers that identify patients with SSc relative to patients that have Other AI diseases recited in Example 1.

Discriminating peptides comprising peptides having sub-motifs provided in FIGS. 16A-16B can be aligned to the human proteome to identify candidate biomarkers that identify patients with SSc relative to patients that have DM.

Discriminating peptides comprising peptides having sub-motifs provided in FIGS. 12A-12B can be aligned to the human proteome to identify candidate biomarkers that identify patients with SSc without renal crisis relative to patients that have SSc with renal crisis. The candidate biomarkers may be useful in predicting which SSc patients may develop renal crisis.

Discriminating peptides comprising peptides having sub-motifs provided in FIGS. 18A-18B can be aligned to the human proteome to identify candidate biomarkers that identify patients with SSc without ILD crisis relative to patients that have SSc with ILD. The candidate biomarkers may be useful in predicting which SSc patients may develop ILD.

Example 4—Precision of Measurements of Binding Signals

The binding precision of 200 array features (different peptides) used to distinguish subjects that tested sera-positive for Chagas disease from sera-negative subjects was estimated using a set of 8 serum samples. Four Chagas positive samples and 3 Chagas negative samples were selected from the full cohort of donors and assayed in triplicate on each slide from multiple wafers in two study designs. One in-house normal donor sample was also assayed in duplicate on each slide.

Within wafer lot: Three wafers from a single production lot were selected and qualified using a one-slide QC sample set. The remaining 12 slides from each wafer were evaluated using the precision study sample set. The slides were run across 3 cassettes per day over 3 days. Slides from each wafer were distributed evenly across the 3 days such that each cassette contained 2 slides from one of the three wafers and 1 slide each from the remaining two wafers.

Between wafer lot: One wafer from each of 4 production lots was selected and qualified using a one-slide QC sample set. The remaining 12 slides from each wafer were evaluated using the precision study sample set. The slides were run across 4 cassettes per day over 3 days. Slides from each wafer were distributed evenly across the 3 days such that each cassette contained 2 slides from two of the four wafers.

Data analysis: A mixed effect model was used to estimate the sources of experimental variance. Donor was treated as a fixed effect. Nested factors 'Wafer', 'slide', and 'array' were crossed with 'day', and were treated as random effects. Models were fit in r using the lme4 package.

TABLE 4

Precision of signal binding measurements

| | CV | % Contribution |
|---|---|---|
| Within wafer-batches | | |
| Inter-array | 11.21 | 59.6 |
| Inter-slide | 4.3 | 8.9 |
| Inter-wafer | 2.7 | 3.5 |
| Inter-day | 7.7 | 28.0 |
| TOTAL | 14.6 | 100 |
| Between wafer-batches | | |
| Inter-array | 14.3 | 38.7 |
| Inter-slide | 7.6 | 11.0 |

TABLE 4-continued

Precision of signal binding measurements

|  | CV | % Contribution |
|---|---|---|
| Inter-wafer | 14.6 | 40.6 |
| Inter-day | 7.1 | 9.7 |
| TOTAL | 22.9 | 100 |

The data show that measurements of binding signals made on arrays within wafer batches can be made with precision varying less than 15%; and that measurements of binding signals made on arrays between wafer batches can be made with precision varying less than 25%".

Example 5—Diagnostic and Prognostic Assays for Infectious Diseases e.g. Chagas Disease Introduction Chagas is the leading cause of death in Latin America and the Caribbean [Perez C J et al., (2014) Trends Parasitol 30:176-182]. Ironically it is also considered the most neglected parasitic disease in the same regions, and epidemiologist are tracking its further spread into nonendemic countries including the US and Europe The etiologic agent, *Trypanosoma* (T) *cruzi*, is a flagellated protozoan transmitted predominantly via blood-feeding triatomine insects into mammalian hosts, where it can multiply in any nucleated cell. Other modes of dissemination include blood transfusion or congenital and oral routes (Steverding D (2104) Parasit Vectors 7:317]. An infected individual initially experiences an acute phase of 4-8 weeks that manifests as periorbital swelling or ulcerative lesions at the entry site and is associated with high-levels of parasite circulating through the bloodstream. This transitions into the asymptomatic, indeterminant phase, which is a life-long infection characterized by loss of blood-parasitemia and sequestration of the protozoa into muscle and fat cells of host organs [Perez et al. 2014]. From 10 to 30 years later, a third or more of these infected individuals will progress to a symptomatic, chronic phase. They succumb to severe cardiac, gastric, or other organ-disease manifestations that lead to irreversible muscular lesions and often death within 2 years (Viotti R, et al. (2006) Ann Intern Med 144: 724-734; Granjon E, et al. (2016) PLoS Negl Trop Dis 10: e0004596; Oliveira G B F et al., (2015) Global Heart 10: 189-192). In recent decades there have been many reports of reactivation of symptomatic disease in immunocompromised patients such as those co-infected with HIV or those under treatment for cancer or autoimmune disorders (Pinazo M J et al. (2013) PLoS Negl Trop Dis 7: e1965; Rassi Jr A, et al (2010) The Lancet 375: 1388-1402). The WHO has recently estimated that approximately 200,000 people will die from Chagasic cardiomyopathy in the next 5 years. That corresponds to the same number of women forecast to die in the US from breast cancer in the same timeframe (Pecoul B et al. (2016) PLoS Negl Trop Dis 10: e0004343.)

There is no vaccine against Chagas and the only mode of prevention is to control spread of the insect-vector. For the past 40 years only the two drugs benznidazole and nifurtimox have been available for treatment (Rassi et al, 2010; Clayton J (2010) Nature 465: S4-S5). They have shown variable but significant effectiveness against acute phase infections but have proven little therapeutic value to those suffering chronic manifestations or to preventing transition from subclinical to symptomatic phases (Issa et al, (2010), The Lancet 376: 768; Morillo C A, et al. (2015) New England Journal of Medicine 373: 1295-1306). The unpredictability of the drugs' efficacy and known side-effects have rendered their prescription to less than 1% of diagnosed Chagas patients. Those that have been treated can experience adverse events that warrant it discontinued [5]. Recently, there has been some increased interest in discovering new drugs against *T. cruzi* infections (De Rycker M, et al. (2016) PLoS Negl Trop Dis 10: e0004584). This is important; however, to date the insurmountable hurtle to new drug development has been the lack of any reliable, practical method to assess their efficacy in the subclinical and chronic phases. Challenges to measuring infection status and therapeutic impact are many (Gomes Y M, et al (2009) Mem Inst Oswaldo Cruz 104 Suppl 1: 115-121). For example, parasitemia is subpatent and low levels of tissue-parasites are anatomically scattered, antigen similarity to other endemic diseases such as Leischmania, no reliable markers of incipient or active disease, and development of symptoms up to 30 years post initial infection (Keating S M, et al. (2015) Int J Cardiol 199: 451-459). There is no tool to identify which patients would most benefit from treatment. Namely, a method is needed to predict those asymptomatic but seropositive individuals whose infection will progress from being clinically silent to causing life-threatening complications.

A number of tests are available for Chagas diagnosis. Direct detection of the parasite can be done by blood microscopy, hemoculture, xenodiagnosis, or PCR of nucleic acids extracted from peripheral blood cells. While very specific, these assays are not sensitive, and considered uninformative in the indeterminant and chronic phases. At both clinics and blood banks, diagnosis is dependent on indirect detection by serology. ELISA tests are available for the detection of *T. cruzi* antibodies against crude parasite lysate (Ortho *T. cruzi* ELISA), semi-purified in vitro-cultured epimastigote fractions, or a mix of four recombinant proteins (Abbott PRISM and ESA Dot Blot). The FDA has approved the Ortho and Abbott tests, which report a signal to cut off value (S/CO) that indicates antigen-binding levels of sera and reflects antibody titers. Unfortunately, inconclusive and discordant results both between and within these test platforms is a persistent problem; cross-reactivity and false positives are common. Consequently, confirmatory serologic tests are helpful in improving the accuracy, although none are FDA approved or considered a reference standard for Chagas diagnosis. The radio-immunoprecipitation assay (*T. cruzi* RIPA) is a qualitative, more specific test for reactive antibodies to epimastigote lysates, and is employed routinely as a confirmatory test by some blood banks (Tobler L H, et al. (2007) Transfusion 47: 90-96.). Newer generation assays are under development based on various mixtures of recombinant proteins and antibody detection methods. For example, the ESA (ELISA strip assay) is an immunoblot-based test that detects reactivity to four chimeric recombinant antigens (Cheng K Y et al (2007) Clinical and Vaccine Immunology 14: 355-361). The Architect Chagas kit uses the same set of recombinant antigens of the ESA in a chemiluminescent ELISA (Praast G et al, (2011) Diagnostic Microbiology and Infectious Disease 69: 74-81). A recently described multiplexed assay allows simultaneous detection of 12 *T. cruzi* antigens printed in a microplate (Granjon et al (2016)). The movement to including additional antigens is important as this eukaryotic pathogen carries a complex proteome and life cycle. The diversity of human immune responses to its infection (Carmona et al (2015) Mol Cell Proteomics 14: 1871-1884) testifies to the need for employing many targets in any test platform that is to capture positivity within any large intended use population, especially those with indeterminant disease. There is a demonstrated need for new markers and new approaches to sensitively measure *T. cruzi* infection status and monitor disease activity during the indeterminate phase (Pinazo et al, (2013)). A pre-requisite for establishing such tests is to develop a single, robust platform that can accurately and reproducibly detect Chagas positivity in a diverse, asymptomatic population.

The ImmunoSignature Technology (IS or IMS) has shown applicability to the classification of many immune mediated diseases, both infectious and non-infectious (Legutki J B, et al., (2010) Vaccine 28: 4529-4537; Restrepo L, et al., (2011) Annals of Neurology 70: 286-295; Hughes A K, et al. (2012) PLoS One 7: e40201; Kukreja M, et al. (2012) Proteomics and Bioinformatics; Stafford P, et al (2014) Proceedings of the National Academy of Sciences 111: E3072-E30800; Sykes K F, et al (2013) Trends Biotechnol 31: 45-51). It is based on diverse yet reproducible patterns of peripheral antibody binding to an array of >100,000 combinatorial peptides designed from chemical sequence space. The assay is performed with a small sample of blood, plasma, or sera (Stafford et al (2014)). A peptide bound by an antibody is not the original target sequence but rather mimics the sequence or structure of the true epitope. Since the diversity of possible sequence space is many orders of magnitude greater than the sequence diversity of proteomes, the probability of any mimetic-peptide corresponding exactly to any protein is extremely low. Furthermore, a combinatorial peptide may not be mimicking a linear sequence but rather a structure, a mutated sequence such as found in tumors, or a non-peptidic biomolecule such as carbohydrate. Each IMS peptide sequence that is selectively bound by an antibody is a functional surrogate of the epitope that the antibody recognizes in vivo. When the mimicked epitope is unique to a health state, the bound antibody becomes a biomarker. These collectively represent highly-informative biomarkers for detecting and monitoring disease. Measuring disease activity would enable treatment response, resolution, or progression to be determined.

Here we demonstrate the development of a simple IMS test that accurately detects Chagas positive individuals within a population of asymptomatic blood donors, and simultaneously distinguishes them from donors that are seropositive but asymptomatic for three other diseases, West Nile, hepatitis B and hepatitis C. The IMS classifications accurately reflect blood bank algorithms of positivity. The signal intensities of the most informative Chagas classifying peptides show an increase as donors with increasing S/CO values are evaluated. This supports a correlation between the IMS test results and disease-specific immune activity and suggests the potential for developing a test for monitoring *T. cruzi* disease status. Next steps will include testing of longitudinally collected samples from Chagas-positive donors annotated with long term infection outcomes, namely the identification of those that eventually sero-reconverted or progressed to life-threatening disease.

Example 6—Immunosignature Methods for the Diagnosis of Infections

Immunosignature assays were developed to detect and differentiate *T. cruzii*, HBV, HCV, and WNV infections according to the following.

Donor Samples.

Donor plasma samples serologically positive for Chagas antibodies, along with age and gender matched healthy donor plasma, and plasma samples that tested seropositive for hepatitis B virus (HBV), hepatitis C virus (HCV) or West Nile virus (WNV), were obtained from Creative Testing Solutions (Tempe, Ariz.). Two cohorts of samples were obtained, one in 2015 and a second set in 2016. Upon receipt, the plasma was thawed, mixed 1:1 with ethylene glycol as a cryoprotectant and aliquoted into single use volumes. Single use aliquots were stored at −20° C. until needed. The remaining sample volume was stored neat at −80° C. Identities of all samples were tracked using 2D barcoded tubes (Micronic, Leystad, the Netherlands). In preparation for assay, sample aliquots were warmed on ice to 4° C. and diluted 1:100 in primary incubation buffer (Phosphate Buffered Saline with 0.05% Tween 20 (PBST) and 1% mannitol). Microtiter plates containing the 1:100 dilutions were then diluted to 1:625 for use in the assay. For the subset of samples selected for evaluating platform performance across wafer lots, the 1:100 dilutions were aliquoted into single use microtiter plates and stored at −80° C. All aliquoting and dilution steps were performed using a BRAVO robotic pipetting station (Agilent, Santa Clara, Calif.). All procedures using de-identified, banked samples were reviewed by the Western Institutional Review Board (protocol no. 20152816).

Arrays.

A combinatorial library of 126,009 peptides with a median length of 9 residues and range from 5 to 13 amino acids was designed to include 99.9% of all possible 4-mers and 48.3% of all possible 5-mers of 16 amino acids (methionine, M; cysteine, C; isoleucine, I; and threonine, T were excluded). These were synthesized on an 200 mm silicon oxide wafer using standard semiconductor photolithography tools adapted for tert-butyloxycarbonyl (BOC) protecting group peptide chemistry (Legutki J B et al., Nature Communications. 2014; 5:4785). Briefly, an aminosilane functionalized wafer was coated with BOC-glycine. Next, photoresist containing a photoacid generator, which is activated by UV light, was applied to the wafer by spin coating. Exposure of the wafer to UV light (365 nm) through a photomask allows for the fixed selection of which features on the wafer will be exposed using a given mask. After exposure to UV light, the wafer was heated, allowing for BOC-deprotection of the exposed features. Subsequent washing, followed the by application of an activated amino acids completes the cycle. With each cycle, a specific amino acid was added to the N-terminus of peptides located at specific locations on the array. These cycles were repeated, varying the mask and amino acids coupled, to achieve the combinatorial peptide library. Thirteen rectangular regions with the dimensions of standard microscope slides, were diced from each wafer. Each completed wafer was diced into 13 rectangular regions with the dimensions of standard microscope slides (25 mm×75 mm). Each of these slides contained 24 arrays in eight rows by three columns. Finally, protecting groups on the side chains of some amino acids were removed using a standard cocktail. The finished slides were stored in a dry nitrogen environment until needed. A number of quality tests are performed ensure arrays are manufactured within process specifications including the use of 3G statistical limits for each step. Wafer batches are sampled intermittently by MALDI-MS to identify that each amino acid was coupled at the correct step, ensuring that the individual steps constituting the combinatorial synthesis are correct. Wafer manufacturing is tracked from beginning to end via an electronic custom Relational Database which is written in Visual Basic and has an access front end with an SQL back end. The front-end user interface allows operators to enter production info into the database with ease. The SQL backend allows us a simple method for database backup and integration with other computer systems for data share as needed. Data typically tracked include chemicals, recipes, time and technician performing tasks. After a wafer is produced the data is reviewed and the records are locked and stored. Finally, each lot is evaluated in a binding assay to confirm performance, as described below.

Plasma Assay.

Production quality manufactured microarrays were obtained and rehydrated prior to use by soaking with gentle agitation in distilled water for 1 h, PBS for 30 min and primary incubation buffer (PBST, 1% mannitol) for 1 h. Slides were loaded into an ArrayIt microarray cassette (ArrayIt, Sunnyvale, Calif.) to adapt the individual microarrays to a microtiter plate footprint. Using a liquid handler, 90 µl of each sample was prepared at a 1:625 dilution in primary incubation buffer (PBST, 1% mannitol) and then transferred to the cassette. This mixture was incubated on the arrays for 1 h at 37° C. with mixing on a TeleShake95 (INHECO, Martinsried, Germany) to drive antibody-peptide binding. Following incubation, the cassette was washed 3× in PBST using a BioTek 405TS (BioTek, Winooski, Vt.). Bound antibody was detected using 4.0 nM goat anti-human IgG (H+L) conjugated to AlexaFluor 555 (Thermo-Invitrogen, Carlsbad, Calif.), or 4.0 nM goat anti-human IgA conjugated to DyLight 550 (Novus Biologicals, Littleton, Colo.) in secondary incubation buffer (0.5% casein in PBST) for 1 h with mixing on a TeleShake95 platform mixer, at 37° C. Following incubation with secondary, the slides were again washed with PBST followed by distilled water, removed from the cassette, sprayed with isopropanol and centrifuged dry. Quantitative signal measurements were obtained by determining a relative fluorescent value for each addressable peptide feature. Separately, ELISAs were conducted to assess cross-reactivity between the anti-IgG and anti-IgA secondary antibody products. A low level of cross-reactivity was noted for the anti-IgG product against an IgA monoclonal; no reactivity was found for the anti IgA product against an IgG monoclonal.

Monoclonal Assay.

Prior to conducting the IST assays with donor plasma, the binding activity of commercial, murine monoclonal antibodies (mAb) to control peptides, corresponding to each mAb's established epitope sequence, was evaluated. The IST arrays were probed in triplicate with 2.0 nM each of antibody clones 4C1 (Genway), p53Ab1 (Mllipore), p53Ab8 (Millipore), and LnkB2 (Absolute Antibody) in primary incubation buffer (1% mannitol, PBST). Secondary incubation and quantification of signal were the same as described above.

Data Acquisition.

Assayed microarrays were imaged using an Innopsys 910AL microarray scanner fitted with a 532 nm laser and 572 nm BP 34 filter (Innopsys, Carbonne, France). The Mapix software application (version 7.2.1) identified regions of the images associated with each peptide feature using an automated gridding algorithm. Median pixel intensities for each peptide feature were saved as a tab-delimitated text file and stored in a database for analysis.

Data Analysis.

The median feature intensities were $\log_{10}$ transformed after adding a constant value of 100 to improve homoscedasticity. The intensities on each array were normalized by subtracting the median intensity of the combinatorial library features for that array.

In the monoclonal assays, selective binding of each monoclonal to its cognate epitope was assessed using a Z-score, calculated as:

$$Z = \frac{\text{mean}(I_{mAb}) - \text{mean}(I_{2°})}{sd(I_{2°})}$$

where $I_{mAb}$ and $I_{2O}$ are the transformed peptide intensities in the presence of monoclonal or secondary antibody only, respectively. Binding to each of the peptides containing an epitope of one of the mAbs was measured on all four mAbs.

In the IST assays, binding of plasma antibodies to each feature was measured by quantifying fluorescent signal. Peptide features that showed differential signal between groups were determined by t-test of mean peptide intensities with the Welch adjustment for unequal variances. For the 2105 Chagas cohort, Chagas seropositive donors (n=146) were compared to seronegative donors (n=189), and peptides with significantly differential signal were identified. A second set of peptides that could discriminate Chagas from other infectious diseases was identified by comparing mean intensities among Chagas seropositive donors (n=88) to Chagas seronegative donors who were positive for HCV (n=71), HBV (n=88) or WNV (n=88) by standard blood panel testing algorithms. Peptides that showed significant discrimination were identified based on 5% threshold for false positives after applying the Bonferroni correction for multiplicity (i.e., p<4e−7). In addition, a Pearson correlation was calculated for the transformed peptide intensities of Chagas-positive donors to their median signal over cut-off value (S/CO) from three *T. cruzi* ELISA assays. Also, peptides correlated to S/CO were identified using a 10% false discovery rate criterion by the Benjamini-Hochberg method (Benjamini Y and Hochberg Y [1995] Journal of the Royal Statistical Society, Series B 57: 289-300) within the 2015 cohort.

To construct a classifier, features were ranked for their ability to discriminate Chagas positive from other samples based on the p value associated with a Welch's t-test comparing Chagas positive to Chagas negative donors, or between the different disease types in the multi-disease model. The number of peptides selected was varied between 5 and 4000 features in steps and each of the selected features was input to a support vector machine (Cortes C, and Vapnik V. Machine Learning. 1995; 20(3):273-97) with a linear kernel and cost parameter of 0.01 to train a classifier. A four-fold or five-fold cross validation repeated 100 times was used to quantify model performance, estimated as the error under the receiver-operating characteristic curve (AUC), and incorporated both feature selection and classifier development to avoid bias.

Finally, a fixed SVM classifier was fit in the 2015 cohort using the optimal number of features based on performance under cross-validation, selected by their t-test p-values. This model was used in assessing precision and reproducibility of the platform, and was also evaluated in the 2016 cohort as an independent verification test of the cross-validation analyses.

All analyses were performed using R version 3.2.5. (Team RC. R: A language and environment for statistical computing. R Foundation for Statistical Computing Vienna 2016. Available from: https://www.R-project.org/.)

Peptide Alignment Scoring.

Library peptides were aligned to the *T. cruzi* CL Bener proteome [Sodre C L et al., (2009) Arch Microbiol 191: 177-184]. The alignment algorithm used a modified BLAST strategy [Altschul S F and Gish W (1996) Methods Enzymol 266: 460-480], requiring a seed of 3 amino acids, a gap penalty of 4 amino acids, and a scoring matrix of BLOSUM62 [Henikoff and, Henikoff J G (1992) Proc Natl Acad Sci USA 89: 10915-10919] modified to reflect the amino acids composition of the array [States D J et al., (1991) Methods 3: 66-70]. These modifications increase the score of similar substitutions, remove penalties for amino acids absent from the array and score all exact matches equally. In one method the discriminating peptides were aligned to the sequences of the proteins. To generate an alignment score to a protein for a set of classifying library peptides i.e. discriminating peptides, those that yield a positive BLAST score are assembled into a matrix, with each row of the matrix corresponding to an aligned peptide and each column corresponding to one of the amino acids in the protein's sequence. Gaps and deletions are permitted within the peptide rows for alignment to the protein. In this way, each position in the matrix receives a score associated with the aligned amino acid of the peptide and protein. Each column, corresponding to an amino acid in the protein, is then summed to create an overlap score; this represents coverage of that amino acids position by the classifying peptides. To correct this score for library composition, another overlap score is calculated using an identical method for a list of all array peptides. This allows for the calculation of a peptide overlap difference score, s, at each amino acids position via the equation:

$$s_d = a - (b/d)*c$$

In this equation, a is the overlap score from the discriminating peptides, b is the number of discriminating peptides, c is the overlap score for the full library of peptides and d is the number of peptides in the library.

To convert these s scores (which were at the amino acids level) to a full-protein statistic, the sum of scores for every possible tiling 20-mer epitope within a protein is calculated. The final protein score, also known as protein epitope score, $S_d$, is the maximum along this rolling window of 20 for each protein. A similar set of scores was calculated for 100 iterative-rounds of randomly selecting peptides from the library, equal in number to the number of discriminating peptides. The p-value for each score, S, is calculated based on the number of times this score is met or exceeded among the randomly selected peptides, controlling for the number of iterations.

Precision, Reproducibility and Performance Analyses. The precision of antibody binding to the array features was characterized for a set of eight plasma samples by measuring the signals of 200 peptides used in a Chagas fixed classifier model. Four Chagas seropositive donors displaying a range of S/CO values and three Chagas seronegative samples were selected from the full cohort of donors. These were assayed in triplicate. A well-characterized in-house plasma sample from a healthy donor was also included in the slide design, assayed in duplicate. As a negative control, one array was incubated without plasma in the primary incubation step but incubated with the secondary detection antibody. These 24 samples were distributed evenly across the array positions on a single slide. This slide layout was then replicated across multiple slides.

To evaluate precision within a batch, three wafers from a single manufacturing lot were selected. Twelve of the thirteen slides from each wafer were evaluated using the one-slide precision design described above. The slides were evaluated across three ArrayIt cassettes per day on three different days. Slides from each wafer were assigned evenly across the three days such that each cassette contained two slides from one of the three wafers and one slide each from the remaining two wafers.

To measure precision between batches one wafer from each of four different production lots was selected. Twelve of the thirteen slides from each wafer were evaluated using the precision study sample-set described above. These slides were distributed for testing across four cassettes per day, spanning three days. Slides from each wafer were distributed evenly across the 3 days such that each cassette contained two slides from two of the four wafers. A mixed effects model was used to estimate the sources of experimental variance. Donor sample was treated as a fixed effect. The nested factors 'wafer', 'slide', and 'array' were crossed with 'day', and these were treated as random effects. Models were fit in R using the lme4 package to derive coefficients of variance (CV).

To assess the robustness of the ImmunoSignature classifier across many wafer manufacturing batches and assays, a quality control (QC) sample-set was selected that could be assayed on a single slide. It was comprised of a representative panel of 11 cases and 11 controls that were assayed on a single slide from 22 different wafers manufactured across 10 synthesis batches. For each of the 22 wafer-slides tested, the fixed model classifier developed in the Chagas trial was applied to this sample set to estimate area under the receiver operator characteristic (ROC) curve. One of these wafers was used for the Chagas trial and another for the mixed cohort (Chagas, HBV, HCV, & WNV) trial.

Example 7—Platform Validation

Experiments were conducted using monoclonal antibodies to evaluate the quality of final in situ synthesized array peptide products with respect to ligand presentation and antibody recognition.

All diagnostic assays were conducted on a validated microarray platform.

A peptide synthesis protocol was developed in which parallel coupling reactions are performed directly on silicon wafers using masks and photolithographic techniques. Arrays displaying a total of 131,712 peptides (median length of 9 amino acids) at features of 14 μm×14 μm each were utilized to query antibody-binding events. The array layout included 125,509 library-peptide features and 6203 control-peptide features attached to the surface via a common linker (see Example 6). The library peptides were designed to evenly sample all possible amino acids combinations. The control peptides include 500 features that correspond to the established epitopes of five different well-characterized monoclonal antibodies (mAb), each replicated 100 times. Another 935 features correspond to four different sequence variants of three of the five epitopes, each replicated from 100 to 280 times. An additional 500 control features were designed with amino acids compositions similar to those of the library peptides, but are uniformly 8-mers and present in triplicate. The median signals of these 500 control features were quantitated and treated as part the library when developing the IST models. The remaining 3,268 controls include fiducial markers to aid grid alignment, analytic control sequences and linker-only features. Aside from the fiducials, all features are distributed evenly across the array.

Experiments were conducted using mAbs that evaluated the quality of final array-synthesized products with respect to ligand presentation and antibody recognition. A panel of four murine antibody clones: 4C1, p53Ab1, p53 Ab8, and LnkB2 were selected with recognition sequences that correspond to four of the five control epitopes designed within the array layout. The sequence contents of the four array-represented epitopes collectively include all 16 amino acids that were used to build the library.

FIGS. 28A-28D present the results from a binding assay conducted described (see Example 6) in which each antibody was individually applied to an array with competitor agent, in triplicate. For each mAb, the control feature intensities were used to calculate a Z score for both the peptide sequence corresponding to its epitope, and the three non-cognate sequences. Each of the cognate sequences were bound with high signal intensity whereas the non-cognates displayed little or no signal above background values (secondary only).

These data validate the integrity of the synthetic library products. The data indicate that the microarrays carry peptides suitable for specific antibody recognition and binding. The use of photolithography and masks for the in situ process provides an opportunity for production scaling and efficient costing. Notably, the exact same library array design can be used to identify peptides that distinguish a variety of different conditions e.g. infections, as is exemplified by the accuracy of classification of Chagas disease, HPV, HCV, and WNV (Tables 8 and 9).

Example 8—Immunosignature Assay Differentiates Subjects that are Seropositive for *T. cruzi* from Subjects that are Seronegative for *T. cruzi*

Two cohorts of plasma samples of asymptomatic donors were obtained from a blood bank repository (Creative Testing Solutions, Tempe, Ariz.), and are shown in Table 5. The 2015 cohort is of 335 donors that were each serologically tested for Chagas disease using the blood bank's algorithm. The testing is intended to prevent entry of samples into the blood supply from any donor with indications of Chagas. First, three ELISAs were serially performed that assayed plasma against whole *T. cruzi* lysate (Ortho). If any one of these is scored positive by a signal to cutoff value (S/CO>1.0), then a confirmatory test is performed. This is an immunoprecipitation assay (*T. cruzi* RIPA) that uses the plasma to precipitate radiolabeled *T. cruzi* lysates. By these criteria 189 donors were seropositive and 146 were seronegative. An S/CO score of >4.0 is considered to be strong positivity [Remesar M et al., (2015) Transfusion 55: 2499-2504], which places 49 (26%) seropositive donors into this high S/CO subgroup. The distributions of gender, age, and ethnicity were those typically observed in a US blood donor population. The 2016 cohort is of 116 donors that were tested for Chagas with the same protocol of serial ELISA and RIPA testing described above. The results identified 58 Chagas seropositive and 58 seronegative participants. A higher proportion of the Chagas positive individuals (31 of 58 (53%) scored into the high S/CO>4 subgroup. The distributions of gender and age are similar although ethnicity was mildly skewed in this second donor population.

TABLE 5

Description of donors in the Chagas Study

| | Training cohort (2015) | | | | Test cohort (2016) | | | |
|---|---|---|---|---|---|---|---|---|
| | all | Chagas neg | Chagas pos | S/CO >4 | all | Chagas neg | Chagas pos | S/CO >4 |
| Group size | 335 | 189 | 146 | 49 | 116 | 58 | 58 | 31 |
| Gender | | | | | | | | |
| female | 90 | 80 | 10 | 2 | 48 | 24 | 24 | 11 |
| male | 127 | 109 | 18 | 6 | 68 | 34 | 34 | 20 |
| unknown | 118 | 0 | 118 | 41 | 0 | 0 | 0 | 0 |
| Ethnicity | | | | | | | | |
| white | 145 | 144 | 1 | 1 | 14 | 8 | 6 | 4 |
| Hispanic | 49 | 32 | 17 | 4 | 84 | 43 | 41 | 24 |
| black | 4 | 4 | 0 | 0 | 3 | 2 | 1 | 0 |
| other | 10 | 9 | 1 | 0 | 2 | 2 | 0 | 0 |
| unknown | 127 | 0 | 127 | 44 | 13 | 3 | 10 | 3 |
| Age bin | | | | | | | | |
| (15-20) | 10 | 9 | 1 | 1 | 16 | 7 | 9 | 5 |
| (20-30) | 29 | 26 | 3 | 0 | 20 | 11 | 9 | 5 |
| (30-40) | 52 | 46 | 6 | 1 | 24 | 14 | 10 | 6 |
| (40-50) | 38 | 33 | 5 | 2 | 26 | 9 | 17 | 7 |
| (50-60) | 38 | 32 | 6 | 1 | 21 | 11 | 10 | 7 |
| (60-70) | 29 | 26 | 3 | 2 | 7 | 4 | 3 | 1 |
| (70-87) | 21 | 17 | 4 | 1 | 2 | 2 | 0 | 0 |
| unknown | 118 | 0 | 118 | 41 | 0 | 0 | 0 | 0 |

The study trial presented here was conducted by using the 2015 cohort as an algorithm-training set to develop a classifier that distinguishes Chagas seropositive from seronegative individuals. This classifier was fixed and then applied to predict the positivity of the 2016 cohort donors. Thus, the 2016 samples represented a training-independent verification set.

Figure 29:
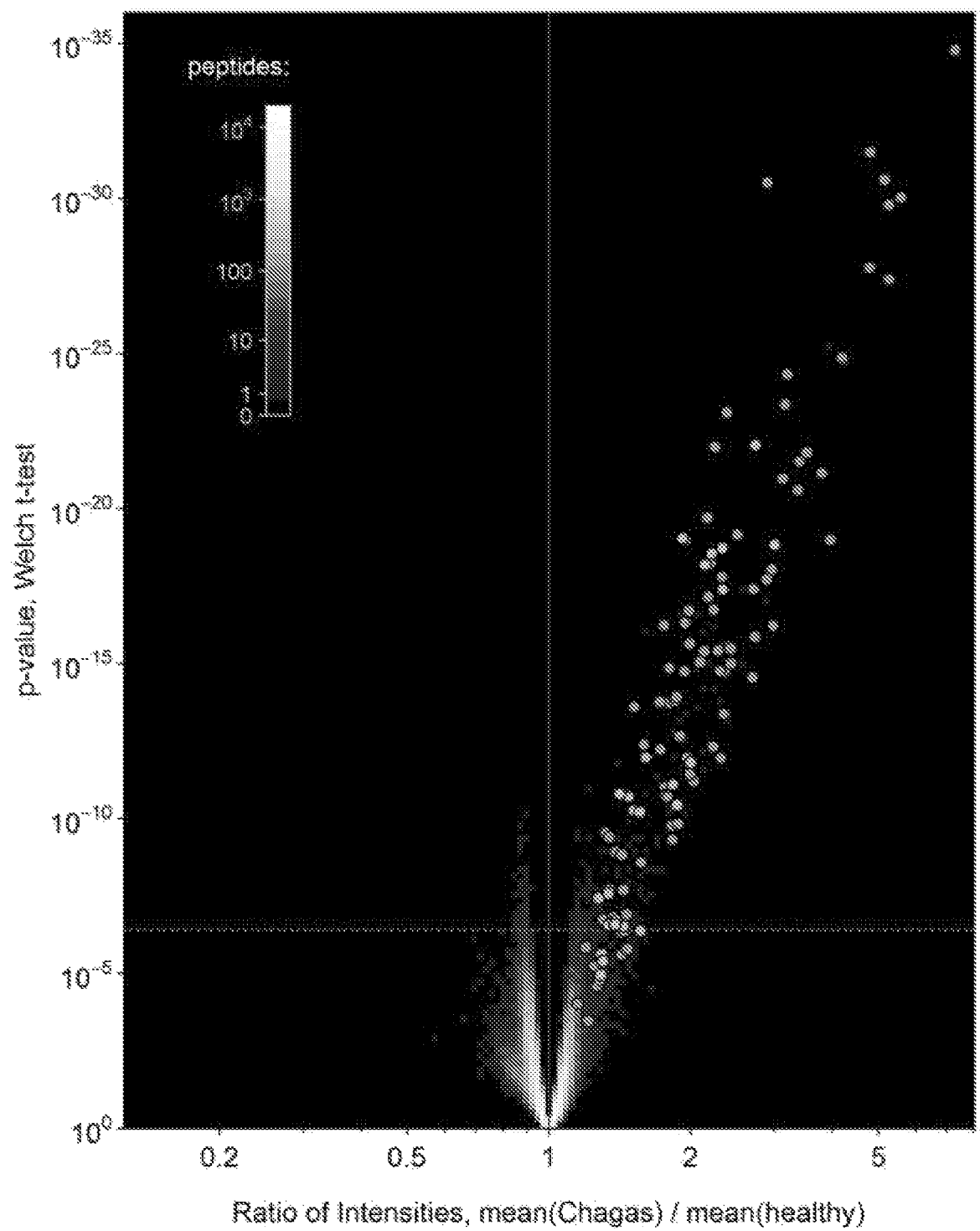
FIG. 29 shows a Volcano plot visualizing a set of library peptides displaying antibody-binding signals that are significantly different between Chagas seropositive and Chagas seronegative subjects. A volcano plot is used to assess this discrimination as the joint distribution of t-test p-values versus log differences in signal intensity means (log of ratios). The density of the peptides at each plotted position is indicated by the heat scale. The 356 peptides above the green dashed white discriminate between positive and negative disease by immunosignature technology (IST) with 95% confidence after applying a Bonferroni adjustment for multiplicity. The colored circles indicate individual peptides with intensities that are significantly correlated to the $T.$ $cruzi$ ELISA-derived signal over cutoff (S/CO) value either by a Bonferroni threshold of p<4e−7 (green) or a false discovery rate of <10% (blue). Most of the S/CO correlated peptides lie above the IST Bonferroni white dashed line.

Evaluating the Performance of the Immunosignature for Determining Chagas Positivity Immunosignature (IST) assays were performed as described in Example 6 and scanned to acquire signal intensity measurements at each feature. Application of Welch's t-test identified 356 individual peptides that had significant differences in mean signal between those donors who were blood-bank scored as seropositive versus seronegative for Chagas. As demarcated in FIG. 29 by a white dotted line, most, but not all, of the significantly distinguishing peptides displayed higher binding intensities in the Chagas positive as compared to Chagas negative donors. Many of these peptides had signals that were also positively correlated to the median *T. cruzi* S/CO value of all Chagas positive donors (shown as blue and green circles). This is consistent with the possibility that some library peptides may bind the same or related plasma-antibodies as those bound by antigen in the ELISA screen. There were 14 peptides that are significantly correlated to S/CO but did not meet the Bonferroni threshold for IST discrimination of Chagas positivity (circles below white dashed line). Notably, many of the 356 peptides that showed the strongest discrimination by IST were not significantly correlated to S/CO values. This demonstrates that the binding data collected by IST (t-test) shares some overlap with that collected by ELISA (S/CO) but indicates that unique interactions were also measured.

A support vector machine (SVM) classifier of Chagas seropositivity was developed in the 2015 cohort. Under cross-validation, the best performance was achieved when the top 500 peptides, as ranked by Welch t-test were input to the model. This number is greater than 356 that met the Bonferroni significance cutoff, indicating that additional information content existed in some of the peptides meeting the less stringent, false discovery rate (FDR) cutoff of significance. FIG. 31A shows the relationship between mean sensitivity and specificity of 100 iterations of five-fold cross validation models, using the top 500 peptides within each training sample, as a function of diagnostic threshold. The area under the curve (AUC) estimates that for a donor chosen at random from within each of the two groups, the seropositive donor would have a 98% probability of being classified with a higher likelihood of Chagas positivity than the seronegative donor, with a 95% confidence interval (CI) of 97%-99%. At the threshold where sensitivity equaled specificity, the accuracy was 93% (CI=91%-95%). The cross-validation estimates were confirmed by application of a single, fixed SVM classifier using the top 500 peptides to the 2016 cohort, where the performance observed (AUC 97%; accuracy 91%) was within the 95% CI of the cross-validation estimates (FIG. 31B).

This same fixed classifier was used to assess the binding precision and reproducibility of the assay using a protocol in which four Chagas seropositive donors and three Chagas seronegative samples were repeatedly assayed as described in the Methods section. Classification accuracy was repeatedly calculated. These precision measurements indicated the following binding signal CVs for the IST assay features which comprise the fixed classifier: inter-array=11%, inter-slide=4%, inter-wafer=2.7%, inter-day=7.7%, and inter-batch=14.6%. Reproducibility of classification was also determined, as described in the Methods, indicating AUCs>0.98 (median AUC=1.0).

Figure 30:
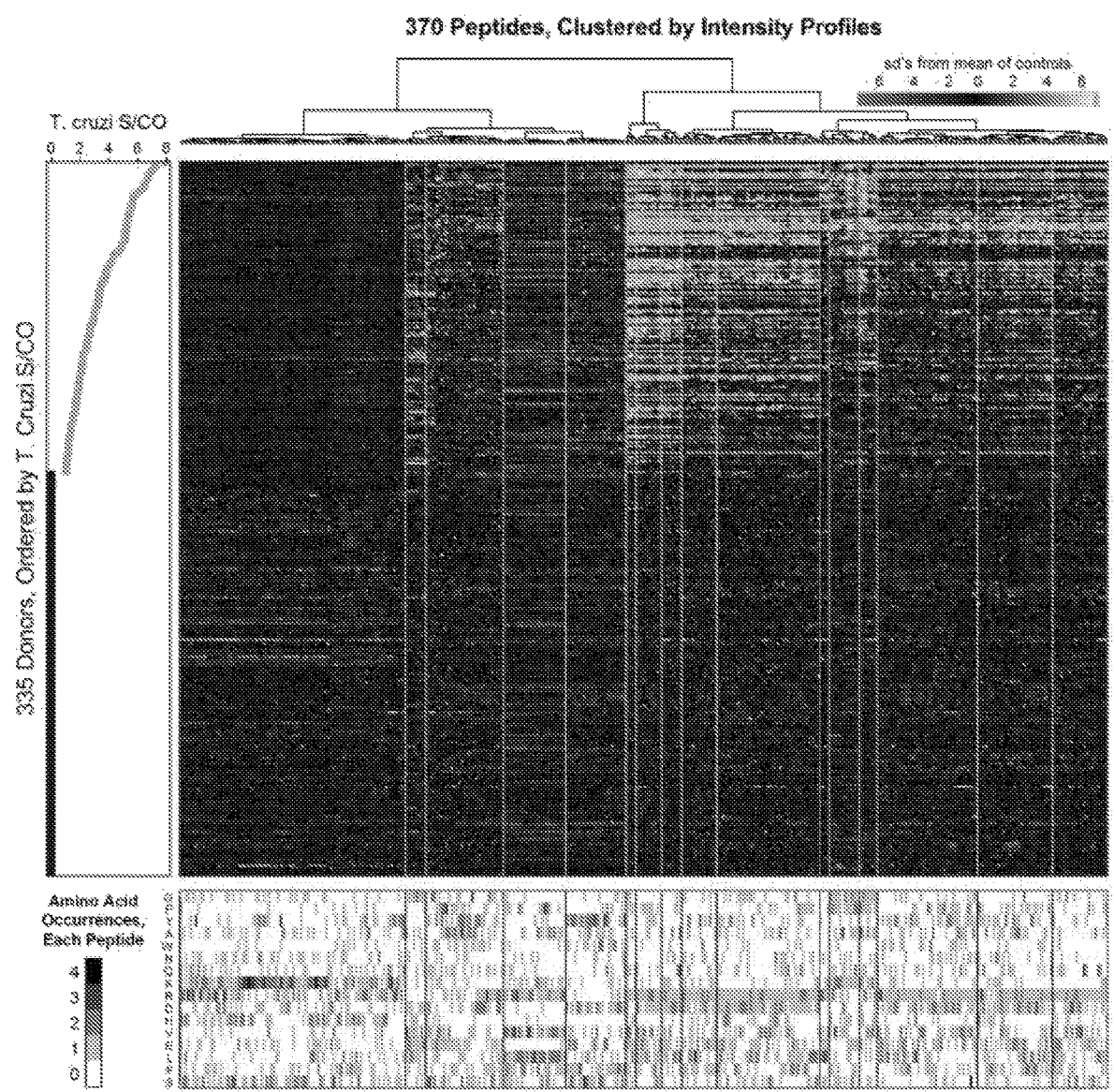
FIG. 30 shows signal intensity patterns displayed by the Chagas-classifying versus donor S/CO value. Heatmap ordering the ranges of signal intensities of the 370 library peptides that distinguish Chagas seropositive from Chagas-negative donors, with a side-bar graph relating these to each donor's ELISA S/CO value.
Figure 32:
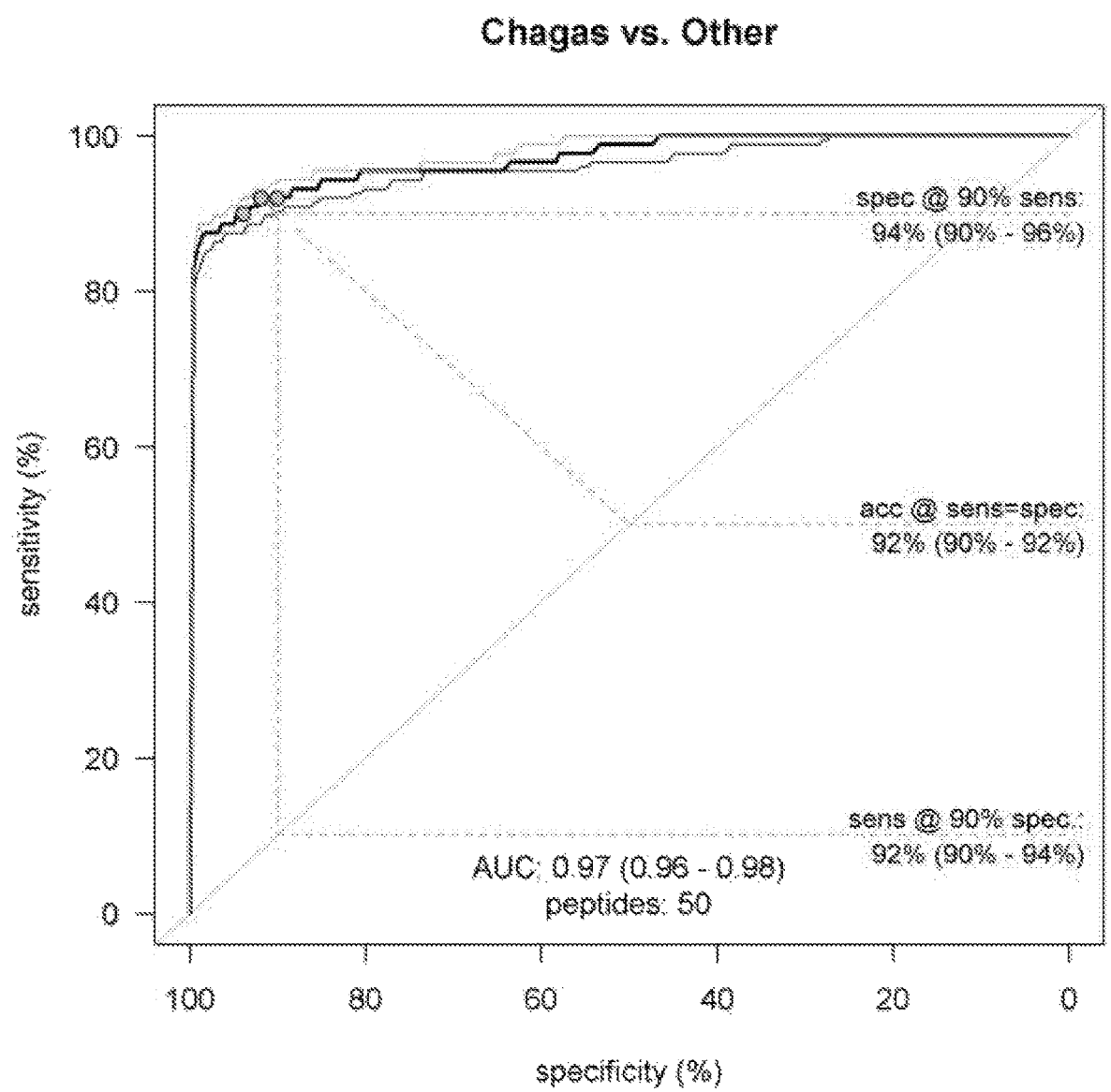
FIG. 32 shows performance of Chagas differential diagnosis classification. Cases are Chagas positive and controls consist of a combination of subjects with West Nile Virus, Hepatitis B, and Hepatitis C. The receiver operating characteristic curve was estimated from the out-of-bag predictions for 100 4-fold cross-validation trials.

The results in FIG. 30 explore the heterogeneity of antibody binding across the 2015 Chagas cohort. The relative signal intensities are displayed for the 370 (356+14) peptides described in FIG. 29 that provided significant discrimination of Chagas positivity by t-test, by correlation to the ELISA S/CO levels or both criteria. The sequence of each of the discriminating peptides identified in comparing the *T. cruzi* seropositive to the *T. cruzi* seronegative binding signals are listed in FIGS. 48 A-48N.

The peptides that discriminated Chagas seropositive from Chagas seronegative samples were found to be enriched by greater than 100% in one or more motifs listed in FIGS. 36B-36F relative to the incidence of the same motifs in the entire peptide library. Additionally, 99% of the peptides that discriminated seropositive from seronegative samples were found to be enriched by greater than 100% in one or more amino acids arginine, aspartic acid, and lysine (FIG. 36A).

Each peptide (x axis) for each donor (y axis) is represented, and is shaded relative to the difference in its intensity compared to the mean intensity of the same peptide in all seronegative donors, which serve as controls. The heatmap color scheme is scaled by the standard deviation (sd) of a feature's signal from that of the controls. The legend has been truncated at 7 sd's to permit smaller, but significant variations to be visualized. The donors were ordered by their median reported ELISA S/CO measurements, and these data are plotted alongside the heatmap. The peptides have been clustered as indicated by the dendrogram at the top. The distinction between ELISA positive and negative donors is evident in the heatmap visualization, as are correlations between some peptides' IST signals and the ELISA signal levels. The Chagas positive samples display at least three distinct binding profiles for a subset of the peptides with i) uniformly lower signal than controls, ii) marginally higher signal than controls and iii) signal that increases as S/CO value increases. Peptide signal heterogeneity in the Chagas negative samples is relatively minor.

These data indicate that the different clusters may correlate with the status of the infection, and/or indicate disease progression.

In addition to measuring the IgG antibodies bound to the IST peptide array, IgA binding activity was determined, by simply detecting the plasma-antibody binding-events with a fluorescently-labeled anti-IgA specific secondary reagent. Fewer library peptides (224) passed the Bonferroni cutoff for significantly different signal levels between the seropositive and negative donors, and these overlapped with 50% of those detected by the anti-IgG secondary reagent. Additionally, all 23 IgA-classifying peptides that correlated to S/CO values were found within the list of 26 IgG-classifying peptides that correlated with S/CO (23/26=88% overlap). The performance of the IgA classification (AUC=0.94) was similar to that of the IgG classifier.

These findings indicate that a correlation exists between the IST test results and the disease-specific immune activity. These findings suggest the use of the immunosignature method as a test for monitoring the status of the *T. cruzi*-induced Chagas disease. A longitudinal study could provide the information necessary for monitoring sero-reconversion of seropositive subjects or long-term development of life-threatening complications of the infection.

Example 9—Proteome Mapping the Chagas-Classifying Peptides

Figure 33:
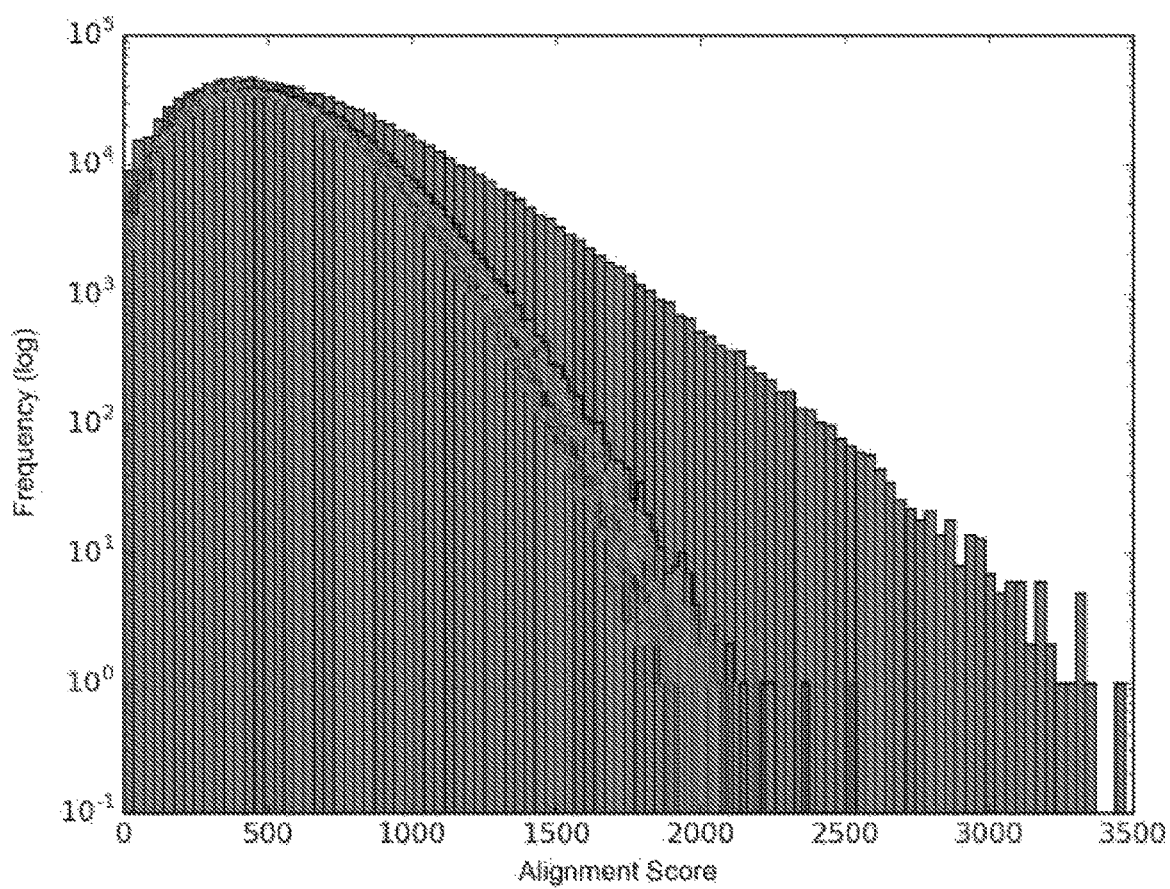
FIG. 33 shows a histogram of the alignment scores from the top 370 peptides against all Chagas proteins (depicted in the blue bars). The mapping algorithm was repeated with 10 equivalent alignments of 370 randomly chosen library peptides. Each yielded histograms that are shown as rainbow-colored line plots.

The 356 IST library peptides that significantly distinguished Chagas positive from negative donors plus the 14 that were correlated to S/CO values were aligned to the *T. cruzi* proteome with a modified BLAST algorithm and scoring system that used a sliding window of 20-mers that overlapped by 10mers (Example 6). This yielded a ranked list of candidate protein-target regions shown in Table 6. Alignmentt of peptides to non-overlapping 20mers of the proteins in the proteome identified the candidate biomarkers provided in Table 7. These classifying peptides display a high frequency of alignment scores that greatly exceed the maximum scores obtained by performing the same analysis with ten equally-sized (370) sets of peptides that were randomly selected from the library (FIG. 33). For example, the maximum score obtained with the randomly selected peptides ranged from less than 2000 to 2500; whereas the classifying peptides generated an alignment score of 3500. Thus, in this instance, the classifying peptides provided a protein score that was at least 28% greater than that of the highest scoring random peptide. Reliable results can also be achieved with a lesser degree of separation.

Figure 34:
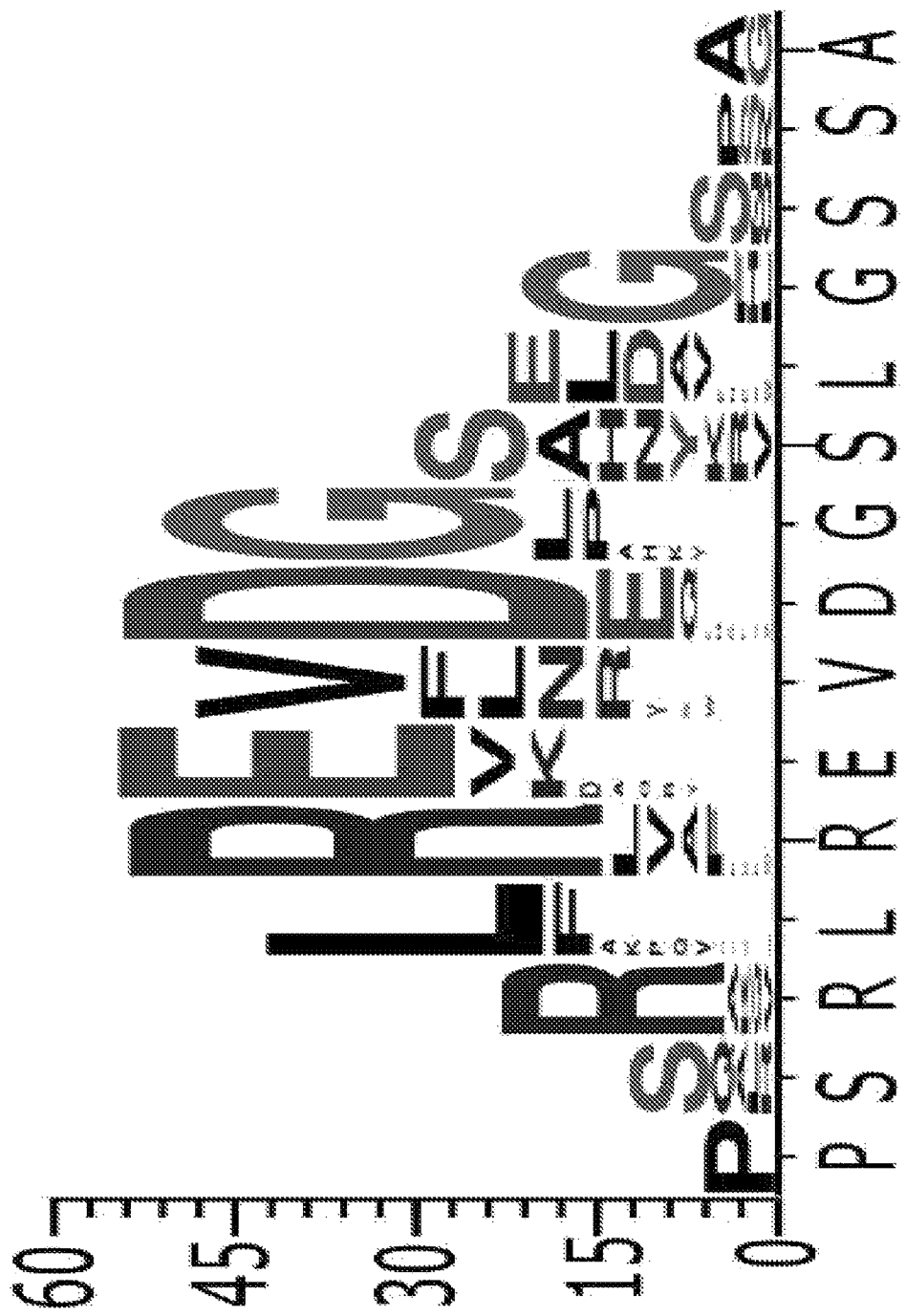
FIG. 34 shows the representation of the levels of similarity of library classifying peptides to a family of *T. cruzi* protein-antigens. Alignment of the top 370 peptides to the mucin II GPI-attachment site is represented as a bar chart in which the bars have been replaced by the amino acid composition at each alignment position, using the standard single-letter code. The x-axis indicates the conserved amino acid at the aligned position in mucin II proteins. The y-axis represents coverage of that amino acid position by the classifying peptides. The height of all letters at a position is the absolute number alignments at each position, where the percent of each letter-bar taken up by a single amino acid equals the percent composition of alignments at that position.

The top-scoring candidate mapped by the Chagas classifying peptides was the C terminus of the Mucin II family of surface glycoproteins. The IST peptide-aligned region includes a glycosylphosphatidylinositol (GPI) attachment site and corresponds to a highly immunogenic epitope in Chagas patients [Buscaglia C A et al., (2004) J Biol Chem 279: 15860-15869]. The amino acids most frequently identified in the Mucin II-aligned IST peptides are summarized in FIG. 34 as a modified WebLogo [Crooks G E et al., (2004) Genome Res 14: 1188-1190]. The corresponding *T. cruzi* mucin sequence (UniProt ID=Q4DXM4) is displayed along the x axis Amino acid substitutions at any one position are shown vertically and the proportional coverage within the mapped library peptides is depicted by the height of the one-letter code. Another member of the Mucin II protein family is identified as the sixth ranked target candidate, and it also maps to the C terminus (UniProt ID=Q4DN88). A member of another *T. cruzi* surface glycoprotein family, the dispersed gene family proteins (DGF-1) [Lander N et al., (2010) Infection and Immunity 78: 231-240], ranked eighth by the aligning algorithm (Q4DQ05), mapping to its C-terminal region and corresponding to the family's consensus sequence. The remaining top 10 scoring alignment regions mapped to proteins involved in calcium signal transduction (calmodulin), vesicle trafficking (vacuolar protein sorting-associated protein, Vps26) [Haft C R et al., (2000) Molecular Biology of the Cell 11: 4105-4116] and uncharacterized proteins. Together these 10 candidate proteome targets accounted for 220 of the aligned 370 IST classifying peptides. Leading candidate biomarkers can also be identified by up to all of the total number of discriminating peptides.

TABLE 6

Candidate biomarkers identified from top ranking alignments of classifying library peptides to *T. cruzi* proteome.

| Rank | *T. cruzi* protein | UniProt ID | Amino acid position |
|---|---|---|---|
| 1 | Mucin TcMUCII | Q4DXM4 | 170-190 |
| 2 | Uncharacterized protein | Q4DLV5 | 170-190 |
| 3 | Uncharacterized protein | K4EBQ9 | 950-970 |
| 4 | Calmodulin | Q4DQ24 | 110-130 |
| 5 | Uncharacterized protein | Q4D6B0 | 910-930 |
| 6 | Mucin TcMUCII | Q4DN88 | 340-360 |
| 7 | Uncharacterized protein | Q4DUA0 | 500-520 |
| 8 | Dispersed gene family protein 1 (DGF-1) | Q4DQ05 | 3380-3400 |
| 9 | Uncharacterized protein | Q4DCE7 | 220-240 |
| 10 | Vacuolar protein sorting-associated protein (Vps26) | K4DSC6 | 10-30 |

Alternatively, were identified with a Welch's T-Test and selected for having a p-value of <4e−7 (Bonferroni). Alternatively, the discriminating peptides were peptides that significantly correlated (by Spearman correlation) to the *T. cruzi* S/CO, where: (a) p<4e−7 when controls are treated as S/CO=0, and (b) FDR<10% when controls are excluded. These discriminating peptides were aligned to the proteome the proteome of T, *cruzi* (Sodré C L et al., Arch Microbiol. [2009] February; 191(2):177-84. Epub 2008 Nov. 11. Proteomic map of *Trypanosoma cruzi* CL Brener: the reference strain of the genome project), and candidate biomarkers were identified (Table 7).

TABLE 7

Additional candidate biomarkers identified using alignmnets to overlapping 20mers nc[1]="Uncharacterized proteinQ4DY21
Q4DY21_TRYCCunreviewedTc00.1047053506357.69*Trypanosoma cruzi* (strain CL Brener)92"
nc[2]="Uncharacterized proteinK4E205
K4E205_TRYCRunreviewedTCSYLVIO_004273*Trypanosoma cruzi*424"
nc[3]="Uncharacterized proteinQ4CYD5
Q4CYD5_TRYCCunreviewedTc00.1047053506123.20*Trypanosoma cruzi* (strain CL Brener)171"
nc[4]="Uncharacterized proteinQ4D0S4
Q4D0S4_TRYCCunreviewedTc00.1047053509231.23*Trypanosoma cruzi* (strain CL Brener)85"
nc[5]="\"Dispersed gene family protein 1 (DGF-1), putative (Fragment)\"K4E9V4K4E9V4_TRYCRunreviewedTCSYLVIO_001440*Trypanosoma cruzi*168"
nc[6]="Uncharacterized proteinQ4E549
Q4E549_TRYCCunreviewedTc00.1047053510359.220*Trypanosoma cruzi* (strain CL Brener)529"
nc[7]="Uncharacterized proteinQ4CTS9
Q4CTS9_TRYCCunreviewedTc00.1047053510647.10*Trypanosoma cruzi* (strain CL Brener)283"
nc[8]="Uncharacterized proteinQ4CZD2
Q4CZD2_TRYCCunreviewedTc00.1047053503779.50*Trypanosoma cruzi* (strain CL Brener)315"
nc[9]="\"Casein kinase, delta isoform, putative (Fragment)\"Q4CN81
Q4CN81_TRYCCunreviewedTc00.1047053504929.15*Trypanosoma cruzi* (strain CL Brener)90"
nc[10]="Uncharacterized proteinQ4CZ70
Q4CZ70_TRYCCunreviewedTc00.1047053509521.10*Trypanosoma cruzi* (strain CL Brener)101"
nc[11]="Alanine--tRNA ligase (EC 6.1.1.7) (Alanyl-tRNA synthetase)Q4DQ33Q4DQ33_TRYCCunreviewedTc00.1047053511825.220*Trypanosoma cruzi* (strain CL Brener)959"
nc[12]="Uncharacterized proteinQ4E5T0
Q4E5T0_TRYCCunreviewedTc00.1047053508221.1020*Trypanosoma cruzi* (strain CL Brener)149"
nc[13]="\ "Retrotransposon hot spot (RHS) protein, putative (Fragment)\"Q4CKR4Q4CKR4_TRYCCunreviewedTc00.1047053400739.10*Trypanosoma cruzi* (strain CL Brener)105"

TABLE 7-continued

Additional candidate biomarkers identified using
alignmnets to overlapping 20mers nc[14]="Uncharacterized proteinQ4CZ70
Q4CZ70_TRYCCunreviewedTc00.1047053509521.10*Trypanosoma cruzi*
(strain CL Brener)101"
nc[15]="Uncharacterized protein (Fragment)Q4DLG1
Q4DLG1_TRYCCunreviewedTc00.1047053510747.5*Trypanosoma cruzi*
(strain CL Brener)73"
nc[16]="Uncharacterized proteinQ4DYI4
Q4DYI4_TRYCCunreviewedTc00.1047053511367.74*Trypanosoma cruzi*
(strain CL Brener)96"

These data show that array peptides that mimic parasitic epitopes were bound differentially by peripheral blood antibodies in Chagas seropositive subjects. These discriminating peptides were mapped to several known immunogenic *T. cruzi* proteins, and to several previously unknown antigens

Example 10—IST Co-Classification of Chagas Positive Donors from Those Testing Positive for Other Blood Infectious Diseases: Chagas Disease, Hepatitis B, Hepatitis C, and West Nile Virus Disease In addition to discriminating Chagas positive samples from Chagas negative samples, the immunosignature method was tested to determine whether Chagas disease could be discriminated from other infectious diseases, and whether the other infectious diseases could be discriminated from each other.

To determine whether Chagas positive samples could be discriminated by IST from other infectious disease samples, a subset of 88 samples from the full Chagas 2015 cohort was re-assayed, alongside 88 HBV, 88 WNV, and 71 HCV disease-positive plasma samples. The virus samples were assigned positivity by both indirect serologic and direct nucleic acid testing at Creative Testing Solutions. All study samples were reported as being positive for only one of the four diseases. The demographic data are presented in Table 8, showing mixed genders and ethnicities and a range of ages. A higher prevalence of Chagas positivity is seen among Hispanic donors, which is consistent with disease prevalence in Central and South America. This higher prevalence was also seen within the full Chagas cohort (Table 5). The distribution of ethnicities for donors testing positive for HBV, HCV and WNV were similar to the distributions found in the general U.S. population.

All IST assays for this study were performed on the same day and scanned immediately to acquire signal intensity measurements at each feature. The raw data was imported into R for analysis.

TABLE 8

Description of donors in the blood panel-positive disease study

| | all | Chagas | HBV | HCV | WNV |
|---|---|---|---|---|---|
| Group size (n) | 335 | 88 | 88 | 71 | 88 |
| Gender | | | | | |
| female | 62 | 27 | 7 | 7 | 21 |
| male | 102 | 30 | 11 | 21 | 40 |
| unknown | 171 | 31 | 70 | 43 | 27 |
| Ethnicity | | | | | |
| white | 70 | 5 | 2 | 16 | 47 |
| Hispanic | 54 | 38 | 1 | 5 | 10 |

TABLE 8-continued

Description of donors in the blood panel-positive disease study

| | all | Chagas | HBV | HCV | WNV |
|---|---|---|---|---|---|
| black | 5 | 0 | 4 | 1 | 0 |
| other | 18 | 4 | 11 | 2 | 1 |
| unknown | 188 | 41 | 70 | 47 | 30 |
| Age bin | | | | | |
| (16-20) | 11 | 3 | 3 | 1 | 4 |
| (20-30) | 30 | 7 | 6 | 7 | 10 |
| (30-40) | 26 | 14 | 2 | 2 | 8 |
| (40-50) | 36 | 11 | 3 | 6 | 16 |
| (50-60) | 35 | 12 | 1 | 10 | 12 |
| (60-70) | 18 | 6 | 3 | 2 | 7 |
| (70-87) | 8 | 4 | 0 | 0 | 4 |
| unknown | 171 | 31 | 70 | 43 | 27 |

Immunosignature assays were performed on all sample to identify the array peptides that were differentially bound by antibodies in samples from subjects infected with *T. cruzi* (Chagas disease), Hepatitis B, Hepatitis C, and West Nile. The array-based assay was performed as described in Example 6, on samples from subjects described in Table 8, and signal intensities of array-bound antibodies in each of the samples was acquired and analyzed as described.

Distinguishing an Infection from Another Infection

Differential antibody binding to array peptides identified peptides that discriminated Chagas (T *cruzii* infection) from HBV, Chagas form HCV, Chagas from WNV, HBV from HCV, HCV from WNV, and WNV from HBV.

Comparisons of signal binding data obtained from samples from Chagas subjects to binding data from a group of subjects with HBV identified peptides that discriminated the Chagas samples from the group HBV were enriched by greater than 100% in one or more motifs listed in FIG. 41A relative to the incidence of the same motifs in the entire peptide library. Additionally, peptides that discriminated Chagas samples from HBV samples were found to be enriched by greater than 100% in one or more amino acids arginine, tyrosine, serine, alanine, valine, glutamine, and glycine (FIG. 41B). The method performance for this contrast was characterized by an 0.98 (0.98-0.99). At 90% sensitivity, the specificity of the assay was 96% (94-97%), the sensitivity of the assay at 90% specificity was 96% (94-97%), and the accuracy of the assay at sensitivity=specificity was 94% (93-96%).

Comparisons of signal binding data obtained from samples from Chagas subjects to binding data from a group of subjects with HCV identified peptides that discriminated the Chagas samples from the group HCV were enriched by greater than 100% in one or more motifs listed in FIG. 42A relative to the incidence of the same motifs in the entire peptide library. Additionally, peptides that discriminated Chagas samples from HCV samples were found to be enriched by greater than 100% in one or more amino acids arginine, tyrosine, serine, valine, and glycine (FIG. 42B). The method performance for this contrast was characterized by an 0.99 (0.98-0.99). At 90% sensitivity, the specificity of the assay was 94% (92-98%), the sensitivity of the assay at 90% specificity was 98% (95-99%), and the accuracy of the assay at sensitivity=specificity was 93% (92-95%).

Comparisons of signal binding data obtained from samples from Chagas subjects to binding data from a group of subjects with WNV identified peptides that discriminated the Chagas samples from the group WVN were enriched by greater than 100% in one or more motifs listed in FIG. 43A relative to the incidence of the same motifs in the entire peptide library. Additionally, peptides that discriminated Chagas samples from WVN samples were found to be enriched by greater than 100% in one or more amino acids lysine, tryptophan, aspartic acid, histidine, arginine, glutamic acid, and glycine (FIG. 43B). The method performance for this contrast was characterized by an 0.95 (0.94-0.97). At 90% sensitivity, the specificity of the assay was 87% (76-94%), the sensitivity of the assay at 90% specificity was 89% (85-92%), and the accuracy of the assay at sensitivity=specificity was 90% (86-91%).

Comparisons of signal binding data obtained from samples from HBV subjects to binding data from a group of subjects with HCV identified peptides that discriminated the HBV samples from the group HCV were enriched by greater than 100% in one or more motifs listed in FIG. 44A relative to the incidence of the same motifs in the entire peptide library. Additionally, peptides that discriminated HBV samples from HCV samples were found to be enriched by greater than 100% in one or more amino acids phenylalanine, tryptophan, valine, leucine, alanine, and histidine (FIG. 44B). The method performance for this contrast was characterized by an 0.91 (0.88-0.94). At 90% sensitivity, the specificity of the assay was 79% (69-86%), the sensitivity of the assay at 90% specificity was 71% (53-83%), and the accuracy of the assay at sensitivity=specificity was 84% (78-87%).

Comparisons of signal binding data obtained from samples from HBV subjects to binding data from a group of subjects with WNV identified peptides that discriminated the HBV samples from the group WNV were enriched by greater than 100% in one or more motifs listed in FIG. 45A relative to the incidence of the same motifs in the entire peptide library. Additionally, peptides that discriminated HBV samples from WNV samples were found to be enriched by greater than 100% in one or more amino acids tryptophan, lysine, phenylalanine, histidine, and valine (FIG. 45B). The method performance for this contrast was characterized by an 0.97 (0.96-0.98). At 90% sensitivity, the specificity of the assay was 96% (90-99%), the sensitivity of the assay at 90% specificity was 94% (90-97%), and the accuracy of the assay at sensitivity=specificity was 93% (90-96%).

Comparisons of signal binding data obtained from samples from HCV subjects to binding data from a group of subjects with WNV identified peptides that discriminated the HCV samples from the group WNV were enriched by greater than 100% in one or more motifs listed in FIG. 46A relative to the incidence of the same motifs in the entire peptide library. Additionally, peptides that discriminated HCV samples from WNV samples were found to be enriched by greater than 100% in one or more amino acids lysine, tryptophan, arginine, tyrosine, and proline (FIG. 46B). The method performance for this contrast was characterized by an 0.97 (0.95-0.98). At 90% sensitivity, the specificity of the assay was 92% (84-97%), the sensitivity of the assay at 90% specificity was 93% (86-97%), and the accuracy of the assay at sensitivity=specificity was 92% (87-94%).

These data show that comparisons of individual infections can be made using the immunosignature assay described herein to differentially diagnose many different infectious conditions.

Distinguishing One Infection from a Group Comprising Two or More Different Types of Infection Binary classifiers were developed for differentiating each of the available infectious diseases from the combination of the others (Table 9). Performance metrics of each disease contrast and their corresponding 95% CI's were determined by four-fold cross-validation analysis. The models generated similar strong AUC's, which ranged from 0.94 to 0.97, and corresponded to accuracies of 87%-92%. Nominally, the contrast of Chagas disease versus the combined class of the remaining three diseases (other) was best performing; however, the parenthetically shown CI's overlapped. Nominally, the hepatitis contrasts were the weakest models. The number of optimal SVM input peptides varied widely from 50 to 16,000 peptides.

Differential antibody binding to array peptides identified peptide that discriminated Chagas samples from a group of mixed samples from subjects having HBV, HCV, and WNV (other). The most discriminating peptides were found to be enriched by greater than 100% in one or more motifs listed in FIG. 37A relative to the incidence of the same motifs in the entire peptide library. Additionally, peptides that discriminated Chagas samples from the group of HBV, HCV, and WNV samples were found to be enriched by greater than 100% in one or more amino acids arginine, aspartic acid, and lysine (FIG. 37B).

A binary classifier was developed based on the binding signal information of discriminating peptides, and was shown to clearly differentiate samples from Chagas disease subjects from samples from the other infectious diseases, HBV, HCV, and WNV, with an assay performance characterized by an AUC=0.97. At a 90% confidence level, the specificity of the assay was 94%, the sensitivity of the assay was 92%, and the accuracy of the assay was 92% (Table 9).

Comparisons of signal binding data obtained from samples from HBV subjects to binding data from a group of subjects with Chagas disease, HCV, and WNV identified peptides that discriminated the HBV samples from the group of Chagas disease, HCV, and WNV, which were enriched by greater than 100% in one or more motifs listed in FIG. 38A relative to the incidence of the same motifs in the entire peptide library. Additionally, peptides that discriminated HBV samples from the group of HBV, HCV, and WNV samples were found to be enriched by greater than 100% in one or more amino acids tryptophan, phenylalanine, lysine, valine, leucine, alanine, and histidine (FIG. 38B). The method performance for this contrast was characterized by an AUC 94%. At a 90% confidence level, the specificity of the assay was 85%, the sensitivity of the assay was 85%, and the accuracy of the assay was 87% (Table 9).

In a third set of contrasts, comparisons of signal binding data obtained from samples from HCV subjects to binding data from a group of subjects with Chagas disease, HBV, and WNV identified peptides that discriminated the HCV samples from the group of Chagas disease, HBV, and WNV, which were enriched by greater than 100% in one or more motifs listed in FIG. 39A relative to the incidence of the same motifs in the entire peptide library. Additionally, peptides that discriminated HCV samples from the group of HBV, HCV, and WNV samples were found to be enriched by greater than 100% in one or more amino acids arginine, tyrosine, aspartic acid, and glycine (FIG. 39B). The method performance for this contrast was characterized by an AUC=96%. At a 90% confidence level, the specificity of the assay was 91%, the sensitivity of the assay was 90%, and the accuracy of the assay was 90% (Table 9).

In a fourth set of contrasts, comparisons of signal binding data obtained from samples from WNV subjects to binding data from a group of subjects with Chagas disease, HBV, and HCV identified peptides that discriminated the WNV samples from the group of Chagas disease, HBV, and HCV, which were enriched by greater than 100% in one or more motifs listed in FIG. 40A relative to the incidence of the same motifs in the entire peptide library. Additionally, peptides that discriminated WNV samples from the group of HBV, HCV, and Chagas samples were found to be enriched by greater than 100% in one or more amino acids lysine, tryptophan histidine, and proline (FIG. 40B). The method performance for this contrast was characterized by an AUC=0.96. At a 90% confidence level, the specificity of the assay was 88%, the sensitivity of the assay was 87%, and the accuracy of the assay was 89% (Table 9).

TABLE 9

Binary classification of each of four disease classes versus a combined class of the remaining three.

|  | AUC | sensitivity @ 90% spec$^a$ | specificity @ 90% sens$^b$ | accuracy @ sens$^b$ = spec$^a$ |
|---|---|---|---|---|
| Chagas vs. Other | 0.97 (0.96-0.98) | 92% (90%-94%) | 94% (90%-96%) | 92% (90%-92%) |
| HBV vs. Other | 0.94 (0.93-0.95) | 85% (78%-90%) | 85% (78%-90%) | 87% (85%-90%) |
| HCV vs. Other | 0.96 (0.94-0.97) | 90% (86%-94%) | 91% (82%-96%) | 90% (88%-93%) |
| WNV vs. Other | 0.96 (0.95-0.97) | 87% (78%-94%) | 88% (84%-92%) | 89% (86%-91%) |

$^a$spec, specificity; $^b$sens, sensitivity

These data show that binary classification of a plurality of different infections based on identified discriminating peptides can distinguish subjects that are seropositive for Chagas from subjects that are seronegative for Chagas, and from subjects that are asymptomatic for WNV, HPV, and HCV. As shown, in every instance, the method performance is greater than 0.94.

Example 11—Simultaneous Classification of Four Different Infections

A multiclassifier model was developed to classify all four infectious disease states simultaneously, with one set of selected peptides, and one algorithm. This multiclass model had similar performance to the binary classifiers shown in Table 9. Namely, the four-fold cross validation analysis yielded multiclass AUC's of 0.98 for Chagas, 0.96 for HBV, 0.95 for HCV, and 0.97 for WNV. Table 10 presents the performance metrics of the assignments of each sample to a class based on its highest predicted probability. In this confusion matrix, each binary contrast is presented. The estimated overall multiclass classification accuracy achieved 87%.

The classifiers for the group contrasts described in the preceding paragraphs and Table 10 were combined to obtain a multiclassifier to determine whether the four infections: Chagas, HBV, HCV, and WNV could be simultaneously discriminated from each other.

Peptides discriminating Chagas, HBV, HCV, and WNV samples from each other in the multiclassifier analysis were enriched by greater than 100% in one or more motifs listed in FIG. 47A relative to the incidence of the same motifs in the entire peptide library. Additionally, the peptides that discriminated Chagas, HBV, HCV, and WNV samples from each other in the multiclassifier analysis were enriched by greater than 100% in one or more amino acids arginine, tyrosine, lysine, tryptophan, valine, and alanine (FIG. 47B).

Figure 35:
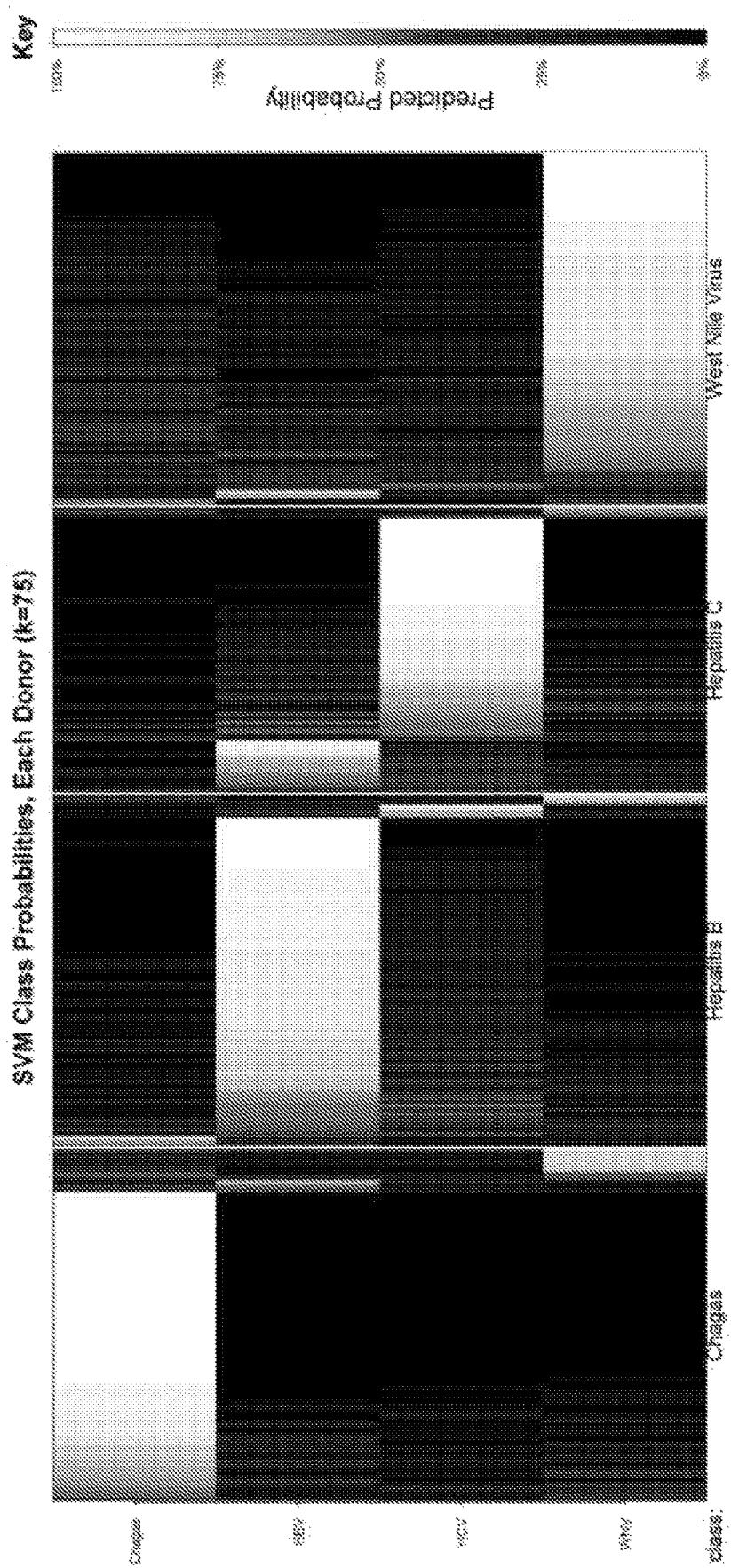
FIG. 35 shows the probabilities of Chagas, Hepatitis B, Hepatitis C and West Nile Virus class assignments. Mean predicted probabilities for each sample were calculated by out-of-bag predictions from four-fold cross-validation analyses using a multiclass SVM machine classifier, iterated 100 times. Each sample has a predicted class membership for each disease class ranging from 0 (black) to 100% (white).

The heat map shown in FIG. 35 visualizes the mean predicted probability of class membership of out of the bag cross validation model predictions (shown in Table 10) for each of the 335 test cohort samples, encompassing all four diseases. This figure demonstrates that the highest predicted probabilities correctly assigned samples to the infectious disease class. Signal intensities of the classifying peptides are visibly more different in the Chagas samples relative to all three of the virus sample. Most, but not all, are higher in Chagas with notable exceptions for a few lower peptide signals relative to HBV and WNV. By contrast, the differences in signal intensities for the same peptides assayed against HBV and HCV samples are less extreme.

Each sample has a predicted class membership for each outcome ranging from 0 (black) to 100% (white). Each sample was assigned to a disease class based on the highest predicted probability presented in FIG. 35 and show in the confusion matrix given in Table 10. The classifications were assigned based on the predicted probabilities shown in FIG. 35 with each sample being assigned to the class with the highest probability. The assay performance for the four contrast ranged from 0.95 to 0.98. The overall accuracy was 87%.

TABLE 10 matrix and Performance Estimates for multiclass predictions

ImmunoSignature Classification

| Confirmed Diagnosis | Chagas pos | HBV pos | HCV pos | WNV pos | Performance Summary | | |
|---|---|---|---|---|---|---|---|
|  |  |  |  |  | Sens | Spec | AUC |
| Chagas | 77 | 3 | 1 | 2 | 93% | 96% | 0.98 |
| HBV | 3 | 79 | 12 | 2 | 82% | 96% | 0.96 |
| HCV | 0 | 3 | 55 | 2 | 92% | 94% | 0.95 |
| WNV | 8 | 3 | 3 | 82 | 85% | 97% | 0.97 |

Overall accuracy = 87%

These data show that the immunosignature assay can simultaneously distinguish one infection from two or more other infections with a high degree of accuracy. In all instances, the method performance as defined by the AUC was greater than 0.95.

Example 12—Identification of Candidate Biomarkers Correlated to Lupus Activity

Background

Although the prognosis of SLE patients has improved, the disease remains a major cause of morbidity and mortality. Prompt treatment of flares not only results in better immediate outcomes, but will prevent cumulative chronic organ damage. Controlling and preventing disease activity are central goals in the management of SLE. Prediction and/or prompt identification of disease flares, and accurate assessment of ongoing activity using current clinical and serologic tools, can be challenging and is often less than optimal. Therefore, sensitive and specific diagnosis of disease activity remains an important unmet clinical need. (Oglesby et al, Impact of early versus late systemic lupus erythematosus diagnosis on clinical and economic outcomes. Applied Health Economics & Health Policy. 12(2):179-90, 2014; Lisnevskaia et al, Systemic lupus erythematosus. Lancet. 384(9957):1878-88, 2014).

As described elsewhere herein, antibody binding to array peptides provides a snapshot of a person's health by their immune system. The disease-specific antibodies in a sample, e.g. blood bind to the peptide array, creating unique detectable Immunosignatures. To determine whether a patient's antibody profile reflects lupus disease activity better than the individual known biomarkers e.g. anti-ds-DNA, C3/C4, and proteinuria, which are currently used in determining SLEDAI score, and to test whether changes in antibody profiles may be used to monitor changes in disease activity, a series of antibody binding assays using plasma samples from patients having varying levels of lupus activity or patients in remission were performed. An array of about 126,000 different peptides was used for the assays, wherein about $10^7$ copies of the same peptide are present within an array feature, was used for the antibody binding assays.

Background/Methods:

The study design consisted of 356 samples obtained from 183 patients who met American College of Rheumatology (ACR) criteria for SLE at the time of diagnosis. The samples were selected to cover a wide range of SLEDAI scores correlated with the collected samples, which ranged from remission (SLEDAI score=0), mild (SLEDAI score=1-4), moderate (SLEDAI score=5-10) and severe (SLEDAI score greater than 11).

The patients met the criteria set by the American College of Rheumatology (ACR) to diagnose and identify patients with SLE. 90% of the subjects were female, ages 11-69 years (median 39), with 52% of the subjects being of Hispanic origin, 31% of African-American origin, 12% of Afro-Caribbean origin, and 5% of other or mixed origin.

Figures 50A, 50B:
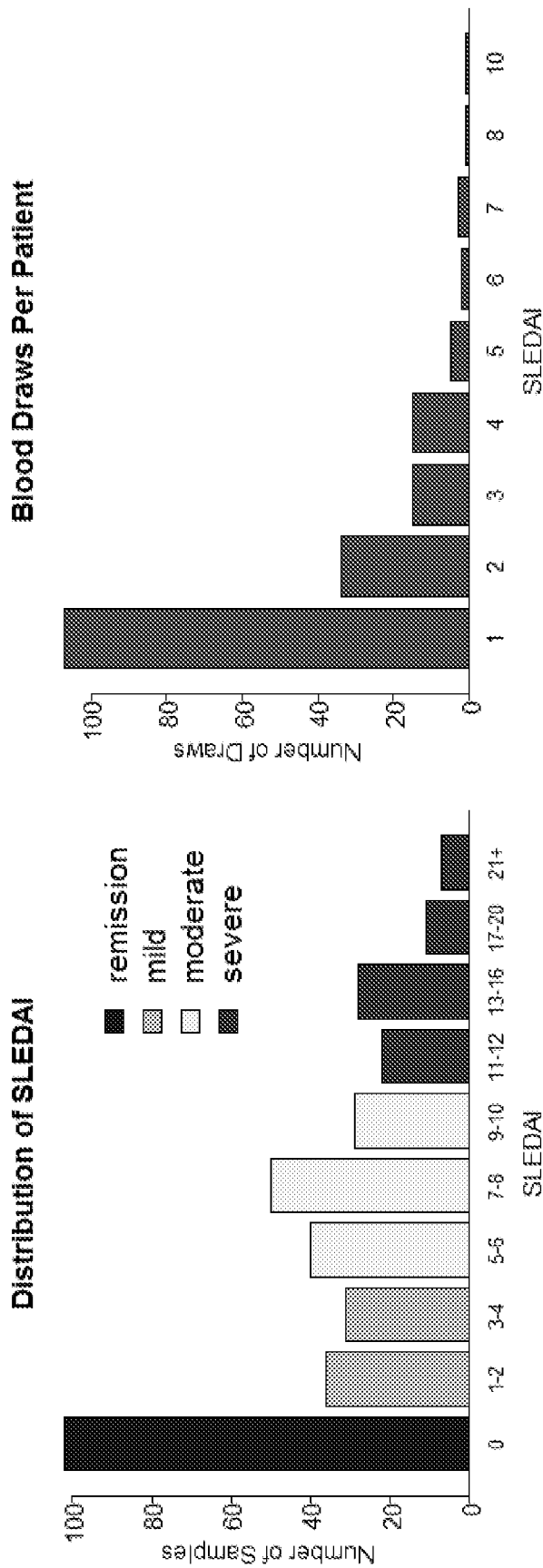
FIGS. 50A-50B shows the distribution of SLEDAI scores by category i.e. remission, mild, moderate, and severe (FIG. 50A), and number of blood draws used for generating immunosignatures (FIG. 50B).

Patients blood samples were drawn as many as 10 different times, with the number of blood draws per patient ranging from 1 to 10. Time between blood draws spanned from 1 week to 4 years (median 6 months). The distribution of SLEDAI scores by category i.e., remission, mild, moderate, and severe, and number of blood draws used for generating immunosignatures are diagrammed in FIGS. 50A-50B.

Binding assays were performed as described above using plasma. The samples were incubated on peptide arrays containing 126,000 unique peptides, washed, incubated with a secondary antibody to fluorescently label the sample antibodies bound to peptides, washed again and imaged. Signal binding intensities were logarithmically transformed, and each sample was normalized by subtracting its median intensity. Discriminating peptides that discriminate samples of donors with low disease activity from samples of donors with high associated with disease activity were identified by t-test and by correlation, and peptides with intensities that correlate to SLEDAI were identified. Support Vector Machine (SVM) classifiers (Cortes, C.; Vapnik, V. (1995). "Support-vector networks". Machine Learning. 20 (3): 273-297. doi:10.1007/BF00994018) were trained to distinguish remission (SLEDAI score=0) from increasing levels of SLE activity. SVMs find the optimal hyperplane that separates classes of peptides, the instant case based on immunosignature peptide signals. In "feature space" each peptide's signal is a dimension that characterizes each sample. "Support Vectors" are training samples that define the boundary between the classes, i.e., those data points hardest to classify).

Figure 4:
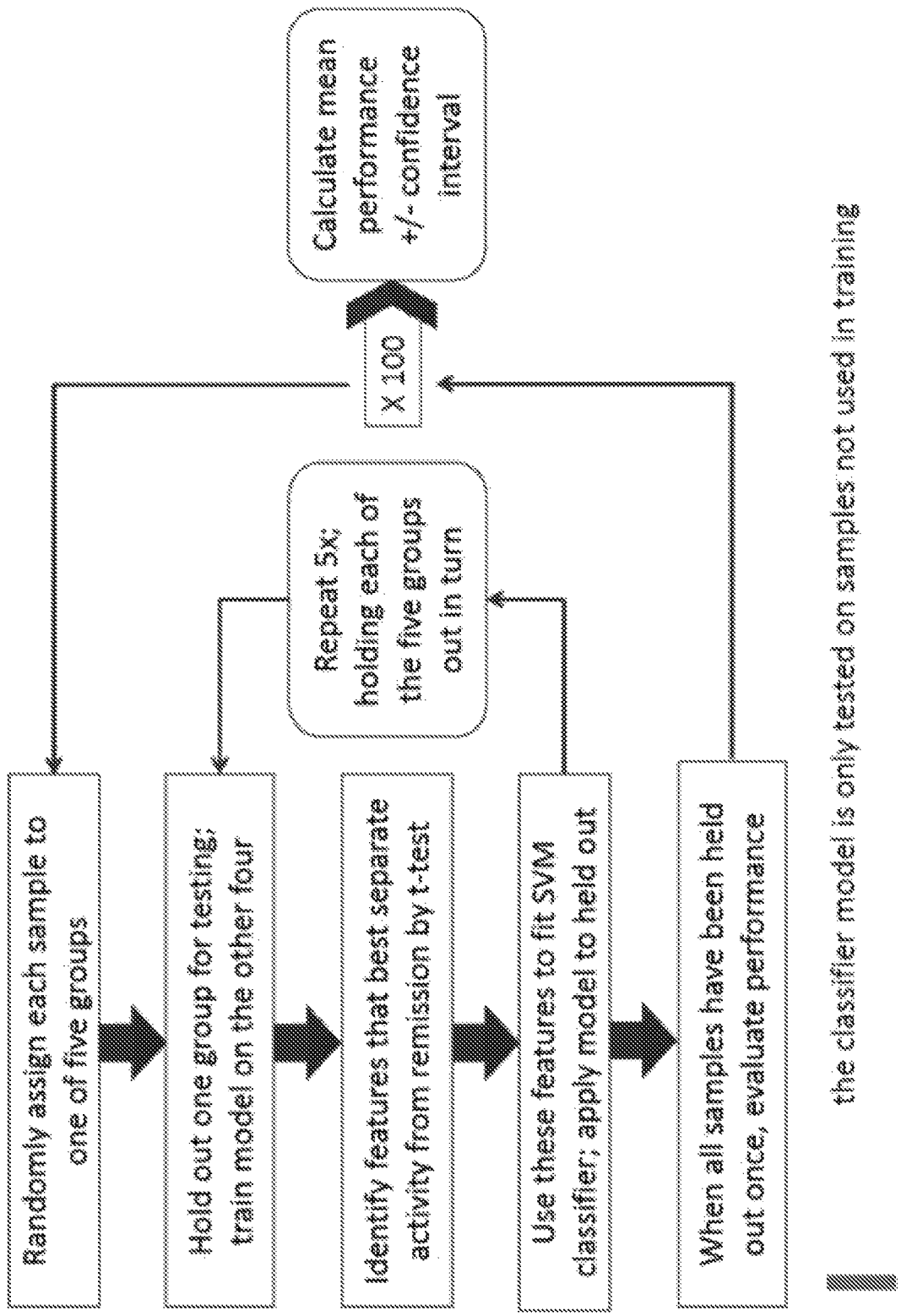
FIG. 4 shows the support vector machines (SVM) process of 5-fold cross validation.

Regression models of SLEDAI were also employed and trained using the Elastic Net Feature selection (see, e.g., Zou, Hui; Hastie, Trevor (2005). "Regularization and Variable Selection via the Elastic Net". Journal of the Royal Statistical Society, Series B: 301-320; Hastie, Tibshirani and Friedman, *The Elements of Statistical Learning*, $2^{nd}$ ed. (2008)) procedure to constrain model complexity. The Elastic Net approach applies Ridge Regression and LASSO penalties to shrink model coefficients and reduce the number of peptide features in the model; correlated features tend to be removed as groups. Briefly, Ridge Regression constrains the sum of coefficients to reduce overfit while reducing magnitude of coefficients, but does not eliminate features. The LASSO approach adds a quadratic term that leads to feature selection, but feature selection is unstable when features are correlated. Five-fold cross validation was used to correct potential estimates for potential overfit. See FIG. 4; see also Frank. E Harrell, Jr., *Regression Modelling Strategies*, Springer Science+Business Media Inc. (2001).

Figure 51:
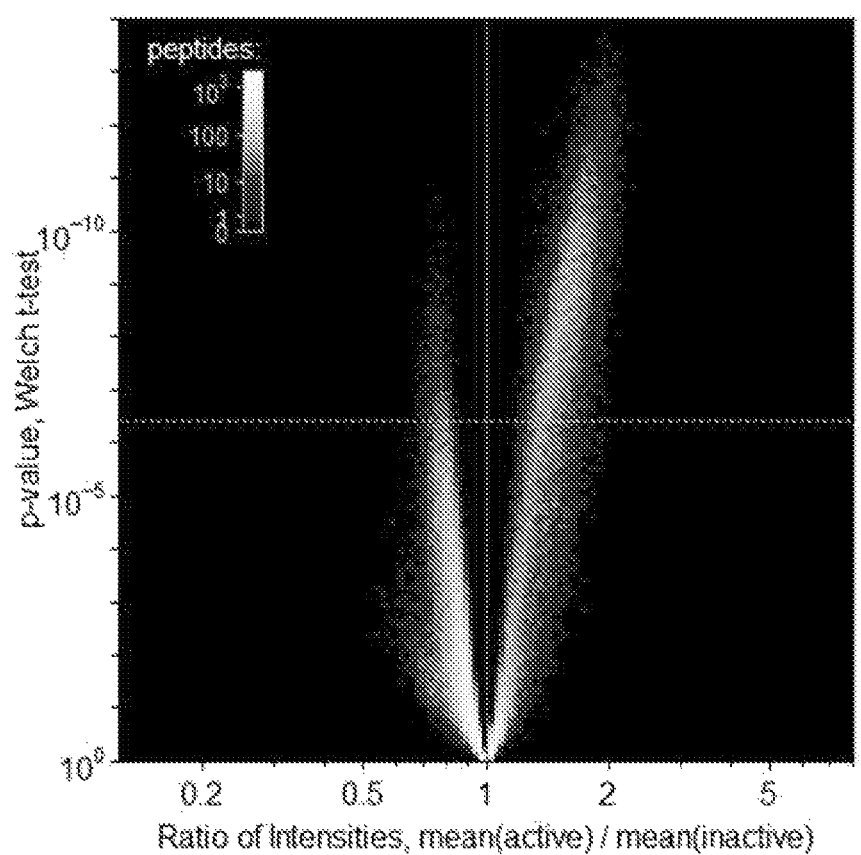
FIG. 51 shows a volcano plot of peptides distinguishing active SLE disease versus inactive SLE disease. The y-axis is the p-value of a t-test for the difference of mean intensities of each peptide between donors who have active SLE and donors within inactive SLE (SLEDAI=0). The x-axis shows the ratio of the mean peptide intensity of the donors with active SLE to the mean peptide intensity of donors with inactive SLE. The color scale indicates the number of peptides with a given combination of p-value and ratio. The green dashed line at p=4e−7 indicates the Bonferroni correction for multiplicity testing; peptides with smaller p-values (above this line) each are more than 95% likely to have a different mean intensity among donors with active disease as compared to the mean of donors with inactive disease.
Figure 52:
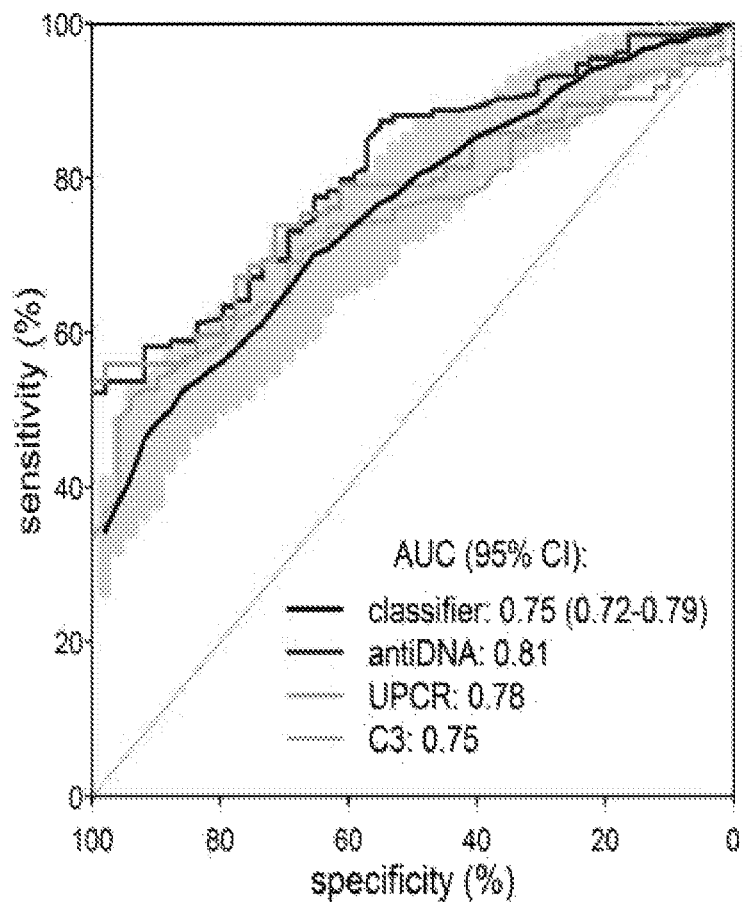
FIG. 52 shows Receiver-Operating Characteristic (ROC) curves for an immunosignature (IMS) model of disease activity as compared to a variety of biomarkers as (anti-dsDNA, UPCR (urine protein/creatinine ratio) and C3 protein) set forth in the SLEDAI index.

Results:

A volcano plot showing the peptides that distinguish active versus inactive (remission) SLE is shown in FIG. 51. Discriminating peptides that showed significant differences in mean intensity between active and inactive disease were identified with a Bonferroni-adjusted cutoff of a p-value <4e−7. The x-axis is the p-value obtained (Welch t-test) for the ratio of mean active disease (mean(active)) vs. mean inactive disease (mean (inactive)). The ability of SVM models incorporating discriminating peptides obtained with immunosignature peptide arrays (IMS) to discriminate donors with active SLE disease from donors in remission was evaluated by plotting Receiver Operating Characteristic (ROC) curves of sensitivity versus specificity for all possible diagnostic thresholds of the model predictions and calculating the area under the ROC curve (AUC). For comparison to known biomarkers, ROC curves were also plotted for anti-ds DNA, UPCR (urine protein/creatinine ratio) and C3 protein biomarker measurements. FIG. 52 shows Receiver-Operator Characteristic curves for an Immunosignature (IS) model of disease activity compared to biomarkers ds-DNA, C3, and proteinuria, for identifying patients with active disease (SLEDAI>0). The gray region indicates the 95% confidence interval of the IS Model, assessed using 5-fold cross validation. Discrimination was improved by training on extreme scores (SLEDAI>8 vs. 0), and performance was greater when applied to extreme contrasts. For example, a classifier of SLEDAI>15 vs. 0 had an AUC of 0.90 (95% CI 0.88-0.92). Preliminary analysis indicates that samples may be binned by IS into low, medium, and high disease activity. Correlations of a linear IS model ($r^2$=0.23), C3 ($r^2$=0.17) and anti-dsDNA ($r^2$=0.13) to SLEDAI were also determined.

Figure 53:
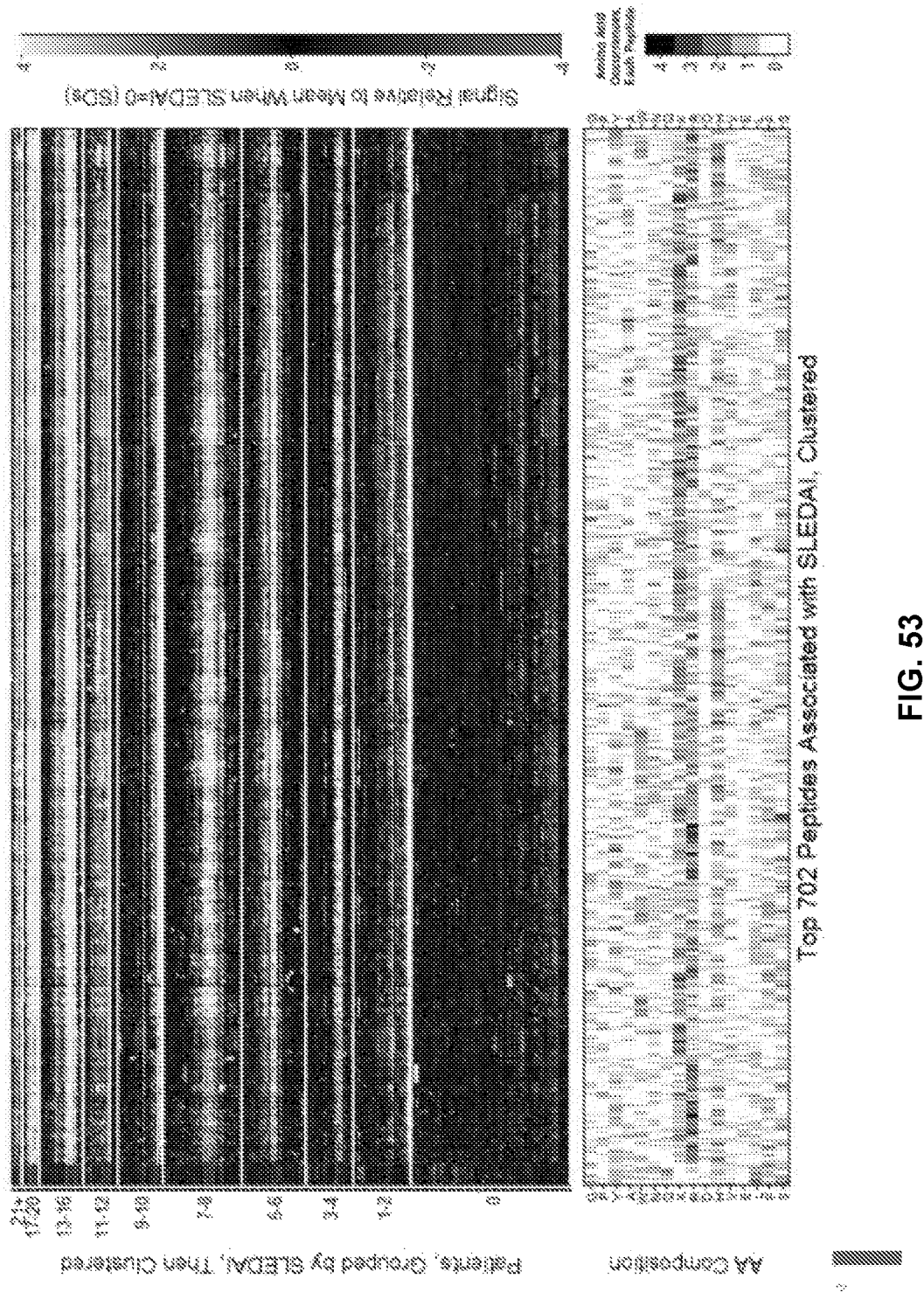
FIG. 53 illustrates a two heat maps. In the top heat map, the colors indicate relative intensity of peptides measured in particular donor's serum as compared to their average intensity among donors with inactive SLE. The plot includes 702 peptides that were selected based on strong correlation between SLEDAI and peptide intensity, and strong correlation between changes in SLEDAI and changes in peptide intensity for pairs of samples (Table 11). Each column of the matrix is a particular peptide, where the peptides have been clustered such that peptides with similar intensity profiles across donors are grouped together. Each row of the matrix is a particular donor, where the donors have been grouped by increasing SLEDAI scores. Each point in the matrix indicates the relative intensity of a particular peptide in a particular donor's serum. Peptides with higher intensities are shown in shades of yellow, meaning that they have more antibodies binding to the particular peptide than observed on average in samples from donors with inactive disease (SLEDAI=0). In the lower heat map, the composition of each of the 702 peptides shown in the upper heat map is presented, where the color scale indicates the number of times each amino acid occurs within each of the peptides.

FIG. 53 shows a clustered heat map showing relative antibody binding to 702 array peptides as the intensity of each peptide in each donor sample relative to the mean intensity of the same peptide across samples from donors in remission, i.e. with SLEDAI scores=0. The heatmap shows the top 702 peptides that are associated with SLEDAI. These are peptides that were significantly correlated with SLEDAI, and/or their changes were significantly correlated with changes in SLEDAI between visits. In both cases, the Bonferroni correction was applied (p<4e−7). The patients were first grouped by SLEDAI test scores, then clustered according to the peptides identified. The heat map shows that as the SLEDAI score increases from 0 to 21 the relative intensities of these peptides also tends to increase (high signal intensity is yellow). These are peptides that were significantly correlated with SLEDAI, and/or their changes were significantly correlated with changes in SLEDAI between visits. In both cases, the Bonferroni correction was applied (p<4e−7). The heatmap shows the top 702 peptides that are associated with SLEDAI. The amino acid composition of each top associated peptide was also identified. The top peptides were used to search a human proteome database to determine the peptides that aligned with known human proteins. See FIGS. 54A-54C.

The peptide sequences of the top 50 of the 702 peptides correlated to SLEDAI activity are provided in FIG. 61.

Figure 54A:
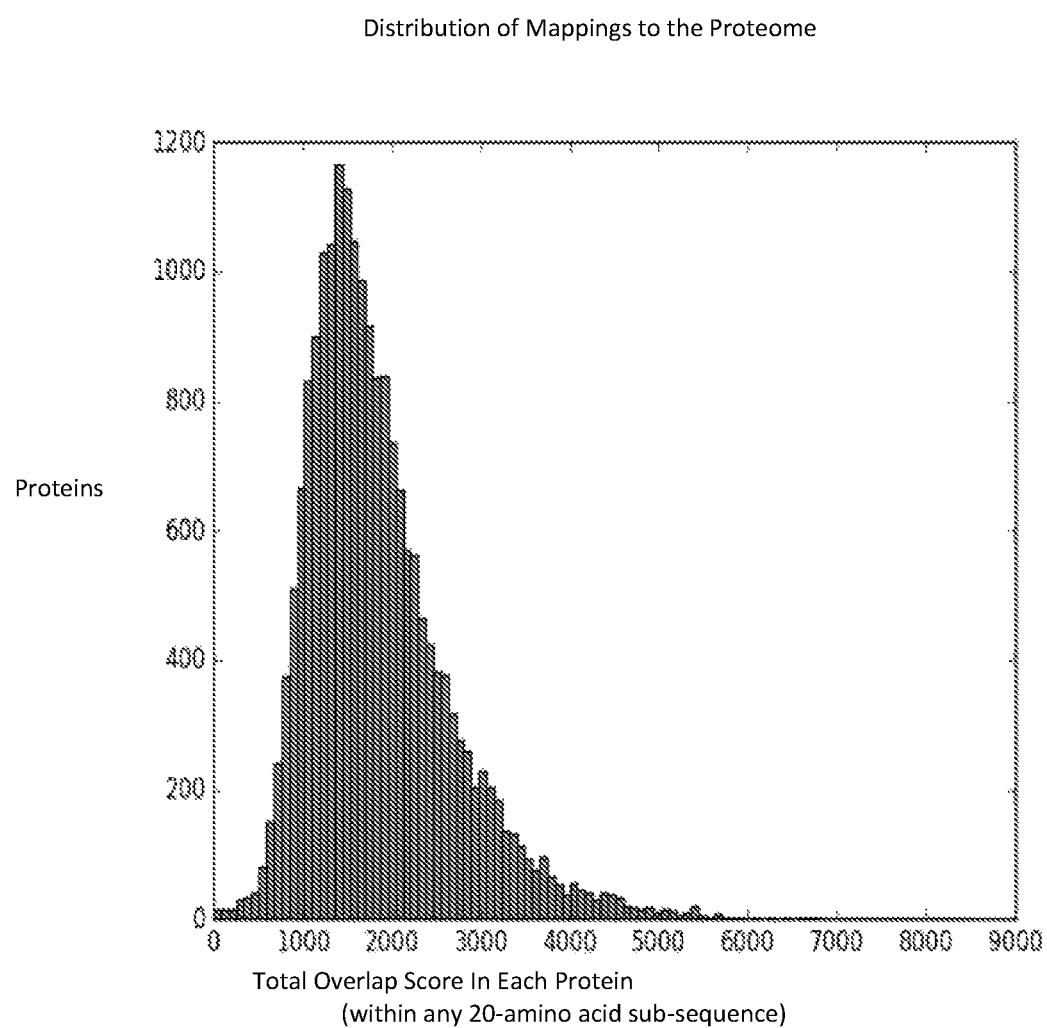
FIGS. 54A-54C show an example of the method using the immunosignature (IMS) peptides that map to known and putative SLE antigens.
Figure 54B:
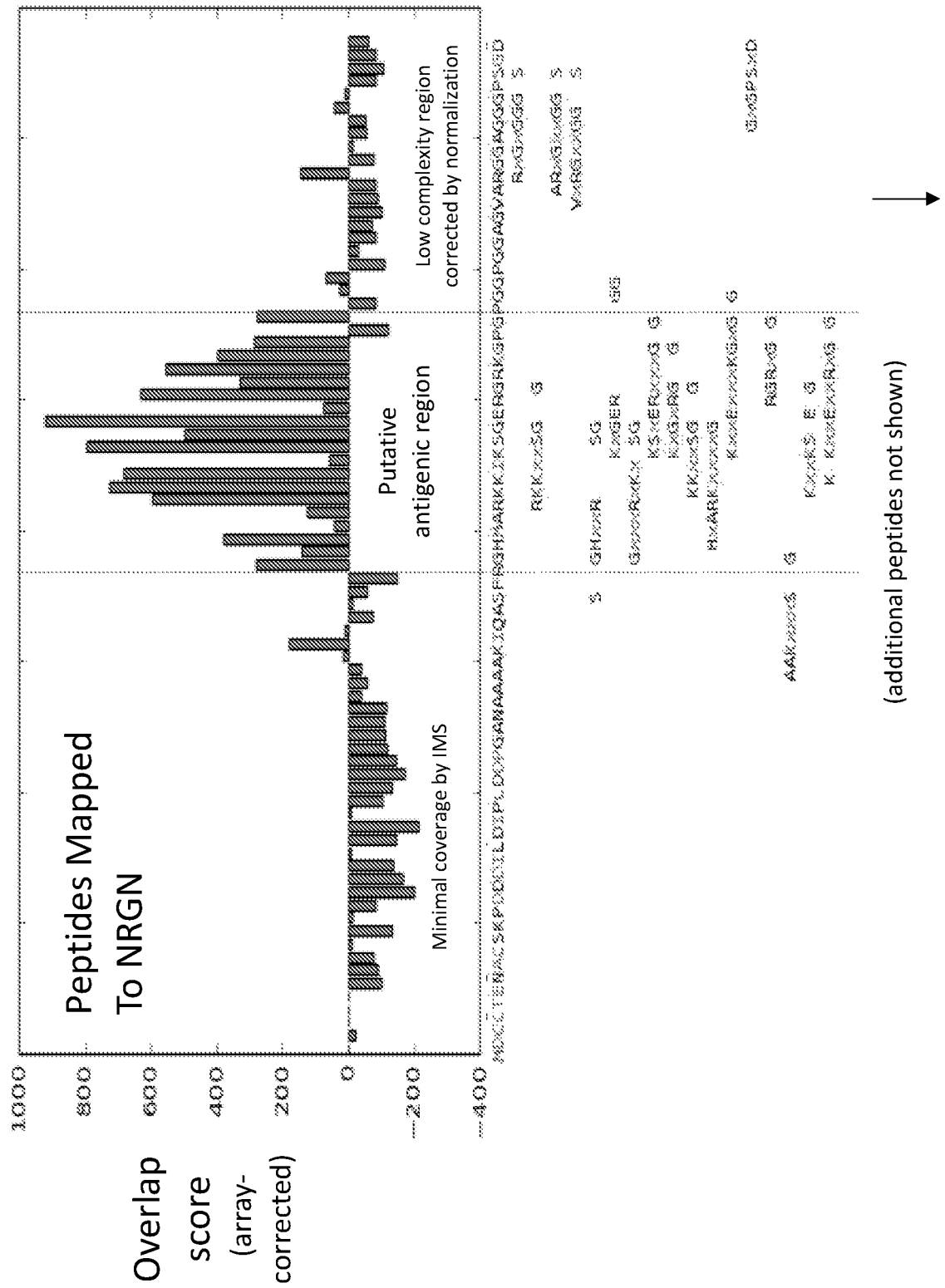
Figure 54C:
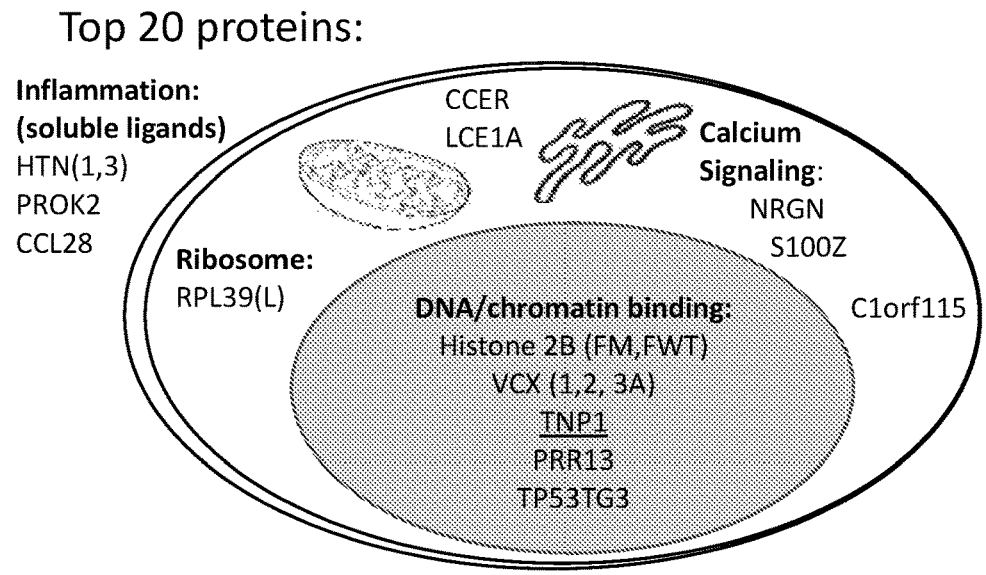

FIG. 54A shows the distribution of all the peptides on the array as aligned to the human proteome by BLAST. The weighted sum of the amino acids at each protein position that aligns with a peptide from the list correlated to SLEDAI score was calculated (overlap score). The overlap score was normalized for the alignments of all the peptides on the array to identify putative antigenic regions that are enriched beyond chance among the SLEDAI-correlated peptides. FIG. 54B shows the overlap scores for the protein NRGN. The left side of the diagram shows that there are very few peptides from the list that align; on the right, there are some alignments, but no more than you would expect by chance because there are many proteins in the proteome with similar sequences. In the middle is a putative antigenic region where more peptides from the list are aligned than one would expect by chance. The actual alignments are shown, where an x indicates an amino acid mismatch in the peptide. All the proteins in the proteome are ranked by their highest sum of positive (enriched) overlap scores within any 20-amino acid subsequence of each protein. The distribution of these total scores is shown at upper left. The 20 proteins with the strongest mappings i.e. top 20 overlap scores, are shown in FIG. 54C, and were found to include proteins known to be involved in inflammation including HTN (1,3), PROK2 and CCL28, as well as calcium signaling (for example, NRGN and S100Z), ribosomal proteins (RPL39(L)), and proteins associated with DNA and chromatin regulation, including Histone 2B (FM, FWT), VCX (1,2, 3A), TNP1, PRR13 and TP53TC3. Proteins that are not known to be associated with SLE are shown in blue: RPL39(L), Histone 2B (FM, FWT), TNP1, NRGN, PROK2, CCL28. Moreover, alignment was also found with uncharacterized proteins, including CCER1, LCE1A and C1orf115. A detailed description of the method for identifying candidate biomarkers is provided in Example 13.

Figure 55:
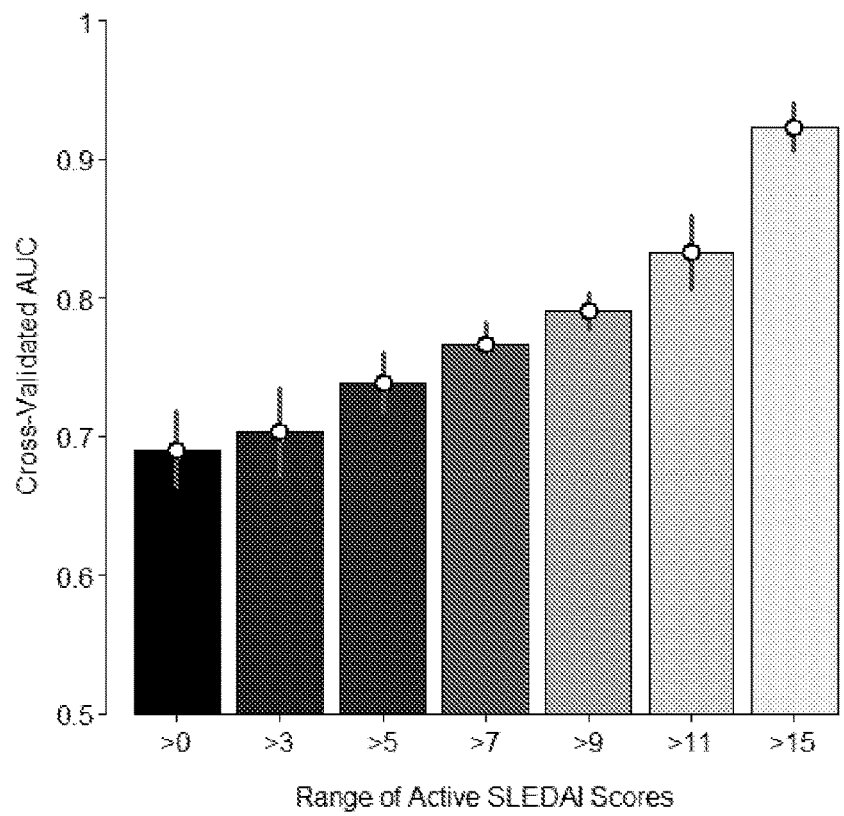
FIG. 55 shows a histogram illustrating the ability of a series of classifier models using discriminating peptides identified from contrasts of active versus inactive SLE to correctly classify donors' disease as active or inactive, as measured by the area under the ROC curve (AUC), estimated by the four-fold cross-validation method. The models use progressively strict definitions of active disease as indicated on the x-axis, such that the first model was applied to donors with SLEDAI of zero or greater than two, while the last model was applied only to donors with SLEDAI of zero or greater than 15. The models classify the donors more accurately when the definition of SLE activity is stricter, indicating that it is easier to distinguish donors with higher activity from those donors in remission (inactive disease), than it is to distinguish donors with a larger range of disease activity, including mild activity, from those in remission.

Performance of the assay using discriminating peptides identified from contrasts of active versus inactive SLE samples show that higher SLEDAI activity is easily distinguished from remission (FIG. 55). Each bar represents the performance of a different support vector machine classifier, as five-fold cross-validated Area Under the ROC Curve (AUC). In each case, the classifier was trained to distinguish patients with active disease from those in remission; in successive bars, the inclusion criteria for patients with active disease were restricted to patients with higher disease activity. Peptide selection was included within the cross-validation loop (i.e., not done as a separate step before cross-validation).

Figure 56:
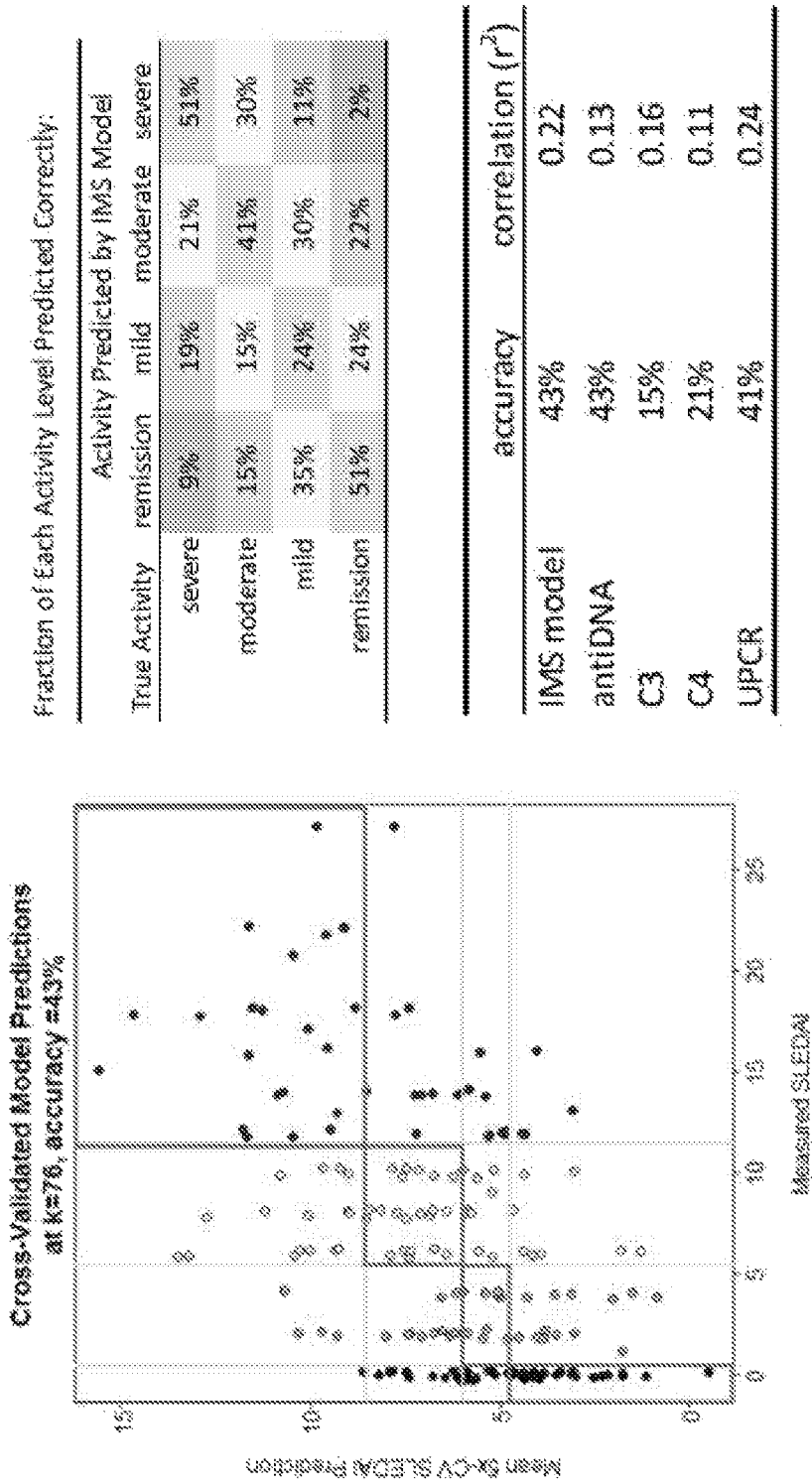
FIG. 56 shows the correlation of the predictive capacity of immunosignature (IMS) with measured SLEDAI score in patients in remission (inactive disease), mild, moderate and severe SLE in the plot on the left. The table at upper right tabulates the fraction of donors with four SLEDAI levels (remission, mild, moderate or severe) who are classified as remission, mild, moderate or severe by the IMS. Agreement between the classification is highlighted in green. The table at bottom right compares the accuracy of the IMS predictions and their correlation to SLEDAI to the accuracy and correlation of known biomarkers of SLEDAI: anti-dsDNA, C3, C4 and UPCR. The data exemplifies that immunosignature models can estimate SLEDAI scores as well or better than these standard biomarkers.
Figure 57A:
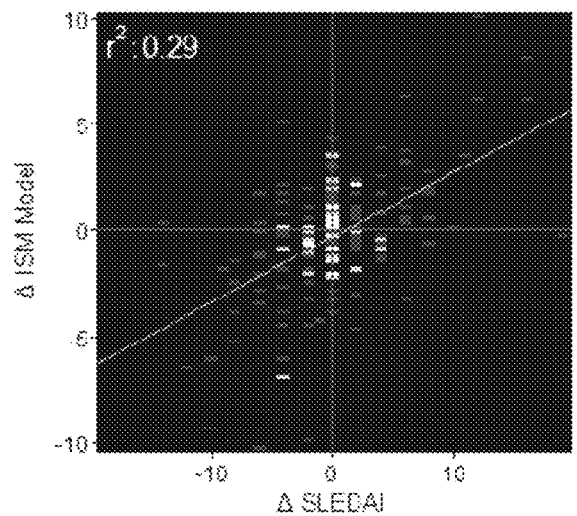
FIGS. 57A-57D show the correlation of changes in antibody binding immunosignature assayed in serum from pairs of blood draws from the same patient samples taken at different times (y-axis) to changes in SLEDAI over the same time (x-axis), for the immunosignature (IMS) (FIG. 57A), and three known SLEDAI biomarkers C3 (FIG. 57B), anti-dsDNA (FIG. 57C) and UPCR (FIG. 57D). This was done by fitting an elastic net model of changes in SLEDAI score against the peptide intensities obtained in the discriminating peptides. The data support that changes in antibody binding are more closely related to changes in SLEDAI than changes in other biomarkers.
Figure 57B:
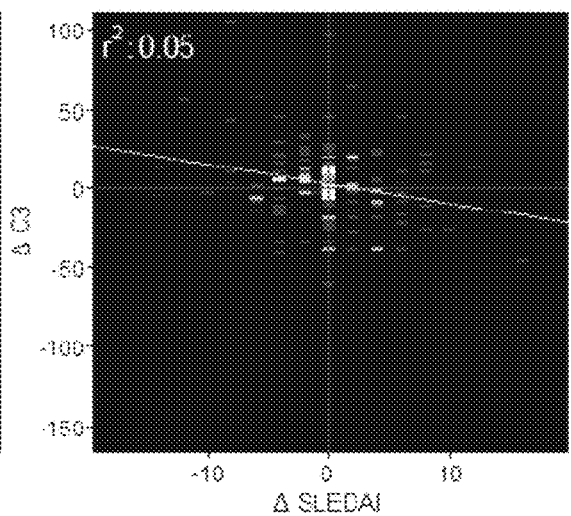
Figure 57C:
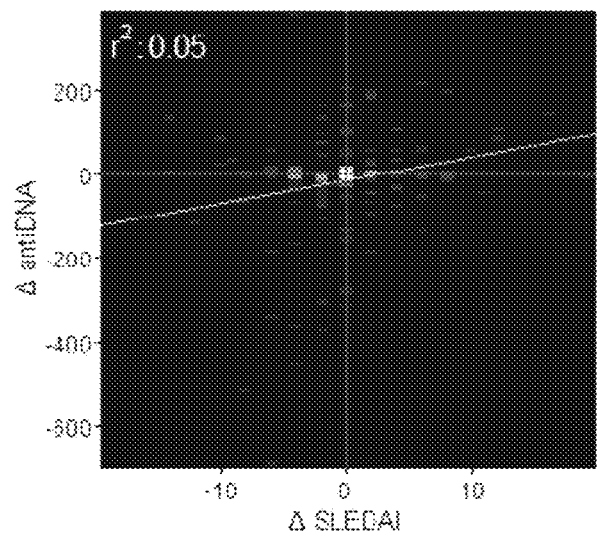
Figure 57D:
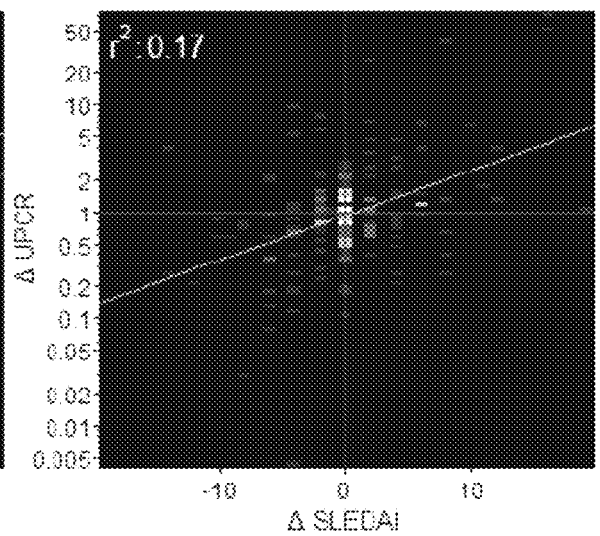

Discriminating peptides of immunosignature models were also shown to estimate SLEDAI score as well or better than standard SLEDAI biomarkers (FIG. 56). Predictions of a linear regression model of SLEDAI values trained using the elastic net technique. Cut points were selected to match the numbers of patients in the remission, mild, moderate and severe categories between the measured SLEDAI scores and the model predictions. Accuracy was calculated as the fraction of predictions that fall within the correct activity category. The fraction of total variance in common between the measured and predicted SLEDAI values was calculated as Pearson's correlation coefficient, squared, also known "coefficient of determination". Correlations of the immunosignature classifications, complement, and anti-dsDNA, C3, C4 and UPCR biomarkers to the SLEDAI scores were determined. The data demonstrates the accuracy of immunosignature models (IMS model) against several biomarkers, including antiDNA, C3, C4 and UPCR biomarkers. Longitudinal results in FIGS. 57A-57D supports that antibody binding in immunosignature models (ISM Model) are more closely related to changes in SLEDAI than changes in other currently used biomarkers, including C3, antiDNA and UPCR.

Figures 58A, 58B, 58C:
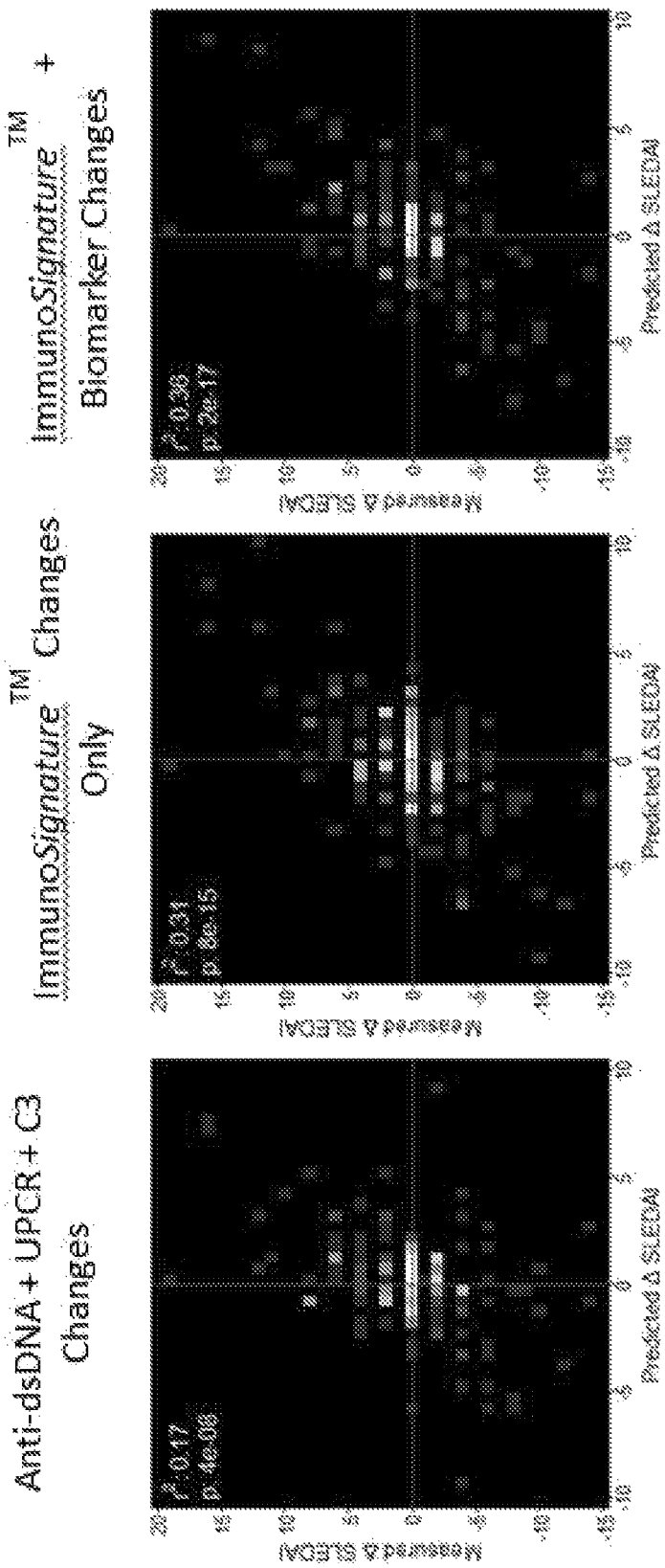
FIGS. 58A-58C show the correlation of changes in antibody binding immunosignature assayed in serum from pairs of blood draws from the same patient samples taken at different times (y-axis) to changes in SLEDAI over the same time (x-axis), for three models: on using the combined measurements of three known biomarkers, one with immunosignature (IMS) alone, and one with the IMS combined with the three biomarkers. The correlation between SLEDAI and the model predictions, $r^2$, is significantly higher for the IMS alone as compared to the three biomarkers, and higher when the IMS is combined with the biomarkers than with either the three markers or IMS alone.

FIGS. 58A-58C further demonstrates the improvement that an immunosignature adds to biomarker predictive capacity, and vice versa. Changes in biomarkers between physician visits are often used to monitor a patient's disease activity. Elastic net models of changes in SLEDAI scores were fit using changes in peptide intensities, and/or changes in anti-dsDNA, UPCR and C3 biomarkers, between successive blood draws (n=167). While as above, changes in antibody binding as seen in immunosignatures (see FIG. 58B) provided a better substitute for changes in SLEDAI state than changes in biomarkers, either individually or combined (i.e., anti-dsDNA+UPCR+C3 (FIG. 58A), immunosignature assay also benefited in improved predictability when combined with biomarker changes. See FIG. 58C.

Figure 59:
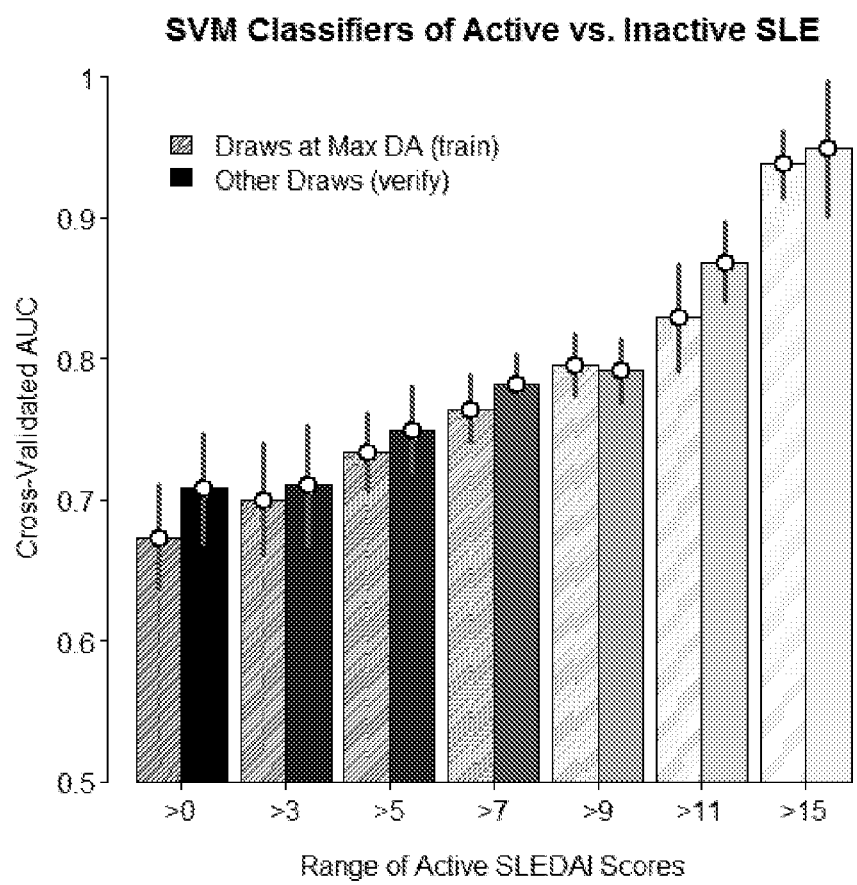
FIG. 59 further demonstrates the difference in immune response that increases with increasing SLEDAI scores, as compared to remission, using the same format used in FIG. 56. In this analysis, the blood draws for each donor have been divided into two groups: the blood draw taken when a donor's SLEDAI was at its maximum value during the study, and all the other blood draws. The models were trained on the former group (cross-hatches), then tested on the latter group (solid). In all cases, the performance on the latter group, by AUC, falls within the 95% confidence intervals of the training group.

FIG. 59 further demonstrates the difference in immune response that increases with increasing SLEDAI scores, as compared to remission. In this study, trained support vector machine (SVM) classifers were employed to distinguish active from inactive disease. A series of models was trained with "active" defined by increasing SLEDAI threshold. This was in comparison to training only on the $1^{st}$ blood draw from each patient. A five-fold cross validation was used to control for overfit in the training set. The models were verified using other blood draws not used in training.

Conclusions:

A simple test that uses specific binding patterns of peripheral-blood antibodies on a peptide array can deliver a single, molecular determination of SLE disease activity. The data show that peptide arrays can differentiate patients by SLE activity. Patients with higher activity are easier to distinguish from remission, and ImmunoSignature model reveals both known and potentially novel lupus antigens, showed correlation to SLEDAI score. Changes in ImmunoSignature signals measured in longitudinal samples from patients showed stronger correlation to changes in SLEDAI score than changes in biomarkers currently used in SLEDAI assessments. Thus, high-throughput, highly multiplexed assays may improve patient activity classification as compared to traditional, single biomarker approaches.

Example 13—Identification of Biomarkers Correlated with SLEDAI

Peptides with signal intensities that are correlated to SLEDAI, and that show correlations between changes in peptide intensity and changes in SLEDAI in pairs of blood draws taken from the same patient at two visits (p<4e−7, all cases). For all donors, the Pearson correlation coefficient between the SLEDAI measured at the donor's first blood draw, and the log 10-transformed intensity of each peptide measured in the serum sample from the first draw was calculated for each peptide and a p-value was calculated assuming the correlation coefficients follow Student's t-distribution with n−2 degrees of freedom, where n is the number of donors.

For all donors, the Pearson correlation coefficient between the SLEDAI measured at the donor's blood draw where their highest SLEDAI score was observed, and the log 10-transformed intensity of each peptide measured in the serum sample from the same blood draw was calculated for each peptide and a p-value was calculated assuming the correlation coefficients follow Student's t-distribution with n−2 degrees of freedom, where n is the number of donors. In cases where the donor's highest SLEDAI was observed at multiple blood draws, the last of these draws was used. The Spearman rank correlation coefficient between changes in SLEDAI and differences in log 10-transformed intensities was calculated for each peptide across all the pairs of draws.

For all donors who had multiple blood draws, the change in their SLEDAI score since the previous draw was calculated for each pair of successive draws. Likewise, the differences between log 10-transformed peptide intensities between the measurements of serum samples from the corresponding blood draw pairs were calculated for each pair of blood draws from each patient. The Spearman rank correlation coefficient between changes in SLEDAI and differences in log 10-transformed intensities was calculated for each peptide across all the pairs of draws. A p-value was calculated assuming the correlation coefficients follow Student's t-distribution with n−2 degrees of freedom, where n is the number of draw-pairs.

A set of peptides was identified where the p-value for all three of these correlation methods was less than 0.05 after applying a Bonferroni adjustment for the 126,009 peptides tested, that is p<4e−7. These peptides were ranked by decreasing mean absolute correlation coefficient across the three methods.

Enriched sub-motifs, k-mers and gapped k-mers, were identified for subsequence lengths k of 1 to 7, within the combined list of correlated peptides. Only sub-motifs with at least two occurrences in the list were considered. The list of sub-motifs was trimmed to include only peptides where the p-value was <0.05 after applying the Holm correction for multiplicity. This is more stringent than the FDR approach of Benjamini-Hochberg.

FIGS. 60A-60G shows the peptide submotifs and amino acids that are enriched in the peptides that correlate SLE with SLEDAI score. In each of the tables of FIGS. 60A-60G:

"n"=the number of times the motif occurs in the top discriminating peptides;

n. lib=the number of times the motif occurs in the array library.

"enrich"=the fold enrichment of a motif in the top discriminating peptides relative to the number of times the motif occurs in the array library.

P is the likelihood of observing a greater enrichment of a motif in the top discriminating peptides compared to the library as a whole by chance, by Fisher's exact test Fold enrichment=(no of times a motif (e.g. ABCD) occurs in the list divided by the number of times the motif (ABCD) occurs in the library)/(Total number of subsequencence i.e. the motif type (e.g. tetramer) occurs in the list/over total number of subsequences of the same type i.e. the motif type (e.g. tetramers) in library). Percent enrichment is "enrichment"×100.

FIG. 61 shows a table listing the top 50 of the 702 significant peptides that correlate with SLEDAI scores. The significant peptides were aligned to a human proteome as described. In FIG. 61: r.Ein.1$^{st}$=Pearson correlation coefficient (r) between the SLEDAI scores and the normalized log-transformed intensity of the peptide, both measured at each donor's first blood draw;

p.Ein. 1$^{st}$=p-value of r.Ein.1st; probability that greater or equal correlation could have arisen by chance;

r.Ein.max=Pearson correlation coefficient (r) between the SLEDAI scores and the normalized log-transformed intensity of the peptide, both measured at each donor's blood draw with the maximum SLEDAI score;

p.Ein.max=p-value of r.Ein.max; probability that greater or equal correlation could have arisen by chance;

r.Ein.chng=Pearson correlation between differences in SLEDAI scores and differences in normalized, log-transformed intensities of all pairs of blood draws from the same patient;

p.Ein.chng=p-value of r.Ein.chng probability that greater or equal correlation could have arisen by chance;

mean.r=mean of r.Ein.1st, r.Ein.max and r.Ein.chng;

min.r2=minimum of r.Ein.1st squared, r.Ein.max squared and r.Ein.chng squared.

Peptides were selected for inclusion in this list if p.Ein.1st, p.Ein.max and p.Ein.chng were all <4e−7 (5% chance of being a false positive after Bonferroni correction). The peptides are ordered by decreasing values of min.r2.

The significant peptides were aligned to a human proteome. Peptides were aligned to 20mer segments of the proteome, and an overlap score was calculated. Proteins identified by the alignments were ranked relative to proteins identified by aligning randomly chosen peptides present of the array as described in Example 6. A partial list showing the top 50 of the candidate biomarkers identified according to the method is provided in Table 11.

TABLE 11

| HTN3 | CLLU1OS | RPS27A | HEYL | IQCF3 |
|---|---|---|---|---|
| H2BFM | CDC42EP2 | RPS26 | RP11-51L5.7 | JDP2 |
| NRGN | PPP1R11 | HEXIM2 | U2AF1 | IL33 |
| C1orf115 | SCG5 | NBPF15 | FAU | AVPI1 |
| HTN1 | TGIF2-C20or | DENR | C10orf99 | SLC16A11 |
| S100Z | UTS2 | XCR1 | NUS1 | BATF3 |
| H2BFWT | GDPD1 | RPL36 | FRG2 | TCEAL8 |
| VCX2 | POP4 | GJB3 | C1orf204 | UBE2QL1 |
| VCX | HEXIM1 | PTMS | MRPS33 | TRBV18 |
| LCE1A | NFYA | RELL1 | NHP2 | PMP22 |
| RPL39L | ARL4C | AC004556.1\n | IGFBP5 | RPL24 |
| TNP1 | HIST1H4A | NXNL1 | CDR1 | RFXAP |
| VCX3A | HIST1H4I | SPIN3 | NACA2 | MS4A4E |
| DAQB-331|12.1 | HIST1H4 | CLEC3A | FAM104 | MRPL15 |
| PROK2 | HIST1H4K | PNRC2 | VEGFA | SHFM1 |
| RPL39 | HIST2H4 | AGTRAP | TAS2R5 | SSR1 |
| CTB-96E2.2\n | HIST1H4F | GATA1 | CXCL9 | FAM174A |
| CCER1 | HIST1H4J | HIST3H2B | C19orf24 | AC011530.4\n |
| PRR13 | HIST1H4L | SPIN4 | TRAT1 | C5orf67 |
| CCL28 | HIST1H4H | AL109927.1\n | LCE4A | ELOF1 |
| VCX3 | HIST1H4D | PDE6H | HTR1E | AC064829.1\n |
| TP53TG3 | HIST2H4A | MEIS1 | HDGFL1 | LIN28A |
| GSX1 | HIST4H4 | C8orf44 | ZNF593 | IGFBP7 |
| AC008686.1\n | HIST1H4E | TEX261 | BMP2 | CCL26 |
| POU2AF1 | HIST1H4C | TOMM20L | NBPF12 | ASIP |
| DDIT3 | SMKR1 | RBM8A | VTN | H2BFS |
| MRPL41 | SLAMF9 | RPS27 | EIF1AY | MRPL36 |
| WFDC13 | RP11-77K12. | RPS8 | FAM72A | COX7A2 |
| GJB2 | TWIST2 | U2AF1L5 | LCNL1 | AEN |
| INSL4 | LCE3E | H2AFB3 | DBI | FAM181 |

TABLE 11-continued

| | | | | |
|---|---|---|---|---|
| AREG | LCE1C | H2AFB2 | FAM204A | LCE2D |
| LCE1F | LCE1D | H2AFB1 | RHOXF1 | ZMAT5 |
| C5orf24 | LCE1 | C11orf87 | NBPF19 | HOXB4 |
| C1orf234 | CCDC3 | TMEM236 | FAM64A | PPP1R16 |
| APLN | VSTM5 | IKZF5 | EIF1AX | ZNF428 |
| SLC10A6 | C14orf37 | SCML1 | PCP4L1 | FXYD2 |
| HBEGF | HEY2 | TWIST1 | FAM132 | DEFB118 |
| MPZL3 | NANOGN | CENPW | LDB1 | NODAL |
| CCDC179 | TMEM100 | EMC6 | LCE1E | LCE3C |
| CXCL17 | TCF21 | LCE3D | MYPOP | UCMA |

Example 14—Immunosignature Methods for Identifying Biomarkers of Autoimmune Diseases Immunosignature assays were used to differentiate autoimmune diseases (AI): Systemic Lupus Erythematosus (SLE) and Rheumatoid Arthritis (RA) from other autoimmune and mimic diseases including Osteoarthritis (OA), Sjogrens' disease (SS), Fibromyalgia (FM).

Donor Samples.

Donor plasma samples were obtained from the Albert Einstein College of Medicine (Bronx, N.Y.). A well-annotated cohort of 400 serum samples was prospectively collected for this study and included SLE (n=75), RA (n=95), Sjogren's (SS) (n=20), Osteo Arthritis (OA) (n=24), Fibromyalgia (n=22), other disease (OD) (n=76), "All Diseases" (AD) (n=237); "Other Rheumatic Diseases" (ORD) (n=144), and healthy controls (HC) (n=59).

Other Autoimmune Diseases and non-autoimmune mimic diseases (OD or Other AI) (n=76): ANCA Vasculitis (2), CIA (4), CNS Vasculitis, Dermatomyositis (6), Discoid Lupus, DMPM (3), DMPM/MCTD, GCA (2), Gout (9), Lupus (4), MCTD (9), Myositis (5), Overlap, Polyarticular Gout, Polychondritis, Polymyositis, Pseudogout, Psoriatic Arthritis (11), Scleroderma (7), Serospon (2), and Vasculitis (4). For SLE, the Other AI+non-AI mimic diseases further include fibromyalgia/RA, lupus/RA, OA/RA/serspon, RA/serspon, RA, and RAVASC. For RA, the Other AI+non-AI mimic diseases further include fibromyalgia/SLE, MCTD/SLE, SLE/MCTD, SLE/scleroderma, and SLE/SS.

"Other Rheumatic Diseases" (ORD) (n=144): SLE, SS, OA, psoriatic arthritis (11), gout (9), seronegative spondyloarthropathy (2), pseudogout (1). Subjects with rheumatological diseases were diagnosed based on ACR criteria.

The "Not" group for SLE are samples of Other AI+non-AI mimic diseases+HC i.e. AI diseases other than SLE plus HC.

The "Not" group for RA are samples of Other AI+non-AI mimic diseases+HC i.e. AI diseases other than RA plus HC.

The "Mixed SLE and Other AI" and the "Mixed RA and Other AI" group indicated in FIG. 72 and FIG. 85, respectively represent a combination os samples from subjects with a mixed diagnosis and samples from subjects with other AI and/or mimic diseases: CIA/OA, gout/OA, OA/RA, OA/RA, OA/RA/serspon/DMPM/FM/SLE/scleroderma/DMPM/SLE, lupus/RA/MCTD/SLE, FM/lupus, FM/OA, FM/RA, FM/SLE, RA/serspon, RA/SLE, RA/SS, RA/vasc., SLE/MCTD, SLE/RA, SLE/scleroderma, SLE/SS, ANCA vasculitis, CIA, CNS vasculitis, dermatomyositis, Discoid lupus, DMPM, DMPM/MCTD, GCA, gout, lupus, MCTD, myositis, overlap, polyarticular gout, polychondritis, polymyositis, pseudogout, psoriatic arthritis, scleroderma, serospon, and vasculitis.

Samples were mixed 1:1 with ethylene glycol as a cryoprotectant and aliquoted into single use volumes. Single use aliquots were stored at −20° C. until needed. In each case, the remaining sample volume was stored neat at −80° C. Identities of all samples were tracked using 2D barcoded tubes (Micronic, Leystad, the Netherlands). In preparation for assay, sample aliquots were warmed on ice to 4° C. and diluted 1:100 in primary incubation buffer (Phosphate Buffered Saline with 0.05% Tween 20 (PBST) and 1% mannitol). Microtiter plates containing the 1:100 dilutions were then diluted to 1:625 for use in the assay.

Arrays. A combinatorial library of 126,009 peptides with a median length of 9 residues and range from 5 to 13 amino acids was designed to include 99.9% of all possible 4-mers and 48.3% of all possible 5-mers of 16 amino acids (methionine, M; cysteine, C; isoleucine, I; and threonine, T were excluded). These were synthesized on an 200 mm silicon oxide wafer using standard semiconductor photolithography tools adapted for tert-butyloxycarbonyl (BOC) protecting group peptide chemistry (Legutki J B et al., Nature Communications. 2014; 5:4785). Briefly, an aminosilane functionalized wafer was coated with BOC-glycine. Next, photoresist containing a photoacid generator, which is activated by UV light, was applied to the wafer by spin coating. Exposure of the wafer to UV light (365 nm) through a photomask allows for the fixed selection of which features on the wafer will be exposed using a given mask. After exposure to UV light, the wafer was heated, allowing for BOC-deprotection of the exposed features. Subsequent washing, followed the by application of an activated amino acids completes the cycle. With each cycle, a specific amino acid was added to the N-terminus of peptides located at specific locations on the array. These cycles were repeated, varying the mask and amino acids coupled, to achieve the combinatorial peptide library. Thirteen rectangular regions with the dimensions of standard microscope slides, were diced from each wafer. Each completed wafer was diced into 13 rectangular regions with the dimensions of standard microscope slides (25 mm×75 mm). Each of these slides contained 24 arrays in eight rows by three columns. Finally, protecting groups on the side chains of some amino acids were removed using a standard cocktail. The finished slides were stored in a dry nitrogen environment until needed. A number of quality tests are performed ensure arrays are manufactured within process specifications including the use of 3G statistical limits for each step. Wafer batches are sampled intermittently by MALDI-MS to identify that each amino acid was coupled at the correct step, ensuring that the individual steps constituting the combinatorial synthesis are correct. Wafer manufacturing is tracked from beginning to end via an electronic custom Relational Database which is written in Visual Basic and has an access front end with an SQL back end. The front-end user interface allows operators to enter production info into the database with ease. The SQL backend allows us a simple method for database backup and integration with other computer systems for data share as needed. Data typically tracked include chemicals, recipes, time and technician performing tasks. After a wafer is produced the data is reviewed and the records are locked and stored. Finally, each lot is evaluated in a binding assay to confirm performance, as described below.

Assay.

Production quality manufactured microarrays were obtained and rehydrated prior to use by soaking with gentle agitation in distilled water for 1 h, PBS for 30 min and primary incubation buffer (PBST, 1% mannitol) for 1 h. Slides were loaded into an ArrayIt microarray cassette (ArrayIt, Sunnyvale, Calif.) to adapt the individual microarrays to a microtiter plate footprint. Using a liquid handler, 90 µl of each sample was prepared at a 1:625 dilution in primary incubation buffer (PBST, 1% mannitol) and then transferred to the cassette. This mixture was incubated on the arrays for 1 h at 37° C. with mixing on a TeleShake95 (INHECO, Martinsried, Germany) to drive antibody-peptide binding. Following incubation, the cassette was washed 3× in PBST using a BioTek 405TS (BioTek, Winooski, Vt.). Bound antibody was detected using 4.0 nM goat anti-human IgG (H+L) conjugated to AlexaFluor 555 (Thermo-Invitrogen, Carlsbad, Calif.), or 4.0 nM goat anti-human IgA conjugated to DyLight 550 (Novus Biologicals, Littleton, Colo.) in secondary incubation buffer (0.5% casein in PBST) for 1 h with mixing on a TeleShake95 platform mixer, at 37° C. Following incubation with secondary antibody, the slides were again washed with PBST followed by distilled water, removed from the cassette, sprayed with isopropanol and centrifuged dry. Quantitative signal measurements were obtained by determining a relative fluorescent value for each addressable peptide feature as described below.

Data Acquisition.

Assayed microarrays were imaged using an Innopsys 910AL microarray scanner fitted with a 532 nm laser and 572 nm BP 34 filter (Innopsys, Carbonne, France). The Mapix software application (version 7.2.1) identified regions of the images associated with each peptide feature using an automated gridding algorithm. Median pixel intensities for each peptide feature were saved as a tab-delimitated text file and stored in a database for analysis.

Data Analysis.

Feature intensities were $\log_{10}$ transformed after adding a constant value of 100 to improve homoscedasticity. The intensities on each array were normalized by subtracting the median intensity of the combinatorial library features for that array and adding back the grand median across all samples.

The binding of plasma antibodies to each feature was measured by quantifying fluorescent signal. Peptide features that showed differential signal between groups were determined by t-test of mean peptide intensities with the Welch adjustment for unequal variances. Binding of antibodies in samples from subjects with a first condition were compared to the binding of antibodies in reference samples from subjects having a different second condition, and peptides showing significantly differential signal were identified. A set of peptides that discriminated the first condition from other conditions was identified by comparing mean intensities among patients having the first condition to the mean intensities among subjects with a second, a third, a fourth etc. condition. Peptides that showed significant discrimination i.e. discriminating peptides, were identified based on 5% threshold for false positives after applying the Bonferroni correction for multiplicity (i.e., p<4e−7).

Figure 3:
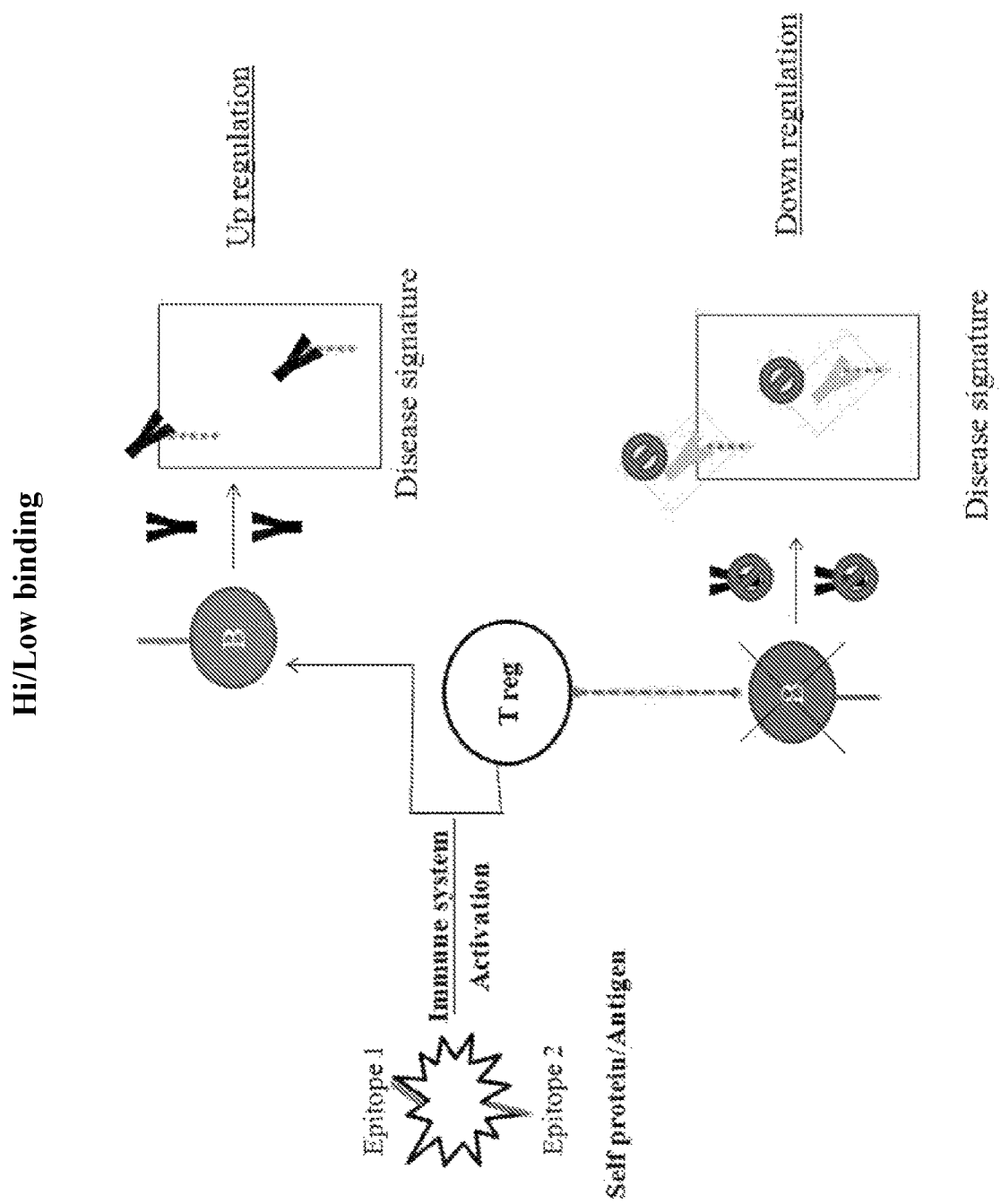
FIG. 3 shows a pathway demonstrating how a self protein/antigen can lead to up-regulation and down-regulation of an immunosignature in peptide microarrays.

To construct a classifier, features of discriminating peptides were ranked for their ability to differentiate a first condition from a second condition based on the p value associated with a Welch's t-test comparing the first condition to the second, or between the different conditions in a multi-disease model. The number of peptides selected for analysis can vary from less than 10 to more than hundreds or thousands varied and each of the selected peptide features was input to a support vector machine (Cortes C, and Vapnik V. Machine Learning. 1995; 20(3):273-97) with a linear kernel and cost parameter of 0.01 to train a classifier. A five-fold cross validation was repeated 100 times and was used to quantify model performance, estimated as the error under the receiver-operating characteristic curve (AUC) (FIG. 3).

Finally, a fixed SVM classifier was fit in the cohort using the optimal number of features based on performance under cross-validation, selected by their t-test p-values. The SVM classifier was used in assessing reproducibility of the platform.

All analyses were performed using R version 3.2.5. (Team RC. R: A language and environment for statistical computing. R Foundation for Statistical Computing Vienna 2016. Available from: https://www.R-project.org/.)

Peptide Alignment Scoring.

Library peptides were aligned to the human proteome RefSeq release 84, corresponding to human genome build GrCh38 (https://www.ncbi.nlm.nih.gov/refseq/), compiled Mar. 10, 2016, using the longest transcript variant for each unique gene ID. Peptides were aligned to overlapping 20 mer portions of proteome sequences; the overlap was of 10mer.

The alignment algorithm used a modified BLAST strategy [Altschul S F and Gish W (1996) Methods Enzymol 266: 460-480], requiring a seed of 3 amino acids, a gap penalty of 4 amino acids, and a scoring matrix of BLOSUM62 [Henikoff and, Henikoff J G (1992) Proc Natl Acad Sci USA 89: 10915-10919] modified to reflect the amino acids composition of the array [States D J et al., (1991) Methods 3: 66-70]. These modifications increase the score of similar substitutions, remove penalties for amino acids absent from the array and score all exact matches equally.

To generate an alignment score for a set of discriminating library peptides, peptides that yielded a positive BLAST score were assembled into a matrix, with each row of the matrix corresponding to an aligned peptide and each column corresponding to one of the amino acids in the protein's sequence. Gaps and deletions were permitted within the peptide rows for alignment to the protein. In this way, each position in the matrix received a score associated with the aligned amino acid of the peptide and protein. Each column, corresponding to an amino acid in the protein, was then summed to create an overlap score; this represents coverage of that amino acids position by the classifying peptides. To correct this score for library composition, another overlap score was calculated using an identical method for a list of all array peptides. This allows for the calculation of a peptide overlap difference score, s, at each amino acids position according to the following equation:

$$s = a - (b/d)*c$$

In this equation, a is the overlap score from the discriminating peptides, b is the number of discriminating peptides, c is the overlap score for the full library of peptides and d is the number of peptides in the library.

To convert these s scores (which were at the amino acids level) to a full-protein statistic, the sum of scores for every possible tiling 20-mer epitope within a protein is calculated. The final protein score, also known as protein epitope score, S, is the maximum along this rolling overlapping windows of 20 for each protein. A similar set of scores was calculated for 100 iterative-rounds of randomly selecting peptides from the library, equal in number to the number of discriminating peptides. The p-value for each score, S, is calculated based on the number of times this score is met or exceeded among proteins identified based on alignments of the randomly selected peptides, controlling for the number of iterations.

The top 25 candidate biomarkers identified from alignments of discriminating peptides that were determined to distinguish samples from subjects having SLE from samples from healthy subjects (HC), Other AI+non-AI mimic diseases, and Not SLE are shown in FIGS. 75A-75C, and the top 25 candidate biomarkers identified from alignments of discriminating peptides that were determined to distinguish samples from subjects having RA from samples from healthy subjects (HC), Other AI+non-AI mimic diseases, and Not RA, are shown in FIGS. 87A-87C, respectively. The candidate biomarkers are listed according to alignment scores.

Example 15—Differential Diagnosis of SLE

Immunosignatures for differentiating subjects in a group of subjects having SLE alone and SLE in patients with mixed diagnosis from different groups of subjects including healthy controls (HC), "All Disease" (AD), subjects with RA, subjects with OA, subjects with Fibromyalgia (FM), and subjects with Sjogrens. The "All Diseases" comprises non-SLE AI diseases and non-AI mimic diseases.

Immunosignature assays were performed as described in Example 14 and scanned to acquire signal intensity measurements at each feature. Peptide features that showed differential signal between groups were determined by t-test of mean peptide intensities with the Welch adjustment for unequal variances. A binary classifier was developed for each of the contrasts.

Table 12 shows the results for the assay performance for each of the contrasts as AUC values.

TABLE 12

Assay performance for discrimination of SLE

| Contrast | # Samples | Significant Peptides | cvAUC (95% CI) |
|---|---|---|---|
| SLE vs. HC | 134 | 5,121 | 0.90 (0.88-0.92) |
| SLE vs. Other AI + non-AI mimic | 312 | 684 | 0.79 (0.77-0.81) |
| SLE vs. RA | 170 | 201 | 0.80 (0.76-0.85) |
| SLE vs. OA | 99 | 455 | 0.88 (0.86-0.91) |
| SLE vs. Fibromyalgia | 97 | 464 | 0.83 (0.78-0.87) |
| SLE vs. Sjögren's | 95 | 0 | 0.65 (0.60-0.70) |
| SLE vs. Not SLE | 400 | 2042 | 0.81 0.79-0.83) |

Significant Peptides that discriminated SLE from each of groups were found to be enriched in some amino acids and peptide motifs. FIGS. 62A-68B show the motifs (A) and amino acids (B) that were enriched in a portion of the discriminating significant peptides in each of the contrasts. The total number of significant i.e. discriminating, peptides identified in the contrasts is indicated in each of the figures. In each of the tables of FIGS. 62A-68B:

"n"=the number of times the motif occurs in the top discriminating peptides;

n. lib=the number of times the motif occurs in the array library

"enrich"=the fold enrichment of a motif in the top discriminating peptides relative to the number of times the motif occurs in the array library.

P=the statistical significance of the occurrence of a motif in the top discriminating peptides Fold enrichment=(no of times a motif (e.g. ABCD) occurs in the list/no of times the motif (ABCD) occurs in the library)/(Total no the motif type (e.g. tetramer) occurs in the list/over total no the motif type (e.g. tetramers) in library). Percent enrichment is "enrichment"×100.

FIGS. 62A-62B shows the peptide motifs (FIG. 62A) and amino acids (FIG. 62B) that are enriched in the peptides that discriminate between the SLE samples from the healthy donor (HC) samples. Comparisons of signal binding data obtained from samples from SLE subjects to binding data from HC group identified peptides that discriminated the SLE samples from the HC group were enriched by greater than 4.2 fold (420%) in one or more motifs listed in FIG. 62A relative to the incidence of the same motifs in the entire peptide library. Additionally, peptides that discriminated SLE samples from HC samples were found to be enriched by greater than 1 (100%) fold in individual amino acids (FIG. 62B).

FIGS. 63A-63B shows the peptide motifs (FIG. 63A) and amino acids (FIG. 63B) that are enriched in the peptides that discriminate between the SLE samples from Other AI+non-AI mimic diseases. Diseases group were enriched by greater than 4.9 fold (490%) in one or more motifs listed in FIG. 63A relative to the incidence of the same motifs in the entire peptide library. Additionally, peptides that discriminated SLE samples from HC samples were found to be enriched by greater than 1.1 (110%) fold in individual amino acids (FIG. 63B).

FIGS. 64A-64B shows the peptide motifs (FIG. 64A) and amino acids (FIG. 64B) that are enriched in the peptides that discriminate between the SLE samples from the "Not SLE" group of samples. Comparisons of signal binding data obtained from samples from SLE subjects to binding data from the "not SLE" group identified peptides that discriminated the SLE samples from the "Not SLE" group were enriched by greater than 5 fold (500% enrichment) in one or more motifs listed in FIG. 64A relative to the incidence of the same motifs in the entire peptide library. Additionally, peptides that discriminated SLE samples from "Not SLE" samples were found to be enriched by greater than 1.00 fold (100% enrichment) in individual amino acids (FIG. 64B).

FIGS. 65A-65B shows the peptide motifs (FIG. 65A) and amino acids (FIG. 65B) that are enriched in the peptides that discriminate between the SLE samples from the RA group of samples. Comparisons of signal binding data obtained from samples from SLE subjects to binding data from HC group identified peptides that discriminated the SLE samples from the RA group were enriched by greater than 3.5 fold (360%) in one or more motifs listed in FIG. 65A relative to the incidence of the same motifs in the entire peptide library. Additionally, peptides that discriminated SLE samples from RA samples were found to be enriched by greater than 1.2 (120%) fold in individual amino acids (FIG. 65B).

FIGS. 66A-66B shows the peptide motifs (FIG. 66A) and amino acids (FIG. 66B) that are enriched in the peptides that discriminate between the SLE samples from the OA group of samples. Comparisons of signal binding data obtained from samples from SLE subjects to binding data from OA group identified peptides that discriminated the SLE samples from the OA group were enriched by greater than 3.8 fold (380%) in one or more motifs listed in FIG. 66A relative to the incidence of the same motifs in the entire peptide library. Additionally, peptides that discriminated SLE samples from OA samples were found to be enriched by greater than 1.2 (120%) fold in individual amino acids (FIG. 66B).

FIGS. 67A-67B shows the peptide motifs (FIG. 67A) and amino acids (FIG. 67B) that are enriched in the peptides that discriminate between the SLE samples from the FM group of samples. Comparisons of signal binding data obtained from samples from SLE subjects to binding data from FM group identified peptides that discriminated the SLE samples from the FM group were enriched by greater than 5 fold (500%) in one or more motifs listed in FIG. 67A relative to the incidence of the same motifs in the entire peptide library. Additionally, peptides that discriminated SLE samples from FM samples were found to be enriched by greater than 1.1 (110%) fold in individual amino acids (FIG. 67B).

FIGS. 68A-68B shows the peptide motifs (FIG. 68A) and amino acids (FIG. 68B) that are enriched in the peptides that discriminate between the SLE samples from the SS group of samples. Comparisons of signal binding data obtained from samples from SLE subjects to binding data from SS group identified peptides that discriminated the SLE samples from the SS group were enriched by greater than 4.2 fold (420%) in one or more motifs listed in FIG. 68A relative to the incidence of the same motifs in the entire peptide library. Additionally, peptides that discriminated SLE samples from SS samples were found to be enriched by greater than 1.3 (130%) fold in individual amino acids (FIG. 68B).

A volcano plot was used to assess the discrimination between samples as the joint distribution of t-test p-values versus log differences in signal intensity means (Fold Change). The density of the peptides at each plotted position is indicated by the heat scale. The peptides above the green dashed line were chosen as discriminating peptides that distinguish between the two groups of each comparison by immunosignature with 95% confidence after applying a Bonferroni adjustment for multiplicity (shown as green line in FIGS. 69A-69C). The Volcano plots show that the majority of the discriminating peptides displayed lower binding intensities in the All SLE group. FIGS. 69A, 69B, and 69C respectively show volcano plots of the median-normalized array peptide intensities.

The Welch's t-test identified the significant peptides, which are individual peptides that had significant differences in mean signal between the samples from the SLE group of subjects and the samples from each of the contrast groups. For example, shown in FIG. 69, the Welch's t-test identified 5121 individual peptides that had significant differences in mean signal between the samples from the SLE group of subjects and the samples from the group of healthy donors (A); 684 significant features that displayed differences between SLE group of subjects and the group of subjects having Other AI+non-AI mimic diseases (B); and 2042 significant features that displayed differences between SLE group of subjects and the group of subjects not having SLE i.e. "Not SLE". Peptides that passed the Bonferroni cut-off in each of eh contrasts are shown in FIG. 70. 478 peptides are common to all contrasts. These 478 peptides comprise two-thirds of the SLE v Other AI+non-AI mimic disease (indicated as "Other AI") contrast, which indicates that these peptides may uniquely identify SLE from similar disorders.

A support vector machine (SVM) classifier was developed for each of the contrasts. Under cross-validation, the best performance (AUC) was determined achieved when the top k peptides, as ranked by Welch t-test were input to the model, where k is allowed to vary between 25 and 10,000 features. FIG. 71 shows the performance of the assay after 100 iterations of five-fold cross validation models, using the top k peptides within each contrast. The optimal k was selected as that k with the highest AUC although AUC itself is very consistent over a wide range of sample sizes. A binary classifier was developed for each of the contrasts. The graph shown in FIG. 71 shows an example that the optimum size of input peptides for each contrast model can be large. For example, the size of input peptides for the contrast of SLE v (HC) was 10000. The graphs also show that the AUCs do not change significantly with increasing number of input peptides.

Support vector machine (SVM) models were used to identify combinations of peptides that can predict the likelihood of SLE versus healthy individuals or other similar diseases. Up to 4000 peptides, as ranked by p-value, were used as SVM inputs. 100 iterations of 5-fold cross-validation minimized the possibility of over-fitting. The histogram in FIG. 72 indicates the area under the receiver operating characteristic curve (AUC) for discriminating between SLE and the listed subgroup: healthy donors (HC), Other AI and non-AI mimic disease ("Other AI"), and the Not SLE group (Other AI+non-AI mimic+HC). The AUC of 0.9 for SLE vs healthy suggests robust discrimination in a diagnostic setting. Discrimination between and SLE and similar diseases can be more difficult, likely because of overlapping etiology and manifestation.

FIG. 73 shows a histogram representing the assay performance in distinguishing SLE from RA, Sjogrens, OA, and FM.

A Multi=class model i.e. simultaneous discrimination of one disease from a group of the remaining related diseases is shown in FIG. 74, yielding AUCs and predictions for these differential diagnoses.

These data show that SLE samples can be discriminated from healthy samples with an AUC of 0.9. These data also show that SLE was easily distinguished from non-autoimmune disease (OA and Fibromyalgia) and from Sjogren's. Additionally, the data also show that SLE can be distinguished from samples of patients having Other AI+non-AI mimic diseases.

Thus, the immunosignature (IS) technology can be used to classify subjects with SLE from healthy controls or subjects with diseases that have common symptoms or underlying immunological dysregulation.

Example 16—Proteome Mapping the SLE-Classifying Peptides Identifies Candidate Biomarkers of SLE Significant discriminating peptides identified by the contrasts described in Example 2 were used to identify candidate biomarkers.

Significant peptides associated with SLE were mapped to putative antigens that included a known immunogenic epitope of SSB.

The library peptides that significantly distinguished SLE from healthy subjects, Other AI+non-AI mimic diseases, and "Not SLE" subjects were aligned to the human proteome RefSeq release 84, corresponding to human genome build GrCh38 (https://www.ncbi.nlm.nih.gov/refseq/), compiled Mar. 10, 2016, using the longest transcript variant for each unique gene ID, with a modified BLAST algorithm and scoring system that used a sliding window of overlapping 20-mers (Example 14). The top 50 significant peptides that discriminate between the SLE samples from the healthy (HC) group of samples are shown in FIG. 90; the top 50 significant peptides that discriminate between SLE samples from the Other Autoimmune and non-Autoimmune mimic diseases (Other AI+non-AI) group of samples are shown in FIG. 91; and the top significant peptides that discriminate between the SLE samples from the Not SLE (Not SLE— Other AI+non-AI+HC) group of samples are shown in FIG. 92.

Peptides were aligned to 20mer segments of the proteins overlapping by 10 mer as described in Example 14. The resulting ranked list of the top 25 candidate biomarkers protein-target regions provided in FIGS. 75A-75C. The gene name/epitope start—alignment scores are provided. These classifying peptides display a high frequency of alignment scores that greatly exceed the maximum scores obtained by performing the same analysis with ten equally-sized sets of peptides that were randomly selected from the library.

Among the top-scoring candidates mapped by the SLE classifying peptides was the surface membrane translocated La/SSB antigen. Notably, the known and clinically used SLE autoantigen SSB is highly ranked on each list. Specifically, one of three immunodominant epitopes, contained in the amino acids at positions 340-360, is identified. The SSB autoantigen maps to amino acids 340-360 of the immunodominant epitope of the intracellular human La protein, which is redistributed from the nucleus to the cell surface, following loss of the nuclear localization signal, during apoptosis [Neufing et al. (2005), Exposure and binding of selected immunodominant La/SSB epitopes on human apoptotic cells. Arthritis & Rheumatism, 52: 3934-3942. doi: 10.1002/art.21486] (FIGS. 75A-75C).

Other top scoring candidate biomarkers mapped by the SLE discriminating peptides included histone proteins. Histones are important target antigens of nuclear antibodies, and anti-nuclear antibodies (ANA), and anti-histone antibody tests are typically performed in detecting autoantibodies that are relevant to the diagnosis of SLE [Manson and Rahman (2006), Systemic Lupus Erythematosus. Orphanet Journal of Rare Diseases 1:6. doi 10.1186/1750-1172-1-6] (FIGS. 75A-75C).

Another top scoring candidate biomarker mapped by the SLE discriminating peptides was identified as the HMGN https://www.ncbi.nlm.nih.gov/pubmed/8318042?dopt=Abstract.

Together the 25 candidate proteome targets in each contrast accounted for the aligned discriminating peptides. Leading candidate biomarkers can also be identified by up to all of the total number of discriminating peptides.

These data show that array peptides that mimic SLE autoantigen epitopes were bound differentially by peripheral blood antibodies in SLE subjects. These discriminating peptides were mapped to several known markers of SLE. Other listed candidate targets could be novel markers of SLE.

Example 17—Differential Diagnosis of RA

Immunosignatures (IS) were obtained for differentiating subjects in a group of RA subjects having RA from groups of subjects including healthy controls (HC), subjects having other rheumatic diseases (ORD), SLE, OA, Fibromyalgia (FM), Sjogrens (SS), a group of subjects with Other AI/non-AI mimic diseases, and Not RA subjects. The Other rheumatic Disease group (ORD) (239) consisted of: RA, SS, OA, psoriatic arthritis, gout, seronegative spondyloarthropathy, and pseudogout. Subjects with rheumatological diseases were diagnosed based on ACR criteria.

The assays were performed as described in Example 14 and scanned to acquire signal intensity measurements at each feature. Peptide features that showed differential signal between groups were determined by t-test of mean peptide intensities with the Welch adjustment for unequal variances, as described previously.

Table 13 shows the results for the assay performance for each of the contrasts as AUC values.

TABLE 13

Assay performance for discrimination of R

| Contrast | # Samples | Significant Peptides | cvAUC (95% CI) |
|---|---|---|---|
| RA vs. HC | 154 | 3,062 | 0.80 (0.78-0.83) |
| RA vs. other rheumatic diseases^ | 239 | 328 | 0.70 (0.66-0.74) |
| RA vs. SLE | 170 | 201 | 0.80 (0.76-0.85) |
| RA vs. OA | 119 | 130 | 0.73 (0.67-0.78) |
| RA vs. Fibromyalgia | 117 | 753 | 0.78 (0.73-0.83) |
| RA vs. SS | 115 | 20 | 0.66 (0.60-0.73) |
| RA vs. Other AI + nonAI mimic | 341 | 742 | 0.70 (0.66-0.73) |
| RA vs. Not RA | 400 | 1564 | 0.70 (0.67-0.72) |

^Other rheumatic diseases = SLE, SS, OA, psoriatic arthritis, gout, pseudogout, serospan Significant Peptides that discriminated RA from each of groups were found to be enriched in some amino acids and peptide motifs. FIGS. 76A-82B show the motifs (A) and amino acids (B) that were enriched in a portion of the discriminating significant peptides in each of the contrasts. The total number of significant peptides is indicated in each of the figures.

FIGS. 76A-76B show the peptide motifs (FIG. 76A) and amino acids (FIG. 76B) that are enriched in the peptides that discriminate between the RA samples from the healthy donor (HC) samples. Comparisons of signal binding data obtained from samples from SLE subjects to binding data from HC group identified peptides that discriminated the SLE samples from the HC group were enriched by greater than 4.6 fold (460%) in one or more motifs listed in FIG. 76A relative to the incidence of the same motifs in the entire peptide library. Additionally, peptides that discriminated SLE samples from HC samples were found to be enriched by greater than 1 (100%) fold in individual amino acids (FIG. 76B).

FIGS. 77A-77B show the peptide motifs (FIG. 77A) and amino acids (FIG. 77B) that are enriched in the peptides that discriminate between the RA samples from the "other Rheumatic Diseases" (ORD) group of samples. Comparisons of signal binding data obtained from samples from RA subjects to binding data from ORD group identified peptides that discriminated the RA samples from the ORD group were enriched by greater than 4.8 fold (480%) in one or more motifs listed in FIG. 77A relative to the incidence of the same motifs in the entire peptide library. Additionally, peptides that discriminated RA samples from ORD samples were found to be enriched by greater than 1.1 (110%) fold in individual amino acids (FIG. 77B).

FIGS. 78A-78B shows the peptide motifs (FIG. 78A) and amino acids (FIG. 78B) that are enriched in the peptides that discriminate between the RA samples from the "Not RA" group of samples. Comparisons of signal binding data obtained from samples from RA subjects to binding data from "Not RA" group identified peptides that discriminated the RA samples from the "Not RA" group were enriched by greater than 4.9 fold (492%) in one or more motifs listed in FIG. 78A relative to the incidence of the same motifs in the entire peptide library. Additionally, peptides that discriminated RA samples from "not RA" samples were found to be enriched by greater than 1.1 (110%) fold in individual amino acids (FIG. 78B).

FIGS. 79A-79B show the peptide motifs (FIG. 79A) and amino acids (FIG. 79B) that are enriched in the peptides that discriminate between the RA samples from the "Other AI+non-AI mimic diseases" group of samples. Comparisons of signal binding data obtained from samples from RA subjects to binding data from the Other AI group identified peptides that discriminated the RA samples from the Other AI+non-AI mimic diseases group were enriched by greater than 4.8 fold (480%) in one or more motifs listed in FIG. 79A relative to the incidence of the same motifs in the entire peptide library. Additionally, peptides that discriminated RA samples from the Other AI+non-AI mimic diseases samples were found to be enriched by greater than 1 (100%) fold in individual amino acids (FIG. 79B).

FIGS. 80A-80B show the peptide motifs (FIG. 80A) and amino acids (FIG. 80B) that are enriched in the peptides that discriminate between the RA samples from the OA group of samples. Comparisons of signal binding data obtained from samples from RA subjects to binding data from OA group identified peptides that discriminated the RA samples from the OA group were enriched by greater than 3.3fold (330%) in one or more motifs listed in FIG. 80A relative to the incidence of the same motifs in the entire peptide library. Additionally, peptides that discriminated RA samples from OA samples were found to be enriched by greater than 1.6 (156%) fold in individual amino acids (FIG. 80B).

FIGS. 81A-81B show the peptide motifs (FIG. 81A) and amino acids (FIG. 81B) that are enriched in the peptides that discriminate between the RA samples from the FM group of samples. Comparisons of signal binding data obtained from samples from RA subjects to binding data from FM group identified peptides that discriminated the RA samples from the FM group were enriched by greater than 3.9 fold (390%) in one or more motifs listed in FIG. 81A relative to the incidence of the same motifs in the entire peptide library. Additionally, peptides that discriminated RA samples from FM samples were found to be enriched by greater than 1.1 (110%) fold in individual amino acids (FIG. 81B).

FIGS. 82A-82B show the peptide motifs (FIG. 82A) and amino acids (FIG. 82B) that are enriched in the peptides that discriminate between the RA samples from the SS group of samples. Comparisons of signal binding data obtained from samples from RA subjects to binding data from SS group identified peptides that discriminated the RA samples from the SS group were enriched by greater than 4.2 fold (420%) in one or more motifs listed in FIG. 82A relative to the incidence of the same motifs in the entire peptide library. Additionally, peptides that discriminated RA samples from SS samples were found to be enriched by greater than 1.3 (130%) fold in individual amino acids (FIG. 82B).

As described for the SLE contrasts, volcano plots were used to assess the discrimination between samples as the joint distribution of t-test p-values versus log differences in signal intensity means (Fold Change). The density of the peptides at each plotted position is indicated by the heat scale. The peptides above the green dashed line were chosen as discriminating peptides that distinguish between the two groups of each comparison by immunosignature with 95% confidence after applying a Bonferroni adjustment for multiplicity (shown as green line in FIGS. 83A-83C). FIGS. 83A, 83B, and 83C respectively show volcano plots of the median-normalized array peptide intensities.

The Welch's t-test identified the significant peptides, which are individual peptides that had significant differences in mean signal between the samples from the RA group of subjects and the samples from each of the contrast groups. For example, shown in FIGS. 83A-83C, the Welch's t-test identified 3062 individual peptides that had significant differences in mean signal between the samples from the RA group of subjects and the samples from the group of healthy donors (FIG. 83A); 742 significant features that displayed differences between RA group of subjects and the group of subjects having "All Diseases" i.e. Other AI+non-AI mimic diseases (FIG. 83B); and 1564 significant features that displayed differences between RA group of subjects and the group of subjects not having RA i.e. "Not RA". Peptides that passed the Bonferroni cut-off in each of the contrasts are shown in FIG. 84. 491 peptides are common to all contrasts. These 491 peptides comprise two-thirds of the RA v Other AI+non-AI mimic diseases indicated as "Other AI" contrast, which indicates that these peptides may uniquely identify RA from similar disorders.

Significant peptides were identified by Welch's t-test and support vector machine (SVM) classifier was developed for each of the contrasts, as described in Example 15. Support vector machine (SVM) models were used to identify combinations of peptides that can predict the likelihood of RA versus healthy individuals or other similar diseases. Up to 4000 peptides, as ranked by p-value, were used as SVM inputs. 100 iterations of 5-fold cross-validation minimized the possibility of over-fitting.

The histogram in FIG. 85 indicates the area under the receiver operating characteristic curve (AUC) for discrimination between RA and the listed subgroup: healthy donors (HC), Other AI and non-AI mimic disease ("Other AI"), and the Not SLE group (Other AI+non-AI mimic+HC). The AUC of 0.9 for SLE vs healthy suggests robust discrimination in a diagnostic setting. The AUC of 0.8 for RA vs healthy indicates discrimination in a diagnostic setting.

Comparisons of signal intensities of array-bound antibodies from samples of subjects with RA showed that RA could be distinguished from other AI and non-AI mimic diseases (Table 2).

A histogram depicting the assay performance in distinguishing RA samples from SLE, Sjogrens, OA and Fibromyalgia is provided in FIG. 86.

Using IS technology, RA is best discriminated from distinct conditions, including patients with lupus and healthy controls. Nevertheless, RA can also be differentiated from closely-related conditions such as SS with modest cvAUCs. The results indicate that IS technology could provide a single test using a small serum sample capable of multi-classification across a range of symptomatically related diseases, or in patients with conditions referred to rheumatologic evaluation.

Example 18—Proteome Mapping the RA-Classifying Peptides Identifies Candidate Biomarkers of RA The top 1000 library peptides, as ranked by p-value) that significantly distinguished RA from healthy subjects, Other AI+non-AI mimic diseases, and "Not RA" subjects, as described in Example 4, were aligned to the human proteome RefSeq release 84, corresponding to human genome build GrCh38 (https://www.ncbi.nlm.nih.gov/refseq/), compiled Mar. 10, 2016, using the longest transcript variant for each unique gene ID, with a modified BLAST algorithm and a BLOSUM62-based scoring system that used a sliding window of overlapping 20-mers (Example 14). The top 50 significant peptides that discriminate between the RA samples from the healthy (HC) group of samples are shown in FIG. 93; the top 50 significant peptides that discriminate between RA samples from the Other Autoimmune and non-Autoimmune mimic diseases (Other AI+non-AI) group of samples are shown in FIG. 94; and the top significant peptides that discriminate between the RA samples from the Not RA (Not RA—Other AI+non-AI+HC) group of samples are shown in FIG. 95.

Peptides were aligned to 20mer segments of the proteins overlapping by 10 mer. The gene name/epitope start—alignment scores are provided.

These classifying peptides display a high frequency of alignment scores that greatly exceed the maximum scores obtained by performing the same analysis with ten equally-sized sets of peptides that were randomly selected from the library.

The resulting ranked list of the top 25 candidate protein-target regions i.e. candidate biomarkers, provided in FIGS. 87A-87C. Among the top-scoring candidates mapped by the RA classifying peptides was the MN1 autoantiboides associated with BrCA cancers [Wang, et al. "Plasma autoantibodies associated with basal-like breast cancers", Cancer Epidemiol Biomarkers Prev. 2015 September; 24(9): 1332-1340.

Together the 25 candidate proteome targets in each contrast accounted for the aligned discriminating peptides. Leading candidate biomarkers can also be identified by up to all of the total number of discriminating peptides.

These data show that array peptides that array peptides, which mimic RA autoantigen epitopes, were bound differentially by peripheral blood antibodies in RA subjects. These discriminating peptides were mapped to several markers that could be novel markers of RA.

Example 19—Simultaneous Classification of Different Health Conditions

Peptides simultaneously discriminating SLE, RA, FM, OA, SS and HC from each other in the multiclassifier analysis were enriched by greater than 100% in one or more motifs listed in FIG. 88A relative to the incidence of the same motifs in the entire peptide library. Additionally, the peptides that discriminated SLE, RA, FM, OA, SS and HC samples from each other in the multiclassifier analysis were enriched by greater than 100% in one or more amino acids listed in FIG. 29B.

The heat map shown in FIG. 89 visualizes the mean predicted probability of class membership of out of the bag cross validation model predictions for each of the test cohort samples, encompassing all six conditions. Each sample has a predicted class membership for each outcome ranging from 0 (black) to 100% (white).

These data show that the immunosignature assay can simultaneously distinguish one health condition from two or more other conditions.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EMBODIMENTS

Provided herein are methods and devices for identifying at least one candidate biomarker for a disease in a subject, the method comprising: (a) providing a peptide array and incubating a biological sample from said subject to the peptide array; (b) identifying a set of discriminating peptides bound to an antibody in the biological sample from said subject, the set of peptides capable of differentiating the disease from at least one different condition; (c) querying a proteome database with each of the peptides in the set of peptides; (d) aligning each of the peptides in the set of peptides to one or more proteins in the proteome database; and (e) obtaining a relevance score and ranking for each of the identified proteins from the proteome database; wherein each of the identified proteins is a candidate biomarker for the disease in the subject.

In some aspects, the methods and devices further comprise obtaining an overlap score, wherein said score corrects for the peptide composition of the peptide library.

In some aspects, the discriminating peptides of the methods and devices herein are identified as having p-values of less than $10^{-5}$, less than $10^{-6}$, less than $10^{-7}$, less than $10^{-8}$, less than $10^{-9}$, less than $10^{-10}$, less than $10^{-11}$, less than $10^{-12}$, less than $10^{-13}$, less than $10^{-14}$, or less than $10^{-15}$. In some aspects, the step of identifying said set of discriminating peptides comprises (i) detecting the binding of antibodies present in samples form a plurality of subjects having said disease to an array of different peptides to obtain a first combination of binding signals; (ii) detecting the binding of antibodies to a same array of peptides, said antibodies being present in samples from one or more reference groups of subjects, each group having a different health condition; (iii) comparing said first to said second combination of binding signals; and (iv) identifying said peptides on said array that are differentially bound by antibodies in samples from subjects having said disease and the antibodies in said samples from one or more reference groups of subjects, thereby identifying said discriminating peptides.

In some aspects, the number of discriminating peptides of the methods and devices disclosed herein corresponds to at least a portion of the total number of peptides on said array. In other aspects, said disease is an autoimmune disease. In some aspects, said autoimmune disease is scleroderma. In some aspects, said discriminating peptides differentiate said scleroderma from a healthy condition. In other aspects, said at least one candidate protein biomarker is selected from the list provided in Table 3. In yet other aspects, said autoimmune disease is lupus. In still other aspects, said discriminating peptides differentiate levels of lupus disease activity and/or a change in lupus disease activity as defined by the SLEDAI score. In still other aspects, said at least one candidate protein biomarker is selected from the list provided in Table 11.

In some aspects of the methods and devices disclosed herein, said disease is an infectious disease. In some instances, the infectious disease is Chagas disease. In yet other instances, the discriminating peptides differentiate said Chagas disease from a healthy condition. In still other aspects, the at least one candidate protein biomarker is selected from the list provided in Tables 6 and 7. In some aspects, the subject is human. In other aspects, the sample is a blood sample. In still other aspects, the blood sample is selected from whole blood, plasma, or serum. In still other instances, the sample is a serum sample. In other aspects, the sample is a plasma sample. In yet other aspects, the sample is a dried blood sample.

In some instances, the different peptides on the peptide array is at least 5 amino acids in length. In other instances, the different peptides on the array is between 5 and 15 amino acids in length. In other aspects, the peptide array comprises at least 10,000 different peptides. In still other aspects, the peptide array comprises at least 50,000 different peptides. In yet other instances, the peptide array comprises at least 100,000 different peptides. In some instances, the peptide array comprises at least 300,000 different peptides. In still other instances, the peptide array comprises at least 500,000 different peptides. In yet other aspects, the peptide array comprises at least 1,000,000 different peptides. In still other instances, the peptide array comprises at least 2,000,000 different peptides. In yet other instances, the peptide array comprises at least 3,000,000 different peptides. In some instances, the different peptides on the array are deposited. In some instances, the different peptides on the array are synthesized in situ. In yet other instances, the different peptides on the array are synthesized from less than 20 amino acids.

What is claimed is:

1. A method for identifying at least one candidate biomarker for an autoimmune disease, the method comprising:

(a) providing a peptide array and contacting a biological sample from a plurality of subjects known to have the autoimmune disease to the peptide array;

(b) identifying a set of discriminating peptides bound to antibodies in the biological sample from the plurality of subjects that differentiate the autoimmune disease from at least one different health condition;

(c) aligning each of the peptides in the set of discriminating peptides to one or more proteins in a proteome; and (d) obtaining a protein score and ranking for each of the identified proteins according to a statistical significance, thereby identifying at least one candidate biomarker for the autoimmune disease, wherein a method performance for differentiating the autoimmune disease from at least one different health condition is characterized by an area under the receiver operator characteristic (ROC) curve (AUC) ranging from 0.60 to 1.00.

2. The method of claim 1, further comprising obtaining an overlap score, wherein said score corrects for composition of the peptides on the peptide array.

3. The method of claim 1, wherein ranking for each of the identified proteins is made relative to the ranking of proteins identified from aligning non-discriminating peptides.

4. The method of claim 1, wherein the identified candidate biomarkers are ranked according to a p-value of less than $10^{-3}$.

5. The method of claim 1, wherein the step of identifying the set of discriminating peptides comprises:

(i) detecting binding of antibodies present in the biological sample from the plurality of subjects having the autoimmune disease to obtain a first combination of binding signals;

(ii) detecting binding of antibodies present in samples from one or more reference groups of subjects to the same peptide array, each reference group having a different health condition to obtain a second combination of binding signals;

(iii) comparing the first combination of binding signals to the second combination of binding signals to obtain a set of differentiating binding signals; and (iv) identifying peptides on the array that are differentially bound by antibodies in samples from subjects having the autoimmune disease and the antibodies in the samples from the one or more reference groups of subjects, thereby identifying said discriminating peptides.

6. The method of claim 5, wherein the discriminating peptides comprise an enrichment of one or more sequence motifs of at least 100% as compared to the remaining peptides on the array.

7. The method of claim 5, wherein the set of differentiating binding signals is obtained by detecting the binding of antibodies present in samples from subjects with the autoimmune disease and the antibodies in the samples from the one or more reference group of subjects to at least 25 peptides on an array of peptides comprising at least 10,000 different peptides.

8. The method of claim 5, wherein the method performance for differentiating the autoimmune disease from the at least one different health condition is characterized by an area under the receiver operator characteristic (ROC) curve (AUC) ranging from 0.60 to 0.70, 0.70 to 0.79, 0.80 to 0.89, or 0.90 to 1.00.

9. The method of claim 5, wherein the autoimmune disease is scleroderma (SSc) and the reference group of subjects are healthy subjects and the discriminating peptides that differentiate the first combination of binding signals from the second combination of binding signals are enriched by at least 100% in one or more sequence motifs listed in FIG. 8A.

10. The method of claim 5, wherein the autoimmune disease is scleroderma and the reference group of subjects are healthy subjects and the discriminating peptides that differentiate the first combination of binding signals from the second combination of binding signals are enriched by at least 100% in one or more amino acids listed in FIG. 8B.

11. The method of claim 5, wherein the autoimmune disease is SSc and the reference group of subjects are healthy subjects and the discriminating peptides that differentiate the first combination of binding signals from the second combination of binding signals comprise at least one peptide of the list provided in Table 3.

12. A set of discriminating peptides, wherein the discriminating peptides comprise one or more sequence motifs provided in FIG. 8A, wherein the discriminating peptides differentiate the binding of antibodies from samples from subjects with SSc from healthy subjects.

13. The set of discriminating peptides of claim 12, wherein the peptides are selected from the list provided in FIG. 8C.

14. The method of claim 5, wherein the autoimmune disease is SLE and the reference group of subjects are healthy subjects, and the discriminating peptides that differentiate the first combination of binding signals from the second combination of binding signals are enriched by at least 100% in one or more sequence motifs listed in FIG. 62A.

15. The method of claim 5, wherein the autoimmune disease is SLE and the reference group of subjects are healthy subjects and the discriminating peptides that differentiate the first combination of binding signals from the second combination of binding signals are selected comprise at least one peptide of the list provided in FIG. 90.

16. A set of discriminating peptides, wherein the discriminating peptides comprise one or more sequence motifs provided in FIG. 62A, wherein the discriminating peptides differentiate the binding of antibodies from samples from subjects with SLE from healthy subjects.

17. The discriminating peptides of claim 16, wherein the peptides are selected from the list provided in FIG. 90.

18. The method of claim 5, wherein the autoimmune disease is RA and the reference group of subjects are healthy subjects, and the discriminating peptides that differentiate the first combination of binding signals from the second combination of binding signals are enriched by at least 100% in one or more sequence motifs listed in FIG. 76A.

19. A set of discriminating peptides, wherein the discriminating peptides comprise one or more sequence motifs provided in FIG. 76A, wherein the discriminating peptides differentiate the binding of antibodies from samples from subjects with RA from healthy subjects.

20. The discriminating peptides of claim 19, wherein the peptides are selected from the list provided in FIG. 93.

\* \* \* \* \*